US009555089B2

(12) United States Patent
Shiratsuchi et al.

(10) Patent No.: US 9,555,089 B2
(45) Date of Patent: Jan. 31, 2017

(54) MODIFICATION OF RECOMBINANT ADENOVIRUS WITH IMMUNOGENIC PLASMODIUM CIRCUMSPOROZOITE PROTEIN EPITOPES

(75) Inventors: Takayuki Shiratsuchi, Tokushima (JP); Moriya Tsuji, New York, NY (US)

(73) Assignee: THE ROCKEFELLER UNIVERSITY, New York, NY (US)

( * ) Notice: Subject to any disclaimer, the term of this patent is extended or adjusted under 35 U.S.C. 154(b) by 441 days.

(21) Appl. No.: 13/399,654

(22) Filed: Feb. 17, 2012

(65) Prior Publication Data

US 2012/0213814 A1 Aug. 23, 2012

Related U.S. Application Data

(63) Continuation of application No. PCT/US2010/045952, filed on Aug. 18, 2010, which is a continuation-in-part of application No. PCT/US2009/054212, filed on Aug. 18, 2009.

(51) Int. Cl.

| | |
|---|---|
| ***A61K 39/015*** | (2006.01) |
| ***C12N 15/861*** | (2006.01) |
| ***A61P 33/06*** | (2006.01) |
| ***C12N 7/01*** | (2006.01) |
| ***A61K 39/00*** | (2006.01) |
| ***C07K 14/005*** | (2006.01) |

(52) U.S. Cl.

CPC ........... *A61K 39/015* (2013.01); *C07K 14/005* (2013.01); *C12N 15/861* (2013.01); *A61K 2039/5256* (2013.01); *A61K 2039/55577* (2013.01); *C07K 2319/00* (2013.01); *C07K 2319/40* (2013.01); *C12N 2710/10322* (2013.01); *C12N 2710/10341* (2013.01); *C12N 2710/10343* (2013.01)

(58) Field of Classification Search

CPC .............. C07K 16/18; A61K 2039/505; A61K 39/0007; C12N 15/86; C12N 2710/10322

USPC .......................................................... 424/199

See application file for complete search history.

(56) References Cited

U.S. PATENT DOCUMENTS

| | | | | |
|---|---|---|---|---|
| 6,066,623 | A | 5/2000 | Hoffman | |
| 2004/0058340 | A1 | 3/2004 | Dai et al. | |
| 2005/0265974 | A1 | 12/2005 | Pau et al. | |
| 2008/0220014 | A1 * | 9/2008 | Pau et al. | 424/199.1 |
| 2009/0148477 | A1 * | 6/2009 | Bruder et al. | 424/272.1 |
| 2010/0166745 | A1 | 7/2010 | Mather et al. | |

FOREIGN PATENT DOCUMENTS

| | | | |
|---|---|---|---|
| EP | 0378881 | * | 9/1993 |
| JP | 2005500336 | A | 1/2005 |
| JP | 2005287309 | A | 10/2005 |
| WO | WO-9310152 | A1 | 5/1993 |
| WO | WO-2004055187 | A1 | 7/2004 |
| WO | 2004101799 | A | 11/2004 |
| WO | WO-2006040330 | A2 | 4/2006 |
| WO | WO2008140474 | * | 11/2008 |
| WO | WO-2008140474 | A1 | 11/2008 |
| WO | WO 2009/009739 | | 1/2009 |

OTHER PUBLICATIONS

Abbink, P., Lemckert, A.A., Ewald, B.A., Lynch, D.M., Denholtz, M., et al. 2007. Comparative seroprevalence and immunogenicity of six rare serotype recombinant adenovirus vaccine vectors from subgroups B and D. *J Virol.* 81:4654-4663.

Alonso, P.L., Sacarlal, J., Aponte, J.J., Leach, A., Macete, E., et al. 2004. Efficacy of the RTS,S/AS02A vaccine against Plasmodium falciparum infection and disease in young African children: randomised controlled trial. *Lancet.* 364:1411-1420.

Alonso, P.L., Sacarlal, J., Aponte, J.J., Leach, A., Macete, E., et al. 2005. Duration of protection with RTS,S/AS02A malaria vaccine in prevention of Plasmodium falciparum disease in Mozambican children: single-blind extended follow-up of a randomised controlled trial. *Lancet.* 366:2012-2018.

Anderson, R.J., Hannan, C.M., Gilbert, S.C., Laidlaw, S.M., Sheu, E.G., et al. 2004. Enhanced CD8+ T cell immune responses and protection elicited against Plasmodium berghei malaria by prime boost immunization regimens using a novel attenuated fowlpox virus. *J Immunol.* 172:3094-3100.

Athappilly, F.K., Murali, R., Rux, J.J., Cai, Z. & Burnett, R.M. The refined crystal structure of Hexon, the major coat protein of adenovirus type 2, at 2.9 a resolution. *Journal of molecular biology* 242, 430-455 (1994).

Barrat, F.J., Meeker, T Gregorio, J Chan, J.H., Uematsu, S., et al. Nucleic acids of mammalian origin can act as endogenous ligands for Toll-like receptors and may promote systemic lupus erythematosus. *J Exp Med.* 202, 1131-1139 (2005).

Bejon, P., Lusingu, J., Olotu, A., Leach, A., Lievens, M., et al. 2008. Efficacy of RTS,S/AS01E vaccine against malaria in children 5 to 17 months of age. *N Engl J Med.* 359:2521-2532.

Belousova, N., Krendelchtchikova, V., Curiel, D.T. & Krasnykh, V. Modulation of adenovirus vector tropism via incorporation of polypeptide ligands into the Fiber protein. *Journal of virology* 76, 8621-8631 (2002).

(Continued)

*Primary Examiner* — Janet L Andres
*Assistant Examiner* — Barry A Chestnut
(74) *Attorney, Agent, or Firm* — Perkins Coie LLP

(57) ABSTRACT

The present disclosure relates to adenovirus protein modifications to augment immune response to a transgene of a recombinant adenovirus and to circumvent pre-existing anti-adenovirus immunity. Some embodiments are directed to a recombinant adenovirus derived from a recombinant adenovirus plasmid vector, wherein the recombinant adenovirus plasmid vector comprises a nucleotide sequence encoding a *Plasmodium* circumsporozoite protein, or antigenic portion thereof, operably linked to a heterologous promoter and a modified capsid or core protein, wherein an immunogenic epitope of *Plasmodium* circumsporozoite is inserted into or replaces at least part of a capsid or core protein. Other embodiments are directed to a pharmaceutical composition or a malaria vaccine composition comprising a recombinant adenovirus according to the above embodiments. Further embodiments include a method of treating, preventing, or diagnosing malaria, comprising administering a therapeutic amount of the pharmaceutical composition or malaria vaccine composition in accordance with the above embodiment.

16 Claims, 101 Drawing Sheets

(56) References Cited

OTHER PUBLICATIONS

Bergelson, J.M. et al. Isolation of a common receptor for Coxsackie B viruses and adenoviruses 2 and 5. *Science* (New York, N.Y 275, 1320-1323 (1997).
Bewley, M.C., Springer, K., Zhang, Y.B., Freimuth, P. & Flanagan, J.M. Structural analysis of the mechanism of adenovirus binding to its human cellular receptor, Car. *Science* (New York, N.Y 286, 1579-1583 (1999).
Bruña-Romero, O., Schmieg, J., Del Val, M., Buschle, M. & Tsuji, M. The dendritic cell-specific chemokine, dendritic cell-derived CC chemokine 1, enhances protective cell-mediated immunity to murine malaria. *J Immunol* 170, 3195-3203 (2003).Hong, S.S., Karayan, L., Tournier, J., Curiel, D.T. & Boulanger, P.A. Adenovirus type 5 Fiber knob binds to MHC class I alpha2 domain at the surface of human epithelial and B lymphoblastoid cells. *The EMBO journal* 16, 2294-2306 (1997).
Bruña-Romero, O., González-Aseguinolaza, G., Hafalla, J.C., Tsuji, M., and Nussenzweig, R.S. 2001. Complete, long-lasting protection against malaria of mice primed and boosted with two distinct viral vectors expressing the same plasmodial antigen. *Proc Natl Acad Sci U S A.* 98:11491-11496.
Bruña-Romero, O., Rocha, C.D., Tsuji, M. & Gazzinelli, R.T. Enhanced protective immunity against malaria by vaccination with a recombinant adenovirus encoding the circumsporozoite protein of Plasmodium lacking the GPI-anchoring motif. *Vaccine* 22, 3575-3584 (2004).
Calvo-Calle, J.M., Oliveira, G.A., Watta, C.O., Soverow, J., Parra-Lopez, C., et al. 2006. A linear peptide containing minimal T- and B-cell epitopes of Plasmodium falciparum circumsporozoite protein elicits protection against transgenic sporozoite challenge. *Infect Immun.* 74:6929-6939.
Clyde, D.F., Most, H., McCarthy, V.C., and Vanderberg, J.P. 1973. Immunization of man against sporozite-induced falciparum malaria. *Am J Med Sci.* 266:169-177.
Chroboczek, J., Ruigrok, R.W. & Cusack, S. Adenovirus Fiber. *Current topics in microbiology and immunology* 199 ( Pt 1), 163-200 (1995).
Chu, Y., Heistad, D., Cybulsky, M.I. & Davidson, B.L. Vascular cell adhesion molecule-1 augments adenovirus-mediated gene transfer. *Arterioscler Thromb Vasc Biol* 21, 238-242 (2001).
Crawford-Miksza, L. & Schnurr, D.P. Analysis of 15 adenovirus Hexon proteins reveals the location and structure of seven hypervariable regions containing serotype-specific residues. *Journal of virology* 70, 1836-1844 (1996).
Crompton, J., Toogood, C.I., Wallis, N. & Hay, R.T. Expression of a foreign epitope on the surface of the adenovirus Hexon. *The Journal of general virology* 75 ( Pt 1), 133-139 (1994).
Crystal, R.G. Transfer of genes to humans: early lessons and obstacles to success. *Science* (New York, N.Y 270, 404-410 (1995).
Douglas, J.T. Adenoviral vectors for gene therapy. *Molecular biotechnology* 36, 71-80 (2007).
Edelman, R., Hoffman, S.L., Davis, J.R., Beier, M., Sztein, M.B., et al. 1993. Long-term persistence of sterile immunity in a volunteer immunized with X-irradiated Plasmodium falciparum sporozoites. *J Infect Dis.* 168:1066-1070.
Grillot, D., Valmori, D., Lambert, P.H., Corradin, G., and Del Giudice, G. 1993. Presentation of T cell epitopes assembled as multiple-antigen peptides to murine and human T lymphocytes. *Infect Immun.* 61:3064-3067.
Graham, F.L. & Prevec, L. Adenovirus-based expression vectors and recombinant vaccines. *Biotechnology* (Reading, Mass 20, 363-390 (1992).
Gwadz, R.W., Cochrane, A.H., Nussenzweig, V., and Nussenzweig, R.S. 1979. Preliminary studies on vaccination of rhesus monkeys with irradiated sporozoites of Plasmodium knowlesi and characterization of surface antigens of these parasites. *Bull World Health Organ.*57 Suppl 1:165-173.
Hackett, N.R. et al. Use of quantitative TaqMan real-time PCR to track the time-dependent distribution of gene transfer vectors in vivo. *Mol Ther* 2, 649-656 (2000).
Harvey, B.G. et al. Airway epithelial CFTR mRNA expression in cystic fibrosis patients after repetitive administration of a recombinant adenovirus. *The Journal of clinical investigation* 104, 1245-1255 (1999).
Heemskerk, B. et al. Adenovirus-specific CD4+ T cell clones recognizing endogenous antigen inhibit viral replication in vitro through cognate interaction. *J Immunol* 177, 8851-8859 (2006).
Henry, L.J., Xia, D., Wilke, M.E., Deisenhofer, J. & Gerard, R.D. Characterization of the knob domain of the adenovirus type 5 Fiber protein expressed in *Escherichia coli. Journal of virology* 68, 5239-5246 (1994).
Hong, S.S., Habib, N.A., Franqueville, L., Jensen, S. & Boulanger, P.A. Identification of adenovirus (ad) penton base neutralizing epitopes by use of sera from patients who had received conditionally replicative ad (addl1520) for treatment of liver tumors. *Journal of virology* 77, 10366-10375 (2003).
Kester, K.E., Cummings, J.F., Ockenhouse, C.F., Nielsen, R., Hall, B.T., et al. 2008. Phase 2a trial of 0, 1, and 3 month and 0, 7, and 28 day immunization schedules of malaria vaccine RTS,S/AS02 in malaria-naïve adults at the Walter Reed Army Institute of Research. *Vaccine.* 26:2191-2202.
Kirby, I. et al. Mutations in the DG loop of adenovirus type 5 Fiber knob protein abolish highaffinity binding to its cellular receptor CAR. *Journal of virology* 73, 9508-9514 (1999).
Koizumi, N., Mizuguchi, H., Utoguchi, N., Watanabe, Y. & Hayakawa, T. Generation of Fiber-modified adenovirus vectors containing heterologous peptides in both the HI loop and C terminus of the Fiber knob. *The Journal of Gene Medicine* 5, 267-276 (2003).
Kozak M. 1987. An analysis of 5'-noncoding sequences from 699 vertebrate messenger RNAs. *Nucleic Acids Res.* 15:8125-148.
Krause, A., Joh, J.H., Hackett, N.R., Roelvink, P.W., Bruder, J.T., et al. 2006. Epitopes expressed in different adenovirus capsid proteins induce different levels of epitope-specific immunity. *J Virol.* 80:5523-5530.
Labow, D., Lee, S., Ginsberg, R.J., Crystal, R.G. & Korst, R.J. Adenovirus vector-mediated gene transfer to regional lymph nodes. *Human gene therapy* 11, 759-769 (2000).
Leen, A.M. et al. Identification of Hexon-specific CD4 and CD8 T cell epitopes for vaccine and immunotherapy. *Journal of virology* 82, 546-554 (2008).
Leopold, P.L. & Crystal, R.G. Intracellular trafficking of adenovirus: many means to many ends. *Advanced drug delivery reviews* 59, 810-821 (2007).
Mastrangeli, A. et al. "Sero-switch" adenovirus-mediated in vivo gene transfer: circumvention of anti-adenovirus humoral immune defenses against repeat adenovirus vector administration by changing the adenovirus serotype. *Human gene therapy* 7, 79-87 (1996).
Mathias, P., Wickham, T., Moore, M. & Nemerow, G. Multiple adenovirus serotypes use alpha v integrins for infection. *Journal of virology* 68, 6811-6814 (1994).
McConnell, M.J., Danthinne, X., and Imperiale, M.J. 2006. Characterization of a permissive epitope insertion site in adenovirus Hexon. *J Virol.* 80:5361-5370.
Meier, O. & Greber, U.F. Adenovirus endocytosis. *The journal of gene medicine* 5, 451-462 (2003).
Miyazawa, N. et al. Fiber swap between adenovirus subgroups B and C alters intracellular trafficking of adenovirus gene transfer vectors. *Journal of virology* 73, 6056-6065 (1999).
Miyazawa, N., Crystal, R.G. & Leopold, P.L. Adenovirus serotype 7 retention in a late endosomal compartment prior to cytosol escape is modulated by Fiber protein. *Journal of virology* 75, 1387-1400 (2001).
Mizuguchi, H. & Hayakawa, T. Targeted adenovirus vectors. *Human gene therapy* 15, 1034-1044 (2004).
Nakano, M.Y., Boucke, K., Suomalainen, M., Stidwill, R.P. & Greber, U.F. The first step of adenovirus type 2 disassembly occurs at the cell surface, independently of endocytosis and escape to the cytosol. *Journal of virology* 74, 7085-7095 (2000).
Nicklin, S.A. et al. Ablating adenovirus type 5 Fiber-Car binding and HI loop insertion of the SIGYPLP peptide generate an endothelial cell-selective adenovirus. *Mol Ther* 4, 534-542 (2001).
Noureddini, S.C. & Curiel, D.T. Genetic targeting strategies for adenovirus. *Molecular pharmaceutics* 2, 341-347 (2005).

(56) References Cited

OTHER PUBLICATIONS

Nussenzweig, R.S., Vanderberg, J., Most, H., and Orton, C. 1967. Protective immunity produced by the injection of x-irradiated sporozoites of plasmodium berghei. *Nature.* 216:160-162.
Nussenzweig, R.S. & Long, C.A. Malaria vaccines: multiple targets. *Science* (New York, N.Y 265, 1381-1383 (1994).
Onion, D. et al. The CD4+ T cell response to adenovirus is focused against conserved residues within the Hexon protein. *The Journal of general virology* 88, 2417-2425 (2007).
Ophorst, O.J., Radosevie, K., Havenga, M.J., Pau, M.G., Holterman, L., et al. 2006. Immunogenicity and protection of a recombinant human adenovirus serotype 35-based malaria vaccine against Plasmodium yoelii in mice. *Infect Immun.* 74:313-320.
Oualikene, W., Gonin, P. & Eloit, M. Short and long term dissemination of deletion mutants of adenovirus in permissive (cotton rat) and non-permissive (mouse) species. *The Journal of general virology* 75 ( Pt 10), 2765-2768 (1994).
Priddy, F.H., Brown, D., Kublin, J., Monahan, K., Wright, D.P., et al. 2008. Safety and immunogenicity of a replication-incompetent adenovirus type 5 HIV-1 clade B gag/pol/nef vaccine in healthy adults. *Clin Infect Dis.* 46:1769-1781.
Roberts, M.M., White, J.L., Grutter, M.G. & Burnett, R.M. Three-dimensional structure of the adenovirus major coat protein Hexon. *Science* (New York, N.Y 232, 1148-1151 (1986).
Roberts, D.M., Nanda, A., Havenga, M.J., Abbink, P., Lynch, D.M., et al. 2006. Hexon-chimaeric adenovirus serotype 5 vectors circumvent pre-existing anti-vector immunity. *Nature.* 441:239-243.
Rodrigues, E.G., Zavala, F., Eichinger, D., Wilson, J.M., and Tsuji, M. 1997. Single immunizing dose of recombinant adenovirus efficiently induces CD8+ T cell-mediated protective immunity against malaria. *J Immunol.* 158:1268-1274.
Rodrigues, E.G., Zavala, F., Nussenzweig, R.S., Wilson, J.M. & Tsuji, M. Efficient induction of protective anti-malaria immunity by recombinant adenovirus. *Vaccine* 16, 1812-1817 (1998).
Roelvink, P.W., Mi Lee, G., Einfeld, D.A., Kovesdi, I. & Wickham, T.J. Identification of a conserved receptor-binding site on the Fiber proteins of CAR-recognizing adenoviridae. *Science* (New York, N.Y 286, 1568-1571 (1999).
Rux, J.J. & Burnett, R.M. Type-specific epitope locations revealed by X-ray crystallographic study of adenovirus type 5 Hexon. *Mol Ther* 1, 18-30 (2000).
Rux, J.J. & Burnett, R.M. Adenovirus structure. *Human gene therapy* 15, 1167-1176 (2004).
Roy, S. et al. Use of chimeric adenoviral vectors to assess capsid neutralization determinants. *Virology* 333, 207-214 (2005).
Shiratsuchi, T., et al. "Replacing adenoviral vector HVR1 with a malaria B cell epitope improves immunogenicity and circumvents preexisting immunity to adenovirus in mice," Journal of Clinical Investigation, vol. 120, No. 10, Oct. 1, 2010, pp. 3688-3701.
Abe, et al., "Advenovirus type 5 with modified hexons induces robust transgene-specific immune responses in mice with pre-existing immunity against advenovirus type 5," The Journal of Gene Medicine, vol. 11, No. 7, Jul. 1, 2009, pp. 570-579.
Silvie, O., Greco, C., Franetich, J.F., Dubart-Kupperschmitt, A., Hannoun, L., et al. 2006. Expression of human CD81 differently affects host cell susceptibility to malaria sporozoites depending on the Plasmodium species. *Cell Microbiol.* 8:1134-1146.
Sumida, S.M., Truitt, D.M., Lemckert, A.A., Vogels, R., Custers, J.H., et al. 2005. Neutralizing antibodies to adenovirus serotype 5 vaccine vectors are directed primarily against the adenovirus Hexon protein. *J Immunol.* 174:7179-7185.
Sun, P., Schwenk, R., White, K., Stoute, J.A., Cohen, J., et al. 2003. Protective immunity induced with malaria vaccine, RTS,S, is linked to Plasmodium falciparum circumsporozoite protein-specific CD4+ and CD8+ T cells producing IFN-gamma. *J Immunol.* 171:6961-6967.
Tao, D., Barba-Spaeth, G., Rai, U., Nussenzweig, V., Rice, C.M., and Nussenzweig, R.S. 2005. Yellow fever 17D as a vaccine vector for microbial CTL epitopes: protection in a rodent malaria model. *J Exp Med.* 201:201-209.
Teramoto, S. et al. Investigation of effects of anesthesia and age on aspiration in mice through LacZ gene transfer by recombinant E1-deleted adenovirus vectors. *American journal of respiratory and critical care medicine* 158, 1914-1919 (1998).
Top, F.H., Jr., Dudding, B.A., Russell, P.K. & Buescher, E.L. Control of respiratory disease in recruits with types 4 and 7 adenovirus vaccines. *American journal of epidemiology* 94, 142-146 (1971).
Top, F.H., Jr. Control of adenovirus acute respiratory disease in U.S. Army trainees. *Yale J Biol Med* 48, 185-195 (1975).
Tsuji, M., Romero, P., Nussenzweig, R.S., and Zavala, F. 1990. CD4+ cytolytic T cell clone confers protection against murine malaria. *J Exp Med.* 172:1353-1357.
Tsuji, M., Rodrigues, E.G. & Nussenzweig, S. Progress toward a malaria vaccine: efficient induction of protective anti-malaria immunity. *Biol Chem* 382, 553-570 (2001).
Valmori, D., et al. "Use of human universally antigenic tetanus toxin T cell epitopes as carriers for human vaccination," The Journal of Immunology, The Amerian Association of Immunologists, US, vol. 140, No. 2, Jul. 15, 1992, pp. 717-712.
Wang, R., et al. "Induction of protective polyclonal antibodies by immunization with a Plasmodium yoelii circumsporozoite protein multiple antigen peptide vaccine," The Journal of Immunology, vol. 15, Mar. 15, 1995, pp. 2784-2784.
Wickham, T.J., Mathias, P., Cheresh, D.A. & Nemerow, G.R. Integrins alpha v beta 3 and alpha v beta 5 promote adenovirus internalization but not virus attachment. *Cell* 73, 309-319 (1993).
Wohlfart, C. Neutralization of adenoviruses: kinetics, stoichiometry, and mechanisms. *Journal of virology* 62, 2321-2328 (1988).
Worgall, S. et al. Modification to the capsid of the adenovirus vector that enhances dendritic cell infection and transgene-specific cellular immune responses. *Journal of virology* 78, 2572-2580 (2004).
Worgall, S., Krause, A., Rivara, M., Hee, K.K., Vintayen, E.V., et al. 2005. Protection against P. aeruginosa with an adenovirus vector containing an OprF epitope in the capsid. *J Clin Invest.* 115:1281-1289.
Worgall, S., Krause, A., Qiu, J., Joh, J., Hackett, N.R., and Crystal, R.G. 2007. Protective immunity to pseudomonas aeruginosa induced with a capsid-modified adenovirus expressing P. aeruginosa OprF. *J Virol.* 81:13801-13808.
Wu, H., Dmitriev, I., Kashentseva, E., Seki, T., Wang, M., et al. 2002. Construction and characterization of adenovirus serotype 5 packaged by serotype 3 Hexon. *J Virol.* 76:12775-12782.
Wu, H. et al. Identification of sites in adenovirus Hexon for foreign peptide incorporation. *Journal of virology* 79, 3382-3390 (2005).
Xia, D., Henry, L., Gerard, R.D. & Deisenhofer, J. Structure of the receptor binding domain of adenovirus type 5 Fiber protein. *Current topics in microbiology and immunology* 199 ( Pt 1), 39-46 (1995).
Yang, Y., Li, Q., Ertl, H.C. & Wilson, J.M. Cellular and humoral immune responses to viral antigens create barriers to lung-directed gene therapy with recombinant adenoviruses. *Journal of virology* 69, 2004-2015 (1995).
Youil, R., Toner, T.J., Su, Q., Chen, M., Tang, A., et al. 2002. Hexon gene switch strategy for the generation of chimeric recombinant adenovirus. *Hum Gene Ther.* 13: 311-320.
International Search Report and Written Opinion of International Application No. PCT/US2009/054212 mailed Feb. 2, 2010, 14 pages.
International Preliminary Report on Patentability of International Application No. PCT/US2009/054212 mailed Oct. 5, 2011, 25 pages.
International Search Report and Written Opinion of International Application No. PCT/US2010/045952 mailed Jan. 11, 2011, 11 pages.
International Preliminary Report on Patentability of International Application No. PCT/US2010/045952 mailed Nov. 4, 2011, 8 pages.
Official Action No. 14592 for Colombian Application No. 12028006, dated Aug. 9, 2013, 13 pages.
English Translation of First Office Action of Chinese Application No. 201080047059.6, mailed Nov. 12, 2013, 6 pages.
Extended Search Report of European Application No. 10810576.8, dated Dec. 20, 2013, 7 pages.

(56) References Cited

OTHER PUBLICATIONS

English translation of Official Action of Ukraine Application No. 201203125, dated Dec. 2, 2013, 8 pages.
English translation of Official Notification of Israeli Application No. 217709, dated May 11, 2014, 2 pages.
Office Action of New Zealand Application No. 598703, dated Nov. 30, 2012, 3 pages.
Akaike H. A new look at the statistical model identification. IEEE Trans Automatic Control 1974;19:716-23.
Akaogi K, Nakajima Y, Ito I, Kawasaki S, Oie SH, Murayama A et al (2009). KLF4 suppresses estrogen-dependent breast cancer growth by inhibiting the transcriptional activity of ERalpha. *Oncogene* 28: 2894-902.
Albergaria A, Paredes J, Sousa B, Milanezi F, Carneiro V, Bastos J et al (2009). Expression of FOXA1 and GATA-3 in breast cancer: the prognostic significance in hormone receptor-negative tumours. *Breast Cancer Res* 11: R40.
Andre F, Job B, Dessen P, et al. Molecular characterization of breast cancer with high-resolution oligonucleotide comparative genomic hybridization array. Clin Cancer Res 2009;15:441-51.
Aslakson CJ, Miller FR. Selective events in the metastatic process defined by analysis of the sequential dissemination of subpopulations of a mouse mammary tumor. Cancer Res 1992;52:1399-405.
Belguise K, Sonenshein GE (2007). PKCtheta promotes c-Rel-driven mammary tumorigenesis in mice and humans by repressing estrogen receptor alpha synthesis. *J Clin Invest* 117: 4009-21.
Berry FB, Saleem RA, Walter MA (2002). FOXC1 transcriptional regulation is mediated by N- and C-terminal activation domains and contains a phosphorylated transcriptional inhibitory domain. *J Biol Chem* 277: 10292-7.
Berry FB, Mirzayans F, Walter MA. Regulation of FOXC1 stability and transcriptional activity by an epidermal growth factor-activated mitogen-activated protein kinase signaling cascade. *J Biol Chem* 2006;281:10098-104.
Biswas DK, Shi Q, Baily S, Strickland I, Ghosh S, Pardee AB et al (2004). NF-kappa B activation in human breast cancer specimens and its role in cell proliferation and apoptosis. *Proc Natl Acad Sci USA* 101: 10137-42.
Biswas DK, Singh S, Shi Q, Pardee AB, Iglehart JD (2005). Crossroads of estrogen receptor and NF-kappaB signaling. *Sci STKE* 2005: pe27.
Bland JM, Altman DG. Survival probabilities (the Kaplan-Meier method). BMJ. Dec. 5, 1998;317(7172):1572.
Bloushtain-Qimron N, Yao J, Snyder EL, et al. Cell type-specific DNA methylation patterns in the human breast. Proc Natl Acad Sci U S A 2008;105:14076-81.
Carey LA, Perou CM, Livasy CA, et al. Race, breast cancer subtypes, and survival in the Carolina Breast Cancer Study. JAMA 2006;295:2492-502.
Carey LA, Dees, EC, Sawyer, L., et al. The Triple Negative Paradox: Primary Tumor Chemosensitivity of Breast Cancer Subtypes. Clin Cancer Res Apr. 15, 2001; 13; 8:2329-2334.
Carroll JS, Liu XS, Brodsky AS, Li W, Meyer CA, Szary AJ et al (2005). Chromosome-wide mapping of estrogen receptor binding reveals long-range regulation requiring the forkhead protein FoxA1. *Cell* 122: 33-43.
Charafe-Jauffret E, Monville F, Bertucci F, et al. Moesin expression is a marker of basal breast carcinomas. Int J Cancer 2007; 121: 1779-85.
Cheang MC, Voduc D, Bajdik C, Leung S, McKinney S, Chia SK, et al. Basal-like breast cancer defined by five biomarkers has superior prognostic value than triple-negative phenotype. Clin Cancer Res. Mar. 1, 2008;14(5):1368-76.
Couse JF, Korach KS (1999). Estrogen receptor null mice: what have we learned and where will they lead us? *Endocr Rev* 20: 358-417.
Cui X, Zhang P, Deng W, Oesterreich S, Lu Y, Mills GB et al (2003). Insulin-like growth factor-I inhibits progesterone receptor expression in breast cancer cells via the phosphatidylinositol 3-kinase/Akt/mammalian target of rapamycin pathway: progesterone receptor as a potential indicator of growth factor activity in breast cancer. *Mol Endocrinol* 17: 575-88.
deConinck EC, McPherson LA, Weigel RJ (1995). Transcriptional regulation of estrogen receptor in breast carcinomas. *Mol Cell Biol* 15: 2191-6.
Dent R, Trudeau M, Pritchard KI, et al. Triple-negative breast cancer: clinical features and patterns of recurrence. Clin Cancer Res 2007; 13:4429-34.
Dhasarathy A, Kajita M, Wade PA (2007). The transcription factor snail mediates epithelial to mesenchymal transitions by repression of estrogen receptor-alpha. *Mol Endocrinol* 21: 2907-18.
Eeckhoute J, Keeton EK, Lupien M, Krum SA, Carroll JS, Brown M (2007). Positive cross-regulatory loop ties GATA-3 to estrogen receptor alpha expression in breast cancer. *Cancer Res* 67: 6477-83.
Elsheikh SE, Green AR, Rakha EA, et al. Caveolin 1 and caveolin 2 are associated with breast cancer basal-like and triple-negative immunophenotype. Br J Cancer 2008;99:327-34.
Farmer P, Bonnefoi H, Becette V, et al. Identification of molecular apocrine breast tumours by microarray analysis. Oncogene 2005; 24:4660-71.
Fuqua SA, Schiff R, Parra I, Moore JT, Mohsin SK, Osborne CK et al (2003). Estrogen receptor beta protein in human breast cancer: correlation with clinical tumor parameters. *Cancer Res* 63: 2434-9.
Ginestier C, Cervera N, Finetti P, Esteyries S, Esterni B, Adelaide J et al (2006). Prognosis and gene expression profiling of 20q13-amplified breast cancers. *Clin Cancer Res* 12: 4533-44.
Gionet N, Jansson D, Mader S, Pratt MA (2009). NF-kappaB and estrogen receptor alpha interactions: Differential function in estrogen receptor-negative and -positive hormone-independent breast cancer cells. *J Cell Biochem* 107: 448-59.
Green S, Walter P, Kumar V, Krust A, Bornert JM, Argos P et al (1986). Human oestrogen receptor cDNA: sequence, expression and homology to v-erb-A. *Nature* 320: 134-9.
Guo S, Sonenshein GE (2004). Forkhead box transcription factor FOXO3a regulates estrogen receptor alpha expression and is repressed by the Her-2/neu/phosphatidylinositol 3-kinase/Akt signaling pathway. *Mol Cell Biol* 24: 8681-90.
Hasegawa M, Moritani S, Murakumo Y, et al. CD109 expression in basal-like breast carcinoma. Pathol Int 2008; 58: 288-94.
Herschkowitz JI, Simin K, Weigman VJ, et al. Identification of conserved gene expression features between murine mammary carcinoma models and human breast tumors. Genome Biol 2007;8:R76.
Hess KR, Anderson K, Symmans WF, et al. Pharmacogenomic predictor of sensitivity to preoperative chemotherapy with paclitaxel and fluorouracil, doxorubicin, and cyclophosphamide in breast cancer. J Clin Oncol 2006;24:4236-44.
Holloway JN, Murthy S, El-Ashry D (2004). A cytoplasmic substrate of mitogen-activated protein kinase is responsible for estrogen receptor-alpha down-regulation in breast cancer cells: the role of nuclear factor-kappaB. *Mol Endocrinol* 18: 1396-410.
Hosey AM, Gorski JJ, Murray MM, Quinn JE, Chung WY, Stewart GE et al (2007). Molecular basis for estrogen receptor alpha deficiency in BRCA1-linked breast cancer. *J Natl Cancer Inst* 99: 1683-94.
Hu Z, Fan C, Oh DS, et al. The molecular portraits of breast tumors are conserved across microarray platforms. BMC Genomics 2006; 7:96.
Ihemelandu CU, Leffall LD, Jr., Dewitty RL, Naab TJ, Mezghebe HM, Makambi KH, et al. Molecular breast cancer subtypes in premenopausal and postmenopausal African-American women: age-specific prevalence and survival. J Surg Res. Nov. 2007;143(1):109-18.
Ihemelandu CU, Naab TJ, Mezghebe HM, Makambi KH, Siram SM, Leffall LD, Jr., et al. Treatment and survival outcome for molecular breast cancer subtypes in black women. Ann Surg. Mar. 2008;247(3):463-9.
International Search Report and Written Opinion for PCT/US10/44817 dated Aug. 6, 2010.
Ivshina AV, George J, Senko O, et al. Genetic reclassification of histologic grade delineates new clinical subtypes of breast cancer. Cancer Res 2006;66:10292-301.

(56) References Cited

OTHER PUBLICATIONS

Karin M, Cao Y, Greten FR, Li ZW (2002). NF-kappaB in cancer: from innocent bystander to major culprit. *Nat Rev Cancer* 2: 301-10.
Keen JC, Davidson NE (2003). The biology of breast carcinoma. *Cancer* 97: 825-33.
Korsching E, Jeffrey SS, Meinerz W, Decker T, Boecker W, Buerger H. Basal carcinoma of the'breast revisited: an old entity with new interpretations. J Clin Pathol 2008; 61: 553-60.
Kos M, Reid G, Denger S, Gannon F (2001). Minireview: genomic organization of the human ERalpha gene promoter region. *Mol Endocrinol* 15: 2057-63.
Kreike B, van Kouwenhove M, Horlings H, et al. Gene expression profiling and histopathological characterization of triple-negative/basal-like breast carcinomas. Breast Cancer Res 2007;9:R65.
Kuiper GG, Carlsson B, Grandien K, Enmark E, Haggblad J, Nilsson S et al (1997). Comparison of the ligand binding specificity and transcript tissue distribution of estrogen receptors alpha and beta. *Endocrinology* 138: 863-70.
Laganiere J, Deblois G, Lefebvre C, Bataille AR, Robert F, Giguere V (2005). From the Cover: Location analysis of estrogen receptor alpha target promoters reveals that FOXA1 defines a domain of the estrogen response. *Proc Natl Acad Sci U S A* 102: 11651-6.
Landis SH, Murray T, Bolden S, Wingo PA (1999). Cancer statistics, 1999. *CA Cancer J Clin* 49: 8-31, 1.
Lin Y, Bai L, Chen W, Xu S the NF-kappaB activation pathways, emerging molecular targets for cancer prevention and therapy. *Expert Opin Ther Targets* 14: 45-55.
Lin Z, Yin P, Reierstad S, O'Halloran M, Coon VJ, Pearson EK et al Adenosine A1 receptor, a target and regulator of estrogen receptoralpha action, mediates the proliferative effects of estradiol in breast cancer. *Oncogene* 29: 1114-22.
Livasy CA, Karaca G, Nanda R, et al. Phenotypic evaluation of the basal-like subtype of invasive breast carcinoma. Mod Pathot 2006; 19:264-71.
Lu S, Simin K, Khan A, Mercurio AM. Analysis of integrin beta4 expression in human breast cancer: association with basal-like tumors and prognostic significance. Clin Cancer Res 2008; 14: 1050-8.
Lu X, Wang ZC, Iglehart JD, Zhang X, Richardson AL (2008). Predicting features of breast cancer with gene expression patterns. *Breast Cancer Res Treat* 108: 191-201.
Lupien M, Eeckhoute J, Meyer CA, Wang Q, Zhang Y, Li W et al (2008). FoxA1 translates epigenetic signatures into enhancer-driven lineage-specific transcription. *Cell* 132: 958-70.
Mahmoodzadeh S, Fritschka S, Dworatzek E, Pham TH, Becher E, Kuehne A et al (2009). Nuclear factor-kappaB regulates estrogen receptor-alpha transcription in the human heart. *J Biol Chem* 284: 24705-14.
Mani SA, Yang J, Brooks M, et al. Mesenchyme Forkhead 1 (FOXC2) plays a key role in metastasis and is associated with aggressive basal-like breast cancers. Proc Natl Acad Sci U S A 2007; 104: 10069-74.
McShane LM, Altman DG, Sauerbrei W, Taube SE, Gion M, Clark GM. REporting recommendations for tumour MARKer prognostic studies (Remark). Br J Cancer. Aug. 22, 2005;93(4):387-91.
Miller LD, Smeds J, George J, et al. An expression signature for p53 status in human breast cancer predicts mutation status, transcriptional effects, and patient survival. Proc. Natl. Acad Sci U S A 2005; 102:13550-5.
Moyano JV, Evans JR, Chen F, et al. AlphaB-crystallin is a novel oncoprotein that predicts poor clinical outcome in breast cancer. J Clin Invest 2006; 116: 261-70.
Nakshatri H, Bhat-Nakshatri P, Martin DA, Goulet RJ, Jr., Sledge GW, Jr. (1997) Constitutive activation of NF-kappaB during progression of breast cancer to hormone-independent growth. *Mol Cell Biol* 17:3629-39.
Nielsen TO, Hsu FD, Jensen K, et al. Immunohistochemical and clinical characterization of the basal-like subtype of invasive breast carcinoma. Clin Cancer Res 2004;10:5367-74.
Nishimura DY, Swiderski RE, Alward WI, Searby CC, Patil SR, Bennet SR et al (1998). The forkhead transcription factor gene FKHL7 is responsible for glaucoma phenotypes which map to 6p25. *Nat Genet* 19: 140-7.
Oh AS, Lorant LA, Holloway JN, Miller DL, Kern FG, El-Ashry D (2001). Hyperactivation of MAPK induces loss of ERalpha expression in breast cancer cells. *Mol Endocrinol* 15: 1344-59.
Osborne CK (1998). Steroid hormone receptors in breast cancer management. *Breast Cancer Res Treat* 51: 227-38.
Panomics. Quantigene FFPE. [online] 2006.
Park WC, Jordan VC (2002). Selective estrogen receptor modulators (SERMS) and their roles in breast cancer prevention. *Trends Mol Med* 8: 82-8.
Parker JS, Mullins M, Cheang MC, et al. Supervised risk predictor of breast cancer based on intrinsic subtypes. J Clin Oncol 2009; 27: 1160-7.
Pawitan Y, Bjohle J, Amler L, et al. Gene expression profiling spares early breast cancer patients from adjuvant therapy: derived and validated in two population-based cohorts. Breast Cancer Res 2005;7: R953-64.
Perou CM, Sorlie T, Eisen MB, et al. Molecular portraits of human breast turnouts. Nature 2000;406:747-52.
Piva R, Bianchini E, Kumar VL, Chambon P, del Senno L (1988). Estrogen induced increase of estrogen receptor RNA in human breast cancer cells. *Biochem Biophys Res Commun* 155: 943-9.
Pollack JR, Sorlie T, Perou CM, Rees CA, Jeffrey SS, Lonning PE et al (2002). Microarray analysis reveals a major direct role of DNA copy number alteration in the transcriptional program of human breast tumors. *Proc Natl Acad Sci U S A* 99: 12963-8.
Qu Y, Wang J, Sim MS, Liu B, Giuliano A, Barsoum J et al (2009). Elesclomol, counteracted by Akt survival signaling, enhances the apoptotic effect of chemotherapy drugs in breast cancer cells. *Breast Cancer Res Treat.* 121:311-21.
Rakha EA, Elsheikh SE, Aleskandarany MA, Habashi Ho, Green AR, Powe DG, et al. Triple-negative breast cancer: distinguishing between basal and nonbasal subtypes. Clin Cancer Res. Apr. 1, 2009;15(7):2302-10.
Rakha, E. A., et al. (2008) Basal-Like Breast Cancer: A Critical Review. J Clin Oncol May 20, 2008; vol. 26; No. 15: 2568-2581.
Ray P, Wang J, Qu Y, Sim M, Shamonki J, Bagaria SP et al (2010). FOXC1 is a Potential Prognostic Biomarker with Functional Significance in Basal-like Breast Cancer. *Cancer Research* 2010; 70:3870-76.
Ray P, Wang J, Qu Y, Sim M, Shamonki J, Liu, B et al (2009). Role of FOXC1 in regulation of basal-like/triple-negative breast cancer. J Clin Oncol 2009 Annual Meeting Proceedings; 27: 15s.
Richardson AL, Wang ZC, De Nicolo A, et al. X chromosomal abnormalities in basal-like like human breast cancer. Cancer Cell 2006;9:121-32.
Rosen EM, Fan S, Isaacs C (2005). BRCA1 in hormonal carcinogenesis: basic and clinical research. *Endocr Relat Cancer* 12: 533-48.
Ryo A, Suizu F, Yoshida Y, Perrem K, Liou YC, Wulf G et al (2003). Regulation of NF-kappaB signaling by Pin1-dependent prolyl isomerization and ubiquitin-mediated proteolysis of p65/RelA. *Mol Cell* 12: 1413-26.
Saceda M, Grunt TW, Colomer R, Lippman ME, Lupu R, Martin MB (1996). Regulation of estrogen receptor concentration and activity by an erbB/HER ligand in breast carcinoma cell lines. *Endocrinology* 137: 4322-30.
Saleem RA, Banerjee-Basu S, Berry FB, Baxevanis AD, Walter MA (2003). Structural and functional analyses of disease-causing missense mutations in the forkhead domain of FOXC1. *Hum Mol Genet* 12: 2993-3005.
Sarrio D, Rodriguez-Pinilla SM, Hardisson D, Cano A, Moreno-Bueno G, Palacios J. Epithelial-mesenchymal transition in breast cancer relates to the basal-like phenotype. Cancer Res 2008;68:989-97.
Schuetz CS, Bonin M, Clare SE, Nieselt K, Sotlar K, Walter M et al (2006). Progression-specific genes identified by expression profiling of matched ductal carcinomas in situ and invasive breast tumors, combining laser capture microdissection and oligonucleotide microarray analysis. *Cancer Res* 66: 5278-86.

(56) References Cited

OTHER PUBLICATIONS

Seewaldt VL, Scott V. Images in clinical medicine. Rapid progression of basal-type breast cancer. N Engl J Med 2007;356:e12.
Shirley SH, Rundhaug JE, Tian J, Cullinan-Ammann N, Lambertz I, Conti CJ et al (2009). Transcriptional regulation of estrogen receptor-alpha by p53 in human breast cancer cells. *Cancer Res* 69: 3405-14.
Singh S, Shi Q, Bailey ST, Palczewski MJ, Pardee AB, Iglehart JD et al (2007). Nuclear factor-kappaB activation: a molecular therapeutic target for estrogen receptor-negative and epidermal growth factor receptor family receptor-positive human breast cancer. *Mol Cancer Ther* 6: 1973-82.
Sorlie T, Perou CM, Tibshirani R, AAS T, Geisler S, Johnsen H et al (2001). Gene expression patterns of breast carcinomas distinguish tumor subclasses with clinical implications. *Proc Natl Acad Sci U S A* 98: 10869-74.
Sorlie T, Tibshirani R, Parker J, et al. Repeated observation of breast tumor subtypes in independent gene expression data sets. Proc Natl Acad Sci U S A 2003;100:8418-23.
Staaf J, Ringner M, Vallon-Christersson J, Jönsson G, Bendahl PO, Holm K, Arason A, Gunnarsson H, Hegardt C, Agnarsson BA, Luts L, Grabau D, Fernö M, Malmstrom PO, Johannsson OT, Loman N, Barkardottir RB, Borg A. Identification of subtypes in human epidermal growth factor receptor 2—positive breast cancer reveals a gene signature prognostic of outcome. J Clin Oncol. Apr. 10, 2010;28(11):1813-20.
Stein B, Yang MX (1995). Repression of the interleukin-6 promoter by estrogen receptor is mediated by NF-kappa B and C/EBP beta. *Mol Cell Biol* 15: 4971-9.
Tanimoto K, Eguchi H, Yoshida T, Hajiro-Nakanishi K, Hayashi S (1999). Regulation of estrogen receptor alpha gene mediated by promoter B responsible for its enhanced expression in human breast cancer. *Nucleic Acids Res* 27: 903-9.
Treilleux, Peloux N, Brown M, Sergeant A (1997). Human estrogen receptor (ER) gene promoter-P1: estradiol-independent activity and estradiol inducibility in Er+ and Er- cells. *Mol Endocrinol* 11: 1319-31.
van der Heul-Nieuwenhuijsen L, Dits NF, Jenster G (2009). Gene expression of forkhead transcription factors in the normal and diseased human prostate. *BJU Int* 103: 1574-80.
van de Vijver MJ, He YD, van't Veer LJ, et al. A gene-expression signature as a predictor of survival in breast cancer. N Engl J Med 2002; 347:1999-2009.
Van Laere SJ, Van der Auwera I, Van den Eynden GG, van Dam P, Van Marck EA, Vermeulen PB et al (2007). NF-kappaB activation in inflammatory breast cancer is associated with oestrogen receptor downregulation, secondary to EGFR and/or ErbB2 overexpression and MAPK hyperactivation. *Br J Cancer* 97: 659-69.
Wang Y, Klijn JG, Zhang Y, et al. Gene-expression profiles to predict distant metastasis of lymph-node-negative primary breast cancer. Lancet 2005;365:671-9.
Yaziji H, Goldstein LC, Barry TS, Werling R, Hwang H, Ellis GK, et al. HER-2 testing in breast cancer using parallel tissue-based methods. JAMA. Apr. 28, 2004:291(16):1972-7.
Yoshida T, Eguchi H, Nakachi K, Tanimoto K, Higashi Y, Suemasu K et al (2000). Distinct mechanisms of loss of estrogen receptor alpha gene expression in human breast cancer: methylation of the gene and alteration of trans-acting factors. *Carcinogenesis* 21 2193-201.
Zhao H, Langerod A, Ji Y, Nowels KW, Nesland JM, Tibshirani R et al (2004). Different gene expression patterns in invasive lobular and ductal carcinomas of the breast. *Mol Biol Cell* 15: 2523-36.
Zhao JJ, Lin J, Yang H, Kong W, He L, Ma X et al (2008). MicroRNA-221/222 negatively regulates estrogen receptor alpha and is associated with tamoxifen resistance in breast cancer. *J Biol Chem* 283: 31079-86.
Bowman S. et al., Database GenBank (Online), Accession No. Q7K740, htto://www.ncbi.nlm.nih.gov/protein, uploaded Jan. 12, 2007, retrieved Nov. 26, 2014, Definition: Circumsporozoite (CS) protein., 2 pages.
Japanese Patent Office, English translation of Official Action of Japanese Application No. 2012-525677, dated Dec. 9, 2014, 8 pages.
State Intellectual Property Office, PRC China, Third Office Action for CN201080047059.6, Apr. 14, 2015 with English Translation, 10 pages.
Wang R., et al., "Induction of Protective Polyclonal Antibodies by Immunization with a Plasmodium yoelii Circumsporozoite Protein Multiple Antigen Peptide Vaccine," J. Immunol., 1995, vol. 154, pp. 2784-2793.
Japanese Patent Office, Decision of Final Rejection for JP 2012-525677, dated Nov. 4, 2015, 12 pages, with English translation.
Rux, John J. et al., Structural and Phylogenetic Analysis of Adenovirus Hexons by Use of High-Resolution X-Ray Crystallographic, Molecular Modeling, and Sequence-Based Methods, J. Virology, vol. 77, 9553-66, Sep. 2003.
Intellectual Property Office of Singapore, Search Report and Written Opinion for SG10201404970P, Apr. 14, 2016, 9 pgs.

* cited by examiner

Structure of capsid-modified PyCS-GFP adenoviruses

Construction of HVR1 and Fiber-modified adenovirus vector

Construction of Fiber and pVII-modified adenovirus vector

Construction of HVR1 and pVII-modified adenovirus vector

Construction of HVR1, Fiber and pVII-Modified adenovirus vector

Codon-optimized Plasmodium yoelii circumsporozoite protein sequence SEQ IDNOS : 1 and 30

```
   1             M  K  K  C  T  I  L  V  V  A  S  L  L  L  V  D
   1  GGTACCGCCACCATGAAGAAGTGCACCATCCTGGTGGTGGCCAGCCTGCTGCTGGTGGAC

  17  S  L  L  P  G  Y  G  Q  N  K  S  V  Q  A  Q  R  N  L  N  E
  61  AGCCTGCTGCCCGGCTACGGCCAGAACAAGAGCGTGCAGGCCCAGAGGAACCTGAACGAG

  37  L  C  Y  N  E  E  N  D  N  K  L  Y  H  V  L  N  S  K  N  G
 121  CTGTGCTACAACGAGGAGAACGACAACAAGCTGTACCACGTGCTGAACAGCAAGAACGGC

  57  K  I  Y  N  R  N  I  V  N  R  L  L  G  D  A  L  N  G  K  P
 181  AAGATCTACAACAGGAACATCGTGAACAGGCTGCTGGGCGACGCCCTGAACGGCAAGCCC

  77  E  E  K  K  D  D  P  P  K  D  D  N  K  D  D  L  P  K  E  E
 241  GAGGAGAAGAAGGACGACCCCCCCAAGGACGACAACAAGGACGACCTGCCCAAGGAGGAG

  97  K  K  D  D  L  P  K  E  E  K  K  D  D  P  P  K  D  P  K  K
 301  AAGAAGGACGACCTGCCCAAGGAGGAGAAGAAGGACGACCCCCCCAAGGACCCCAAGAAG

 117  D  D  P  P  K  E  A  Q  N  K  L  N  Q  P  V  V  A  D  E  N
 361  GACGACCCCCCCAAGGAGGCCCAGAACAAGCTGAACCAGCCCGTAGTGGCAGATGAAAAT

 137  V  D  Q  G  P  G  A  P  Q  G  P  G  A  P  Q  G  P  G  A  P
 421  GTAGATCAAGGGCCAGGAGCACCACAAGGGCCAGGAGCACCACAAGGGCCAGGAGCACCA

 157  Q  G  P  G  A  P  Q  G  P  G  A  P  Q  G  P  G  A  P  Q  G
 481  CAGGGGCCAGGAGCACCACAGGGGCCAGGAGCACCACAAGGGCCAGGAGCACCACAAGGA

 177  P  G  A  P  Q  G  P  G  A  P  Q  G  P  G  A  P  Q  G  P  G
 541  CCAGGAGCACCACAAGGGCCAGGAGCACCACAAGGGCCAGGAGCACCACAAGGGCCAGGA

 197  A  P  Q  G  P  G  A  P  Q  G  P  G  A  P  Q  G  P  G  A  P
 601  GCACCCCAGGGGCCAGGAGCACCACAAGGGCCAGGAGCACCACAAGGACCAGGAGCACCA

 217  Q  G  P  G  A  P  Q  G  P  G  A  P  Q  G  P  G  A  P  Q  G
 661  CAGGGTCCAGGAGCACCACAAGGACCAGGAGCACCACAAGGACCAGGAGCACCACAAGGT

 237  P  G  A  P  Q  G  P  G  A  P  Q  G  P  G  A  P  Q  E  P  P
 721  CCAGGAGCACCACAGGGGCCAGGAGCACCACAAGGGCCAGGAGCACCACAAGAACCACCC

 257  Q  Q  P  P  Q  Q  P  P  Q  Q  P  P  Q  Q  P  P  Q  Q  P  P
 781  CAACAACCCCCACAACAGCCACCACAACAGCCACCACAACAGCCACCACAACAGCCACCA

 277  Q  Q  P  N  N  N  N  N  N  N  G  N  N  N  E  D  S  Y  V  P
 841  CAACAACCAAACAACAACAACAACAACAACGGCAACAACAACGAGGACAGCTACGTGCCC

 297  S  A  E  Q  I  L  E  F  V  K  Q  I  S  S  Q  L  T  E  E  W
 901  AGCGCCGAGCAGATCCTGGAGTTCGTGAAGCAGATCAGCAGCCAGCTGACCGAGGAGTGG

 317  S  Q  C  S  V  T  C  G  S  G  V  R  V  R  K  R  K  N  V  N
 961  AGCCAGTGCAGCGTGACCTGCGGCAGCGGCGTGAGGGTGAGGAAGAGGAAGAACGTGAAC

 337  K  Q  P  E  N  L  T  L  E  D  I  D  T  E  I  C  K  M  D  K
1021  AAGCAGCCCGAGAACCTGACCCTGGAGGACATCGACACCGAGATCTGCAAGATGGACAAG

 357  C  S  S  I  F  N  I  V  S  N  S  L  G
1081  TGCAGCAGCATCTTCAACATCGTGAGCAACAGCCTGGGCTAAAGCTT
```

Fig. 9

Codon-optimized Plasmodium falciparum circumsporozoite protein sequence SEQ IDNOS : 2 and 43

1 M M R K L A I L S V S S F L F V
1 GGTACCGCCACCATGATGCGCAAGCTGGCCATACTGTCTGTTAGTAGCTTTCTCTTTGTA

17 E A L F Q E Y Q C Y G S S S N T R V L N
61 GAGGCCCTGTTTCAGGAATACCAGTGCTATGGCAGCAGCAGCAACACTCGTGTGCTGAAC

37 E L N Y D N A G T N L Y N E L E M N Y Y
121 GAACTTAACTATGATAATGCAGGAACAAATTTATATAACGAACTGGAGATGAATTACTAT

57 G K Q E N W Y S L K K N S R S L G E N D
181 GGTAAGCAGGAAAATTGGTACTCTCTGAAAAAGAACTCTAGATCTCTGGGCGAGAACGAC

77 D G N N E D N E K L R K P K H K K L K Q
241 GACGGCAATAATGAAGACAATGAAAAGCTGAGGAAGCCAAAGCACAAAAAACTAAAGCAG

97 P A D G N P D P N A N P N V D P N A N P
301 CCCGCAGACGGCAATCCAGACCCCAATGCTAACCCAAACGTGGACCCCAATGCTAATCCA

117 N V D P N A N P N V D P N A N P N A N P
361 AACGTGGATCCTAACGCTAACCCGAATGTGGACCCTAACGCCAATCCAAATGCGAATCCG

137 N A N P N A N P N A N P N A N P N A N P
421 AACGCTAATCCTAACGCAAACCCGAATGCTAACCCTAACGCAAACCCGAACGCTAACCCG

157 N A N P N A N P N A N P N A N P N A N P
481 AACGCGAACCCCAATGCCAACCCCAACGCCAACCCGAACGCCAATCCAAACGCTAACCCT

177 N A N P N A N P N A N P N A N P N A N P
541 AATGCCAATCCTAATGCCAATCCGAACGCCAATCCAAATGCCAATCCAAATGCTAATCCC

197 N V D P N A N P N A N P N A N P N A N P
601 AACGTGGACCCCAACGCGAACCCTAATGCCAACCCCAACGCTAATCCAAATGCGAACCCT

217 N A N P N A N P N A N P N A N P N A N P
661 AACGCCAACCCGAATGCTAATCCCAATGCCAACCCCAATGCTAATCCGAATGCGAACCCT

237 N A N P N A N P N A N P N A N P N A N P
721 AATGCCAATCCCAACGCCAACCCCAACGCAAACCCTAATGCTAACCCGAACGCCAATCCG

257 N A N P N A N P N A N P N A N P N K N N
781 AACGCAAATCCTAATGCTAATCCTAACGCTAACCCCAACGCCAATCCAAATAAGAACAAT

277 Q G N G Q G H N M P N D P N R N V D E N
841 CAAGGCAACGGGCAGGGCCACAATATGCCAAATGACCCTAACCGGAATGTGGACGAGAAT

297 A N A N S A V K N N N N E E P S D K H I
901 GCAAATGCCAATAGCGCCGTGAAAAATAATAATAACGAGGAGCCAAGTGACAAACACATT

317 K E Y L N K I Q N S L S T E W S P C S V
961 AAGGAATATTTGAACAAGATTCAAAACTCCCTCTCAACAGAATGGTCTCCTTGCAGCGTG

337 T C G N G I Q V R I K P G S A N K P K D
1021 ACTTGTGGAAATGGCATCCAGGTTCGTATTAAACCAGGTAGTGCCAACAAGCCCAAGGAT

357 E L D Y A N D I E K K I C K M E K C --
1081 GAACTAGACTATGCCAATGATATAGAGAAAAAAATCTGTAAGATGGAGAAATGCTAGCTT

1141 CTAGA

Fig. 10

Hexon sequence of (QGPGAP)$_3$-HVR1 adenovirus SEQ IDNOS : 3 and 31

```
   1  M  A  T  P  S  M  M  P  Q  W  S  Y  M  H  I  S  G  Q  D  A
   1  ATGGCTACCCCTTCGATGATGCCGCAGTGGTCTTACATGCACATCTCGGGCCAGGACGCC

  21  S  E  Y  L  S  P  G  L  V  Q  F  A  R  A  T  E  T  Y  F  S
  61  TCGGAGTACCTGAGCCCCGGGCTGGTGCAGTTTGCCCGCGCCACCGAGACGTACTTCAGC

  41  L  N  N  K  F  R  N  P  T  V  A  P  T  H  D  V  T  T  D  R
 121  CTGAATAACAAGTTTAGAAACCCCACGGTGGCGCCTACGCACGACGTGACCACAGACCGG

  61  S  Q  R  L  T  L  R  F  I  P  V  D  R  E  D  T  A  Y  S  Y
 181  TCCCAGCGTTTGACGCTGCGGTTCATCCCTGTGGACCGTGAGGATACTGCGTACTCGTAC

  81  K  A  R  F  T  L  A  V  G  D  N  R  V  L  D  M  A  S  T  Y
 241  AAGGCGCGGTTCACCCTAGCTGTGGGTGATAACCGTGTGCTGGACATGGCTTCCACGTAC

 101  F  D  I  R  G  V  L  D  R  G  P  T  F  K  P  Y  S  G  T  A
 301  TTTGACATCCGCGGCGTGCTGGACAGGGGCCCTACTTTTAAGCCCTACTCTGGCACTGCC

 121  Y  N  A  L  A  P  K  G  A  P  N  P  C  E  W  D  E  Q  G  P
 361  TACAACGCCCTGGCTCCCAAGGGTGCCCCAAATCCTTGCGAATGGGATGAACAGGGCCCT

 141  G  A  P  Q  G  P  G  A  P  Q  G  P  G  A  P  K  T  H  V  F
 421  GGAGCTCCACAGGGACCAGGTGCACCTCAAGGGCCTGGAGCCCCTAAAACTCACGTATTT

 161  G  Q  A  P  Y  S  G  I  N  I  T  K  E  G  I  Q  I  G  V  E
 481  GGGCAGGCGCCTTATTCTGGTATAAATATTACAAAGGAGGGTATTCAAATAGGTGTCGAA

 181  G  Q  T  P  K  Y  A  D  K  T  F  Q  P  E  P  Q  I  G  E  S
 541  GGTCAAACACCTAAATATGCCGATAAAACATTTCAACCTGAACCTCAAATAGGAGAATCT

 201  Q  W  Y  E  T  E  I  N  H  A  A  G  R  V  L  K  K  T  T  P
 601  CAGTGGTACGAAACAGAAATTAATCATGCAGCTGGGAGAGTCCTAAAAAAGACTACCCCA

 221  M  K  P  C  Y  G  S  Y  A  K  P  T  N  E  N  G  G  Q  G  I
 661  ATGAAACCATGTTACGGTTCATATGCAAAACCCACAAATGAAAATGGAGGGCAAGGCATT

 241  L  V  K  Q  Q  N  G  K  L  E  S  Q  V  E  M  Q  F  F  S  T
 721  CTTGTAAAGCAACAAAATGGAAAGCTAGAAAGTCAAGTGGAAATGCAATTTTTCTCAACT

 261  T  E  A  A  A  G  N  G  D  N  L  T  P  K  V  V  L  Y  S  E
 781  ACTGAGGCAGCCGCAGGCAATGGTGATAACTTGACTCCTAAAGTGGTATTGTACAGTGAA

 281  D  V  D  I  E  T  P  D  T  H  I  S  Y  M  P  T  I  K  E  G
 841  GATGTAGATATAGAAACCCCAGACACTCATATTTCTTACATGCCCACTATTAAGGAAGGT

 301  N  S  R  E  L  M  G  Q  Q  S  M  P  N  R  P  N  Y  I  A  F
 901  AACTCACGAGAACTAATGGGCCAACAATCTATGCCCAACAGGCCTAATTACATTGCTTTT

 321  R  D  N  F  I  G  L  M  Y  Y  N  S  T  G  N  M  G  V  L  A
 961  AGGGACAATTTTATTGGTCTAATGTATTACAACAGCACGGGTAATATGGGTGTTCTGGCG

 341  G  Q  A  S  Q  L  N  A  V  V  D  L  Q  D  R  N  T  E  L  S
1021  GGCCAAGCATCGCAGTTGAATGCTGTTGTAGATTTGCAAGACAGAAACACAGAGCTTTCA

 361  Y  Q  L  L  L  D  S  I  G  D  R  T  R  Y  F  S  M  W  N  Q
1081  TACCAGCTTTTGCTTGATTCCATTGGTGATAGAACCAGGTACTTTTCTATGTGGAATCAG

 381  A  V  D  S  Y  D  P  D  V  R  I  I  E  N  H  G  T  E  D  E
1141  GCTGTTGACAGCTATGATCCAGATGTTAGAATTATTGAAAATCATGGAACTGAAGATGAA
```

Fig. 11A

```
 401  L  P  N  Y  C  F  P  L  G  G  V  I  N  T  E  T  L  T  K  V
1201  CTTCCAAATTACTGCTTTCCACTGGGAGGTGTGATTAATACAGAGACTCTTACCAAGGTA

 421  K  P  K  T  G  Q  E  N  G  W  E  K  D  A  T  E  F  S  D  K
1261  AAACCTAAAACAGGTCAGGAAAATGGATGGGAAAAAGATGCTACAGAATTTTCAGATAAA

 441  N  E  I  R  V  G  N  N  F  A  M  E  I  N  L  N  A  N  L  W
1321  AATGAAATAAGAGTTGGAAATAATTTTGCCATGGAAATCAATCTAAATGCCAACCTGTGG

 461  R  N  F  L  Y  S  N  I  A  L  Y  L  P  D  K  L  K  Y  S  P
1381  AGAAATTTCCTGTACTCCAACATAGCGCTGTATTTGCCCGACAAGCTAAAGTACAGTCCT

 481  S  N  V  K  I  S  D  N  P  N  T  Y  D  Y  M  N  K  R  V  V
1441  TCCAACGTAAAAATTTCTGATAACCCAAACACCTACGACTACATGAACAAGCGAGTGGTG

 501  A  P  G  L  V  D  C  Y  I  N  L  G  A  R  W  S  L  D  Y  M
1501  GCTCCCGGGCTAGTGGACTGCTACATTAACCTTGGAGCACGCTGGTCCCTTGACTATATG

 521  D  N  V  N  P  F  N  H  H  R  N  A  G  L  R  Y  R  S  M  L
1561  GACAACGTCAACCCATTTAACCACCACCGCAATGCTGGCCTGCGCTACCGCTCAATGTTG

 541  L  G  N  G  R  Y  V  P  F  H  I  Q  V  P  Q  K  F  F  A  I
1621  CTGGGCAATGGTCGCTATGTGCCCTTCCACATCCAGGTGCCTCAGAAGTTCTTTGCCATT

 561  K  N  L  L  L  L  P  G  S  Y  T  Y  E  W  N  F  R  K  D  V
1681  AAAAACCTCCTTCTCCTGCCGGGCTCATACACCTACGAGTGGAACTTCAGGAAGGATGTT

 581  N  M  V  L  Q  S  S  L  G  N  D  L  R  V  D  G  A  S  I  K
1741  AACATGGTTCTGCAGAGCTCCCTAGGAAATGACCTAAGGGTTGACGGAGCCAGCATTAAG

 601  F  D  S  I  C  L  Y  A  T  F  F  P  M  A  H  N  T  A  S  T
1801  TTTGATAGCATTTGCCTTTACGCCACCTTCTTCCCCATGGCCCACAACACCGCCTCCACG

 621  L  E  A  M  L  R  N  D  T  N  D  Q  S  F  N  D  Y  L  S  A
1861  CTTGAGGCCATGCTTAGAAACGACACCAACGACCAGTCCTTTAACGACTATCTCTCCGCC

 641  A  N  M  L  Y  P  I  P  A  N  A  T  N  V  P  I  S  I  P  S
1921  GCCAACATGCTCTACCCTATACCCGCCAACGCTACCAACGTGCCCATATCCATCCCCTCC

 661  R  N  W  A  A  F  R  G  W  A  F  T  R  L  K  T  K  E  T  P
1981  CGCAACTGGGCGGCTTTCCGCGGCTGGGCCTTCACGCGCCTTAAGACTAAGGAAACCCCA

 681  S  L  G  S  G  Y  D  P  Y  Y  T  Y  S  G  S  I  P  Y  L  D
2041  TCACTGGGCTCGGGCTACGACCCTTATTACACCTACTCTGGCTCTATACCCTACCTAGAT

 701  G  T  F  Y  L  N  H  T  F  K  K  V  A  I  T  F  D  S  S  V
2101  GGAACCTTTTACCTCAACCACACCTTTAAGAAGGTGGCCATTACCTTTGACTCTTCTGTC

 721  S  W  P  G  N  D  R  L  L  T  P  N  E  F  E  I  K  R  S  V
2161  AGCTGGCCTGGCAATGACCGCCTGCTTACCCCCAACGAGTTTGAAATTAAGCGCTCAGTT

 741  D  G  E  G  Y  N  V  A  Q  C  N  M  T  K  D  W  F  L  V  Q
2221  GACGGGGAGGGTTACAACGTTGCCCAGTGTAACATGACCAAAGACTGGTTCCTGGTACAA

 761  M  L  A  N  Y  N  I  G  Y  Q  G  F  Y  I  P  E  S  Y  K  D
2281  ATGCTAGCTAACTATAACATTGGCTACCAGGGCTTCTATATCCCAGAGAGCTACAAGGAC

 781  R  M  Y  S  F  F  R  N  F  Q  P  M  S  R  Q  V  V  D  D  T
2341  CGCATGTACTCCTTCTTTAGAAACTTCCAGCCCATGAGCCGTCAGGTGGTGGATGATACT
```

Fig. 11B

```
 801  K  Y  K  D  Y  Q  Q  V  G  I  L  H  Q  H  N  N  S  G  F  V
2401  AAATACAAGGACTACCAACAGGTGGGCATCCTACACCAACACAACAACTCTGGATTTGTT

 821  G  Y  L  A  P  T  M  R  E  G  Q  A  Y  P  A  N  F  P  Y  P
2461  GGCTACCTTGCCCCCACCATGCGCGAAGGACAGGCCTACCCTGCTAACTTCCCCTATCCG

 841  L  I  G  K  T  A  V  D  S  I  T  Q  K  K  F  L  C  D  R  T
2521  CTTATAGGCAAGACCGCAGTTGACAGCATTACCCAGAAAAAGTTTCTTTGCGATCGCACC

 861  L  W  R  I  P  F  S  S  N  F  M  S  M  G  A  L  T  D  L  G
2581  CTTTGGCGCATCCCATTCTCCAGTAACTTTATGTCCATGGGCGCACTCACAGACCTGGGC

 881  Q  N  L  L  Y  A  N  S  A  H  A  L  D  M  T  F  E  V  D  P
2641  CAAAACCTTCTCTACGCCAACTCCGCCCACGCGCTAGACATGACTTTTGAGGTGGATCCC

 901  M  D  E  P  T  L  L  Y  V  L  F  E  V  F  D  V  V  R  V  H
2701  ATGGACGAGCCCACCCTTCTTTATGTTTTGTTTGAAGTCTTTGACGTGGTCCGTGTGCAC

 921  Q  P  H  R  G  V  I  E  T  V  Y  L  R  T  P  F  S  A  G  N
2761  CAGCCGCACCGCGGCGTCATCGAAACCGTGTACCTGCGCACGCCCTTCTCGGCCGGCAAC

 941  A  T  T  -
2821  GCCACAACATAA
```

Fig. 11C

Hexon sequence of $(QGPGAP)_4$-HVR1 adenovirus SEQ IDNOS : 4 and 32

```
1    M A T P S M M P Q W S Y M H I S G Q D A
1    ATGGCTACCCCTTCGATGATGCCGCAGTGGTCTTACATGCACATCTCGGGCCAGGACGCC

21   S E Y L S P G L V Q F A R A T E T Y F S
61   TCGGAGTACCTGAGCCCCGGGCTGGTGCAGTTTGCCCGCGCCACCGAGACGTACTTCAGC

41   L N N K F R N P T V A P T H D V T T D R
121  CTGAATAACAAGTTTAGAAACCCCACGGTGGCGCCTACGCACGACGTGACCACAGACCGG

61   S Q R L T L R F I P V D R E D T A Y S Y
181  TCCCAGCGTTTGACGCTGCGGTTCATCCCTGTGGACCGTGAGGATACTGCGTACTCGTAC

81   K A R F T L A V G D N R V L D M A S T Y
241  AAGGCGCGGTTCACCCTAGCTGTGGGTGATAACCGTGTGCTGGACATGGCTTCCACGTAC

101  F D I R G V L D R G P T F K P Y S G T A
301  TTTGACATCCGCGGCGTGCTGGACAGGGGCCCTACTTTTAAGCCCTACTCTGGCACTGCC

121  Y N A L A P K G A P N P C E W D E Q G P
361  TACAACGCCCTGGCTCCCAAGGGTGCCCCAAATCCTTGCGAATGGGATGAACAGGGACCA

141  G A P Q G P G A P Q G P G A P Q G P G A
421  GGAGCACCACAGGGACCAGGAGCACCACAGGGACCAGGAGCACCGCAAGGTCCTGGTGCT

161  P K T H V F G Q A P Y S G I N I T K E G
481  CCTAAAACTCACGTATTTGGGCAGGCGCCTTATTCTGGTATAAATATTACAAAGGAGGGT

181  I Q I G V E G Q T P K Y A D K T F Q P E
541  ATTCAAATAGGTGTCGAAGGTCAAACACCTAAATATGCCGATAAAACATTTCAACCTGAA

201  P Q I G E S Q W Y E T E I N H A A G R V
601  CCTCAAATAGGAGAATCTCAGTGGTACGAAACAGAAATTAATCATGCAGCTGGGAGAGTC

221  L K K T T P M K P C Y G S Y A K P T N E
661  CTAAAAAAGACTACCCCAATGAAACCATGTTACGGTTCATATGCAAAACCCACAAATGAA

241  N G G Q G I L V K Q Q N G K L E S Q V E
721  AATGGAGGGCAAGGCATTCTTGTAAAGCAACAAAATGGAAAGCTAGAAAGTCAAGTGGAA

261  M Q F F S T T E A A A G N G D N L T P K
781  ATGCAATTTTTCTCAACTACTGAGGCAGCCGCAGGCAATGGTGATAACTTGACTCCTAAA

281  V V L Y S E D V D I E T P D T H I S Y M
841  GTGGTATTGTACAGTGAAGATGTAGATATAGAAACCCCAGACACTCATATTTCTTACATG

301  P T I K E G N S R E L M G Q Q S M P N R
901  CCCACTATTAAGGAAGGTAACTCACGAGAACTAATGGGCCAACAATCTATGCCCAACAGG

321  P N Y I A F R D N F I G L M Y Y N S T G
961  CCTAATTACATTGCTTTTAGGGACAATTTTATTGGTCTAATGTATTACAACAGCACGGGT

341  N M G V L A G Q A S Q L N A V V D L Q D
1021 AATATGGGTGTTCTGGCGGGCCAAGCATCGCAGTTGAATGCTGTTGTAGATTTGCAAGAC

361  R N T E L S Y Q L L L D S I G D R T R Y
1081 AGAAACACAGAGCTTTCATACCAGCTTTTGCTTGATTCCATTGGTGATAGAACCAGGTAC

381  F S M W N Q L P N Y C F P L G G V I N T
1141 TTTTCTATGTGGAATCAGCTTCCAAATTACTGCTTTCCACTGGGAGGTGTGATTAATACA
```

1201 GAGACTCTTACCAAGGTAAAACCTAAAACAGGTCAGGAAAATGGATGGGAAAAAGATGCT

421 T E F S D K N E I R V G N N F A M E I N

1261 ACAGAATTTTCAGATAAAAATGAAATAAGAGTTGGAAATAATTTTGCCATGGAAATCAAT

441 L N A N L W R N F L Y S N I A L Y L P D

1321 CTAAATGCCAACCTGTGGAGAAATTTCCTGTACTCCAACATAGCGCTGTATTTGCCCGAC

461 K L K Y S P S N V K I S D N P N T Y D Y

1381 AAGCTAAAGTACAGTCCTTCCAACGTAAAAATTTCTGATAACCCAAACACCTACGACTAC

481 M N K R V V A P G L V D C Y I N L G A R

1441 ATGAACAAGCGAGTGGTGGCTCCCGGGCTAGTGGACTGCTACATTAACCTTGGAGCACGC

501 W S L D Y M D N V N P F N H H R N A G L

1501 TGGTCCCTTGACTATATGGACAACGTCAACCCATTTAACCACCACCGCAATGCTGGCCTG

521 R Y R S M L L G N G R Y V P F H I Q V P

1561 CGCTACCGCTCAATGTTGCTGGGCAATGGTCGCTATGTGCCCTTCCACATCCAGGTGCCT

541 Q K F F A I K N L L L L P G S Y T Y E W

1621 CAGAAGTTCTTTGCCATTAAAAACCTCCTTCTCCTGCCGGGCTCATACACCTACGAGTGG

561 N F R K D V N M V L Q S S L G N D L R V

1681 AACTTCAGGAAGGATGTTAACATGGTTCTGCAGAGCTCCCTAGGAAATGACCTAAGGGTT

581 D G A S I K F D S I C L Y A T F F P M A

1741 GACGGAGCCAGCATTAAGTTTGATAGCATTTGCCTTTACGCCACCTTCTTCCCCATGGCC

601 H N T A S T L E A M L R N D T N D Q S F

1801 CACAACACCGCCTCCACGCTTGAGGCCATGCTTAGAAACGACACCAACGACCAGTCCTTT

621 N D Y L S A A N M L Y P I P A N A T N V

1861 AACGACTATCTCTCCGCCGCCAACATGCTCTACCCTATACCGCCAACGCTACCAACGTG

641 P I S I P S R N W A A F R G W A F T R L

1921 CCCATATCCATCCCCTCCCGCAACTGGGCGGCTTTCCGCGGCTGGGCCTTCACGCGCCTT

661 K T K E T P S L G S G Y D P Y Y T Y S G

1981 AAGACTAAGGAAACCCCATCACTGGGCTCGGGCTACGACCCTTATTACACCTACTCTGGC

681 S I P Y L D G T F Y L N H T F K K V A I

2041 TCTATACCCTACCTAGATGGAACCTTTTACCTCAACCACACCTTTAAGAAGGTGGCCATT

701 T F D S S V S W P G N D R L L T P N E F

2101 ACCTTTGACTCTTCTGTCAGCTGGCCTGGCAATGACCGCCTGCTTACCCCCAACGAGTTT

721 E I K R S V D G E G Y N V A Q C N M T K

2161 GAAATTAAGCGCTCAGTTGACGGGGAGGGTTACAACGTTGCCCAGTGTAACATGACCAAA

741 D W F L V Q M L A N Y N I G Y Q G F Y I

2221 GACTGGTTCCTGGTACAAATGCTAGCTAACTATAACATTGGCTACCAGGGCTTCTATATC

761 P E S Y K D R M Y S F F R N F Q P M S R

2281 CCAGAGAGCTACAAGGACCGCATGTACTCCTTCTTTAGAAACTTCCAGCCCATGAGCCGT

781 Q V V D D T K Y K D Y Q Q V G I L H Q H

2341 CAGGTGGTGGATGATACTAAATACAAGGACTACCAACAGGTGGGCATCCTACACCAACAC

801 N N S G F V G Y L A P T M R E G Q A Y P

2401 AACAACTCTGGATTTGTTGGCTACCTTGCCCCCACCATGCGCGAAGGACAGGCCTACCCT

Fig. 12B

```
 821  A  N  F  P  Y  P  L  I  G  K  T  A  V  D  S  I  T  Q  K  K
2461  GCTAACTTCCCCTATCCGCTTATAGGCAAGACCGCAGTTGACAGCATTACCCAGAAAAAG

 841  F  L  C  D  R  T  L  W  R  I  P  F  S  S  N  F  M  S  M  G
2521  TTTCTTTGCGATCGCACCCTTTGGCGCATCCCATTCTCCAGTAACTTTATGTCCATGGGC

 861  A  L  T  D  L  G  Q  N  L  L  Y  A  N  S  A  H  A  L  D  M
2581  GCACTCACAGACCTGGGCCAAAACCTTCTCTACGCCAACTCCGCCCACGCGCTAGACATG

 881  T  F  E  V  D  P  M  D  E  P  T  L  L  Y  V  L  F  E  V  F
2641  ACTTTTGAGGTGGATCCCATGGACGAGCCCACCCTTCTTTATGTTTTGTTTGAAGTCTTT

 901  D  V  V  R  V  H  Q  P  H  R  G  V  I  E  T  V  Y  L  R  T
2701  GACGTGGTCCGTGTGCACCAGCCGCACCGCGGCGTCATCGAAACCGTGTACCTGCGCACG

 921  P  F  S  A  G  N  A  T  T  -
2761  CCCTTCTCGGCCGGCAACGCCACAACATAA
```

Fig. 12C

Hexon sequence of (QGPGAP)$_5$-HVR1 adenovirus SEQ IDNOS : 5 and 33

```
   1 M A T P S M M P Q W S Y M H I S G Q D A
   1 ATGGCTACCCCTTCGATGATGCCGCAGTGGTCTTACATGCACATCTCGGGCCAGGACGCC

  21 S E Y L S P G L V Q F A R A T E T Y F S
  61 TCGGAGTACCTGAGCCCCGGGCTGGTGCAGTTTGCCCGCGCCACCGAGACGTACTTCAGC

  41 L N N K F R N P T V A P T H D V T T D R
 121 CTGAATAACAAGTTTAGAAACCCCACGGTGGCGCCTACGCACGACGTGACCACAGACCGG

  61 S Q R L T L R F I P V D R E D T A Y S Y
 181 TCCCAGCGTTTGACGCTGCGGTTCATCCCTGTGGACCGTGAGGATACTGCGTACTCGTAC

  81 K A R F T L A V G D N R V L D M A S T Y
 241 AAGGCGCGGTTCACCCTAGCTGTGGGTGATAACCGTGTGCTGGACATGGCTTCCACGTAC

 101 F D I R G V L D R G P T F K P Y S G T A
 301 TTTGACATCCGCGGCGTGCTGGACAGGGGCCCTACTTTTAAGCCCTACTCTGGCACTGCC

 121 Y N A L A P K G A P N P C E W D E Q G P
 361 TACAACGCCCTGGCTCCCAAGGGTGCCCCAAATCCTTGCGAATGGGATGAACAGGGACCA

 141 G A P Q G P G A P Q G P G A P Q G P G A
 421 GGAGCACCACAGGGACCAGGAGCACCACAGGGACCAGGAGCACCGCAAGGTCCTGGTGCT

 161 P Q G P G A P K T H V F G Q A P Y S G I
 481 CCTCAGGGACCAGGAGCACCAAAAACTCACGTATTTGGGCAGGCGCCTTATTCTGGTATA

 181 N I T K E G I Q I G V E G Q T P K Y A D
 541 AATATTACAAAGGAGGGTATTCAAATAGGTGTCGAAGGTCAAACACCTAAATATGCCGAT

 201 K T F Q P E P Q I G E S Q W Y E T E I N
 601 AAAACATTTCAACCTGAACCTCAAATAGGAGAATCTCAGTGGTACGAAACAGAAATTAAT

 221 H A A G R V L K K T T P M K P C Y G S Y
 661 CATGCAGCTGGGAGAGTCCTAAAAAAGACTACCCCAATGAAACCATGTTACGGTTCATAT

 241 A K P T N E N G G Q G I L V K Q Q N G K
 721 GCAAAACCCACAAATGAAAATGGAGGGCAAGGCATTCTTGTAAAGCAACAAAATGGAAAG

 261 L E S Q V E M Q F F S T T E A A A G N G
 781 CTAGAAAGTCAAGTGGAAATGCAATTTTTCTCAACTACTGAGGCAGCCGCAGGCAATGGT

 281 D N L T P K V V L Y S E D V D I E T P D
 841 GATAACTTGACTCCTAAAGTGGTATTGTACAGTGAAGATGTAGATATAGAAACCCCAGAC

 301 T H I S Y M P T I K E G N S R E L M G Q
 901 ACTCATATTTCTTACATGCCCACTATTAAGGAAGGTAACTCACGAGAACTAATGGGCCAA

 321 Q S M P N R P N Y I A F R D N F I G L M
 961 CAATCTATGCCCAACAGGCCTAATTACATTGCTTTTAGGGACAATTTTATTGGTCTAATG

 341 Y Y N S T G N M G V L A G Q A S Q L N A
1021 TATTACAACAGCACGGGTAATATGGGTGTTCTGGCGGGCCAAGCATCGCAGTTGAATGCT

 361 V V D L Q D R N T E L S Y Q L L L D S I
1081 GTTGTAGATTTGCAAGACAGAAACACAGAGCTTTCATACCAGCTTTTGCTTGATTCCATT

 381 G D R T R Y F S M W N Q L P N Y C F P L
1141 GGTGATAGAACCAGGTACTTTTCTATGTGGAATCAGCTTCCAAATTACTGCTTTCCACTG
```

Fig. 13A

```
 401  G  G  V  I  N  T  E  T  L  T  K  V  K  P  K  T  G  Q  E  N
1201  GGAGGTGTGATTAATACAGAGACTCTTACCAAGGTAAAACCTAAAACAGGTCAGGAAAAT

 421  G  W  E  K  D  A  T  E  F  S  D  K  N  E  I  R  V  G  N  N
1261  GGATGGGAAAAAGATGCTACAGAATTTTCAGATAAAAATGAAATAAGAGTTGGAAATAAT

 441  F  A  M  E  I  N  L  N  A  N  L  W  R  N  F  L  Y  S  N  I
1321  TTTGCCATGGAAATCAATCTAAATGCCAACCTGTGGAGAAATTTCCTGTACTCCAACATA

 461  A  L  Y  L  P  D  K  L  K  Y  S  P  S  N  V  K  I  S  D  N
1381  GCGCTGTATTTGCCCGACAAGCTAAAGTACAGTCCTTCCAACGTAAAAATTTCTGATAAC

 481  P  N  T  Y  D  Y  M  N  K  R  V  V  A  P  G  L  V  D  C  Y
1441  CCAAACACCTACGACTACATGAACAAGCGAGTGGTGGCTCCCGGGCTAGTGGACTGCTAC

 501  I  N  L  G  A  R  W  S  L  D  Y  M  D  N  V  N  P  F  N  H
1501  ATTAACCTTGGAGCACGCTGGTCCCTTGACTATATGGACAACGTCAACCCATTTAACCAC

 521  H  R  N  A  G  L  R  Y  R  S  M  L  L  G  N  G  R  Y  V  P
1561  CACCGCAATGCTGGCCTGCGCTACCGCTCAATGTTGCTGGGCAATGGTCGCTATGTGCCC

 541  F  H  I  Q  V  P  Q  K  F  F  A  I  K  N  L  L  L  L  P  G
1621  TTCCACATCCAGGTGCCTCAGAAGTTCTTTGCCATTAAAAACCTCCTTCTCCTGCCGGGC

 561  S  Y  T  Y  E  W  N  F  R  K  D  V  N  M  V  L  Q  S  S  L
1681  TCATACACCTACGAGTGGAACTTCAGGAAGGATGTTAACATGGTTCTGCAGAGCTCCCTA

 581  G  N  D  L  R  V  D  G  A  S  I  K  F  D  S  I  C  L  Y  A
1741  GGAAATGACCTAAGGGTTGACGGAGCCAGCATTAAGTTTGATAGCATTTGCCTTTACGCC

 601  T  F  F  P  M  A  H  N  T  A  S  T  L  E  A  M  L  R  N  D
1801  ACCTTCTTCCCCATGGCCCACAACACCGCCTCCACGCTTGAGGCCATGCTTAGAAACGAC

 621  T  N  D  Q  S  F  N  D  Y  L  S  A  A  N  M  L  Y  P  I  P
1861  ACCAACGACCAGTCCTTTAACGACTATCTCTCCGCCGCCAACATGCTCTACCCTATACCC

 641  A  N  A  T  N  V  P  I  S  I  P  S  R  N  W  A  A  F  R  G
1921  GCCAACGCTACCAACGTGCCCATATCCATCCCCTCCCGCAACTGGGCGGCTTTCCGCGGC

 661  W  A  F  T  R  L  K  T  K  E  T  P  S  L  G  S  G  Y  D  P
1981  TGGGCCTTCACGCGCCTTAAGACTAAGGAAACCCCATCACTGGGCTCGGGCTACGACCCT

 681  Y  Y  T  Y  S  G  S  I  P  Y  L  D  G  T  F  Y  L  N  H  T
2041  TATTACACCTACTCTGGCTCTATACCCTACCTAGATGGAACCTTTTACCTCAACCACACC

 701  F  K  K  V  A  I  T  F  D  S  S  V  S  W  P  G  N  D  R  L
2101  TTTAAGAAGGTGGCCATTACCTTTGACTCTTCTGTCAGCTGGCCTGGCAATGACCGCCTG

 721  L  T  P  N  E  F  E  I  K  R  S  V  D  G  E  G  Y  N  V  A
2161  CTTACCCCCAACGAGTTTGAAATTAAGCGCTCAGTTGACGGGGAGGGTTACAACGTTGCC

 741  Q  C  N  M  T  K  D  W  F  L  V  Q  M  L  A  N  Y  N  I  G
2221  CAGTGTAACATGACCAAAGACTGGTTCCTGGTACAAATGCTAGCTAACTATAACATTGGC

 761  Y  Q  G  F  Y  I  P  E  S  Y  K  D  R  M  Y  S  F  F  R  N
2281  TACCAGGGCTTCTATATCCCAGAGAGCTACAAGGACCGCATGTACTCCTTCTTTAGAAAC

 781  F  Q  P  M  S  R  Q  V  V  D  D  T  K  Y  K  D  Y  Q  Q  V
2341  TTCCAGCCCATGAGCCGTCAGGTGGTGGATGATACTAAATACAAGGACTACCAACAGGTG

 801  G  I  L  H  Q  H  N  N  S  G  F  V  G  Y  L  A  P  T  M  R
2401  GGCATCCTACACCAACACAACAACTCTGGATTTGTTGGCTACCTTGCCCCCACCATGCGC
```

Fig. 13B

```
 821  E  G  Q  A  Y  P  A  N  F  P  Y  P  L  I  G  K  T  A  V  D
2461  GAAGGACAGGCCTACCCTGCTAACTTCCCCTATCCGCTTATAGGCAAGACCGCAGTTGAC

 841  S  I  T  Q  K  K  F  L  C  D  R  T  L  W  R  I  P  F  S  S
2521  AGCATTACCCAGAAAAAGTTTCTTTGCGATCGCACCCTTTGGCGCATCCCATTCTCCAGT

 861  N  F  M  S  M  G  A  L  T  D  L  G  Q  N  L  L  Y  A  N  S
2581  AACTTTATGTCCATGGGCGCACTCACAGACCTGGGCCAAAACCTTCTCTACGCCAACTCC

 881  A  H  A  L  D  M  T  F  E  V  D  P  M  D  E  P  T  L  L  Y
2641  GCCCACGCGCTAGACATGACTTTTGAGGTGGATCCCATGGACGAGCCCACCCTTCTTTAT

 901  V  L  F  E  V  F  D  V  V  R  V  H  Q  P  H  R  G  V  I  E
2701  GTTTTGTTTGAAGTCTTTGACGTGGTCCGTGTGCACCAGCCGCACCGCGGCGTCATCGAA

 921  T  V  Y  L  R  T  P  F  S  A  G  N  A  T  T  -
2761  ACCGTGTACCTGCGCACGCCCTTCTCGGCCGGCAACGCCACAACATAA
```

Fig. 13C

Hexon sequence of (QGPGAP)$_6$-HVR1 adenovirus SEQ IDNOS : 6 and 34

```
   1  M  A  T  P  S  M  M  P  Q  W  S  Y  M  H  I  S  G  Q  D  A
   1  ATGGCTACCCCTTCGATGATGCCGCAGTGGTCTTACATGCACATCTCGGGCCAGGACGCC

  21  S  E  Y  L  S  P  G  L  V  Q  F  A  R  A  T  E  T  Y  F  S
  61  TCGGAGTACCTGAGCCCCGGGCTGGTGCAGTTTGCCCGCGCCACCGAGACGTACTTCAGC

  41  L  N  N  K  F  R  N  P  T  V  A  P  T  H  D  V  T  T  D  R
 121  CTGAATAACAAGTTTAGAAACCCCACGGTGGCGCCTACGCACGACGTGACCACAGACCGG

  61  S  Q  R  L  T  L  R  F  I  P  V  D  R  E  D  T  A  Y  S  Y
 181  TCCCAGCGTTTGACGCTGCGGTTCATCCCTGTGGACCGTGAGGATACTGCGTACTCGTAC

  81  K  A  R  F  T  L  A  V  G  D  N  R  V  L  D  M  A  S  T  Y
 241  AAGGCGCGGTTCACCCTAGCTGTGGGTGATAACCGTGTGCTGGACATGGCTTCCACGTAC

 101  F  D  I  R  G  V  L  D  R  G  P  T  F  K  P  Y  S  G  T  A
 301  TTTGACATCCGCGGCGTGCTGGACAGGGGCCCTACTTTTAAGCCCTACTCTGGCACTGCC

 121  Y  N  A  L  A  P  K  G  A  P  N  P  C  E  W  D  E  Q  G  P
 361  TACAACGCCCTGGCTCCCAAGGGTGCCCCAAATCCTTGCGAATGGGATGAACAGGGACCA

 141  G  A  P  Q  G  P  G  A  P  Q  G  P  G  A  P  Q  G  P  G  A
 421  GGAGCACCACAGGGACCAGGAGCACCACAGGGACCAGGAGCACCGCAAGGTCCTGGTGCT

 161  P  Q  G  P  G  A  P  Q  G  P  G  A  P  K  T  H  V  F  G  Q
 481  CCTCAGGGACCAGGAGCACCACAGGGACCAGGAGCACCAAAAACTCACGTATTTGGGCAG

 181  A  P  Y  S  G  I  N  I  T  K  E  G  I  Q  I  G  V  E  G  Q
 541  GCGCCTTATTCTGGTATAAATATTACAAAGGAGGGTATTCAAATAGGTGTCGAAGGTCAA

 201  T  P  K  Y  A  D  K  T  F  Q  P  E  P  Q  I  G  E  S  Q  W
 601  ACACCTAAATATGCCGATAAAACATTTCAACCTGAACCTCAAATAGGAGAATCTCAGTGG

 221  Y  E  T  E  I  N  H  A  A  G  R  V  L  K  K  T  T  P  M  K
 661  TACGAAACAGAAATTAATCATGCAGCTGGGAGAGTCCTAAAAAAGACTACCCCAATGAAA

 241  P  C  Y  G  S  Y  A  K  P  T  N  E  N  G  G  Q  G  I  L  V
 721  CCATGTTACGGTTCATATGCAAAACCCACAAATGAAAATGGAGGGCAAGGCATTCTTGTA

 261  K  Q  Q  N  G  K  L  E  S  Q  V  E  M  Q  F  F  S  T  T  E
 781  AAGCAACAAAATGGAAAGCTAGAAAGTCAAGTGGAAATGCAATTTTTCTCAACTACTGAG

 281  A  A  A  G  N  G  D  N  L  T  P  K  V  V  L  Y  S  E  D  V
 841  GCAGCCGCAGGCAATGGTGATAACTTGACTCCTAAAGTGGTATTGTACAGTGAAGATGTA

 301  D  I  E  T  P  D  T  H  I  S  Y  M  P  T  I  K  E  G  N  S
 901  GATATAGAAACCCCAGACACTCATATTTCTTACATGCCCACTATTAAGGAAGGTAACTCA

 321  R  E  L  M  G  Q  Q  S  M  P  N  R  P  N  Y  I  A  F  R  D
 961  CGAGAACTAATGGGCCAACAATCTATGCCCAACAGGCCTAATTACATTGCTTTTAGGGAC

 341  N  F  I  G  L  M  Y  Y  N  S  T  G  N  M  G  V  L  A  G  Q
1021  AATTTTATTGGTCTAATGTATTACAACAGCACGGGTAATATGGGTGTTCTGGCGGGCCAA

 361  A  S  Q  L  N  A  V  V  D  L  Q  D  R  N  T  E  L  S  Y  Q
1081  GCATCGCAGTTGAATGCTGTTGTAGATTTGCAAGACAGAAACACAGAGCTTTCATACCAG

 381  L  L  L  D  S  I  G  D  R  T  R  Y  F  S  M  W  N  Q  L  P
1141  CTTTTGCTTGATTCCATTGGTGATAGAACCAGGTACTTTTCTATGTGGAATCAGCTTCCA
```

Fig. 14A

```
 401  N  Y  C  F  P  L  G  G  V  I  N  T  E  T  L  T  K  V  K  P
1201  AATTACTGCTTTCCACTGGGAGGTGTGATTAATACAGAGACTCTTACCAAGGTAAAACCT

 421  K  T  G  Q  E  N  G  W  E  K  D  A  T  E  F  S  D  K  N  E
1261  AAAACAGGTCAGGAAAATGGATGGGAAAAAGATGCTACAGAATTTTCAGATAAAAATGAA

 441  I  R  V  G  N  N  F  A  M  E  I  N  L  N  A  N  L  W  R  N
1321  ATAAGAGTTGGAAATAATTTTGCCATGGAAATCAATCTAAATGCCAACCTGTGGAGAAAT

 461  F  L  Y  S  N  I  A  L  Y  L  P  D  K  L  K  Y  S  P  S  N
1381  TTCCTGTACTCCAACATAGCGCTGTATTTGCCCGACAAGCTAAAGTACAGTCCTTCCAAC

 481  V  K  I  S  D  N  P  N  T  Y  D  Y  M  N  K  R  V  V  A  P
1441  GTAAAAATTTCTGATAACCCAAACACCTACGACTACATGAACAAGCGAGTGGTGGCTCCC

 501  G  L  V  D  C  Y  I  N  L  G  A  R  W  S  L  D  Y  M  D  N
1501  GGGCTAGTGGACTGCTACATTAACCTTGGAGCACGCTGGTCCCTTGACTATATGGACAAC

 521  V  N  P  F  N  H  H  R  N  A  G  L  R  Y  R  S  M  L  L  G
1561  GTCAACCCATTTAACCACCACCGCAATGCTGGCCTGCGCTACCGCTCAATGTTGCTGGGC

 541  N  G  R  Y  V  P  F  H  I  Q  V  P  Q  K  F  F  A  I  K  N
1621  AATGGTCGCTATGTGCCCTTCCACATCCAGGTGCCTCAGAAGTTCTTTGCCATTAAAAAC

 561  L  L  L  L  P  G  S  Y  T  Y  E  W  N  F  R  K  D  V  N  M
1681  CTCCTTCTCCTGCCGGGCTCATACACCTACGAGTGGAACTTCAGGAAGGATGTTAACATG

 581  V  L  Q  S  S  L  G  N  D  L  R  V  D  G  A  S  I  K  F  D
1741  GTTCTGCAGAGCTCCCTAGGAAATGACCTAAGGGTTGACGGAGCCAGCATTAAGTTTGAT

 601  S  I  C  L  Y  A  T  F  F  P  M  A  H  N  T  A  S  T  L  E
1801  AGCATTTGCCTTTACGCCACCTTCTTCCCCATGGCCCACAACACCGCCTCCACGCTTGAG

 621  A  M  L  R  N  D  T  N  D  Q  S  F  N  D  Y  L  S  A  A  N
1861  GCCATGCTTAGAAACGACACCAACGACCAGTCCTTTAACGACTATCTCTCCGCCGCCAAC

 641  M  L  Y  P  I  P  A  N  A  T  N  V  P  I  S  I  P  S  R  N
1921  ATGCTCTACCCTATACCCGCCAACGCTACCAACGTGCCCATATCCATCCCCTCCCGCAAC

 661  W  A  A  F  R  G  W  A  F  T  R  L  K  T  K  E  T  P  S  L
1981  TGGGCGGCTTTCCGCGGCTGGGCCTTCACGCGCCTTAAGACTAAGGAAACCCCATCACTG

 681  G  S  G  Y  D  P  Y  Y  T  Y  S  G  S  I  P  Y  L  D  G  T
2041  GGCTCGGGCTACGACCCTTATTACACCTACTCTGGCTCTATACCCTACCTAGATGGAACC

 701  F  Y  L  N  H  T  F  K  K  V  A  I  T  F  D  S  S  V  S  W
2101  TTTTACCTCAACCACACCTTTAAGAAGGTGGCCATTACCTTTGACTCTTCTGTCAGCTGG

 721  P  G  N  D  R  L  L  T  P  N  E  F  E  I  K  R  S  V  D  G
2161  CCTGGCAATGACCGCCTGCTTACCCCCAACGAGTTTGAAATTAAGCGCTCAGTTGACGGG

 741  E  G  Y  N  V  A  Q  C  N  M  T  K  D  W  F  L  V  Q  M  L
2221  GAGGGTTACAACGTTGCCCAGTGTAACATGACCAAAGACTGGTTCCTGGTACAAATGCTA

 761  A  N  Y  N  I  G  Y  Q  G  F  Y  I  P  E  S  Y  K  D  R  M
2281  GCTAACTATAACATTGGCTACCAGGGCTTCTATATCCCAGAGAGCTACAAGGACCGCATG

 781  Y  S  F  F  R  N  F  Q  P  M  S  R  Q  V  V  D  D  T  K  Y
2341  TACTCCTTCTTTAGAAACTTCCAGCCCATGAGCCGTCAGGTGGTGGATGATACTAAATAC

 801  K  D  Y  Q  Q  V  G  I  L  H  Q  H  N  N  S  G  F  V  G  Y
2401  AAGGACTACCAACAGGTGGGCATCCTACACCAACACAACAACTCTGGATTTGTTGGCTAC
```

Fig. 14B

```
 821  L  A  P  T  M  R  E  G  Q  A  Y  P  A  N  F  P  Y  P  L  I
2461  CTTGCCCCCACCATGCGCGAAGGACAGGCCTACCCTGCTAACTTCCCCTATCCGCTTATA

 841  G  K  T  A  V  D  S  I  T  Q  K  K  F  L  C  D  R  T  L  W
2521  GGCAAGACCGCAGTTGACAGCATTACCCAGAAAAAGTTTCTTTGCGATCGCACCCTTTGG

 861  R  I  P  F  S  S  N  F  M  S  M  G  A  L  T  D  L  G  Q  N
2581  CGCATCCCATTCTCCAGTAACTTTATGTCCATGGGCGCACTCACAGACCTGGGCCAAAAC

 881  L  L  Y  A  N  S  A  H  A  L  D  M  T  F  E  V  D  P  M  D
2641  CTTCTCTACGCCAACTCCGCCCACGCGCTAGACATGACTTTTGAGGTGGATCCCATGGAC

 901  E  P  T  L  L  Y  V  L  F  E  V  F  D  V  V  R  V  H  Q  P
2701  GAGCCCACCCTTCTTTATGTTTTGTTTGAAGTCTTTGACGTGGTCCGTGTGCACCAGCCG

 921  H  R  G  V  I  E  T  V  Y  L  R  T  P  F  S  A  G  N  A  T
2761  CACCGCGGCGTCATCGAAACCGTGTACCTGCGCACGCCCTTCTCGGCCGGCAACGCCACA

 941  T  -
2821  ACATAA
```

Fig. 14C

Hexon sequence of (QGPGAP)$_7$-HVR1 adenovirus SEQ IDNOS : 7 and 35

```
   1  M  A  T  P  S  M  M  P  Q  W  S  Y  M  H  I  S  G  Q  D  A
   1  ATGGCTACCCCTTCGATGATGCCGCAGTGGTCTTACATGCACATCTCGGGCCAGGACGCC

  21  S  E  Y  L  S  P  G  L  V  Q  F  A  R  A  T  E  T  Y  F  S
  61  TCGGAGTACCTGAGCCCCGGGCTGGTGCAGTTTGCCCGCGCCACCGAGACGTACTTCAGC

  41  L  N  N  K  F  R  N  P  T  V  A  P  T  H  D  V  T  T  D  R
 121  CTGAATAACAAGTTTAGAAACCCCACGGTGGCGCCTACGCACGACGTGACCACAGACCGG

  61  S  Q  R  L  T  L  R  F  I  P  V  D  R  E  D  T  A  Y  S  Y
 181  TCCCAGCGTTTGACGCTGCGGTTCATCCCTGTGGACCGTGAGGATACTGCGTACTCGTAC

  81  K  A  R  F  T  L  A  V  G  D  N  R  V  L  D  M  A  S  T  Y
 241  AAGGCGCGGTTCACCCTAGCTGTGGGTGATAACCGTGTGCTGGACATGGCTTCCACGTAC

 101  F  D  I  R  G  V  L  D  R  G  P  T  F  K  P  Y  S  G  T  A
 301  TTTGACATCCGCGGCGTGCTGGACAGGGGCCCTACTTTTAAGCCCTACTCTGGCACTGCC

 121  Y  N  A  L  A  P  K  G  A  P  N  P  C  E  W  D  E  Q  G  P
 361  TACAACGCCCTGGCTCCCAAGGGTGCCCCAAATCCTTGCGAATGGGATGAACAGGGACCA

 141  G  A  P  Q  G  P  G  A  P  Q  G  P  G  A  P  Q  G  P  G  A
 421  GGAGCACCACAGGGACCAGGAGCACCACAGGGACCAGGAGCACCACAGGGACCAGGAGCA

 161  P  Q  G  P  G  A  P  Q  G  P  G  A  P  Q  G  P  G  A  P  K
 481  CCACAGGGACCAGGAGCACCACAGGGACCAGGAGCACCGCAAGGTCCTGGTGCTCCTAAA

 181  T  H  V  F  G  Q  A  P  Y  S  G  I  N  I  T  K  E  G  I  Q
 541  ACTCACGTATTTGGGCAGGCGCCTTATTCTGGTATAAATATTACAAAGGAGGGTATTCAA

 201  I  G  V  E  G  Q  T  P  K  Y  A  D  K  T  F  Q  P  E  P  Q
 601  ATAGGTGTCGAAGGTCAAACACCTAAATATGCCGATAAAACATTTCAACCTGAACCTCAA

 221  I  G  E  S  Q  W  Y  E  T  E  I  N  H  A  A  G  R  V  L  K
 661  ATAGGAGAATCTCAGTGGTACGAAACAGAAATTAATCATGCAGCTGGGAGAGTCCTAAAA

 241  K  T  T  P  M  K  P  C  Y  G  S  Y  A  K  P  T  N  E  N  G
 721  AAGACTACCCCAATGAAACCATGTTACGGTTCATATGCAAAACCCACAAATGAAAATGGA

 261  G  Q  G  I  L  V  K  Q  Q  N  G  K  L  E  S  Q  V  E  M  Q
 781  GGGCAAGGCATTCTTGTAAAGCAACAAAATGGAAAGCTAGAAAGTCAAGTGGAAATGCAA

 281  F  F  S  T  T  E  A  A  A  G  N  G  D  N  L  T  P  K  V  V
 841  TTTTTCTCAACTACTGAGGCAGCCGCAGGCAATGGTGATAACTTGACTCCTAAAGTGGTA

 301  L  Y  S  E  D  V  D  I  E  T  P  D  T  H  I  S  Y  M  P  T
 901  TTGTACAGTGAAGATGTAGATATAGAAACCCCAGACACTCATATTTCTTACATGCCCACT

 321  I  K  E  G  N  S  R  E  L  M  G  Q  Q  S  M  P  N  R  P  N
 961  ATTAAGGAAGGTAACTCACGAGAACTAATGGGCCAACAATCTATGCCCAACAGGCCTAAT

 341  Y  I  A  F  R  D  N  F  I  G  L  M  Y  Y  N  S  T  G  N  M
1021  TACATTGCTTTTAGGGACAATTTTATTGGTCTAATGTATTACAACAGCACGGGTAATATG

 361  G  V  L  A  G  Q  A  S  Q  L  N  A  V  V  D  L  Q  D  R  N
1081  GGTGTTCTGGCGGGCCAAGCATCGCAGTTGAATGCTGTTGTAGATTTGCAAGACAGAAAC

 381  T  E  L  S  Y  Q  L  L  L  D  S  I  G  D  R  T  R  Y  F  S
1141  ACAGAGCTTTCATACCAGCTTTTGCTTGATTCCATTGGTGATAGAACCAGGTACTTTTCT
```

Fig. 15A

```
401   M  W  N  Q  L  P  N  Y  C  F  P  L  G  G  V  I  N  T  E  T
1201  ATGTGGAATCAGCTTCCAAATTACTGCTTTCCACTGGGAGGTGTGATTAATACAGAGACT

421   L  T  K  V  K  P  K  T  G  Q  E  N  G  W  E  K  D  A  T  E
1261  CTTACCAAGGTAAAACCTAAAACAGGTCAGGAAAATGGATGGGAAAAAGATGCTACAGAA

441   F  S  D  K  N  E  I  R  V  G  N  N  F  A  M  E  I  N  L  N
1321  TTTTCAGATAAAAATGAAATAAGAGTTGGAAATAATTTTGCCATGGAAATCAATCTAAAT

461   A  N  L  W  R  N  F  L  Y  S  N  I  A  L  Y  L  P  D  K  L
1381  GCCAACCTGTGGAGAAATTTCCTGTACTCCAACATAGCGCTGTATTTGCCCGACAAGCTA

481   K  Y  S  P  S  N  V  K  I  S  D  N  P  N  T  Y  D  Y  M  N
1441  AAGTACAGTCCTTCCAACGTAAAAATTTCTGATAACCCAAACACCTACGACTACATGAAC

501   K  R  V  V  A  P  G  L  V  D  C  Y  I  N  L  G  A  R  W  S
1501  AAGCGAGTGGTGGCTCCCGGGCTAGTGGACTGCTACATTAACCTTGGAGCACGCTGGTCC

521   L  D  Y  M  D  N  V  N  P  F  N  H  H  R  N  A  G  L  R  Y
1561  CTTGACTATATGGACAACGTCAACCCATTTAACCACCACCGCAATGCTGGCCTGCGCTAC

541   R  S  M  L  L  G  N  G  R  Y  V  P  F  H  I  Q  V  P  Q  K
1621  CGCTCAATGTTGCTGGGCAATGGTCGCTATGTGCCCTTCCACATCCAGGTGCCTCAGAAG

561   F  F  A  I  K  N  L  L  L  L  P  G  S  Y  T  Y  E  W  N  F
1681  TTCTTTGCCATTAAAAACCTCCTTCTCCTGCCGGGCTCATACACCTACGAGTGGAACTTC

581   R  K  D  V  N  M  V  L  Q  S  S  L  G  N  D  L  R  V  D  G
1741  AGGAAGGATGTTAACATGGTTCTGCAGAGCTCCCTAGGAAATGACCTAAGGGTTGACGGA

601   A  S  I  K  F  D  S  I  C  L  Y  A  T  F  F  P  M  A  H  N
1801  GCCAGCATTAAGTTTGATAGCATTTGCCTTTACGCCACCTTCTTCCCCATGGCCCACAAC

621   T  A  S  T  L  E  A  M  L  R  N  D  T  N  D  Q  S  F  N  D
1861  ACCGCCTCCACGCTTGAGGCCATGCTTAGAAACGACACCAACGACCAGTCCTTTAACGAC

641   Y  L  S  A  A  N  M  L  Y  P  I  P  A  N  A  T  N  V  P  I
1921  TATCTCTCCGCCGCCAACATGCTCTACCCTATACCCGCCAACGCTACCAACGTGCCCATA

661   S  I  P  S  R  N  W  A  A  F  R  G  W  A  F  T  R  L  K  T
1981  TCCATCCCCTCCCGCAACTGGGCGGCTTTCCGCGGCTGGGCCTTCACGCGCCTTAAGACT

681   K  E  T  P  S  L  G  S  G  Y  D  P  Y  Y  T  Y  S  G  S  I
2041  AAGGAAACCCCATCACTGGGCTCGGGCTACGACCCTTATTACACCTACTCTGGCTCTATA

701   P  Y  L  D  G  T  F  Y  L  N  H  T  F  K  K  V  A  I  T  F
2101  CCCTACCTAGATGGAACCTTTTACCTCAACCACACCTTTAAGAAGGTGGCCATTACCTTT

721   D  S  S  V  S  W  P  G  N  D  R  L  L  T  P  N  E  F  E  I
2161  GACTCTTCTGTCAGCTGGCCTGGCAATGACCGCCTGCTTACCCCCAACGAGTTTGAAATT

741   K  R  S  V  D  G  E  G  Y  N  V  A  Q  C  N  M  T  K  D  W
2221  AAGCGCTCAGTTGACGGGGAGGGTTACAACGTTGCCCAGTGTAACATGACCAAAGACTGG

761   F  L  V  Q  M  L  A  N  Y  N  I  G  Y  Q  G  F  Y  I  P  E
2281  TTCCTGGTACAAATGCTAGCTAACTATAACATTGGCTACCAGGGCTTCTATATCCCAGAG

781   S  Y  K  D  R  M  Y  S  F  F  R  N  F  Q  P  M  S  R  Q  V
2341  AGCTACAAGGACCGCATGTACTCCTTCTTTAGAAACTTCCAGCCCATGAGCCGTCAGGTG

801   V  D  D  T  K  Y  K  D  Y  Q  Q  V  G  I  L  H  Q  H  N  N
2401  GTGGATGATACTAAATACAAGGACTACCAACAGGTGGGCATCCTACACCAACACAACAAC
```

Fig. 15B

```
 821  S  G  F  V  G  Y  L  A  P  T  M  R  E  G  Q  A  Y  P  A  N
2461  TCTGGATTTGTTGGCTACCTTGCCCCCACCATGCGCGAAGGACAGGCCTACCCTGCTAAC

 841  F  P  Y  P  L  I  G  K  T  A  V  D  S  I  T  Q  K  K  F  L
2521  TTCCCCTATCCGCTTATAGGCAAGACCGCAGTTGACAGCATTACCCAGAAAAAGTTTCTT

 861  C  D  R  T  L  W  R  I  P  F  S  S  N  F  M  S  M  G  A  L
2581  TGCGATCGCACCCTTTGGCGCATCCCATTCTCCAGTAACTTTATGTCCATGGGCGCACTC

 881  T  D  L  G  Q  N  L  L  Y  A  N  S  A  H  A  L  D  M  T  F
2641  ACAGACCTGGGCCAAAACCTTCTCTACGCCAACTCCGCCCACGCGCTAGACATGACTTTT

 901  E  V  D  P  M  D  E  P  T  L  L  Y  V  L  F  E  V  F  D  V
2701  GAGGTGGATCCCATGGACGAGCCCACCCTTCTTTATGTTTTGTTTGAAGTCTTTGACGTG

 921  V  R  V  H  Q  P  H  R  G  V  I  E  T  V  Y  L  R  T  P  F
2761  GTCCGTGTGCACCAGCCGCACCGCGGCGTCATCGAAACCGTGTACCTGCGCACGCCCTTC

 941  S  A  G  N  A  T  T  -
2821  TCGGCCGGCAACGCCACAACATAA
```

Fig. 15C

Hexon sequence of $(QGPGAP)_8$-HVR1 adenovirus SEQ IDNOS : 8 and 36

```
   1  M  A  T  P  S  M  M  P  Q  W  S  Y  M  H  I  S  G  Q  D  A
   1  ATGGCTACCCCTTCGATGATGCCGCAGTGGTCTTACATGCACATCTCGGGCCAGGACGCC

  21  S  E  Y  L  S  P  G  L  V  Q  F  A  R  A  T  E  T  Y  F  S
  61  TCGGAGTACCTGAGCCCCGGGCTGGTGCAGTTTGCCCGCGCCACCGAGACGTACTTCAGC

  41  L  N  N  K  F  R  N  P  T  V  A  P  T  H  D  V  T  T  D  R
 121  CTGAATAACAAGTTTAGAAACCCCACGGTGGCGCCTACGCACGACGTGACCACAGACCGG

  61  S  Q  R  L  T  L  R  F  I  P  V  D  R  E  D  T  A  Y  S  Y
 181  TCCCAGCGTTTGACGCTGCGGTTCATCCCTGTGGACCGTGAGGATACTGCGTACTCGTAC

  81  K  A  R  F  T  L  A  V  G  D  N  R  V  L  D  M  A  S  T  Y
 241  AAGGCGCGGTTCACCCTAGCTGTGGGTGATAACCGTGTGCTGGACATGGCTTCCACGTAC

 101  F  D  I  R  G  V  L  D  R  G  P  T  F  K  P  Y  S  G  T  A
 301  TTTGACATCCGCGGCGTGCTGGACAGGGGCCCTACTTTTAAGCCCTACTCTGGCACTGCC

 121  Y  N  A  L  A  P  K  G  A  P  N  P  C  E  W  D  E  Q  G  P
 361  TACAACGCCCTGGCTCCCAAGGGTGCCCCAAATCCTTGCGAATGGGATGAACAGGGACCA

 141  G  A  P  Q  G  P  G  A  P  Q  G  P  G  A  P  Q  G  P  G  A
 421  GGAGCACCACAGGGACCAGGAGCACCACAGGGACCAGGAGCACCACAGGGACCAGGAGCA

 161  P  Q  G  P  G  A  P  Q  G  P  G  A  P  Q  G  P  G  A  P  Q
 481  CCACAGGGACCAGGAGCACCACAGGGACCAGGAGCACCGCAAGGTCCTGGTGCTCCTCAG

 181  G  P  G  A  P  K  T  H  V  F  G  Q  A  P  Y  S  G  I  N  I
 541  GGACCAGGAGCACCAAAAACTCACGTATTTGGGCAGGCGCCTTATTCTGGTATAAATATT

 201  T  K  E  G  I  Q  I  G  V  E  G  Q  T  P  K  Y  A  D  K  T
 601  ACAAAGGAGGGTATTCAAATAGGTGTCGAAGGTCAAACACCTAAATATGCCGATAAAACA

 221  F  Q  P  E  P  Q  I  G  E  S  Q  W  Y  E  T  E  I  N  H  A
 661  TTTCAACCTGAACCTCAAATAGGAGAATCTCAGTGGTACGAAACAGAAATTAATCATGCA

 241  A  G  R  V  L  K  K  T  T  P  M  K  P  C  Y  G  S  Y  A  K
 721  GCTGGGAGAGTCCTAAAAAAGACTACCCCAATGAAACCATGTTACGGTTCATATGCAAAA

 261  P  T  N  E  N  G  G  Q  G  I  L  V  K  Q  Q  N  G  K  L  E
 781  CCCACAAATGAAAATGGAGGGCAAGGCATTCTTGTAAAGCAACAAAATGGAAAGCTAGAA

 281  S  Q  V  E  M  Q  F  F  S  T  T  E  A  A  A  G  N  G  D  N
 841  AGTCAAGTGGAAATGCAATTTTTCTCAACTACTGAGGCAGCCGCAGGCAATGGTGATAAC

 301  L  T  P  K  V  V  L  Y  S  E  D  V  D  I  E  T  P  D  T  H
 901  TTGACTCCTAAAGTGGTATTGTACAGTGAAGATGTAGATATAGAAACCCCAGACACTCAT

 321  I  S  Y  M  P  T  I  K  E  G  N  S  R  E  L  M  G  Q  Q  S
 961  ATTTCTTACATGCCCACTATTAAGGAAGGTAACTCACGAGAACTAATGGGCCAACAATCT

 341  M  P  N  R  P  N  Y  I  A  F  R  D  N  F  I  G  L  M  Y  Y
1021  ATGCCCAACAGGCCTAATTACATTGCTTTTAGGGACAATTTTATTGGTCTAATGTATTAC

 361  N  S  T  G  N  M  G  V  L  A  G  Q  A  S  Q  L  N  A  V  V
1081  AACAGCACGGGTAATATGGGTGTTCTGGCGGGCCAAGCATCGCAGTTGAATGCTGTTGTA

 381  D  L  Q  D  R  N  T  E  L  S  Y  Q  L  L  L  D  S  I  G  D
1141  GATTTGCAAGACAGAAACACAGAGCTTTCATACCAGCTTTTGCTTGATTCCATTGGTGAT
```

Fig. 16A

```
 401  R  T  R  Y  F  S  M  W  N  Q  L  P  N  Y  C  F  P  L  G  G
1201  AGAACCAGGTACTTTTCTATGTGGAATCAGCTTCCAAATTACTGCTTTCCACTGGGAGGT

 421  V  I  N  T  E  T  L  T  K  V  K  P  K  T  G  Q  E  N  G  W
1261  GTGATTAATACAGAGACTCTTACCAAGGTAAAACCTAAAACAGGTCAGGAAAATGGATGG

 441  E  K  D  A  T  E  F  S  D  K  N  E  I  R  V  G  N  N  F  A
1321  GAAAAAGATGCTACAGAATTTTCAGATAAAAATGAAATAAGAGTTGGAAATAATTTTGCC

 461  M  E  I  N  L  N  A  N  L  W  R  N  F  L  Y  S  N  I  A  L
1381  ATGGAAATCAATCTAAATGCCAACCTGTGGAGAAATTTCCTGTACTCCAACATAGCGCTG

 481  Y  L  P  D  K  L  K  Y  S  P  S  N  V  K  I  S  D  N  P  N
1441  TATTTGCCCGACAAGCTAAAGTACAGTCCTTCCAACGTAAAAATTTCTGATAACCCAAAC

 501  T  Y  D  Y  M  N  K  R  V  V  A  P  G  L  V  D  C  Y  I  N
1501  ACCTACGACTACATGAACAAGCGAGTGGTGGCTCCCGGGCTAGTGGACTGCTACATTAAC

 521  L  G  A  R  W  S  L  D  Y  M  D  N  V  N  P  F  N  H  H  R
1561  CTTGGAGCACGCTGGTCCCTTGACTATATGGACAACGTCAACCCATTTAACCACCACCGC

 541  N  A  G  L  R  Y  R  S  M  L  L  G  N  G  R  Y  V  P  F  H
1621  AATGCTGGCCTGCGCTACCGCTCAATGTTGCTGGGCAATGGTCGCTATGTGCCCTTCCAC

 561  I  Q  V  P  Q  K  F  F  A  I  K  N  L  L  L  L  P  G  S  Y
1681  ATCCAGGTGCCTCAGAAGTTCTTTGCCATTAAAAACCTCCTTCTCCTGCCGGGCTCATAC

 581  T  Y  E  W  N  F  R  K  D  V  N  M  V  L  Q  S  S  L  G  N
1741  ACCTACGAGTGGAACTTCAGGAAGGATGTTAACATGGTTCTGCAGAGCTCCCTAGGAAAT

 601  D  L  R  V  D  G  A  S  I  K  F  D  S  I  C  L  Y  A  T  F
1801  GACCTAAGGGTTGACGGAGCCAGCATTAAGTTTGATAGCATTTGCCTTTACGCCACCTTC

 621  F  P  M  A  H  N  T  A  S  T  L  E  A  M  L  R  N  D  T  N
1861  TTCCCCATGGCCCACAACACCGCCTCCACGCTTGAGGCCATGCTTAGAAACGACACCAAC

 641  D  Q  S  F  N  D  Y  L  S  A  A  N  M  L  Y  P  I  P  A  N
1921  GACCAGTCCTTTAACGACTATCTCTCCGCCGCCAACATGCTCTACCCTATACCCGCCAAC

 661  A  T  N  V  P  I  S  I  P  S  R  N  W  A  A  F  R  G  W  A
1981  GCTACCAACGTGCCCATATCCATCCCCTCCCGCAACTGGGCGGCTTTCCGCGGCTGGGCC

 681  F  T  R  L  K  T  K  E  T  P  S  L  G  S  G  Y  D  P  Y  Y
2041  TTCACGCGCCTTAAGACTAAGGAAACCCCATCACTGGGCTCGGGCTACGACCCTTATTAC

 701  T  Y  S  G  S  I  P  Y  L  D  G  T  F  Y  L  N  H  T  F  K
2101  ACCTACTCTGGCTCTATACCCTACCTAGATGGAACCTTTTACCTCAACCACACCTTTAAG

 721  K  V  A  I  T  F  D  S  S  V  S  W  P  G  N  D  R  L  L  T
2161  AAGGTGGCCATTACCTTTGACTCTTCTGTCAGCTGGCCTGGCAATGACCGCCTGCTTACC

 741  P  N  E  F  E  I  K  R  S  V  D  G  E  G  Y  N  V  A  Q  C
2221  CCCAACGAGTTTGAAATTAAGCGCTCAGTTGACGGGGAGGGTTACAACGTTGCCCAGTGT

 761  N  M  T  K  D  W  F  L  V  Q  M  L  A  N  Y  N  I  G  Y  Q
2281  AACATGACCAAAGACTGGTTCCTGGTACAAATGCTAGCTAACTATAACATTGGCTACCAG

 781  G  F  Y  I  P  E  S  Y  K  D  R  M  Y  S  F  F  R  N  F  Q
2341  GGCTTCTATATCCCAGAGAGCTACAAGGACCGCATGTACTCCTTCTTTAGAAACTTCCAG

 801  P  M  S  R  Q  V  V  D  D  T  K  Y  K  D  Y  Q  Q  V  G  I
2401  CCCATGAGCCGTCAGGTGGTGGATGATACTAAATACAAGGACTACCAACAGGTGGGCATC
```

Fig. 16B

```
 821  L  H  Q  H  N  N  S  G  F  V  G  Y  L  A  P  T  M  R  E  G
2461  CTACACCAACACAACAACTCTGGATTTGTTGGCTACCTTGCCCCCACCATGCGCGAAGGA

 841  Q  A  Y  P  A  N  F  P  Y  P  L  I  G  K  T  A  V  D  S  I
2521  CAGGCCTACCCTGCTAACTTCCCCTATCCGCTTATAGGCAAGACCGCAGTTGACAGCATT

 861  T  Q  K  K  F  L  C  D  R  T  L  W  R  I  P  F  S  S  N  F
2581  ACCCAGAAAAAGTTTCTTTGCGATCGCACCCTTTGGCGCATCCCATTCTCCAGTAACTTT

 881  M  S  M  G  A  L  T  D  L  G  Q  N  L  L  Y  A  N  S  A  H
2641  ATGTCCATGGGCGCACTCACAGACCTGGGCCAAAACCTTCTCTACGCCAACTCCGCCCAC

 901  A  L  D  M  T  F  E  V  D  P  M  D  E  P  T  L  L  Y  V  L
2701  GCGCTAGACATGACTTTTGAGGTGGATCCCATGGACGAGCCCACCCTTCTTTATGTTTTG

 921  F  E  V  F  D  V  V  R  V  H  Q  P  H  R  G  V  I  E  T  V
2761  TTTGAAGTCTTTGACGTGGTCCGTGTGCACCAGCCGCACCGCGGCGTCATCGAAACCGTG

 941  Y  L  R  T  P  F  S  A  G  N  A  T  T  -
2821  TACCTGCGCACGCCCTTCTCGGCCGGCAACGCCACAACATAA
```

Fig. 16C

Hexon sequence of $(QGPGAP)_9$-HVR1 adenovirus SEQ IDNOS : 9 and 37

```
   1  M  A  T  P  S  M  M  P  Q  W  S  Y  M  H  I  S  G  Q  D  A
   1  ATGGCTACCCCTTCGATGATGCCGCAGTGGTCTTACATGCACATCTCGGGCCAGGACGCC

  21  S  E  Y  L  S  P  G  L  V  Q  F  A  R  A  T  E  T  Y  F  S
  61  TCGGAGTACCTGAGCCCCGGGCTGGTGCAGTTTGCCCGCGCCACCGAGACGTACTTCAGC

  41  L  N  N  K  F  R  N  P  T  V  A  P  T  H  D  V  T  T  D  R
 121  CTGAATAACAAGTTTAGAAACCCCACGGTGGCGCCTACGCACGACGTGACCACAGACCGG

  61  S  Q  R  L  T  L  R  F  I  P  V  D  R  E  D  T  A  Y  S  Y
 181  TCCCAGCGTTTGACGCTGCGGTTCATCCCTGTGGACCGTGAGGATACTGCGTACTCGTAC

  81  K  A  R  F  T  L  A  V  G  D  N  R  V  L  D  M  A  S  T  Y
 241  AAGGCGCGGTTCACCCTAGCTGTGGGTGATAACCGTGTGCTGGACATGGCTTCCACGTAC

 101  F  D  I  R  G  V  L  D  R  G  P  T  F  K  P  Y  S  G  T  A
 301  TTTGACATCCGCGGCGTGCTGGACAGGGGCCCTACTTTTAAGCCCTACTCTGGCACTGCC

 121  Y  N  A  L  A  P  K  G  A  P  N  P  C  E  W  D  E  Q  G  P
 361  TACAACGCCCTGGCTCCCAAGGGTGCCCCAAATCCTTGCGAATGGGATGAACAGGGACCA

 141  G  A  P  Q  G  P  G  A  P  Q  G  P  G  A  P  Q  G  P  G  A
 421  GGAGCACCACAGGGACCAGGAGCACCACAGGGACCAGGAGCACCACAGGGACCAGGAGCA

 161  P  Q  G  P  G  A  P  Q  G  P  G  A  P  Q  G  P  G  A  P  Q
 481  CCACAGGGACCAGGAGCACCACAGGGACCAGGAGCACCGCAAGGTCCTGGTGCTCCTCAG

 181  G  P  G  A  P  Q  G  P  G  A  P  K  T  H  V  F  G  Q  A  P
 541  GGACCAGGAGCACCACAGGGACCAGGAGCACCAAAAACTCACGTATTTGGGCAGGCGCCT

 201  Y  S  G  I  N  I  T  K  E  G  I  Q  I  G  V  E  G  Q  T  P
 601  TATTCTGGTATAAATATTACAAAGGAGGGTATTCAAATAGGTGTCGAAGGTCAAACACCT

 221  K  Y  A  D  K  T  F  Q  P  E  P  Q  I  G  E  S  Q  W  Y  E
 661  AAATATGCCGATAAAACATTTCAACCTGAACCTCAAATAGGAGAATCTCAGTGGTACGAA

 241  T  E  I  N  H  A  A  G  R  V  L  K  K  T  T  P  M  K  P  C
 721  ACAGAAATTAATCATGCAGCTGGGAGAGTCCTAAAAAAGACTACCCCAATGAAACCATGT

 261  Y  G  S  Y  A  K  P  T  N  E  N  G  G  Q  G  I  L  V  K  Q
 781  TACGGTTCATATGCAAAACCCACAAATGAAAATGGAGGGCAAGGCATTCTTGTAAAGCAA

 281  Q  N  G  K  L  E  S  Q  V  E  M  Q  F  F  S  T  T  E  A  A
 841  CAAAATGGAAAGCTAGAAAGTCAAGTGGAAATGCAATTTTTCTCAACTACTGAGGCAGCC

 301  A  G  N  G  D  N  L  T  P  K  V  V  L  Y  S  E  D  V  D  I
 901  GCAGGCAATGGTGATAACTTGACTCCTAAAGTGGTATTGTACAGTGAAGATGTAGATATA

 321  E  T  P  D  T  H  I  S  Y  M  P  T  I  K  E  G  N  S  R  E
 961  GAAACCCCAGACACTCATATTTCTTACATGCCCACTATTAAGGAAGGTAACTCACGAGAA

 341  L  M  G  Q  Q  S  M  P  N  R  P  N  Y  I  A  F  R  D  N  F
1021  CTAATGGGCCAACAATCTATGCCCAACAGGCCTAATTACATTGCTTTTAGGGACAATTTT

 361  I  G  L  M  Y  Y  N  S  T  G  N  M  G  V  L  A  G  Q  A  S
1081  ATTGGTCTAATGTATTACAACAGCACGGGTAATATGGGTGTTCTGGCGGGCCAAGCATCG

 381  Q  L  N  A  V  V  D  L  Q  D  R  N  T  E  L  S  Y  Q  L  L
1141  CAGTTGAATGCTGTTGTAGATTTGCAAGACAGAAACACAGAGCTTTCATACCAGCTTTTG
```

Fig. 17A

```
 401 L D S I G D R T R Y F S M W N Q L P N Y
1201 CTTGATTCCATTGGTGATAGAACCAGGTACTTTTCTATGTGGAATCAGCTTCCAAATTAC

 421 C F P L G G V I N T E T L T K V K P K T
1261 TGCTTTCCACTGGGAGGTGTGATTAATACAGAGACTCTTACCAAGGTAAAACCTAAAACA

 441 G Q E N G W E K D A T E F S D K N E I R
1321 GGTCAGGAAAATGGATGGGAAAAAGATGCTACAGAATTTTCAGATAAAAATGAAATAAGA

 461 V G N N F A M E I N L N A N L W R N F L
1381 GTTGGAAATAATTTTGCCATGGAAATCAATCTAAATGCCAACCTGTGGAGAAATTTCCTG

 481 Y S N I A L Y L P D K L K Y S P S N V K
1441 TACTCCAACATAGCGCTGTATTTGCCCGACAAGCTAAAGTACAGTCCTTCCAACGTAAAA

 501 I S D N P N T Y D Y M N K R V V A P G L
1501 ATTTCTGATAACCCAAACACCTACGACTACATGAACAAGCGAGTGGTGGCTCCCGGGCTA

 521 V D C Y I N L G A R W S L D Y M D N V N
1561 GTGGACTGCTACATTAACCTTGGAGCACGCTGGTCCCTTGACTATATGGACAACGTCAAC

 541 P F N H H R N A G L R Y R S M L L G N G
1621 CCATTTAACCACCACCGCAATGCTGGCCTGCGCTACCGCTCAATGTTGCTGGGCAATGGT

 561 R Y V P F H I Q V P Q K F F A I K N L L
1681 CGCTATGTGCCCTTCCACATCCAGGTGCCTCAGAAGTTCTTTGCCATTAAAAACCTCCTT

 581 L L P G S Y T Y E W N F R K D V N M V L
1741 CTCCTGCCGGGCTCATACACCTACGAGTGGAACTTCAGGAAGGATGTTAACATGGTTCTG

 601 Q S S L G N D L R V D G A S I K F D S I
1801 CAGAGCTCCCTAGGAAATGACCTAAGGGTTGACGGAGCCAGCATTAAGTTTGATAGCATT

 621 C L Y A T F F P M A H N T A S T L E A M
1861 TGCCTTTACGCCACCTTCTTCCCCATGGCCCACAACACCGCCTCCACGCTTGAGGCCATG

 641 L R N D T N D Q S F N D Y L S A A N M L
1921 CTTAGAAACGACACCAACGACCAGTCCTTTAACGACTATCTCTCCGCCGCCAACATGCTC

 661 Y P I P A N A T N V P I S I P S R N W A
1981 TACCCTATACCCGCCAACGCTACCAACGTGCCCATATCCATCCCCTCCCGCAACTGGGCG

 681 A F R G W A F T R L K T K E T P S L G S
2041 GCTTTCCGCGGCTGGGCCTTCACGCGCCTTAAGACTAAGGAAACCCCATCACTGGGCTCG

 701 G Y D P Y Y T Y S G S I P Y L D G T F Y
2101 GGCTACGACCCTTATTACACCTACTCTGGCTCTATACCCTACCTAGATGGAACCTTTTAC

 721 L N H T F K K V A I T F D S S V S W P G
2161 CTCAACCACACCTTTAAGAAGGTGGCCATTACCTTTGACTCTTCTGTCAGCTGGCCTGGC

 741 N D R L L T P N E F E I K R S V D G E G
2221 AATGACCGCCTGCTTACCCCCAACGAGTTTGAAATTAAGCGCTCAGTTGACGGGGAGGGT

 761 Y N V A Q C N M T K D W F L V Q M L A N
2281 TACAACGTTGCCCAGTGTAACATGACCAAAGACTGGTTCCTGGTACAAATGCTAGCTAAC

 781 Y N I G Y Q G F Y I P E S Y K D R M Y S
2341 TATAACATTGGCTACCAGGGCTTCTATATCCCAGAGAGCTACAAGGACCGCATGTACTCC

 801 F F R N F Q P M S R Q V V D D T K Y K D
2401 TTCTTTAGAAACTTCCAGCCCATGAGCCGTCAGGTGGTGGATGATACTAAATACAAGGAC
```

Fig. 17B

```
 821  Y  Q  Q  V  G  I  L  H  Q  H  N  N  S  G  F  V  G  Y  L  A
2461  TACCAACAGGTGGGCATCCTACACCAACACAACAACTCTGGATTTGTTGGCTACCTTGCC

 841  P  T  M  R  E  G  Q  A  Y  P  A  N  F  P  Y  P  L  I  G  K
2521  CCCACCATGCGCGAAGGACAGGCCTACCCTGCTAACTTCCCCTATCCGCTTATAGGCAAG

 861  T  A  V  D  S  I  T  Q  K  K  F  L  C  D  R  T  L  W  R  I
2581  ACCGCAGTTGACAGCATTACCCAGAAAAAGTTTCTTTGCGATCGCACCCTTTGGCGCATC

 881  P  F  S  S  N  F  M  S  M  G  A  L  T  D  L  G  Q  N  L  L
2641  CCATTCTCCAGTAACTTTATGTCCATGGGCGCACTCACAGACCTGGGCCAAAACCTTCTC

 901  Y  A  N  S  A  H  A  L  D  M  T  F  E  V  D  P  M  D  E  P
2701  TACGCCAACTCCGCCCACGCGCTAGACATGACTTTTGAGGTGGATCCCATGGACGAGCCC

 921  T  L  L  Y  V  L  F  E  V  F  D  V  V  R  V  H  Q  P  H  R
2761  ACCCTTCTTTATGTTTTGTTTGAAGTCTTTGACGTGGTCCGTGTGCACCAGCCGCACCGC

 941  G  V  I  E  T  V  Y  L  R  T  P  F  S  A  G  N  A  T  T  -
2821  GGCGTCATCGAAACCGTGTACCTGCGCACGCCCTTCTCGGCCGGCAACGCCACAACATAA
```

Fig. 17C

Hexon sequence of $(QGPGAP)_{11}$-HVR1 adenovirus SEQ IDNOS : 10 and 38

```
   1  M  A  T  P  S  M  M  P  Q  W  S  Y  M  H  I  S  G  Q  D  A
   1  ATGGCTACCCCTTCGATGATGCCGCAGTGGTCTTACATGCACATCTCGGGCCAGGACGCC

  21  S  E  Y  L  S  P  G  L  V  Q  F  A  R  A  T  E  T  Y  F  S
  61  TCGGAGTACCTGAGCCCCGGGCTGGTGCAGTTTGCCCGCGCCACCGAGACGTACTTCAGC

  41  L  N  N  K  F  R  N  P  T  V  A  P  T  H  D  V  T  T  D  R
 121  CTGAATAACAAGTTTAGAAACCCCACGGTGGCGCCTACGCACGACGTGACCACAGACCGG

  61  S  Q  R  L  T  L  R  F  I  P  V  D  R  E  D  T  A  Y  S  Y
 181  TCCCAGCGTTTGACGCTGCGGTTCATCCCTGTGGACCGTGAGGATACTGCGTACTCGTAC

  81  K  A  R  F  T  L  A  V  G  D  N  R  V  L  D  M  A  S  T  Y
 241  AAGGCGCGGTTCACCCTAGCTGTGGGTGATAACCGTGTGCTGGACATGGCTTCCACGTAC

 101  F  D  I  R  G  V  L  D  R  G  P  T  F  K  P  Y  S  G  T  A
 301  TTTGACATCCGCGGCGTGCTGGACAGGGGCCCTACTTTTAAGCCCTACTCTGGCACTGCC

 121  Y  N  A  L  A  P  K  G  A  P  N  P  C  E  W  D  E  Q  G  P
 361  TACAACGCCCTGGCTCCCAAGGGTGCCCCAAATCCTTGCGAATGGGATGAACAGGGACCA

 141  G  A  P  Q  G  P  G  A  P  Q  G  P  G  A  P  Q  G  P  G  A
 421  GGAGCACCACAGGGACCAGGAGCACCACAGGGACCAGGAGCACCACAGGGACCAGGAGCA

 161  P  Q  G  P  G  A  P  Q  G  P  G  A  P  Q  G  P  G  A  P  Q
 481  CCACAGGGACCAGGAGCACCACAGGGACCAGGAGCACCACAGGGACCAGGAGCACCACAG

 181  G  P  G  A  P  Q  G  P  G  A  P  Q  G  P  G  A  P  Q  G  P
 541  GGACCAGGAGCACCGCAAGGTCCTGGTGCTCCTCAGGGACCAGGAGCACCACAGGGACCA

 201  G  A  P  K  T  H  V  F  G  Q  A  P  Y  S  G  I  N  I  T  K
 601  GGAGCACCAAAAACTCACGTATTTGGGCAGGCGCCTTATTCTGGTATAAATATTACAAAG

 221  E  G  I  Q  I  G  V  E  G  Q  T  P  K  Y  A  D  K  T  F  Q
 661  GAGGGTATTCAAATAGGTGTCGAAGGTCAAACACCTAAATATGCCGATAAAACATTTCAA

 241  P  E  P  Q  I  G  E  S  Q  W  Y  E  T  E  I  N  H  A  A  G
 721  CCTGAACCTCAAATAGGAGAATCTCAGTGGTACGAAACAGAAATTAATCATGCAGCTGGG

 261  R  V  L  K  K  T  T  P  M  K  P  C  Y  G  S  Y  A  K  P  T
 781  AGAGTCCTAAAAAAGACTACCCCAATGAAACCATGTTACGGTTCATATGCAAAACCCACA

 281  N  E  N  G  G  Q  G  I  L  V  K  Q  Q  N  G  K  L  E  S  Q
 841  AATGAAAATGGAGGGCAAGGCATTCTTGTAAAGCAACAAAATGGAAAGCTAGAAAGTCAA

 301  V  E  M  Q  F  F  S  T  T  E  A  A  A  G  N  G  D  N  L  T
 901  GTGGAAATGCAATTTTTCTCAACTACTGAGGCAGCCGCAGGCAATGGTGATAACTTGACT

 321  P  K  V  V  L  Y  S  E  D  V  D  I  E  T  P  D  T  H  I  S
 961  CCTAAAGTGGTATTGTACAGTGAAGATGTAGATATAGAAACCCCAGACACTCATATTTCT

 341  Y  M  P  T  I  K  E  G  N  S  R  E  L  M  G  Q  Q  S  M  P
1021  TACATGCCCACTATTAAGGAAGGTAACTCACGAGAACTAATGGGCCAACAATCTATGCCC

 361  N  R  P  N  Y  I  A  F  R  D  N  F  I  G  L  M  Y  Y  N  S
1081  AACAGGCCTAATTACATTGCTTTTAGGGACAATTTTATTGGTCTAATGTATTACAACAGC

 381  T  G  N  M  G  V  L  A  G  Q  A  S  Q  L  N  A  V  V  D  L
1141  ACGGGTAATATGGGTGTTCTGGCGGGCCAAGCATCGCAGTTGAATGCTGTTGTAGATTTG
```

Fig. 18A

```
 401  Q  D  R  N  T  E  L  S  Y  Q  L  L  L  D  S  I  G  D  R  T
1201  CAAGACAGAAACACAGAGCTTTCATACCAGCTTTTGCTTGATTCCATTGGTGATAGAACC

 421  R  Y  F  S  M  W  N  Q  L  P  N  Y  C  F  P  L  G  G  V  I
1261  AGGTACTTTTCTATGTGGAATCAGCTTCCAAATTACTGCTTTCCACTGGGAGGTGTGATT

 441  N  T  E  T  L  T  K  V  K  P  K  T  G  Q  E  N  G  W  E  K
1321  AATACAGAGACTCTTACCAAGGTAAAACCTAAAACAGGTCAGGAAAATGGATGGGAAAAA

 461  D  A  T  E  F  S  D  K  N  E  I  R  V  G  N  N  F  A  M  E
1381  GATGCTACAGAATTTTCAGATAAAAATGAAATAAGAGTTGGAAATAATTTTGCCATGGAA

 481  I  N  L  N  A  N  L  W  R  N  F  L  Y  S  N  I  A  L  Y  L
1441  ATCAATCTAAATGCCAACCTGTGGAGAAATTTCCTGTACTCCAACATAGCGCTGTATTTG

 501  P  D  K  L  K  Y  S  P  S  N  V  K  I  S  D  N  P  N  T  Y
1501  CCCGACAAGCTAAAGTACAGTCCTTCCAACGTAAAAATTTCTGATAACCCAAACACCTAC

 521  D  Y  M  N  K  R  V  V  A  P  G  L  V  D  C  Y  I  N  L  G
1561  GACTACATGAACAAGCGAGTGGTGGCTCCCGGGCTAGTGGACTGCTACATTAACCTTGGA

 541  A  R  W  S  L  D  Y  M  D  N  V  N  P  F  N  H  H  R  N  A
1621  GCACGCTGGTCCCTTGACTATATGGACAACGTCAACCCATTTAACCACCACCGCAATGCT

 561  G  L  R  Y  R  S  M  L  L  G  N  G  R  Y  V  P  F  H  I  Q
1681  GGCCTGCGCTACCGCTCAATGTTGCTGGGCAATGGTCGCTATGTGCCCTTCCACATCCAG

 581  V  P  Q  K  F  F  A  I  K  N  L  L  L  L  P  G  S  Y  T  Y
1741  GTGCCTCAGAAGTTCTTTGCCATTAAAAACCTCCTTCTCCTGCCGGGCTCATACACCTAC

 601  E  W  N  F  R  K  D  V  N  M  V  L  Q  S  S  L  G  N  D  L
1801  GAGTGGAACTTCAGGAAGGATGTTAACATGGTTCTGCAGAGCTCCCTAGGAAATGACCTA

 621  R  V  D  G  A  S  I  K  F  D  S  I  C  L  Y  A  T  F  F  P
1861  AGGGTTGACGGAGCCAGCATTAAGTTTGATAGCATTTGCCTTTACGCCACCTTCTTCCCC

 641  M  A  H  N  T  A  S  T  L  E  A  M  L  R  N  D  T  N  D  Q
1921  ATGGCCCACAACACCGCCTCCACGCTTGAGGCCATGCTTAGAAACGACACCAACGACCAG

 661  S  F  N  D  Y  L  S  A  A  N  M  L  Y  P  I  P  A  N  A  T
1981  TCCTTTAACGACTATCTCTCCGCCGCCAACATGCTCTACCCTATACCCGCCAACGCTACC

 681  N  V  P  I  S  I  P  S  R  N  W  A  A  F  R  G  W  A  F  T
2041  AACGTGCCCATATCCATCCCCTCCCGCAACTGGGCGGCTTTCCGCGGCTGGGCCTTCACG

 701  R  L  K  T  K  E  T  P  S  L  G  S  G  Y  D  P  Y  Y  T  Y
2101  CGCCTTAAGACTAAGGAAACCCCATCACTGGGCTCGGGCTACGACCCTTATTACACCTAC

 721  S  G  S  I  P  Y  L  D  G  T  F  Y  L  N  H  T  F  K  K  V
2161  TCTGGCTCTATACCCTACCTAGATGGAACCTTTTACCTCAACCACACCTTTAAGAAGGTG

 741  A  I  T  F  D  S  S  V  S  W  P  G  N  D  R  L  L  T  P  N
2221  GCCATTACCTTTGACTCTTCTGTCAGCTGGCCTGGCAATGACCGCCTGCTTACCCCCAAC

 761  E  F  E  I  K  R  S  V  D  G  E  G  Y  N  V  A  Q  C  N  M
2281  GAGTTTGAAATTAAGCGCTCAGTTGACGGGGAGGGTTACAACGTTGCCCAGTGTAACATG

 781  T  K  D  W  F  L  V  Q  M  L  A  N  Y  N  I  G  Y  Q  G  F
2341  ACCAAAGACTGGTTCCTGGTACAAATGCTAGCTAACTATAACATTGGCTACCAGGGCTTC

 801  Y  I  P  E  S  Y  K  D  R  M  Y  S  F  F  R  N  F  Q  P  M
2401  TATATCCCAGAGAGCTACAAGGACCGCATGTACTCCTTCTTTAGAAACTTCCAGCCCATG
```

Fig. 18B

```
821   S  R  Q  V  V  D  D  T  K  Y  K  D  Y  Q  Q  V  G  I  L  H
2461  AGCCGTCAGGTGGTGGATGATACTAAATACAAGGACTACCAACAGGTGGGCATCCTACAC

841   Q  H  N  N  S  G  F  V  G  Y  L  A  P  T  M  R  E  G  Q  A
2521  CAACACAACAACTCTGGATTTGTTGGCTACCTTGCCCCCACCATGCGCGAAGGACAGGCC

861   Y  P  A  N  F  P  Y  P  L  I  G  K  T  A  V  D  S  I  T  Q
2581  TACCCTGCTAACTTCCCCTATCCGCTTATAGGCAAGACCGCAGTTGACAGCATTACCCAG

881   K  K  F  L  C  D  R  T  L  W  R  I  P  F  S  S  N  F  M  S
2641  AAAAAGTTTCTTTGCGATCGCACCCTTTGGCGCATCCCATTCTCCAGTAACTTTATGTCC

901   M  G  A  L  T  D  L  G  Q  N  L  L  Y  A  N  S  A  H  A  L
2701  ATGGGCGCACTCACAGACCTGGGCCAAAACCTTCTCTACGCCAACTCCGCCCACGCGCTA

921   D  M  T  F  E  V  D  P  M  D  E  P  T  L  L  Y  V  L  F  E
2761  GACATGACTTTTGAGGTGGATCCCATGGACGAGCCCACCCTTCTTTATGTTTTGTTTGAA

941   V  F  D  V  V  R  V  H  Q  P  H  R  G  V  I  E  T  V  Y  L
2821  GTCTTTGACGTGGTCCGTGTGCACCAGCCGCACCGCGGCGTCATCGAAACCGTGTACCTG

961   R  T  P  F  S  A  G  N  A  T  T  -
2881  CGCACGCCCTTCTCGGCCGGCAACGCCACAACATAA
```

Fig. 18C

Hexon sequence of $(QGPGAP)_{12}$-HVR1 adenovirus SEQ IDNOS : 11 and 39

```
   1  M  A  T  P  S  M  M  P  Q  W  S  Y  M  H  I  S  G  Q  D  A
   1  ATGGCTACCCCTTCGATGATGCCGCAGTGGTCTTACATGCACATCTCGGGCCAGGACGCC

  21  S  E  Y  L  S  P  G  L  V  Q  F  A  R  A  T  E  T  Y  F  S
  61  TCGGAGTACCTGAGCCCCGGGCTGGTGCAGTTTGCCCGCGCCACCGAGACGTACTTCAGC

  41  L  N  N  K  F  R  N  P  T  V  A  P  T  H  D  V  T  T  D  R
 121  CTGAATAACAAGTTTAGAAACCCCACGGTGGCGCCTACGCACGACGTGACCACAGACCGG

  61  S  Q  R  L  T  L  R  F  I  P  V  D  R  E  D  T  A  Y  S  Y
 181  TCCCAGCGTTTGACGCTGCGGTTCATCCCTGTGGACCGTGAGGATACTGCGTACTCGTAC

  81  K  A  R  F  T  L  A  V  G  D  N  R  V  L  D  M  A  S  T  Y
 241  AAGGCGCGGTTCACCCTAGCTGTGGGTGATAACCGTGTGCTGGACATGGCTTCCACGTAC

 101  F  D  I  R  G  V  L  D  R  G  P  T  F  K  P  Y  S  G  T  A
 301  TTTGACATCCGCGGCGTGCTGGACAGGGGCCCTACTTTTAAGCCCTACTCTGGCACTGCC

 121  Y  N  A  L  A  P  K  G  A  P  N  P  C  E  W  D  E  Q  G  P
 361  TACAACGCCCTGGCTCCCAAGGGTGCCCCAAATCCTTGCGAATGGGATGAACAGGGACCA

 141  G  A  P  Q  G  P  G  A  P  Q  G  P  G  A  P  Q  G  P  G  A
 421  GGAGCACCACAGGGACCAGGAGCACCACAGGGACCAGGAGCACCACAGGGACCAGGAGCA

 161  P  Q  G  P  G  A  P  Q  G  P  G  A  P  Q  G  P  G  A  P  Q
 481  CCACAGGGACCAGGAGCACCACAGGGACCAGGAGCACCACAGGGACCAGGAGCACCACAG

 181  G  P  G  A  P  Q  G  P  G  A  P  Q  G  P  G  A  P  Q  G  P
 541  GGACCAGGAGCACCGCAAGGTCCTGGTGCTCCTCAGGGACCAGGAGCACCACAGGGACCA

 201  G  A  P  Q  G  P  G  A  P  K  T  H  V  F  G  Q  A  P  Y  S
 601  GGAGCACCACAGGGACCAGGAGCACCAAAAACTCACGTATTTGGGCAGGCGCCTTATTCT

 221  G  I  N  I  T  K  E  G  I  Q  I  G  V  E  G  Q  T  P  K  Y
 661  GGTATAAATATTACAAAGGAGGGTATTCAAATAGGTGTCGAAGGTCAAACACCTAAATAT

 241  A  D  K  T  F  Q  P  E  P  Q  I  G  E  S  Q  W  Y  E  T  E
 721  GCCGATAAAACATTTCAACCTGAACCTCAAATAGGAGAATCTCAGTGGTACGAAACAGAA

 261  I  N  H  A  A  G  R  V  L  K  K  T  T  P  M  K  P  C  Y  G
 781  ATTAATCATGCAGCTGGGAGAGTCCTAAAAAAGACTACCCCAATGAAACCATGTTACGGT

 281  S  Y  A  K  P  T  N  E  N  G  G  Q  G  I  L  V  K  Q  Q  N
 841  TCATATGCAAAACCCACAAATGAAAATGGAGGGCAAGGCATTCTTGTAAAGCAACAAAAT

 301  G  K  L  E  S  Q  V  E  M  Q  F  F  S  T  T  E  A  A  A  G
 901  GGAAAGCTAGAAAGTCAAGTGGAAATGCAATTTTTCTCAACTACTGAGGCAGCCGCAGGC

 321  N  G  D  N  L  T  P  K  V  V  L  Y  S  E  D  V  D  I  E  T
 961  AATGGTGATAACTTGACTCCTAAAGTGGTATTGTACAGTGAAGATGTAGATATAGAAACC

 341  P  D  T  H  I  S  Y  M  P  T  I  K  E  G  N  S  R  E  L  M
1021  CCAGACACTCATATTTCTTACATGCCCACTATTAAGGAAGGTAACTCACGAGAACTAATG

 361  G  Q  Q  S  M  P  N  R  P  N  Y  I  A  F  R  D  N  F  I  G
1081  GGCCAACAATCTATGCCCAACAGGCCTAATTACATTGCTTTTAGGGACAATTTTATTGGT

 381  L  M  Y  Y  N  S  T  G  N  M  G  V  L  A  G  Q  A  S  Q  L
1141  CTAATGTATTACAACAGCACGGGTAATATGGGTGTTCTGGCGGGCCAAGCATCGCAGTTG
```

Fig. 19A

401 N A V V D L Q D R N T E L S Y Q L L L D
1201 AATGCTGTTGTAGATTTGCAAGACAGAAACACAGAGCTTTCATACCAGCTTTTGCTTGAT

421 S I G D R T R Y F S M W N Q L P N Y C F
1261 TCCATTGGTGATAGAACCAGGTACTTTTCTATGTGGAATCAGCTTCCAAATTACTGCTTT

441 P L G G V I N T E T L T K V K P K T G Q
1321 CCACTGGGAGGTGTGATTAATACAGAGACTCTTACCAAGGTAAAACCTAAAACAGGTCAG

461 E N G W E K D A T E F S D K N E I R V G
1381 GAAAATGGATGGGAAAAAGATGCTACAGAATTTTCAGATAAAAATGAAATAAGAGTTGGA

481 N N F A M E I N L N A N L W R N F L Y S
1441 AATAATTTTGCCATGGAAATCAATCTAAATGCCAACCTGTGGAGAAATTTCCTGTACTCC

501 N I A L Y L P D K L K Y S P S N V K I S
1501 AACATAGCGCTGTATTTGCCCGACAAGCTAAAGTACAGTCCTTCCAACGTAAAAATTTCT

521 D N P N T Y D Y M N K R V V A P G L V D
1561 GATAACCCAAACACCTACGACTACATGAACAAGCGAGTGGTGGCTCCCGGGCTAGTGGAC

541 C Y I N L G A R W S L D Y M D N V N P F
1621 TGCTACATTAACCTTGGAGCACGCTGGTCCCTTGACTATATGGACAACGTCAACCCATTT

561 N H H R N A G L R Y R S M L L G N G R Y
1681 AACCACCACCGCAATGCTGGCCTGCGCTACCGCTCAATGTTGCTGGGCAATGGTCGCTAT

581 V P F H I Q V P Q K F F A I K N L L L L
1741 GTGCCCTTCCACATCCAGGTGCCTCAGAAGTTCTTTGCCATTAAAAACCTCCTTCTCCTG

601 P G S Y T Y E W N F R K D V N M V L Q S
1801 CCGGGCTCATACACCTACGAGTGGAACTTCAGGAAGGATGTTAACATGGTTCTGCAGAGC

621 S L G N D L R V D G A S I K F D S I C L
1861 TCCCTAGGAAATGACCTAAGGGTTGACGGAGCCAGCATTAAGTTTGATAGCATTTGCCTT

641 Y A T F F P M A H N T A S T L E A M L R
1921 TACGCCACCTTCTTCCCCATGGCCCACAACACCGCCTCCACGCTTGAGGCCATGCTTAGA

661 N D T N D Q S F N D Y L S A A N M L Y P
1981 AACGACACCAACGACCAGTCCTTTAACGACTATCTCTCCGCCGCCAACATGCTCTACCCT

681 I P A N A T N V P I S I P S R N W A A F
2041 ATACCCGCCAACGCTACCAACGTGCCCATATCCATCCCCTCCCGCAACTGGGCGGCTTTC

701 R G W A F T R L K T K E T P S L G S G Y
2101 CGCGGCTGGGCCTTCACGCGCCTTAAGACTAAGGAAACCCCATCACTGGGCTCGGGCTAC

721 D P Y Y T Y S G S I P Y L D G T F Y L N
2161 GACCCTTATTACACCTACTCTGGCTCTATACCCTACCTAGATGGAACCTTTTACCTCAAC

741 H T F K K V A I T F D S S V S W P G N D
2221 CACACCTTTAAGAAGGTGGCCATTACCTTTGACTCTTCTGTCAGCTGGCCTGGCAATGAC

761 R L L T P N E F E I K R S V D G E G Y N
2281 CGCCTGCTTACCCCCAACGAGTTTGAAATTAAGCGCTCAGTTGACGGGGAGGGTTACAAC

781 V A Q C N M T K D W F L V Q M L A N Y N
2341 GTTGCCCAGTGTAACATGACCAAAGACTGGTTCCTGGTACAAATGCTAGCTAACTATAAC

Fig. 19B

801 I G Y Q G F Y I P E S Y K D R M Y S F F
2401 ATTGGCTACCAGGGCTTCTATATCCCAGAGAGCTACAAGGACCGCATGTACTCCTTCTTT

```
 821  R  N  F  Q  P  M  S  R  Q  V  V  D  D  T  K  Y  K  D  Y  Q
2461  AGAAACTTCCAGCCCATGAGCCGTCAGGTGGTGGATGATACTAAATACAAGGACTACCAA

 841  Q  V  G  I  L  H  Q  H  N  N  S  G  F  V  G  Y  L  A  P  T
2521  CAGGTGGGCATCCTACACCAACACAACAACTCTGGATTTGTTGGCTACCTTGCCCCCACC

 861  M  R  E  G  Q  A  Y  P  A  N  F  P  Y  P  L  I  G  K  T  A
2581  ATGCGCGAAGGACAGGCCTACCCTGCTAACTTCCCCTATCCGCTTATAGGCAAGACCGCA

 881  V  D  S  I  T  Q  K  K  F  L  C  D  R  T  L  W  R  I  P  F
2641  GTTGACAGCATTACCCAGAAAAAGTTTCTTTGCGATCGCACCCTTTGGCGCATCCCATTC

 901  S  S  N  F  M  S  M  G  A  L  T  D  L  G  Q  N  L  L  Y  A
2701  TCCAGTAACTTTATGTCCATGGGCGCACTCACAGACCTGGGCCAAAACCTTCTCTACGCC

 921  N  S  A  H  A  L  D  M  T  F  E  V  D  P  M  D  E  P  T  L
2761  AACTCCGCCCACGCGCTAGACATGACTTTTGAGGTGGATCCCATGGACGAGCCCACCCTT

 941  L  Y  V  L  F  E  V  F  D  V  V  R  V  H  Q  P  H  R  G  V
2821  CTTTATGTTTTGTTTGAAGTCTTTGACGTGGTCCGTGTGCACCAGCCGCACCGCGGCGTC

 961  I  E  T  V  Y  L  R  T  P  F  S  A  G  N  A  T  T  -
2881  ATCGAAACCGTGTACCTGCGCACGCCCTTCTCGGCCGGCAACGCCACAACATAA
```

Fig. 19C

Hexon sequence of $(NANP)_4$-HVR1 adenovirus SEQ IDNOS : 12 and 44

```
   1  M  A  T  P  S  M  M  P  Q  W  S  Y  M  H  I  S  G  Q  D  A
   1  ATGGCTACCCCTTCGATGATGCCGCAGTGGTCTTACATGCACATCTCGGGCCAGGACGCC

  21  S  E  Y  L  S  P  G  L  V  Q  F  A  R  A  T  E  T  Y  F  S
  61  TCGGAGTACCTGAGCCCCGGGCTGGTGCAGTTTGCCCGCGCCACCGAGACGTACTTCAGC

  41  L  N  N  K  F  R  N  P  T  V  A  P  T  H  D  V  T  T  D  R
 121  CTGAATAACAAGTTTAGAAACCCCACGGTGGCGCCTACGCACGACGTGACCACAGACCGG

  61  S  Q  R  L  T  L  R  F  I  P  V  D  R  E  D  T  A  Y  S  Y
 181  TCCCAGCGTTTGACGCTGCGGTTCATCCCTGTGGACCGTGAGGATACTGCGTACTCGTAC

  81  K  A  R  F  T  L  A  V  G  D  N  R  V  L  D  M  A  S  T  Y
 241  AAGGCGCGGTTCACCCTAGCTGTGGGTGATAACCGTGTGCTGGACATGGCTTCCACGTAC

 101  F  D  I  R  G  V  L  D  R  G  P  T  F  K  P  Y  S  G  T  A
 301  TTTGACATCCGCGGCGTGCTGGACAGGGGCCCTACTTTTAAGCCCTACTCTGGCACTGCC

 121  Y  N  A  L  A  P  K  G  A  P  N  P  C  E  W  D  E  N  A  N
 361  TACAACGCCCTGGCTCCCAAGGGTGCCCCAAATCCTTGCGAATGGGATGAAAACGCTAAT

 141  P  N  A  N  P  N  A  N  P  N  A  N  P  K  T  H  V  F  G  Q
 421  CCCAACGCTAACCCAAATGCAAATCCTAATGCCAACCCCAAAACTCACGTATTTGGGCAG

 161  A  P  Y  S  G  I  N  I  T  K  E  G  I  Q  I  G  V  E  G  Q
 481  GCGCCTTATTCTGGTATAAATATTACAAAGGAGGGTATTCAAATAGGTGTCGAAGGTCAA

 181  T  P  K  Y  A  D  K  T  F  Q  P  E  P  Q  I  G  E  S  Q  W
 541  ACACCTAAATATGCCGATAAAACATTTCAACCTGAACCTCAAATAGGAGAATCTCAGTGG

 201  Y  E  T  E  I  N  H  A  A  G  R  V  L  K  K  T  T  P  M  K
 601  TACGAAACAGAAATTAATCATGCAGCTGGGAGAGTCCTAAAAAAGACTACCCCAATGAAA

 221  P  C  Y  G  S  Y  A  K  P  T  N  E  N  G  G  Q  G  I  L  V
 661  CCATGTTACGGTTCATATGCAAAACCCACAAATGAAAATGGAGGGCAAGGCATTCTTGTA

 241  K  Q  Q  N  G  K  L  E  S  Q  V  E  M  Q  F  F  S  T  T  E
 721  AAGCAACAAAATGGAAAGCTAGAAAGTCAAGTGGAAATGCAATTTTTCTCAACTACTGAG

 261  A  A  A  G  N  G  D  N  L  T  P  K  V  V  L  Y  S  E  D  V
 781  GCAGCCGCAGGCAATGGTGATAACTTGACTCCTAAAGTGGTATTGTACAGTGAAGATGTA

 281  D  I  E  T  P  D  T  H  I  S  Y  M  P  T  I  K  E  G  N  S
 841  GATATAGAAACCCCAGACACTCATATTTCTTACATGCCCACTATTAAGGAAGGTAACTCA

 301  R  E  L  M  G  Q  Q  S  M  P  N  R  P  N  Y  I  A  F  R  D
 901  CGAGAACTAATGGGCCAACAATCTATGCCCAACAGGCCTAATTACATTGCTTTTAGGGAC

 321  N  F  I  G  L  M  Y  Y  N  S  T  G  N  M  G  V  L  A  G  Q
 961  AATTTTATTGGTCTAATGTATTACAACAGCACGGGTAATATGGGTGTTCTGGCGGGCCAA

 341  A  S  Q  L  N  A  V  V  D  L  Q  D  R  N  T  E  L  S  Y  Q
1021  GCATCGCAGTTGAATGCTGTTGTAGATTTGCAAGACAGAAACACAGAGCTTTCATACCAG

 361  L  L  L  D  S  I  G  D  R  T  R  Y  F  S  M  W  N  Q  A  V
1081  CTTTTGCTTGATTCCATTGGTGATAGAACCAGGTACTTTTCTATGTGGAATCAGGCTGTT

 381  D  S  Y  D  P  D  V  R  I  I  E  N  H  G  T  E  D  E  L  P
1141  GACAGCTATGATCCAGATGTTAGAATTATTGAAAATCATGGAACTGAAGATGAACTTCCA
```

Fig. 20A

401 N Y C F P L G G V I N T E T L T K V K P
1201 AATTACTGCTTTCCACTGGGAGGTGTGATTAATACAGAGACTCTTACCAAGGTAAAACCT

421 K T G Q E N G W E K D A T E F S D K N E
1261 AAAACAGGTCAGGAAAATGGATGGGAAAAAGATGCTACAGAATTTTCAGATAAAAATGAA

441 I R V G N N F A M E I N L N A N L W R N
1321 ATAAGAGTTGGAAATAATTTTGCCATGGAAATCAATCTAAATGCCAACCTGTGGAGAAAT

461 F L Y S N I A L Y L P D K L K Y S P S N
1381 TTCCTGTACTCCAACATAGCGCTGTATTTGCCCGACAAGCTAAAGTACAGTCCTTCCAAC

481 V K I S D N P N T Y D Y M N K R V V A P
1441 GTAAAAATTTCTGATAACCCAAACACCTACGACTACATGAACAAGCGAGTGGTGGCTCCC

501 G L V D C Y I N L G A R W S L D Y M D N
1501 GGGCTAGTGGACTGCTACATTAACCTTGGAGCACGCTGGTCCCTTGACTATATGGACAAC

521 V N P F N H H R N A G L R Y R S M L L G
1561 GTCAACCCATTTAACCACCACCGCAATGCTGGCCTGCGCTACCGCTCAATGTTGCTGGGC

541 N G R Y V P F H I Q V P Q K F F A I K N
1621 AATGGTCGCTATGTGCCCTTCCACATCCAGGTGCCTCAGAAGTTCTTTGCCATTAAAAAC

561 L L L L P G S Y T Y E W N F R K D V N M
1681 CTCCTTCTCCTGCCGGGCTCATACACCTACGAGTGGAACTTCAGGAAGGATGTTAACATG

581 V L Q S S L G N D L R V D G A S I K F D
1741 GTTCTGCAGAGCTCCCTAGGAAATGACCTAAGGGTTGACGGAGCCAGCATTAAGTTTGAT

601 S I C L Y A T F F P M A H N T A S T L E
1801 AGCATTTGCCTTTACGCCACCTTCTTCCCCATGGCCCACAACACCGCCTCCACGCTTGAG

621 A M L R N D T N D Q S F N D Y L S A A N
1861 GCCATGCTTAGAAACGACACCAACGACCAGTCCTTTAACGACTATCTCTCCGCCGCCAAC

641 M L Y P I P A N A T N V P I S I P S R N
1921 ATGCTCTACCCTATACCGGCCAACGCTACCAACGTGCCCATATCCATCCCCTCCCGCAAC

661 W A A F R G W A F T R L K T K E T P S L
1981 TGGGCGGCTTTCCGCGGCTGGGCCTTCACGCGCCTTAAGACTAAGGAAACCCCATCACTG
681 G S G Y D P Y Y T Y S G S I P Y L D G T
2041 GGCTCGGGCTACGACCCTTATTACACCTACTCTGGCTCTATACCCTACCTAGATGGAACC

701 F Y L N H T F K K V A I T F D S S V S W
2101 TTTTACCTCAACCACACCTTTAAGAAGGTGGCCATTACCTTTGACTCTTCTGTCAGCTGG

721 P G N D R L L T P N E F E I K R S V D G
2161 CCTGGCAATGACCGCCTGCTTACCCCCAACGAGTTTGAAATTAAGCGCTCAGTTGACGGG

741 E G Y N V A Q C N M T K D W F L V Q M L
2221 GAGGGTTACAACGTTGCCCAGTGTAACATGACCAAAGACTGGTTCCTGGTACAAATGCTA

761 A N Y N I G Y Q G F Y I P E S Y K D R M
2281 GCTAACTATAACATTGGCTACCAGGGCTTCTATATCCCAGAGAGCTACAAGGACCGCATG

781 Y S F F R N F Q P M S R Q V V D D T K Y
2341 TACTCCTTCTTTAGAAACTTCCAGCCCATGAGCCGTCAGGTGGTGGATGATACTAAATAC

801 K D Y Q Q V G I L H Q H N N S G F V G Y
2401 AAGGACTACCAACAGGTGGGCATCCTACACCAACACAACAACTCTGGATTTGTTGGCTAC

Fig. 20B

```
 821  L  A  P  T  M  R  E  G  Q  A  Y  P  A  N  F  P  Y  P  L  I
2461  CTTGCCCCCACCATGCGCGAAGGACAGGCCTACCCTGCTAACTTCCCCTATCCGCTTATA

 841  G  K  T  A  V  D  S  I  T  Q  K  K  F  L  C  D  R  T  L  W
2521  GGCAAGACCGCAGTTGACAGCATTACCCAGAAAAAGTTTCTTTGCGATCGCACCCTTTGG

 861  R  I  P  F  S  S  N  F  M  S  M  G  A  L  T  D  L  G  Q  N
2581  CGCATCCCATTCTCCAGTAACTTTATGTCCATGGGCGCACTCACAGACCTGGGCCAAAAC

 881  L  L  Y  A  N  S  A  H  A  L  D  M  T  F  E  V  D  P  M  D
2641  CTTCTCTACGCCAACTCCGCCCACGCGCTAGACATGACTTTTGAGGTGGATCCCATGGAC

 901  E  P  T  L  L  Y  V  L  F  E  V  F  D  V  V  R  V  H  Q  P
2701  GAGCCCACCCTTCTTTATGTTTTGTTTGAAGTCTTTGACGTGGTCCGTGTGCACCAGCCG

 921  H  R  G  V  I  E  T  V  Y  L  R  T  P  F  S  A  G  N  A  T
2761  CACCGCGGCGTCATCGAAACCGTGTACCTGCGCACGCCCTTCTCGGCCGGCAACGCCACA

 941  T  -
2821  ACATAA
```

Fig. 20C

Hexon sequence of $(NANP)_6$-HVR1 adenovirus SEQ IDNOS : 13 and 45

```
   1  M  A  T  P  S  M  M  P  Q  W  S  Y  M  H  I  S  G  Q  D  A
   1  ATGGCTACCCCTTCGATGATGCCGCAGTGGTCTTACATGCACATCTCGGGCCAGGACGCC

  21  S  E  Y  L  S  P  G  L  V  Q  F  A  R  A  T  E  T  Y  F  S
  61  TCGGAGTACCTGAGCCCCGGGCTGGTGCAGTTTGCCCGCGCCACCGAGACGTACTTCAGC

  41  L  N  N  K  F  R  N  P  T  V  A  P  T  H  D  V  T  T  D  R
 121  CTGAATAACAAGTTTAGAAACCCCACGGTGGCGCCTACGCACGACGTGACCACAGACCGG

  61  S  Q  R  L  T  L  R  F  I  P  V  D  R  E  D  T  A  Y  S  Y
 181  TCCCAGCGTTTGACGCTGCGGTTCATCCCTGTGGACCGTGAGGATACTGCGTACTCGTAC

  81  K  A  R  F  T  L  A  V  G  D  N  R  V  L  D  M  A  S  T  Y
 241  AAGGCGCGGTTCACCCTAGCTGTGGGTGATAACCGTGTGCTGGACATGGCTTCCACGTAC

 101  F  D  I  R  G  V  L  D  R  G  P  T  F  K  P  Y  S  G  T  A
 301  TTTGACATCCGCGGCGTGCTGGACAGGGGCCCTACTTTTAAGCCCTACTCTGGCACTGCC

 121  Y  N  A  L  A  P  K  G  A  P  N  P  C  E  W  D  E  N  A  N
 361  TACAACGCCCTGGCTCCCAAGGGTGCCCCAAATCCTTGCGAATGGGATGAAAATGCAAAT

 141  P  N  A  N  P  N  A  N  P  N  A  N  P  N  A  N  P  N  A  N
 421  CCAAATGCAAATCCAAATGCAAATCCAAATGCAAATCCAAACGCGAACCCGAATGCTAAT

 161  P  K  T  H  V  F  G  Q  A  P  Y  S  G  I  N  I  T  K  E  G
 481  CCTAAAACTCACGTATTTGGGCAGGCGCCTTATTCTGGTATAAATATTACAAAGGAGGGT

 181  I  Q  I  G  V  E  G  Q  T  P  K  Y  A  D  K  T  F  Q  P  E
 541  ATTCAAATAGGTGTCGAAGGTCAAACACCTAAATATGCCGATAAAACATTTCAACCTGAA

 201  P  Q  I  G  E  S  Q  W  Y  E  T  E  I  N  H  A  A  G  R  V
 601  CCTCAAATAGGAGAATCTCAGTGGTACGAAACAGAAATTAATCATGCAGCTGGGAGAGTC

 221  L  K  K  T  T  P  M  K  P  C  Y  G  S  Y  A  K  P  T  N  E
 661  CTAAAAAAGACTACCCCAATGAAACCATGTTACGGTTCATATGCAAAACCCACAAATGAA

 241  N  G  G  Q  G  I  L  V  K  Q  Q  N  G  K  L  E  S  Q  V  E
 721  AATGGAGGGCAAGGCATTCTTGTAAAGCAACAAAATGGAAAGCTAGAAAGTCAAGTGGAA

 261  M  Q  F  F  S  T  T  E  A  A  A  G  N  G  D  N  L  T  P  K
 781  ATGCAATTTTTCTCAACTACTGAGGCAGCCGCAGGCAATGGTGATAACTTGACTCCTAAA

 281  V  V  L  Y  S  E  D  V  D  I  E  T  P  D  T  H  I  S  Y  M
 841  GTGGTATTGTACAGTGAAGATGTAGATATAGAAACCCCAGACACTCATATTTCTTACATG

 301  P  T  I  K  E  G  N  S  R  E  L  M  G  Q  Q  S  M  P  N  R
 901  CCCACTATTAAGGAAGGTAACTCACGAGAACTAATGGGCCAACAATCTATGCCCAACAGG

 321  P  N  Y  I  A  F  R  D  N  F  I  G  L  M  Y  Y  N  S  T  G
 961  CCTAATTACATTGCTTTTAGGGACAATTTTATTGGTCTAATGTATTACAACAGCACGGGT

 341  N  M  G  V  L  A  G  Q  A  S  Q  L  N  A  V  V  D  L  Q  D
1021  AATATGGGTGTTCTGGCGGGCCAAGCATCGCAGTTGAATGCTGTTGTAGATTTGCAAGAC

 361  R  N  T  E  L  S  Y  Q  L  L  L  D  S  I  G  D  R  T  R  Y
1081  AGAAACACAGAGCTTTCATACCAGCTTTTGCTTGATTCCATTGGTGATAGAACCAGGTAC

 381  F  S  M  W  N  Q  L  P  N  Y  C  F  P  L  G  G  V  I  N  T
1141  TTTTCTATGTGGAATCAGCTTCCAAATTACTGCTTTCCACTGGGAGGTGTGATTAATACA
```

Fig. 21A

```
 401  E  T  L  T  K  V  K  P  K  T  G  Q  E  N  G  W  E  K  D  A
1201  GAGACTCTTACCAAGGTAAAACCTAAAACAGGTCAGGAAAATGGATGGGAAAAAGATGCT

 421  T  E  F  S  D  K  N  E  I  R  V  G  N  N  F  A  M  E  I  N
1261  ACAGAATTTTCAGATAAAAATGAAATAAGAGTTGGAAATAATTTTGCCATGGAAATCAAT

 441  L  N  A  N  L  W  R  N  F  L  Y  S  N  I  A  L  Y  L  P  D
1321  CTAAATGCCAACCTGTGGAGAAATTTCCTGTACTCCAACATAGCGCTGTATTTGCCCGAC

 461  K  L  K  Y  S  P  S  N  V  K  I  S  D  N  P  N  T  Y  D  Y
1381  AAGCTAAAGTACAGTCCTTCCAACGTAAAAATTTCTGATAACCCAAACACCTACGACTAC

 481  M  N  K  R  V  V  A  P  G  L  V  D  C  Y  I  N  L  G  A  R
1441  ATGAACAAGCGAGTGGTGGCTCCCGGGCTAGTGGACTGCTACATTAACCTTGGAGCACGC

 501  W  S  L  D  Y  M  D  N  V  N  P  F  N  H  H  R  N  A  G  L
1501  TGGTCCCTTGACTATATGGACAACGTCAACCCATTTAACCACCACCGCAATGCTGGCCTG

 521  R  Y  R  S  M  L  L  G  N  G  R  Y  V  P  F  H  I  Q  V  P
1561  CGCTACCGCTCAATGTTGCTGGGCAATGGTCGCTATGTGCCCTTCCACATCCAGGTGCCT

 541  Q  K  F  F  A  I  K  N  L  L  L  L  P  G  S  Y  T  Y  E  W
1621  CAGAAGTTCTTTGCCATTAAAAACCTCCTTCTCCTGCCGGGCTCATACACCTACGAGTGG

 561  N  F  R  K  D  V  N  M  V  L  Q  S  S  L  G  N  D  L  R  V
1681  AACTTCAGGAAGGATGTTAACATGGTTCTGCAGAGCTCCCTAGGAAATGACCTAAGGGTT

 581  D  G  A  S  I  K  F  D  S  I  C  L  Y  A  T  F  F  P  M  A
1741  GACGGAGCCAGCATTAAGTTTGATAGCATTTGCCTTTACGCCACCTTCTTCCCCATGGCC

 601  H  N  T  A  S  T  L  E  A  M  L  R  N  D  T  N  D  Q  S  F
1801  CACAACACCGCCTCCACGCTTGAGGCCATGCTTAGAAACGACACCAACGACCAGTCCTTT

 621  N  D  Y  L  S  A  A  N  M  L  Y  P  I  P  A  N  A  T  N  V
1861  AACGACTATCTCTCCGCCGCCAACATGCTCTACCCTATACCCGCCAACGCTACCAACGTG

 641  P  I  S  I  P  S  R  N  W  A  A  F  R  G  W  A  F  T  R  L
1921  CCCATATCCATCCCCTCCCGCAACTGGGCGGCTTTCCGCGGCTGGGCCTTCACGCGCCTT

 661  K  T  K  E  T  P  S  L  G  S  G  Y  D  P  Y  Y  T  Y  S  G
1981  AAGACTAAGGAAACCCCATCACTGGGCTCGGGCTACGACCCTTATTACACCTACTCTGGC

 681  S  I  P  Y  L  D  G  T  F  Y  L  N  H  T  F  K  K  V  A  I
2041  TCTATACCCTACCTAGATGGAACCTTTTACCTCAACCACACCTTTAAGAAGGTGGCCATT

 701  T  F  D  S  S  V  S  W  P  G  N  D  R  L  L  T  P  N  E  F
2101  ACCTTTGACTCTTCTGTCAGCTGGCCTGGCAATGACCGCCTGCTTACCCCCAACGAGTTT

 721  E  I  K  R  S  V  D  G  E  G  Y  N  V  A  Q  C  N  M  T  K
2161  GAAATTAAGCGCTCAGTTGACGGGGAGGGTTACAACGTTGCCCAGTGTAACATGACCAAA

 741  D  W  F  L  V  Q  M  L  A  N  Y  N  I  G  Y  Q  G  F  Y  I
2221  GACTGGTTCCTGGTACAAATGCTAGCTAACTATAACATTGGCTACCAGGGCTTCTATATC

 761  P  E  S  Y  K  D  R  M  Y  S  F  F  R  N  F  Q  P  M  S  R
2281  CCAGAGAGCTACAAGGACCGCATGTACTCCTTCTTTAGAAACTTCCAGCCCATGAGCCGT

 781  Q  V  V  D  D  T  K  Y  K  D  Y  Q  Q  V  G  I  L  H  Q  H
2341  CAGGTGGTGGATGATACTAAATACAAGGACTACCAACAGGTGGGCATCCTACACCAACAC

 801  N  N  S  G  F  V  G  Y  L  A  P  T  M  R  E  G  Q  A  Y  P
2401  AACAACTCTGGATTTGTTGGCTACCTTGCCCCCACCATGCGCGAAGGACAGGCCTACCCT
```

Fig. 21B

```
 821  A  N  F  P  Y  P  L  I  G  K  T  A  V  D  S  I  T  Q  K  K
2461  GCTAACTTCCCCTATCCGCTTATAGGCAAGACCGCAGTTGACAGCATTACCCAGAAAAAG

 841  F  L  C  D  R  T  L  W  R  I  P  F  S  S  N  F  M  S  M  G
2521  TTTCTTTGCGATCGCACCCTTTGGCGCATCCCATTCTCCAGTAACTTTATGTCCATGGGC

 861  A  L  T  D  L  G  Q  N  L  L  Y  A  N  S  A  H  A  L  D  M
2581  GCACTCACAGACCTGGGCCAAAACCTTCTCTACGCCAACTCCGCCCACGCGCTAGACATG

 881  T  F  E  V  D  P  M  D  E  P  T  L  L  Y  V  L  F  E  V  F
2641  ACTTTTGAGGTGGATCCCATGGACGAGCCCACCCTTCTTTATGTTTTGTTTGAAGTCTTT

 901  D  V  V  R  V  H  Q  P  H  R  G  V  I  E  T  V  Y  L  R  T
2701  GACGTGGTCCGTGTGCACCAGCCGCACCGCGGCGTCATCGAAACCGTGTACCTGCGCACG

 921  P  F  S  A  G  N  A  T  T  -
2761  CCCTTCTCGGCCGGCAACGCCACAACATAA
```

Fig. 21C

Hexon sequence of $(NANP)_8$-HVR1 adenovirus SEQ IDNOS : 14 and 46

```
   1  M  A  T  P  S  M  M  P  Q  W  S  Y  M  H  I  S  G  Q  D  A
   1  ATGGCTACCCCTTCGATGATGCCGCAGTGGTCTTACATGCACATCTCGGGCCAGGACGCC

  21  S  E  Y  L  S  P  G  L  V  Q  F  A  R  A  T  E  T  Y  F  S
  61  TCGGAGTACCTGAGCCCCGGGCTGGTGCAGTTTGCCCGCGCCACCGAGACGTACTTCAGC

  41  L  N  N  K  F  R  N  P  T  V  A  P  T  H  D  V  T  T  D  R
 121  CTGAATAACAAGTTTAGAAACCCCACGGTGGCGCCTACGCACGACGTGACCACAGACCGG

  61  S  Q  R  L  T  L  R  F  I  P  V  D  R  E  D  T  A  Y  S  Y
 181  TCCCAGCGTTTGACGCTGCGGTTCATCCCTGTGGACCGTGAGGATACTGCGTACTCGTAC

  81  K  A  R  F  T  L  A  V  G  D  N  R  V  L  D  M  A  S  T  Y
 241  AAGGCGCGGTTCACCCTAGCTGTGGGTGATAACCGTGTGCTGGACATGGCTTCCACGTAC

 101  F  D  I  R  G  V  L  D  R  G  P  T  F  K  P  Y  S  G  T  A
 301  TTTGACATCCGCGGCGTGCTGGACAGGGGCCCTACTTTTAAGCCCTACTCTGGCACTGCC

 121  Y  N  A  L  A  P  K  G  A  P  N  P  C  E  W  D  E  N  A  N
 361  TACAACGCCCTGGCTCCCAAGGGTGCCCCAAATCCTTGCGAATGGGATGAAAATGCAAAT

 141  P  N  A  N  P  N  A  N  P  N  A  N  P  N  A  N  P  N  A  N
 421  CCAAATGCAAATCCAAATGCAAATCCAAATGCAAATCCAAACGCGAACCCGAATGCTAAT

 161  P  N  A  N  P  N  A  N  P  K  T  H  V  F  G  Q  A  P  Y  S
 481  CCTAATGCAAATCCAAATGCAAATCCAAAAACTCACGTATTTGGGCAGGCGCCTTATTCT

 181  G  I  N  I  T  K  E  G  I  Q  I  G  V  E  G  Q  T  P  K  Y
 541  GGTATAAATATTACAAAGGAGGGTATTCAAATAGGTGTCGAAGGTCAAACACCTAAATAT

 201  A  D  K  T  F  Q  P  E  P  Q  I  G  E  S  Q  W  Y  E  T  E
 601  GCCGATAAAACATTTCAACCTGAACCTCAAATAGGAGAATCTCAGTGGTACGAAACAGAA

 221  I  N  H  A  A  G  R  V  L  K  K  T  T  P  M  K  P  C  Y  G
 661  ATTAATCATGCAGCTGGGAGAGTCCTAAAAAAGACTACCCCAATGAAACCATGTTACGGT

 241  S  Y  A  K  P  T  N  E  N  G  G  Q  G  I  L  V  K  Q  Q  N
 721  TCATATGCAAAACCCACAAATGAAAATGGAGGGCAAGGCATTCTTGTAAAGCAACAAAAT

 261  G  K  L  E  S  Q  V  E  M  Q  F  F  S  T  T  E  A  A  A  G
 781  GGAAAGCTAGAAAGTCAAGTGGAAATGCAATTTTTCTCAACTACTGAGGCAGCCGCAGGC

 281  N  G  D  N  L  T  P  K  V  V  L  Y  S  E  D  V  D  I  E  T
 841  AATGGTGATAACTTGACTCCTAAAGTGGTATTGTACAGTGAAGATGTAGATATAGAAACC

 301  P  D  T  H  I  S  Y  M  P  T  I  K  E  G  N  S  R  E  L  M
 901  CCAGACACTCATATTTCTTACATGCCCACTATTAAGGAAGGTAACTCACGAGAACTAATG

 321  G  Q  Q  S  M  P  N  R  P  N  Y  I  A  F  R  D  N  F  I  G
 961  GGCCAACAATCTATGCCCAACAGGCCTAATTACATTGCTTTTAGGGACAATTTTATTGGT

 341  L  M  Y  Y  N  S  T  G  N  M  G  V  L  A  G  Q  A  S  Q  L
1021  CTAATGTATTACAACAGCACGGGTAATATGGGTGTTCTGGCGGGCCAAGCATCGCAGTTG

 361  N  A  V  V  D  L  Q  D  R  N  T  E  L  S  Y  Q  L  L  L  D
1081  AATGCTGTTGTAGATTTGCAAGACAGAAACACAGAGCTTTCATACCAGCTTTTGCTTGAT

 381  S  I  G  D  R  T  R  Y  F  S  M  W  N  Q  L  P  N  Y  C  F
1141  TCCATTGGTGATAGAACCAGGTACTTTTCTATGTGGAATCAGCTTCCAAATTACTGCTTT
```

Fig. 22A

```
 401  P  L  G  G  V  I  N  T  E  T  L  T  K  V  K  P  K  T  G  Q
1201  CCACTGGGAGGTGTGATTAATACAGAGACTCTTACCAAGGTAAAACCTAAAACAGGTCAG

 421  E  N  G  W  E  K  D  A  T  E  F  S  D  K  N  E  I  R  V  G
1261  GAAAATGGATGGGAAAAAGATGCTACAGAATTTTCAGATAAAAATGAAATAAGAGTTGGA

 441  N  N  F  A  M  E  I  N  L  N  A  N  L  W  R  N  F  L  Y  S
1321  AATAATTTTGCCATGGAAATCAATCTAAATGCCAACCTGTGGAGAAATTTCCTGTACTCC

 461  N  I  A  L  Y  L  P  D  K  L  K  Y  S  P  S  N  V  K  I  S
1381  AACATAGCGCTGTATTTGCCCGACAAGCTAAAGTACAGTCCTTCCAACGTAAAAATTTCT

 481  D  N  P  N  T  Y  D  Y  M  N  K  R  V  V  A  P  G  L  V  D
1441  GATAACCCAAACACCTACGACTACATGAACAAGCGAGTGGTGGCTCCCGGGCTAGTGGAC

 501  C  Y  I  N  L  G  A  R  W  S  L  D  Y  M  D  N  V  N  P  F
1501  TGCTACATTAACCTTGGAGCACGCTGGTCCCTTGACTATATGGACAACGTCAACCCATTT

 521  N  H  H  R  N  A  G  L  R  Y  R  S  M  L  L  G  N  G  R  Y
1561  AACCACCACCGCAATGCTGGCCTGCGCTACCGCTCAATGTTGCTGGGCAATGGTCGCTAT

 541  V  P  F  H  I  Q  V  P  Q  K  F  F  A  I  K  N  L  L  L  L
1621  GTGCCCTTCCACATCCAGGTGCCTCAGAAGTTCTTTGCCATTAAAAACCTCCTTCTCCTG

 561  P  G  S  Y  T  Y  E  W  N  F  R  K  D  V  N  M  V  L  Q  S
1681  CCGGGCTCATACACCTACGAGTGGAACTTCAGGAAGGATGTTAACATGGTTCTGCAGAGC

 581  S  L  G  N  D  L  R  V  D  G  A  S  I  K  F  D  S  I  C  L
1741  TCCCTAGGAAATGACCTAAGGGTTGACGGAGCCAGCATTAAGTTTGATAGCATTTGCCTT

 601  Y  A  T  F  F  P  M  A  H  N  T  A  S  T  L  E  A  M  L  R
1801  TACGCCACCTTCTTCCCCATGGCCCACAACACCGCCTCCACGCTTGAGGCCATGCTTAGA

 621  N  D  T  N  D  Q  S  F  N  D  Y  L  S  A  A  N  M  L  Y  P
1861  AACGACACCAACGACCAGTCCTTTAACGACTATCTCTCCGCCGCCAACATGCTCTACCCT

 641  I  P  A  N  A  T  N  V  P  I  S  I  P  S  R  N  W  A  A  F
1921  ATACCCGCCAACGCTACCAACGTGCCCATATCCATCCCCTCCCGCAACTGGGCGGCTTTC

 661  R  G  W  A  F  T  R  L  K  T  K  E  T  P  S  L  G  S  G  Y
1981  CGCGGCTGGGCCTTCACGCGCCTTAAGACTAAGGAAACCCCATCACTGGGCTCGGGCTAC

 681  D  P  Y  Y  T  Y  S  G  S  I  P  Y  L  D  G  T  F  Y  L  N
2041  GACCCTTATTACACCTACTCTGGCTCTATACCCTACCTAGATGGAACCTTTTACCTCAAC

 701  H  T  F  K  K  V  A  I  T  F  D  S  S  V  S  W  P  G  N  D
2101  CACACCTTTAAGAAGGTGGCCATTACCTTTGACTCTTCTGTCAGCTGGCCTGGCAATGAC

 721  R  L  L  T  P  N  E  F  E  I  K  R  S  V  D  G  E  G  Y  N
2161  CGCCTGCTTACCCCCAACGAGTTTGAAATTAAGCGCTCAGTTGACGGGGAGGGTTACAAC

 741  V  A  Q  C  N  M  T  K  D  W  F  L  V  Q  M  L  A  N  Y  N
2221  GTTGCCCAGTGTAACATGACCAAAGACTGGTTCCTGGTACAAATGCTAGCTAACTATAAC

 761  I  G  Y  Q  G  F  Y  I  P  E  S  Y  K  D  R  M  Y  S  F  F
2281  ATTGGCTACCAGGGCTTCTATATCCCAGAGAGCTACAAGGACCGCATGTACTCCTTCTTT

 781  R  N  F  Q  P  M  S  R  Q  V  V  D  D  T  K  Y  K  D  Y  Q
2341  AGAAACTTCCAGCCCATGAGCCGTCAGGTGGTGGATGATACTAAATACAAGGACTACCAA

 801  Q  V  G  I  L  H  Q  H  N  N  S  G  F  V  G  Y  L  A  P  T
2401  CAGGTGGGCATCCTACACCAACACAACAACTCTGGATTTGTTGGCTACCTTGCCCCCACC
```

Fig. 22B

```
 821  M  R  E  G  Q  A  Y  P  A  N  F  P  Y  P  L  I  G  K  T  A
2461  ATGCGCGAAGGACAGGCCTACCCTGCTAACTTCCCCTATCCGCTTATAGGCAAGACCGCA

 841  V  D  S  I  T  Q  K  K  F  L  C  D  R  T  L  W  R  I  P  F
2521  GTTGACAGCATTACCCAGAAAAAGTTTCTTTGCGATCGCACCCTTTGGCGCATCCCATTC

 861  S  S  N  F  M  S  M  G  A  L  T  D  L  G  Q  N  L  L  Y  A
2581  TCCAGTAACTTTATGTCCATGGGCGCACTCACAGACCTGGGCCAAAACCTTCTCTACGCC

 881  N  S  A  H  A  L  D  M  T  F  E  V  D  P  M  D  E  P  T  L
2641  AACTCCGCCCACGCGCTAGACATGACTTTTGAGGTGGATCCCATGGACGAGCCCACCCTT

 901  L  Y  V  L  F  E  V  F  D  V  V  R  V  H  Q  P  H  R  G  V
2701  CTTTATGTTTTGTTTGAAGTCTTTGACGTGGTCCGTGTGCACCAGCCGCACCGCGGCGTC

 921  I  E  T  V  Y  L  R  T  P  F  S  A  G  N  A  T  T  -
2761  ATCGAAACCGTGTACCTGCGCACGCCCTTCTCGGCCGGCAACGCCACAACATAA
```

Fig. 22C

Hexon sequence of $(NANP)_{10}$-HVR1 adenovirus SEQ IDNOS : 15 and 47

```
   1  M  A  T  P  S  M  M  P  Q  W  S  Y  M  H  I  S  G  Q  D  A
   1  ATGGCTACCCCTTCGATGATGCCGCAGTGGTCTTACATGCACATCTCGGGCCAGGACGCC

  21  S  E  Y  L  S  P  G  L  V  Q  F  A  R  A  T  E  T  Y  F  S
  61  TCGGAGTACCTGAGCCCCGGGCTGGTGCAGTTTGCCCGCGCCACCGAGACGTACTTCAGC

  41  L  N  N  K  F  R  N  P  T  V  A  P  T  H  D  V  T  T  D  R
 121  CTGAATAACAAGTTTAGAAACCCCACGGTGGCGCCTACGCACGACGTGACCACAGACCGG

  61  S  Q  R  L  T  L  R  F  I  P  V  D  R  E  D  T  A  Y  S  Y
 181  TCCCAGCGTTTGACGCTGCGGTTCATCCCTGTGGACCGTGAGGATACTGCGTACTCGTAC

  81  K  A  R  F  T  L  A  V  G  D  N  R  V  L  D  M  A  S  T  Y
 241  AAGGCGCGGTTCACCCTAGCTGTGGGTGATAACCGTGTGCTGGACATGGCTTCCACGTAC

 101  F  D  I  R  G  V  L  D  R  G  P  T  F  K  P  Y  S  G  T  A
 301  TTTGACATCCGCGGCGTGCTGGACAGGGGCCCTACTTTTAAGCCCTACTCTGGCACTGCC

 121  Y  N  A  L  A  P  K  G  A  P  N  P  C  E  W  D  E  N  A  N
 361  TACAACGCCCTGGCTCCCAAGGGTGCCCCAAATCCTTGCGAATGGGATGAAAATGCAAAT

 141  P  N  A  N  P  N  A  N  P  N  A  N  P  N  A  N  P  N  A  N
 421  CCAAATGCAAATCCAAATGCAAATCCAAATGCAAATCCAAACGCGAACCCGAATGCTAAT

 161  P  N  A  N  P  N  A  N  P  N  A  N  P  N  A  N  P  K  T  H
 481  CCTAATGCAAATCCAAATGCAAATCCAAATGCAAATCCAAATGCAAATCCAAAAACTCAC

 181  V  F  G  Q  A  P  Y  S  G  I  N  I  T  K  E  G  I  Q  I  G
 541  GTATTTGGGCAGGCGCCTTATTCTGGTATAAATATTACAAAGGAGGGTATTCAAATAGGT

 201  V  E  G  Q  T  P  K  Y  A  D  K  T  F  Q  P  E  P  Q  I  G
 601  GTCGAAGGTCAAACACCTAAATATGCCGATAAAACATTTCAACCTGAACCTCAAATAGGA

 221  E  S  Q  W  Y  E  T  E  I  N  H  A  A  G  R  V  L  K  K  T
 661  GAATCTCAGTGGTACGAAACAGAAATTAATCATGCAGCTGGGAGAGTCCTAAAAAAGACT

 241  T  P  M  K  P  C  Y  G  S  Y  A  K  P  T  N  E  N  G  G  Q
 721  ACCCCAATGAAACCATGTTACGGTTCATATGCAAAACCCACAAATGAAAATGGAGGGCAA

 261  G  I  L  V  K  Q  Q  N  G  K  L  E  S  Q  V  E  M  Q  F  F
 781  GGCATTCTTGTAAAGCAACAAAATGGAAAGCTAGAAAGTCAAGTGGAAATGCAATTTTTC

 281  S  T  T  E  A  A  A  G  N  G  D  N  L  T  P  K  V  V  L  Y
 841  TCAACTACTGAGGCAGCCGCAGGCAATGGTGATAACTTGACTCCTAAAGTGGTATTGTAC

 301  S  E  D  V  D  I  E  T  P  D  T  H  I  S  Y  M  P  T  I  K
 901  AGTGAAGATGTAGATATAGAAACCCCAGACACTCATATTTCTTACATGCCCACTATTAAG

 321  E  G  N  S  R  E  L  M  G  Q  Q  S  M  P  N  R  P  N  Y  I
 961  GAAGGTAACTCACGAGAACTAATGGGCCAACAATCTATGCCCAACAGGCCTAATTACATT

 341  A  F  R  D  N  F  I  G  L  M  Y  Y  N  S  T  G  N  M  G  V
1021  GCTTTTAGGGACAATTTTATTGGTCTAATGTATTACAACAGCACGGGTAATATGGGTGTT

 361  L  A  G  Q  A  S  Q  L  N  A  V  V  D  L  Q  D  R  N  T  E
1081  CTGGCGGGCCAAGCATCGCAGTTGAATGCTGTTGTAGATTTGCAAGACAGAAACACAGAG

 381  L  S  Y  Q  L  L  L  D  S  I  G  D  R  T  R  Y  F  S  M  W
1141  CTTTCATACCAGCTTTTGCTTGATTCCATTGGTGATAGAACCAGGTACTTTTCTATGTGG
```

Fig. 23A

401 N Q L P N Y C F P L G G V I N T E T L T
1201 AATCAGCTTCCAAATTACTGCTTTCCACTGGGAGGTGTGATTAATACAGAGACTCTTACC

421 K V K P K T G Q E N G W E K D A T E F S
1261 AAGGTAAAACCTAAAACAGGTCAGGAAAATGGATGGGAAAAAGATGCTACAGAATTTTCA

441 D K N E I R V G N N F A M E I N L N A N
1321 GATAAAAATGAAATAAGAGTTGGAAATAATTTTGCCATGGAAATCAATCTAAATGCCAAC

461 L W R N F L Y S N I A L Y L P D K L K Y
1381 CTGTGGAGAAATTTCCTGTACTCCAACATAGCGCTGTATTTGCCCGACAAGCTAAAGTAC

481 S P S N V K I S D N P N T Y D Y M N K R
1441 AGTCCTTCCAACGTAAAAATTTCTGATAACCCAAACACCTACGACTACATGAACAAGCGA

501 V V A P G L V D C Y I N L G A R W S L D
1501 GTGGTGGCTCCCGGGCTAGTGGACTGCTACATTAACCTTGGAGCACGCTGGTCCCTTGAC

521 Y M D N V N P F N H H R N A G L R Y R S
1561 TATATGGACAACGTCAACCCATTTAACCACCACCGCAATGCTGGCCTGCGCTACCGCTCA

541 M L L G N G R Y V P F H I Q V P Q K F F
1621 ATGTTGCTGGGCAATGGTCGCTATGTGCCCTTCCACATCCAGGTGCCTCAGAAGTTCTTT

561 A I K N L L L L P G S Y T Y E W N F R K
1681 GCCATTAAAAACCTCCTTCTCCTGCCGGGCTCATACACCTACGAGTGGAACTTCAGGAAG

581 D V N M V L Q S S L G N D L R V D G A S
1741 GATGTTAACATGGTTCTGCAGAGCTCCCTAGGAAATGACCTAAGGGTTGACGGAGCCAGC

601 I K F D S I C L Y A T F F P M A H N T A
1801 ATTAAGTTTGATAGCATTTGCCTTTACGCCACCTTCTTCCCCATGGCCCACAACACCGCC

621 S T L E A M L R N D T N D Q S F N D Y L
1861 TCCACGCTTGAGGCCATGCTTAGAAACGACACCAACGACCAGTCCTTTAACGACTATCTC

641 S A A N M L Y P I P A N A T N V P I S I
1921 TCCGCCGCCAACATGCTCTACCCTATACCCGCCAACGCTACCAACGTGCCCATATCCATC

661 P S R N W A A F R G W A F T R L K T K E
1981 CCCTCCCGCAACTGGGCGGCTTTCCGCGGCTGGGCCTTCACGCGCCTTAAGACTAAGGAA

681 T P S L G S G Y D P Y Y T Y S G S I P Y
2041 ACCCCATCACTGGGCTCGGGCTACGACCCTTATTACACCTACTCTGGCTCTATACCCTAC

701 L D G T F Y L N H T F K K V A I T F D S
2101 CTAGATGGAACCTTTTACCTCAACCACACCTTTAAGAAGGTGGCCATTACCTTTGACTCT

721 S V S W P G N D R L L T P N E F E I K R
2161 TCTGTCAGCTGGCCTGGCAATGACCGCCTGCTTACCCCCAACGAGTTTGAAATTAAGCGC

741 S V D G E G Y N V A Q C N M T K D W F L
2221 TCAGTTGACGGGGAGGGTTACAACGTTGCCCAGTGTAACATGACCAAAGACTGGTTCCTG

761 V Q M L A N Y N I G Y Q G F Y I P E S Y
2281 GTACAAATGCTAGCTAACTATAACATTGGCTACCAGGGCTTCTATATCCCAGAGAGCTAC

781 K D R M Y S F F R N F Q P M S R Q V V D
2341 AAGGACCGCATGTACTCCTTCTTTAGAAACTTCCAGCCCATGAGCCGTCAGGTGGTGGAT

Fig. 23B

801 D T K Y K D Y Q Q V G I L H Q H N N S G
2401 GATACTAAATACAAGGACTACCAACAGGTGGGCATCCTACACCAACACAACAACTCTGGA

```
 821  F  V  G  Y  L  A  P  T  M  R  E  G  Q  A  Y  P  A  N  F  P
2461  TTTGTTGGCTACCTTGCCCCCACCATGCGCGAAGGACAGGCCTACCCTGCTAACTTCCCC

 841  Y  P  L  I  G  K  T  A  V  D  S  I  T  Q  K  K  F  L  C  D
2521  TATCCGCTTATAGGCAAGACCGCAGTTGACAGCATTACCCAGAAAAAGTTTCTTTGCGAT

 861  R  T  L  W  R  I  P  F  S  S  N  F  M  S  M  G  A  L  T  D
2581  CGCACCCTTTGGCGCATCCCATTCTCCAGTAACTTTATGTCCATGGGCGCACTCACAGAC

 881  L  G  Q  N  L  L  Y  A  N  S  A  H  A  L  D  M  T  F  E  V
2641  CTGGGCCAAAACCTTCTCTACGCCAACTCCGCCCACGCGCTAGACATGACTTTTGAGGTG

 901  D  P  M  D  E  P  T  L  L  Y  V  L  F  E  V  F  D  V  V  R
2701  GATCCCATGGACGAGCCCACCCTTCTTTATGTTTTGTTTGAAGTCTTTGACGTGGTCCGT

 921  V  H  Q  P  H  R  G  V  I  E  T  V  Y  L  R  T  P  F  S  A
2761  GTGCACCAGCCGCACCGCGGCGTCATCGAAACCGTGTACCTGCGCACGCCCTTCTCGGCC

 941  G  N  A  T  T  -
2821  GGCAACGCCACAACATAA
```

Fig. 23C

Hexon sequence of $(NANP)_{12}$-HVR1 adenovirus SEQ IDNOS : 16 and 48

```
   1  M  A  T  P  S  M  M  P  Q  W  S  Y  M  H  I  S  G  Q  D  A
   1  ATGGCTACCCCTTCGATGATGCCGCAGTGGTCTTACATGCACATCTCGGGCCAGGACGCC

  21  S  E  Y  L  S  P  G  L  V  Q  F  A  R  A  T  E  T  Y  F  S
  61  TCGGAGTACCTGAGCCCCGGGCTGGTGCAGTTTGCCCGCGCCACCGAGACGTACTTCAGC

  41  L  N  N  K  F  R  N  P  T  V  A  P  T  H  D  V  T  T  D  R
 121  CTGAATAACAAGTTTAGAAACCCCACGGTGGCGCCTACGCACGACGTGACCACAGACCGG

  61  S  Q  R  L  T  L  R  F  I  P  V  D  R  E  D  T  A  Y  S  Y
 181  TCCCAGCGTTTGACGCTGCGGTTCATCCCTGTGGACCGTGAGGATACTGCGTACTCGTAC

  81  K  A  R  F  T  L  A  V  G  D  N  R  V  L  D  M  A  S  T  Y
 241  AAGGCGCGGTTCACCCTAGCTGTGGGTGATAACCGTGTGCTGGACATGGCTTCCACGTAC

 101  F  D  I  R  G  V  L  D  R  G  P  T  F  K  P  Y  S  G  T  A
 301  TTTGACATCCGCGGCGTGCTGGACAGGGGCCCTACTTTTAAGCCCTACTCTGGCACTGCC

 121  Y  N  A  L  A  P  K  G  A  P  N  P  C  E  W  D  E  N  A  N
 361  TACAACGCCCTGGCTCCCAAGGGTGCCCCAAATCCTTGCGAATGGGATGAAAATGCAAAT

 141  P  N  A  N  P  N  A  N  P  N  A  N  P  N  A  N  P  N  A  N
 421  CCAAATGCAAATCCAAATGCAAATCCAAATGCAAATCCAAATGCAAATCCAAATGCAAAT

 161  P  N  A  N  P  N  A  N  P  N  A  N  P  N  A  N  P  N  A  N
 481  CCAAATGCAAATCCAAATGCAAATCCAAACGCGAACCCGAATGCTAATCCTAATGCAAAT

 181  P  N  A  N  P  K  T  H  V  F  G  Q  A  P  Y  S  G  I  N  I
 541  CCAAATGCAAATCCAAAAACTCACGTATTTGGGCAGGCGCCTTATTCTGGTATAAATATT

 201  T  K  E  G  I  Q  I  G  V  E  G  Q  T  P  K  Y  A  D  K  T
 601  ACAAAGGAGGGTATTCAAATAGGTGTCGAAGGTCAAACACCTAAATATGCCGATAAAACA

 221  F  Q  P  E  P  Q  I  G  E  S  Q  W  Y  E  T  E  I  N  H  A
 661  TTTCAACCTGAACCTCAAATAGGAGAATCTCAGTGGTACGAAACAGAAATTAATCATGCA

 241  A  G  R  V  L  K  K  T  T  P  M  K  P  C  Y  G  S  Y  A  K
 721  GCTGGGAGAGTCCTAAAAAAGACTACCCCAATGAAACCATGTTACGGTTCATATGCAAAA

 261  P  T  N  E  N  G  G  Q  G  I  L  V  K  Q  Q  N  G  K  L  E
 781  CCCACAAATGAAAATGGAGGGCAAGGCATTCTTGTAAAGCAACAAAATGGAAAGCTAGAA

 281  S  Q  V  E  M  Q  F  F  S  T  T  E  A  A  A  G  N  G  D  N
 841  AGTCAAGTGGAAATGCAATTTTTCTCAACTACTGAGGCAGCCGCAGGCAATGGTGATAAC

 301  L  T  P  K  V  V  L  Y  S  E  D  V  D  I  E  T  P  D  T  H
 901  TTGACTCCTAAAGTGGTATTGTACAGTGAAGATGTAGATATAGAAACCCCAGACACTCAT

 321  I  S  Y  M  P  T  I  K  E  G  N  S  R  E  L  M  G  Q  Q  S
 961  ATTTCTTACATGCCCACTATTAAGGAAGGTAACTCACGAGAACTAATGGGCCAACAATCT

 341  M  P  N  R  P  N  Y  I  A  F  R  D  N  F  I  G  L  M  Y  Y
1021  ATGCCCAACAGGCCTAATTACATTGCTTTTAGGGACAATTTTATTGGTCTAATGTATTAC

 361  N  S  T  G  N  M  G  V  L  A  G  Q  A  S  Q  L  N  A  V  V
1081  AACAGCACGGGTAATATGGGTGTTCTGGCGGGCCAAGCATCGCAGTTGAATGCTGTTGTA

 381  D  L  Q  D  R  N  T  E  L  S  Y  Q  L  L  L  D  S  I  G  D
1141  GATTTGCAAGACAGAAACACAGAGCTTTCATACCAGCTTTTGCTTGATTCCATTGGTGAT
```

Fig. 24A

```
 401  R T R Y F S M W N Q L P N Y C F P L G G
1201  AGAACCAGGTACTTTTCTATGTGGAATCAGCTTCCAAATTACTGCTTTCCACTGGGAGGT

 421  V I N T E T L T K V K P K T G Q E N G W
1261  GTGATTAATACAGAGACTCTTACCAAGGTAAAACCTAAAACAGGTCAGGAAAATGGATGG

 441  E K D A T E F S D K N E I R V G N N F A
1321  GAAAAAGATGCTACAGAATTTTCAGATAAAAATGAAATAAGAGTTGGAAATAATTTTGCC

 461  M E I N L N A N L W R N F L Y S N I A L
1381  ATGGAAATCAATCTAAATGCCAACCTGTGGAGAAATTTCCTGTACTCCAACATAGCGCTG

 481  Y L P D K L K Y S P S N V K I S D N P N
1441  TATTTGCCCGACAAGCTAAAGTACAGTCCTTCCAACGTAAAAATTTCTGATAACCCAAAC

 501  T Y D Y M N K R V V A P G L V D C Y I N
1501  ACCTACGACTACATGAACAAGCGAGTGGTGGCTCCCGGGCTAGTGGACTGCTACATTAAC

 521  L G A R W S L D Y M D N V N P F N H H R
1561  CTTGGAGCACGCTGGTCCCTTGACTATATGGACAACGTCAACCCATTTAACCACCACCGC

 541  N A G L R Y R S M L L G N G R Y V P F H
1621  AATGCTGGCCTGCGCTACCGCTCAATGTTGCTGGGCAATGGTCGCTATGTGCCCTTCCAC

 561  I Q V P Q K F F A I K N L L L L P G S Y
1681  ATCCAGGTGCCTCAGAAGTTCTTTGCCATTAAAAACCTCCTTCTCCTGCCGGGCTCATAC

 581  T Y E W N F R K D V N M V L Q S S L G N
1741  ACCTACGAGTGGAACTTCAGGAAGGATGTTAACATGGTTCTGCAGAGCTCCCTAGGAAAT

 601  D L R V D G A S I K F D S I C L Y A T F
1801  GACCTAAGGGTTGACGGAGCCAGCATTAAGTTTGATAGCATTTGCCTTTACGCCACCTTC

 621  F P M A H N T A S T L E A M L R N D T N
1861  TTCCCCATGGCCCACAACACCGCCTCCACGCTTGAGGCCATGCTTAGAAACGACACCAAC

 641  D Q S F N D Y L S A A N M L Y P I P A N
1921  GACCAGTCCTTTAACGACTATCTCTCCGCCGCCAACATGCTCTACCCTATACCCGCCAAC

 661  A T N V P I S I P S R N W A A F R G W A
1981  GCTACCAACGTGCCCATATCCATCCCCTCCCGCAACTGGGCGGCTTTCCGCGGCTGGGCC

 681  F T R L K T K E T P S L G S G Y D P Y Y
2041  TTCACGCGCCTTAAGACTAAGGAAACCCCATCACTGGGCTCGGGCTACGACCCTTATTAC

 701  T Y S G S I P Y L D G T F Y L N H T F K
2101  ACCTACTCTGGCTCTATACCCTACCTAGATGGAACCTTTTACCTCAACCACACCTTTAAG

 721  K V A I T F D S S V S W P G N D R L L T
2161  AAGGTGGCCATTACCTTTGACTCTTCTGTCAGCTGGCCTGGCAATGACCGCCTGCTTACC

 741  P N E F E I K R S V D G E G Y N V A Q C
2221  CCCAACGAGTTTGAAATTAAGCGCTCAGTTGACGGGGAGGGTTACAACGTTGCCCAGTGT

 761  N M T K D W F L V Q M L A N Y N I G Y Q
2281  AACATGACCAAAGACTGGTTCCTGGTACAAATGCTAGCTAACTATAACATTGGCTACCAG

 781  G F Y I P E S Y K D R M Y S F F R N F Q
2341  GGCTTCTATATCCCAGAGAGCTACAAGGACCGCATGTACTCCTTCTTTAGAAACTTCCAG

 801  P M S R Q V V D D T K Y K D Y Q Q V G I
2401  CCCATGAGCCGTCAGGTGGTGGATGATACTAAATACAAGGACTACCAACAGGTGGGCATC
```

Fig. 24B

```
 821  L  H  Q  H  N  N  S  G  F  V  G  Y  L  A  P  T  M  R  E  G
2461  CTACACCAACACAACAACTCTGGATTTGTTGGCTACCTTGCCCCCACCATGCGCGAAGGA

 841  Q  A  Y  P  A  N  F  P  Y  P  L  I  G  K  T  A  V  D  S  I
2521  CAGGCCTACCCTGCTAACTTCCCCTATCCGCTTATAGGCAAGACCGCAGTTGACAGCATT

 861  T  Q  K  K  F  L  C  D  R  T  L  W  R  I  P  F  S  S  N  F
2581  ACCCAGAAAAAGTTTCTTTGCGATCGCACCCTTTGGCGCATCCCATTCTCCAGTAACTTT

 881  M  S  M  G  A  L  T  D  L  G  Q  N  L  L  Y  A  N  S  A  H
2641  ATGTCCATGGGCGCACTCACAGACCTGGGCCAAAACCTTCTCTACGCCAACTCCGCCCAC

 901  A  L  D  M  T  F  E  V  D  P  M  D  E  P  T  L  L  Y  V  L
2701  GCGCTAGACATGACTTTTGAGGTGGATCCCATGGACGAGCCCACCCTTCTTTATGTTTTG

 921  F  E  V  F  D  V  V  R  V  H  Q  P  H  R  G  V  I  E  T  V
2761  TTTGAAGTCTTTGACGTGGTCCGTGTGCACCAGCCGCACCGCGGCGTCATCGAAACCGTG

 941  Y  L  R  T  P  F  S  A  G  N  A  T  T  -
2821  TACCTGCGCACGCCCTTCTCGGCCGGCAACGCCACAACATAA
```

Fig. 24C

Hexon sequence of $(NANP)_{14}$-HVR1 adenovirus SEQ IDNOS : 17 and 49

```
   1  M  A  T  P  S  M  M  P  Q  W  S  Y  M  H  I  S  G  Q  D  A
   1  ATGGCTACCCCTTCGATGATGCCGCAGTGGTCTTACATGCACATCTCGGGCCAGGACGCC

  21  S  E  Y  L  S  P  G  L  V  Q  F  A  R  A  T  E  T  Y  F  S
  61  TCGGAGTACCTGAGCCCCGGGCTGGTGCAGTTTGCCCGCGCCACCGAGACGTACTTCAGC

  41  L  N  N  K  F  R  N  P  T  V  A  P  T  H  D  V  T  T  D  R
 121  CTGAATAACAAGTTTAGAAACCCCACGGTGGCGCCTACGCACGACGTGACCACAGACCGG

  61  S  Q  R  L  T  L  R  F  I  P  V  D  R  E  D  T  A  Y  S  Y
 181  TCCCAGCGTTTGACGCTGCGGTTCATCCCTGTGGACCGTGAGGATACTGCGTACTCGTAC

  81  K  A  R  F  T  L  A  V  G  D  N  R  V  L  D  M  A  S  T  Y
 241  AAGGCGCGGTTCACCCTAGCTGTGGGTGATAACCGTGTGCTGGACATGGCTTCCACGTAC

 101  F  D  I  R  G  V  L  D  R  G  P  T  F  K  P  Y  S  G  T  A
 301  TTTGACATCCGCGGCGTGCTGGACAGGGGCCCTACTTTTAAGCCCTACTCTGGCACTGCC

 121  Y  N  A  L  A  P  K  G  A  P  N  P  C  E  W  D  E  N  A  N
 361  TACAACGCCCTGGCTCCCAAGGGTGCCCCAAATCCTTGCGAATGGGATGAAAATGCAAAT

 141  P  N  A  N  P  N  A  N  P  N  A  N  P  N  A  N  P  N  A  N
 421  CCAAATGCAAATCCAAATGCAAATCCAAATGCAAATCCAAATGCAAATCCAAATGCAAAT

 161  P  N  A  N  P  N  A  N  P  N  A  N  P  N  A  N  P  N  A  N
 481  CCAAATGCAAATCCAAATGCAAATCCAAACGCGAACCCGAATGCTAATCCTAATGCAAAT

 181  P  N  A  N  P  N  A  N  P  N  A  N  P  K  T  H  V  F  G  Q
 541  CCAAATGCAAATCCAAATGCAAATCCAAATGCAAATCCAAAAACTCACGTATTTGGGCAG

 201  A  P  Y  S  G  I  N  I  T  K  E  G  I  Q  I  G  V  E  G  Q
 601  GCGCCTTATTCTGGTATAAATATTACAAAGGAGGGTATTCAAATAGGTGTCGAAGGTCAA

 221  T  P  K  Y  A  D  K  T  F  Q  P  E  P  Q  I  G  E  S  Q  W
 661  ACACCTAAATATGCCGATAAAACATTTCAACCTGAACCTCAAATAGGAGAATCTCAGTGG

 241  Y  E  T  E  I  N  H  A  A  G  R  V  L  K  K  T  T  P  M  K
 721  TACGAAACAGAAATTAATCATGCAGCTGGGAGAGTCCTAAAAAAGACTACCCCAATGAAA

 261  P  C  Y  G  S  Y  A  K  P  T  N  E  N  G  G  Q  G  I  L  V
 781  CCATGTTACGGTTCATATGCAAAACCCACAAATGAAAATGGAGGGCAAGGCATTCTTGTA

 281  K  Q  Q  N  G  K  L  E  S  Q  V  E  M  Q  F  F  S  T  T  E
 841  AAGCAACAAAATGGAAAGCTAGAAAGTCAAGTGGAAATGCAATTTTTCTCAACTACTGAG

 301  A  A  A  G  N  G  D  N  L  T  P  K  V  V  L  Y  S  E  D  V
 901  GCAGCCGCAGGCAATGGTGATAACTTGACTCCTAAAGTGGTATTGTACAGTGAAGATGTA

 321  D  I  E  T  P  D  T  H  I  S  Y  M  P  T  I  K  E  G  N  S
 961  GATATAGAAACCCCAGACACTCATATTTCTTACATGCCCACTATTAAGGAAGGTAACTCA

 341  R  E  L  M  G  Q  Q  S  M  P  N  R  P  N  Y  I  A  F  R  D
1021  CGAGAACTAATGGGCCAACAATCTATGCCCAACAGGCCTAATTACATTGCTTTTAGGGAC

 361  N  F  I  G  L  M  Y  Y  N  S  T  G  N  M  G  V  L  A  G  Q
1081  AATTTTATTGGTCTAATGTATTACAACAGCACGGGTAATATGGGTGTTCTGGCGGGCCAA

 381  A  S  Q  L  N  A  V  V  D  L  Q  D  R  N  T  E  L  S  Y  Q
1141  GCATCGCAGTTGAATGCTGTTGTAGATTTGCAAGACAGAAACACAGAGCTTTCATACCAG
```

Fig. 25A

```
 401  L  L  L  D  S  I  G  D  R  T  R  Y  F  S  M  W  N  Q  L  P
1201  CTTTTGCTTGATTCCATTGGTGATAGAACCAGGTACTTTTCTATGTGGAATCAGCTTCCA

 421  N  Y  C  F  P  L  G  G  V  I  N  T  E  T  L  T  K  V  K  P
1261  AATTACTGCTTTCCACTGGGAGGTGTGATTAATACAGAGACTCTTACCAAGGTAAAACCT

 441  K  T  G  Q  E  N  G  W  E  K  D  A  T  E  F  S  D  K  N  E
1321  AAAACAGGTCAGGAAAATGGATGGGAAAAAGATGCTACAGAATTTTCAGATAAAAATGAA

 461  I  R  V  G  N  N  F  A  M  E  I  N  L  N  A  N  L  W  R  N
1381  ATAAGAGTTGGAAATAATTTTGCCATGGAAATCAATCTAAATGCCAACCTGTGGAGAAAT

 481  F  L  Y  S  N  I  A  L  Y  L  P  D  K  L  K  Y  S  P  S  N
1441  TTCCTGTACTCCAACATAGCGCTGTATTTGCCCGACAAGCTAAAGTACAGTCCTTCCAAC

 501  V  K  I  S  D  N  P  N  T  Y  D  Y  M  N  K  R  V  V  A  P
1501  GTAAAAATTTCTGATAACCCAAACACCTACGACTACATGAACAAGCGAGTGGTGGCTCCC

 521  G  L  V  D  C  Y  I  N  L  G  A  R  W  S  L  D  Y  M  D  N
1561  GGGCTAGTGGACTGCTACATTAACCTTGGAGCACGCTGGTCCCTTGACTATATGGACAAC

 541  V  N  P  F  N  H  H  R  N  A  G  L  R  Y  R  S  M  L  L  G
1621  GTCAACCCATTTAACCACCACCGCAATGCTGGCCTGCGCTACCGCTCAATGTTGCTGGGC

 561  N  G  R  Y  V  P  F  H  I  Q  V  P  Q  K  F  F  A  I  K  N
1681  AATGGTCGCTATGTGCCCTTCCACATCCAGGTGCCTCAGAAGTTCTTTGCCATTAAAAAC

 581  L  L  L  L  P  G  S  Y  T  Y  E  W  N  F  R  K  D  V  N  M
1741  CTCCTTCTCCTGCCGGGCTCATACACCTACGAGTGGAACTTCAGGAAGGATGTTAACATG

 601  V  L  Q  S  S  L  G  N  D  L  R  V  D  G  A  S  I  K  F  D
1801  GTTCTGCAGAGCTCCCTAGGAAATGACCTAAGGGTTGACGGAGCCAGCATTAAGTTTGAT

 621  S  I  C  L  Y  A  T  F  F  P  M  A  H  N  T  A  S  T  L  E
1861  AGCATTTGCCTTTACGCCACCTTCTTCCCCATGGCCCACAACACCGCCTCCACGCTTGAG

 641  A  M  L  R  N  D  T  N  D  Q  S  F  N  D  Y  L  S  A  A  N
1921  GCCATGCTTAGAAACGACACCAACGACCAGTCCTTTAACGACTATCTCTCCGCCGCCAAC

 661  M  L  Y  P  I  P  A  N  A  T  N  V  P  I  S  I  P  S  R  N
1981  ATGCTCTACCCTATACCCGCCAACGCTACCAACGTGCCCATATCCATCCCCTCCCGCAAC

 681  W  A  A  F  R  G  W  A  F  T  R  L  K  T  K  E  T  P  S  L
2041  TGGGCGGCTTTCCGCGGCTGGGCCTTCACGCGCCTTAAGACTAAGGAAACCCCATCACTG

 701  G  S  G  Y  D  P  Y  Y  T  Y  S  G  S  I  P  Y  L  D  G  T
2101  GGCTCGGGCTACGACCCTTATTACACCTACTCTGGCTCTATACCCTACCTAGATGGAACC

 721  F  Y  L  N  H  T  F  K  K  V  A  I  T  F  D  S  S  V  S  W
2161  TTTTACCTCAACCACACCTTTAAGAAGGTGGCCATTACCTTTGACTCTTCTGTCAGCTGG

 741  P  G  N  D  R  L  L  T  P  N  E  F  E  I  K  R  S  V  D  G
2221  CCTGGCAATGACCGCCTGCTTACCCCCAACGAGTTTGAAATTAAGCGCTCAGTTGACGGG

 761  E  G  Y  N  V  A  Q  C  N  M  T  K  D  W  F  L  V  Q  M  L
2281  GAGGGTTACAACGTTGCCCAGTGTAACATGACCAAAGACTGGTTCCTGGTACAAATGCTA

 781  A  N  Y  N  I  G  Y  Q  G  F  Y  I  P  E  S  Y  K  D  R  M
2341  GCTAACTATAACATTGGCTACCAGGGCTTCTATATCCCAGAGAGCTACAAGGACCGCATG

 801  Y  S  F  F  R  N  F  Q  P  M  S  R  Q  V  V  D  D  T  K  Y
2401  TACTCCTTCTTTAGAAACTTCCAGCCCATGAGCCGTCAGGTGGTGGATGATACTAAATAC
```

Fig. 25B

```
 821  K  D  Y  Q  Q  V  G  I  L  H  Q  H  N  N  S  G  F  V  G  Y
2461  AAGGACTACCAACAGGTGGGCATCCTACACCAACACAACAACTCTGGATTTGTTGGCTAC

 841  L  A  P  T  M  R  E  G  Q  A  Y  P  A  N  F  P  Y  P  L  I
2521  CTTGCCCCCACCATGCGCGAAGGACAGGCCTACCCTGCTAACTTCCCCTATCCGCTTATA

 861  G  K  T  A  V  D  S  I  T  Q  K  K  F  L  C  D  R  T  L  W
2581  GGCAAGACCGCAGTTGACAGCATTACCCAGAAAAAGTTTCTTTGCGATCGCACCCTTTGG

 881  R  I  P  F  S  S  N  F  M  S  M  G  A  L  T  D  L  G  Q  N
2641  CGCATCCCATTCTCCAGTAACTTTATGTCCATGGGCGCACTCACAGACCTGGGCCAAAAC

 901  L  L  Y  A  N  S  A  H  A  L  D  M  T  F  E  V  D  P  M  D
2701  CTTCTCTACGCCAACTCCGCCCACGCGCTAGACATGACTTTTGAGGTGGATCCCATGGAC

 921  E  P  T  L  L  Y  V  L  F  E  V  F  D  V  V  R  V  H  Q  P
2761  GAGCCCACCCTTCTTTATGTTTTGTTTGAAGTCTTTGACGTGGTCCGTGTGCACCAGCCG

 941  H  R  G  V  I  E  T  V  Y  L  R  T  P  F  S  A  G  N  A  T
2821  CACCGCGGCGTCATCGAAACCGTGTACCTGCGCACGCCCTTCTCGGCCGGCAACGCCACA

 961  T  -
2881  ACATAA
```

Fig. 25C

Hexon sequence of $(NANP)_{16}$-HVR1 adenovirus SEQ IDNOS : 18 and 50

```
   1  M A T P S M M P Q W S Y M H I S G Q D A
   1  ATGGCTACCCCTTCGATGATGCCGCAGTGGTCTTACATGCACATCTCGGGCCAGGACGCC

  21  S E Y L S P G L V Q F A R A T E T Y F S
  61  TCGGAGTACCTGAGCCCCGGGCTGGTGCAGTTTGCCCGCGCCACCGAGACGTACTTCAGC

  41  L N N K F R N P T V A P T H D V T T D R
 121  CTGAATAACAAGTTTAGAAACCCCACGGTGGCGCCTACGCACGACGTGACCACAGACCGG

  61  S Q R L T L R F I P V D R E D T A Y S Y
 181  TCCCAGCGTTTGACGCTGCGGTTCATCCCTGTGGACCGTGAGGATACTGCGTACTCGTAC

  81  K A R F T L A V G D N R V L D M A S T Y
 241  AAGGCGCGGTTCACCCTAGCTGTGGGTGATAACCGTGTGCTGGACATGGCTTCCACGTAC

 101  F D I R G V L D R G P T F K P Y S G T A
 301  TTTGACATCCGCGGCGTGCTGGACAGGGGCCCTACTTTTAAGCCCTACTCTGGCACTGCC

 121  Y N A L A P K G A P N P C E W D E N A N
 361  TACAACGCCCTGGCTCCCAAGGGTGCCCCAAATCCTTGCGAATGGGATGAAAATGCAAAT

 141  P N A N P N A N P N A N P N A N P N A N
 421  CCAAATGCAAATCCAAATGCAAATCCAAATGCAAATCCAAATGCAAATCCAAATGCAAAT

 161  P N A N P N A N P N A N P N A N P N A N
 481  CCAAATGCAAATCCAAATGCAAATCCAAACGCGAACCCGAATGCTAATCCTAATGCAAAT

 181  P N A N P N A N P N A N P N A N P N A N
 541  CCAAATGCAAATCCAAATGCAAATCCAAATGCAAATCCAAATGCAAATCCAAATGCAAAT

 201  P K T H V F G Q A P Y S G I N I T K E G
 601  CCAAAAACTCACGTATTTGGGCAGGCGCCTTATTCTGGTATAAATATTACAAAGGAGGGT

 221  I Q I G V E G Q T P K Y A D K T F Q P E
 661  ATTCAAATAGGTGTCGAAGGTCAAACACCTAAATATGCCGATAAAACATTTCAACCTGAA

 241  P Q I G E S Q W Y E T E I N H A A G R V
 721  CCTCAAATAGGAGAATCTCAGTGGTACGAAACAGAAATTAATCATGCAGCTGGGAGAGTC

 261  L K K T T P M K P C Y G S Y A K P T N E
 781  CTAAAAAAGACTACCCCAATGAAACCATGTTACGGTTCATATGCAAAACCCACAAATGAA

 281  N G G Q G I L V K Q Q N G K L E S Q V E
 841  AATGGAGGGCAAGGCATTCTTGTAAAGCAACAAAATGGAAAGCTAGAAAGTCAAGTGGAA

 301  M Q F F S T T E A A A G N G D N L T P K
 901  ATGCAATTTTTCTCAACTACTGAGGCAGCCGCAGGCAATGGTGATAACTTGACTCCTAAA

 321  V V L Y S E D V D I E T P D T H I S Y M
 961  GTGGTATTGTACAGTGAAGATGTAGATATAGAAACCCCAGACACTCATATTTCTTACATG

 341  P T I K E G N S R E L M G Q Q S M P N R
1021  CCCACTATTAAGGAAGGTAACTCACGAGAACTAATGGGCCAACAATCTATGCCCAACAGG

 361  P N Y I A F R D N F I G L M Y Y N S T G
1081  CCTAATTACATTGCTTTTAGGGACAATTTTATTGGTCTAATGTATTACAACAGCACGGGT

 381  N M G V L A G Q A S Q L N A V V D L Q D
1141  AATATGGGTGTTCTGGCGGGCCAAGCATCGCAGTTGAATGCTGTTGTAGATTTGCAAGAC
```

Fig. 26A

```
 401  R  N  T  E  L  S  Y  Q  L  L  L  D  S  I  G  D  R  T  R  Y
1201  AGAAACACAGAGCTTTCATACCAGCTTTTGCTTGATTCCATTGGTGATAGAACCAGGTAC

 421  F  S  M  W  N  Q  L  P  N  Y  C  F  P  L  G  G  V  I  N  T
1261  TTTTCTATGTGGAATCAGCTTCCAAATTACTGCTTTCCACTGGGAGGTGTGATTAATACA

 441  E  T  L  T  K  V  K  P  K  T  G  Q  E  N  G  W  E  K  D  A
1321  GAGACTCTTACCAAGGTAAAACCTAAAACAGGTCAGGAAAATGGATGGGAAAAAGATGCT

 461  T  E  F  S  D  K  N  E  I  R  V  G  N  N  F  A  M  E  I  N
1381  ACAGAATTTTCAGATAAAAATGAAATAAGAGTTGGAAATAATTTTGCCATGGAAATCAAT

 481  L  N  A  N  L  W  R  N  F  L  Y  S  N  I  A  L  Y  L  P  D
1441  CTAAATGCCAACCTGTGGAGAAATTTCCTGTACTCCAACATAGCGCTGTATTTGCCCGAC

 501  K  L  K  Y  S  P  S  N  V  K  I  S  D  N  P  N  T  Y  D  Y
1501  AAGCTAAAGTACAGTCCTTCCAACGTAAAAATTTCTGATAACCCAAACACCTACGACTAC

 521  M  N  K  R  V  V  A  P  G  L  V  D  C  Y  I  N  L  G  A  R
1561  ATGAACAAGCGAGTGGTGGCTCCCGGGCTAGTGGACTGCTACATTAACCTTGGAGCACGC

 541  W  S  L  D  Y  M  D  N  V  N  P  F  N  H  H  R  N  A  G  L
1621  TGGTCCCTTGACTATATGGACAACGTCAACCCATTTAACCACCACCGCAATGCTGGCCTG

 561  R  Y  R  S  M  L  L  G  N  G  R  Y  V  P  F  H  I  Q  V  P
1681  CGCTACCGCTCAATGTTGCTGGGCAATGGTCGCTATGTGCCCTTCCACATCCAGGTGCCT

 581  Q  K  F  F  A  I  K  N  L  L  L  L  P  G  S  Y  T  Y  E  W
1741  CAGAAGTTCTTTGCCATTAAAAACCTCCTTCTCCTGCCGGGCTCATACACCTACGAGTGG

 601  N  F  R  K  D  V  N  M  V  L  Q  S  S  L  G  N  D  L  R  V
1801  AACTTCAGGAAGGATGTTAACATGGTTCTGCAGAGCTCCCTAGGAAATGACCTAAGGGTT

 621  D  G  A  S  I  K  F  D  S  I  C  L  Y  A  T  F  F  P  M  A
1861  GACGGAGCCAGCATTAAGTTTGATAGCATTTGCCTTTACGCCACCTTCTTCCCCATGGCC

 641  H  N  T  A  S  T  L  E  A  M  L  R  N  D  T  N  D  Q  S  F
1921  CACAACACCGCCTCCACGCTTGAGGCCATGCTTAGAAACGACACCAACGACCAGTCCTTT

 661  N  D  Y  L  S  A  A  N  M  L  Y  P  I  P  A  N  A  T  N  V
1981  AACGACTATCTCTCCGCCGCCAACATGCTCTACCCTATACCCGCCAACGCTACCAACGTG

 681  P  I  S  I  P  S  R  N  W  A  A  F  R  G  W  A  F  T  R  L
2041  CCCATATCCATCCCCTCCCGCAACTGGGCGGCTTTCCGCGGCTGGGCCTTCACGCGCCTT

 701  K  T  K  E  T  P  S  L  G  S  G  Y  D  P  Y  Y  T  Y  S  G
2101  AAGACTAAGGAAACCCCATCACTGGGCTCGGGCTACGACCCTTATTACACCTACTCTGGC

 721  S  I  P  Y  L  D  G  T  F  Y  L  N  H  T  F  K  K  V  A  I
2161  TCTATACCCTACCTAGATGGAACCTTTTACCTCAACCACACCTTTAAGAAGGTGGCCATT

 741  T  F  D  S  S  V  S  W  P  G  N  D  R  L  L  T  P  N  E  F
2221  ACCTTTGACTCTTCTGTCAGCTGGCCTGGCAATGACCGCCTGCTTACCCCCAACGAGTTT

 761  E  I  K  R  S  V  D  G  E  G  Y  N  V  A  Q  C  N  M  T  K
2281  GAAATTAAGCGCTCAGTTGACGGGGAGGGTTACAACGTTGCCCAGTGTAACATGACCAAA

 781  D  W  F  L  V  Q  M  L  A  N  Y  N  I  G  Y  Q  G  F  Y  I
2341  GACTGGTTCCTGGTACAAATGCTAGCTAACTATAACATTGGCTACCAGGGCTTCTATATC

 801  P  E  S  Y  K  D  R  M  Y  S  F  F  R  N  F  Q  P  M  S  R
2401  CCAGAGAGCTACAAGGACCGCATGTACTCCTTCTTTAGAAACTTCCAGCCCATGAGCCGT
```

Fig. 26B

```
 821  Q  V  V  D  D  T  K  Y  K  D  Y  Q  Q  V  G  I  L  H  Q  H
2461  CAGGTGGTGGATGATACTAAATACAAGGACTACCAACAGGTGGGCATCCTACACCAACAC

 841  N  N  S  G  F  V  G  Y  L  A  P  T  M  R  E  G  Q  A  Y  P
2521  AACAACTCTGGATTTGTTGGCTACCTTGCCCCCACCATGCGCGAAGGACAGGCCTACCCT

 861  A  N  F  P  Y  P  L  I  G  K  T  A  V  D  S  I  T  Q  K  K
2581  GCTAACTTCCCCTATCCGCTTATAGGCAAGACCGCAGTTGACAGCATTACCCAGAAAAAG

 881  F  L  C  D  R  T  L  W  R  I  P  F  S  S  N  F  M  S  M  G
2641  TTTCTTTGCGATCGCACCCTTTGGCGCATCCCATTCTCCAGTAACTTTATGTCCATGGGC

 901  A  L  T  D  L  G  Q  N  L  L  Y  A  N  S  A  H  A  L  D  M
2701  GCACTCACAGACCTGGGCCAAAACCTTCTCTACGCCAACTCCGCCCACGCGCTAGACATG

 921  T  F  E  V  D  P  M  D  E  P  T  L  L  Y  V  L  F  E  V  F
2761  ACTTTTGAGGTGGATCCCATGGACGAGCCCACCCTTCTTTATGTTTTGTTTGAAGTCTTT

 941  D  V  V  R  V  H  Q  P  H  R  G  V  I  E  T  V  Y  L  R  T
2821  GACGTGGTCCGTGTGCACCAGCCGCACCGCGGCGTCATCGAAACCGTGTACCTGCGCACG

 961  P  F  S  A  G  N  A  T  T  -
2881  CCCTTCTCGGCCGGCAACGCCACAACATAA
```

Fig. 26C

Hexon sequence of $(NANP)_{18}$-HVR1 adenovirus SEQ IDNOS : 19 and 51

```
   1  M  A  T  P  S  M  M  P  Q  W  S  Y  M  H  I  S  G  Q  D  A
   1  ATGGCTACCCCTTCGATGATGCCGCAGTGGTCTTACATGCACATCTCGGGCCAGGACGCC

  21  S  E  Y  L  S  P  G  L  V  Q  F  A  R  A  T  E  T  Y  F  S
  61  TCGGAGTACCTGAGCCCCGGGCTGGTGCAGTTTGCCCGCGCCACCGAGACGTACTTCAGC

  41  L  N  N  K  F  R  N  P  T  V  A  P  T  H  D  V  T  T  D  R
 121  CTGAATAACAAGTTTAGAAACCCCACGGTGGCGCCTACGCACGACGTGACCACAGACCGG

  61  S  Q  R  L  T  L  R  F  I  P  V  D  R  E  D  T  A  Y  S  Y
 181  TCCCAGCGTTTGACGCTGCGGTTCATCCCTGTGGACCGTGAGGATACTGCGTACTCGTAC

  81  K  A  R  F  T  L  A  V  G  D  N  R  V  L  D  M  A  S  T  Y
 241  AAGGCGCGGTTCACCCTAGCTGTGGGTGATAACCGTGTGCTGGACATGGCTTCCACGTAC

 101  F  D  I  R  G  V  L  D  R  G  P  T  F  K  P  Y  S  G  T  A
 301  TTTGACATCCGCGGCGTGCTGGACAGGGGCCCTACTTTTAAGCCCTACTCTGGCACTGCC

 121  Y  N  A  L  A  P  K  G  A  P  N  P  C  E  W  D  E  N  A  N
 361  TACAACGCCCTGGCTCCCAAGGGTGCCCCAAATCCTTGCGAATGGGATGAAAATGCAAAT

 141  P  N  A  N  P  N  A  N  P  N  A  N  P  N  A  N  P  N  A  N
 421  CCAAATGCAAATCCAAATGCAAATCCAAATGCAAATCCAAATGCAAATCCAAATGCAAAT

 161  P  N  A  N  P  N  A  N  P  N  A  N  P  N  A  N  P  N  A  N
 481  CCAAATGCAAATCCAAATGCAAATCCAAATGCAAATCCAAATGCAAATCCAAATGCAAAT

 181  P  N  A  N  P  N  A  N  P  N  A  N  P  N  A  N  P  N  A  N
 541  CCAAATGCAAATCCAAACGCGAACCCGAATGCTAATCCTAATGCAAATCCAAATGCAAAT

 201  P  N  A  N  P  N  A  N  P  K  T  H  V  F  G  Q  A  P  Y  S
 601  CCAAATGCAAATCCAAATGCAAATCCAAAAACTCACGTATTTGGGCAGGCGCCTTATTCT

 221  G  I  N  I  T  K  E  G  I  Q  I  G  V  E  G  Q  T  P  K  Y
 661  GGTATAAATATTACAAAGGAGGGTATTCAAATAGGTGTCGAAGGTCAAACACCTAAATAT

 241  A  D  K  T  F  Q  P  E  P  Q  I  G  E  S  Q  W  Y  E  T  E
 721  GCCGATAAAACATTTCAACCTGAACCTCAAATAGGAGAATCTCAGTGGTACGAAACAGAA

 261  I  N  H  A  A  G  R  V  L  K  K  T  T  P  M  K  P  C  Y  G
 781  ATTAATCATGCAGCTGGGAGAGTCCTAAAAAAGACTACCCCAATGAAACCATGTTACGGT

 281  S  Y  A  K  P  T  N  E  N  G  G  Q  G  I  L  V  K  Q  Q  N
 841  TCATATGCAAAACCCACAAATGAAAATGGAGGGCAAGGCATTCTTGTAAAGCAACAAAAT

 301  G  K  L  E  S  Q  V  E  M  Q  F  F  S  T  T  E  A  A  A  G
 901  GGAAAGCTAGAAAGTCAAGTGGAAATGCAATTTTTCTCAACTACTGAGGCAGCCGCAGGC

 321  N  G  D  N  L  T  P  K  V  V  L  Y  S  E  D  V  D  I  E  T
 961  AATGGTGATAACTTGACTCCTAAAGTGGTATTGTACAGTGAAGATGTAGATATAGAAACC

 341  P  D  T  H  I  S  Y  M  P  T  I  K  E  G  N  S  R  E  L  M
1021  CCAGACACTCATATTTCTTACATGCCCACTATTAAGGAAGGTAACTCACGAGAACTAATG

 361  G  Q  Q  S  M  P  N  R  P  N  Y  I  A  F  R  D  N  F  I  G
1081  GGCCAACAATCTATGCCCAACAGGCCTAATTACATTGCTTTTAGGGACAATTTTATTGGT

 381  L  M  Y  Y  N  S  T  G  N  M  G  V  L  A  G  Q  A  S  Q  L
1141  CTAATGTATTACAACAGCACGGGTAATATGGGTGTTCTGGCGGGCCAAGCATCGCAGTTG
```

Fig. 27A

```
401  N A V V D L Q D R N T E L S Y Q L L L D
1201 AATGCTGTTGTAGATTTGCAAGACAGAAACACAGAGCTTTCATACCAGCTTTTGCTTGAT

421  S I G D R T R Y F S M W N Q L P N Y C F
1261 TCCATTGGTGATAGAACCAGGTACTTTTCTATGTGGAATCAGCTTCCAAATTACTGCTTT

441  P L G G V I N T E T L T K V K P K T G Q
1321 CCACTGGGAGGTGTGATTAATACAGAGACTCTTACCAAGGTAAAACCTAAAACAGGTCAG

461  E N G W E K D A T E F S D K N E I R V G
1381 GAAAATGGATGGGAAAAAGATGCTACAGAATTTTCAGATAAAAATGAAATAAGAGTTGGA

481  N N F A M E I N L N A N L W R N F L Y S
1441 AATAATTTTGCCATGGAAATCAATCTAAATGCCAACCTGTGGAGAAATTTCCTGTACTCC

501  N I A L Y L P D K L K Y S P S N V K I S
1501 AACATAGCGCTGTATTTGCCCGACAAGCTAAAGTACAGTCCTTCCAACGTAAAAATTTCT

521  D N P N T Y D Y M N K R V V A P G L V D
1561 GATAACCCAAACACCTACGACTACATGAACAAGCGAGTGGTGGCTCCCGGGCTAGTGGAC

541  C Y I N L G A R W S L D Y M D N V N P F
1621 TGCTACATTAACCTTGGAGCACGCTGGTCCCTTGACTATATGGACAACGTCAACCCATTT

561  N H H R N A G L R Y R S M L L G N G R Y
1681 AACCACCACCGCAATGCTGGCCTGCGCTACCGCTCAATGTTGCTGGGCAATGGTCGCTAT

581  V P F H I Q V P Q K F F A I K N L L L L
1741 GTGCCCTTCCACATCCAGGTGCCTCAGAAGTTCTTTGCCATTAAAAACCTCCTTCTCCTG

601  P G S Y T Y E W N F R K D V N M V L Q S
1801 CCGGGCTCATACACCTACGAGTGGAACTTCAGGAAGGATGTTAACATGGTTCTGCAGAGC

621  S L G N D L R V D G A S I K F D S I C L
1861 TCCCTAGGAAATGACCTAAGGGTTGACGGAGCCAGCATTAAGTTTGATAGCATTTGCCTT

641  Y A T F F P M A H N T A S T L E A M L R
1921 TACGCCACCTTCTTCCCCATGGCCCACAACACCGCCTCCACGCTTGAGGCCATGCTTAGA

661  N D T N D Q S F N D Y L S A A N M L Y P
1981 AACGACACCAACGACCAGTCCTTTAACGACTATCTCTCCGCCGCCAACATGCTCTACCCT

681  I P A N A T N V P I S I P S R N W A A F
2041 ATACCCGCCAACGCTACCAACGTGCCCATATCCATCCCCTCCCGCAACTGGGCGGCTTTC

701  R G W A F T R L K T K E T P S L G S G Y
2101 CGCGGCTGGGCCTTCACGCGCCTTAAGACTAAGGAAACCCCATCACTGGGCTCGGGCTAC

721  D P Y Y T Y S G S I P Y L D G T F Y L N
2161 GACCCTTATTACACCTACTCTGGCTCTATACCCTACCTAGATGGAACCTTTTACCTCAAC

741  H T F K K V A I T F D S S V S W P G N D
2221 CACACCTTTAAGAAGGTGGCCATTACCTTTGACTCTTCTGTCAGCTGGCCTGGCAATGAC

761  R L L T P N E F E I K R S V D G E G Y N
2281 CGCCTGCTTACCCCCAACGAGTTTGAAATTAAGCGCTCAGTTGACGGGGAGGGTTACAAC

781  V A Q C N M T K D W F L V Q M L A N Y N
2341 GTTGCCCAGTGTAACATGACCAAAGACTGGTTCCTGGTACAAATGCTAGCTAACTATAAC

801  I G Y Q G F Y I P E S Y K D R M Y S F F
2401 ATTGGCTACCAGGGCTTCTATATCCCAGAGAGCTACAAGGACCGCATGTACTCCTTCTTT
```

Fig. 27B

```
 821  R  N  F  Q  P  M  S  R  Q  V  V  D  D  T  K  Y  K  D  Y  Q
2461  AGAAACTTCCAGCCCATGAGCCGTCAGGTGGTGGATGATACTAAATACAAGGACTACCAA

 841  Q  V  G  I  L  H  Q  H  N  N  S  G  F  V  G  Y  L  A  P  T
2521  CAGGTGGGCATCCTACACCAACACAACAACTCTGGATTTGTTGGCTACCTTGCCCCCACC

 861  M  R  E  G  Q  A  Y  P  A  N  F  P  Y  P  L  I  G  K  T  A
2581  ATGCGCGAAGGACAGGCCTACCCTGCTAACTTCCCCTATCCGCTTATAGGCAAGACCGCA

 881  V  D  S  I  T  Q  K  K  F  L  C  D  R  T  L  W  R  I  P  F
2641  GTTGACAGCATTACCCAGAAAAAGTTTCTTTGCGATCGCACCCTTTGGCGCATCCCATTC

 901  S  S  N  F  M  S  M  G  A  L  T  D  L  G  Q  N  L  L  Y  A
2701  TCCAGTAACTTTATGTCCATGGGCGCACTCACAGACCTGGGCCAAAACCTTCTCTACGCC

 921  N  S  A  H  A  L  D  M  T  F  E  V  D  P  M  D  E  P  T  L
2761  AACTCCGCCCACGCGCTAGACATGACTTTTGAGGTGGATCCCATGGACGAGCCCACCCTT

 941  L  Y  V  L  F  E  V  F  D  V  V  R  V  H  Q  P  H  R  G  V
2821  CTTTATGTTTTGTTTGAAGTCTTTGACGTGGTCCGTGTGCACCAGCCGCACCGCGGCGTC

 961  I  E  T  V  Y  L  R  T  P  F  S  A  G  N  A  T  T  -
2881  ATCGAAACCGTGTACCTGCGCACGCCCTTCTCGGCCGGCAACGCCACAACATAA
```

Fig. 27C

Hexon sequence of $(NANP)_{20}$-HVR1 adenovirus SEQ IDNOS : 20 and 52

```
   1  M  A  T  P  S  M  M  P  Q  W  S  Y  M  H  I  S  G  Q  D  A
   1  ATGGCTACCCCTTCGATGATGCCGCAGTGGTCTTACATGCACATCTCGGGCCAGGACGCC

  21  S  E  Y  L  S  P  G  L  V  Q  F  A  R  A  T  E  T  Y  F  S
  61  TCGGAGTACCTGAGCCCCGGGCTGGTGCAGTTTGCCCGCGCCACCGAGACGTACTTCAGC

  41  L  N  N  K  F  R  N  P  T  V  A  P  T  H  D  V  T  T  D  R
 121  CTGAATAACAAGTTTAGAAACCCCACGGTGGCGCCTACGCACGACGTGACCACAGACCGG

  61  S  Q  R  L  T  L  R  F  I  P  V  D  R  E  D  T  A  Y  S  Y
 181  TCCCAGCGTTTGACGCTGCGGTTCATCCCTGTGGACCGTGAGGATACTGCGTACTCGTAC

  81  K  A  R  F  T  L  A  V  G  D  N  R  V  L  D  M  A  S  T  Y
 241  AAGGCGCGGTTCACCCTAGCTGTGGGTGATAACCGTGTGCTGGACATGGCTTCCACGTAC

 101  F  D  I  R  G  V  L  D  R  G  P  T  F  K  P  Y  S  G  T  A
 301  TTTGACATCCGCGGCGTGCTGGACAGGGGCCCTACTTTTAAGCCCTACTCTGGCACTGCC

 121  Y  N  A  L  A  P  K  G  A  P  N  P  C  E  W  D  E  N  A  N
 361  TACAACGCCCTGGCTCCCAAGGGTGCCCCAAATCCTTGCGAATGGGATGAAAATGCAAAT

 141  P  N  A  N  P  N  A  N  P  N  A  N  P  N  A  N  P  N  A  N
 421  CCAAATGCAAATCCAAATGCAAATCCAAATGCAAATCCAAATGCAAATCCAAATGCAAAT

 161  P  N  A  N  P  N  A  N  P  N  A  N  P  N  A  N  P  N  A  N
 481  CCAAATGCAAATCCAAATGCAAATCCAAATGCAAATCCAAATGCAAATCCAAATGCAAAT

 181  P  N  A  N  P  N  A  N  P  N  A  N  P  N  A  N  P  N  A  N
 541  CCAAATGCAAATCCAAACGCGAACCCGAATGCTAATCCTAATGCAAATCCAAATGCAAAT

 201  P  N  A  N  P  N  A  N  P  N  A  N  P  N  A  N  P  K  T  H
 601  CCAAATGCAAATCCAAATGCAAATCCAAATGCAAATCCAAATGCAAATCCAAAAACTCAC

 221  V  F  G  Q  A  P  Y  S  G  I  N  I  T  K  E  G  I  Q  I  G
 661  GTATTTGGGCAGGCGCCTTATTCTGGTATAAATATTACAAAGGAGGGTATTCAAATAGGT

 241  V  E  G  Q  T  P  K  Y  A  D  K  T  F  Q  P  E  P  Q  I  G
 721  GTCGAAGGTCAAACACCTAAATATGCCGATAAAACATTTCAACCTGAACCTCAAATAGGA

 261  E  S  Q  W  Y  E  T  E  I  N  H  A  A  G  R  V  L  K  K  T
 781  GAATCTCAGTGGTACGAAACAGAAATTAATCATGCAGCTGGGAGAGTCCTAAAAAAGACT

 281  T  P  M  K  P  C  Y  G  S  Y  A  K  P  T  N  E  N  G  G  Q
 841  ACCCCAATGAAACCATGTTACGGTTCATATGCAAAACCCACAAATGAAAATGGAGGGCAA

 301  G  I  L  V  K  Q  Q  N  G  K  L  E  S  Q  V  E  M  Q  F  F
 901  GGCATTCTTGTAAAGCAACAAAATGGAAAGCTAGAAAGTCAAGTGGAAATGCAATTTTTC

 321  S  T  T  E  A  A  A  G  N  G  D  N  L  T  P  K  V  V  L  Y
 961  TCAACTACTGAGGCAGCCGCAGGCAATGGTGATAACTTGACTCCTAAAGTGGTATTGTAC

 341  S  E  D  V  D  I  E  T  P  D  T  H  I  S  Y  M  P  T  I  K
1021  AGTGAAGATGTAGATATAGAAACCCCAGACACTCATATTTCTTACATGCCCACTATTAAG

 361  E  G  N  S  R  E  L  M  G  Q  Q  S  M  P  N  R  P  N  Y  I
1081  GAAGGTAACTCACGAGAACTAATGGGCCAACAATCTATGCCCAACAGGCCTAATTACATT

 381  A  F  R  D  N  F  I  G  L  M  Y  Y  N  S  T  G  N  M  G  V
1141  GCTTTTAGGGACAATTTTATTGGTCTAATGTATTACAACAGCACGGGTAATATGGGTGTT
```

Fig. 28A

```
 401  L  A  G  Q  A  S  Q  L  N  A  V  V  D  L  Q  D  R  N  T  E
1201  CTGGCGGGCCAAGCATCGCAGTTGAATGCTGTTGTAGATTTGCAAGACAGAAACACAGAG

 421  L  S  Y  Q  L  L  L  D  S  I  G  D  R  T  R  Y  F  S  M  W
1261  CTTTCATACCAGCTTTTGCTTGATTCCATTGGTGATAGAACCAGGTACTTTTCTATGTGG

 441  N  Q  L  P  N  Y  C  F  P  L  G  G  V  I  N  T  E  T  L  T
1321  AATCAGCTTCCAAATTACTGCTTTCCACTGGGAGGTGTGATTAATACAGAGACTCTTACC

 461  K  V  K  P  K  T  G  Q  E  N  G  W  E  K  D  A  T  E  F  S
1381  AAGGTAAAACCTAAAACAGGTCAGGAAAATGGATGGGAAAAAGATGCTACAGAATTTTCA

 481  D  K  N  E  I  R  V  G  N  N  F  A  M  E  I  N  L  N  A  N
1441  GATAAAAATGAAATAAGAGTTGGAAATAATTTTGCCATGGAAATCAATCTAAATGCCAAC

 501  L  W  R  N  F  L  Y  S  N  I  A  L  Y  L  P  D  K  L  K  Y
1501  CTGTGGAGAAATTTCCTGTACTCCAACATAGCGCTGTATTTGCCCGACAAGCTAAAGTAC

 521  S  P  S  N  V  K  I  S  D  N  P  N  T  Y  D  Y  M  N  K  R
1561  AGTCCTTCCAACGTAAAAATTTCTGATAACCCAAACACCTACGACTACATGAACAAGCGA

 541  V  V  A  P  G  L  V  D  C  Y  I  N  L  G  A  R  W  S  L  D
1621  GTGGTGGCTCCCGGGCTAGTGGACTGCTACATTAACCTTGGAGCACGCTGGTCCCTTGAC

 561  Y  M  D  N  V  N  P  F  N  H  H  R  N  A  G  L  R  Y  R  S
1681  TATATGGACAACGTCAACCCATTTAACCACCACCGCAATGCTGGCCTGCGCTACCGCTCA

 581  M  L  L  G  N  G  R  Y  V  P  F  H  I  Q  V  P  Q  K  F  F
1741  ATGTTGCTGGGCAATGGTCGCTATGTGCCCTTCCACATCCAGGTGCCTCAGAAGTTCTTT

 601  A  I  K  N  L  L  L  L  P  G  S  Y  T  Y  E  W  N  F  R  K
1801  GCCATTAAAAACCTCCTTCTCCTGCCGGGCTCATACACCTACGAGTGGAACTTCAGGAAG

 621  D  V  N  M  V  L  Q  S  S  L  G  N  D  L  R  V  D  G  A  S
1861  GATGTTAACATGGTTCTGCAGAGCTCCCTAGGAAATGACCTAAGGGTTGACGGAGCCAGC

 641  I  K  F  D  S  I  C  L  Y  A  T  F  F  P  M  A  H  N  T  A
1921  ATTAAGTTTGATAGCATTTGCCTTTACGCCACCTTCTTCCCCATGGCCCACAACACCGCC

 661  S  T  L  E  A  M  L  R  N  D  T  N  D  Q  S  F  N  D  Y  L
1981  TCCACGCTTGAGGCCATGCTTAGAAACGACACCAACGACCAGTCCTTTAACGACTATCTC

 681  S  A  A  N  M  L  Y  P  I  P  A  N  A  T  N  V  P  I  S  I
2041  TCCGCCGCCAACATGCTCTACCCTATACCCGCCAACGCTACCAACGTGCCCATATCCATC

 701  P  S  R  N  W  A  A  F  R  G  W  A  F  T  R  L  K  T  K  E
2101  CCCTCCCGCAACTGGGCGGCTTTCCGCGGCTGGGCCTTCACGCGCCTTAAGACTAAGGAA

 721  T  P  S  L  G  S  G  Y  D  P  Y  Y  T  Y  S  G  S  I  P  Y
2161  ACCCCATCACTGGGCTCGGGCTACGACCCTTATTACACCTACTCTGGCTCTATACCCTAC

 741  L  D  G  T  F  Y  L  N  H  T  F  K  K  V  A  I  T  F  D  S
2221  CTAGATGGAACCTTTTACCTCAACCACACCTTTAAGAAGGTGGCCATTACCTTTGACTCT

 761  S  V  S  W  P  G  N  D  R  L  L  T  P  N  E  F  E  I  K  R
2281  TCTGTCAGCTGGCCTGGCAATGACCGCCTGCTTACCCCCAACGAGTTTGAAATTAAGCGC

 781  S  V  D  G  E  G  Y  N  V  A  Q  C  N  M  T  K  D  W  F  L
2341  TCAGTTGACGGGGAGGGTTACAACGTTGCCCAGTGTAACATGACCAAAGACTGGTTCCTG

 801  V  Q  M  L  A  N  Y  N  I  G  Y  Q  G  F  Y  I  P  E  S  Y
2401  GTACAAATGCTAGCTAACTATAACATTGGCTACCAGGGCTTCTATATCCCAGAGAGCTAC
```

Fig. 28B

```
 821  K D R M Y S F F R N F Q P M S R Q V V D
2461  AAGGACCGCATGTACTCCTTCTTTAGAAACTTCCAGCCCATGAGCCGTCAGGTGGTGGAT

 841  D T K Y K D Y Q Q V G I L H Q H N N S G
2521  GATACTAAATACAAGGACTACCAACAGGTGGGCATCCTACACCAACACAACAACTCTGGA

 861  F V G Y L A P T M R E G Q A Y P A N F P
2581  TTTGTTGGCTACCTTGCCCCCACCATGCGCGAAGGACAGGCCTACCCTGCTAACTTCCCC

 881  Y P L I G K T A V D S I T Q K K F L C D
2641  TATCCGCTTATAGGCAAGACCGCAGTTGACAGCATTACCCAGAAAAAGTTTCTTTGCGAT

 901  R T L W R I P F S S N F M S M G A L T D
2701  CGCACCCTTTGGCGCATCCCATTCTCCAGTAACTTTATGTCCATGGGCGCACTCACAGAC

 921  L G Q N L L Y A N S A H A L D M T F E V
2761  CTGGGCCAAAACCTTCTCTACGCCAACTCCGCCCACGCGCTAGACATGACTTTTGAGGTG

 941  D P M D E P T L L Y V L F E V F D V V R
2821  GATCCCATGGACGAGCCCACCCTTCTTTATGTTTTGTTTGAAGTCTTTGACGTGGTCCGT

 961  V H Q P H R G V I E T V Y L R T P F S A
2881  GTGCACCAGCCGCACCGCGGCGTCATCGAAACCGTGTACCTGCGCACGCCCTTCTCGGCC

 981  G N A T T -
2941  GGCAACGCCACAACATAA
```

Fig. 28C

Hexon sequence of $(NANP)_{22}$-HVR1 adenovirus SEQ IDNOS : 21 and 53

```
   1  M  A  T  P  S  M  M  P  Q  W  S  Y  M  H  I  S  G  Q  D  A
   1  ATGGCTACCCCTTCGATGATGCCGCAGTGGTCTTACATGCACATCTCGGGCCAGGACGCC

  21  S  E  Y  L  S  P  G  L  V  Q  F  A  R  A  T  E  T  Y  F  S
  61  TCGGAGTACCTGAGCCCCGGGCTGGTGCAGTTTGCCCGCGCCACCGAGACGTACTTCAGC

  41  L  N  N  K  F  R  N  P  T  V  A  P  T  H  D  V  T  T  D  R
 121  CTGAATAACAAGTTTAGAAACCCCACGGTGGCGCCTACGCACGACGTGACCACAGACCGG

  61  S  Q  R  L  T  L  R  F  I  P  V  D  R  E  D  T  A  Y  S  Y
 181  TCCCAGCGTTTGACGCTGCGGTTCATCCCTGTGGACCGTGAGGATACTGCGTACTCGTAC

  81  K  A  R  F  T  L  A  V  G  D  N  R  V  L  D  M  A  S  T  Y
 241  AAGGCGCGGTTCACCCTAGCTGTGGGTGATAACCGTGTGCTGGACATGGCTTCCACGTAC

 101  F  D  I  R  G  V  L  D  R  G  P  T  F  K  P  Y  S  G  T  A
 301  TTTGACATCCGCGGCGTGCTGGACAGGGGCCCTACTTTTAAGCCCTACTCTGGCACTGCC

 121  Y  N  A  L  A  P  K  G  A  P  N  P  C  E  W  D  E  N  A  N
 361  TACAACGCCCTGGCTCCCAAGGGTGCCCCAAATCCTTGCGAATGGGATGAAAATGCAAAT

 141  P  N  A  N  P  N  A  N  P  N  A  N  P  N  A  N  P  N  A  N
 421  CCAAATGCAAATCCAAATGCAAATCCAAATGCAAATCCAAATGCAAATCCAAATGCAAAT

 161  P  N  A  N  P  N  A  N  P  N  A  N  P  N  A  N  P  N  A  N
 481  CCAAATGCAAATCCAAATGCAAATCCAAATGCAAATCCAAATGCAAATCCAAATGCAAAT

 181  P  N  A  N  P  N  A  N  P  N  A  N  P  N  A  N  P  N  A  N
 541  CCAAATGCAAATCCAAACGCGAACCCGAATGCTAATCCTAATGCAAATCCAAATGCAAAT

 201  P  N  A  N  P  N  A  N  P  N  A  N  P  N  A  N  P  N  A  N
 601  CCAAATGCAAATCCAAATGCAAATCCAAATGCAAATCCAAATGCAAATCCAAATGCAAAT

 221  P  N  A  N  P  K  T  H  V  F  G  Q  A  P  Y  S  G  I  N  I
 661  CCAAATGCAAATCCAAAAACTCACGTATTTGGGCAGGCGCCTTATTCTGGTATAAATATT

 241  T  K  E  G  I  Q  I  G  V  E  G  Q  T  P  K  Y  A  D  K  T
 721  ACAAAGGAGGGTATTCAAATAGGTGTCGAAGGTCAAACACCTAAATATGCCGATAAAACA

 261  F  Q  P  E  P  Q  I  G  E  S  Q  W  Y  E  T  E  I  N  H  A
 781  TTTCAACCTGAACCTCAAATAGGAGAATCTCAGTGGTACGAAACAGAAATTAATCATGCA

 281  A  G  R  V  L  K  K  T  T  P  M  K  P  C  Y  G  S  Y  A  K
 841  GCTGGGAGAGTCCTAAAAAAGACTACCCCAATGAAACCATGTTACGGTTCATATGCAAAA

 301  P  T  N  E  N  G  G  Q  G  I  L  V  K  Q  Q  N  G  K  L  E
 901  CCCACAAATGAAAATGGAGGGCAAGGCATTCTTGTAAAGCAACAAAATGGAAAGCTAGAA

 321  S  Q  V  E  M  Q  F  F  S  T  T  E  A  A  A  G  N  G  D  N
 961  AGTCAAGTGGAAATGCAATTTTTCTCAACTACTGAGGCAGCCGCAGGCAATGGTGATAAC

 341  L  T  P  K  V  V  L  Y  S  E  D  V  D  I  E  T  P  D  T  H
1021  TTGACTCCTAAAGTGGTATTGTACAGTGAAGATGTAGATATAGAAACCCCAGACACTCAT

 361  I  S  Y  M  P  T  I  K  E  G  N  S  R  E  L  M  G  Q  Q  S
1081  ATTTCTTACATGCCCACTATTAAGGAAGGTAACTCACGAGAACTAATGGGCCAACAATCT

 381  M  P  N  R  P  N  Y  I  A  F  R  D  N  F  I  G  L  M  Y  Y
1141  ATGCCCAACAGGCCTAATTACATTGCTTTTAGGGACAATTTTATTGGTCTAATGTATTAC
```

Fig. 29A

```
 401  N  S  T  G  N  M  G  V  L  A  G  Q  A  S  Q  L  N  A  V  V
1201  AACAGCACGGGTAATATGGGTGTTCTGGCGGGCCAAGCATCGCAGTTGAATGCTGTTGTA

 421  D  L  Q  D  R  N  T  E  L  S  Y  Q  L  L  L  D  S  I  G  D
1261  GATTTGCAAGACAGAAACACAGAGCTTTCATACCAGCTTTTGCTTGATTCCATTGGTGAT

 441  R  T  R  Y  F  S  M  W  N  Q  L  P  N  Y  C  F  P  L  G  G
1321  AGAACCAGGTACTTTTCTATGTGGAATCAGCTTCCAAATTACTGCTTTCCACTGGGAGGT

 461  V  I  N  T  E  T  L  T  K  V  K  P  K  T  G  Q  E  N  G  W
1381  GTGATTAATACAGAGACTCTTACCAAGGTAAAACCTAAAACAGGTCAGGAAAATGGATGG

 481  E  K  D  A  T  E  F  S  D  K  N  E  I  R  V  G  N  N  F  A
1441  GAAAAAGATGCTACAGAATTTTCAGATAAAAATGAAATAAGAGTTGGAAATAATTTTGCC

 501  M  E  I  N  L  N  A  N  L  W  R  N  F  L  Y  S  N  I  A  L
1501  ATGGAAATCAATCTAAATGCCAACCTGTGGAGAAATTTCCTGTACTCCAACATAGCGCTG

 521  Y  L  P  D  K  L  K  Y  S  P  S  N  V  K  I  S  D  N  P  N
1561  TATTTGCCCGACAAGCTAAAGTACAGTCCTTCCAACGTAAAAATTTCTGATAACCCAAAC

 541  T  Y  D  Y  M  N  K  R  V  V  A  P  G  L  V  D  C  Y  I  N
1621  ACCTACGACTACATGAACAAGCGAGTGGTGGCTCCCGGGCTAGTGGACTGCTACATTAAC

 561  L  G  A  R  W  S  L  D  Y  M  D  N  V  N  P  F  N  H  H  R
1681  CTTGGAGCACGCTGGTCCCTTGACTATATGGACAACGTCAACCCATTTAACCACCACCGC

 581  N  A  G  L  R  Y  R  S  M  L  L  G  N  G  R  Y  V  P  F  H
1741  AATGCTGGCCTGCGCTACCGCTCAATGTTGCTGGGCAATGGTCGCTATGTGCCCTTCCAC

 601  I  Q  V  P  Q  K  F  F  A  I  K  N  L  L  L  L  P  G  S  Y
1801  ATCCAGGTGCCTCAGAAGTTCTTTGCCATTAAAAACCTCCTTCTCCTGCCGGGCTCATAC

 621  T  Y  E  W  N  F  R  K  D  V  N  M  V  L  Q  S  S  L  G  N
1861  ACCTACGAGTGGAACTTCAGGAAGGATGTTAACATGGTTCTGCAGAGCTCCCTAGGAAAT

 641  D  L  R  V  D  G  A  S  I  K  F  D  S  I  C  L  Y  A  T  F
1921  GACCTAAGGGTTGACGGAGCCAGCATTAAGTTTGATAGCATTTGCCTTTACGCCACCTTC

 661  F  P  M  A  H  N  T  A  S  T  L  E  A  M  L  R  N  D  T  N
1981  TTCCCCATGGCCCACAACACCGCCTCCACGCTTGAGGCCATGCTTAGAAACGACACCAAC

 681  D  Q  S  F  N  D  Y  L  S  A  A  N  M  L  Y  P  I  P  A  N
2041  GACCAGTCCTTTAACGACTATCTCTCCGCCGCCAACATGCTCTACCCTATACCCGCCAAC

 701  A  T  N  V  P  I  S  I  P  S  R  N  W  A  A  F  R  G  W  A
2101  GCTACCAACGTGCCCATATCCATCCCCTCCCGCAACTGGGCGGCTTTCCGCGGCTGGGCC

 721  F  T  R  L  K  T  K  E  T  P  S  L  G  S  G  Y  D  P  Y  Y
2161  TTCACGCGCCTTAAGACTAAGGAAACCCCATCACTGGGCTCGGGCTACGACCCTTATTAC

 741  T  Y  S  G  S  I  P  Y  L  D  G  T  F  Y  L  N  H  T  F  K
2221  ACCTACTCTGGCTCTATACCCTACCTAGATGGAACCTTTTACCTCAACCACACCTTTAAG

 761  K  V  A  I  T  F  D  S  S  V  S  W  P  G  N  D  R  L  L  T
2281  AAGGTGGCCATTACCTTTGACTCTTCTGTCAGCTGGCCTGGCAATGACCGCCTGCTTACC

 781  P  N  E  F  E  I  K  R  S  V  D  G  E  G  Y  N  V  A  Q  C
2341  CCCAACGAGTTTGAAATTAAGCGCTCAGTTGACGGGGAGGGTTACAACGTTGCCCAGTGT

 801  N  M  T  K  D  W  F  L  V  Q  M  L  A  N  Y  N  I  G  Y  Q
2401  AACATGACCAAAGACTGGTTCCTGGTACAAATGCTAGCTAACTATAACATTGGCTACCAG
```

Fig. 29B

```
 821  G  F  Y  I  P  E  S  Y  K  D  R  M  Y  S  F  F  R  N  F  Q
2461  GGCTTCTATATCCCAGAGAGCTACAAGGACCGCATGTACTCCTTCTTTAGAAACTTCCAG

 841  P  M  S  R  Q  V  V  D  D  T  K  Y  K  D  Y  Q  Q  V  G  I
2521  CCCATGAGCCGTCAGGTGGTGGATGATACTAAATACAAGGACTACCAACAGGTGGGCATC

 861  L  H  Q  H  N  N  S  G  F  V  G  Y  L  A  P  T  M  R  E  G
2581  CTACACCAACACAACAACTCTGGATTTGTTGGCTACCTTGCCCCCACCATGCGCGAAGGA

 881  Q  A  Y  P  A  N  F  P  Y  P  L  I  G  K  T  A  V  D  S  I
2641  CAGGCCTACCCTGCTAACTTCCCCTATCCGCTTATAGGCAAGACCGCAGTTGACAGCATT

 901  T  Q  K  K  F  L  C  D  R  T  L  W  R  I  P  F  S  S  N  F
2701  ACCCAGAAAAAGTTTCTTTGCGATCGCACCCTTTGGCGCATCCCATTCTCCAGTAACTTT

 921  M  S  M  G  A  L  T  D  L  G  Q  N  L  L  Y  A  N  S  A  H
2761  ATGTCCATGGGCGCACTCACAGACCTGGGCCAAAACCTTCTCTACGCCAACTCCGCCCAC

 941  A  L  D  M  T  F  E  V  D  P  M  D  E  P  T  L  L  Y  V  L
2821  GCGCTAGACATGACTTTTGAGGTGGATCCCATGGACGAGCCCACCCTTCTTTATGTTTTG

 961  F  E  V  F  D  V  V  R  V  H  Q  P  H  R  G  V  I  E  T  V
2881  TTTGAAGTCTTTGACGTGGTCCGTGTGCACCAGCCGCACCGCGGCGTCATCGAAACCGTG

 981  Y  L  R  T  P  F  S  A  G  N  A  T  T  -
2941  TACCTGCGCACGCCCTTCTCGGCCGGCAACGCCACAACATAA
```

Fig. 29C

Hexon sequence of $(NANP)_{28}$-HVR1 adenovirus SEQ IDNOS : 22 and 54

```
   1  M  A  T  P  S  M  M  P  Q  W  S  Y  M  H  I  S  G  Q  D  A
   1  ATGGCTACCCCTTCGATGATGCCGCAGTGGTCTTACATGCACATCTCGGGCCAGGACGCC

  21  S  E  Y  L  S  P  G  L  V  Q  F  A  R  A  T  E  T  Y  F  S
  61  TCGGAGTACCTGAGCCCCGGGCTGGTGCAGTTTGCCCGCGCCACCGAGACGTACTTCAGC

  41  L  N  N  K  F  R  N  P  T  V  A  P  T  H  D  V  T  T  D  R
 121  CTGAATAACAAGTTTAGAAACCCCACGGTGGCGCCTACGCACGACGTGACCACAGACCGG

  61  S  Q  R  L  T  L  R  F  I  P  V  D  R  E  D  T  A  Y  S  Y
 181  TCCCAGCGTTTGACGCTGCGGTTCATCCCTGTGGACCGTGAGGATACTGCGTACTCGTAC

  81  K  A  R  F  T  L  A  V  G  D  N  R  V  L  D  M  A  S  T  Y
 241  AAGGCGCGGTTCACCCTAGCTGTGGGTGATAACCGTGTGCTGGACATGGCTTCCACGTAC

 101  F  D  I  R  G  V  L  D  R  G  P  T  F  K  P  Y  S  G  T  A
 301  TTTGACATCCGCGGCGTGCTGGACAGGGGCCCTACTTTTAAGCCCTACTCTGGCACTGCC

 121  Y  N  A  L  A  P  K  G  A  P  N  P  C  E  W  D  E  N  A  N
 361  TACAACGCCCTGGCTCCCAAGGGTGCCCCAAATCCTTGCGAATGGGATGAAAACGCCAAT

 141  P  N  A  N  P  N  A  N  P  N  A  N  P  N  A  N  P  N  A  N
 421  CCAAATGCGAATCCCAACGCTAATCCTAACGCAAACCCGAATGCTAACCCTAACGCAAAC

 161  P  N  A  N  P  N  A  N  P  N  A  N  P  N  A  N  P  N  A  N
 481  CCCAACGCTAACCCCAACGCGAACCCCAATGCCAACCCCAACGCCAACCCGAACGCCAAT

 181  P  N  A  N  P  N  A  N  P  N  A  N  P  N  A  N  P  N  A  N
 541  CCAAACGCTAACCCTAATGCCAATCCTAATGCCAATCCGAACGCCAATCCAAATGCCAAT

 201  P  N  A  N  P  N  V  D  P  N  A  N  P  N  A  N  P  N  A  N
 601  CCAAATGCTAATCCCAACGTGGACCCCAACGCGAACCCTAATGCCAACCCCAACGCTAAT

 221  P  N  A  N  P  N  A  N  P  N  A  N  P  N  A  N  P  N  A  N
 661  CCAAATGCGAACCCTAACGCCAACCCGAATGCTAATCCCAATGCCAACCCCAATGCTAAT

 241  P  N  A  N  P  N  A  N  P  K  T  H  V  F  G  Q  A  P  Y  S
 721  CCCAATGCGAACCCTAATGCCAATCCCAAAACTCACGTATTTGGGCAGGCGCCTTATTCT

 261  G  I  N  I  T  K  E  G  I  Q  I  G  V  E  G  Q  T  P  K  Y
 781  GGTATAAATATTACAAAGGAGGGTATTCAAATAGGTGTCGAAGGTCAAACACCTAAATAT

 281  A  D  K  T  F  Q  P  E  P  Q  I  G  E  S  Q  W  Y  E  T  E
 841  GCCGATAAAACATTTCAACCTGAACCTCAAATAGGAGAATCTCAGTGGTACGAAACAGAA

 301  I  N  H  A  A  G  R  V  L  K  K  T  T  P  M  K  P  C  Y  G
 901  ATTAATCATGCAGCTGGGAGAGTCCTAAAAAAGACTACCCCAATGAAACCATGTTACGGT

 321  S  Y  A  K  P  T  N  E  N  G  G  Q  G  I  L  V  K  Q  Q  N
 961  TCATATGCAAAACCCACAAATGAAAATGGAGGGCAAGGCATTCTTGTAAAGCAACAAAAT

 341  G  K  L  E  S  Q  V  E  M  Q  F  F  S  T  T  E  A  A  A  G
1021  GGAAAGCTAGAAAGTCAAGTGGAAATGCAATTTTTCTCAACTACTGAGGCAGCCGCAGGC

 361  N  G  D  N  L  T  P  K  V  V  L  Y  S  E  D  V  D  I  E  T
1081  AATGGTGATAACTTGACTCCTAAAGTGGTATTGTACAGTGAAGATGTAGATATAGAAACC

 381  P  D  T  H  I  S  Y  M  P  T  I  K  E  G  N  S  R  E  L  M
1141  CCAGACACTCATATTTCTTACATGCCCACTATTAAGGAAGGTAACTCACGAGAACTAATG
```

Fig. 30A

```
 401  G  Q  Q  S  M  P  N  R  P  N  Y  I  A  F  R  D  N  F  I  G
1201  GGCCAACAATCTATGCCCAACAGGCCTAATTACATTGCTTTTAGGGACAATTTTATTGGT

 421  L  M  Y  Y  N  S  T  G  N  M  G  V  L  A  G  Q  A  S  Q  L
1261  CTAATGTATTACAACAGCACGGGTAATATGGGTGTTCTGGCGGGCCAAGCATCGCAGTTG

 441  N  A  V  V  D  L  Q  D  R  N  T  E  L  S  Y  Q  L  L  L  D
1321  AATGCTGTTGTAGATTTGCAAGACAGAAACACAGAGCTTTCATACCAGCTTTTGCTTGAT

 461  S  I  G  D  R  T  R  Y  F  S  M  W  N  Q  L  P  N  Y  C  F
1381  TCCATTGGTGATAGAACCAGGTACTTTTCTATGTGGAATCAGCTTCCAAATTACTGCTTT

 481  P  L  G  G  V  I  N  T  E  T  L  T  K  V  K  P  K  T  G  Q
1441  CCACTGGGAGGTGTGATTAATACAGAGACTCTTACCAAGGTAAAACCTAAAACAGGTCAG

 501  E  N  G  W  E  K  D  A  T  E  F  S  D  K  N  E  I  R  V  G
1501  GAAAATGGATGGGAAAAAGATGCTACAGAATTTTCAGATAAAAATGAAATAAGAGTTGGA

 521  N  N  F  A  M  E  I  N  L  N  A  N  L  W  R  N  F  L  Y  S
1561  AATAATTTTGCCATGGAAATCAATCTAAATGCCAACCTGTGGAGAAATTTCCTGTACTCC

 541  N  I  A  L  Y  L  P  D  K  L  K  Y  S  P  S  N  V  K  I  S
1621  AACATAGCGCTGTATTTGCCCGACAAGCTAAAGTACAGTCCTTCCAACGTAAAAATTTCT

 561  D  N  P  N  T  Y  D  Y  M  N  K  R  V  V  A  P  G  L  V  D
1681  GATAACCCAAACACCTACGACTACATGAACAAGCGAGTGGTGGCTCCCGGGCTAGTGGAC

 581  C  Y  I  N  L  G  A  R  W  S  L  D  Y  M  D  N  V  N  P  F
1741  TGCTACATTAACCTTGGAGCACGCTGGTCCCTTGACTATATGGACAACGTCAACCCATTT

 601  N  H  H  R  N  A  G  L  R  Y  R  S  M  L  L  G  N  G  R  Y
1801  AACCACCACCGCAATGCTGGCCTGCGCTACCGCTCAATGTTGCTGGGCAATGGTCGCTAT

 621  V  P  F  H  I  Q  V  P  Q  K  F  F  A  I  K  N  L  L  L  L
1861  GTGCCCTTCCACATCCAGGTGCCTCAGAAGTTCTTTGCCATTAAAAACCTCCTTCTCCTG

 641  P  G  S  Y  T  Y  E  W  N  F  R  K  D  V  N  M  V  L  Q  S
1921  CCGGGCTCATACACCTACGAGTGGAACTTCAGGAAGGATGTTAACATGGTTCTGCAGAGC

 661  S  L  G  N  D  L  R  V  D  G  A  S  I  K  F  D  S  I  C  L
1981  TCCCTAGGAAATGACCTAAGGGTTGACGGAGCCAGCATTAAGTTTGATAGCATTTGCCTT

 681  Y  A  T  F  F  P  M  A  H  N  T  A  S  T  L  E  A  M  L  R
2041  TACGCCACCTTCTTCCCCATGGCCCACAACACCGCCTCCACGCTTGAGGCCATGCTTAGA

 701  N  D  T  N  D  Q  S  F  N  D  Y  L  S  A  A  N  M  L  Y  P
2101  AACGACACCAACGACCAGTCCTTTAACGACTATCTCTCCGCCGCCAACATGCTCTACCCT

 721  I  P  A  N  A  T  N  V  P  I  S  I  P  S  R  N  W  A  A  F
2161  ATACCCGCCAACGCTACCAACGTGCCCATATCCATCCCCTCCCGCAACTGGGCGGCTTTC

 741  R  G  W  A  F  T  R  L  K  T  K  E  T  P  S  L  G  S  G  Y
2221  CGCGGCTGGGCCTTCACGCGCCTTAAGACTAAGGAAACCCCATCACTGGGCTCGGGCTAC

 761  D  P  Y  Y  T  Y  S  G  S  I  P  Y  L  D  G  T  F  Y  L  N
2281  GACCCTTATTACACCTACTCTGGCTCTATACCCTACCTAGATGGAACCTTTTACCTCAAC

 781  H  T  F  K  K  V  A  I  T  F  D  S  S  V  S  W  P  G  N  D
2341  CACACCTTTAAGAAGGTGGCCATTACCTTTGACTCTTCTGTCAGCTGGCCTGGCAATGAC

 801  R  L  L  T  P  N  E  F  E  I  K  R  S  V  D  G  E  G  Y  N
2401  CGCCTGCTTACCCCCAACGAGTTTGAAATTAAGCGCTCAGTTGACGGGGAGGGTTACAAC
```

Fig. 30B

```
821   V  A  Q  C  N  M  T  K  D  W  F  L  V  Q  M  L  A  N  Y  N
2461  GTTGCCCAGTGTAACATGACCAAAGACTGGTTCCTGGTACAAATGCTAGCTAACTATAAC

841   I  G  Y  Q  G  F  Y  I  P  E  S  Y  K  D  R  M  Y  S  F  F
2521  ATTGGCTACCAGGGCTTCTATATCCCAGAGAGCTACAAGGACCGCATGTACTCCTTCTTT

861   R  N  F  Q  P  M  S  R  Q  V  V  D  D  T  K  Y  K  D  Y  Q
2581  AGAAACTTCCAGCCCATGAGCCGTCAGGTGGTGGATGATACTAAATACAAGGACTACCAA

881   Q  V  G  I  L  H  Q  H  N  N  S  G  F  V  G  Y  L  A  P  T
2641  CAGGTGGGCATCCTACACCAACACAACAACTCTGGATTTGTTGGCTACCTTGCCCCCACC

901   M  R  E  G  Q  A  Y  P  A  N  F  P  Y  P  L  I  G  K  T  A
2701  ATGCGCGAAGGACAGGCCTACCCTGCTAACTTCCCCTATCCGCTTATAGGCAAGACCGCA

921   V  D  S  I  T  Q  K  K  F  L  C  D  R  T  L  W  R  I  P  F
2761  GTTGACAGCATTACCCAGAAAAAGTTTCTTTGCGATCGCACCCTTTGGCGCATCCCATTC

941   S  S  N  F  M  S  M  G  A  L  T  D  L  G  Q  N  L  L  Y  A
2821  TCCAGTAACTTTATGTCCATGGGCGCACTCACAGACCTGGGCCAAAACCTTCTCTACGCC

961   N  S  A  H  A  L  D  M  T  F  E  V  D  P  M  D  E  P  T  L
2881  AACTCCGCCCACGCGCTAGACATGACTTTTGAGGTGGATCCCATGGACGAGCCCACCCTT

981   L  Y  V  L  F  E  V  F  D  V  V  R  V  H  Q  P  H  R  G  V
2941  CTTTATGTTTTGTTTGAAGTCTTTGACGTGGTCCGTGTGCACCAGCCGCACCGCGGCGTC

1001  I  E  T  V  Y  L  R  T  P  F  S  A  G  N  A  T  T  -
3001  ATCGAAACCGTGTACCTGCGCACGCCCTTCTCGGCCGGCAACGCCACAACATAA
```

Fig. 30C

Hexon sequence of (QGPGAP)$_3$-HVR5 adenovirus SEQ IDNOS : 23 and 40

1 M A T P S M M P Q W S Y M H I S G Q D A
1 ATGGCTACCCCTTCGATGATGCCGCAGTGGTCTTACATGCACATCTCGGGCCAGGACGCC

21 S E Y L S P G L V Q F A R A T E T Y F S
61 TCGGAGTACCTGAGCCCCGGGCTGGTGCAGTTTGCCCGCGCCACCGAGACGTACTTCAGC

41 L N N K F R N P T V A P T H D V T T D R
121 CTGAATAACAAGTTTAGAAACCCCACGGTGGCGCCTACGCACGACGTGACCACAGACCGG

61 S Q R L T L R F I P V D R E D T A Y S Y
181 TCCCAGCGTTTGACGCTGCGGTTCATCCCTGTGGACCGTGAGGATACTGCGTACTCGTAC

81 K A R F T L A V G D N R V L D M A S T Y
241 AAGGCGCGGTTCACCCTAGCTGTGGGTGATAACCGTGTGCTGGACATGGCTTCCACGTAC

101 F D I R G V L D R G P T F K P Y S G T A
301 TTTGACATCCGCGGCGTGCTGGACAGGGGCCCTACTTTTAAGCCCTACTCTGGCACTGCC

121 Y N A L A P K G A P N P C E W D E A A T
361 TACAACGCCCTGGCTCCCAAGGGTGCCCCAAATCCTTGCGAATGGGATGAAGCTGCTACT

141 A L E I N L E E E D D D N E D E V D E Q
421 GCTCTTGAAATAAACCTAGAAGAAGAGGACGATGACAACGAAGACGAAGTAGACGAGCAA

161 A E Q Q K T H V F G Q A P Y S G I N I T
481 GCTGAGCAGCAAAAAACTCACGTATTTGGGCAGGCGCCTTATTCTGGTATAAATATTACA

181 K E G I Q I G V E G Q T P K Y A D K T F
541 AAGGAGGGTATTCAAATAGGTGTCGAAGGTCAAACACCTAAATATGCCGATAAAACATTT

201 Q P E P Q I G E S Q W Y E T E I N H A A
601 CAACCTGAACCTCAAATAGGAGAATCTCAGTGGTACGAAACAGAAATTAATCATGCAGCT

221 G R V L K K T T P M K P C Y G S Y A K P
661 GGGAGAGTCCTAAAAAAGACTACCCCAATGAAACCATGTTACGGTTCATATGCAAAACCC

241 T N E N G G Q G I L V K Q Q N G K L E S
721 ACAAATGAAAATGGAGGGCAAGGCATTCTTGTAAAGCAACAAAATGGAAAGCTAGAAAGT

261 Q V E M Q F F S A S <u>Q G P G A P Q G P G</u>
781 CAAGTGGAAATGCAATTTTTCTCAGCTAGC<u>CAGGGCCCTGGAGCTCCACAGGGACCAGGT</u>

281 <u>A P Q G P G A P</u> G T S T T E A A A G N G
841 <u>GCACCTCAAGGGCCTGGAGCCCCT</u>GGCACTAGCACTACTGAGGCAGCCGCAGGCAATGGT

301 D N L T P K V V L Y S E D V D I E T P D
901 GATAACTTGACTCCTAAAGTGGTATTGTACAGTGAAGATGTAGATATAGAAACCCCAGAC

321 T H I S Y M P T I K E G N S R E L M G Q
961 ACTCATATTTCTTACATGCCCACTATTAAGGAAGGTAACTCACGAGAACTAATGGGCCAA

341 Q S M P N R P N Y I A F R D N F I G L M
1021 CAATCTATGCCCAACAGGCCTAATTACATTGCTTTTAGGGACAATTTTATTGGTCTAATG

361 Y Y N S T G N M G V L A G Q A S Q L N A
1081 TATTACAACAGCACGGGTAATATGGGTGTTCTGGCGGGCCAAGCATCGCAGTTGAATGCT

381 V V D L Q D R N T E L S Y Q L L L D S I
1141 GTTGTAGATTTGCAAGACAGAAACACAGAGCTTTCATACCAGCTTTTGCTTGATTCCATT

Fig. 31A

```
 401  G  D  R  T  R  Y  F  S  M  W  N  Q  A  V  D  S  Y  D  P  D
1201  GGTGATAGAACCAGGTACTTTTCTATGTGGAATCAGGCTGTTGACAGCTATGATCCAGAT

 421  V  R  I  I  E  N  H  G  T  E  D  E  L  P  N  Y  C  F  P  L
1261  GTTAGAATTATTGAAAATCATGGAACTGAAGATGAACTTCCAAATTACTGCTTTCCACTG

 441  G  G  V  I  N  T  E  T  L  T  K  V  K  P  K  T  G  Q  E  N
1321  GGAGGTGTGATTAATACAGAGACTCTTACCAAGGTAAAACCTAAAACAGGTCAGGAAAAT

 461  G  W  E  K  D  A  T  E  F  S  D  K  N  E  I  R  V  G  N  N
1381  GGATGGGAAAAAGATGCTACAGAATTTTCAGATAAAAATGAAATAAGAGTTGGAAATAAT

 481  F  A  M  E  I  N  L  N  A  N  L  W  R  N  F  L  Y  S  N  I
1441  TTTGCCATGGAAATCAATCTAAATGCCAACCTGTGGAGAAATTTCCTGTACTCCAACATA

 501  A  L  Y  L  P  D  K  L  K  Y  S  P  S  N  V  K  I  S  D  N
1501  GCGCTGTATTTGCCCGACAAGCTAAAGTACAGTCCTTCCAACGTAAAAATTTCTGATAAC

 521  P  N  T  Y  D  Y  M  N  K  R  V  V  A  P  G  L  V  D  C  Y
1561  CCAAACACCTACGACTACATGAACAAGCGAGTGGTGGCTCCCGGGCTAGTGGACTGCTAC

 541  I  N  L  G  A  R  W  S  L  D  Y  M  D  N  V  N  P  F  N  H
1621  ATTAACCTTGGAGCACGCTGGTCCCTTGACTATATGGACAACGTCAACCCATTTAACCAC

 561  H  R  N  A  G  L  R  Y  R  S  M  L  L  G  N  G  R  Y  V  P
1681  CACCGCAATGCTGGCCTGCGCTACCGCTCAATGTTGCTGGGCAATGGTCGCTATGTGCCC

 581  F  H  I  Q  V  P  Q  K  F  F  A  I  K  N  L  L  L  L  P  G
1741  TTCCACATCCAGGTGCCTCAGAAGTTCTTTGCCATTAAAAACCTCCTTCTCCTGCCGGGC

 601  S  Y  T  Y  E  W  N  F  R  K  D  V  N  M  V  L  Q  S  S  L
1801  TCATACACCTACGAGTGGAACTTCAGGAAGGATGTTAACATGGTTCTGCAGAGCTCCCTA

 621  G  N  D  L  R  V  D  G  A  S  I  K  F  D  S  I  C  L  Y  A
1861  GGAAATGACCTAAGGGTTGACGGAGCCAGCATTAAGTTTGATAGCATTTGCCTTTACGCC

 641  T  F  F  P  M  A  H  N  T  A  S  T  L  E  A  M  L  R  N  D
1921  ACCTTCTTCCCCATGGCCCACAACACCGCCTCCACGCTTGAGGCCATGCTTAGAAACGAC

 661  T  N  D  Q  S  F  N  D  Y  L  S  A  A  N  M  L  Y  P  I  P
1981  ACCAACGACCAGTCCTTTAACGACTATCTCTCCGCCGCCAACATGCTCTACCCTATACCC

 681  A  N  A  T  N  V  P  I  S  I  P  S  R  N  W  A  A  F  R  G
2041  GCCAACGCTACCAACGTGCCCATATCCATCCCCTCCCGCAACTGGGCGGCTTTCCGCGGC

 701  W  A  F  T  R  L  K  T  K  E  T  P  S  L  G  S  G  Y  D  P
2101  TGGGCCTTCACGCGCCTTAAGACTAAGGAAACCCCATCACTGGGCTCGGGCTACGACCCT

 721  Y  Y  T  Y  S  G  S  I  P  Y  L  D  G  T  F  Y  L  N  H  T
2161  TATTACACCTACTCTGGCTCTATACCCTACCTAGATGGAACCTTTTACCTCAACCACACC

 741  F  K  K  V  A  I  T  F  D  S  S  V  S  W  P  G  N  D  R  L
2221  TTTAAGAAGGTGGCCATTACCTTTGACTCTTCTGTCAGCTGGCCTGGCAATGACCGCCTG

 761  L  T  P  N  E  F  E  I  K  R  S  V  D  G  E  G  Y  N  V  A
2281  CTTACCCCCAACGAGTTTGAAATTAAGCGCTCAGTTGACGGGGAGGGTTACAACGTTGCC

 781  Q  C  N  M  T  K  D  W  F  L  V  Q  M  L  A  N  Y  N  I  G
2341  CAGTGTAACATGACCAAAGACTGGTTCCTGGTACAAATGCTAGCTAACTATAACATTGGC
```

Fig. 31B

```
801   Y  Q  G  F  Y  I  P  E  S  Y  K  D  R  M  Y  S  F  F  R  N
2401  TACCAGGGCTTCTATATCCCAGAGAGCTACAAGGACCGCATGTACTCCTTCTTTAGAAAC

821   F  Q  P  M  S  R  Q  V  V  D  D  T  K  Y  K  D  Y  Q  Q  V
2461  TTCCAGCCCATGAGCCGTCAGGTGGTGGATGATACTAAATACAAGGACTACCAACAGGTG

841   G  I  L  H  Q  H  N  N  S  G  F  V  G  Y  L  A  P  T  M  R
2521  GGCATCCTACACCAACACAACAACTCTGGATTTGTTGGCTACCTTGCCCCCACCATGCGC

861   E  G  Q  A  Y  P  A  N  F  P  Y  P  L  I  G  K  T  A  V  D
2581  GAAGGACAGGCCTACCCTGCTAACTTCCCCTATCCGCTTATAGGCAAGACCGCAGTTGAC

881   S  I  T  Q  K  K  F  L  C  D  R  T  L  W  R  I  P  F  S  S
2641  AGCATTACCCAGAAAAAGTTTCTTTGCGATCGCACCCTTTGGCGCATCCCATTCTCCAGT

901   N  F  M  S  M  G  A  L  T  D  L  G  Q  N  L  L  Y  A  N  S
2701  AACTTTATGTCCATGGGCGCACTCACAGACCTGGGCCAAAACCTTCTCTACGCCAACTCC

921   A  H  A  L  D  M  T  F  E  V  D  P  M  D  E  P  T  L  L  Y
2761  GCCCACGCGCTAGACATGACTTTTGAGGTGGATCCCATGGACGAGCCCACCCTTCTTTAT

941   V  L  F  E  V  F  D  V  V  R  V  H  Q  P  H  R  G  V  I  E
2821  GTTTTGTTTGAAGTCTTTGACGTGGTCCGTGTGCACCAGCCGCACCGCGGCGTCATCGAA

961   T  V  Y  L  R  T  P  F  S  A  G  N  A  T  T  -
2881  ACCGTGTACCTGCGCACGCCCTTCTCGGCCGGCAACGCCACAACATAA
```

Fig. 31C

Fiber sequence of $(QGPGAP)_3$-Fib adenovirus SEQ IDNOS : 24 and 41

```
   1  M  K  R  A  R  P  S  E  D  T  F  N  P  V  Y  P  Y  D  T  E
   1  ATGAAGCGCGCAAGACCGTCTGAAGATACCTTCAACCCCGTGTATCCATATGACACGGAA

  21  T  G  P  P  T  V  P  F  L  T  P  P  F  V  S  P  N  G  F  Q
  61  ACCGGTCCTCCAACTGTGCCTTTTCTTACTCCTCCCTTTGTATCCCCCAATGGGTTTCAA

  41  E  S  P  P  G  V  L  S  L  R  L  S  E  P  L  V  T  S  N  G
 121  GAGAGTCCCCCTGGGGTACTCTCTTTGCGCCTATCCGAACCTCTAGTTACCTCCAATGGC

  61  M  L  A  L  K  M  G  N  G  L  S  L  D  E  A  G  N  L  T  S
 181  ATGCTTGCGCTCAAAATGGGCAACGGCCTCTCTCTGGACGAGGCCGGCAACCTTACCTCC

  81  Q  N  V  T  T  V  S  P  P  L  K  K  T  K  S  N  I  N  L  E
 241  CAAAATGTAACCACTGTGAGCCCACCTCTCAAAAAAACCAAGTCAAACATAAACCTGGAA

 101  I  S  A  P  L  T  V  T  S  E  A  L  T  V  A  A  A  A  P  L
 301  ATATCTGCACCCCTCACAGTTACCTCAGAAGCCCTAACTGTGGCTGCCGCCGCACCTCTA

 121  M  V  A  G  N  T  L  T  M  Q  S  Q  A  P  L  T  V  H  D  S
 361  ATGGTCGCGGGCAACACACTCACCATGCAATCACAGGCCCCGCTAACCGTGCACGACTCC

 141  K  L  S  I  A  T  Q  G  P  L  T  V  S  E  G  K  L  A  L  Q
 421  AAACTTAGCATTGCCACCCAAGGACCCCTCACAGTGTCAGAAGGAAAGCTAGCCCTGCAA

 161  T  S  G  P  L  T  T  T  D  S  S  T  L  T  I  T  A  S  P  P
 481  ACATCAGGCCCCCTCACCACCACCGATAGCAGTACCCTTACTATCACTGCCTCACCCCCT

 181  L  T  T  A  T  G  S  L  G  I  D  L  K  E  P  I  Y  T  Q  N
 541  CTAACTACTGCCACTGGTAGCTTGGGCATTGACTTGAAAGAGCCCATTTATACACAAAAT

 201  G  K  L  G  L  K  Y  G  A  P  L  H  V  T  D  D  L  N  T  L
 601  GGAAAACTAGGACTAAAGTACGGGGCTCCTTTGCATGTAACAGACGACCTAAACACTTTG

 221  T  V  A  T  G  P  G  V  T  I  N  N  T  S  L  Q  T  K  V  T
 661  ACCGTAGCAACTGGTCCAGGTGTGACTATTAATAATACTTCCTTGCAAACTAAAGTTACT

 241  G  A  L  G  F  D  S  Q  G  N  M  Q  L  N  V  A  G  G  L  R
 721  GGAGCCTTGGGTTTTGATTCACAAGGCAATATGCAACTTAATGTAGCAGGAGGACTAAGG

 261  I  D  S  Q  N  R  R  L  I  L  D  V  S  Y  P  F  D  A  Q  N
 781  ATTGATTCTCAAAACAGACGCCTTATACTTGATGTTAGTTATCCGTTTGATGCTCAAAAC

 281  Q  L  N  L  R  L  G  Q  G  P  L  F  I  N  S  A  H  N  L  D
 841  CAACTAAATCTAAGACTAGGACAGGGCCCTCTTTTTATAAACTCAGCCCACAACTTGGAT

 301  I  N  Y  N  K  G  L  Y  L  F  T  A  S  N  N  S  K  K  L  E
 901  ATTAACTACAACAAAGGCCTTTACTTGTTTACAGCTTCAAACAATTCCAAAAAGCTTGAG

 321  V  N  L  S  T  A  K  G  L  M  F  D  A  T  A  I  A  I  N  A
 961  GTTAACCTAAGCACTGCCAAGGGGTTGATGTTTGACGCTACAGCCATAGCCATTAATGCA

 341  G  D  G  L  E  F  G  S  P  N  A  P  N  T  N  P  L  K  T  K
1021  GGAGATGGGCTTGAATTTGGTTCACCTAATGCACCAAACACAAATCCCCTCAAAACAAAA

 361  I  G  H  G  L  E  F  D  S  N  K  A  M  V  P  K  L  G  T  G
1081  ATTGGCCATGGCCTAGAATTTGATTCAAACAAGGCTATGGTTCCTAAACTAGGAACTGGC

 381  L  S  F  D  S  T  G  A  I  T  V  G  N  K  N  N  D  K  L  T
1141  CTTAGTTTTGACAGCACAGGTGCCATTACAGTAGGAAACAAAAATAATGATAAGCTAACT
```

Fig. 32A

```
 401  L W T T P A P S P N C R L N A E K D A K
1201  TTGTGGACCACACCAGCTCCATCTCCTAACTGTAGACTAAATGCAGAGAAAGATGCTAAA

 421  L T L V L T K C G S Q I L A T V S V L A
1261  CTCACTTTGGTCTTAACAAAATGTGGCAGTCAAATACTTGCTACAGTTTCAGTTTTGGCT

 441  V K G S L A P I S G T V Q S A H L I I R
1321  GTTAAAGGCAGTTTGGCTCCAATATCTGGAACAGTTCAAAGTGCTCATCTTATTATAAGA

 461  F D E N G V L L N N S F L D P E Y W N F
1381  TTTGACGAAAATGGAGTGCTACTAAACAATTCCTTCCTGGACCCAGAATATTGGAACTTT

 481  R N G D L T E G T A Y T N A V G F M P N
1441  AGAAATGGAGATCTTACTGAAGGCACAGCCTATACAAACGCTGTTGGATTTATGCCTAAC

 501  L S A Y P K S H G K T A K S N I V S Q V
1501  CTATCAGCTTATCCAAAATCTCACGGTAAAACTGCCAAAAGTAACATTGTCAGTCAAGTT

 521  Y L N G D K T K P V T L T I T L N G T Q
1561  TACTTAAACGGAGACAAAACTAAACCTGTAACACTAACCATTACACTAAACGGTACACAG

 541  E T G Q G P G A P Q G P G A P Q G P G A
1621  GAAACAGGACAGGGCCCTGGAGCTCCACAGGGACCAGGTGCACCTCAAGGGCCTGGAGCC

 561  P D T T P S A Y S M S F S W D W S G H N
1681  CCTGACACAACTCCAAGTGCATACTCTATGTCATTTTCATGGGACTGGTCTGGCCACAAC

 581  Y I N E I F A T S S Y T F S Y I A Q E -
1741  TACATTAATGAAATATTTGCCACATCCTCTTACACTTTTTCATACATTGCCCAAGAATAA
```

Fig. 32B

Fiber sequence of $(NANP)_4$-Fib adenovirus SEQ IDNOS : 25 and 55

```
   1  M  K  R  A  R  P  S  E  D  T  F  N  P  V  Y  P  Y  D  T  E
   1  ATGAAGCGCGCAAGACCGTCTGAAGATACCTTCAACCCCGTGTATCCATATGACACGGAA

  21  T  G  P  P  T  V  P  F  L  T  P  P  F  V  S  P  N  G  F  Q
  61  ACCGGTCCTCCAACTGTGCCTTTTCTTACTCCTCCCTTTGTATCCCCCAATGGGTTTCAA

  41  E  S  P  P  G  V  L  S  L  R  L  S  E  P  L  V  T  S  N  G
 121  GAGAGTCCCCCTGGGGTACTCTCTTTGCGCCTATCCGAACCTCTAGTTACCTCCAATGGC

  61  M  L  A  L  K  M  G  N  G  L  S  L  D  E  A  G  N  L  T  S
 181  ATGCTTGCGCTCAAAATGGGCAACGGCCTCTCTCTGGACGAGGCCGGCAACCTTACCTCC

  81  Q  N  V  T  T  V  S  P  P  L  K  K  T  K  S  N  I  N  L  E
 241  CAAAATGTAACCACTGTGAGCCCACCTCTCAAAAAAACCAAGTCAAACATAAACCTGGAA

 101  I  S  A  P  L  T  V  T  S  E  A  L  T  V  A  A  A  A  P  L
 301  ATATCTGCACCCCTCACAGTTACCTCAGAAGCCCTAACTGTGGCTGCCGCCGCACCTCTA

 121  M  V  A  G  N  T  L  T  M  Q  S  Q  A  P  L  T  V  H  D  S
 361  ATGGTCGCGGGCAACACACTCACCATGCAATCACAGGCCCCGCTAACCGTGCACGACTCC

 141  K  L  S  I  A  T  Q  G  P  L  T  V  S  E  G  K  L  A  L  Q
 421  AAACTTAGCATTGCCACCCAAGGACCCCTCACAGTGTCAGAAGGAAAGCTAGCCCTGCAA

 161  T  S  G  P  L  T  T  T  D  S  S  T  L  T  I  T  A  S  P  P
 481  ACATCAGGCCCCCTCACCACCACCGATAGCAGTACCCTTACTATCACTGCCTCACCCCCT

 181  L  T  T  A  T  G  S  L  G  I  D  L  K  E  P  I  Y  T  Q  N
 541  CTAACTACTGCCACTGGTAGCTTGGGCATTGACTTGAAAGAGCCCATTTATACACAAAAT

 201  G  K  L  G  L  K  Y  G  A  P  L  H  V  T  D  D  L  N  T  L
 601  GGAAAACTAGGACTAAAGTACGGGGCTCCTTTGCATGTAACAGACGACCTAAACACTTTG

 221  T  V  A  T  G  P  G  V  T  I  N  N  T  S  L  Q  T  K  V  T
 661  ACCGTAGCAACTGGTCCAGGTGTGACTATTAATAATACTTCCTTGCAAACTAAAGTTACT

 241  G  A  L  G  F  D  S  Q  G  N  M  Q  L  N  V  A  G  G  L  R
 721  GGAGCCTTGGGTTTTGATTCACAAGGCAATATGCAACTTAATGTAGCAGGAGGACTAAGG

 261  I  D  S  Q  N  R  R  L  I  L  D  V  S  Y  P  F  D  A  Q  N
 781  ATTGATTCTCAAAACAGACGCCTTATACTTGATGTTAGTTATCCGTTTGATGCTCAAAAC

 281  Q  L  N  L  R  L  G  Q  G  P  L  F  I  N  S  A  H  N  L  D
 841  CAACTAAATCTAAGACTAGGACAGGGCCCTCTTTTTATAAACTCAGCCCACAACTTGGAT

 301  I  N  Y  N  K  G  L  Y  L  F  T  A  S  N  N  S  K  K  L  E
 901  ATTAACTACAACAAAGGCCTTTACTTGTTTACAGCTTCAAACAATTCCAAAAAGCTTGAG

 321  V  N  L  S  T  A  K  G  L  M  F  D  A  T  A  I  A  I  N  A
 961  GTTAACCTAAGCACTGCCAAGGGGTTGATGTTTGACGCTACAGCCATAGCCATTAATGCA

 341  G  D  G  L  E  F  G  S  P  N  A  P  N  T  N  P  L  K  T  K
1021  GGAGATGGGCTTGAATTTGGTTCACCTAATGCACCAAACACAAATCCCCTCAAAACAAAA

 361  I  G  H  G  L  E  F  D  S  N  K  A  M  V  P  K  L  G  T  G
1081  ATTGGCCATGGCCTAGAATTTGATTCAAACAAGGCTATGGTTCCTAAACTAGGAACTGGC

 381  L  S  F  D  S  T  G  A  I  T  V  G  N  K  N  N  D  K  L  T
1141  CTTAGTTTTGACAGCACAGGTGCCATTACAGTAGGAAACAAAAATAATGATAAGCTAACT
```

Fig. 33A

```
 401  L  W  T  T  P  A  P  S  P  N  C  R  L  N  A  E  K  D  A  K
1201  TTGTGGACCACACCAGCTCCATCTCCTAACTGTAGACTAAATGCAGAGAAAGATGCTAAA

 421  L  T  L  V  L  T  K  C  G  S  Q  I  L  A  T  V  S  V  L  A
1261  CTCACTTTGGTCTTAACAAAATGTGGCAGTCAAATACTTGCTACAGTTTCAGTTTTGGCT

 441  V  K  G  S  L  A  P  I  S  G  T  V  Q  S  A  H  L  I  I  R
1321  GTTAAAGGCAGTTTGGCTCCAATATCTGGAACAGTTCAAAGTGCTCATCTTATTATAAGA

 461  F  D  E  N  G  V  L  L  N  N  S  F  L  D  P  E  Y  W  N  F
1381  TTTGACGAAAATGGAGTGCTACTAAACAATTCCTTCCTGGACCCAGAATATTGGAACTTT

 481  R  N  G  D  L  T  E  G  T  A  Y  T  N  A  V  G  F  M  P  N
1441  AGAAATGGAGATCTTACTGAAGGCACAGCCTATACAAACGCTGTTGGATTTATGCCTAAC

 501  L  S  A  Y  P  K  S  H  G  K  T  A  K  S  N  I  V  S  Q  V
1501  CTATCAGCTTATCCAAAATCTCACGGTAAAACTGCCAAAAGTAACATTGTCAGTCAAGTT

 521  Y  L  N  G  D  K  T  K  P  V  T  L  T  I  T  L  N  G  T  Q
1561  TACTTAAACGGAGACAAAACTAAACCTGTAACACTAACCATTACACTAAACGGTACACAG

 541  E  T  G  N  A  N  P  N  A  N  P  N  A  N  P  N  A  N  P  D
1621  GAAACAGGAAACGCTAATCCCAACGCTAACCCAAATGCAAATCCTAATGCCAACCCCGAC

 561  T  T  P  S  A  Y  S  M  S  F  S  W  D  W  S  G  H  N  Y  I
1681  ACAACTCCAAGTGCATACTCTATGTCATTTTCATGGGACTGGTCTGGCCACAACTACATT

 581  N  E  I  F  A  T  S  S  Y  T  F  S  Y  I  A  Q  E  -
1741  AATGAAATATTTGCCACATCCTCTTACACTTTTTCATACATTGCCCAAGAATAA
```

Fig. 33B pVII sequence of PyCSCD4-pVII adenovirus SEQ IDNOS : 26 and 42

```
  1  M  S  I  L  I  S  P  S  N  N  T  G  W  G  L  R  F  P  S  K
  1  ATGTCCATCCTTATATCGCCCAGCAATAACACAGGCTGGGGCCTGCGCTTCCCAAGCAAG

 21  M  F  G  G  A  K  K  R  S  D  Q  H  P  V  R  V  R  G  H  Y
 61  ATGTTTGGCGGCGCCAAGAAGCGCTCCGACCAACACCCAGTGCGCGTGCGCGGGCACTAC

 41  R  A  P  W  G  A  H  K  R  G  R  T  G  R  T  T  V  D  D  A
121  CGCGCGCCCTGGGGCGCGCACAAACGCGGCCGCACTGGGCGCACCACCGTCGATGACGCG

 61  I  D  A  V  V  E  E  A  R  N  Y  T  P  T  P  P  P  V  S  T
181  ATCGACGCGGTGGTGGAGGAGGCGCGCAACTACACGCCCACGCCGCCACCAGTGTCCACA

 81  V  D  A  A  I  Q  T  V  V  R  G  A  R  R  Y  A  K  M  K  R
241  GTGGACGCGGCCATTCAGACCGTGGTGCGCGGAGCCCGCCGCTATGCTAAAATGAAGAGA

101  R  R  R  R  V  A  R  R  H  R  R  R  P  S  T  A  A  Q  R  A
301  CGGCGGAGGCGCGTAGCACGTCGCCACCGCCGCCGACCCGGCACTGCCGCCCAACGCGCG

121  A  A  A  L  L  N  R  A  R  R  T  G  R  R  A  A  M  R  A  A
361  GCGGCGGCCCTGCTTAACCGCGCACGTCGCACCGGCCGACGGGCGGCCATGCGGGCCGCT

141  R  R  L  A  A  G  I  V  T  V  P  P  R  S  R  R  R  A  A  A
421  CGAAGGCTGGCCGCGGGTATTGTCACTGTGCCCCCCAGGTCCAGGCGACGAGCGGCCGCC

161  A  A  A  A  A  I  S  A  M  T  Q  G  R  R  G  N  V  Y  W  V
481  GCAGCAGCCGCGGCCATTAGTGCTATGACTCAGGGTCGCAGGGGCAACGTGTATTGGGTG

181  R  D  S  V  S  G  L  R  V  P  V  R  T  R  P  P  R  N  V  R
541  CGCGACTCGGTTAGCGGCCTGCGCGTGCCCGTGCGCACCCGCCCCCCGCGCAACGTGCGC

201  T  R  P  P  R  N  Y  N  R  N  I  V  N  R  L  L  G  D  A  L
601  ACCCGCCCCCCCCGCAACTACAACAGGAACATCGTGAACAGGCTGCTGGGCGACGCCCTG

221  N  G  K  P  E  E  K  ~
661  AACGGCAAGCCCGAGGAGAAGTAG
```

Fig. 34 pVII sequence of PfCSPCD4-pVII-1 adenovirus SEQ IDNOS : 27 and 56

```
  1  M  S  I  L  I  S  P  S  N  N  T  G  W  G  L  R  F  P  S  K
  1  ATGTCCATCCTTATATCGCCCAGCAATAACACAGGCTGGGGCCTGCGCTTCCCAAGCAAG

 21  M  F  G  G  A  K  K  R  S  D  Q  H  P  V  R  V  R  G  H  Y
 61  ATGTTTGGCGGGGCCAAGAAGCGCTCCGACCAACACCCAGTGCGCGTGCGCGGGCACTAC

 41  R  A  P  W  G  A  H  K  R  G  R  T  G  R  T  T  V  D  D  A
121  CGCGCCCCTTGGGGCGCGCACAAACGCGGCCGCACTGGGCGCACGACCGTCGATGACGCC

 61  I  D  A  V  V  E  E  A  R  N  Y  T  P  T  P  P  P  V  S  T
181  ATCGACGCGGTGGTGGAGGAGGCGCGCAACTACACGCCCACGCCGCCACCAGTGTCCACA

 81  V  D  A  A  I  Q  T  V  V  R  G  A  R  R  Y  A  K  M  K  R
241  GTGGACGCGGCCATTCAGACCGTGGTGCGCGGAGCCCGGCGCTATGCTAAAATGAAGAGA

101  R  R  R  R  Y  A  R  R  H  R  R  R  P  G  T  A  A  Q  R  A
301  CGGCGGAGGCGGTACGCACGGCGCCACCGCCGCCGACCCGGCACTGCCGCCCAACGCGCG

121  A  A  A  L  L  N  R  A  R  R  T  G  R  R  A  A  M  R  A  A
361  GCGGCGGCCCTGCTTAACCGCGCACGTCGCACCGGCCGACGGGCGGCCATGCGGGCCGCT

141  R  R  L  A  A  G  I  V  T  V  P  P  R  S  R  R  R  A  A  A
421  CGAAGGCTGGCCGCGGGCATTGTCACTGTGCCCCCCAGGTCCAGGCGACGAGCGGCCGCC

161  A  A  A  A  A  I  S  A  M  T  Q  G  R  R  G  N  V  Y  W  V
481  GCAGCAGCCGCGGCCATTAGTGCTATGACTCAGGGTCGCAGGGGCAACGTGTATTGGGTG

181  R  D  S  V  S  G  L  R  V  P  V  R  T  R  P  P  R  N  E  Y
541  CGGGACTCGGTTAGCGGCCTGCGCGTGCCCGTGCGCACCCGCCCCCCGCGCAACGAATAT

201  L  N  K  I  Q  N  S  L  S  T  E  W  S  P  C  S  V  T  -
601  TTGAACAAGATTCAAAACTCGCTGTCAACAGAATGGTCTCCTTGCAGCGTGACTTAG
```

Fig. 35 pVII sequence of PfCSPCD4-pVII-2 adenovirus SEQ IDNOS : 28 and 57

```
1    M  S  I  L  I  S  P  S  N  N  T  G  W  G  L  R  F  P  S  K
1    ATGTCCATCCTTATATCGCCCAGCAATAACACAGGCTGGGGCCTGCGCTTCCCAAGCAAG

21   M  F  G  G  A  K  K  R  S  D  Q  H  P  V  R  V  R  G  H  Y
61   ATGTTTGGCGGGGCCAAGAAGCGCTCCGACCAACACCCAGTGCGGGTGCGGGGGCACTAC

41   R  A  P  W  G  A  H  K  R  G  R  T  G  R  T  T  V  D  D  A
121  CGCGCGCCCTGGGGCGCGCACAAACGCGGCCGCACTGGGCGCACCACCGTCGATGACGCC

61   I  D  A  V  V  E  E  A  R  N  Y  T  P  T  P  P  P  V  S  T
181  ATCGACGCGGTGGTGGAGGAGGCGCGCAACTACACGCCCACGCCGCCACCAGTGTCCACA

81   V  D  A  A  I  Q  T  V  V  R  G  A  E  Y  L  N  K  I  Q  N
241  GTGGACGCGGCCATTCAGACCGTGGTGCGCGGAGCCGAATATTTGAACAAGATTCAAAAC

101  S  L  S  T  E  W  S  P  C  S  V  T  R  R  Y  A  K  M  K  R
301  TCCCTCTCAACAGAATGGTCTCCTTGCAGCGTGACTCGGCGCTATGCTAAAATGAAGAGA

121  R  R  R  R  V  A  R  R  H  R  R  R  P  G  T  A  A  Q  R  A
361  CGCCGGAGGCGCGTAGCACGTCGGCACCGCCGCCGACCGGGCACTGCCGCCCAACGCGCG

141  A  A  A  L  L  N  R  A  R  R  T  G  R  R  A  A  M  R  A  A
421  GCGGCGGCGCTGCTTAACCGGGCACGTCGCACCGGCCGACGGGCGGCCATGCGGGCCGCT

161  R  R  L  A  A  G  I  V  T  V  P  P  R  S  R  R  R  A  A  A
481  CGAAGGCTGGCCGCGGGTATTGTCACTGTGCCCCCCAGGTCCAGGCGACGAGCGGCCGCC

181  A  A  A  A  A  I  S  A  M  T  Q  G  R  R  G  N  V  Y  W  V
541  GCAGCAGCCGCGGCCATTAGTGCTATGACTCAGGGTCGCAGGGGCAACGTGTATTGGGTG

201  R  D  S  V  S  G  L  R  V  P  V  R  T  R  P  P  R  N  V  R
601  CGCGACTCGGTTAGCGGCCTGCGCGTGCCCGTGCGCACCCGCCCCCCGCGCAACGTGCGC

221  T  R  P  P  R  N  Y  N  R  N  I  V  N  R  L  L  G  D  A  L
661  ACCCGCCCCCCGCGCAACTACAACAGGAACATCGTGAACAGGCTGCTGGGCGACGCCCTG

241  T  R  P  P  R  N  -
721  ACCCGCCCCCCGCGCAACTAG
```

Fig. 36 pVII sequence of PfCSPCD4-pVII-3 adenovirus SEQ IDNOS : 29 and 58

```
  1  M  S  I  L  I  S  P  S  N  N  T  G  W  G  L  R  F  P  S  K
  1  ATGTCCATCCTTATATCGCCCAGCAATAACACAGGCTGGGGCCTGCGCTTCCCAAGCAAG

 21  M  F  G  G  A  K  K  R  S  D  Q  H  P  V  R  V  R  G  H  Y
 61  ATGTTTGGCGGGGCCAAGAAGCGCTCCGACCAACACCCAGTGCGCGTGCGCGGGCACTAC

 41  R  A  P  W  G  A  H  K  R  G  R  T  G  R  T  T  V  D  D  A
121  CGCGCGCCCTGGGGCGCGCACAAACGCGGCCGCACTGGGCGCACCACCGTCGATGACGCC

 61  I  D  A  V  V  E  E  A  R  N  Y  T  P  T  P  P  P  V  S  T
181  ATCGACGCGGTGGTGGAGGAGGCGCGCAACTACACGCCCACGCCGCCGCCAGTGTCCACA

 81  V  D  A  A  I  Q  T  V  V  R  G  A  R  R  Y  A  K  M  K  R
241  GTGGACGCGGCCATTCAGACCGTGGTGCGCGGAGCCCGGCGCTATGCTAAAATGAAGAGA

101  R  R  R  R  V  A  R  R  H  R  R  R  P  G  T  A  A  Q  R  A
301  CGGCGGAGGCGCGTAGCACGTCGCCACCGCCGCCGACCCGGCACTGCCGCCCAACGCGCG

121  A  A  A  L  L  N  R  A  R  R  T  G  R  R  A  A  M  R  A  A
361  GCGGCGGCCCTGCTTAACCGCGCACGTCGCACCGGCCGACGGGCGGCCATGCGGGCCGCT

141  E  Y  L  N  K  I  Q  N  S  L  S  T  E  W  S  P  C  S  V  T
421  GAATATTTGAACAAGATTCAAAACTCCCTGTCAACAGAATGGTCTCCTTGCAGCGTGACT

161  R  R  L  A  A  G  I  V  T  V  P  P  R  S  R  R  R  A  A  A
481  CGAAGGCTGGCCGCGGGTATTGTCACTGTGCCCCCCAGGTCCAGGCGACGAGCGGCCGCC

181  A  A  A  A  A  I  S  A  M  T  Q  G  G  R  G  N  V  Y  W  V
541  GCAGCAGCCGCGGCCATTAGTGCTATGACTCAGGGTGGCAGGGGCAACGTGTATTGGGTG

201  R  D  S  V  S  G  L  R  V  P  V  R  T  R  P  P  R  N  V  R
601  CGCGACTCGGTTAGCGGCCTGCGCGTGCCCGTGCGCACCCGCCCCCCGCGCAACGTGCGC

221  T  R  P  P  R  N  -
661  ACCCGCCCCCCGCGCAACTAG
```

Fig. 37

A
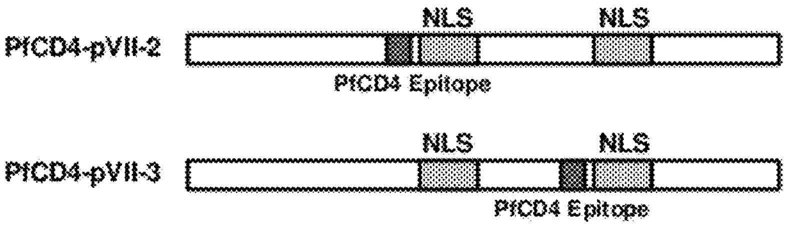
B
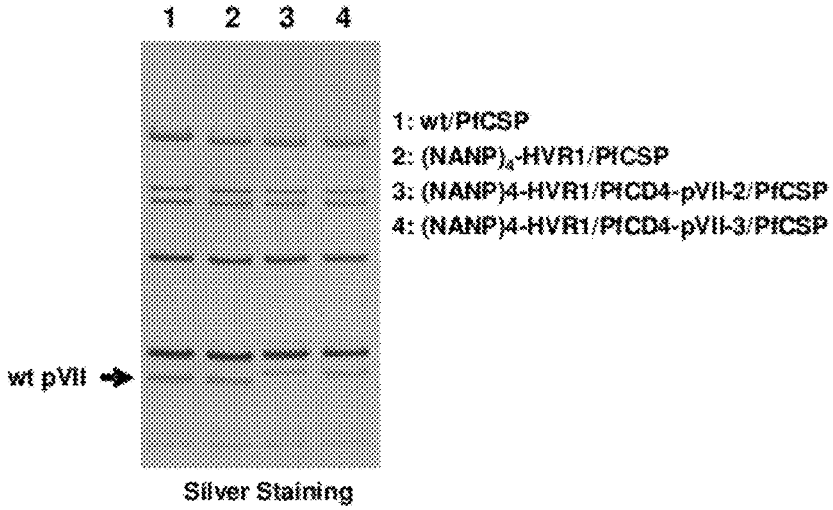
Fig. 53

SEQUENCE LISTING

```
<160> NUMBER OF SEQ ID NOS: 66

<210> SEQ ID NO 1
<211> LENGTH: 1127
<212> TYPE: DNA
<213> ORGANISM: Artificial Sequence
<220> FEATURE:
<223> OTHER INFORMATION: Codon-optimized Plasmodium yoelii
      circumsporozoite protein
<220> FEATURE:
<221> NAME/KEY: CDS
<222> LOCATION: (13)..(1119)

<400> SEQUENCE: 1

ggtaccgcca cc atg aag aag tgc acc atc ctg gtg gtg gcc agc ctg ctg      51
              Met Lys Lys Cys Thr Ile Leu Val Val Ala Ser Leu Leu
              1               5                   10

ctg gtg gac agc ctg ctg ccc ggc tac ggc cag aac aag agc gtg cag        99
Leu Val Asp Ser Leu Leu Pro Gly Tyr Gly Gln Asn Lys Ser Val Gln
    15                  20                  25

gcc cag agg aac ctg aac gag ctg tgc tac aac gag gag aac gac aac       147
Ala Gln Arg Asn Leu Asn Glu Leu Cys Tyr Asn Glu Glu Asn Asp Asn
30                  35                  40                  45

aag ctg tac cac gtg ctg aac agc aag aac ggc aag atc tac aac agg       195
Lys Leu Tyr His Val Leu Asn Ser Lys Asn Gly Lys Ile Tyr Asn Arg
                50                  55                  60

aac atc gtg aac agg ctg ctg ggc gac gcc ctg aac ggc aag ccc gag       243
Asn Ile Val Asn Arg Leu Leu Gly Asp Ala Leu Asn Gly Lys Pro Glu
            65                  70                  75

gag aag aag gac gac ccc ccc aag gac gac aac aag gac gac ctg ccc       291
Glu Lys Lys Asp Asp Pro Pro Lys Asp Asp Asn Lys Asp Asp Leu Pro
        80                  85                  90

aag gag gag aag aag gac gac ctg ccc aag gag gag aag aag gac gac       339
Lys Glu Glu Lys Lys Asp Asp Leu Pro Lys Glu Glu Lys Lys Asp Asp
    95                  100                 105

ccc ccc aag gac ccc aag aag gac gac ccc ccc aag gag gcc cag aac       387
Pro Pro Lys Asp Pro Lys Lys Asp Asp Pro Pro Lys Glu Ala Gln Asn
110                 115                 120                 125

aag ctg aac cag ccc gta gtg gca gat gaa aat gta gat caa ggg cca       435
Lys Leu Asn Gln Pro Val Val Ala Asp Glu Asn Val Asp Gln Gly Pro
                130                 135                 140

gga gca cca caa ggg cca gga gca cca caa ggg cca gga gca cca cag       483
Gly Ala Pro Gln Gly Pro Gly Ala Pro Gln Gly Pro Gly Ala Pro Gln
            145                 150                 155

ggg cca gga gca cca cag ggg cca gga gca cca caa ggg cca gga gca       531
Gly Pro Gly Ala Pro Gln Gly Pro Gly Ala Pro Gln Gly Pro Gly Ala
        160                 165                 170

cca caa gga cca gga gca cca caa ggg cca gga gca cca caa ggg cca       579
Pro Gln Gly Pro Gly Ala Pro Gln Gly Pro Gly Ala Pro Gln Gly Pro
    175                 180                 185

gga gca cca caa ggg cca gga gca ccg cag ggg cca gga gca cca caa       627
Gly Ala Pro Gln Gly Pro Gly Ala Pro Gln Gly Pro Gly Ala Pro Gln
190                 195                 200                 205

ggg cca gga gca cca caa gga cca gga gca cca cag ggt cca gga gca       675
Gly Pro Gly Ala Pro Gln Gly Pro Gly Ala Pro Gln Gly Pro Gly Ala
                210                 215                 220
```

-continued

```
cca caa gga cca gga gca cca caa gga cca gga gca cca caa ggt cca      723
Pro Gln Gly Pro Gly Ala Pro Gln Gly Pro Gly Ala Pro Gln Gly Pro
            225                 230                 235

gga gca cca cag ggg cca gga gca cca caa ggg cca gga gca cca caa      771
Gly Ala Pro Gln Gly Pro Gly Ala Pro Gln Gly Pro Gly Ala Pro Gln
        240                 245                 250

gaa cca ccc caa caa ccc cca caa cag cca cca caa cag cca cca caa      819
Glu Pro Pro Gln Gln Pro Pro Gln Gln Pro Pro Gln Gln Pro Pro Gln
    255                 260                 265

cag cca cca caa cag cca cca caa caa cca aac aac aac aac aac aac      867
Gln Pro Pro Gln Gln Pro Pro Gln Gln Pro Asn Asn Asn Asn Asn Asn
270                 275                 280                 285

aac ggc aac aac aac gag gac agc tac gtg ccc agc gcc gag cag atc      915
Asn Gly Asn Asn Asn Glu Asp Ser Tyr Val Pro Ser Ala Glu Gln Ile
                290                 295                 300

ctg gag ttc gtg aag cag atc agc agc cag ctg acc gag gag tgg agc      963
Leu Glu Phe Val Lys Gln Ile Ser Ser Gln Leu Thr Glu Glu Trp Ser
            305                 310                 315

cag tgc agc gtg acc tgc ggc agc ggc gtg agg gtg agg aag agg aag     1011
Gln Cys Ser Val Thr Cys Gly Ser Gly Val Arg Val Arg Lys Arg Lys
        320                 325                 330

aac gtg aac aag cag ccc gag aac ctg acc ctg gag gac atc gac acc     1059
Asn Val Asn Lys Gln Pro Glu Asn Leu Thr Leu Glu Asp Ile Asp Thr
    335                 340                 345

gag atc tgc aag atg gac aag tgc agc agc atc ttc aac atc gtg agc     1107
Glu Ile Cys Lys Met Asp Lys Cys Ser Ser Ile Phe Asn Ile Val Ser
350                 355                 360                 365

aac agc ctg ggc taaagctt                                            1127
Asn Ser Leu Gly
```

<210> SEQ ID NO 2
<211> LENGTH: 1145
<212> TYPE: DNA
<213> ORGANISM: Artificial Sequence
<220> FEATURE:
<223> OTHER INFORMATION: Codon-optimized Plasmodium falciparus circumsporozoite protein
<220> FEATURE:
<221> NAME/KEY: CDS
<222> LOCATION: (13)..(1134)

<400> SEQUENCE: 2

```
ggtaccgcca cc atg atg cgc aag ctc gcc ata ctg tct gtt agt agc ttt      51
              Met Met Arg Lys Leu Ala Ile Leu Ser Val Ser Ser Phe
              1               5                   10

ctc ttt gta gag gcc ctg ttt cag gaa tac cag tgc tat ggc agc agc       99
Leu Phe Val Glu Ala Leu Phe Gln Glu Tyr Gln Cys Tyr Gly Ser Ser
    15                  20                  25

agc aac act cgt gtg ctg aac gaa ctt aac tat gat aat gca gga aca      147
Ser Asn Thr Arg Val Leu Asn Glu Leu Asn Tyr Asp Asn Ala Gly Thr
30                  35                  40                  45

aat tta tat aac gaa ctg gag atg aat tac tat ggt aag cag gaa aat      195
Asn Leu Tyr Asn Glu Leu Glu Met Asn Tyr Tyr Gly Lys Gln Glu Asn
                50                  55                  60

tgg tac tct ctg aaa aag aac tct aga tct ctg ggc gag aac gac gac      243
Trp Tyr Ser Leu Lys Lys Asn Ser Arg Ser Leu Gly Glu Asn Asp Asp
            65                  70                  75

ggc aat aat gaa gac aat gaa aag ctg agg aag cca aag cac aaa aaa      291
Gly Asn Asn Glu Asp Asn Glu Lys Leu Arg Lys Pro Lys His Lys Lys
        80                  85                  90

cta aag cag ccc gca gac ggc aat cca gac ccc aat gct aac cca aac      339
```

-continued

```
Leu Lys Gln Pro Ala Asp Gly Asn Pro Asp Pro Asn Ala Asn Pro Asn
    95                  100                 105

gtg gac ccc aat gct aat cca aac gtg gat cct aac gct aac ccg aat      387
Val Asp Pro Asn Ala Asn Pro Asn Val Asp Pro Asn Ala Asn Pro Asn
110                 115                 120                 125

gtg gac cct aac gcc aat cca aat gcg aat ccc aac gct aat cct aac      435
Val Asp Pro Asn Ala Asn Pro Asn Ala Asn Pro Asn Ala Asn Pro Asn
                130                 135                 140

gca aac ccg aat gct aac cct aac gca aac ccc aac gct aac ccc aac      483
Ala Asn Pro Asn Ala Asn Pro Asn Ala Asn Pro Asn Ala Asn Pro Asn
            145                 150                 155

gcg aac ccc aat gcc aac ccc aac gcc aac ccg aac gcc aat cca aac      531
Ala Asn Pro Asn Ala Asn Pro Asn Ala Asn Pro Asn Ala Asn Pro Asn
        160                 165                 170

gct aac cct aat gcc aat cct aat gcc aat ccg aac gcc aat cca aat      579
Ala Asn Pro Asn Ala Asn Pro Asn Ala Asn Pro Asn Ala Asn Pro Asn
    175                 180                 185

gcc aat cca aat gct aat ccc aac gtg gac ccc aac gcg aac cct aat      627
Ala Asn Pro Asn Ala Asn Pro Asn Val Asp Pro Asn Ala Asn Pro Asn
190                 195                 200                 205

gcc aac ccc aac gct aat cca aat gcg aac cct aac gcc aac ccg aat      675
Ala Asn Pro Asn Ala Asn Pro Asn Ala Asn Pro Asn Ala Asn Pro Asn
                210                 215                 220

gct aat ccc aat gcc aac ccc aat gct aat ccc aat gcg aac cct aat      723
Ala Asn Pro Asn Ala Asn Pro Asn Ala Asn Pro Asn Ala Asn Pro Asn
            225                 230                 235

gcc aat ccc aac gcc aac ccc aac gca aac cct aat gct aac ccg aac      771
Ala Asn Pro Asn Ala Asn Pro Asn Ala Asn Pro Asn Ala Asn Pro Asn
        240                 245                 250

gcc aat ccg aac gca aat cct aat gct aat cct aac gct aac ccc aac      819
Ala Asn Pro Asn Ala Asn Pro Asn Ala Asn Pro Asn Ala Asn Pro Asn
    255                 260                 265

gcc aat cca aat aag aac aat caa ggc aac ggg cag ggg cac aat atg      867
Ala Asn Pro Asn Lys Asn Asn Gln Gly Asn Gly Gln Gly His Asn Met
270                 275                 280                 285

cca aat gac cct aac cgg aat gtc gac gag aat gca aat gcc aat agc      915
Pro Asn Asp Pro Asn Arg Asn Val Asp Glu Asn Ala Asn Ala Asn Ser
                290                 295                 300

gcc gtg aaa aat aat aat aac gag gag cca agt gac aaa cac att aag      963
Ala Val Lys Asn Asn Asn Asn Glu Glu Pro Ser Asp Lys His Ile Lys
            305                 310                 315

gaa tat ttg aac aag att caa aac tcc ctc tca aca gaa tgg tct cct     1011
Glu Tyr Leu Asn Lys Ile Gln Asn Ser Leu Ser Thr Glu Trp Ser Pro
        320                 325                 330

tgc agc gtg act tgt gga aat ggc atc cag gtt cgt att aaa cca ggt     1059
Cys Ser Val Thr Cys Gly Asn Gly Ile Gln Val Arg Ile Lys Pro Gly
    335                 340                 345

agt gcc aac aag ccc aag gat gaa cta gac tat gcg aat gat ata gag     1107
Ser Ala Asn Lys Pro Lys Asp Glu Leu Asp Tyr Ala Asn Asp Ile Glu
350                 355                 360                 365

aaa aaa atc tgt aag atg gag aaa tgc tagcttctag a                    1145
Lys Lys Ile Cys Lys Met Glu Lys Cys
                370
```

<210> SEQ ID NO 3
<211> LENGTH: 2832
<212> TYPE: DNA
<213> ORGANISM: Artificial Sequence
<220> FEATURE:
<223> OTHER INFORMATION: (QGPGAP)3-HVR1 modified Hexon protein
<220> FEATURE:

```
<221> NAME/KEY: CDS
<222> LOCATION: (1)..(2829)

<400> SEQUENCE: 3

atg gct acc cct tcg atg atg ccg cag tgg tct tac atg cac atc tcg       48
Met Ala Thr Pro Ser Met Met Pro Gln Trp Ser Tyr Met His Ile Ser
1               5                   10                  15

ggc cag gac gcc tcg gag tac ctg agc ccc ggg ctg gtg cag ttt gcc       96
Gly Gln Asp Ala Ser Glu Tyr Leu Ser Pro Gly Leu Val Gln Phe Ala
            20                  25                  30

cgc gcc acc gag acg tac ttc agc ctg aat aac aag ttt aga aac ccc      144
Arg Ala Thr Glu Thr Tyr Phe Ser Leu Asn Asn Lys Phe Arg Asn Pro
        35                  40                  45

acg gtg gcg cct acg cac gac gtg acc aca gac cgg tcc cag cgt ttg      192
Thr Val Ala Pro Thr His Asp Val Thr Thr Asp Arg Ser Gln Arg Leu
    50                  55                  60

acg ctg cgg ttc atc cct gtg gac cgt gag gat act gcg tac tcg tac      240
Thr Leu Arg Phe Ile Pro Val Asp Arg Glu Asp Thr Ala Tyr Ser Tyr
65                  70                  75                  80

aag gcg cgg ttc acc cta gct gtg ggt gat aac cgt gtg ctg gac atg      288
Lys Ala Arg Phe Thr Leu Ala Val Gly Asp Asn Arg Val Leu Asp Met
                85                  90                  95

gct tcc acg tac ttt gac atc cgc ggc gtg ctg gac agg ggc cct act      336
Ala Ser Thr Tyr Phe Asp Ile Arg Gly Val Leu Asp Arg Gly Pro Thr
            100                 105                 110

ttt aag ccc tac tct ggc act gcc tac aac gcc ctg gct ccc aag ggt      384
Phe Lys Pro Tyr Ser Gly Thr Ala Tyr Asn Ala Leu Ala Pro Lys Gly
        115                 120                 125

gcc cca aat cct tgc gaa tgg gat gaa cag ggc cct gga gct cca cag      432
Ala Pro Asn Pro Cys Glu Trp Asp Glu Gln Gly Pro Gly Ala Pro Gln
    130                 135                 140

gga cca ggt gca cct caa ggg cct gga gcc cct aaa act cac gta ttt      480
Gly Pro Gly Ala Pro Gln Gly Pro Gly Ala Pro Lys Thr His Val Phe
145                 150                 155                 160

ggg cag gcg cct tat tct ggt ata aat att aca aag gag ggt att caa      528
Gly Gln Ala Pro Tyr Ser Gly Ile Asn Ile Thr Lys Glu Gly Ile Gln
                165                 170                 175

ata ggt gtc gaa ggt caa aca cct aaa tat gcc gat aaa aca ttt caa      576
Ile Gly Val Glu Gly Gln Thr Pro Lys Tyr Ala Asp Lys Thr Phe Gln
            180                 185                 190

cct gaa cct caa ata gga gaa tct cag tgg tac gaa aca gaa att aat      624
Pro Glu Pro Gln Ile Gly Glu Ser Gln Trp Tyr Glu Thr Glu Ile Asn
        195                 200                 205

cat gca gct ggg aga gtc cta aaa aag act acc cca atg aaa cca tgt      672
His Ala Ala Gly Arg Val Leu Lys Lys Thr Thr Pro Met Lys Pro Cys
    210                 215                 220

tac ggt tca tat gca aaa ccc aca aat gaa aat gga ggg caa ggc att      720
Tyr Gly Ser Tyr Ala Lys Pro Thr Asn Glu Asn Gly Gly Gln Gly Ile
225                 230                 235                 240

ctt gta aag caa caa aat gga aag cta gaa agt caa gtg gaa atg caa      768
Leu Val Lys Gln Gln Asn Gly Lys Leu Glu Ser Gln Val Glu Met Gln
                245                 250                 255

ttt ttc tca act act gag gca gcc gca ggc aat ggt gat aac ttg act      816
Phe Phe Ser Thr Thr Glu Ala Ala Ala Gly Asn Gly Asp Asn Leu Thr
            260                 265                 270

cct aaa gtg gta ttg tac agt gaa gat gta gat ata gaa acc cca gac      864
Pro Lys Val Val Leu Tyr Ser Glu Asp Val Asp Ile Glu Thr Pro Asp
        275                 280                 285

act cat att tct tac atg ccc act att aag gaa ggt aac tca cga gaa      912
Thr His Ile Ser Tyr Met Pro Thr Ile Lys Glu Gly Asn Ser Arg Glu
```

-continued

```
    290                 295                 300

cta atg ggc caa caa tct atg ccc aac agg cct aat tac att gct ttt      960
Leu Met Gly Gln Gln Ser Met Pro Asn Arg Pro Asn Tyr Ile Ala Phe
305                 310                 315                 320

agg gac aat ttt att ggt cta atg tat tac aac agc acg ggt aat atg     1008
Arg Asp Asn Phe Ile Gly Leu Met Tyr Tyr Asn Ser Thr Gly Asn Met
                325                 330                 335

ggt gtt ctg gcg ggc caa gca tcg cag ttg aat gct gtt gta gat ttg     1056
Gly Val Leu Ala Gly Gln Ala Ser Gln Leu Asn Ala Val Val Asp Leu
            340                 345                 350

caa gac aga aac aca gag ctt tca tac cag ctt ttg ctt gat tcc att     1104
Gln Asp Arg Asn Thr Glu Leu Ser Tyr Gln Leu Leu Leu Asp Ser Ile
        355                 360                 365

ggt gat aga acc agg tac ttt tct atg tgg aat cag gct gtt gac agc     1152
Gly Asp Arg Thr Arg Tyr Phe Ser Met Trp Asn Gln Ala Val Asp Ser
    370                 375                 380

tat gat cca gat gtt aga att att gaa aat cat gga act gaa gat gaa     1200
Tyr Asp Pro Asp Val Arg Ile Ile Glu Asn His Gly Thr Glu Asp Glu
385                 390                 395                 400

ctt cca aat tac tgc ttt cca ctg gga ggt gtg att aat aca gag act     1248
Leu Pro Asn Tyr Cys Phe Pro Leu Gly Gly Val Ile Asn Thr Glu Thr
                405                 410                 415

ctt acc aag gta aaa cct aaa aca ggt cag gaa aat gga tgg gaa aaa     1296
Leu Thr Lys Val Lys Pro Lys Thr Gly Gln Glu Asn Gly Trp Glu Lys
            420                 425                 430

gat gct aca gaa ttt tca gat aaa aat gaa ata aga gtt gga aat aat     1344
Asp Ala Thr Glu Phe Ser Asp Lys Asn Glu Ile Arg Val Gly Asn Asn
        435                 440                 445

ttt gcc atg gaa atc aat cta aat gcc aac ctg tgg aga aat ttc ctg     1392
Phe Ala Met Glu Ile Asn Leu Asn Ala Asn Leu Trp Arg Asn Phe Leu
    450                 455                 460

tac tcc aac ata gcg ctg tat ttg ccc gac aag cta aag tac agt cct     1440
Tyr Ser Asn Ile Ala Leu Tyr Leu Pro Asp Lys Leu Lys Tyr Ser Pro
465                 470                 475                 480

tcc aac gta aaa att tct gat aac cca aac acc tac gac tac atg aac     1488
Ser Asn Val Lys Ile Ser Asp Asn Pro Asn Thr Tyr Asp Tyr Met Asn
                485                 490                 495

aag cga gtg gtg gct ccc ggg cta gtg gac tgc tac att aac ctt gga     1536
Lys Arg Val Val Ala Pro Gly Leu Val Asp Cys Tyr Ile Asn Leu Gly
            500                 505                 510

gca cgc tgg tcc ctt gac tat atg gac aac gtc aac cca ttt aac cac     1584
Ala Arg Trp Ser Leu Asp Tyr Met Asp Asn Val Asn Pro Phe Asn His
        515                 520                 525

cac cgc aat gct ggc ctg cgc tac cgc tca atg ttg ctg ggc aat ggt     1632
His Arg Asn Ala Gly Leu Arg Tyr Arg Ser Met Leu Leu Gly Asn Gly
    530                 535                 540

cgc tat gtg ccc ttc cac atc cag gtg cct cag aag ttc ttt gcc att     1680
Arg Tyr Val Pro Phe His Ile Gln Val Pro Gln Lys Phe Phe Ala Ile
545                 550                 555                 560

aaa aac ctc ctt ctc ctg ccg ggc tca tac acc tac gag tgg aac ttc     1728
Lys Asn Leu Leu Leu Leu Pro Gly Ser Tyr Thr Tyr Glu Trp Asn Phe
                565                 570                 575

agg aag gat gtt aac atg gtt ctg cag agc tcc cta gga aat gac cta     1776
Arg Lys Asp Val Asn Met Val Leu Gln Ser Ser Leu Gly Asn Asp Leu
            580                 585                 590

agg gtt gac gga gcc agc att aag ttt gat agc att tgc ctt tac gcc     1824
Arg Val Asp Gly Ala Ser Ile Lys Phe Asp Ser Ile Cys Leu Tyr Ala
        595                 600                 605

acc ttc ttc ccc atg gcc cac aac acc gcc tcc acg ctt gag gcc atg     1872
```

-continued

```
Thr Phe Phe Pro Met Ala His Asn Thr Ala Ser Thr Leu Glu Ala Met
    610                 615                 620

ctt aga aac gac acc aac gac cag tcc ttt aac gac tat ctc tcc gcc      1920
Leu Arg Asn Asp Thr Asn Asp Gln Ser Phe Asn Asp Tyr Leu Ser Ala
625                 630                 635                 640

gcc aac atg ctc tac cct ata ccc gcc aac gct acc aac gtg ccc ata      1968
Ala Asn Met Leu Tyr Pro Ile Pro Ala Asn Ala Thr Asn Val Pro Ile
                645                 650                 655

tcc atc ccc tcc cgc aac tgg gcg gct ttc cgc ggc tgg gcc ttc acg      2016
Ser Ile Pro Ser Arg Asn Trp Ala Ala Phe Arg Gly Trp Ala Phe Thr
            660                 665                 670

cgc ctt aag act aag gaa acc cca tca ctg ggc tcg ggc tac gac cct      2064
Arg Leu Lys Thr Lys Glu Thr Pro Ser Leu Gly Ser Gly Tyr Asp Pro
        675                 680                 685

tat tac acc tac tct ggc tct ata ccc tac cta gat gga acc ttt tac      2112
Tyr Tyr Thr Tyr Ser Gly Ser Ile Pro Tyr Leu Asp Gly Thr Phe Tyr
    690                 695                 700

ctc aac cac acc ttt aag aag gtg gcc att acc ttt gac tct tct gtc      2160
Leu Asn His Thr Phe Lys Lys Val Ala Ile Thr Phe Asp Ser Ser Val
705                 710                 715                 720

agc tgg cct ggc aat gac cgc ctg ctt acc ccc aac gag ttt gaa att      2208
Ser Trp Pro Gly Asn Asp Arg Leu Leu Thr Pro Asn Glu Phe Glu Ile
                725                 730                 735

aag cgc tca gtt gac ggg gag ggt tac aac gtt gcc cag tgt aac atg      2256
Lys Arg Ser Val Asp Gly Glu Gly Tyr Asn Val Ala Gln Cys Asn Met
            740                 745                 750

acc aaa gac tgg ttc ctg gta caa atg cta gct aac tat aac att ggc      2304
Thr Lys Asp Trp Phe Leu Val Gln Met Leu Ala Asn Tyr Asn Ile Gly
        755                 760                 765

tac cag ggc ttc tat atc cca gag agc tac aag gac cgc atg tac tcc      2352
Tyr Gln Gly Phe Tyr Ile Pro Glu Ser Tyr Lys Asp Arg Met Tyr Ser
    770                 775                 780

ttc ttt aga aac ttc cag ccc atg agc cgt cag gtg gtg gat gat act      2400
Phe Phe Arg Asn Phe Gln Pro Met Ser Arg Gln Val Val Asp Asp Thr
785                 790                 795                 800

aaa tac aag gac tac caa cag gtg ggc atc cta cac caa cac aac aac      2448
Lys Tyr Lys Asp Tyr Gln Gln Val Gly Ile Leu His Gln His Asn Asn
                805                 810                 815

tct gga ttt gtt ggc tac ctt gcc ccc acc atg cgc gaa gga cag gcc      2496
Ser Gly Phe Val Gly Tyr Leu Ala Pro Thr Met Arg Glu Gly Gln Ala
            820                 825                 830

tac cct gct aac ttc ccc tat ccg ctt ata ggc aag acc gca gtt gac      2544
Tyr Pro Ala Asn Phe Pro Tyr Pro Leu Ile Gly Lys Thr Ala Val Asp
        835                 840                 845

agc att acc cag aaa aag ttt ctt tgc gat cgc acc ctt tgg cgc atc      2592
Ser Ile Thr Gln Lys Lys Phe Leu Cys Asp Arg Thr Leu Trp Arg Ile
    850                 855                 860

cca ttc tcc agt aac ttt atg tcc atg ggc gca ctc aca gac ctg ggc      2640
Pro Phe Ser Ser Asn Phe Met Ser Met Gly Ala Leu Thr Asp Leu Gly
865                 870                 875                 880

caa aac ctt ctc tac gcc aac tcc gcc cac gcg cta gac atg act ttt      2688
Gln Asn Leu Leu Tyr Ala Asn Ser Ala His Ala Leu Asp Met Thr Phe
                885                 890                 895

gag gtg gat ccc atg gac gag ccc acc ctt ctt tat gtt ttg ttt gaa      2736
Glu Val Asp Pro Met Asp Glu Pro Thr Leu Leu Tyr Val Leu Phe Glu
            900                 905                 910

gtc ttt gac gtg gtc cgt gtg cac cag ccg cac cgc ggc gtc atc gaa      2784
Val Phe Asp Val Val Arg Val His Gln Pro His Arg Gly Val Ile Glu
        915                 920                 925
```

-continued

```
acc gtg tac ctg cgc acg ccc ttc tcg gcc ggc aac gcc aca aca taa     2832
Thr Val Tyr Leu Arg Thr Pro Phe Ser Ala Gly Asn Ala Thr Thr
    930                 935                 940


<210> SEQ ID NO 4
<211> LENGTH: 2790
<212> TYPE: DNA
<213> ORGANISM: Artificial Sequence
<220> FEATURE:
<223> OTHER INFORMATION: (QGPGAP)4-HVR1 modified Hexon protein
<220> FEATURE:
<221> NAME/KEY: CDS
<222> LOCATION: (1)..(2787)

<400> SEQUENCE: 4

atg gct acc cct tcg atg atg ccg cag tgg tct tac atg cac atc tcg       48
Met Ala Thr Pro Ser Met Met Pro Gln Trp Ser Tyr Met His Ile Ser
1               5                   10                  15

ggc cag gac gcc tcg gag tac ctg agc ccc ggg ctg gtg cag ttt gcc       96
Gly Gln Asp Ala Ser Glu Tyr Leu Ser Pro Gly Leu Val Gln Phe Ala
            20                  25                  30

cgc gcc acc gag acg tac ttc agc ctg aat aac aag ttt aga aac ccc      144
Arg Ala Thr Glu Thr Tyr Phe Ser Leu Asn Asn Lys Phe Arg Asn Pro
        35                  40                  45

acg gtg gcg cct acg cac gac gtg acc aca gac cgg tcc cag cgt ttg      192
Thr Val Ala Pro Thr His Asp Val Thr Thr Asp Arg Ser Gln Arg Leu
    50                  55                  60

acg ctg cgg ttc atc cct gtg gac cgt gag gat act gcg tac tcg tac      240
Thr Leu Arg Phe Ile Pro Val Asp Arg Glu Asp Thr Ala Tyr Ser Tyr
65                  70                  75                  80

aag gcg cgg ttc acc cta gct gtg ggt gat aac cgt gtg ctg gac atg      288
Lys Ala Arg Phe Thr Leu Ala Val Gly Asp Asn Arg Val Leu Asp Met
                85                  90                  95

gct tcc acg tac ttt gac atc cgc ggc gtg ctg gac agg ggc cct act      336
Ala Ser Thr Tyr Phe Asp Ile Arg Gly Val Leu Asp Arg Gly Pro Thr
            100                 105                 110

ttt aag ccc tac tct ggc act gcc tac aac gcc ctg gct ccc aag ggt      384
Phe Lys Pro Tyr Ser Gly Thr Ala Tyr Asn Ala Leu Ala Pro Lys Gly
        115                 120                 125

gcc cca aat cct tgc gaa tgg gat gaa cag gga cca gga gca cca cag      432
Ala Pro Asn Pro Cys Glu Trp Asp Glu Gln Gly Pro Gly Ala Pro Gln
    130                 135                 140

gga cca gga gca cca cag gga cca gga gca ccg caa ggt cct ggt gct      480
Gly Pro Gly Ala Pro Gln Gly Pro Gly Ala Pro Gln Gly Pro Gly Ala
145                 150                 155                 160

cct aaa act cac gta ttt ggg cag gcg cct tat tct ggt ata aat att      528
Pro Lys Thr His Val Phe Gly Gln Ala Pro Tyr Ser Gly Ile Asn Ile
                165                 170                 175

aca aag gag ggt att caa ata ggt gtc gaa ggt caa aca cct aaa tat      576
Thr Lys Glu Gly Ile Gln Ile Gly Val Glu Gly Gln Thr Pro Lys Tyr
            180                 185                 190

gcc gat aaa aca ttt caa cct gaa cct caa ata gga gaa tct cag tgg      624
Ala Asp Lys Thr Phe Gln Pro Glu Pro Gln Ile Gly Glu Ser Gln Trp
        195                 200                 205

tac gaa aca gaa att aat cat gca gct ggg aga gtc cta aaa aag act      672
Tyr Glu Thr Glu Ile Asn His Ala Ala Gly Arg Val Leu Lys Lys Thr
    210                 215                 220

acc cca atg aaa cca tgt tac ggt tca tat gca aaa ccc aca aat gaa      720
Thr Pro Met Lys Pro Cys Tyr Gly Ser Tyr Ala Lys Pro Thr Asn Glu
225                 230                 235                 240

aat gga ggg caa ggc att ctt gta aag caa caa aat gga aag cta gaa      768
Asn Gly Gly Gln Gly Ile Leu Val Lys Gln Gln Asn Gly Lys Leu Glu
```

-continued

```
                245                 250                 255

agt caa gtg gaa atg caa ttt ttc tca act act gag gca gcc gca ggc      816
Ser Gln Val Glu Met Gln Phe Phe Ser Thr Thr Glu Ala Ala Ala Gly
            260                 265                 270

aat ggt gat aac ttg act cct aaa gtg gta ttg tac agt gaa gat gta      864
Asn Gly Asp Asn Leu Thr Pro Lys Val Val Leu Tyr Ser Glu Asp Val
        275                 280                 285

gat ata gaa acc cca gac act cat att tct tac atg ccc act att aag      912
Asp Ile Glu Thr Pro Asp Thr His Ile Ser Tyr Met Pro Thr Ile Lys
    290                 295                 300

gaa ggt aac tca cga gaa cta atg ggc caa caa tct atg ccc aac agg      960
Glu Gly Asn Ser Arg Glu Leu Met Gly Gln Gln Ser Met Pro Asn Arg
305                 310                 315                 320

cct aat tac att gct ttt agg gac aat ttt att ggt cta atg tat tac     1008
Pro Asn Tyr Ile Ala Phe Arg Asp Asn Phe Ile Gly Leu Met Tyr Tyr
                325                 330                 335

aac agc acg ggt aat atg ggt gtt ctg gcg ggc caa gca tcg cag ttg     1056
Asn Ser Thr Gly Asn Met Gly Val Leu Ala Gly Gln Ala Ser Gln Leu
            340                 345                 350

aat gct gtt gta gat ttg caa gac aga aac aca gag ctt tca tac cag     1104
Asn Ala Val Val Asp Leu Gln Asp Arg Asn Thr Glu Leu Ser Tyr Gln
        355                 360                 365

ctt ttg ctt gat tcc att ggt gat aga acc agg tac ttt tct atg tgg     1152
Leu Leu Leu Asp Ser Ile Gly Asp Arg Thr Arg Tyr Phe Ser Met Trp
    370                 375                 380

aat cag ctt cca aat tac tgc ttt cca ctg gga ggt gtg att aat aca     1200
Asn Gln Leu Pro Asn Tyr Cys Phe Pro Leu Gly Gly Val Ile Asn Thr
385                 390                 395                 400

gag act ctt acc aag gta aaa cct aaa aca ggt cag gaa aat gga tgg     1248
Glu Thr Leu Thr Lys Val Lys Pro Lys Thr Gly Gln Glu Asn Gly Trp
                405                 410                 415

gaa aaa gat gct aca gaa ttt tca gat aaa aat gaa ata aga gtt gga     1296
Glu Lys Asp Ala Thr Glu Phe Ser Asp Lys Asn Glu Ile Arg Val Gly
            420                 425                 430

aat aat ttt gcc atg gaa atc aat cta aat gcc aac ctg tgg aga aat     1344
Asn Asn Phe Ala Met Glu Ile Asn Leu Asn Ala Asn Leu Trp Arg Asn
        435                 440                 445

ttc ctg tac tcc aac ata gcg ctg tat ttg ccc gac aag cta aag tac     1392
Phe Leu Tyr Ser Asn Ile Ala Leu Tyr Leu Pro Asp Lys Leu Lys Tyr
    450                 455                 460

agt cct tcc aac gta aaa att tct gat aac cca aac acc tac gac tac     1440
Ser Pro Ser Asn Val Lys Ile Ser Asp Asn Pro Asn Thr Tyr Asp Tyr
465                 470                 475                 480

atg aac aag cga gtg gtg gct ccc ggg cta gtg gac tgc tac att aac     1488
Met Asn Lys Arg Val Val Ala Pro Gly Leu Val Asp Cys Tyr Ile Asn
                485                 490                 495

ctt gga gca cgc tgg tcc ctt gac tat atg gac aac gtc aac cca ttt     1536
Leu Gly Ala Arg Trp Ser Leu Asp Tyr Met Asp Asn Val Asn Pro Phe
            500                 505                 510

aac cac cac cgc aat gct ggc ctg cgc tac cgc tca atg ttg ctg ggc     1584
Asn His His Arg Asn Ala Gly Leu Arg Tyr Arg Ser Met Leu Leu Gly
        515                 520                 525

aat ggt cgc tat gtg ccc ttc cac atc cag gtg cct cag aag ttc ttt     1632
Asn Gly Arg Tyr Val Pro Phe His Ile Gln Val Pro Gln Lys Phe Phe
    530                 535                 540

gcc att aaa aac ctc ctt ctc ctg ccg ggc tca tac acc tac gag tgg     1680
Ala Ile Lys Asn Leu Leu Leu Leu Pro Gly Ser Tyr Thr Tyr Glu Trp
545                 550                 555                 560

aac ttc agg aag gat gtt aac atg gtt ctg cag agc tcc cta gga aat     1728
```

-continued

```
Asn Phe Arg Lys Asp Val Asn Met Val Leu Gln Ser Ser Leu Gly Asn
                565                 570                 575

gac cta agg gtt gac gga gcc agc att aag ttt gat agc att tgc ctt      1776
Asp Leu Arg Val Asp Gly Ala Ser Ile Lys Phe Asp Ser Ile Cys Leu
            580                 585                 590

tac gcc acc ttc ttc ccc atg gcc cac aac acc gcc tcc acg ctt gag      1824
Tyr Ala Thr Phe Phe Pro Met Ala His Asn Thr Ala Ser Thr Leu Glu
        595                 600                 605

gcc atg ctt aga aac gac acc aac gac cag tcc ttt aac gac tat ctc      1872
Ala Met Leu Arg Asn Asp Thr Asn Asp Gln Ser Phe Asn Asp Tyr Leu
    610                 615                 620

tcc gcc gcc aac atg ctc tac cct ata ccc gcc aac gct acc aac gtg      1920
Ser Ala Ala Asn Met Leu Tyr Pro Ile Pro Ala Asn Ala Thr Asn Val
625                 630                 635                 640

ccc ata tcc atc ccc tcc cgc aac tgg gcg gct ttc cgc ggc tgg gcc      1968
Pro Ile Ser Ile Pro Ser Arg Asn Trp Ala Ala Phe Arg Gly Trp Ala
                645                 650                 655

ttc acg cgc ctt aag act aag gaa acc cca tca ctg ggc tcg ggc tac      2016
Phe Thr Arg Leu Lys Thr Lys Glu Thr Pro Ser Leu Gly Ser Gly Tyr
            660                 665                 670

gac cct tat tac acc tac tct ggc tct ata ccc tac cta gat gga acc      2064
Asp Pro Tyr Tyr Thr Tyr Ser Gly Ser Ile Pro Tyr Leu Asp Gly Thr
        675                 680                 685

ttt tac ctc aac cac acc ttt aag aag gtg gcc att acc ttt gac tct      2112
Phe Tyr Leu Asn His Thr Phe Lys Lys Val Ala Ile Thr Phe Asp Ser
    690                 695                 700

tct gtc agc tgg cct ggc aat gac cgc ctg ctt acc ccc aac gag ttt      2160
Ser Val Ser Trp Pro Gly Asn Asp Arg Leu Leu Thr Pro Asn Glu Phe
705                 710                 715                 720

gaa att aag cgc tca gtt gac ggg gag ggt tac aac gtt gcc cag tgt      2208
Glu Ile Lys Arg Ser Val Asp Gly Glu Gly Tyr Asn Val Ala Gln Cys
                725                 730                 735

aac atg acc aaa gac tgg ttc ctg gta caa atg cta gct aac tat aac      2256
Asn Met Thr Lys Asp Trp Phe Leu Val Gln Met Leu Ala Asn Tyr Asn
            740                 745                 750

att ggc tac cag ggc ttc tat atc cca gag agc tac aag gac cgc atg      2304
Ile Gly Tyr Gln Gly Phe Tyr Ile Pro Glu Ser Tyr Lys Asp Arg Met
        755                 760                 765

tac tcc ttc ttt aga aac ttc cag ccc atg agc cgt cag gtg gtg gat      2352
Tyr Ser Phe Phe Arg Asn Phe Gln Pro Met Ser Arg Gln Val Val Asp
    770                 775                 780

gat act aaa tac aag gac tac caa cag gtg ggc atc cta cac caa cac      2400
Asp Thr Lys Tyr Lys Asp Tyr Gln Gln Val Gly Ile Leu His Gln His
785                 790                 795                 800

aac aac tct gga ttt gtt ggc tac ctt gcc ccc acc atg cgc gaa gga      2448
Asn Asn Ser Gly Phe Val Gly Tyr Leu Ala Pro Thr Met Arg Glu Gly
                805                 810                 815

cag gcc tac cct gct aac ttc ccc tat ccg ctt ata ggc aag acc gca      2496
Gln Ala Tyr Pro Ala Asn Phe Pro Tyr Pro Leu Ile Gly Lys Thr Ala
            820                 825                 830

gtt gac agc att acc cag aaa aag ttt ctt tgc gat cgc acc ctt tgg      2544
Val Asp Ser Ile Thr Gln Lys Lys Phe Leu Cys Asp Arg Thr Leu Trp
        835                 840                 845

cgc atc cca ttc tcc agt aac ttt atg tcc atg ggc gca ctc aca gac      2592
Arg Ile Pro Phe Ser Ser Asn Phe Met Ser Met Gly Ala Leu Thr Asp
    850                 855                 860

ctg ggc caa aac ctt ctc tac gcc aac tcc gcc cac gcg cta gac atg      2640
Leu Gly Gln Asn Leu Leu Tyr Ala Asn Ser Ala His Ala Leu Asp Met
865                 870                 875                 880
```

act ttt gag gtg gat ccc atg gac gag ccc acc ctt ctt tat gtt ttg 2688
Thr Phe Glu Val Asp Pro Met Asp Glu Pro Thr Leu Leu Tyr Val Leu
885 890 895 ttt gaa gtc ttt gac gtg gtc cgt gtg cac cag ccg cac cgc ggc gtc 2736
Phe Glu Val Phe Asp Val Val Arg Val His Gln Pro His Arg Gly Val
900 905 910 atc gaa acc gtg tac ctg cgc acg ccc ttc tcg gcc ggc aac gcc aca 2784
Ile Glu Thr Val Tyr Leu Arg Thr Pro Phe Ser Ala Gly Asn Ala Thr
915 920 925 aca taa 2790
Thr

<210> SEQ ID NO 5
<211> LENGTH: 2808
<212> TYPE: DNA
<213> ORGANISM: Artificial Sequence
<220> FEATURE:
<223> OTHER INFORMATION: (QPGGAP)5-HVR1 modified Hexon protein
<220> FEATURE:
<221> NAME/KEY: CDS
<222> LOCATION: (1)..(2805)

<400> SEQUENCE: 5 atg gct acc cct tcg atg atg ccg cag tgg tct tac atg cac atc tcg 48
Met Ala Thr Pro Ser Met Met Pro Gln Trp Ser Tyr Met His Ile Ser
1 5 10 15 ggc cag gac gcc tcg gag tac ctg agc ccc ggg ctg gtg cag ttt gcc 96
Gly Gln Asp Ala Ser Glu Tyr Leu Ser Pro Gly Leu Val Gln Phe Ala
20 25 30 cgc gcc acc gag acg tac ttc agc ctg aat aac aag ttt aga aac ccc 144
Arg Ala Thr Glu Thr Tyr Phe Ser Leu Asn Asn Lys Phe Arg Asn Pro
35 40 45 acg gtg gcg cct acg cac gac gtg acc aca gac cgg tcc cag cgt ttg 192
Thr Val Ala Pro Thr His Asp Val Thr Thr Asp Arg Ser Gln Arg Leu
50 55 60 acg ctg cgg ttc atc cct gtg gac cgt gag gat act gcg tac tcg tac 240
Thr Leu Arg Phe Ile Pro Val Asp Arg Glu Asp Thr Ala Tyr Ser Tyr
65 70 75 80 aag gcg cgg ttc acc cta gct gtg ggt gat aac cgt gtg ctg gac atg 288
Lys Ala Arg Phe Thr Leu Ala Val Gly Asp Asn Arg Val Leu Asp Met
85 90 95 gct tcc acg tac ttt gac atc cgc ggc gtg ctg gac agg ggc cct act 336
Ala Ser Thr Tyr Phe Asp Ile Arg Gly Val Leu Asp Arg Gly Pro Thr
100 105 110 ttt aag ccc tac tct ggc act gcc tac aac gcc ctg gct ccc aag ggt 384
Phe Lys Pro Tyr Ser Gly Thr Ala Tyr Asn Ala Leu Ala Pro Lys Gly
115 120 125 gcc cca aat cct tgc gaa tgg gat gaa cag gga cca gga gca cca cag 432
Ala Pro Asn Pro Cys Glu Trp Asp Glu Gln Gly Pro Gly Ala Pro Gln
130 135 140 gga cca gga gca cca cag gga cca gga gca ccg caa ggt cct ggt gct 480
Gly Pro Gly Ala Pro Gln Gly Pro Gly Ala Pro Gln Gly Pro Gly Ala
145 150 155 160 cct cag gga cca gga gca cca aaa act cac gta ttt ggg cag gcg cct 528
Pro Gln Gly Pro Gly Ala Pro Lys Thr His Val Phe Gly Gln Ala Pro
165 170 175 tat tct ggt ata aat att aca aag gag ggt att caa ata ggt gtc gaa 576
Tyr Ser Gly Ile Asn Ile Thr Lys Glu Gly Ile Gln Ile Gly Val Glu
180 185 190 ggt caa aca cct aaa tat gcc gat aaa aca ttt caa cct gaa cct caa 624
Gly Gln Thr Pro Lys Tyr Ala Asp Lys Thr Phe Gln Pro Glu Pro Gln
195 200 205

```
ata gga gaa tct cag tgg tac gaa aca gaa att aat cat gca gct ggg      672
Ile Gly Glu Ser Gln Trp Tyr Glu Thr Glu Ile Asn His Ala Ala Gly
    210                 215                 220

aga gtc cta aaa aag act acc cca atg aaa cca tgt tac ggt tca tat      720
Arg Val Leu Lys Lys Thr Thr Pro Met Lys Pro Cys Tyr Gly Ser Tyr
225                 230                 235                 240

gca aaa ccc aca aat gaa aat gga ggg caa ggc att ctt gta aag caa      768
Ala Lys Pro Thr Asn Glu Asn Gly Gly Gln Gly Ile Leu Val Lys Gln
                245                 250                 255

caa aat gga aag cta gaa agt caa gtg gaa atg caa ttt ttc tca act      816
Gln Asn Gly Lys Leu Glu Ser Gln Val Glu Met Gln Phe Phe Ser Thr
            260                 265                 270

act gag gca gcc gca ggc aat ggt gat aac ttg act cct aaa gtg gta      864
Thr Glu Ala Ala Ala Gly Asn Gly Asp Asn Leu Thr Pro Lys Val Val
        275                 280                 285

ttg tac agt gaa gat gta gat ata gaa acc cca gac act cat att tct      912
Leu Tyr Ser Glu Asp Val Asp Ile Glu Thr Pro Asp Thr His Ile Ser
    290                 295                 300

tac atg ccc act att aag gaa ggt aac tca cga gaa cta atg ggc caa      960
Tyr Met Pro Thr Ile Lys Glu Gly Asn Ser Arg Glu Leu Met Gly Gln
305                 310                 315                 320

caa tct atg ccc aac agg cct aat tac att gct ttt agg gac aat ttt     1008
Gln Ser Met Pro Asn Arg Pro Asn Tyr Ile Ala Phe Arg Asp Asn Phe
                325                 330                 335

att ggt cta atg tat tac aac agc acg ggt aat atg ggt gtt ctg gcg     1056
Ile Gly Leu Met Tyr Tyr Asn Ser Thr Gly Asn Met Gly Val Leu Ala
            340                 345                 350

ggc caa gca tcg cag ttg aat gct gtt gta gat ttg caa gac aga aac     1104
Gly Gln Ala Ser Gln Leu Asn Ala Val Val Asp Leu Gln Asp Arg Asn
        355                 360                 365

aca gag ctt tca tac cag ctt ttg ctt gat tcc att ggt gat aga acc     1152
Thr Glu Leu Ser Tyr Gln Leu Leu Leu Asp Ser Ile Gly Asp Arg Thr
    370                 375                 380

agg tac ttt tct atg tgg aat cag ctt cca aat tac tgc ttt cca ctg     1200
Arg Tyr Phe Ser Met Trp Asn Gln Leu Pro Asn Tyr Cys Phe Pro Leu
385                 390                 395                 400

gga ggt gtg att aat aca gag act ctt acc aag gta aaa cct aaa aca     1248
Gly Gly Val Ile Asn Thr Glu Thr Leu Thr Lys Val Lys Pro Lys Thr
                405                 410                 415

ggt cag gaa aat gga tgg gaa aaa gat gct aca gaa ttt tca gat aaa     1296
Gly Gln Glu Asn Gly Trp Glu Lys Asp Ala Thr Glu Phe Ser Asp Lys
            420                 425                 430

aat gaa ata aga gtt gga aat aat ttt gcc atg gaa atc aat cta aat     1344
Asn Glu Ile Arg Val Gly Asn Asn Phe Ala Met Glu Ile Asn Leu Asn
        435                 440                 445

gcc aac ctg tgg aga aat ttc ctg tac tcc aac ata gcg ctg tat ttg     1392
Ala Asn Leu Trp Arg Asn Phe Leu Tyr Ser Asn Ile Ala Leu Tyr Leu
    450                 455                 460

ccc gac aag cta aag tac agt cct tcc aac gta aaa att tct gat aac     1440
Pro Asp Lys Leu Lys Tyr Ser Pro Ser Asn Val Lys Ile Ser Asp Asn
465                 470                 475                 480

cca aac acc tac gac tac atg aac aag cga gtg gtg gct ccc ggg cta     1488
Pro Asn Thr Tyr Asp Tyr Met Asn Lys Arg Val Val Ala Pro Gly Leu
                485                 490                 495

gtg gac tgc tac att aac ctt gga gca cgc tgg tcc ctt gac tat atg     1536
Val Asp Cys Tyr Ile Asn Leu Gly Ala Arg Trp Ser Leu Asp Tyr Met
            500                 505                 510

gac aac gtc aac cca ttt aac cac cac cgc aat gct ggc ctg cgc tac     1584
Asp Asn Val Asn Pro Phe Asn His His Arg Asn Ala Gly Leu Arg Tyr
```

-continued

```
        515                 520                 525

cgc tca atg ttg ctg ggc aat ggt cgc tat gtg ccc ttc cac atc cag      1632
Arg Ser Met Leu Leu Gly Asn Gly Arg Tyr Val Pro Phe His Ile Gln
    530                 535                 540

gtg cct cag aag ttc ttt gcc att aaa aac ctc ctt ctc ctg ccg ggc      1680
Val Pro Gln Lys Phe Phe Ala Ile Lys Asn Leu Leu Leu Leu Pro Gly
545                 550                 555                 560

tca tac acc tac gag tgg aac ttc agg aag gat gtt aac atg gtt ctg      1728
Ser Tyr Thr Tyr Glu Trp Asn Phe Arg Lys Asp Val Asn Met Val Leu
                565                 570                 575

cag agc tcc cta gga aat gac cta agg gtt gac gga gcc agc att aag      1776
Gln Ser Ser Leu Gly Asn Asp Leu Arg Val Asp Gly Ala Ser Ile Lys
            580                 585                 590

ttt gat agc att tgc ctt tac gcc acc ttc ttc ccc atg gcc cac aac      1824
Phe Asp Ser Ile Cys Leu Tyr Ala Thr Phe Phe Pro Met Ala His Asn
        595                 600                 605

acc gcc tcc acg ctt gag gcc atg ctt aga aac gac acc aac gac cag      1872
Thr Ala Ser Thr Leu Glu Ala Met Leu Arg Asn Asp Thr Asn Asp Gln
    610                 615                 620

tcc ttt aac gac tat ctc tcc gcc gcc aac atg ctc tac cct ata ccc      1920
Ser Phe Asn Asp Tyr Leu Ser Ala Ala Asn Met Leu Tyr Pro Ile Pro
625                 630                 635                 640

gcc aac gct acc aac gtg ccc ata tcc atc ccc tcc cgc aac tgg gcg      1968
Ala Asn Ala Thr Asn Val Pro Ile Ser Ile Pro Ser Arg Asn Trp Ala
                645                 650                 655

gct ttc cgc ggc tgg gcc ttc acg cgc ctt aag act aag gaa acc cca      2016
Ala Phe Arg Gly Trp Ala Phe Thr Arg Leu Lys Thr Lys Glu Thr Pro
            660                 665                 670

tca ctg ggc tcg ggc tac gac cct tat tac acc tac tct ggc tct ata      2064
Ser Leu Gly Ser Gly Tyr Asp Pro Tyr Tyr Thr Tyr Ser Gly Ser Ile
        675                 680                 685

ccc tac cta gat gga acc ttt tac ctc aac cac acc ttt aag aag gtg      2112
Pro Tyr Leu Asp Gly Thr Phe Tyr Leu Asn His Thr Phe Lys Lys Val
    690                 695                 700

gcc att acc ttt gac tct tct gtc agc tgg cct ggc aat gac cgc ctg      2160
Ala Ile Thr Phe Asp Ser Ser Val Ser Trp Pro Gly Asn Asp Arg Leu
705                 710                 715                 720

ctt acc ccc aac gag ttt gaa att aag cgc tca gtt gac ggg gag ggt      2208
Leu Thr Pro Asn Glu Phe Glu Ile Lys Arg Ser Val Asp Gly Glu Gly
                725                 730                 735

tac aac gtt gcc cag tgt aac atg acc aaa gac tgg ttc ctg gta caa      2256
Tyr Asn Val Ala Gln Cys Asn Met Thr Lys Asp Trp Phe Leu Val Gln
            740                 745                 750

atg cta gct aac tat aac att ggc tac cag ggc ttc tat atc cca gag      2304
Met Leu Ala Asn Tyr Asn Ile Gly Tyr Gln Gly Phe Tyr Ile Pro Glu
        755                 760                 765

agc tac aag gac cgc atg tac tcc ttc ttt aga aac ttc cag ccc atg      2352
Ser Tyr Lys Asp Arg Met Tyr Ser Phe Phe Arg Asn Phe Gln Pro Met
    770                 775                 780

agc cgt cag gtg gtg gat gat act aaa tac aag gac tac caa cag gtg      2400
Ser Arg Gln Val Val Asp Asp Thr Lys Tyr Lys Asp Tyr Gln Gln Val
785                 790                 795                 800

ggc atc cta cac caa cac aac aac tct gga ttt gtt ggc tac ctt gcc      2448
Gly Ile Leu His Gln His Asn Asn Ser Gly Phe Val Gly Tyr Leu Ala
                805                 810                 815

ccc acc atg cgc gaa gga cag gcc tac cct gct aac ttc ccc tat ccg      2496
Pro Thr Met Arg Glu Gly Gln Ala Tyr Pro Ala Asn Phe Pro Tyr Pro
            820                 825                 830

ctt ata ggc aag acc gca gtt gac agc att acc cag aaa aag ttt ctt      2544
```

```
Leu Ile Gly Lys Thr Ala Val Asp Ser Ile Thr Gln Lys Lys Phe Leu
        835                 840                 845

tgc gat cgc acc ctt tgg cgc atc cca ttc tcc agt aac ttt atg tcc      2592
Cys Asp Arg Thr Leu Trp Arg Ile Pro Phe Ser Ser Asn Phe Met Ser
    850                 855                 860

atg ggc gca ctc aca gac ctg ggc caa aac ctt ctc tac gcc aac tcc      2640
Met Gly Ala Leu Thr Asp Leu Gly Gln Asn Leu Leu Tyr Ala Asn Ser
865                 870                 875                 880

gcc cac gcg cta gac atg act ttt gag gtg gat ccc atg gac gag ccc      2688
Ala His Ala Leu Asp Met Thr Phe Glu Val Asp Pro Met Asp Glu Pro
                885                 890                 895

acc ctt ctt tat gtt ttg ttt gaa gtc ttt gac gtg gtc cgt gtg cac      2736
Thr Leu Leu Tyr Val Leu Phe Glu Val Phe Asp Val Val Arg Val His
            900                 905                 910

cag ccg cac cgc ggc gtc atc gaa acc gtg tac ctg cgc acg ccc ttc      2784
Gln Pro His Arg Gly Val Ile Glu Thr Val Tyr Leu Arg Thr Pro Phe
        915                 920                 925

tcg gcc ggc aac gcc aca aca taa                                      2808
Ser Ala Gly Asn Ala Thr Thr
    930                 935


<210> SEQ ID NO 6
<211> LENGTH: 2826
<212> TYPE: DNA
<213> ORGANISM: Artificial Sequence
<220> FEATURE:
<223> OTHER INFORMATION: (QGPGAP)6-HVR1 modified Hexon protein
<220> FEATURE:
<221> NAME/KEY: CDS
<222> LOCATION: (1)..(2823)

<400> SEQUENCE: 6

atg gct acc cct tcg atg atg ccg cag tgg tct tac atg cac atc tcg        48
Met Ala Thr Pro Ser Met Met Pro Gln Trp Ser Tyr Met His Ile Ser
1               5                   10                  15

ggc cag gac gcc tcg gag tac ctg agc ccc ggg ctg gtg cag ttt gcc        96
Gly Gln Asp Ala Ser Glu Tyr Leu Ser Pro Gly Leu Val Gln Phe Ala
            20                  25                  30

cgc gcc acc gag acg tac ttc agc ctg aat aac aag ttt aga aac ccc       144
Arg Ala Thr Glu Thr Tyr Phe Ser Leu Asn Asn Lys Phe Arg Asn Pro
        35                  40                  45

acg gtg gcg cct acg cac gac gtg acc aca gac cgg tcc cag cgt ttg       192
Thr Val Ala Pro Thr His Asp Val Thr Thr Asp Arg Ser Gln Arg Leu
    50                  55                  60

acg ctg cgg ttc atc cct gtg gac cgt gag gat act gcg tac tcg tac       240
Thr Leu Arg Phe Ile Pro Val Asp Arg Glu Asp Thr Ala Tyr Ser Tyr
65                  70                  75                  80

aag gcg cgg ttc acc cta gct gtg ggt gat aac cgt gtg ctg gac atg       288
Lys Ala Arg Phe Thr Leu Ala Val Gly Asp Asn Arg Val Leu Asp Met
                85                  90                  95

gct tcc acg tac ttt gac atc cgc ggc gtg ctg gac agg ggc cct act       336
Ala Ser Thr Tyr Phe Asp Ile Arg Gly Val Leu Asp Arg Gly Pro Thr
            100                 105                 110

ttt aag ccc tac tct ggc act gcc tac aac gcc ctg gct ccc aag ggt       384
Phe Lys Pro Tyr Ser Gly Thr Ala Tyr Asn Ala Leu Ala Pro Lys Gly
        115                 120                 125

gcc cca aat cct tgc gaa tgg gat gaa cag gga cca gga gca cca cag       432
Ala Pro Asn Pro Cys Glu Trp Asp Glu Gln Gly Pro Gly Ala Pro Gln
    130                 135                 140

gga cca gga gca cca cag gga cca gga gca ccg caa ggt cct ggt gct       480
Gly Pro Gly Ala Pro Gln Gly Pro Gly Ala Pro Gln Gly Pro Gly Ala
145                 150                 155                 160
```

-continued

```
cct cag gga cca gga gca cca cag gga cca gga gca cca aaa act cac      528
Pro Gln Gly Pro Gly Ala Pro Gln Gly Pro Gly Ala Pro Lys Thr His
                165                 170                 175

gta ttt ggg cag gcg cct tat tct ggt ata aat att aca aag gag ggt      576
Val Phe Gly Gln Ala Pro Tyr Ser Gly Ile Asn Ile Thr Lys Glu Gly
            180                 185                 190

att caa ata ggt gtc gaa ggt caa aca cct aaa tat gcc gat aaa aca      624
Ile Gln Ile Gly Val Glu Gly Gln Thr Pro Lys Tyr Ala Asp Lys Thr
        195                 200                 205

ttt caa cct gaa cct caa ata gga gaa tct cag tgg tac gaa aca gaa      672
Phe Gln Pro Glu Pro Gln Ile Gly Glu Ser Gln Trp Tyr Glu Thr Glu
    210                 215                 220

att aat cat gca gct ggg aga gtc cta aaa aag act acc cca atg aaa      720
Ile Asn His Ala Ala Gly Arg Val Leu Lys Lys Thr Thr Pro Met Lys
225                 230                 235                 240

cca tgt tac ggt tca tat gca aaa ccc aca aat gaa aat gga ggg caa      768
Pro Cys Tyr Gly Ser Tyr Ala Lys Pro Thr Asn Glu Asn Gly Gly Gln
                245                 250                 255

ggc att ctt gta aag caa caa aat gga aag cta gaa agt caa gtg gaa      816
Gly Ile Leu Val Lys Gln Gln Asn Gly Lys Leu Glu Ser Gln Val Glu
            260                 265                 270

atg caa ttt ttc tca act act gag gca gcc gca ggc aat ggt gat aac      864
Met Gln Phe Phe Ser Thr Thr Glu Ala Ala Ala Gly Asn Gly Asp Asn
        275                 280                 285

ttg act cct aaa gtg gta ttg tac agt gaa gat gta gat ata gaa acc      912
Leu Thr Pro Lys Val Val Leu Tyr Ser Glu Asp Val Asp Ile Glu Thr
    290                 295                 300

cca gac act cat att tct tac atg ccc act att aag gaa ggt aac tca      960
Pro Asp Thr His Ile Ser Tyr Met Pro Thr Ile Lys Glu Gly Asn Ser
305                 310                 315                 320

cga gaa cta atg ggc caa caa tct atg ccc aac agg cct aat tac att     1008
Arg Glu Leu Met Gly Gln Gln Ser Met Pro Asn Arg Pro Asn Tyr Ile
                325                 330                 335

gct ttt agg gac aat ttt att ggt cta atg tat tac aac agc acg ggt     1056
Ala Phe Arg Asp Asn Phe Ile Gly Leu Met Tyr Tyr Asn Ser Thr Gly
            340                 345                 350

aat atg ggt gtt ctg gcg ggc caa gca tcg cag ttg aat gct gtt gta     1104
Asn Met Gly Val Leu Ala Gly Gln Ala Ser Gln Leu Asn Ala Val Val
        355                 360                 365

gat ttg caa gac aga aac aca gag ctt tca tac cag ctt ttg ctt gat     1152
Asp Leu Gln Asp Arg Asn Thr Glu Leu Ser Tyr Gln Leu Leu Leu Asp
    370                 375                 380

tcc att ggt gat aga acc agg tac ttt tct atg tgg aat cag ctt cca     1200
Ser Ile Gly Asp Arg Thr Arg Tyr Phe Ser Met Trp Asn Gln Leu Pro
385                 390                 395                 400

aat tac tgc ttt cca ctg gga ggt gtg att aat aca gag act ctt acc     1248
Asn Tyr Cys Phe Pro Leu Gly Gly Val Ile Asn Thr Glu Thr Leu Thr
                405                 410                 415

aag gta aaa cct aaa aca ggt cag gaa aat gga tgg gaa aaa gat gct     1296
Lys Val Lys Pro Lys Thr Gly Gln Glu Asn Gly Trp Glu Lys Asp Ala
            420                 425                 430

aca gaa ttt tca gat aaa aat gaa ata aga gtt gga aat aat ttt gcc     1344
Thr Glu Phe Ser Asp Lys Asn Glu Ile Arg Val Gly Asn Asn Phe Ala
        435                 440                 445

atg gaa atc aat cta aat gcc aac ctg tgg aga aat ttc ctg tac tcc     1392
Met Glu Ile Asn Leu Asn Ala Asn Leu Trp Arg Asn Phe Leu Tyr Ser
    450                 455                 460

aac ata gcg ctg tat ttg ccc gac aag cta aag tac agt cct tcc aac     1440
Asn Ile Ala Leu Tyr Leu Pro Asp Lys Leu Lys Tyr Ser Pro Ser Asn
```

-continued

```
465                 470                 475                 480

gta aaa att tct gat aac cca aac acc tac gac tac atg aac aag cga      1488
Val Lys Ile Ser Asp Asn Pro Asn Thr Tyr Asp Tyr Met Asn Lys Arg
                485                 490                 495

gtg gtg gct ccc ggg cta gtg gac tgc tac att aac ctt gga gca cgc      1536
Val Val Ala Pro Gly Leu Val Asp Cys Tyr Ile Asn Leu Gly Ala Arg
            500                 505                 510

tgg tcc ctt gac tat atg gac aac gtc aac cca ttt aac cac cac cgc      1584
Trp Ser Leu Asp Tyr Met Asp Asn Val Asn Pro Phe Asn His His Arg
        515                 520                 525

aat gct ggc ctg cgc tac cgc tca atg ttg ctg ggc aat ggt cgc tat      1632
Asn Ala Gly Leu Arg Tyr Arg Ser Met Leu Leu Gly Asn Gly Arg Tyr
    530                 535                 540

gtg ccc ttc cac atc cag gtg cct cag aag ttc ttt gcc att aaa aac      1680
Val Pro Phe His Ile Gln Val Pro Gln Lys Phe Phe Ala Ile Lys Asn
545                 550                 555                 560

ctc ctt ctc ctg ccg ggc tca tac acc tac gag tgg aac ttc agg aag      1728
Leu Leu Leu Leu Pro Gly Ser Tyr Thr Tyr Glu Trp Asn Phe Arg Lys
                565                 570                 575

gat gtt aac atg gtt ctg cag agc tcc cta gga aat gac cta agg gtt      1776
Asp Val Asn Met Val Leu Gln Ser Ser Leu Gly Asn Asp Leu Arg Val
            580                 585                 590

gac gga gcc agc att aag ttt gat agc att tgc ctt tac gcc acc ttc      1824
Asp Gly Ala Ser Ile Lys Phe Asp Ser Ile Cys Leu Tyr Ala Thr Phe
        595                 600                 605

ttc ccc atg gcc cac aac acc gcc tcc acg ctt gag gcc atg ctt aga      1872
Phe Pro Met Ala His Asn Thr Ala Ser Thr Leu Glu Ala Met Leu Arg
    610                 615                 620

aac gac acc aac gac cag tcc ttt aac gac tat ctc tcc gcc gcc aac      1920
Asn Asp Thr Asn Asp Gln Ser Phe Asn Asp Tyr Leu Ser Ala Ala Asn
625                 630                 635                 640

atg ctc tac cct ata ccc gcc aac gct acc aac gtg ccc ata tcc atc      1968
Met Leu Tyr Pro Ile Pro Ala Asn Ala Thr Asn Val Pro Ile Ser Ile
                645                 650                 655

ccc tcc cgc aac tgg gcg gct ttc cgc ggc tgg gcc ttc acg cgc ctt      2016
Pro Ser Arg Asn Trp Ala Ala Phe Arg Gly Trp Ala Phe Thr Arg Leu
            660                 665                 670

aag act aag gaa acc cca tca ctg ggc tcg ggc tac gac cct tat tac      2064
Lys Thr Lys Glu Thr Pro Ser Leu Gly Ser Gly Tyr Asp Pro Tyr Tyr
        675                 680                 685

acc tac tct ggc tct ata ccc tac cta gat gga acc ttt tac ctc aac      2112
Thr Tyr Ser Gly Ser Ile Pro Tyr Leu Asp Gly Thr Phe Tyr Leu Asn
    690                 695                 700

cac acc ttt aag aag gtg gcc att acc ttt gac tct tct gtc agc tgg      2160
His Thr Phe Lys Lys Val Ala Ile Thr Phe Asp Ser Ser Val Ser Trp
705                 710                 715                 720

cct ggc aat gac cgc ctg ctt acc ccc aac gag ttt gaa att aag cgc      2208
Pro Gly Asn Asp Arg Leu Leu Thr Pro Asn Glu Phe Glu Ile Lys Arg
                725                 730                 735

tca gtt gac ggg gag ggt tac aac gtt gcc cag tgt aac atg acc aaa      2256
Ser Val Asp Gly Glu Gly Tyr Asn Val Ala Gln Cys Asn Met Thr Lys
            740                 745                 750

gac tgg ttc ctg gta caa atg cta gct aac tat aac att ggc tac cag      2304
Asp Trp Phe Leu Val Gln Met Leu Ala Asn Tyr Asn Ile Gly Tyr Gln
        755                 760                 765

ggc ttc tat atc cca gag agc tac aag gac cgc atg tac tcc ttc ttt      2352
Gly Phe Tyr Ile Pro Glu Ser Tyr Lys Asp Arg Met Tyr Ser Phe Phe
    770                 775                 780

aga aac ttc cag ccc atg agc cgt cag gtg gtg gat gat act aaa tac      2400
```

-continued

```
Arg Asn Phe Gln Pro Met Ser Arg Gln Val Val Asp Asp Thr Lys Tyr
785                 790                 795                 800

aag gac tac caa cag gtg ggc atc cta cac caa cac aac aac tct gga     2448
Lys Asp Tyr Gln Gln Val Gly Ile Leu His Gln His Asn Asn Ser Gly
                805                 810                 815

ttt gtt ggc tac ctt gcc ccc acc atg cgc gaa gga cag gcc tac cct     2496
Phe Val Gly Tyr Leu Ala Pro Thr Met Arg Glu Gly Gln Ala Tyr Pro
            820                 825                 830

gct aac ttc ccc tat ccg ctt ata ggc aag acc gca gtt gac agc att     2544
Ala Asn Phe Pro Tyr Pro Leu Ile Gly Lys Thr Ala Val Asp Ser Ile
        835                 840                 845

acc cag aaa aag ttt ctt tgc gat cgc acc ctt tgg cgc atc cca ttc     2592
Thr Gln Lys Lys Phe Leu Cys Asp Arg Thr Leu Trp Arg Ile Pro Phe
    850                 855                 860

tcc agt aac ttt atg tcc atg ggc gca ctc aca gac ctg ggc caa aac     2640
Ser Ser Asn Phe Met Ser Met Gly Ala Leu Thr Asp Leu Gly Gln Asn
865                 870                 875                 880

ctt ctc tac gcc aac tcc gcc cac gcg cta gac atg act ttt gag gtg     2688
Leu Leu Tyr Ala Asn Ser Ala His Ala Leu Asp Met Thr Phe Glu Val
                885                 890                 895

gat ccc atg gac gag ccc acc ctt ctt tat gtt ttg ttt gaa gtc ttt     2736
Asp Pro Met Asp Glu Pro Thr Leu Leu Tyr Val Leu Phe Glu Val Phe
            900                 905                 910

gac gtg gtc cgt gtg cac cag ccg cac cgc ggc gtc atc gaa acc gtg     2784
Asp Val Val Arg Val His Gln Pro His Arg Gly Val Ile Glu Thr Val
        915                 920                 925

tac ctg cgc acg ccc ttc tcg gcc ggc aac gcc aca aca taa             2826
Tyr Leu Arg Thr Pro Phe Ser Ala Gly Asn Ala Thr Thr
    930                 935                 940


<210> SEQ ID NO 7
<211> LENGTH: 2844
<212> TYPE: DNA
<213> ORGANISM: Artificial Sequence
<220> FEATURE:
<223> OTHER INFORMATION: (QGPGAP)7-HVR1 modified Hexon protein
<220> FEATURE:
<221> NAME/KEY: CDS
<222> LOCATION: (1)..(2841)

<400> SEQUENCE: 7

atg gct acc cct tcg atg atg ccg cag tgg tct tac atg cac atc tcg       48
Met Ala Thr Pro Ser Met Met Pro Gln Trp Ser Tyr Met His Ile Ser
1               5                   10                  15

ggc cag gac gcc tcg gag tac ctg agc ccc ggg ctg gtg cag ttt gcc       96
Gly Gln Asp Ala Ser Glu Tyr Leu Ser Pro Gly Leu Val Gln Phe Ala
            20                  25                  30

cgc gcc acc gag acg tac ttc agc ctg aat aac aag ttt aga aac ccc      144
Arg Ala Thr Glu Thr Tyr Phe Ser Leu Asn Asn Lys Phe Arg Asn Pro
        35                  40                  45

acg gtg gcg cct acg cac gac gtg acc aca gac cgg tcc cag cgt ttg      192
Thr Val Ala Pro Thr His Asp Val Thr Thr Asp Arg Ser Gln Arg Leu
    50                  55                  60

acg ctg cgg ttc atc cct gtg gac cgt gag gat act gcg tac tcg tac      240
Thr Leu Arg Phe Ile Pro Val Asp Arg Glu Asp Thr Ala Tyr Ser Tyr
65                  70                  75                  80

aag gcg cgg ttc acc cta gct gtg ggt gat aac cgt gtg ctg gac atg      288
Lys Ala Arg Phe Thr Leu Ala Val Gly Asp Asn Arg Val Leu Asp Met
                85                  90                  95

gct tcc acg tac ttt gac atc cgc ggc gtg ctg gac agg ggc cct act      336
Ala Ser Thr Tyr Phe Asp Ile Arg Gly Val Leu Asp Arg Gly Pro Thr
            100                 105                 110
```

-continued

```
ttt aag ccc tac tct ggc act gcc tac aac gcc ctg gct ccc aag ggt      384
Phe Lys Pro Tyr Ser Gly Thr Ala Tyr Asn Ala Leu Ala Pro Lys Gly
        115                 120                 125

gcc cca aat cct tgc gaa tgg gat gaa cag gga cca gga gca cca cag      432
Ala Pro Asn Pro Cys Glu Trp Asp Glu Gln Gly Pro Gly Ala Pro Gln
    130                 135                 140

gga cca gga gca cca cag gga cca gga gca cca cag gga cca gga gca      480
Gly Pro Gly Ala Pro Gln Gly Pro Gly Ala Pro Gln Gly Pro Gly Ala
145                 150                 155                 160

cca cag gga cca gga gca cca cag gga cca gga gca ccg caa ggt cct      528
Pro Gln Gly Pro Gly Ala Pro Gln Gly Pro Gly Ala Pro Gln Gly Pro
                165                 170                 175

ggt gct cct aaa act cac gta ttt ggg cag gcg cct tat tct ggt ata      576
Gly Ala Pro Lys Thr His Val Phe Gly Gln Ala Pro Tyr Ser Gly Ile
            180                 185                 190

aat att aca aag gag ggt att caa ata ggt gtc gaa ggt caa aca cct      624
Asn Ile Thr Lys Glu Gly Ile Gln Ile Gly Val Glu Gly Gln Thr Pro
        195                 200                 205

aaa tat gcc gat aaa aca ttt caa cct gaa cct caa ata gga gaa tct      672
Lys Tyr Ala Asp Lys Thr Phe Gln Pro Glu Pro Gln Ile Gly Glu Ser
    210                 215                 220

cag tgg tac gaa aca gaa att aat cat gca gct ggg aga gtc cta aaa      720
Gln Trp Tyr Glu Thr Glu Ile Asn His Ala Ala Gly Arg Val Leu Lys
225                 230                 235                 240

aag act acc cca atg aaa cca tgt tac ggt tca tat gca aaa ccc aca      768
Lys Thr Thr Pro Met Lys Pro Cys Tyr Gly Ser Tyr Ala Lys Pro Thr
                245                 250                 255

aat gaa aat gga ggg caa ggc att ctt gta aag caa caa aat gga aag      816
Asn Glu Asn Gly Gly Gln Gly Ile Leu Val Lys Gln Gln Asn Gly Lys
            260                 265                 270

cta gaa agt caa gtg gaa atg caa ttt ttc tca act act gag gca gcc      864
Leu Glu Ser Gln Val Glu Met Gln Phe Phe Ser Thr Thr Glu Ala Ala
        275                 280                 285

gca ggc aat ggt gat aac ttg act cct aaa gtg gta ttg tac agt gaa      912
Ala Gly Asn Gly Asp Asn Leu Thr Pro Lys Val Val Leu Tyr Ser Glu
    290                 295                 300

gat gta gat ata gaa acc cca gac act cat att tct tac atg ccc act      960
Asp Val Asp Ile Glu Thr Pro Asp Thr His Ile Ser Tyr Met Pro Thr
305                 310                 315                 320

att aag gaa ggt aac tca cga gaa cta atg ggc caa caa tct atg ccc     1008
Ile Lys Glu Gly Asn Ser Arg Glu Leu Met Gly Gln Gln Ser Met Pro
                325                 330                 335

aac agg cct aat tac att gct ttt agg gac aat ttt att ggt cta atg     1056
Asn Arg Pro Asn Tyr Ile Ala Phe Arg Asp Asn Phe Ile Gly Leu Met
            340                 345                 350

tat tac aac agc acg ggt aat atg ggt gtt ctg gcg ggc caa gca tcg     1104
Tyr Tyr Asn Ser Thr Gly Asn Met Gly Val Leu Ala Gly Gln Ala Ser
        355                 360                 365

cag ttg aat gct gtt gta gat ttg caa gac aga aac aca gag ctt tca     1152
Gln Leu Asn Ala Val Val Asp Leu Gln Asp Arg Asn Thr Glu Leu Ser
    370                 375                 380

tac cag ctt ttg ctt gat tcc att ggt gat aga acc agg tac ttt tct     1200
Tyr Gln Leu Leu Leu Asp Ser Ile Gly Asp Arg Thr Arg Tyr Phe Ser
385                 390                 395                 400

atg tgg aat cag ctt cca aat tac tgc ttt cca ctg gga ggt gtg att     1248
Met Trp Asn Gln Leu Pro Asn Tyr Cys Phe Pro Leu Gly Gly Val Ile
                405                 410                 415

aat aca gag act ctt acc aag gta aaa cct aaa aca ggt cag gaa aat     1296
Asn Thr Glu Thr Leu Thr Lys Val Lys Pro Lys Thr Gly Gln Glu Asn
```

-continued

```
            420                 425                 430

gga tgg gaa aaa gat gct aca gaa ttt tca gat aaa aat gaa ata aga     1344
Gly Trp Glu Lys Asp Ala Thr Glu Phe Ser Asp Lys Asn Glu Ile Arg
        435                 440                 445

gtt gga aat aat ttt gcc atg gaa atc aat cta aat gcc aac ctg tgg     1392
Val Gly Asn Asn Phe Ala Met Glu Ile Asn Leu Asn Ala Asn Leu Trp
    450                 455                 460

aga aat ttc ctg tac tcc aac ata gcg ctg tat ttg ccc gac aag cta     1440
Arg Asn Phe Leu Tyr Ser Asn Ile Ala Leu Tyr Leu Pro Asp Lys Leu
465                 470                 475                 480

aag tac agt cct tcc aac gta aaa att tct gat aac cca aac acc tac     1488
Lys Tyr Ser Pro Ser Asn Val Lys Ile Ser Asp Asn Pro Asn Thr Tyr
                485                 490                 495

gac tac atg aac aag cga gtg gtg gct ccc ggg cta gtg gac tgc tac     1536
Asp Tyr Met Asn Lys Arg Val Val Ala Pro Gly Leu Val Asp Cys Tyr
            500                 505                 510

att aac ctt gga gca cgc tgg tcc ctt gac tat atg gac aac gtc aac     1584
Ile Asn Leu Gly Ala Arg Trp Ser Leu Asp Tyr Met Asp Asn Val Asn
        515                 520                 525

cca ttt aac cac cac cgc aat gct ggc ctg cgc tac cgc tca atg ttg     1632
Pro Phe Asn His His Arg Asn Ala Gly Leu Arg Tyr Arg Ser Met Leu
    530                 535                 540

ctg ggc aat ggt cgc tat gtg ccc ttc cac atc cag gtg cct cag aag     1680
Leu Gly Asn Gly Arg Tyr Val Pro Phe His Ile Gln Val Pro Gln Lys
545                 550                 555                 560

ttc ttt gcc att aaa aac ctc ctt ctc ctg ccg ggc tca tac acc tac     1728
Phe Phe Ala Ile Lys Asn Leu Leu Leu Leu Pro Gly Ser Tyr Thr Tyr
                565                 570                 575

gag tgg aac ttc agg aag gat gtt aac atg gtt ctg cag agc tcc cta     1776
Glu Trp Asn Phe Arg Lys Asp Val Asn Met Val Leu Gln Ser Ser Leu
            580                 585                 590

gga aat gac cta agg gtt gac gga gcc agc att aag ttt gat agc att     1824
Gly Asn Asp Leu Arg Val Asp Gly Ala Ser Ile Lys Phe Asp Ser Ile
        595                 600                 605

tgc ctt tac gcc acc ttc ttc ccc atg gcc cac aac acc gcc tcc acg     1872
Cys Leu Tyr Ala Thr Phe Phe Pro Met Ala His Asn Thr Ala Ser Thr
    610                 615                 620

ctt gag gcc atg ctt aga aac gac acc aac gac cag tcc ttt aac gac     1920
Leu Glu Ala Met Leu Arg Asn Asp Thr Asn Asp Gln Ser Phe Asn Asp
625                 630                 635                 640

tat ctc tcc gcc gcc aac atg ctc tac cct ata ccc gcc aac gct acc     1968
Tyr Leu Ser Ala Ala Asn Met Leu Tyr Pro Ile Pro Ala Asn Ala Thr
                645                 650                 655

aac gtg ccc ata tcc atc ccc tcc cgc aac tgg gcg gct ttc cgc ggc     2016
Asn Val Pro Ile Ser Ile Pro Ser Arg Asn Trp Ala Ala Phe Arg Gly
            660                 665                 670

tgg gcc ttc acg cgc ctt aag act aag gaa acc cca tca ctg ggc tcg     2064
Trp Ala Phe Thr Arg Leu Lys Thr Lys Glu Thr Pro Ser Leu Gly Ser
        675                 680                 685

ggc tac gac cct tat tac acc tac tct ggc tct ata ccc tac cta gat     2112
Gly Tyr Asp Pro Tyr Tyr Thr Tyr Ser Gly Ser Ile Pro Tyr Leu Asp
    690                 695                 700

gga acc ttt tac ctc aac cac acc ttt aag aag gtg gcc att acc ttt     2160
Gly Thr Phe Tyr Leu Asn His Thr Phe Lys Lys Val Ala Ile Thr Phe
705                 710                 715                 720

gac tct tct gtc agc tgg cct ggc aat gac cgc ctg ctt acc ccc aac     2208
Asp Ser Ser Val Ser Trp Pro Gly Asn Asp Arg Leu Leu Thr Pro Asn
                725                 730                 735

gag ttt gaa att aag cgc tca gtt gac ggg gag ggt tac aac gtt gcc     2256
```

-continued

```
Glu Phe Glu Ile Lys Arg Ser Val Asp Gly Glu Gly Tyr Asn Val Ala
            740                 745                 750

cag tgt aac atg acc aaa gac tgg ttc ctg gta caa atg cta gct aac     2304
Gln Cys Asn Met Thr Lys Asp Trp Phe Leu Val Gln Met Leu Ala Asn
        755                 760                 765

tat aac att ggc tac cag ggc ttc tat atc cca gag agc tac aag gac     2352
Tyr Asn Ile Gly Tyr Gln Gly Phe Tyr Ile Pro Glu Ser Tyr Lys Asp
    770                 775                 780

cgc atg tac tcc ttc ttt aga aac ttc cag ccc atg agc cgt cag gtg     2400
Arg Met Tyr Ser Phe Phe Arg Asn Phe Gln Pro Met Ser Arg Gln Val
785                 790                 795                 800

gtg gat gat act aaa tac aag gac tac caa cag gtg ggc atc cta cac     2448
Val Asp Asp Thr Lys Tyr Lys Asp Tyr Gln Gln Val Gly Ile Leu His
            805                 810                 815

caa cac aac aac tct gga ttt gtt ggc tac ctt gcc ccc acc atg cgc     2496
Gln His Asn Asn Ser Gly Phe Val Gly Tyr Leu Ala Pro Thr Met Arg
            820                 825                 830

gaa gga cag gcc tac cct gct aac ttc ccc tat ccg ctt ata ggc aag     2544
Glu Gly Gln Ala Tyr Pro Ala Asn Phe Pro Tyr Pro Leu Ile Gly Lys
        835                 840                 845

acc gca gtt gac agc att acc cag aaa aag ttt ctt tgc gat cgc acc     2592
Thr Ala Val Asp Ser Ile Thr Gln Lys Lys Phe Leu Cys Asp Arg Thr
    850                 855                 860

ctt tgg cgc atc cca ttc tcc agt aac ttt atg tcc atg ggc gca ctc     2640
Leu Trp Arg Ile Pro Phe Ser Ser Asn Phe Met Ser Met Gly Ala Leu
865                 870                 875                 880

aca gac ctg ggc caa aac ctt ctc tac gcc aac tcc gcc cac gcg cta     2688
Thr Asp Leu Gly Gln Asn Leu Leu Tyr Ala Asn Ser Ala His Ala Leu
            885                 890                 895

gac atg act ttt gag gtg gat ccc atg gac gag ccc acc ctt ctt tat     2736
Asp Met Thr Phe Glu Val Asp Pro Met Asp Glu Pro Thr Leu Leu Tyr
            900                 905                 910

gtt ttg ttt gaa gtc ttt gac gtg gtc cgt gtg cac cag ccg cac cgc     2784
Val Leu Phe Glu Val Phe Asp Val Val Arg Val His Gln Pro His Arg
        915                 920                 925

ggc gtc atc gaa acc gtg tac ctg cgc acg ccc ttc tcg gcc ggc aac     2832
Gly Val Ile Glu Thr Val Tyr Leu Arg Thr Pro Phe Ser Ala Gly Asn
    930                 935                 940

gcc aca aca taa                                                     2844
Ala Thr Thr
945


<210> SEQ ID NO 8
<211> LENGTH: 2862
<212> TYPE: DNA
<213> ORGANISM: Artificial Sequence
<220> FEATURE:
<223> OTHER INFORMATION: (QGPGAP)8-HVR1 modified Hexon protein
<220> FEATURE:
<221> NAME/KEY: CDS
<222> LOCATION: (1)..(2859)

<400> SEQUENCE: 8

atg gct acc cct tcg atg atg ccg cag tgg tct tac atg cac atc tcg       48
Met Ala Thr Pro Ser Met Met Pro Gln Trp Ser Tyr Met His Ile Ser
1               5                   10                  15

ggc cag gac gcc tcg gag tac ctg agc ccc ggg ctg gtg cag ttt gcc       96
Gly Gln Asp Ala Ser Glu Tyr Leu Ser Pro Gly Leu Val Gln Phe Ala
            20                  25                  30

cgc gcc acc gag acg tac ttc agc ctg aat aac aag ttt aga aac ccc      144
Arg Ala Thr Glu Thr Tyr Phe Ser Leu Asn Asn Lys Phe Arg Asn Pro
        35                  40                  45
```

-continued

```
acg gtg gcg cct acg cac gac gtg acc aca gac cgg tcc cag cgt ttg      192
Thr Val Ala Pro Thr His Asp Val Thr Thr Asp Arg Ser Gln Arg Leu
    50                  55                  60

acg ctg cgg ttc atc cct gtg gac cgt gag gat act gcg tac tcg tac      240
Thr Leu Arg Phe Ile Pro Val Asp Arg Glu Asp Thr Ala Tyr Ser Tyr
65                  70                  75                  80

aag gcg cgg ttc acc cta gct gtg ggt gat aac cgt gtg ctg gac atg      288
Lys Ala Arg Phe Thr Leu Ala Val Gly Asp Asn Arg Val Leu Asp Met
                85                  90                  95

gct tcc acg tac ttt gac atc cgc ggc gtg ctg gac agg ggc cct act      336
Ala Ser Thr Tyr Phe Asp Ile Arg Gly Val Leu Asp Arg Gly Pro Thr
            100                 105                 110

ttt aag ccc tac tct ggc act gcc tac aac gcc ctg gct ccc aag ggt      384
Phe Lys Pro Tyr Ser Gly Thr Ala Tyr Asn Ala Leu Ala Pro Lys Gly
        115                 120                 125

gcc cca aat cct tgc gaa tgg gat gaa cag gga cca gga gca cca cag      432
Ala Pro Asn Pro Cys Glu Trp Asp Glu Gln Gly Pro Gly Ala Pro Gln
    130                 135                 140

gga cca gga gca cca cag gga cca gga gca cca cag gga cca gga gca      480
Gly Pro Gly Ala Pro Gln Gly Pro Gly Ala Pro Gln Gly Pro Gly Ala
145                 150                 155                 160

cca cag gga cca gga gca cca cag gga cca gga gca ccg caa ggt cct      528
Pro Gln Gly Pro Gly Ala Pro Gln Gly Pro Gly Ala Pro Gln Gly Pro
                165                 170                 175

ggt gct cct cag gga cca gga gca cca aaa act cac gta ttt ggg cag      576
Gly Ala Pro Gln Gly Pro Gly Ala Pro Lys Thr His Val Phe Gly Gln
            180                 185                 190

gcg cct tat tct ggt ata aat att aca aag gag ggt att caa ata ggt      624
Ala Pro Tyr Ser Gly Ile Asn Ile Thr Lys Glu Gly Ile Gln Ile Gly
        195                 200                 205

gtc gaa ggt caa aca cct aaa tat gcc gat aaa aca ttt caa cct gaa      672
Val Glu Gly Gln Thr Pro Lys Tyr Ala Asp Lys Thr Phe Gln Pro Glu
    210                 215                 220

cct caa ata gga gaa tct cag tgg tac gaa aca gaa att aat cat gca      720
Pro Gln Ile Gly Glu Ser Gln Trp Tyr Glu Thr Glu Ile Asn His Ala
225                 230                 235                 240

gct ggg aga gtc cta aaa aag act acc cca atg aaa cca tgt tac ggt      768
Ala Gly Arg Val Leu Lys Lys Thr Thr Pro Met Lys Pro Cys Tyr Gly
                245                 250                 255

tca tat gca aaa ccc aca aat gaa aat gga ggg caa ggc att ctt gta      816
Ser Tyr Ala Lys Pro Thr Asn Glu Asn Gly Gly Gln Gly Ile Leu Val
            260                 265                 270

aag caa caa aat gga aag cta gaa agt caa gtg gaa atg caa ttt ttc      864
Lys Gln Gln Asn Gly Lys Leu Glu Ser Gln Val Glu Met Gln Phe Phe
        275                 280                 285

tca act act gag gca gcc gca ggc aat ggt gat aac ttg act cct aaa      912
Ser Thr Thr Glu Ala Ala Ala Gly Asn Gly Asp Asn Leu Thr Pro Lys
    290                 295                 300

gtg gta ttg tac agt gaa gat gta gat ata gaa acc cca gac act cat      960
Val Val Leu Tyr Ser Glu Asp Val Asp Ile Glu Thr Pro Asp Thr His
305                 310                 315                 320

att tct tac atg ccc act att aag gaa ggt aac tca cga gaa cta atg     1008
Ile Ser Tyr Met Pro Thr Ile Lys Glu Gly Asn Ser Arg Glu Leu Met
                325                 330                 335

ggc caa caa tct atg ccc aac agg cct aat tac att gct ttt agg gac     1056
Gly Gln Gln Ser Met Pro Asn Arg Pro Asn Tyr Ile Ala Phe Arg Asp
            340                 345                 350

aat ttt att ggt cta atg tat tac aac agc acg ggt aat atg ggt gtt     1104
Asn Phe Ile Gly Leu Met Tyr Tyr Asn Ser Thr Gly Asn Met Gly Val
```

```
        355                 360                 365

ctg gcg ggc caa gca tcg cag ttg aat gct gtt gta gat ttg caa gac      1152
Leu Ala Gly Gln Ala Ser Gln Leu Asn Ala Val Val Asp Leu Gln Asp
    370                 375                 380

aga aac aca gag ctt tca tac cag ctt ttg ctt gat tcc att ggt gat      1200
Arg Asn Thr Glu Leu Ser Tyr Gln Leu Leu Leu Asp Ser Ile Gly Asp
385                 390                 395                 400

aga acc agg tac ttt tct atg tgg aat cag ctt cca aat tac tgc ttt      1248
Arg Thr Arg Tyr Phe Ser Met Trp Asn Gln Leu Pro Asn Tyr Cys Phe
                405                 410                 415

cca ctg gga ggt gtg att aat aca gag act ctt acc aag gta aaa cct      1296
Pro Leu Gly Gly Val Ile Asn Thr Glu Thr Leu Thr Lys Val Lys Pro
            420                 425                 430

aaa aca ggt cag gaa aat gga tgg gaa aaa gat gct aca gaa ttt tca      1344
Lys Thr Gly Gln Glu Asn Gly Trp Glu Lys Asp Ala Thr Glu Phe Ser
        435                 440                 445

gat aaa aat gaa ata aga gtt gga aat aat ttt gcc atg gaa atc aat      1392
Asp Lys Asn Glu Ile Arg Val Gly Asn Asn Phe Ala Met Glu Ile Asn
    450                 455                 460

cta aat gcc aac ctg tgg aga aat ttc ctg tac tcc aac ata gcg ctg      1440
Leu Asn Ala Asn Leu Trp Arg Asn Phe Leu Tyr Ser Asn Ile Ala Leu
465                 470                 475                 480

tat ttg ccc gac aag cta aag tac agt cct tcc aac gta aaa att tct      1488
Tyr Leu Pro Asp Lys Leu Lys Tyr Ser Pro Ser Asn Val Lys Ile Ser
                485                 490                 495

gat aac cca aac acc tac gac tac atg aac aag cga gtg gtg gct ccc      1536
Asp Asn Pro Asn Thr Tyr Asp Tyr Met Asn Lys Arg Val Val Ala Pro
            500                 505                 510

ggg cta gtg gac tgc tac att aac ctt gga gca cgc tgg tcc ctt gac      1584
Gly Leu Val Asp Cys Tyr Ile Asn Leu Gly Ala Arg Trp Ser Leu Asp
        515                 520                 525

tat atg gac aac gtc aac cca ttt aac cac cac cgc aat gct ggc ctg      1632
Tyr Met Asp Asn Val Asn Pro Phe Asn His His Arg Asn Ala Gly Leu
    530                 535                 540

cgc tac cgc tca atg ttg ctg ggc aat ggt cgc tat gtg ccc ttc cac      1680
Arg Tyr Arg Ser Met Leu Leu Gly Asn Gly Arg Tyr Val Pro Phe His
545                 550                 555                 560

atc cag gtg cct cag aag ttc ttt gcc att aaa aac ctc ctt ctc ctg      1728
Ile Gln Val Pro Gln Lys Phe Phe Ala Ile Lys Asn Leu Leu Leu Leu
                565                 570                 575

ccg ggc tca tac acc tac gag tgg aac ttc agg aag gat gtt aac atg      1776
Pro Gly Ser Tyr Thr Tyr Glu Trp Asn Phe Arg Lys Asp Val Asn Met
            580                 585                 590

gtt ctg cag agc tcc cta gga aat gac cta agg gtt gac gga gcc agc      1824
Val Leu Gln Ser Ser Leu Gly Asn Asp Leu Arg Val Asp Gly Ala Ser
        595                 600                 605

att aag ttt gat agc att tgc ctt tac gcc acc ttc ttc ccc atg gcc      1872
Ile Lys Phe Asp Ser Ile Cys Leu Tyr Ala Thr Phe Phe Pro Met Ala
    610                 615                 620

cac aac acc gcc tcc acg ctt gag gcc atg ctt aga aac gac acc aac      1920
His Asn Thr Ala Ser Thr Leu Glu Ala Met Leu Arg Asn Asp Thr Asn
625                 630                 635                 640

gac cag tcc ttt aac gac tat ctc tcc gcc gcc aac atg ctc tac cct      1968
Asp Gln Ser Phe Asn Asp Tyr Leu Ser Ala Ala Asn Met Leu Tyr Pro
                645                 650                 655

ata ccc gcc aac gct acc aac gtg ccc ata tcc atc ccc tcc cgc aac      2016
Ile Pro Ala Asn Ala Thr Asn Val Pro Ile Ser Ile Pro Ser Arg Asn
            660                 665                 670

tgg gcg gct ttc cgc ggc tgg gcc ttc acg cgc ctt aag act aag gaa      2064
```

-continued

```
Trp Ala Ala Phe Arg Gly Trp Ala Phe Thr Arg Leu Lys Thr Lys Glu
        675                 680                 685

acc cca tca ctg ggc tcg ggc tac gac cct tat tac acc tac tct ggc      2112
Thr Pro Ser Leu Gly Ser Gly Tyr Asp Pro Tyr Tyr Thr Tyr Ser Gly
    690                 695                 700

tct ata ccc tac cta gat gga acc ttt tac ctc aac cac acc ttt aag      2160
Ser Ile Pro Tyr Leu Asp Gly Thr Phe Tyr Leu Asn His Thr Phe Lys
705                 710                 715                 720

aag gtg gcc att acc ttt gac tct tct gtc agc tgg cct ggc aat gac      2208
Lys Val Ala Ile Thr Phe Asp Ser Ser Val Ser Trp Pro Gly Asn Asp
                725                 730                 735

cgc ctg ctt acc ccc aac gag ttt gaa att aag cgc tca gtt gac ggg      2256
Arg Leu Leu Thr Pro Asn Glu Phe Glu Ile Lys Arg Ser Val Asp Gly
            740                 745                 750

gag ggt tac aac gtt gcc cag tgt aac atg acc aaa gac tgg ttc ctg      2304
Glu Gly Tyr Asn Val Ala Gln Cys Asn Met Thr Lys Asp Trp Phe Leu
        755                 760                 765

gta caa atg cta gct aac tat aac att ggc tac cag ggc ttc tat atc      2352
Val Gln Met Leu Ala Asn Tyr Asn Ile Gly Tyr Gln Gly Phe Tyr Ile
    770                 775                 780

cca gag agc tac aag gac cgc atg tac tcc ttc ttt aga aac ttc cag      2400
Pro Glu Ser Tyr Lys Asp Arg Met Tyr Ser Phe Phe Arg Asn Phe Gln
785                 790                 795                 800

ccc atg agc cgt cag gtg gtg gat gat act aaa tac aag gac tac caa      2448
Pro Met Ser Arg Gln Val Val Asp Asp Thr Lys Tyr Lys Asp Tyr Gln
                805                 810                 815

cag gtg ggc atc cta cac caa cac aac aac tct gga ttt gtt ggc tac      2496
Gln Val Gly Ile Leu His Gln His Asn Asn Ser Gly Phe Val Gly Tyr
            820                 825                 830

ctt gcc ccc acc atg cgc gaa gga cag gcc tac cct gct aac ttc ccc      2544
Leu Ala Pro Thr Met Arg Glu Gly Gln Ala Tyr Pro Ala Asn Phe Pro
        835                 840                 845

tat ccg ctt ata ggc aag acc gca gtt gac agc att acc cag aaa aag      2592
Tyr Pro Leu Ile Gly Lys Thr Ala Val Asp Ser Ile Thr Gln Lys Lys
    850                 855                 860

ttt ctt tgc gat cgc acc ctt tgg cgc atc cca ttc tcc agt aac ttt      2640
Phe Leu Cys Asp Arg Thr Leu Trp Arg Ile Pro Phe Ser Ser Asn Phe
865                 870                 875                 880

atg tcc atg ggc gca ctc aca gac ctg ggc caa aac ctt ctc tac gcc      2688
Met Ser Met Gly Ala Leu Thr Asp Leu Gly Gln Asn Leu Leu Tyr Ala
                885                 890                 895

aac tcc gcc cac gcg cta gac atg act ttt gag gtg gat ccc atg gac      2736
Asn Ser Ala His Ala Leu Asp Met Thr Phe Glu Val Asp Pro Met Asp
            900                 905                 910

gag ccc acc ctt ctt tat gtt ttg ttt gaa gtc ttt gac gtg gtc cgt      2784
Glu Pro Thr Leu Leu Tyr Val Leu Phe Glu Val Phe Asp Val Val Arg
        915                 920                 925

gtg cac cag ccg cac cgc ggc gtc atc gaa acc gtg tac ctg cgc acg      2832
Val His Gln Pro His Arg Gly Val Ile Glu Thr Val Tyr Leu Arg Thr
    930                 935                 940

ccc ttc tcg gcc ggc aac gcc aca aca taa                              2862
Pro Phe Ser Ala Gly Asn Ala Thr Thr
945                 950
```

<210> SEQ ID NO 9
<211> LENGTH: 2880
<212> TYPE: DNA
<213> ORGANISM: Artificial Sequence
<220> FEATURE:
<223> OTHER INFORMATION: (QGPGAP)9-HVR1 modified Hexon protein
<220> FEATURE:

```
<221> NAME/KEY: CDS
<222> LOCATION: (1)..(2877)

<400> SEQUENCE: 9

atg gct acc cct tcg atg atg ccg cag tgg tct tac atg cac atc tcg       48
Met Ala Thr Pro Ser Met Met Pro Gln Trp Ser Tyr Met His Ile Ser
1               5                   10                  15

ggc cag gac gcc tcg gag tac ctg agc ccc ggg ctg gtg cag ttt gcc       96
Gly Gln Asp Ala Ser Glu Tyr Leu Ser Pro Gly Leu Val Gln Phe Ala
            20                  25                  30

cgc gcc acc gag acg tac ttc agc ctg aat aac aag ttt aga aac ccc      144
Arg Ala Thr Glu Thr Tyr Phe Ser Leu Asn Asn Lys Phe Arg Asn Pro
        35                  40                  45

acg gtg gcg cct acg cac gac gtg acc aca gac cgg tcc cag cgt ttg      192
Thr Val Ala Pro Thr His Asp Val Thr Thr Asp Arg Ser Gln Arg Leu
    50                  55                  60

acg ctg cgg ttc atc cct gtg gac cgt gag gat act gcg tac tcg tac      240
Thr Leu Arg Phe Ile Pro Val Asp Arg Glu Asp Thr Ala Tyr Ser Tyr
65                  70                  75                  80

aag gcg cgg ttc acc cta gct gtg ggt gat aac cgt gtg ctg gac atg      288
Lys Ala Arg Phe Thr Leu Ala Val Gly Asp Asn Arg Val Leu Asp Met
                85                  90                  95

gct tcc acg tac ttt gac atc cgc ggc gtg ctg gac agg ggc cct act      336
Ala Ser Thr Tyr Phe Asp Ile Arg Gly Val Leu Asp Arg Gly Pro Thr
            100                 105                 110

ttt aag ccc tac tct ggc act gcc tac aac gcc ctg gct ccc aag ggt      384
Phe Lys Pro Tyr Ser Gly Thr Ala Tyr Asn Ala Leu Ala Pro Lys Gly
        115                 120                 125

gcc cca aat cct tgc gaa tgg gat gaa cag gga cca gga gca cca cag      432
Ala Pro Asn Pro Cys Glu Trp Asp Glu Gln Gly Pro Gly Ala Pro Gln
    130                 135                 140

gga cca gga gca cca cag gga cca gga gca cca cag gga cca gga gca      480
Gly Pro Gly Ala Pro Gln Gly Pro Gly Ala Pro Gln Gly Pro Gly Ala
145                 150                 155                 160

cca cag gga cca gga gca cca cag gga cca gga gca ccg caa ggt cct      528
Pro Gln Gly Pro Gly Ala Pro Gln Gly Pro Gly Ala Pro Gln Gly Pro
                165                 170                 175

ggt gct cct cag gga cca gga gca cca cag gga cca gga gca cca aaa      576
Gly Ala Pro Gln Gly Pro Gly Ala Pro Gln Gly Pro Gly Ala Pro Lys
            180                 185                 190

act cac gta ttt ggg cag gcg cct tat tct ggt ata aat att aca aag      624
Thr His Val Phe Gly Gln Ala Pro Tyr Ser Gly Ile Asn Ile Thr Lys
        195                 200                 205

gag ggt att caa ata ggt gtc gaa ggt caa aca cct aaa tat gcc gat      672
Glu Gly Ile Gln Ile Gly Val Glu Gly Gln Thr Pro Lys Tyr Ala Asp
    210                 215                 220

aaa aca ttt caa cct gaa cct caa ata gga gaa tct cag tgg tac gaa      720
Lys Thr Phe Gln Pro Glu Pro Gln Ile Gly Glu Ser Gln Trp Tyr Glu
225                 230                 235                 240

aca gaa att aat cat gca gct ggg aga gtc cta aaa aag act acc cca      768
Thr Glu Ile Asn His Ala Ala Gly Arg Val Leu Lys Lys Thr Thr Pro
                245                 250                 255

atg aaa cca tgt tac ggt tca tat gca aaa ccc aca aat gaa aat gga      816
Met Lys Pro Cys Tyr Gly Ser Tyr Ala Lys Pro Thr Asn Glu Asn Gly
            260                 265                 270

ggg caa ggc att ctt gta aag caa caa aat gga aag cta gaa agt caa      864
Gly Gln Gly Ile Leu Val Lys Gln Gln Asn Gly Lys Leu Glu Ser Gln
        275                 280                 285

gtg gaa atg caa ttt ttc tca act act gag gca gcc gca ggc aat ggt      912
Val Glu Met Gln Phe Phe Ser Thr Thr Glu Ala Ala Ala Gly Asn Gly
```

-continued

```
    290                 295                 300

gat aac ttg act cct aaa gtg gta ttg tac agt gaa gat gta gat ata      960
Asp Asn Leu Thr Pro Lys Val Val Leu Tyr Ser Glu Asp Val Asp Ile
305                 310                 315                 320

gaa acc cca gac act cat att tct tac atg ccc act att aag gaa ggt     1008
Glu Thr Pro Asp Thr His Ile Ser Tyr Met Pro Thr Ile Lys Glu Gly
                325                 330                 335

aac tca cga gaa cta atg ggc caa caa tct atg ccc aac agg cct aat     1056
Asn Ser Arg Glu Leu Met Gly Gln Gln Ser Met Pro Asn Arg Pro Asn
            340                 345                 350

tac att gct ttt agg gac aat ttt att ggt cta atg tat tac aac agc     1104
Tyr Ile Ala Phe Arg Asp Asn Phe Ile Gly Leu Met Tyr Tyr Asn Ser
        355                 360                 365

acg ggt aat atg ggt gtt ctg gcg ggc caa gca tcg cag ttg aat gct     1152
Thr Gly Asn Met Gly Val Leu Ala Gly Gln Ala Ser Gln Leu Asn Ala
    370                 375                 380

gtt gta gat ttg caa gac aga aac aca gag ctt tca tac cag ctt ttg     1200
Val Val Asp Leu Gln Asp Arg Asn Thr Glu Leu Ser Tyr Gln Leu Leu
385                 390                 395                 400

ctt gat tcc att ggt gat aga acc agg tac ttt tct atg tgg aat cag     1248
Leu Asp Ser Ile Gly Asp Arg Thr Arg Tyr Phe Ser Met Trp Asn Gln
                405                 410                 415

ctt cca aat tac tgc ttt cca ctg gga ggt gtg att aat aca gag act     1296
Leu Pro Asn Tyr Cys Phe Pro Leu Gly Gly Val Ile Asn Thr Glu Thr
            420                 425                 430

ctt acc aag gta aaa cct aaa aca ggt cag gaa aat gga tgg gaa aaa     1344
Leu Thr Lys Val Lys Pro Lys Thr Gly Gln Glu Asn Gly Trp Glu Lys
        435                 440                 445

gat gct aca gaa ttt tca gat aaa aat gaa ata aga gtt gga aat aat     1392
Asp Ala Thr Glu Phe Ser Asp Lys Asn Glu Ile Arg Val Gly Asn Asn
    450                 455                 460

ttt gcc atg gaa atc aat cta aat gcc aac ctg tgg aga aat ttc ctg     1440
Phe Ala Met Glu Ile Asn Leu Asn Ala Asn Leu Trp Arg Asn Phe Leu
465                 470                 475                 480

tac tcc aac ata gcg ctg tat ttg ccc gac aag cta aag tac agt cct     1488
Tyr Ser Asn Ile Ala Leu Tyr Leu Pro Asp Lys Leu Lys Tyr Ser Pro
                485                 490                 495

tcc aac gta aaa att tct gat aac cca aac acc tac gac tac atg aac     1536
Ser Asn Val Lys Ile Ser Asp Asn Pro Asn Thr Tyr Asp Tyr Met Asn
            500                 505                 510

aag cga gtg gtg gct ccc ggg cta gtg gac tgc tac att aac ctt gga     1584
Lys Arg Val Val Ala Pro Gly Leu Val Asp Cys Tyr Ile Asn Leu Gly
        515                 520                 525

gca cgc tgg tcc ctt gac tat atg gac aac gtc aac cca ttt aac cac     1632
Ala Arg Trp Ser Leu Asp Tyr Met Asp Asn Val Asn Pro Phe Asn His
    530                 535                 540

cac cgc aat gct ggc ctg cgc tac cgc tca atg ttg ctg ggc aat ggt     1680
His Arg Asn Ala Gly Leu Arg Tyr Arg Ser Met Leu Leu Gly Asn Gly
545                 550                 555                 560

cgc tat gtg ccc ttc cac atc cag gtg cct cag aag ttc ttt gcc att     1728
Arg Tyr Val Pro Phe His Ile Gln Val Pro Gln Lys Phe Phe Ala Ile
                565                 570                 575

aaa aac ctc ctt ctc ctg ccg ggc tca tac acc tac gag tgg aac ttc     1776
Lys Asn Leu Leu Leu Leu Pro Gly Ser Tyr Thr Tyr Glu Trp Asn Phe
            580                 585                 590

agg aag gat gtt aac atg gtt ctg cag agc tcc cta gga aat gac cta     1824
Arg Lys Asp Val Asn Met Val Leu Gln Ser Ser Leu Gly Asn Asp Leu
        595                 600                 605

agg gtt gac gga gcc agc att aag ttt gat agc att tgc ctt tac gcc     1872
```

-continued

```
Arg Val Asp Gly Ala Ser Ile Lys Phe Asp Ser Ile Cys Leu Tyr Ala
    610                 615                 620

acc ttc ttc ccc atg gcc cac aac acc gcc tcc acg ctt gag gcc atg      1920
Thr Phe Phe Pro Met Ala His Asn Thr Ala Ser Thr Leu Glu Ala Met
625                 630                 635                 640

ctt aga aac gac acc aac gac cag tcc ttt aac gac tat ctc tcc gcc      1968
Leu Arg Asn Asp Thr Asn Asp Gln Ser Phe Asn Asp Tyr Leu Ser Ala
                645                 650                 655

gcc aac atg ctc tac cct ata ccc gcc aac gct acc aac gtg ccc ata      2016
Ala Asn Met Leu Tyr Pro Ile Pro Ala Asn Ala Thr Asn Val Pro Ile
            660                 665                 670

tcc atc ccc tcc cgc aac tgg gcg gct ttc cgc ggc tgg gcc ttc acg      2064
Ser Ile Pro Ser Arg Asn Trp Ala Ala Phe Arg Gly Trp Ala Phe Thr
        675                 680                 685

cgc ctt aag act aag gaa acc cca tca ctg ggc tcg ggc tac gac cct      2112
Arg Leu Lys Thr Lys Glu Thr Pro Ser Leu Gly Ser Gly Tyr Asp Pro
    690                 695                 700

tat tac acc tac tct ggc tct ata ccc tac cta gat gga acc ttt tac      2160
Tyr Tyr Thr Tyr Ser Gly Ser Ile Pro Tyr Leu Asp Gly Thr Phe Tyr
705                 710                 715                 720

ctc aac cac acc ttt aag aag gtg gcc att acc ttt gac tct tct gtc      2208
Leu Asn His Thr Phe Lys Lys Val Ala Ile Thr Phe Asp Ser Ser Val
                725                 730                 735

agc tgg cct ggc aat gac cgc ctg ctt acc ccc aac gag ttt gaa att      2256
Ser Trp Pro Gly Asn Asp Arg Leu Leu Thr Pro Asn Glu Phe Glu Ile
            740                 745                 750

aag cgc tca gtt gac ggg gag ggt tac aac gtt gcc cag tgt aac atg      2304
Lys Arg Ser Val Asp Gly Glu Gly Tyr Asn Val Ala Gln Cys Asn Met
        755                 760                 765

acc aaa gac tgg ttc ctg gta caa atg cta gct aac tat aac att ggc      2352
Thr Lys Asp Trp Phe Leu Val Gln Met Leu Ala Asn Tyr Asn Ile Gly
    770                 775                 780

tac cag ggc ttc tat atc cca gag agc tac aag gac cgc atg tac tcc      2400
Tyr Gln Gly Phe Tyr Ile Pro Glu Ser Tyr Lys Asp Arg Met Tyr Ser
785                 790                 795                 800

ttc ttt aga aac ttc cag ccc atg agc cgt cag gtg gtg gat gat act      2448
Phe Phe Arg Asn Phe Gln Pro Met Ser Arg Gln Val Val Asp Asp Thr
                805                 810                 815

aaa tac aag gac tac caa cag gtg ggc atc cta cac caa cac aac aac      2496
Lys Tyr Lys Asp Tyr Gln Gln Val Gly Ile Leu His Gln His Asn Asn
            820                 825                 830

tct gga ttt gtt ggc tac ctt gcc ccc acc atg cgc gaa gga cag gcc      2544
Ser Gly Phe Val Gly Tyr Leu Ala Pro Thr Met Arg Glu Gly Gln Ala
        835                 840                 845

tac cct gct aac ttc ccc tat ccg ctt ata ggc aag acc gca gtt gac      2592
Tyr Pro Ala Asn Phe Pro Tyr Pro Leu Ile Gly Lys Thr Ala Val Asp
    850                 855                 860

agc att acc cag aaa aag ttt ctt tgc gat cgc acc ctt tgg cgc atc      2640
Ser Ile Thr Gln Lys Lys Phe Leu Cys Asp Arg Thr Leu Trp Arg Ile
865                 870                 875                 880

cca ttc tcc agt aac ttt atg tcc atg ggc gca ctc aca gac ctg ggc      2688
Pro Phe Ser Ser Asn Phe Met Ser Met Gly Ala Leu Thr Asp Leu Gly
                885                 890                 895

caa aac ctt ctc tac gcc aac tcc gcc cac gcg cta gac atg act ttt      2736
Gln Asn Leu Leu Tyr Ala Asn Ser Ala His Ala Leu Asp Met Thr Phe
            900                 905                 910

gag gtg gat ccc atg gac gag ccc acc ctt ctt tat gtt ttg ttt gaa      2784
Glu Val Asp Pro Met Asp Glu Pro Thr Leu Leu Tyr Val Leu Phe Glu
        915                 920                 925
```

-continued

```
gtc ttt gac gtg gtc cgt gtg cac cag ccg cac cgc ggc gtc atc gaa     2832
Val Phe Asp Val Val Arg Val His Gln Pro His Arg Gly Val Ile Glu
    930                 935                 940

acc gtg tac ctg cgc acg ccc ttc tcg gcc ggc aac gcc aca aca taa     2880
Thr Val Tyr Leu Arg Thr Pro Phe Ser Ala Gly Asn Ala Thr Thr
945                 950                 955


<210> SEQ ID NO 10
<211> LENGTH: 2916
<212> TYPE: DNA
<213> ORGANISM: Artificial Sequence
<220> FEATURE:
<223> OTHER INFORMATION: (QGPGAP)11-HVR1 modified Hexon protein
<220> FEATURE:
<221> NAME/KEY: CDS
<222> LOCATION: (1)..(2913)

<400> SEQUENCE: 10

atg gct acc cct tcg atg atg ccg cag tgg tct tac atg cac atc tcg       48
Met Ala Thr Pro Ser Met Met Pro Gln Trp Ser Tyr Met His Ile Ser
1               5                   10                  15

ggc cag gac gcc tcg gag tac ctg agc ccc ggg ctg gtg cag ttt gcc       96
Gly Gln Asp Ala Ser Glu Tyr Leu Ser Pro Gly Leu Val Gln Phe Ala
            20                  25                  30

cgc gcc acc gag acg tac ttc agc ctg aat aac aag ttt aga aac ccc      144
Arg Ala Thr Glu Thr Tyr Phe Ser Leu Asn Asn Lys Phe Arg Asn Pro
        35                  40                  45

acg gtg gcg cct acg cac gac gtg acc aca gac cgg tcc cag cgt ttg      192
Thr Val Ala Pro Thr His Asp Val Thr Thr Asp Arg Ser Gln Arg Leu
    50                  55                  60

acg ctg cgg ttc atc cct gtg gac cgt gag gat act gcg tac tcg tac      240
Thr Leu Arg Phe Ile Pro Val Asp Arg Glu Asp Thr Ala Tyr Ser Tyr
65                  70                  75                  80

aag gcg cgg ttc acc cta gct gtg ggt gat aac cgt gtg ctg gac atg      288
Lys Ala Arg Phe Thr Leu Ala Val Gly Asp Asn Arg Val Leu Asp Met
                85                  90                  95

gct tcc acg tac ttt gac atc cgc ggc gtg ctg gac agg ggc cct act      336
Ala Ser Thr Tyr Phe Asp Ile Arg Gly Val Leu Asp Arg Gly Pro Thr
            100                 105                 110

ttt aag ccc tac tct ggc act gcc tac aac gcc ctg gct ccc aag ggt      384
Phe Lys Pro Tyr Ser Gly Thr Ala Tyr Asn Ala Leu Ala Pro Lys Gly
        115                 120                 125

gcc cca aat cct tgc gaa tgg gat gaa cag gga cca gga gca cca cag      432
Ala Pro Asn Pro Cys Glu Trp Asp Glu Gln Gly Pro Gly Ala Pro Gln
    130                 135                 140

gga cca gga gca cca cag gga cca gga gca cca cag gga cca gga gca      480
Gly Pro Gly Ala Pro Gln Gly Pro Gly Ala Pro Gln Gly Pro Gly Ala
145                 150                 155                 160

cca cag gga cca gga gca cca cag gga cca gga gca cca cag gga cca      528
Pro Gln Gly Pro Gly Ala Pro Gln Gly Pro Gly Ala Pro Gln Gly Pro
                165                 170                 175

gga gca cca cag gga cca gga gca ccg caa ggt cct ggt gct cct cag      576
Gly Ala Pro Gln Gly Pro Gly Ala Pro Gln Gly Pro Gly Ala Pro Gln
            180                 185                 190

gga cca gga gca cca cag gga cca gga gca cca aaa act cac gta ttt      624
Gly Pro Gly Ala Pro Gln Gly Pro Gly Ala Pro Lys Thr His Val Phe
        195                 200                 205

ggg cag gcg cct tat tct ggt ata aat att aca aag gag ggt att caa      672
Gly Gln Ala Pro Tyr Ser Gly Ile Asn Ile Thr Lys Glu Gly Ile Gln
    210                 215                 220

ata ggt gtc gaa ggt caa aca cct aaa tat gcc gat aaa aca ttt caa      720
Ile Gly Val Glu Gly Gln Thr Pro Lys Tyr Ala Asp Lys Thr Phe Gln
```

-continued

```
225                 230                 235                 240

cct gaa cct caa ata gga gaa tct cag tgg tac gaa aca gaa att aat      768
Pro Glu Pro Gln Ile Gly Glu Ser Gln Trp Tyr Glu Thr Glu Ile Asn
                245                 250                 255

cat gca gct ggg aga gtc cta aaa aag act acc cca atg aaa cca tgt      816
His Ala Ala Gly Arg Val Leu Lys Lys Thr Thr Pro Met Lys Pro Cys
            260                 265                 270

tac ggt tca tat gca aaa ccc aca aat gaa aat gga ggg caa ggc att      864
Tyr Gly Ser Tyr Ala Lys Pro Thr Asn Glu Asn Gly Gly Gln Gly Ile
        275                 280                 285

ctt gta aag caa caa aat gga aag cta gaa agt caa gtg gaa atg caa      912
Leu Val Lys Gln Gln Asn Gly Lys Leu Glu Ser Gln Val Glu Met Gln
    290                 295                 300

ttt ttc tca act act gag gca gcc gca ggc aat ggt gat aac ttg act      960
Phe Phe Ser Thr Thr Glu Ala Ala Ala Gly Asn Gly Asp Asn Leu Thr
305                 310                 315                 320

cct aaa gtg gta ttg tac agt gaa gat gta gat ata gaa acc cca gac     1008
Pro Lys Val Val Leu Tyr Ser Glu Asp Val Asp Ile Glu Thr Pro Asp
                325                 330                 335

act cat att tct tac atg ccc act att aag gaa ggt aac tca cga gaa     1056
Thr His Ile Ser Tyr Met Pro Thr Ile Lys Glu Gly Asn Ser Arg Glu
            340                 345                 350

cta atg ggc caa caa tct atg ccc aac agg cct aat tac att gct ttt     1104
Leu Met Gly Gln Gln Ser Met Pro Asn Arg Pro Asn Tyr Ile Ala Phe
        355                 360                 365

agg gac aat ttt att ggt cta atg tat tac aac agc acg ggt aat atg     1152
Arg Asp Asn Phe Ile Gly Leu Met Tyr Tyr Asn Ser Thr Gly Asn Met
    370                 375                 380

ggt gtt ctg gcg ggc caa gca tcg cag ttg aat gct gtt gta gat ttg     1200
Gly Val Leu Ala Gly Gln Ala Ser Gln Leu Asn Ala Val Val Asp Leu
385                 390                 395                 400

caa gac aga aac aca gag ctt tca tac cag ctt ttg ctt gat tcc att     1248
Gln Asp Arg Asn Thr Glu Leu Ser Tyr Gln Leu Leu Leu Asp Ser Ile
                405                 410                 415

ggt gat aga acc agg tac ttt tct atg tgg aat cag ctt cca aat tac     1296
Gly Asp Arg Thr Arg Tyr Phe Ser Met Trp Asn Gln Leu Pro Asn Tyr
            420                 425                 430

tgc ttt cca ctg gga ggt gtg att aat aca gag act ctt acc aag gta     1344
Cys Phe Pro Leu Gly Gly Val Ile Asn Thr Glu Thr Leu Thr Lys Val
        435                 440                 445

aaa cct aaa aca ggt cag gaa aat gga tgg gaa aaa gat gct aca gaa     1392
Lys Pro Lys Thr Gly Gln Glu Asn Gly Trp Glu Lys Asp Ala Thr Glu
    450                 455                 460

ttt tca gat aaa aat gaa ata aga gtt gga aat aat ttt gcc atg gaa     1440
Phe Ser Asp Lys Asn Glu Ile Arg Val Gly Asn Asn Phe Ala Met Glu
465                 470                 475                 480

atc aat cta aat gcc aac ctg tgg aga aat ttc ctg tac tcc aac ata     1488
Ile Asn Leu Asn Ala Asn Leu Trp Arg Asn Phe Leu Tyr Ser Asn Ile
                485                 490                 495

gcg ctg tat ttg ccc gac aag cta aag tac agt cct tcc aac gta aaa     1536
Ala Leu Tyr Leu Pro Asp Lys Leu Lys Tyr Ser Pro Ser Asn Val Lys
            500                 505                 510

att tct gat aac cca aac acc tac gac tac atg aac aag cga gtg gtg     1584
Ile Ser Asp Asn Pro Asn Thr Tyr Asp Tyr Met Asn Lys Arg Val Val
        515                 520                 525

gct ccc ggg cta gtg gac tgc tac att aac ctt gga gca cgc tgg tcc     1632
Ala Pro Gly Leu Val Asp Cys Tyr Ile Asn Leu Gly Ala Arg Trp Ser
    530                 535                 540

ctt gac tat atg gac aac gtc aac cca ttt aac cac cac cgc aat gct     1680
```

-continued

```
Leu Asp Tyr Met Asp Asn Val Asn Pro Phe Asn His His Arg Asn Ala
545                 550                 555                 560

ggc ctg cgc tac cgc tca atg ttg ctg ggc aat ggt cgc tat gtg ccc     1728
Gly Leu Arg Tyr Arg Ser Met Leu Leu Gly Asn Gly Arg Tyr Val Pro
                565                 570                 575

ttc cac atc cag gtg cct cag aag ttc ttt gcc att aaa aac ctc ctt     1776
Phe His Ile Gln Val Pro Gln Lys Phe Phe Ala Ile Lys Asn Leu Leu
            580                 585                 590

ctc ctg ccg ggc tca tac acc tac gag tgg aac ttc agg aag gat gtt     1824
Leu Leu Pro Gly Ser Tyr Thr Tyr Glu Trp Asn Phe Arg Lys Asp Val
        595                 600                 605

aac atg gtt ctg cag agc tcc cta gga aat gac cta agg gtt gac gga     1872
Asn Met Val Leu Gln Ser Ser Leu Gly Asn Asp Leu Arg Val Asp Gly
    610                 615                 620

gcc agc att aag ttt gat agc att tgc ctt tac gcc acc ttc ttc ccc     1920
Ala Ser Ile Lys Phe Asp Ser Ile Cys Leu Tyr Ala Thr Phe Phe Pro
625                 630                 635                 640

atg gcc cac aac acc gcc tcc acg ctt gag gcc atg ctt aga aac gac     1968
Met Ala His Asn Thr Ala Ser Thr Leu Glu Ala Met Leu Arg Asn Asp
                645                 650                 655

acc aac gac cag tcc ttt aac gac tat ctc tcc gcc gcc aac atg ctc     2016
Thr Asn Asp Gln Ser Phe Asn Asp Tyr Leu Ser Ala Ala Asn Met Leu
            660                 665                 670

tac cct ata ccc gcc aac gct acc aac gtg ccc ata tcc atc ccc tcc     2064
Tyr Pro Ile Pro Ala Asn Ala Thr Asn Val Pro Ile Ser Ile Pro Ser
        675                 680                 685

cgc aac tgg gcg gct ttc cgc ggc tgg gcc ttc acg cgc ctt aag act     2112
Arg Asn Trp Ala Ala Phe Arg Gly Trp Ala Phe Thr Arg Leu Lys Thr
    690                 695                 700

aag gaa acc cca tca ctg ggc tcg ggc tac gac cct tat tac acc tac     2160
Lys Glu Thr Pro Ser Leu Gly Ser Gly Tyr Asp Pro Tyr Tyr Thr Tyr
705                 710                 715                 720

tct ggc tct ata ccc tac cta gat gga acc ttt tac ctc aac cac acc     2208
Ser Gly Ser Ile Pro Tyr Leu Asp Gly Thr Phe Tyr Leu Asn His Thr
                725                 730                 735

ttt aag aag gtg gcc att acc ttt gac tct tct gtc agc tgg cct ggc     2256
Phe Lys Lys Val Ala Ile Thr Phe Asp Ser Ser Val Ser Trp Pro Gly
            740                 745                 750

aat gac cgc ctg ctt acc ccc aac gag ttt gaa att aag cgc tca gtt     2304
Asn Asp Arg Leu Leu Thr Pro Asn Glu Phe Glu Ile Lys Arg Ser Val
        755                 760                 765

gac ggg gag ggt tac aac gtt gcc cag tgt aac atg acc aaa gac tgg     2352
Asp Gly Glu Gly Tyr Asn Val Ala Gln Cys Asn Met Thr Lys Asp Trp
    770                 775                 780

ttc ctg gta caa atg cta gct aac tat aac att ggc tac cag ggc ttc     2400
Phe Leu Val Gln Met Leu Ala Asn Tyr Asn Ile Gly Tyr Gln Gly Phe
785                 790                 795                 800

tat atc cca gag agc tac aag gac cgc atg tac tcc ttc ttt aga aac     2448
Tyr Ile Pro Glu Ser Tyr Lys Asp Arg Met Tyr Ser Phe Phe Arg Asn
                805                 810                 815

ttc cag ccc atg agc cgt cag gtg gtg gat gat act aaa tac aag gac     2496
Phe Gln Pro Met Ser Arg Gln Val Val Asp Asp Thr Lys Tyr Lys Asp
            820                 825                 830

tac caa cag gtg ggc atc cta cac caa cac aac aac tct gga ttt gtt     2544
Tyr Gln Gln Val Gly Ile Leu His Gln His Asn Asn Ser Gly Phe Val
        835                 840                 845

ggc tac ctt gcc ccc acc atg cgc gaa gga cag gcc tac cct gct aac     2592
Gly Tyr Leu Ala Pro Thr Met Arg Glu Gly Gln Ala Tyr Pro Ala Asn
    850                 855                 860
```

-continued

```
ttc ccc tat ccg ctt ata ggc aag acc gca gtt gac agc att acc cag     2640
Phe Pro Tyr Pro Leu Ile Gly Lys Thr Ala Val Asp Ser Ile Thr Gln
865                 870                 875                 880

aaa aag ttt ctt tgc gat cgc acc ctt tgg cgc atc cca ttc tcc agt     2688
Lys Lys Phe Leu Cys Asp Arg Thr Leu Trp Arg Ile Pro Phe Ser Ser
                885                 890                 895

aac ttt atg tcc atg ggc gca ctc aca gac ctg ggc caa aac ctt ctc     2736
Asn Phe Met Ser Met Gly Ala Leu Thr Asp Leu Gly Gln Asn Leu Leu
            900                 905                 910

tac gcc aac tcc gcc cac gcg cta gac atg act ttt gag gtg gat ccc     2784
Tyr Ala Asn Ser Ala His Ala Leu Asp Met Thr Phe Glu Val Asp Pro
        915                 920                 925

atg gac gag ccc acc ctt ctt tat gtt ttg ttt gaa gtc ttt gac gtg     2832
Met Asp Glu Pro Thr Leu Leu Tyr Val Leu Phe Glu Val Phe Asp Val
    930                 935                 940

gtc cgt gtg cac cag ccg cac cgc ggc gtc atc gaa acc gtg tac ctg     2880
Val Arg Val His Gln Pro His Arg Gly Val Ile Glu Thr Val Tyr Leu
945                 950                 955                 960

cgc acg ccc ttc tcg gcc ggc aac gcc aca aca taa                     2916
Arg Thr Pro Phe Ser Ala Gly Asn Ala Thr Thr
                965                 970


<210> SEQ ID NO 11
<211> LENGTH: 2934
<212> TYPE: DNA
<213> ORGANISM: Artificial Sequence
<220> FEATURE:
<223> OTHER INFORMATION: (QGPGAP)12-HVR1 modified Hexon protein
<220> FEATURE:
<221> NAME/KEY: CDS
<222> LOCATION: (1)..(2931)

<400> SEQUENCE: 11

atg gct acc cct tcg atg atg ccg cag tgg tct tac atg cac atc tcg       48
Met Ala Thr Pro Ser Met Met Pro Gln Trp Ser Tyr Met His Ile Ser
1               5                   10                  15

ggc cag gac gcc tcg gag tac ctg agc ccc ggg ctg gtg cag ttt gcc       96
Gly Gln Asp Ala Ser Glu Tyr Leu Ser Pro Gly Leu Val Gln Phe Ala
            20                  25                  30

cgc gcc acc gag acg tac ttc agc ctg aat aac aag ttt aga aac ccc      144
Arg Ala Thr Glu Thr Tyr Phe Ser Leu Asn Asn Lys Phe Arg Asn Pro
        35                  40                  45

acg gtg gcg cct acg cac gac gtg acc aca gac cgg tcc cag cgt ttg      192
Thr Val Ala Pro Thr His Asp Val Thr Thr Asp Arg Ser Gln Arg Leu
    50                  55                  60

acg ctg cgg ttc atc cct gtg gac cgt gag gat act gcg tac tcg tac      240
Thr Leu Arg Phe Ile Pro Val Asp Arg Glu Asp Thr Ala Tyr Ser Tyr
65                  70                  75                  80

aag gcg cgg ttc acc cta gct gtg ggt gat aac cgt gtg ctg gac atg      288
Lys Ala Arg Phe Thr Leu Ala Val Gly Asp Asn Arg Val Leu Asp Met
                85                  90                  95

gct tcc acg tac ttt gac atc cgc ggc gtg ctg gac agg ggc cct act      336
Ala Ser Thr Tyr Phe Asp Ile Arg Gly Val Leu Asp Arg Gly Pro Thr
            100                 105                 110

ttt aag ccc tac tct ggc act gcc tac aac gcc ctg gct ccc aag ggt      384
Phe Lys Pro Tyr Ser Gly Thr Ala Tyr Asn Ala Leu Ala Pro Lys Gly
        115                 120                 125

gcc cca aat cct tgc gaa tgg gat gaa cag gga cca gga gca cca cag      432
Ala Pro Asn Pro Cys Glu Trp Asp Glu Gln Gly Pro Gly Ala Pro Gln
    130                 135                 140

gga cca gga gca cca cag gga cca gga gca cca cag gga cca gga gca      480
Gly Pro Gly Ala Pro Gln Gly Pro Gly Ala Pro Gln Gly Pro Gly Ala
```

-continued

```
145                 150                 155                 160

cca cag gga cca gga gca cca cag gga cca gga gca cca cag gga cca      528
Pro Gln Gly Pro Gly Ala Pro Gln Gly Pro Gly Ala Pro Gln Gly Pro
                165                 170                 175

gga gca cca cag gga cca gga gca ccg caa ggt cct ggt gct cct cag      576
Gly Ala Pro Gln Gly Pro Gly Ala Pro Gln Gly Pro Gly Ala Pro Gln
            180                 185                 190

gga cca gga gca cca cag gga cca gga gca cca cag gga cca gga gca      624
Gly Pro Gly Ala Pro Gln Gly Pro Gly Ala Pro Gln Gly Pro Gly Ala
        195                 200                 205

cca aaa act cac gta ttt ggg cag gcg cct tat tct ggt ata aat att      672
Pro Lys Thr His Val Phe Gly Gln Ala Pro Tyr Ser Gly Ile Asn Ile
    210                 215                 220

aca aag gag ggt att caa ata ggt gtc gaa ggt caa aca cct aaa tat      720
Thr Lys Glu Gly Ile Gln Ile Gly Val Glu Gly Gln Thr Pro Lys Tyr
225                 230                 235                 240

gcc gat aaa aca ttt caa cct gaa cct caa ata gga gaa tct cag tgg      768
Ala Asp Lys Thr Phe Gln Pro Glu Pro Gln Ile Gly Glu Ser Gln Trp
                245                 250                 255

tac gaa aca gaa att aat cat gca gct ggg aga gtc cta aaa aag act      816
Tyr Glu Thr Glu Ile Asn His Ala Ala Gly Arg Val Leu Lys Lys Thr
            260                 265                 270

acc cca atg aaa cca tgt tac ggt tca tat gca aaa ccc aca aat gaa      864
Thr Pro Met Lys Pro Cys Tyr Gly Ser Tyr Ala Lys Pro Thr Asn Glu
        275                 280                 285

aat gga ggg caa ggc att ctt gta aag caa caa aat gga aag cta gaa      912
Asn Gly Gly Gln Gly Ile Leu Val Lys Gln Gln Asn Gly Lys Leu Glu
    290                 295                 300

agt caa gtg gaa atg caa ttt ttc tca act act gag gca gcc gca ggc      960
Ser Gln Val Glu Met Gln Phe Phe Ser Thr Thr Glu Ala Ala Ala Gly
305                 310                 315                 320

aat ggt gat aac ttg act cct aaa gtg gta ttg tac agt gaa gat gta     1008
Asn Gly Asp Asn Leu Thr Pro Lys Val Val Leu Tyr Ser Glu Asp Val
                325                 330                 335

gat ata gaa acc cca gac act cat att tct tac atg ccc act att aag     1056
Asp Ile Glu Thr Pro Asp Thr His Ile Ser Tyr Met Pro Thr Ile Lys
            340                 345                 350

gaa ggt aac tca cga gaa cta atg ggc caa caa tct atg ccc aac agg     1104
Glu Gly Asn Ser Arg Glu Leu Met Gly Gln Gln Ser Met Pro Asn Arg
        355                 360                 365

cct aat tac att gct ttt agg gac aat ttt att ggt cta atg tat tac     1152
Pro Asn Tyr Ile Ala Phe Arg Asp Asn Phe Ile Gly Leu Met Tyr Tyr
    370                 375                 380

aac agc acg ggt aat atg ggt gtt ctg gcg ggc caa gca tcg cag ttg     1200
Asn Ser Thr Gly Asn Met Gly Val Leu Ala Gly Gln Ala Ser Gln Leu
385                 390                 395                 400

aat gct gtt gta gat ttg caa gac aga aac aca gag ctt tca tac cag     1248
Asn Ala Val Val Asp Leu Gln Asp Arg Asn Thr Glu Leu Ser Tyr Gln
                405                 410                 415

ctt ttg ctt gat tcc att ggt gat aga acc agg tac ttt tct atg tgg     1296
Leu Leu Leu Asp Ser Ile Gly Asp Arg Thr Arg Tyr Phe Ser Met Trp
            420                 425                 430

aat cag ctt cca aat tac tgc ttt cca ctg gga ggt gtg att aat aca     1344
Asn Gln Leu Pro Asn Tyr Cys Phe Pro Leu Gly Gly Val Ile Asn Thr
        435                 440                 445

gag act ctt acc aag gta aaa cct aaa aca ggt cag gaa aat gga tgg     1392
Glu Thr Leu Thr Lys Val Lys Pro Lys Thr Gly Gln Glu Asn Gly Trp
    450                 455                 460

gaa aaa gat gct aca gaa ttt tca gat aaa aat gaa ata aga gtt gga     1440
```

-continued

```
Glu Lys Asp Ala Thr Glu Phe Ser Asp Lys Asn Glu Ile Arg Val Gly
465                 470                 475                 480

aat aat ttt gcc atg gaa atc aat cta aat gcc aac ctg tgg aga aat      1488
Asn Asn Phe Ala Met Glu Ile Asn Leu Asn Ala Asn Leu Trp Arg Asn
                485                 490                 495

ttc ctg tac tcc aac ata gcg ctg tat ttg ccc gac aag cta aag tac      1536
Phe Leu Tyr Ser Asn Ile Ala Leu Tyr Leu Pro Asp Lys Leu Lys Tyr
            500                 505                 510

agt cct tcc aac gta aaa att tct gat aac cca aac acc tac gac tac      1584
Ser Pro Ser Asn Val Lys Ile Ser Asp Asn Pro Asn Thr Tyr Asp Tyr
        515                 520                 525

atg aac aag cga gtg gtg gct ccc ggg cta gtg gac tgc tac att aac      1632
Met Asn Lys Arg Val Val Ala Pro Gly Leu Val Asp Cys Tyr Ile Asn
    530                 535                 540

ctt gga gca cgc tgg tcc ctt gac tat atg gac aac gtc aac cca ttt      1680
Leu Gly Ala Arg Trp Ser Leu Asp Tyr Met Asp Asn Val Asn Pro Phe
545                 550                 555                 560

aac cac cac cgc aat gct ggc ctg cgc tac cgc tca atg ttg ctg ggc      1728
Asn His His Arg Asn Ala Gly Leu Arg Tyr Arg Ser Met Leu Leu Gly
                565                 570                 575

aat ggt cgc tat gtg ccc ttc cac atc cag gtg cct cag aag ttc ttt      1776
Asn Gly Arg Tyr Val Pro Phe His Ile Gln Val Pro Gln Lys Phe Phe
            580                 585                 590

gcc att aaa aac ctc ctt ctc ctg ccg ggc tca tac acc tac gag tgg      1824
Ala Ile Lys Asn Leu Leu Leu Leu Pro Gly Ser Tyr Thr Tyr Glu Trp
        595                 600                 605

aac ttc agg aag gat gtt aac atg gtt ctg cag agc tcc cta gga aat      1872
Asn Phe Arg Lys Asp Val Asn Met Val Leu Gln Ser Ser Leu Gly Asn
    610                 615                 620

gac cta agg gtt gac gga gcc agc att aag ttt gat agc att tgc ctt      1920
Asp Leu Arg Val Asp Gly Ala Ser Ile Lys Phe Asp Ser Ile Cys Leu
625                 630                 635                 640

tac gcc acc ttc ttc ccc atg gcc cac aac acc gcc tcc acg ctt gag      1968
Tyr Ala Thr Phe Phe Pro Met Ala His Asn Thr Ala Ser Thr Leu Glu
                645                 650                 655

gcc atg ctt aga aac gac acc aac gac cag tcc ttt aac gac tat ctc      2016
Ala Met Leu Arg Asn Asp Thr Asn Asp Gln Ser Phe Asn Asp Tyr Leu
            660                 665                 670

tcc gcc gcc aac atg ctc tac cct ata ccc gcc aac gct acc aac gtg      2064
Ser Ala Ala Asn Met Leu Tyr Pro Ile Pro Ala Asn Ala Thr Asn Val
        675                 680                 685

ccc ata tcc atc ccc tcc cgc aac tgg gcg gct ttc cgc ctg ctt acc      2112
Pro Ile Ser Ile Pro Ser Arg Asn Trp Ala Ala Phe Arg Leu Leu Thr
    690                 695                 700

ccc aac gag ttt gaa att aag cgc tca gtt gac ggg gag ggt tac aac      2160
Pro Asn Glu Phe Glu Ile Lys Arg Ser Val Asp Gly Glu Gly Tyr Asn
705                 710                 715                 720

gac cct tat tac acc tac tct ggc tct ata ccc tac cta gat gga acc      2208
Asp Pro Tyr Tyr Thr Tyr Ser Gly Ser Ile Pro Tyr Leu Asp Gly Thr
                725                 730                 735

ttt tac ctc aac cac acc ttt aag aag gtg gcc att acc ttt gac tct      2256
Phe Tyr Leu Asn His Thr Phe Lys Lys Val Ala Ile Thr Phe Asp Ser
            740                 745                 750

tct gtc agc tgg cct ggc aat gac cgc ctg ctt acc ccc aac gag ttt      2304
Ser Val Ser Trp Pro Gly Asn Asp Arg Leu Leu Thr Pro Asn Glu Phe
        755                 760                 765

gaa att aag cgc tca gtt gac ggg gag ggt tac aac gtt gcc cag tgt      2352
Glu Ile Lys Arg Ser Val Asp Gly Glu Gly Tyr Asn Val Ala Gln Cys
    770                 775                 780
```

-continued

```
aac atg acc aaa gac tgg ttc ctg gta caa atg cta gct aac tat aac     2400
Asn Met Thr Lys Asp Trp Phe Leu Val Gln Met Leu Ala Asn Tyr Asn
785                 790                 795                 800

att ggc tac cag ggc ttc tat atc cca gag agc tac aag gac cgc atg     2448
Ile Gly Tyr Gln Gly Phe Tyr Ile Pro Glu Ser Tyr Lys Asp Arg Met
                805                 810                 815

tac tcc ttc ttt aga aac ttc cag ccc atg agc cgt cag gtg gtg gat     2496
Tyr Ser Phe Phe Arg Asn Phe Gln Pro Met Ser Arg Gln Val Val Asp
            820                 825                 830

gat act aaa tac aag gac tac caa cag gtg ggc atc cta cac caa cac     2544
Asp Thr Lys Tyr Lys Asp Tyr Gln Gln Val Gly Ile Leu His Gln His
        835                 840                 845

aac aac tct gga ttt gtt ggc tac ctt gcc ccc acc atg cgc gaa gga     2592
Asn Asn Ser Gly Phe Val Gly Tyr Leu Ala Pro Thr Met Arg Glu Gly
    850                 855                 860

cag gcc tac cct gct aac ttc ccc tat ccg ctt ata ggc aag acc gca     2640
Gln Ala Tyr Pro Ala Asn Phe Pro Tyr Pro Leu Ile Gly Lys Thr Ala
865                 870                 875                 880

gtt gac agc att acc cag aaa aag ttt ctt tgc gat cgc acc ctt tgg     2688
Val Asp Ser Ile Thr Gln Lys Lys Phe Leu Cys Asp Arg Thr Leu Trp
                885                 890                 895

cgc atc cca ttc tcc agt aac ttt atg tcc atg ggc gca ctc aca gac     2736
Arg Ile Pro Phe Ser Ser Asn Phe Met Ser Met Gly Ala Leu Thr Asp
            900                 905                 910

ctg ggc caa aac ctt ctc tac gcc aac tcc gcc cac gcg cta gac atg     2784
Leu Gly Gln Asn Leu Leu Tyr Ala Asn Ser Ala His Ala Leu Asp Met
        915                 920                 925

act ttt gag gtg gat ccc atg gac gag ccc acc ctt ctt tat gtt ttg     2832
Thr Phe Glu Val Asp Pro Met Asp Glu Pro Thr Leu Leu Tyr Val Leu
    930                 935                 940

ttt gaa gtc ttt gac gtg gtc cgt gtg cac cag ccg cac cgc ggc gtc     2880
Phe Glu Val Phe Asp Val Val Arg Val His Gln Pro His Arg Gly Val
945                 950                 955                 960

atc gaa acc gtg tac ctg cgc acg ccc ttc tcg gcc ggc aac gcc aca     2928
Ile Glu Thr Val Tyr Leu Arg Thr Pro Phe Ser Ala Gly Asn Ala Thr
                965                 970                 975

aca taa                                                             2934
Thr
```

```
<210> SEQ ID NO 12
<211> LENGTH: 2826
<212> TYPE: DNA
<213> ORGANISM: Artificial Sequence
<220> FEATURE:
<223> OTHER INFORMATION: (NANP)4-HVR1 modified Hexon protein
<220> FEATURE:
<221> NAME/KEY: CDS
<222> LOCATION: (1)..(2823)

<400> SEQUENCE: 12
```

```
atg gct acc cct tcg atg atg ccg cag tgg tct tac atg cac atc tcg       48
Met Ala Thr Pro Ser Met Met Pro Gln Trp Ser Tyr Met His Ile Ser
1               5                   10                  15

ggc cag gac gcc tcg gag tac ctg agc ccc ggg ctg gtg cag ttt gcc       96
Gly Gln Asp Ala Ser Glu Tyr Leu Ser Pro Gly Leu Val Gln Phe Ala
            20                  25                  30

cgc gcc acc gag acg tac ttc agc ctg aat aac aag ttt aga aac ccc      144
Arg Ala Thr Glu Thr Tyr Phe Ser Leu Asn Asn Lys Phe Arg Asn Pro
        35                  40                  45

acg gtg gcg cct acg cac gac gtg acc aca gac cgg tcc cag cgt ttg      192
Thr Val Ala Pro Thr His Asp Val Thr Thr Asp Arg Ser Gln Arg Leu
    50                  55                  60
```

-continued

```
acg ctg cgg ttc atc cct gtg gac cgt gag gat act gcg tac tcg tac      240
Thr Leu Arg Phe Ile Pro Val Asp Arg Glu Asp Thr Ala Tyr Ser Tyr
65                  70                  75                  80

aag gcg cgg ttc acc cta gct gtg ggt gat aac cgt gtg ctg gac atg      288
Lys Ala Arg Phe Thr Leu Ala Val Gly Asp Asn Arg Val Leu Asp Met
                85                  90                  95

gct tcc acg tac ttt gac atc cgc ggc gtg ctg gac agg ggc cct act      336
Ala Ser Thr Tyr Phe Asp Ile Arg Gly Val Leu Asp Arg Gly Pro Thr
            100                 105                 110

ttt aag ccc tac tct ggc act gcc tac aac gcc ctg gct ccc aag ggt      384
Phe Lys Pro Tyr Ser Gly Thr Ala Tyr Asn Ala Leu Ala Pro Lys Gly
        115                 120                 125

gcc cca aat cct tgc gaa tgg gat gaa aac gct aat ccc aac gct aac      432
Ala Pro Asn Pro Cys Glu Trp Asp Glu Asn Ala Asn Pro Asn Ala Asn
    130                 135                 140

cca aat gca aat cct aat gcc aac ccc aaa act cac gta ttt ggg cag      480
Pro Asn Ala Asn Pro Asn Ala Asn Pro Lys Thr His Val Phe Gly Gln
145                 150                 155                 160

gcg cct tat tct ggt ata aat att aca aag gag ggt att caa ata ggt      528
Ala Pro Tyr Ser Gly Ile Asn Ile Thr Lys Glu Gly Ile Gln Ile Gly
                165                 170                 175

gtc gaa ggt caa aca cct aaa tat gcc gat aaa aca ttt caa cct gaa      576
Val Glu Gly Gln Thr Pro Lys Tyr Ala Asp Lys Thr Phe Gln Pro Glu
            180                 185                 190

cct caa ata gga gaa tct cag tgg tac gaa aca gaa att aat cat gca      624
Pro Gln Ile Gly Glu Ser Gln Trp Tyr Glu Thr Glu Ile Asn His Ala
        195                 200                 205

gct ggg aga gtc cta aaa aag act acc cca atg aaa cca tgt tac ggt      672
Ala Gly Arg Val Leu Lys Lys Thr Thr Pro Met Lys Pro Cys Tyr Gly
    210                 215                 220

tca tat gca aaa ccc aca aat gaa aat gga ggg caa ggc att ctt gta      720
Ser Tyr Ala Lys Pro Thr Asn Glu Asn Gly Gly Gln Gly Ile Leu Val
225                 230                 235                 240

aag caa caa aat gga aag cta gaa agt caa gtg gaa atg caa ttt ttc      768
Lys Gln Gln Asn Gly Lys Leu Glu Ser Gln Val Glu Met Gln Phe Phe
                245                 250                 255

tca act act gag gca gcc gca ggc aat ggt gat aac ttg act cct aaa      816
Ser Thr Thr Glu Ala Ala Ala Gly Asn Gly Asp Asn Leu Thr Pro Lys
            260                 265                 270

gtg gta ttg tac agt gaa gat gta gat ata gaa acc cca gac act cat      864
Val Val Leu Tyr Ser Glu Asp Val Asp Ile Glu Thr Pro Asp Thr His
        275                 280                 285

att tct tac atg ccc act att aag gaa ggt aac tca cga gaa cta atg      912
Ile Ser Tyr Met Pro Thr Ile Lys Glu Gly Asn Ser Arg Glu Leu Met
    290                 295                 300

ggc caa caa tct atg ccc aac agg cct aat tac att gct ttt agg gac      960
Gly Gln Gln Ser Met Pro Asn Arg Pro Asn Tyr Ile Ala Phe Arg Asp
305                 310                 315                 320

aat ttt att ggt cta atg tat tac aac agc acg ggt aat atg ggt gtt     1008
Asn Phe Ile Gly Leu Met Tyr Tyr Asn Ser Thr Gly Asn Met Gly Val
                325                 330                 335

ctg gcg ggc caa gca tcg cag ttg aat gct gtt gta gat ttg caa gac     1056
Leu Ala Gly Gln Ala Ser Gln Leu Asn Ala Val Val Asp Leu Gln Asp
            340                 345                 350

aga aac aca gag ctt tca tac cag ctt ttg ctt gat tcc att ggt gat     1104
Arg Asn Thr Glu Leu Ser Tyr Gln Leu Leu Leu Asp Ser Ile Gly Asp
        355                 360                 365

aga acc agg tac ttt tct atg tgg aat cag gct gtt gac agc tat gat     1152
Arg Thr Arg Tyr Phe Ser Met Trp Asn Gln Ala Val Asp Ser Tyr Asp
```

```
    370                 375                 380

cca gat gtt aga att att gaa aat cat gga act gaa gat gaa ctt cca      1200
Pro Asp Val Arg Ile Ile Glu Asn His Gly Thr Glu Asp Glu Leu Pro
385                 390                 395                 400

aat tac tgc ttt cca ctg gga ggt gtg att aat aca gag act ctt acc      1248
Asn Tyr Cys Phe Pro Leu Gly Gly Val Ile Asn Thr Glu Thr Leu Thr
                405                 410                 415

aag gta aaa cct aaa aca ggt cag gaa aat gga tgg gaa aaa gat gct      1296
Lys Val Lys Pro Lys Thr Gly Gln Glu Asn Gly Trp Glu Lys Asp Ala
            420                 425                 430

aca gaa ttt tca gat aaa aat gaa ata aga gtt gga aat aat ttt gcc      1344
Thr Glu Phe Ser Asp Lys Asn Glu Ile Arg Val Gly Asn Asn Phe Ala
        435                 440                 445

atg gaa atc aat cta aat gcc aac ctg tgg aga aat ttc ctg tac tcc      1392
Met Glu Ile Asn Leu Asn Ala Asn Leu Trp Arg Asn Phe Leu Tyr Ser
    450                 455                 460

aac ata gcg ctg tat ttg ccc gac aag cta aag tac agt cct tcc aac      1440
Asn Ile Ala Leu Tyr Leu Pro Asp Lys Leu Lys Tyr Ser Pro Ser Asn
465                 470                 475                 480

gta aaa att tct gat aac cca aac acc tac gac tac atg aac aag cga      1488
Val Lys Ile Ser Asp Asn Pro Asn Thr Tyr Asp Tyr Met Asn Lys Arg
                485                 490                 495

gtg gtg gct ccc ggg cta gtg gac tgc tac att aac ctt gga gca cgc      1536
Val Val Ala Pro Gly Leu Val Asp Cys Tyr Ile Asn Leu Gly Ala Arg
            500                 505                 510

tgg tcc ctt gac tat atg gac aac gtc aac cca ttt aac cac cac cgc      1584
Trp Ser Leu Asp Tyr Met Asp Asn Val Asn Pro Phe Asn His His Arg
        515                 520                 525

aat gct ggc ctg cgc tac cgc tca atg ttg ctg ggc aat ggt cgc tat      1632
Asn Ala Gly Leu Arg Tyr Arg Ser Met Leu Leu Gly Asn Gly Arg Tyr
    530                 535                 540

gtg ccc ttc cac atc cag gtg cct cag aag ttc ttt gcc att aaa aac      1680
Val Pro Phe His Ile Gln Val Pro Gln Lys Phe Phe Ala Ile Lys Asn
545                 550                 555                 560

ctc ctt ctc ctg ccg ggc tca tac acc tac gag tgg aac ttc agg aag      1728
Leu Leu Leu Leu Pro Gly Ser Tyr Thr Tyr Glu Trp Asn Phe Arg Lys
                565                 570                 575

gat gtt aac atg gtt ctg cag agc tcc cta gga aat gac cta agg gtt      1776
Asp Val Asn Met Val Leu Gln Ser Ser Leu Gly Asn Asp Leu Arg Val
            580                 585                 590

gac gga gcc agc att aag ttt gat agc att tgc ctt tac gcc acc ttc      1824
Asp Gly Ala Ser Ile Lys Phe Asp Ser Ile Cys Leu Tyr Ala Thr Phe
        595                 600                 605

ttc ccc atg gcc cac aac acc gcc tcc acg ctt gag gcc atg ctt aga      1872
Phe Pro Met Ala His Asn Thr Ala Ser Thr Leu Glu Ala Met Leu Arg
    610                 615                 620

aac gac acc aac gac cag tcc ttt aac gac tat ctc tcc gcc gcc aac      1920
Asn Asp Thr Asn Asp Gln Ser Phe Asn Asp Tyr Leu Ser Ala Ala Asn
625                 630                 635                 640

atg ctc tac cct ata ccc gcc aac gct acc aac gtg ccc ata tcc atc      1968
Met Leu Tyr Pro Ile Pro Ala Asn Ala Thr Asn Val Pro Ile Ser Ile
                645                 650                 655

ccc tcc cgc aac tgg gcg gct ttc cgc ggc tgg gcc ttc acg cgc ctt      2016
Pro Ser Arg Asn Trp Ala Ala Phe Arg Gly Trp Ala Phe Thr Arg Leu
            660                 665                 670

aag act aag gaa acc cca tca ctg ggc tcg ggc tac gac cct tat tac      2064
Lys Thr Lys Glu Thr Pro Ser Leu Gly Ser Gly Tyr Asp Pro Tyr Tyr
        675                 680                 685

acc tac tct ggc tct ata ccc tac cta gat gga acc ttt tac ctc aac      2112
```

```
Thr Tyr Ser Gly Ser Ile Pro Tyr Leu Asp Gly Thr Phe Tyr Leu Asn
    690                 695                 700

cac acc ttt aag aag gtg gcc att acc ttt gac tct tct gtc agc tgg     2160
His Thr Phe Lys Lys Val Ala Ile Thr Phe Asp Ser Ser Val Ser Trp
705                 710                 715                 720

cct ggc aat gac cgc ctg ctt acc ccc aac gag ttt gaa att aag cgc     2208
Pro Gly Asn Asp Arg Leu Leu Thr Pro Asn Glu Phe Glu Ile Lys Arg
                725                 730                 735

tca gtt gac ggg gag ggt tac aac gtt gcc cag tgt aac atg acc aaa     2256
Ser Val Asp Gly Glu Gly Tyr Asn Val Ala Gln Cys Asn Met Thr Lys
            740                 745                 750

gac tgg ttc ctg gta caa atg cta gct aac tat aac att ggc tac cag     2304
Asp Trp Phe Leu Val Gln Met Leu Ala Asn Tyr Asn Ile Gly Tyr Gln
        755                 760                 765

ggc ttc tat atc cca gag agc tac aag gac cgc atg tac tcc ttc ttt     2352
Gly Phe Tyr Ile Pro Glu Ser Tyr Lys Asp Arg Met Tyr Ser Phe Phe
    770                 775                 780

aga aac ttc cag ccc atg agc cgt cag gtg gtg gat gat act aaa tac     2400
Arg Asn Phe Gln Pro Met Ser Arg Gln Val Val Asp Asp Thr Lys Tyr
785                 790                 795                 800

aag gac tac caa cag gtg ggc atc cta cac caa cac aac aac tct gga     2448
Lys Asp Tyr Gln Gln Val Gly Ile Leu His Gln His Asn Asn Ser Gly
                805                 810                 815

ttt gtt ggc tac ctt gcc ccc acc atg cgc gaa gga cag gcc tac cct     2496
Phe Val Gly Tyr Leu Ala Pro Thr Met Arg Glu Gly Gln Ala Tyr Pro
            820                 825                 830

gct aac ttc ccc tat ccg ctt ata ggc aag acc gca gtt gac agc att     2544
Ala Asn Phe Pro Tyr Pro Leu Ile Gly Lys Thr Ala Val Asp Ser Ile
        835                 840                 845

acc cag aaa aag ttt ctt tgc gat cgc acc ctt tgg cgc atc cca ttc     2592
Thr Gln Lys Lys Phe Leu Cys Asp Arg Thr Leu Trp Arg Ile Pro Phe
    850                 855                 860

tcc agt aac ttt atg tcc atg ggc gca ctc aca gac ctg ggc caa aac     2640
Ser Ser Asn Phe Met Ser Met Gly Ala Leu Thr Asp Leu Gly Gln Asn
865                 870                 875                 880

ctt ctc tac gcc aac tcc gcc cac gcg cta gac atg act ttt gag gtg     2688
Leu Leu Tyr Ala Asn Ser Ala His Ala Leu Asp Met Thr Phe Glu Val
                885                 890                 895

gat ccc atg gac gag ccc acc ctt ctt tat gtt ttg ttt gaa gtc ttt     2736
Asp Pro Met Asp Glu Pro Thr Leu Leu Tyr Val Leu Phe Glu Val Phe
            900                 905                 910

gac gtg gtc cgt gtg cac cag ccg cac cgc ggc gtc atc gaa acc gtg     2784
Asp Val Val Arg Val His Gln Pro His Arg Gly Val Ile Glu Thr Val
        915                 920                 925

tac ctg cgc acg ccc ttc tcg gcc ggc aac gcc aca aca taa             2826
Tyr Leu Arg Thr Pro Phe Ser Ala Gly Asn Ala Thr Thr
    930                 935                 940


<210> SEQ ID NO 13
<211> LENGTH: 2790
<212> TYPE: DNA
<213> ORGANISM: Artificial Sequence
<220> FEATURE:
<223> OTHER INFORMATION: (NANP)6-HVR1 modified Hexon protein
<220> FEATURE:
<221> NAME/KEY: CDS
<222> LOCATION: (1)..(2787)

<400> SEQUENCE: 13

atg gct acc cct tcg atg atg ccg cag tgg tct tac atg cac atc tcg       48
Met Ala Thr Pro Ser Met Met Pro Gln Trp Ser Tyr Met His Ile Ser
1               5                   10                  15
```

```
ggc cag gac gcc tcg gag tac ctg agc ccc ggg ctg gtg cag ttt gcc       96
Gly Gln Asp Ala Ser Glu Tyr Leu Ser Pro Gly Leu Val Gln Phe Ala
            20                  25                  30

cgc gcc acc gag acg tac ttc agc ctg aat aac aag ttt aga aac ccc      144
Arg Ala Thr Glu Thr Tyr Phe Ser Leu Asn Asn Lys Phe Arg Asn Pro
        35                  40                  45

acg gtg gcg cct acg cac gac gtg acc aca gac cgg tcc cag cgt ttg      192
Thr Val Ala Pro Thr His Asp Val Thr Thr Asp Arg Ser Gln Arg Leu
    50                  55                  60

acg ctg cgg ttc atc cct gtg gac cgt gag gat act gcg tac tcg tac      240
Thr Leu Arg Phe Ile Pro Val Asp Arg Glu Asp Thr Ala Tyr Ser Tyr
65                  70                  75                  80

aag gcg cgg ttc acc cta gct gtg ggt gat aac cgt gtg ctg gac atg      288
Lys Ala Arg Phe Thr Leu Ala Val Gly Asp Asn Arg Val Leu Asp Met
                85                  90                  95

gct tcc acg tac ttt gac atc cgc ggc gtg ctg gac agg ggc cct act      336
Ala Ser Thr Tyr Phe Asp Ile Arg Gly Val Leu Asp Arg Gly Pro Thr
            100                 105                 110

ttt aag ccc tac tct ggc act gcc tac aac gcc ctg gct ccc aag ggt      384
Phe Lys Pro Tyr Ser Gly Thr Ala Tyr Asn Ala Leu Ala Pro Lys Gly
        115                 120                 125

gcc cca aat cct tgc gaa tgg gat gaa aat gca aat cca aat gca aat      432
Ala Pro Asn Pro Cys Glu Trp Asp Glu Asn Ala Asn Pro Asn Ala Asn
    130                 135                 140

cca aat gca aat cca aat gca aat cca aac gcg aac ccg aat gct aat      480
Pro Asn Ala Asn Pro Asn Ala Asn Pro Asn Ala Asn Pro Asn Ala Asn
145                 150                 155                 160

cct aaa act cac gta ttt ggg cag gcg cct tat tct ggt ata aat att      528
Pro Lys Thr His Val Phe Gly Gln Ala Pro Tyr Ser Gly Ile Asn Ile
                165                 170                 175

aca aag gag ggt att caa ata ggt gtc gaa ggt caa aca cct aaa tat      576
Thr Lys Glu Gly Ile Gln Ile Gly Val Glu Gly Gln Thr Pro Lys Tyr
            180                 185                 190

gcc gat aaa aca ttt caa cct gaa cct caa ata gga gaa tct cag tgg      624
Ala Asp Lys Thr Phe Gln Pro Glu Pro Gln Ile Gly Glu Ser Gln Trp
        195                 200                 205

tac gaa aca gaa att aat cat gca gct ggg aga gtc cta aaa aag act      672
Tyr Glu Thr Glu Ile Asn His Ala Ala Gly Arg Val Leu Lys Lys Thr
    210                 215                 220

acc cca atg aaa cca tgt tac ggt tca tat gca aaa ccc aca aat gaa      720
Thr Pro Met Lys Pro Cys Tyr Gly Ser Tyr Ala Lys Pro Thr Asn Glu
225                 230                 235                 240

aat gga ggg caa ggc att ctt gta aag caa caa aat gga aag cta gaa      768
Asn Gly Gly Gln Gly Ile Leu Val Lys Gln Gln Asn Gly Lys Leu Glu
                245                 250                 255

agt caa gtg gaa atg caa ttt ttc tca act act gag gca gcc gca ggc      816
Ser Gln Val Glu Met Gln Phe Phe Ser Thr Thr Glu Ala Ala Ala Gly
            260                 265                 270

aat ggt gat aac ttg act cct aaa gtg gta ttg tac agt gaa gat gta      864
Asn Gly Asp Asn Leu Thr Pro Lys Val Val Leu Tyr Ser Glu Asp Val
        275                 280                 285

gat ata gaa acc cca gac act cat att tct tac atg ccc act att aag      912
Asp Ile Glu Thr Pro Asp Thr His Ile Ser Tyr Met Pro Thr Ile Lys
    290                 295                 300

gaa ggt aac tca cga gaa cta atg ggc caa caa tct atg ccc aac agg      960
Glu Gly Asn Ser Arg Glu Leu Met Gly Gln Gln Ser Met Pro Asn Arg
305                 310                 315                 320

cct aat tac att gct ttt agg gac aat ttt att ggt cta atg tat tac     1008
Pro Asn Tyr Ile Ala Phe Arg Asp Asn Phe Ile Gly Leu Met Tyr Tyr
```

-continued

```
                325                 330                 335

aac agc acg ggt aat atg ggt gtt ctg gcg ggc caa gca tcg cag ttg      1056
Asn Ser Thr Gly Asn Met Gly Val Leu Ala Gly Gln Ala Ser Gln Leu
            340                 345                 350

aat gct gtt gta gat ttg caa gac aga aac aca gag ctt tca tac cag      1104
Asn Ala Val Val Asp Leu Gln Asp Arg Asn Thr Glu Leu Ser Tyr Gln
        355                 360                 365

ctt ttg ctt gat tcc att ggt gat aga acc agg tac ttt tct atg tgg      1152
Leu Leu Leu Asp Ser Ile Gly Asp Arg Thr Arg Tyr Phe Ser Met Trp
    370                 375                 380

aat cag ctt cca aat tac tgc ttt cca ctg gga ggt gtg att aat aca      1200
Asn Gln Leu Pro Asn Tyr Cys Phe Pro Leu Gly Gly Val Ile Asn Thr
385                 390                 395                 400

gag act ctt acc aag gta aaa cct aaa aca ggt cag gaa aat gga tgg      1248
Glu Thr Leu Thr Lys Val Lys Pro Lys Thr Gly Gln Glu Asn Gly Trp
                405                 410                 415

gaa aaa gat gct aca gaa ttt tca gat aaa aat gaa ata aga gtt gga      1296
Glu Lys Asp Ala Thr Glu Phe Ser Asp Lys Asn Glu Ile Arg Val Gly
            420                 425                 430

aat aat ttt gcc atg gaa atc aat cta aat gcc aac ctg tgg aga aat      1344
Asn Asn Phe Ala Met Glu Ile Asn Leu Asn Ala Asn Leu Trp Arg Asn
        435                 440                 445

ttc ctg tac tcc aac ata gcg ctg tat ttg ccc gac aag cta aag tac      1392
Phe Leu Tyr Ser Asn Ile Ala Leu Tyr Leu Pro Asp Lys Leu Lys Tyr
    450                 455                 460

agt cct tcc aac gta aaa att tct gat aac cca aac acc tac gac tac      1440
Ser Pro Ser Asn Val Lys Ile Ser Asp Asn Pro Asn Thr Tyr Asp Tyr
465                 470                 475                 480

atg aac aag cga gtg gtg gct ccc ggg cta gtg gac tgc tac att aac      1488
Met Asn Lys Arg Val Val Ala Pro Gly Leu Val Asp Cys Tyr Ile Asn
                485                 490                 495

ctt gga gca cgc tgg tcc ctt gac tat atg gac aac gtc aac cca ttt      1536
Leu Gly Ala Arg Trp Ser Leu Asp Tyr Met Asp Asn Val Asn Pro Phe
            500                 505                 510

aac cac cac cgc aat gct ggc ctg cgc tac cgc tca atg ttg ctg ggc      1584
Asn His His Arg Asn Ala Gly Leu Arg Tyr Arg Ser Met Leu Leu Gly
        515                 520                 525

aat ggt cgc tat gtg ccc ttc cac atc cag gtg cct cag aag ttc ttt      1632
Asn Gly Arg Tyr Val Pro Phe His Ile Gln Val Pro Gln Lys Phe Phe
    530                 535                 540

gcc att aaa aac ctc ctt ctc ctg ccg ggc tca tac acc tac gag tgg      1680
Ala Ile Lys Asn Leu Leu Leu Leu Pro Gly Ser Tyr Thr Tyr Glu Trp
545                 550                 555                 560

aac ttc agg aag gat gtt aac atg gtt ctg cag agc tcc cta gga aat      1728
Asn Phe Arg Lys Asp Val Asn Met Val Leu Gln Ser Ser Leu Gly Asn
                565                 570                 575

gac cta agg gtt gac gga gcc agc att aag ttt gat agc att tgc ctt      1776
Asp Leu Arg Val Asp Gly Ala Ser Ile Lys Phe Asp Ser Ile Cys Leu
            580                 585                 590

tac gcc acc ttc ttc ccc atg gcc cac aac acc gcc tcc acg ctt gag      1824
Tyr Ala Thr Phe Phe Pro Met Ala His Asn Thr Ala Ser Thr Leu Glu
        595                 600                 605

gcc atg ctt aga aac gac acc aac gac cag tcc ttt aac gac tat ctc      1872
Ala Met Leu Arg Asn Asp Thr Asn Asp Gln Ser Phe Asn Asp Tyr Leu
    610                 615                 620

tcc gcc gcc aac atg ctc tac cct ata ccc gcc aac gct acc aac gtg      1920
Ser Ala Ala Asn Met Leu Tyr Pro Ile Pro Ala Asn Ala Thr Asn Val
625                 630                 635                 640

ccc ata tcc atc ccc tcc cgc aac tgg gcg gct ttc cgc ggc tgg gcc      1968
```

```
Pro Ile Ser Ile Pro Ser Arg Asn Trp Ala Ala Phe Arg Gly Trp Ala
                645                 650                 655

ttc acg cgc ctt aag act aag gaa acc cca tca ctg ggc tcg ggc tac      2016
Phe Thr Arg Leu Lys Thr Lys Glu Thr Pro Ser Leu Gly Ser Gly Tyr
            660                 665                 670

gac cct tat tac acc tac tct ggc tct ata ccc tac cta gat gga acc      2064
Asp Pro Tyr Tyr Thr Tyr Ser Gly Ser Ile Pro Tyr Leu Asp Gly Thr
        675                 680                 685

ttt tac ctc aac cac acc ttt aag aag gtg gcc att acc ttt gac tct      2112
Phe Tyr Leu Asn His Thr Phe Lys Lys Val Ala Ile Thr Phe Asp Ser
    690                 695                 700

tct gtc agc tgg cct ggc aat gac cgc ctg ctt acc ccc aac gag ttt      2160
Ser Val Ser Trp Pro Gly Asn Asp Arg Leu Leu Thr Pro Asn Glu Phe
705                 710                 715                 720

gaa att aag cgc tca gtt gac ggg gag ggt tac aac gtt gcc cag tgt      2208
Glu Ile Lys Arg Ser Val Asp Gly Glu Gly Tyr Asn Val Ala Gln Cys
                725                 730                 735

aac atg acc aaa gac tgg ttc ctg gta caa atg cta gct aac tat aac      2256
Asn Met Thr Lys Asp Trp Phe Leu Val Gln Met Leu Ala Asn Tyr Asn
            740                 745                 750

att ggc tac cag ggc ttc tat atc cca gag agc tac aag gac cgc atg      2304
Ile Gly Tyr Gln Gly Phe Tyr Ile Pro Glu Ser Tyr Lys Asp Arg Met
        755                 760                 765

tac tcc ttc ttt aga aac ttc cag ccc atg agc cgt cag gtg gtg gat      2352
Tyr Ser Phe Phe Arg Asn Phe Gln Pro Met Ser Arg Gln Val Val Asp
    770                 775                 780

gat act aaa tac aag gac tac caa cag gtg ggc atc cta cac caa cac      2400
Asp Thr Lys Tyr Lys Asp Tyr Gln Gln Val Gly Ile Leu His Gln His
785                 790                 795                 800

aac aac tct gga ttt gtt ggc tac ctt gcc ccc acc atg cgc gaa gga      2448
Asn Asn Ser Gly Phe Val Gly Tyr Leu Ala Pro Thr Met Arg Glu Gly
                805                 810                 815

cag gcc tac cct gct aac ttc ccc tat ccg ctt ata ggc aag acc gca      2496
Gln Ala Tyr Pro Ala Asn Phe Pro Tyr Pro Leu Ile Gly Lys Thr Ala
            820                 825                 830

gtt gac agc att acc cag aaa aag ttt ctt tgc gat cgc acc ctt tgg      2544
Val Asp Ser Ile Thr Gln Lys Lys Phe Leu Cys Asp Arg Thr Leu Trp
        835                 840                 845

cgc atc cca ttc tcc agt aac ttt atg tcc atg ggc gca ctc aca gac      2592
Arg Ile Pro Phe Ser Ser Asn Phe Met Ser Met Gly Ala Leu Thr Asp
    850                 855                 860

ctg ggc caa aac ctt ctc tac gcc aac tcc gcc cac gcg cta gac atg      2640
Leu Gly Gln Asn Leu Leu Tyr Ala Asn Ser Ala His Ala Leu Asp Met
865                 870                 875                 880

act ttt gag gtg gat ccc atg gac gag ccc acc ctt ctt tat gtt ttg      2688
Thr Phe Glu Val Asp Pro Met Asp Glu Pro Thr Leu Leu Tyr Val Leu
                885                 890                 895

ttt gaa gtc ttt gac gtg gtc cgt gtg cac cag ccg cac cgc ggc gtc      2736
Phe Glu Val Phe Asp Val Val Arg Val His Gln Pro His Arg Gly Val
            900                 905                 910

atc gaa acc gtg tac ctg cgc acg ccc ttc tcg gcc ggc aac gcc aca      2784
Ile Glu Thr Val Tyr Leu Arg Thr Pro Phe Ser Ala Gly Asn Ala Thr
        915                 920                 925

aca taa                                                              2790
Thr
```

<210> SEQ ID NO 14
<211> LENGTH: 2814
<212> TYPE: DNA
<213> ORGANISM: Artificial Sequence

```
<220> FEATURE:
<223> OTHER INFORMATION: (NANP)8-HVR1 modified Hexon protein
<220> FEATURE:
<221> NAME/KEY: CDS
<222> LOCATION: (1)..(2811)

<400> SEQUENCE: 14

atg gct acc cct tcg atg atg ccg cag tgg tct tac atg cac atc tcg       48
Met Ala Thr Pro Ser Met Met Pro Gln Trp Ser Tyr Met His Ile Ser
1               5                   10                  15

ggc cag gac gcc tcg gag tac ctg agc ccc ggg ctg gtg cag ttt gcc       96
Gly Gln Asp Ala Ser Glu Tyr Leu Ser Pro Gly Leu Val Gln Phe Ala
            20                  25                  30

cgc gcc acc gag acg tac ttc agc ctg aat aac aag ttt aga aac ccc      144
Arg Ala Thr Glu Thr Tyr Phe Ser Leu Asn Asn Lys Phe Arg Asn Pro
        35                  40                  45

acg gtg gcg cct acg cac gac gtg acc aca gac cgg tcc cag cgt ttg      192
Thr Val Ala Pro Thr His Asp Val Thr Thr Asp Arg Ser Gln Arg Leu
    50                  55                  60

acg ctg cgg ttc atc cct gtg gac cgt gag gat act gcg tac tcg tac      240
Thr Leu Arg Phe Ile Pro Val Asp Arg Glu Asp Thr Ala Tyr Ser Tyr
65                  70                  75                  80

aag gcg cgg ttc acc cta gct gtg ggt gat aac cgt gtg ctg gac atg      288
Lys Ala Arg Phe Thr Leu Ala Val Gly Asp Asn Arg Val Leu Asp Met
                85                  90                  95

gct tcc acg tac ttt gac atc cgc ggc gtg ctg gac agg ggc cct act      336
Ala Ser Thr Tyr Phe Asp Ile Arg Gly Val Leu Asp Arg Gly Pro Thr
            100                 105                 110

ttt aag ccc tac tct ggc act gcc tac aac gcc ctg gct ccc aag ggt      384
Phe Lys Pro Tyr Ser Gly Thr Ala Tyr Asn Ala Leu Ala Pro Lys Gly
        115                 120                 125

gcc cca aat cct tgc gaa tgg gat gaa aat gca aat cca aat gca aat      432
Ala Pro Asn Pro Cys Glu Trp Asp Glu Asn Ala Asn Pro Asn Ala Asn
    130                 135                 140

cca aat gca aat cca aat gca aat cca aac gcg aac ccg aat gct aat      480
Pro Asn Ala Asn Pro Asn Ala Asn Pro Asn Ala Asn Pro Asn Ala Asn
145                 150                 155                 160

cct aat gca aat cca aat gca aat cca aaa act cac gta ttt ggg cag      528
Pro Asn Ala Asn Pro Asn Ala Asn Pro Lys Thr His Val Phe Gly Gln
                165                 170                 175

gcg cct tat tct ggt ata aat att aca aag gag ggt att caa ata ggt      576
Ala Pro Tyr Ser Gly Ile Asn Ile Thr Lys Glu Gly Ile Gln Ile Gly
            180                 185                 190

gtc gaa ggt caa aca cct aaa tat gcc gat aaa aca ttt caa cct gaa      624
Val Glu Gly Gln Thr Pro Lys Tyr Ala Asp Lys Thr Phe Gln Pro Glu
        195                 200                 205

cct caa ata gga gaa tct cag tgg tac gaa aca gaa att aat cat gca      672
Pro Gln Ile Gly Glu Ser Gln Trp Tyr Glu Thr Glu Ile Asn His Ala
    210                 215                 220

gct ggg aga gtc cta aaa aag act acc cca atg aaa cca tgt tac ggt      720
Ala Gly Arg Val Leu Lys Lys Thr Thr Pro Met Lys Pro Cys Tyr Gly
225                 230                 235                 240

tca tat gca aaa ccc aca aat gaa aat gga ggg caa ggc att ctt gta      768
Ser Tyr Ala Lys Pro Thr Asn Glu Asn Gly Gly Gln Gly Ile Leu Val
                245                 250                 255

aag caa caa aat gga aag cta gaa agt caa gtg gaa atg caa ttt ttc      816
Lys Gln Gln Asn Gly Lys Leu Glu Ser Gln Val Glu Met Gln Phe Phe
            260                 265                 270

tca act act gag gca gcc gca ggc aat ggt gat aac ttg act cct aaa      864
Ser Thr Thr Glu Ala Ala Ala Gly Asn Gly Asp Asn Leu Thr Pro Lys
        275                 280                 285
```

```
gtg gta ttg tac agt gaa gat gta gat ata gaa acc cca gac act cat      912
Val Val Leu Tyr Ser Glu Asp Val Asp Ile Glu Thr Pro Asp Thr His
    290                 295                 300

att tct tac atg ccc act att aag gaa ggt aac tca cga gaa cta atg      960
Ile Ser Tyr Met Pro Thr Ile Lys Glu Gly Asn Ser Arg Glu Leu Met
305                 310                 315                 320

ggc caa caa tct atg ccc aac agg cct aat tac att gct ttt agg gac     1008
Gly Gln Gln Ser Met Pro Asn Arg Pro Asn Tyr Ile Ala Phe Arg Asp
                325                 330                 335

aat ttt att ggt cta atg tat tac aac agc acg ggt aat atg ggt gtt     1056
Asn Phe Ile Gly Leu Met Tyr Tyr Asn Ser Thr Gly Asn Met Gly Val
            340                 345                 350

ctg gcg ggc caa gca tcg cag ttg aat gct gtt gta gat ttg caa gac     1104
Leu Ala Gly Gln Ala Ser Gln Leu Asn Ala Val Val Asp Leu Gln Asp
        355                 360                 365

aga aac aca gag ctt tca tac cag ctt ttg ctt gat tcc att ggt gat     1152
Arg Asn Thr Glu Leu Ser Tyr Gln Leu Leu Leu Asp Ser Ile Gly Asp
    370                 375                 380

aga acc agg tac ttt tct atg tgg aat cag ctt cca aat tac tgc ttt     1200
Arg Thr Arg Tyr Phe Ser Met Trp Asn Gln Leu Pro Asn Tyr Cys Phe
385                 390                 395                 400

cca ctg gga ggt gtg att aat aca gag act ctt acc aag gta aaa cct     1248
Pro Leu Gly Gly Val Ile Asn Thr Glu Thr Leu Thr Lys Val Lys Pro
                405                 410                 415

aaa aca ggt cag gaa aat gga tgg gaa aaa gat gct aca gaa ttt tca     1296
Lys Thr Gly Gln Glu Asn Gly Trp Glu Lys Asp Ala Thr Glu Phe Ser
            420                 425                 430

gat aaa aat gaa ata aga gtt gga aat aat ttt gcc atg gaa atc aat     1344
Asp Lys Asn Glu Ile Arg Val Gly Asn Asn Phe Ala Met Glu Ile Asn
        435                 440                 445

cta aat gcc aac ctg tgg aga aat ttc ctg tac tcc aac ata gcg ctg     1392
Leu Asn Ala Asn Leu Trp Arg Asn Phe Leu Tyr Ser Asn Ile Ala Leu
    450                 455                 460

tat ttg ccc gac aag cta aag tac agt cct tcc aac gta aaa att tct     1440
Tyr Leu Pro Asp Lys Leu Lys Tyr Ser Pro Ser Asn Val Lys Ile Ser
465                 470                 475                 480

gat aac cca aac acc tac gac tac atg aac aag cga gtg gtg gct ccc     1488
Asp Asn Pro Asn Thr Tyr Asp Tyr Met Asn Lys Arg Val Val Ala Pro
                485                 490                 495

ggg cta gtg gac tgc tac att aac ctt gga gca cgc tgg tcc ctt gac     1536
Gly Leu Val Asp Cys Tyr Ile Asn Leu Gly Ala Arg Trp Ser Leu Asp
            500                 505                 510

tat atg gac aac gtc aac cca ttt aac cac cac cgc aat gct ggc ctg     1584
Tyr Met Asp Asn Val Asn Pro Phe Asn His His Arg Asn Ala Gly Leu
        515                 520                 525

cgc tac cgc tca atg ttg ctg ggc aat ggt cgc tat gtg ccc ttc cac     1632
Arg Tyr Arg Ser Met Leu Leu Gly Asn Gly Arg Tyr Val Pro Phe His
    530                 535                 540

atc cag gtg cct cag aag ttc ttt gcc att aaa aac ctc ctt ctc ctg     1680
Ile Gln Val Pro Gln Lys Phe Phe Ala Ile Lys Asn Leu Leu Leu Leu
545                 550                 555                 560

ccg ggc tca tac acc tac gag tgg aac ttc agg aag gat gtt aac atg     1728
Pro Gly Ser Tyr Thr Tyr Glu Trp Asn Phe Arg Lys Asp Val Asn Met
                565                 570                 575

gtt ctg cag agc tcc cta gga aat gac cta agg gtt gac gga gcc agc     1776
Val Leu Gln Ser Ser Leu Gly Asn Asp Leu Arg Val Asp Gly Ala Ser
            580                 585                 590

att aag ttt gat agc att tgc ctt tac gcc acc ttc ttc ccc atg gcc     1824
Ile Lys Phe Asp Ser Ile Cys Leu Tyr Ala Thr Phe Phe Pro Met Ala
```

-continued

```
        595                 600                 605

cac aac acc gcc tcc acg ctt gag gcc atg ctt aga aac gac acc aac      1872
His Asn Thr Ala Ser Thr Leu Glu Ala Met Leu Arg Asn Asp Thr Asn
    610                 615                 620

gac cag tcc ttt aac gac tat ctc tcc gcc gcc aac atg ctc tac cct      1920
Asp Gln Ser Phe Asn Asp Tyr Leu Ser Ala Ala Asn Met Leu Tyr Pro
625                 630                 635                 640

ata ccc gcc aac gct acc aac gtg ccc ata tcc atc ccc tcc cgc aac      1968
Ile Pro Ala Asn Ala Thr Asn Val Pro Ile Ser Ile Pro Ser Arg Asn
                645                 650                 655

tgg gcg gct ttc cgc ggc tgg gcc ttc acg cgc ctt aag act aag gaa      2016
Trp Ala Ala Phe Arg Gly Trp Ala Phe Thr Arg Leu Lys Thr Lys Glu
            660                 665                 670

acc cca tca ctg ggc tcg ggc tac gac cct tat tac acc tac tct ggc      2064
Thr Pro Ser Leu Gly Ser Gly Tyr Asp Pro Tyr Tyr Thr Tyr Ser Gly
        675                 680                 685

tct ata ccc tac cta gat gga acc ttt tac ctc aac cac acc ttt aag      2112
Ser Ile Pro Tyr Leu Asp Gly Thr Phe Tyr Leu Asn His Thr Phe Lys
    690                 695                 700

aag gtg gcc att acc ttt gac tct tct gtc agc tgg cct ggc aat gac      2160
Lys Val Ala Ile Thr Phe Asp Ser Ser Val Ser Trp Pro Gly Asn Asp
705                 710                 715                 720

cgc ctg ctt acc ccc aac gag ttt gaa att aag cgc tca gtt gac ggg      2208
Arg Leu Leu Thr Pro Asn Glu Phe Glu Ile Lys Arg Ser Val Asp Gly
                725                 730                 735

gag ggt tac aac gtt gcc cag tgt aac atg acc aaa gac tgg ttc ctg      2256
Glu Gly Tyr Asn Val Ala Gln Cys Asn Met Thr Lys Asp Trp Phe Leu
            740                 745                 750

gta caa atg cta gct aac tat aac att ggc tac cag ggc ttc tat atc      2304
Val Gln Met Leu Ala Asn Tyr Asn Ile Gly Tyr Gln Gly Phe Tyr Ile
        755                 760                 765

cca gag agc tac aag gac cgc atg tac tcc ttc ttt aga aac ttc cag      2352
Pro Glu Ser Tyr Lys Asp Arg Met Tyr Ser Phe Phe Arg Asn Phe Gln
    770                 775                 780

ccc atg agc cgt cag gtg gtg gat gat act aaa tac aag gac tac caa      2400
Pro Met Ser Arg Gln Val Val Asp Asp Thr Lys Tyr Lys Asp Tyr Gln
785                 790                 795                 800

cag gtg ggc atc cta cac caa cac aac aac tct gga ttt gtt ggc tac      2448
Gln Val Gly Ile Leu His Gln His Asn Asn Ser Gly Phe Val Gly Tyr
                805                 810                 815

ctt gcc ccc acc atg cgc gaa gga cag gcc tac cct gct aac ttc ccc      2496
Leu Ala Pro Thr Met Arg Glu Gly Gln Ala Tyr Pro Ala Asn Phe Pro
            820                 825                 830

tat ccg ctt ata ggc aag acc gca gtt gac agc att acc cag aaa aag      2544
Tyr Pro Leu Ile Gly Lys Thr Ala Val Asp Ser Ile Thr Gln Lys Lys
        835                 840                 845

ttt ctt tgc gat cgc acc ctt tgg cgc atc cca ttc tcc agt aac ttt      2592
Phe Leu Cys Asp Arg Thr Leu Trp Arg Ile Pro Phe Ser Ser Asn Phe
    850                 855                 860

atg tcc atg ggc gca ctc aca gac ctg ggc caa aac ctt ctc tac gcc      2640
Met Ser Met Gly Ala Leu Thr Asp Leu Gly Gln Asn Leu Leu Tyr Ala
865                 870                 875                 880

aac tcc gcc cac gcg cta gac atg act ttt gag gtg gat ccc atg gac      2688
Asn Ser Ala His Ala Leu Asp Met Thr Phe Glu Val Asp Pro Met Asp
                885                 890                 895

gag ccc acc ctt ctt tat gtt ttg ttt gaa gtc ttt gac gtg gtc cgt      2736
Glu Pro Thr Leu Leu Tyr Val Leu Phe Glu Val Phe Asp Val Val Arg
            900                 905                 910

gtg cac cag ccg cac cgc ggc gtc atc gaa acc gtg tac ctg cgc acg      2784
```

```
Val His Gln Pro His Arg Gly Val Ile Glu Thr Val Tyr Leu Arg Thr
        915                 920                 925

ccc ttc tcg gcc ggc aac gcc aca aca taa                          2814
Pro Phe Ser Ala Gly Asn Ala Thr Thr
    930                 935
```

<210> SEQ ID NO 15
<211> LENGTH: 2838
<212> TYPE: DNA
<213> ORGANISM: Artificial Sequence
<220> FEATURE:
<223> OTHER INFORMATION: (NANP)10-HVR1 modified Hexon protein
<220> FEATURE:
<221> NAME/KEY: CDS
<222> LOCATION: (1)..(2835)

<400> SEQUENCE: 15

```
atg gct acc cct tcg atg atg ccg cag tgg tct tac atg cac atc tcg       48
Met Ala Thr Pro Ser Met Met Pro Gln Trp Ser Tyr Met His Ile Ser
1               5                   10                  15

ggc cag gac gcc tcg gag tac ctg agc ccc ggg ctg gtg cag ttt gcc       96
Gly Gln Asp Ala Ser Glu Tyr Leu Ser Pro Gly Leu Val Gln Phe Ala
            20                  25                  30

cgc gcc acc gag acg tac ttc agc ctg aat aac aag ttt aga aac ccc      144
Arg Ala Thr Glu Thr Tyr Phe Ser Leu Asn Asn Lys Phe Arg Asn Pro
        35                  40                  45

acg gtg gcg cct acg cac gac gtg acc aca gac cgg tcc cag cgt ttg      192
Thr Val Ala Pro Thr His Asp Val Thr Thr Asp Arg Ser Gln Arg Leu
    50                  55                  60

acg ctg cgg ttc atc cct gtg gac cgt gag gat act gcg tac tcg tac      240
Thr Leu Arg Phe Ile Pro Val Asp Arg Glu Asp Thr Ala Tyr Ser Tyr
65                  70                  75                  80

aag gcg cgg ttc acc cta gct gtg ggt gat aac cgt gtg ctg gac atg      288
Lys Ala Arg Phe Thr Leu Ala Val Gly Asp Asn Arg Val Leu Asp Met
                85                  90                  95

gct tcc acg tac ttt gac atc cgc ggc gtg ctg gac agg ggc cct act      336
Ala Ser Thr Tyr Phe Asp Ile Arg Gly Val Leu Asp Arg Gly Pro Thr
            100                 105                 110

ttt aag ccc tac tct ggc act gcc tac aac gcc ctg gct ccc aag ggt      384
Phe Lys Pro Tyr Ser Gly Thr Ala Tyr Asn Ala Leu Ala Pro Lys Gly
        115                 120                 125

gcc cca aat cct tgc gaa tgg gat gaa aat gca aat cca aat gca aat      432
Ala Pro Asn Pro Cys Glu Trp Asp Glu Asn Ala Asn Pro Asn Ala Asn
    130                 135                 140

cca aat gca aat cca aat gca aat cca aac gcg aac ccg aat gct aat      480
Pro Asn Ala Asn Pro Asn Ala Asn Pro Asn Ala Asn Pro Asn Ala Asn
145                 150                 155                 160

cct aat gca aat cca aat gca aat cca aat gca aat cca aat gca aat      528
Pro Asn Ala Asn Pro Asn Ala Asn Pro Asn Ala Asn Pro Asn Ala Asn
                165                 170                 175

cca aaa act cac gta ttt ggg cag gcg cct tat tct ggt ata aat att      576
Pro Lys Thr His Val Phe Gly Gln Ala Pro Tyr Ser Gly Ile Asn Ile
            180                 185                 190

aca aag gag ggt att caa ata ggt gtc gaa ggt caa aca cct aaa tat      624
Thr Lys Glu Gly Ile Gln Ile Gly Val Glu Gly Gln Thr Pro Lys Tyr
        195                 200                 205

gcc gat aaa aca ttt caa cct gaa cct caa ata gga gaa tct cag tgg      672
Ala Asp Lys Thr Phe Gln Pro Glu Pro Gln Ile Gly Glu Ser Gln Trp
    210                 215                 220

tac gaa aca gaa att aat cat gca gct ggg aga gtc cta aaa aag act      720
Tyr Glu Thr Glu Ile Asn His Ala Ala Gly Arg Val Leu Lys Lys Thr
225                 230                 235                 240
```

-continued

```
acc cca atg aaa cca tgt tac ggt tca tat gca aaa ccc aca aat gaa      768
Thr Pro Met Lys Pro Cys Tyr Gly Ser Tyr Ala Lys Pro Thr Asn Glu
                245                 250                 255

aat gga ggg caa ggc att ctt gta aag caa caa aat gga aag cta gaa      816
Asn Gly Gly Gln Gly Ile Leu Val Lys Gln Gln Asn Gly Lys Leu Glu
            260                 265                 270

agt caa gtg gaa atg caa ttt ttc tca act act gag gca gcc gca ggc      864
Ser Gln Val Glu Met Gln Phe Phe Ser Thr Thr Glu Ala Ala Ala Gly
        275                 280                 285

aat ggt gat aac ttg act cct aaa gtg gta ttg tac agt gaa gat gta      912
Asn Gly Asp Asn Leu Thr Pro Lys Val Val Leu Tyr Ser Glu Asp Val
    290                 295                 300

gat ata gaa acc cca gac act cat att tct tac atg ccc act att aag      960
Asp Ile Glu Thr Pro Asp Thr His Ile Ser Tyr Met Pro Thr Ile Lys
305                 310                 315                 320

gaa ggt aac tca cga gaa cta atg ggc caa caa tct atg ccc aac agg     1008
Glu Gly Asn Ser Arg Glu Leu Met Gly Gln Gln Ser Met Pro Asn Arg
                325                 330                 335

cct aat tac att gct ttt agg gac aat ttt att ggt cta atg tat tac     1056
Pro Asn Tyr Ile Ala Phe Arg Asp Asn Phe Ile Gly Leu Met Tyr Tyr
            340                 345                 350

aac agc acg ggt aat atg ggt gtt ctg gcg ggc caa gca tcg cag ttg     1104
Asn Ser Thr Gly Asn Met Gly Val Leu Ala Gly Gln Ala Ser Gln Leu
        355                 360                 365

aat gct gtt gta gat ttg caa gac aga aac aca gag ctt tca tac cag     1152
Asn Ala Val Val Asp Leu Gln Asp Arg Asn Thr Glu Leu Ser Tyr Gln
    370                 375                 380

ctt ttg ctt gat tcc att ggt gat aga acc agg tac ttt tct atg tgg     1200
Leu Leu Leu Asp Ser Ile Gly Asp Arg Thr Arg Tyr Phe Ser Met Trp
385                 390                 395                 400

aat cag ctt cca aat tac tgc ttt cca ctg gga ggt gtg att aat aca     1248
Asn Gln Leu Pro Asn Tyr Cys Phe Pro Leu Gly Gly Val Ile Asn Thr
                405                 410                 415

gag act ctt acc aag gta aaa cct aaa aca ggt cag gaa aat gga tgg     1296
Glu Thr Leu Thr Lys Val Lys Pro Lys Thr Gly Gln Glu Asn Gly Trp
            420                 425                 430

gaa aaa gat gct aca gaa ttt tca gat aaa aat gaa ata aga gtt gga     1344
Glu Lys Asp Ala Thr Glu Phe Ser Asp Lys Asn Glu Ile Arg Val Gly
        435                 440                 445

aat aat ttt gcc atg gaa atc aat cta aat gcc aac ctg tgg aga aat     1392
Asn Asn Phe Ala Met Glu Ile Asn Leu Asn Ala Asn Leu Trp Arg Asn
    450                 455                 460

ttc ctg tac tcc aac ata gcg ctg tat ttg ccc gac aag cta aag tac     1440
Phe Leu Tyr Ser Asn Ile Ala Leu Tyr Leu Pro Asp Lys Leu Lys Tyr
465                 470                 475                 480

agt cct tcc aac gta aaa att tct gat aac cca aac acc tac gac tac     1488
Ser Pro Ser Asn Val Lys Ile Ser Asp Asn Pro Asn Thr Tyr Asp Tyr
                485                 490                 495

atg aac aag cga gtg gtg gct ccc ggg cta gtg gac tgc tac att aac     1536
Met Asn Lys Arg Val Val Ala Pro Gly Leu Val Asp Cys Tyr Ile Asn
            500                 505                 510

ctt gga gca cgc tgg tcc ctt gac tat atg gac aac gtc aac cca ttt     1584
Leu Gly Ala Arg Trp Ser Leu Asp Tyr Met Asp Asn Val Asn Pro Phe
        515                 520                 525

aac cac cac cgc aat gct ggc ctg cgc tac cgc tca atg ttg ctg ggc     1632
Asn His His Arg Asn Ala Gly Leu Arg Tyr Arg Ser Met Leu Leu Gly
    530                 535                 540

aat ggt cgc tat gtg ccc ttc cac atc cag gtg cct cag aag ttc ttt     1680
Asn Gly Arg Tyr Val Pro Phe His Ile Gln Val Pro Gln Lys Phe Phe
```

-continued

```
545                 550                 555                 560

gcc att aaa aac ctc ctt ctc ctg ccg ggc tca tac acc tac gag tgg      1728
Ala Ile Lys Asn Leu Leu Leu Leu Pro Gly Ser Tyr Thr Tyr Glu Trp
                565                 570                 575

aac ttc agg aag gat gtt aac atg gtt ctg cag agc tcc cta gga aat      1776
Asn Phe Arg Lys Asp Val Asn Met Val Leu Gln Ser Ser Leu Gly Asn
            580                 585                 590

gac cta agg gtt gac gga gcc agc att aag ttt gat agc att tgc ctt      1824
Asp Leu Arg Val Asp Gly Ala Ser Ile Lys Phe Asp Ser Ile Cys Leu
        595                 600                 605

tac gcc acc ttc ttc ccc atg gcc cac aac acc gcc tcc acg ctt gag      1872
Tyr Ala Thr Phe Phe Pro Met Ala His Asn Thr Ala Ser Thr Leu Glu
    610                 615                 620

gcc atg ctt aga aac gac acc aac gac cag tcc ttt aac gac tat ctc      1920
Ala Met Leu Arg Asn Asp Thr Asn Asp Gln Ser Phe Asn Asp Tyr Leu
625                 630                 635                 640

tcc gcc gcc aac atg ctc tac cct ata ccc gcc aac gct acc aac gtg      1968
Ser Ala Ala Asn Met Leu Tyr Pro Ile Pro Ala Asn Ala Thr Asn Val
                645                 650                 655

ccc ata tcc atc ccc tcc cgc aac tgg gcg gct ttc cgc ggc tgg gcc      2016
Pro Ile Ser Ile Pro Ser Arg Asn Trp Ala Ala Phe Arg Gly Trp Ala
            660                 665                 670

ttc acg cgc ctt aag act aag gaa acc cca tca ctg ggc tcg ggc tac      2064
Phe Thr Arg Leu Lys Thr Lys Glu Thr Pro Ser Leu Gly Ser Gly Tyr
        675                 680                 685

gac cct tat tac acc tac tct ggc tct ata ccc tac cta gat gga acc      2112
Asp Pro Tyr Tyr Thr Tyr Ser Gly Ser Ile Pro Tyr Leu Asp Gly Thr
    690                 695                 700

ttt tac ctc aac cac acc ttt aag aag gtg gcc att acc ttt gac tct      2160
Phe Tyr Leu Asn His Thr Phe Lys Lys Val Ala Ile Thr Phe Asp Ser
705                 710                 715                 720

tct gtc agc tgg cct ggc aat gac cgc ctg ctt acc ccc aac gag ttt      2208
Ser Val Ser Trp Pro Gly Asn Asp Arg Leu Leu Thr Pro Asn Glu Phe
                725                 730                 735

gaa att aag cgc tca gtt gac ggg gag ggt tac aac gtt gcc cag tgt      2256
Glu Ile Lys Arg Ser Val Asp Gly Glu Gly Tyr Asn Val Ala Gln Cys
            740                 745                 750

aac atg acc aaa gac tgg ttc ctg gta caa atg cta gct aac tat aac      2304
Asn Met Thr Lys Asp Trp Phe Leu Val Gln Met Leu Ala Asn Tyr Asn
        755                 760                 765

att ggc tac cag ggc ttc tat atc cca gag agc tac aag gac cgc atg      2352
Ile Gly Tyr Gln Gly Phe Tyr Ile Pro Glu Ser Tyr Lys Asp Arg Met
    770                 775                 780

tac tcc ttc ttt aga aac ttc cag ccc atg agc cgt cag gtg gtg gat      2400
Tyr Ser Phe Phe Arg Asn Phe Gln Pro Met Ser Arg Gln Val Val Asp
785                 790                 795                 800

gat act aaa tac aag gac tac caa cag gtg ggc atc cta cac caa cac      2448
Asp Thr Lys Tyr Lys Asp Tyr Gln Gln Val Gly Ile Leu His Gln His
                805                 810                 815

aac aac tct gga ttt gtt ggc tac ctt gcc ccc acc atg cgc gaa gga      2496
Asn Asn Ser Gly Phe Val Gly Tyr Leu Ala Pro Thr Met Arg Glu Gly
            820                 825                 830

cag gcc tac cct gct aac ttc ccc tat ccg ctt ata ggc aag acc gca      2544
Gln Ala Tyr Pro Ala Asn Phe Pro Tyr Pro Leu Ile Gly Lys Thr Ala
        835                 840                 845

gtt gac agc att acc cag aaa aag ttt ctt tgc gat cgc acc ctt tgg      2592
Val Asp Ser Ile Thr Gln Lys Lys Phe Leu Cys Asp Arg Thr Leu Trp
    850                 855                 860

cgc atc cca ttc tcc agt aac ttt atg tcc atg ggc gca ctc aca gac      2640
```

```
Arg Ile Pro Phe Ser Ser Asn Phe Met Ser Met Gly Ala Leu Thr Asp
865                 870                 875                 880

ctg ggc caa aac ctt ctc tac gcc aac tcc gcc cac gcg cta gac atg     2688
Leu Gly Gln Asn Leu Leu Tyr Ala Asn Ser Ala His Ala Leu Asp Met
                885                 890                 895

act ttt gag gtg gat ccc atg gac gag ccc acc ctt ctt tat gtt ttg     2736
Thr Phe Glu Val Asp Pro Met Asp Glu Pro Thr Leu Leu Tyr Val Leu
            900                 905                 910

ttt gaa gtc ttt gac gtg gtc cgt gtg cac cag ccg cac cgc ggc gtc     2784
Phe Glu Val Phe Asp Val Val Arg Val His Gln Pro His Arg Gly Val
        915                 920                 925

atc gaa acc gtg tac ctg cgc acg ccc ttc tcg gcc ggc aac gcc aca     2832
Ile Glu Thr Val Tyr Leu Arg Thr Pro Phe Ser Ala Gly Asn Ala Thr
    930                 935                 940

aca taa                                                             2838
Thr
945


<210> SEQ ID NO 16
<211> LENGTH: 2862
<212> TYPE: DNA
<213> ORGANISM: Artificial Sequence
<220> FEATURE:
<223> OTHER INFORMATION: (NANP)12-HVR1 modified Hexon protein
<220> FEATURE:
<221> NAME/KEY: CDS
<222> LOCATION: (1)..(2859)

<400> SEQUENCE: 16

atg gct acc cct tcg atg atg ccg cag tgg tct tac atg cac atc tcg       48
Met Ala Thr Pro Ser Met Met Pro Gln Trp Ser Tyr Met His Ile Ser
1               5                   10                  15

ggc cag gac gcc tcg gag tac ctg agc ccc ggg ctg gtg cag ttt gcc       96
Gly Gln Asp Ala Ser Glu Tyr Leu Ser Pro Gly Leu Val Gln Phe Ala
            20                  25                  30

cgc gcc acc gag acg tac ttc agc ctg aat aac aag ttt aga aac ccc      144
Arg Ala Thr Glu Thr Tyr Phe Ser Leu Asn Asn Lys Phe Arg Asn Pro
        35                  40                  45

acg gtg gcg cct acg cac gac gtg acc aca gac cgg tcc cag cgt ttg      192
Thr Val Ala Pro Thr His Asp Val Thr Thr Asp Arg Ser Gln Arg Leu
    50                  55                  60

acg ctg cgg ttc atc cct gtg gac cgt gag gat act gcg tac tcg tac      240
Thr Leu Arg Phe Ile Pro Val Asp Arg Glu Asp Thr Ala Tyr Ser Tyr
65                  70                  75                  80

aag gcg cgg ttc acc cta gct gtg ggt gat aac cgt gtg ctg gac atg      288
Lys Ala Arg Phe Thr Leu Ala Val Gly Asp Asn Arg Val Leu Asp Met
                85                  90                  95

gct tcc acg tac ttt gac atc cgc ggc gtg ctg gac agg ggc cct act      336
Ala Ser Thr Tyr Phe Asp Ile Arg Gly Val Leu Asp Arg Gly Pro Thr
            100                 105                 110

ttt aag ccc tac tct ggc act gcc tac aac gcc ctg gct ccc aag ggt      384
Phe Lys Pro Tyr Ser Gly Thr Ala Tyr Asn Ala Leu Ala Pro Lys Gly
        115                 120                 125

gcc cca aat cct tgc gaa tgg gat gaa aat gca aat cca aat gca aat      432
Ala Pro Asn Pro Cys Glu Trp Asp Glu Asn Ala Asn Pro Asn Ala Asn
    130                 135                 140

cca aat gca aat cca aat gca aat cca aat gca aat cca aat gca aat      480
Pro Asn Ala Asn Pro Asn Ala Asn Pro Asn Ala Asn Pro Asn Ala Asn
145                 150                 155                 160

cca aat gca aat cca aat gca aat cca aac gcg aac ccg aat gct aat      528
Pro Asn Ala Asn Pro Asn Ala Asn Pro Asn Ala Asn Pro Asn Ala Asn
                165                 170                 175
```

-continued

```
cct aat gca aat cca aat gca aat cca aaa act cac gta ttt ggg cag      576
Pro Asn Ala Asn Pro Asn Ala Asn Pro Lys Thr His Val Phe Gly Gln
            180                 185                 190

gcg cct tat tct ggt ata aat att aca aag gag ggt att caa ata ggt      624
Ala Pro Tyr Ser Gly Ile Asn Ile Thr Lys Glu Gly Ile Gln Ile Gly
        195                 200                 205

gtc gaa ggt caa aca cct aaa tat gcc gat aaa aca ttt caa cct gaa      672
Val Glu Gly Gln Thr Pro Lys Tyr Ala Asp Lys Thr Phe Gln Pro Glu
    210                 215                 220

cct caa ata gga gaa tct cag tgg tac gaa aca gaa att aat cat gca      720
Pro Gln Ile Gly Glu Ser Gln Trp Tyr Glu Thr Glu Ile Asn His Ala
225                 230                 235                 240

gct ggg aga gtc cta aaa aag act acc cca atg aaa cca tgt tac ggt      768
Ala Gly Arg Val Leu Lys Lys Thr Thr Pro Met Lys Pro Cys Tyr Gly
                245                 250                 255

tca tat gca aaa ccc aca aat gaa aat gga ggg caa ggc att ctt gta      816
Ser Tyr Ala Lys Pro Thr Asn Glu Asn Gly Gly Gln Gly Ile Leu Val
            260                 265                 270

aag caa caa aat gga aag cta gaa agt caa gtg gaa atg caa ttt ttc      864
Lys Gln Gln Asn Gly Lys Leu Glu Ser Gln Val Glu Met Gln Phe Phe
        275                 280                 285

tca act act gag gca gcc gca ggc aat ggt gat aac ttg act cct aaa      912
Ser Thr Thr Glu Ala Ala Ala Gly Asn Gly Asp Asn Leu Thr Pro Lys
    290                 295                 300

gtg gta ttg tac agt gaa gat gta gat ata gaa acc cca gac act cat      960
Val Val Leu Tyr Ser Glu Asp Val Asp Ile Glu Thr Pro Asp Thr His
305                 310                 315                 320

att tct tac atg ccc act att aag gaa ggt aac tca cga gaa cta atg     1008
Ile Ser Tyr Met Pro Thr Ile Lys Glu Gly Asn Ser Arg Glu Leu Met
                325                 330                 335

ggc caa caa tct atg ccc aac agg cct aat tac att gct ttt agg gac     1056
Gly Gln Gln Ser Met Pro Asn Arg Pro Asn Tyr Ile Ala Phe Arg Asp
            340                 345                 350

aat ttt att ggt cta atg tat tac aac agc acg ggt aat atg ggt gtt     1104
Asn Phe Ile Gly Leu Met Tyr Tyr Asn Ser Thr Gly Asn Met Gly Val
        355                 360                 365

ctg gcg ggc caa gca tcg cag ttg aat gct gtt gta gat ttg caa gac     1152
Leu Ala Gly Gln Ala Ser Gln Leu Asn Ala Val Val Asp Leu Gln Asp
    370                 375                 380

aga aac aca gag ctt tca tac cag ctt ttg ctt gat tcc att ggt gat     1200
Arg Asn Thr Glu Leu Ser Tyr Gln Leu Leu Leu Asp Ser Ile Gly Asp
385                 390                 395                 400

aga acc agg tac ttt tct atg tgg aat cag ctt cca aat tac tgc ttt     1248
Arg Thr Arg Tyr Phe Ser Met Trp Asn Gln Leu Pro Asn Tyr Cys Phe
                405                 410                 415

cca ctg gga ggt gtg att aat aca gag act ctt acc aag gta aaa cct     1296
Pro Leu Gly Gly Val Ile Asn Thr Glu Thr Leu Thr Lys Val Lys Pro
            420                 425                 430

aaa aca ggt cag gaa aat gga tgg gaa aaa gat gct aca gaa ttt tca     1344
Lys Thr Gly Gln Glu Asn Gly Trp Glu Lys Asp Ala Thr Glu Phe Ser
        435                 440                 445

gat aaa aat gaa ata aga gtt gga aat aat ttt gcc atg gaa atc aat     1392
Asp Lys Asn Glu Ile Arg Val Gly Asn Asn Phe Ala Met Glu Ile Asn
    450                 455                 460

cta aat gcc aac ctg tgg aga aat ttc ctg tac tcc aac ata gcg ctg     1440
Leu Asn Ala Asn Leu Trp Arg Asn Phe Leu Tyr Ser Asn Ile Ala Leu
465                 470                 475                 480

tat ttg ccc gac aag cta aag tac agt cct tcc aac gta aaa att tct     1488
Tyr Leu Pro Asp Lys Leu Lys Tyr Ser Pro Ser Asn Val Lys Ile Ser
```

-continued

```
                485                 490                 495

gat aac cca aac acc tac gac tac atg aac aag cga gtg gtg gct ccc      1536
Asp Asn Pro Asn Thr Tyr Asp Tyr Met Asn Lys Arg Val Val Ala Pro
            500                 505                 510

ggg cta gtg gac tgc tac att aac ctt gga gca cgc tgg tcc ctt gac      1584
Gly Leu Val Asp Cys Tyr Ile Asn Leu Gly Ala Arg Trp Ser Leu Asp
        515                 520                 525

tat atg gac aac gtc aac cca ttt aac cac cac cgc aat gct ggc ctg      1632
Tyr Met Asp Asn Val Asn Pro Phe Asn His His Arg Asn Ala Gly Leu
    530                 535                 540

cgc tac cgc tca atg ttg ctg ggc aat ggt cgc tat gtg ccc ttc cac      1680
Arg Tyr Arg Ser Met Leu Leu Gly Asn Gly Arg Tyr Val Pro Phe His
545                 550                 555                 560

atc cag gtg cct cag aag ttc ttt gcc att aaa aac ctc ctt ctc ctg      1728
Ile Gln Val Pro Gln Lys Phe Phe Ala Ile Lys Asn Leu Leu Leu Leu
                565                 570                 575

ccg ggc tca tac acc tac gag tgg aac ttc agg aag gat gtt aac atg      1776
Pro Gly Ser Tyr Thr Tyr Glu Trp Asn Phe Arg Lys Asp Val Asn Met
            580                 585                 590

gtt ctg cag agc tcc cta gga aat gac cta agg gtt gac gga gcc agc      1824
Val Leu Gln Ser Ser Leu Gly Asn Asp Leu Arg Val Asp Gly Ala Ser
        595                 600                 605

att aag ttt gat agc att tgc ctt tac gcc acc ttc ttc ccc atg gcc      1872
Ile Lys Phe Asp Ser Ile Cys Leu Tyr Ala Thr Phe Phe Pro Met Ala
    610                 615                 620

cac aac acc gcc tcc acg ctt gag gcc atg ctt aga aac gac acc aac      1920
His Asn Thr Ala Ser Thr Leu Glu Ala Met Leu Arg Asn Asp Thr Asn
625                 630                 635                 640

gac cag tcc ttt aac gac tat ctc tcc gcc gcc aac atg ctc tac cct      1968
Asp Gln Ser Phe Asn Asp Tyr Leu Ser Ala Ala Asn Met Leu Tyr Pro
                645                 650                 655

ata ccc gcc aac gct acc aac gtg ccc ata tcc atc ccc tcc cgc aac      2016
Ile Pro Ala Asn Ala Thr Asn Val Pro Ile Ser Ile Pro Ser Arg Asn
            660                 665                 670

tgg gcg gct ttc cgc ggc tgg gcc ttc acg cgc ctt aag act aag gaa      2064
Trp Ala Ala Phe Arg Gly Trp Ala Phe Thr Arg Leu Lys Thr Lys Glu
        675                 680                 685

acc cca tca ctg ggc tcg ggc tac gac cct tat tac acc tac tct ggc      2112
Thr Pro Ser Leu Gly Ser Gly Tyr Asp Pro Tyr Tyr Thr Tyr Ser Gly
    690                 695                 700

tct ata ccc tac cta gat gga acc ttt tac ctc aac cac acc ttt aag      2160
Ser Ile Pro Tyr Leu Asp Gly Thr Phe Tyr Leu Asn His Thr Phe Lys
705                 710                 715                 720

aag gtg gcc att acc ttt gac tct tct gtc agc tgg cct ggc aat gac      2208
Lys Val Ala Ile Thr Phe Asp Ser Ser Val Ser Trp Pro Gly Asn Asp
                725                 730                 735

cgc ctg ctt acc ccc aac gag ttt gaa att aag cgc tca gtt gac ggg      2256
Arg Leu Leu Thr Pro Asn Glu Phe Glu Ile Lys Arg Ser Val Asp Gly
            740                 745                 750

gag ggt tac aac gtt gcc cag tgt aac atg acc aaa gac tgg ttc ctg      2304
Glu Gly Tyr Asn Val Ala Gln Cys Asn Met Thr Lys Asp Trp Phe Leu
        755                 760                 765

gta caa atg cta gct aac tat aac att ggc tac cag ggc ttc tat atc      2352
Val Gln Met Leu Ala Asn Tyr Asn Ile Gly Tyr Gln Gly Phe Tyr Ile
    770                 775                 780

cca gag agc tac aag gac cgc atg tac tcc ttc ttt aga aac ttc cag      2400
Pro Glu Ser Tyr Lys Asp Arg Met Tyr Ser Phe Phe Arg Asn Phe Gln
785                 790                 795                 800

ccc atg agc cgt cag gtg gtg gat gat act aaa tac aag gac tac caa      2448
```

-continued

```
Pro Met Ser Arg Gln Val Val Asp Asp Thr Lys Tyr Lys Asp Tyr Gln
            805                 810                 815

cag gtg ggc atc cta cac caa cac aac aac tct gga ttt gtt ggc tac     2496
Gln Val Gly Ile Leu His Gln His Asn Asn Ser Gly Phe Val Gly Tyr
            820                 825                 830

ctt gcc ccc acc atg cgc gaa gga cag gcc tac cct gct aac ttc ccc     2544
Leu Ala Pro Thr Met Arg Glu Gly Gln Ala Tyr Pro Ala Asn Phe Pro
        835                 840                 845

tat ccg ctt ata ggc aag acc gca gtt gac agc att acc cag aaa aag     2592
Tyr Pro Leu Ile Gly Lys Thr Ala Val Asp Ser Ile Thr Gln Lys Lys
    850                 855                 860

ttt ctt tgc gat cgc acc ctt tgg cgc atc cca ttc tcc agt aac ttt     2640
Phe Leu Cys Asp Arg Thr Leu Trp Arg Ile Pro Phe Ser Ser Asn Phe
865                 870                 875                 880

atg tcc atg ggc gca ctc aca gac ctg ggc caa aac ctt ctc tac gcc     2688
Met Ser Met Gly Ala Leu Thr Asp Leu Gly Gln Asn Leu Leu Tyr Ala
            885                 890                 895

aac tcc gcc cac gcg cta gac atg act ttt gag gtg gat ccc atg gac     2736
Asn Ser Ala His Ala Leu Asp Met Thr Phe Glu Val Asp Pro Met Asp
            900                 905                 910

gag ccc acc ctt ctt tat gtt ttg ttt gaa gtc ttt gac gtg gtc cgt     2784
Glu Pro Thr Leu Leu Tyr Val Leu Phe Glu Val Phe Asp Val Val Arg
        915                 920                 925

gtg cac cag ccg cac cgc ggc gtc atc gaa acc gtg tac ctg cgc acg     2832
Val His Gln Pro His Arg Gly Val Ile Glu Thr Val Tyr Leu Arg Thr
    930                 935                 940

ccc ttc tcg gcc ggc aac gcc aca aca taa                             2862
Pro Phe Ser Ala Gly Asn Ala Thr Thr
945                 950


<210> SEQ ID NO 17
<211> LENGTH: 2886
<212> TYPE: DNA
<213> ORGANISM: Artificial Sequence
<220> FEATURE:
<223> OTHER INFORMATION: (NANP)14-HVR1 modified Hexon protein
<220> FEATURE:
<221> NAME/KEY: CDS
<222> LOCATION: (1)..(2883)

<400> SEQUENCE: 17

atg gct acc cct tcg atg atg ccg cag tgg tct tac atg cac atc tcg       48
Met Ala Thr Pro Ser Met Met Pro Gln Trp Ser Tyr Met His Ile Ser
1               5                   10                  15

ggc cag gac gcc tcg gag tac ctg agc ccc ggg ctg gtg cag ttt gcc       96
Gly Gln Asp Ala Ser Glu Tyr Leu Ser Pro Gly Leu Val Gln Phe Ala
            20                  25                  30

cgc gcc acc gag acg tac ttc agc ctg aat aac aag ttt aga aac ccc      144
Arg Ala Thr Glu Thr Tyr Phe Ser Leu Asn Asn Lys Phe Arg Asn Pro
        35                  40                  45

acg gtg gcg cct acg cac gac gtg acc aca gac cgg tcc cag cgt ttg      192
Thr Val Ala Pro Thr His Asp Val Thr Thr Asp Arg Ser Gln Arg Leu
    50                  55                  60

acg ctg cgg ttc atc cct gtg gac cgt gag gat act gcg tac tcg tac      240
Thr Leu Arg Phe Ile Pro Val Asp Arg Glu Asp Thr Ala Tyr Ser Tyr
65                  70                  75                  80

aag gcg cgg ttc acc cta gct gtg ggt gat aac cgt gtg ctg gac atg      288
Lys Ala Arg Phe Thr Leu Ala Val Gly Asp Asn Arg Val Leu Asp Met
            85                  90                  95

gct tcc acg tac ttt gac atc cgc ggc gtg ctg gac agg ggc cct act      336
Ala Ser Thr Tyr Phe Asp Ile Arg Gly Val Leu Asp Arg Gly Pro Thr
            100                 105                 110
```

```
ttt aag ccc tac tct ggc act gcc tac aac gcc ctg gct ccc aag ggt      384
Phe Lys Pro Tyr Ser Gly Thr Ala Tyr Asn Ala Leu Ala Pro Lys Gly
        115                 120                 125

gcc cca aat cct tgc gaa tgg gat gaa aat gca aat cca aat gca aat      432
Ala Pro Asn Pro Cys Glu Trp Asp Glu Asn Ala Asn Pro Asn Ala Asn
    130                 135                 140

cca aat gca aat cca aat gca aat cca aat gca aat cca aat gca aat      480
Pro Asn Ala Asn Pro Asn Ala Asn Pro Asn Ala Asn Pro Asn Ala Asn
145                 150                 155                 160

cca aat gca aat cca aat gca aat cca aac gcg aac ccg aat gct aat      528
Pro Asn Ala Asn Pro Asn Ala Asn Pro Asn Ala Asn Pro Asn Ala Asn
                165                 170                 175

cct aat gca aat cca aat gca aat cca aat gca aat cca aat gca aat      576
Pro Asn Ala Asn Pro Asn Ala Asn Pro Asn Ala Asn Pro Asn Ala Asn
            180                 185                 190

cca aaa act cac gta ttt ggg cag gcg cct tat tct ggt ata aat att      624
Pro Lys Thr His Val Phe Gly Gln Ala Pro Tyr Ser Gly Ile Asn Ile
        195                 200                 205

aca aag gag ggt att caa ata ggt gtc gaa ggt caa aca cct aaa tat      672
Thr Lys Glu Gly Ile Gln Ile Gly Val Glu Gly Gln Thr Pro Lys Tyr
    210                 215                 220

gcc gat aaa aca ttt caa cct gaa cct caa ata gga gaa tct cag tgg      720
Ala Asp Lys Thr Phe Gln Pro Glu Pro Gln Ile Gly Glu Ser Gln Trp
225                 230                 235                 240

tac gaa aca gaa att aat cat gca gct ggg aga gtc cta aaa aag act      768
Tyr Glu Thr Glu Ile Asn His Ala Ala Gly Arg Val Leu Lys Lys Thr
                245                 250                 255

acc cca atg aaa cca tgt tac ggt tca tat gca aaa ccc aca aat gaa      816
Thr Pro Met Lys Pro Cys Tyr Gly Ser Tyr Ala Lys Pro Thr Asn Glu
            260                 265                 270

aat gga ggg caa ggc att ctt gta aag caa caa aat gga aag cta gaa      864
Asn Gly Gly Gln Gly Ile Leu Val Lys Gln Gln Asn Gly Lys Leu Glu
        275                 280                 285

agt caa gtg gaa atg caa ttt ttc tca act act gag gca gcc gca ggc      912
Ser Gln Val Glu Met Gln Phe Phe Ser Thr Thr Glu Ala Ala Ala Gly
    290                 295                 300

aat ggt gat aac ttg act cct aaa gtg gta ttg tac agt gaa gat gta      960
Asn Gly Asp Asn Leu Thr Pro Lys Val Val Leu Tyr Ser Glu Asp Val
305                 310                 315                 320

gat ata gaa acc cca gac act cat att tct tac atg ccc act att aag     1008
Asp Ile Glu Thr Pro Asp Thr His Ile Ser Tyr Met Pro Thr Ile Lys
                325                 330                 335

gaa ggt aac tca cga gaa cta atg ggc caa caa tct atg ccc aac agg     1056
Glu Gly Asn Ser Arg Glu Leu Met Gly Gln Gln Ser Met Pro Asn Arg
            340                 345                 350

cct aat tac att gct ttt agg gac aat ttt att ggt cta atg tat tac     1104
Pro Asn Tyr Ile Ala Phe Arg Asp Asn Phe Ile Gly Leu Met Tyr Tyr
        355                 360                 365

aac agc acg ggt aat atg ggt gtt ctg gcg ggc caa gca tcg cag ttg     1152
Asn Ser Thr Gly Asn Met Gly Val Leu Ala Gly Gln Ala Ser Gln Leu
    370                 375                 380

aat gct gtt gta gat ttg caa gac aga aac aca gag ctt tca tac cag     1200
Asn Ala Val Val Asp Leu Gln Asp Arg Asn Thr Glu Leu Ser Tyr Gln
385                 390                 395                 400

ctt ttg ctt gat tcc att ggt gat aga acc agg tac ttt tct atg tgg     1248
Leu Leu Leu Asp Ser Ile Gly Asp Arg Thr Arg Tyr Phe Ser Met Trp
                405                 410                 415

aat cag ctt cca aat tac tgc ttt cca ctg gga ggt gtg att aat aca     1296
Asn Gln Leu Pro Asn Tyr Cys Phe Pro Leu Gly Gly Val Ile Asn Thr
```

-continued

```
            420                 425                 430

gag act ctt acc aag gta aaa cct aaa aca ggt cag gaa aat gga tgg      1344
Glu Thr Leu Thr Lys Val Lys Pro Lys Thr Gly Gln Glu Asn Gly Trp
        435                 440                 445

gaa aaa gat gct aca gaa ttt tca gat aaa aat gaa ata aga gtt gga      1392
Glu Lys Asp Ala Thr Glu Phe Ser Asp Lys Asn Glu Ile Arg Val Gly
    450                 455                 460

aat aat ttt gcc atg gaa atc aat cta aat gcc aac ctg tgg aga aat      1440
Asn Asn Phe Ala Met Glu Ile Asn Leu Asn Ala Asn Leu Trp Arg Asn
465                 470                 475                 480

ttc ctg tac tcc aac ata gcg ctg tat ttg ccc gac aag cta aag tac      1488
Phe Leu Tyr Ser Asn Ile Ala Leu Tyr Leu Pro Asp Lys Leu Lys Tyr
                485                 490                 495

agt cct tcc aac gta aaa att tct gat aac cca aac acc tac gac tac      1536
Ser Pro Ser Asn Val Lys Ile Ser Asp Asn Pro Asn Thr Tyr Asp Tyr
            500                 505                 510

atg aac aag cga gtg gtg gct ccc ggg cta gtg gac tgc tac att aac      1584
Met Asn Lys Arg Val Val Ala Pro Gly Leu Val Asp Cys Tyr Ile Asn
        515                 520                 525

ctt gga gca cgc tgg tcc ctt gac tat atg gac aac gtc aac cca ttt      1632
Leu Gly Ala Arg Trp Ser Leu Asp Tyr Met Asp Asn Val Asn Pro Phe
    530                 535                 540

aac cac cac cgc aat gct ggc ctg cgc tac cgc tca atg ttg ctg ggc      1680
Asn His His Arg Asn Ala Gly Leu Arg Tyr Arg Ser Met Leu Leu Gly
545                 550                 555                 560

aat ggt cgc tat gtg ccc ttc cac atc cag gtg cct cag aag ttc ttt      1728
Asn Gly Arg Tyr Val Pro Phe His Ile Gln Val Pro Gln Lys Phe Phe
                565                 570                 575

gcc att aaa aac ctc ctt ctc ctg ccg ggc tca tac acc tac gag tgg      1776
Ala Ile Lys Asn Leu Leu Leu Leu Pro Gly Ser Tyr Thr Tyr Glu Trp
            580                 585                 590

aac ttc agg aag gat gtt aac atg gtt ctg cag agc tcc cta gga aat      1824
Asn Phe Arg Lys Asp Val Asn Met Val Leu Gln Ser Ser Leu Gly Asn
        595                 600                 605

gac cta agg gtt gac gga gcc agc att aag ttt gat agc att tgc ctt      1872
Asp Leu Arg Val Asp Gly Ala Ser Ile Lys Phe Asp Ser Ile Cys Leu
    610                 615                 620

tac gcc acc ttc ttc ccc atg gcc cac aac acc gcc tcc acg ctt gag      1920
Tyr Ala Thr Phe Phe Pro Met Ala His Asn Thr Ala Ser Thr Leu Glu
625                 630                 635                 640

gcc atg ctt aga aac gac acc aac gac cag tcc ttt aac gac tat ctc      1968
Ala Met Leu Arg Asn Asp Thr Asn Asp Gln Ser Phe Asn Asp Tyr Leu
                645                 650                 655

tcc gcc gcc aac atg ctc tac cct ata ccc gcc aac gct acc aac gtg      2016
Ser Ala Ala Asn Met Leu Tyr Pro Ile Pro Ala Asn Ala Thr Asn Val
            660                 665                 670

ccc ata tcc atc ccc tcc cgc aac tgg gcg gct ttc cgc ggc tgg gcc      2064
Pro Ile Ser Ile Pro Ser Arg Asn Trp Ala Ala Phe Arg Gly Trp Ala
        675                 680                 685

ttc acg cgc ctt aag act aag gaa acc cca tca ctg ggc tcg ggc tac      2112
Phe Thr Arg Leu Lys Thr Lys Glu Thr Pro Ser Leu Gly Ser Gly Tyr
    690                 695                 700

gac cct tat tac acc tac tct ggc tct ata ccc tac cta gat gga acc      2160
Asp Pro Tyr Tyr Thr Tyr Ser Gly Ser Ile Pro Tyr Leu Asp Gly Thr
705                 710                 715                 720

ttt tac ctc aac cac acc ttt aag aag gtg gcc att acc ttt gac tct      2208
Phe Tyr Leu Asn His Thr Phe Lys Lys Val Ala Ile Thr Phe Asp Ser
                725                 730                 735

tct gtc agc tgg cct ggc aat gac cgc ctg ctt acc ccc aac gag ttt      2256
```

-continued

```
Ser Val Ser Trp Pro Gly Asn Asp Arg Leu Leu Thr Pro Asn Glu Phe
            740                 745                 750

gaa att aag cgc tca gtt gac ggg gag ggt tac aac gtt gcc cag tgt     2304
Glu Ile Lys Arg Ser Val Asp Gly Glu Gly Tyr Asn Val Ala Gln Cys
        755                 760                 765

aac atg acc aaa gac tgg ttc ctg gta caa atg cta gct aac tat aac     2352
Asn Met Thr Lys Asp Trp Phe Leu Val Gln Met Leu Ala Asn Tyr Asn
    770                 775                 780

att ggc tac cag ggc ttc tat atc cca gag agc tac aag gac cgc atg     2400
Ile Gly Tyr Gln Gly Phe Tyr Ile Pro Glu Ser Tyr Lys Asp Arg Met
785                 790                 795                 800

tac tcc ttc ttt aga aac ttc cag ccc atg agc cgt cag gtg gtg gat     2448
Tyr Ser Phe Phe Arg Asn Phe Gln Pro Met Ser Arg Gln Val Val Asp
                805                 810                 815

gat act aaa tac aag gac tac caa cag gtg ggc atc cta cac caa cac     2496
Asp Thr Lys Tyr Lys Asp Tyr Gln Gln Val Gly Ile Leu His Gln His
            820                 825                 830

aac aac tct gga ttt gtt ggc tac ctt gcc ccc acc atg cgc gaa gga     2544
Asn Asn Ser Gly Phe Val Gly Tyr Leu Ala Pro Thr Met Arg Glu Gly
        835                 840                 845

cag gcc tac cct gct aac ttc ccc tat ccg ctt ata ggc aag acc gca     2592
Gln Ala Tyr Pro Ala Asn Phe Pro Tyr Pro Leu Ile Gly Lys Thr Ala
    850                 855                 860

gtt gac agc att acc cag aaa aag ttt ctt tgc gat cgc acc ctt tgg     2640
Val Asp Ser Ile Thr Gln Lys Lys Phe Leu Cys Asp Arg Thr Leu Trp
865                 870                 875                 880

cgc atc cca ttc tcc agt aac ttt atg tcc atg ggc gca ctc aca gac     2688
Arg Ile Pro Phe Ser Ser Asn Phe Met Ser Met Gly Ala Leu Thr Asp
                885                 890                 895

ctg ggc caa aac ctt ctc tac gcc aac tcc gcc cac gcg cta gac atg     2736
Leu Gly Gln Asn Leu Leu Tyr Ala Asn Ser Ala His Ala Leu Asp Met
            900                 905                 910

act ttt gag gtg gat ccc atg gac gag ccc acc ctt ctt tat gtt ttg     2784
Thr Phe Glu Val Asp Pro Met Asp Glu Pro Thr Leu Leu Tyr Val Leu
        915                 920                 925

ttt gaa gtc ttt gac gtg gtc cgt gtg cac cag ccg cac cgc ggc gtc     2832
Phe Glu Val Phe Asp Val Val Arg Val His Gln Pro His Arg Gly Val
    930                 935                 940

atc gaa acc gtg tac ctg cgc acg ccc ttc tcg gcc ggc aac gcc aca     2880
Ile Glu Thr Val Tyr Leu Arg Thr Pro Phe Ser Ala Gly Asn Ala Thr
945                 950                 955                 960

aca taa                                                             2886
Thr


<210> SEQ ID NO 18
<211> LENGTH: 2910
<212> TYPE: DNA
<213> ORGANISM: Artificial Sequence
<220> FEATURE:
<223> OTHER INFORMATION: (NANP)16-HVR1 modified Hexon protein
<220> FEATURE:
<221> NAME/KEY: CDS
<222> LOCATION: (1)..(2907)

<400> SEQUENCE: 18

atg gct acc cct tcg atg atg ccg cag tgg tct tac atg cac atc tcg       48
Met Ala Thr Pro Ser Met Met Pro Gln Trp Ser Tyr Met His Ile Ser
1               5                   10                  15

ggc cag gac gcc tcg gag tac ctg agc ccc ggg ctg gtg cag ttt gcc       96
Gly Gln Asp Ala Ser Glu Tyr Leu Ser Pro Gly Leu Val Gln Phe Ala
            20                  25                  30
```

-continued

```
cgc gcc acc gag acg tac ttc agc ctg aat aac aag ttt aga aac ccc      144
Arg Ala Thr Glu Thr Tyr Phe Ser Leu Asn Asn Lys Phe Arg Asn Pro
        35                  40                  45

acg gtg gcg cct acg cac gac gtg acc aca gac cgg tcc cag cgt ttg      192
Thr Val Ala Pro Thr His Asp Val Thr Thr Asp Arg Ser Gln Arg Leu
    50                  55                  60

acg ctg cgg ttc atc cct gtg gac cgt gag gat act gcg tac tcg tac      240
Thr Leu Arg Phe Ile Pro Val Asp Arg Glu Asp Thr Ala Tyr Ser Tyr
65                  70                  75                  80

aag gcg cgg ttc acc cta gct gtg ggt gat aac cgt gtg ctg gac atg      288
Lys Ala Arg Phe Thr Leu Ala Val Gly Asp Asn Arg Val Leu Asp Met
                85                  90                  95

gct tcc acg tac ttt gac atc cgc ggc gtg ctg gac agg ggc cct act      336
Ala Ser Thr Tyr Phe Asp Ile Arg Gly Val Leu Asp Arg Gly Pro Thr
            100                 105                 110

ttt aag ccc tac tct ggc act gcc tac aac gcc ctg gct ccc aag ggt      384
Phe Lys Pro Tyr Ser Gly Thr Ala Tyr Asn Ala Leu Ala Pro Lys Gly
        115                 120                 125

gcc cca aat cct tgc gaa tgg gat gaa aat gca aat cca aat gca aat      432
Ala Pro Asn Pro Cys Glu Trp Asp Glu Asn Ala Asn Pro Asn Ala Asn
    130                 135                 140

cca aat gca aat cca aat gca aat cca aat gca aat cca aat gca aat      480
Pro Asn Ala Asn Pro Asn Ala Asn Pro Asn Ala Asn Pro Asn Ala Asn
145                 150                 155                 160

cca aat gca aat cca aat gca aat cca aac gcg aac ccg aat gct aat      528
Pro Asn Ala Asn Pro Asn Ala Asn Pro Asn Ala Asn Pro Asn Ala Asn
                165                 170                 175

cct aat gca aat cca aat gca aat cca aat gca aat cca aat gca aat      576
Pro Asn Ala Asn Pro Asn Ala Asn Pro Asn Ala Asn Pro Asn Ala Asn
            180                 185                 190

cca aat gca aat cca aat gca aat cca aaa act cac gta ttt ggg cag      624
Pro Asn Ala Asn Pro Asn Ala Asn Pro Lys Thr His Val Phe Gly Gln
        195                 200                 205

gcg cct tat tct ggt ata aat att aca aag gag ggt att caa ata ggt      672
Ala Pro Tyr Ser Gly Ile Asn Ile Thr Lys Glu Gly Ile Gln Ile Gly
    210                 215                 220

gtc gaa ggt caa aca cct aaa tat gcc gat aaa aca ttt caa cct gaa      720
Val Glu Gly Gln Thr Pro Lys Tyr Ala Asp Lys Thr Phe Gln Pro Glu
225                 230                 235                 240

cct caa ata gga gaa tct cag tgg tac gaa aca gaa att aat cat gca      768
Pro Gln Ile Gly Glu Ser Gln Trp Tyr Glu Thr Glu Ile Asn His Ala
                245                 250                 255

gct ggg aga gtc cta aaa aag act acc cca atg aaa cca tgt tac ggt      816
Ala Gly Arg Val Leu Lys Lys Thr Thr Pro Met Lys Pro Cys Tyr Gly
            260                 265                 270

tca tat gca aaa ccc aca aat gaa aat gga ggg caa ggc att ctt gta      864
Ser Tyr Ala Lys Pro Thr Asn Glu Asn Gly Gly Gln Gly Ile Leu Val
        275                 280                 285

aag caa caa aat gga aag cta gaa agt caa gtg gaa atg caa ttt ttc      912
Lys Gln Gln Asn Gly Lys Leu Glu Ser Gln Val Glu Met Gln Phe Phe
    290                 295                 300

tca act act gag gca gcc gca ggc aat ggt gat aac ttg act cct aaa      960
Ser Thr Thr Glu Ala Ala Ala Gly Asn Gly Asp Asn Leu Thr Pro Lys
305                 310                 315                 320

gtg gta ttg tac agt gaa gat gta gat ata gaa acc cca gac act cat     1008
Val Val Leu Tyr Ser Glu Asp Val Asp Ile Glu Thr Pro Asp Thr His
                325                 330                 335

att tct tac atg ccc act att aag gaa ggt aac tca cga gaa cta atg     1056
Ile Ser Tyr Met Pro Thr Ile Lys Glu Gly Asn Ser Arg Glu Leu Met
            340                 345                 350
```

-continued

```
ggc caa caa tct atg ccc aac agg cct aat tac att gct ttt agg gac     1104
Gly Gln Gln Ser Met Pro Asn Arg Pro Asn Tyr Ile Ala Phe Arg Asp
        355                 360                 365

aat ttt att ggt cta atg tat tac aac agc acg ggt aat atg ggt gtt     1152
Asn Phe Ile Gly Leu Met Tyr Tyr Asn Ser Thr Gly Asn Met Gly Val
    370                 375                 380

ctg gcg ggc caa gca tcg cag ttg aat gct gtt gta gat ttg caa gac     1200
Leu Ala Gly Gln Ala Ser Gln Leu Asn Ala Val Val Asp Leu Gln Asp
385                 390                 395                 400

aga aac aca gag ctt tca tac cag ctt ttg ctt gat tcc att ggt gat     1248
Arg Asn Thr Glu Leu Ser Tyr Gln Leu Leu Leu Asp Ser Ile Gly Asp
                405                 410                 415

aga acc agg tac ttt tct atg tgg aat cag ctt cca aat tac tgc ttt     1296
Arg Thr Arg Tyr Phe Ser Met Trp Asn Gln Leu Pro Asn Tyr Cys Phe
            420                 425                 430

cca ctg gga ggt gtg att aat aca gag act ctt acc aag gta aaa cct     1344
Pro Leu Gly Gly Val Ile Asn Thr Glu Thr Leu Thr Lys Val Lys Pro
        435                 440                 445

aaa aca ggt cag gaa aat gga tgg gaa aaa gat gct aca gaa ttt tca     1392
Lys Thr Gly Gln Glu Asn Gly Trp Glu Lys Asp Ala Thr Glu Phe Ser
    450                 455                 460

gat aaa aat gaa ata aga gtt gga aat aat ttt gcc atg gaa atc aat     1440
Asp Lys Asn Glu Ile Arg Val Gly Asn Asn Phe Ala Met Glu Ile Asn
465                 470                 475                 480

cta aat gcc aac ctg tgg aga aat ttc ctg tac tcc aac ata gcg ctg     1488
Leu Asn Ala Asn Leu Trp Arg Asn Phe Leu Tyr Ser Asn Ile Ala Leu
                485                 490                 495

tat ttg ccc gac aag cta aag tac agt cct tcc aac gta aaa att tct     1536
Tyr Leu Pro Asp Lys Leu Lys Tyr Ser Pro Ser Asn Val Lys Ile Ser
            500                 505                 510

gat aac cca aac acc tac gac tac atg aac aag cga gtg gtg gct ccc     1584
Asp Asn Pro Asn Thr Tyr Asp Tyr Met Asn Lys Arg Val Val Ala Pro
        515                 520                 525

ggg cta gtg gac tgc tac att aac ctt gga gca cgc tgg tcc ctt gac     1632
Gly Leu Val Asp Cys Tyr Ile Asn Leu Gly Ala Arg Trp Ser Leu Asp
    530                 535                 540

tat atg gac aac gtc aac cca ttt aac cac cac cgc aat gct ggc ctg     1680
Tyr Met Asp Asn Val Asn Pro Phe Asn His His Arg Asn Ala Gly Leu
545                 550                 555                 560

cgc tac cgc tca atg ttg ctg ggc aat ggt cgc tat gtg ccc ttc cac     1728
Arg Tyr Arg Ser Met Leu Leu Gly Asn Gly Arg Tyr Val Pro Phe His
                565                 570                 575

atc cag gtg cct cag aag ttc ttt gcc att aaa aac ctc ctt ctc ctg     1776
Ile Gln Val Pro Gln Lys Phe Phe Ala Ile Lys Asn Leu Leu Leu Leu
            580                 585                 590

ccg ggc tca tac acc tac gag tgg aac ttc agg aag gat gtt aac atg     1824
Pro Gly Ser Tyr Thr Tyr Glu Trp Asn Phe Arg Lys Asp Val Asn Met
        595                 600                 605

gtt ctg cag agc tcc cta gga aat gac cta agg gtt gac gga gcc agc     1872
Val Leu Gln Ser Ser Leu Gly Asn Asp Leu Arg Val Asp Gly Ala Ser
    610                 615                 620

att aag ttt gat agc att tgc ctt tac gcc acc ttc ttc ccc atg gcc     1920
Ile Lys Phe Asp Ser Ile Cys Leu Tyr Ala Thr Phe Phe Pro Met Ala
625                 630                 635                 640

cac aac acc gcc tcc acg ctt gag gcc atg ctt aga aac gac acc aac     1968
His Asn Thr Ala Ser Thr Leu Glu Ala Met Leu Arg Asn Asp Thr Asn
                645                 650                 655

gac cag tcc ttt aac gac tat ctc tcc gcc gcc aac atg ctc tac cct     2016
Asp Gln Ser Phe Asn Asp Tyr Leu Ser Ala Ala Asn Met Leu Tyr Pro
```

-continued

```
            660                 665                 670

ata ccc gcc aac gct acc aac gtg ccc ata tcc atc ccc tcc cgc aac      2064
Ile Pro Ala Asn Ala Thr Asn Val Pro Ile Ser Ile Pro Ser Arg Asn
        675                 680                 685

tgg gcg gct ttc cgc ggc tgg gcc ttc acg cgc ctt aag act aag gaa      2112
Trp Ala Ala Phe Arg Gly Trp Ala Phe Thr Arg Leu Lys Thr Lys Glu
    690                 695                 700

acc cca tca ctg ggc tcg ggc tac gac cct tat tac acc tac tct ggc      2160
Thr Pro Ser Leu Gly Ser Gly Tyr Asp Pro Tyr Tyr Thr Tyr Ser Gly
705                 710                 715                 720

tct ata ccc tac cta gat gga acc ttt tac ctc aac cac acc ttt aag      2208
Ser Ile Pro Tyr Leu Asp Gly Thr Phe Tyr Leu Asn His Thr Phe Lys
                725                 730                 735

aag gtg gcc att acc ttt gac tct tct gtc agc tgg cct ggc aat gac      2256
Lys Val Ala Ile Thr Phe Asp Ser Ser Val Ser Trp Pro Gly Asn Asp
            740                 745                 750

cgc ctg ctt acc ccc aac gag ttt gaa att aag cgc tca gtt gac ggg      2304
Arg Leu Leu Thr Pro Asn Glu Phe Glu Ile Lys Arg Ser Val Asp Gly
        755                 760                 765

gag ggt tac aac gtt gcc cag tgt aac atg acc aaa gac tgg ttc ctg      2352
Glu Gly Tyr Asn Val Ala Gln Cys Asn Met Thr Lys Asp Trp Phe Leu
    770                 775                 780

gta caa atg cta gct aac tat aac att ggc tac cag ggc ttc tat atc      2400
Val Gln Met Leu Ala Asn Tyr Asn Ile Gly Tyr Gln Gly Phe Tyr Ile
785                 790                 795                 800

cca gag agc tac aag gac cgc atg tac tcc ttc ttt aga aac ttc cag      2448
Pro Glu Ser Tyr Lys Asp Arg Met Tyr Ser Phe Phe Arg Asn Phe Gln
                805                 810                 815

ccc atg agc cgt cag gtg gtg gat gat act aaa tac aag gac tac caa      2496
Pro Met Ser Arg Gln Val Val Asp Asp Thr Lys Tyr Lys Asp Tyr Gln
            820                 825                 830

cag gtg ggc atc cta cac caa cac aac aac tct gga ttt gtt ggc tac      2544
Gln Val Gly Ile Leu His Gln His Asn Asn Ser Gly Phe Val Gly Tyr
        835                 840                 845

ctt gcc ccc acc atg cgc gaa gga cag gcc tac cct gct aac ttc ccc      2592
Leu Ala Pro Thr Met Arg Glu Gly Gln Ala Tyr Pro Ala Asn Phe Pro
    850                 855                 860

tat ccg ctt ata ggc aag acc gca gtt gac agc att acc cag aaa aag      2640
Tyr Pro Leu Ile Gly Lys Thr Ala Val Asp Ser Ile Thr Gln Lys Lys
865                 870                 875                 880

ttt ctt tgc gat cgc acc ctt tgg cgc atc cca ttc tcc agt aac ttt      2688
Phe Leu Cys Asp Arg Thr Leu Trp Arg Ile Pro Phe Ser Ser Asn Phe
                885                 890                 895

atg tcc atg ggc gca ctc aca gac ctg ggc caa aac ctt ctc tac gcc      2736
Met Ser Met Gly Ala Leu Thr Asp Leu Gly Gln Asn Leu Leu Tyr Ala
            900                 905                 910

aac tcc gcc cac gcg cta gac atg act ttt gag gtg gat ccc atg gac      2784
Asn Ser Ala His Ala Leu Asp Met Thr Phe Glu Val Asp Pro Met Asp
        915                 920                 925

gag ccc acc ctt ctt tat gtt ttg ttt gaa gtc ttt gac gtg gtc cgt      2832
Glu Pro Thr Leu Leu Tyr Val Leu Phe Glu Val Phe Asp Val Val Arg
    930                 935                 940

gtg cac cag ccg cac cgc ggc gtc atc gaa acc gtg tac ctg cgc acg      2880
Val His Gln Pro His Arg Gly Val Ile Glu Thr Val Tyr Leu Arg Thr
945                 950                 955                 960

ccc ttc tcg gcc ggc aac gcc aca aca taa                              2910
Pro Phe Ser Ala Gly Asn Ala Thr Thr
                965
```

```
<210> SEQ ID NO 19
<211> LENGTH: 2934
<212> TYPE: DNA
<213> ORGANISM: Artificial Sequence
<220> FEATURE:
<223> OTHER INFORMATION: (NANP)18-HVR1 modified Hexon protein
<220> FEATURE:
<221> NAME/KEY: CDS
<222> LOCATION: (1)..(2931)

<400> SEQUENCE: 19

atg gct acc cct tcg atg atg ccg cag tgg tct tac atg cac atc tcg       48
Met Ala Thr Pro Ser Met Met Pro Gln Trp Ser Tyr Met His Ile Ser
1               5                   10                  15

ggc cag gac gcc tcg gag tac ctg agc ccc ggg ctg gtg cag ttt gcc       96
Gly Gln Asp Ala Ser Glu Tyr Leu Ser Pro Gly Leu Val Gln Phe Ala
            20                  25                  30

cgc gcc acc gag acg tac ttc agc ctg aat aac aag ttt aga aac ccc      144
Arg Ala Thr Glu Thr Tyr Phe Ser Leu Asn Asn Lys Phe Arg Asn Pro
        35                  40                  45

acg gtg gcg cct acg cac gac gtg acc aca gac cgg tcc cag cgt ttg      192
Thr Val Ala Pro Thr His Asp Val Thr Thr Asp Arg Ser Gln Arg Leu
    50                  55                  60

acg ctg cgg ttc atc cct gtg gac cgt gag gat act gcg tac tcg tac      240
Thr Leu Arg Phe Ile Pro Val Asp Arg Glu Asp Thr Ala Tyr Ser Tyr
65                  70                  75                  80

aag gcg cgg ttc acc cta gct gtg ggt gat aac cgt gtg ctg gac atg      288
Lys Ala Arg Phe Thr Leu Ala Val Gly Asp Asn Arg Val Leu Asp Met
                85                  90                  95

gct tcc acg tac ttt gac atc cgc ggc gtg ctg gac agg ggc cct act      336
Ala Ser Thr Tyr Phe Asp Ile Arg Gly Val Leu Asp Arg Gly Pro Thr
            100                 105                 110

ttt aag ccc tac tct ggc act gcc tac aac gcc ctg gct ccc aag ggt      384
Phe Lys Pro Tyr Ser Gly Thr Ala Tyr Asn Ala Leu Ala Pro Lys Gly
        115                 120                 125

gcc cca aat cct tgc gaa tgg gat gaa aat gca aat cca aat gca aat      432
Ala Pro Asn Pro Cys Glu Trp Asp Glu Asn Ala Asn Pro Asn Ala Asn
    130                 135                 140

cca aat gca aat cca aat gca aat cca aat gca aat cca aat gca aat      480
Pro Asn Ala Asn Pro Asn Ala Asn Pro Asn Ala Asn Pro Asn Ala Asn
145                 150                 155                 160

cca aat gca aat cca aat gca aat cca aat gca aat cca aat gca aat      528
Pro Asn Ala Asn Pro Asn Ala Asn Pro Asn Ala Asn Pro Asn Ala Asn
                165                 170                 175

cca aat gca aat cca aat gca aat cca aac gcg aac ccg aat gct aat      576
Pro Asn Ala Asn Pro Asn Ala Asn Pro Asn Ala Asn Pro Asn Ala Asn
            180                 185                 190

cct aat gca aat cca aat gca aat cca aat gca aat cca aat gca aat      624
Pro Asn Ala Asn Pro Asn Ala Asn Pro Asn Ala Asn Pro Asn Ala Asn
        195                 200                 205

cca aaa act cac gta ttt ggg cag gcg cct tat tct ggt ata aat att      672
Pro Lys Thr His Val Phe Gly Gln Ala Pro Tyr Ser Gly Ile Asn Ile
    210                 215                 220

aca aag gag ggt att caa ata ggt gtc gaa ggt caa aca cct aaa tat      720
Thr Lys Glu Gly Ile Gln Ile Gly Val Glu Gly Gln Thr Pro Lys Tyr
225                 230                 235                 240

gcc gat aaa aca ttt caa cct gaa cct caa ata gga gaa tct cag tgg      768
Ala Asp Lys Thr Phe Gln Pro Glu Pro Gln Ile Gly Glu Ser Gln Trp
                245                 250                 255

tac gaa aca gaa att aat cat gca gct ggg aga gtc cta aaa aag act      816
Tyr Glu Thr Glu Ile Asn His Ala Ala Gly Arg Val Leu Lys Lys Thr
            260                 265                 270
```

```
acc cca atg aaa cca tgt tac ggt tca tat gca aaa ccc aca aat gaa      864
Thr Pro Met Lys Pro Cys Tyr Gly Ser Tyr Ala Lys Pro Thr Asn Glu
        275                 280                 285

aat gga ggg caa ggc att ctt gta aag caa caa aat gga aag cta gaa      912
Asn Gly Gly Gln Gly Ile Leu Val Lys Gln Gln Asn Gly Lys Leu Glu
    290                 295                 300

agt caa gtg gaa atg caa ttt ttc tca act act gag gca gcc gca ggc      960
Ser Gln Val Glu Met Gln Phe Phe Ser Thr Thr Glu Ala Ala Ala Gly
305                 310                 315                 320

aat ggt gat aac ttg act cct aaa gtg gta ttg tac agt gaa gat gta     1008
Asn Gly Asp Asn Leu Thr Pro Lys Val Val Leu Tyr Ser Glu Asp Val
                325                 330                 335

gat ata gaa acc cca gac act cat att tct tac atg ccc act att aag     1056
Asp Ile Glu Thr Pro Asp Thr His Ile Ser Tyr Met Pro Thr Ile Lys
            340                 345                 350

gaa ggt aac tca cga gaa cta atg ggc caa caa tct atg ccc aac agg     1104
Glu Gly Asn Ser Arg Glu Leu Met Gly Gln Gln Ser Met Pro Asn Arg
        355                 360                 365

cct aat tac att gct ttt agg gac aat ttt att ggt cta atg tat tac     1152
Pro Asn Tyr Ile Ala Phe Arg Asp Asn Phe Ile Gly Leu Met Tyr Tyr
    370                 375                 380

aac agc acg ggt aat atg ggt gtt ctg gcg ggc caa gca tcg cag ttg     1200
Asn Ser Thr Gly Asn Met Gly Val Leu Ala Gly Gln Ala Ser Gln Leu
385                 390                 395                 400

aat gct gtt gta gat ttg caa gac aga aac aca gag ctt tca tac cag     1248
Asn Ala Val Val Asp Leu Gln Asp Arg Asn Thr Glu Leu Ser Tyr Gln
                405                 410                 415

ctt ttg ctt gat tcc att ggt gat aga acc agg tac ttt tct atg tgg     1296
Leu Leu Leu Asp Ser Ile Gly Asp Arg Thr Arg Tyr Phe Ser Met Trp
            420                 425                 430

aat cag ctt cca aat tac tgc ttt cca ctg gga ggt gtg att aat aca     1344
Asn Gln Leu Pro Asn Tyr Cys Phe Pro Leu Gly Gly Val Ile Asn Thr
        435                 440                 445

gag act ctt acc aag gta aaa cct aaa aca ggt cag gaa aat gga tgg     1392
Glu Thr Leu Thr Lys Val Lys Pro Lys Thr Gly Gln Glu Asn Gly Trp
    450                 455                 460

gaa aaa gat gct aca gaa ttt tca gat aaa aat gaa ata aga gtt gga     1440
Glu Lys Asp Ala Thr Glu Phe Ser Asp Lys Asn Glu Ile Arg Val Gly
465                 470                 475                 480

aat aat ttt gcc atg gaa atc aat cta aat gcc aac ctg tgg aga aat     1488
Asn Asn Phe Ala Met Glu Ile Asn Leu Asn Ala Asn Leu Trp Arg Asn
                485                 490                 495

ttc ctg tac tcc aac ata gcg ctg tat ttg ccc gac aag cta aag tac     1536
Phe Leu Tyr Ser Asn Ile Ala Leu Tyr Leu Pro Asp Lys Leu Lys Tyr
            500                 505                 510

agt cct tcc aac gta aaa att tct gat aac cca aac acc tac gac tac     1584
Ser Pro Ser Asn Val Lys Ile Ser Asp Asn Pro Asn Thr Tyr Asp Tyr
        515                 520                 525

atg aac aag cga gtg gtg gct ccc ggg cta gtg gac tgc tac att aac     1632
Met Asn Lys Arg Val Val Ala Pro Gly Leu Val Asp Cys Tyr Ile Asn
    530                 535                 540

ctt gga gca cgc tgg tcc ctt gac tat atg gac aac gtc aac cca ttt     1680
Leu Gly Ala Arg Trp Ser Leu Asp Tyr Met Asp Asn Val Asn Pro Phe
545                 550                 555                 560

aac cac cac cgc aat gct ggc ctg cgc tac cgc tca atg ttg ctg ggc     1728
Asn His His Arg Asn Ala Gly Leu Arg Tyr Arg Ser Met Leu Leu Gly
                565                 570                 575

aat ggt cgc tat gtg ccc ttc cac atc cag gtg cct cag aag ttc ttt     1776
Asn Gly Arg Tyr Val Pro Phe His Ile Gln Val Pro Gln Lys Phe Phe
```

-continued

```
            580                 585                 590

gcc att aaa aac ctc ctt ctc ctg ccg ggc tca tac acc tac gag tgg      1824
Ala Ile Lys Asn Leu Leu Leu Leu Pro Gly Ser Tyr Thr Tyr Glu Trp
        595                 600                 605

aac ttc agg aag gat gtt aac atg gtt ctg cag agc tcc cta gga aat      1872
Asn Phe Arg Lys Asp Val Asn Met Val Leu Gln Ser Ser Leu Gly Asn
    610                 615                 620

gac cta agg gtt gac gga gcc agc att aag ttt gat agc att tgc ctt      1920
Asp Leu Arg Val Asp Gly Ala Ser Ile Lys Phe Asp Ser Ile Cys Leu
625                 630                 635                 640

tac gcc acc ttc ttc ccc atg gcc cac aac acc gcc tcc acg ctt gag      1968
Tyr Ala Thr Phe Phe Pro Met Ala His Asn Thr Ala Ser Thr Leu Glu
                645                 650                 655

gcc atg ctt aga aac gac acc aac gac cag tcc ttt aac gac tat ctc      2016
Ala Met Leu Arg Asn Asp Thr Asn Asp Gln Ser Phe Asn Asp Tyr Leu
            660                 665                 670

tcc gcc gcc aac atg ctc tac cct ata ccc gcc aac gct acc aac gtg      2064
Ser Ala Ala Asn Met Leu Tyr Pro Ile Pro Ala Asn Ala Thr Asn Val
        675                 680                 685

ccc ata tcc atc ccc tcc cgc aac tgg gcg gct ttc cgc ggc tgg gcc      2112
Pro Ile Ser Ile Pro Ser Arg Asn Trp Ala Ala Phe Arg Gly Trp Ala
    690                 695                 700

ttc acg cgc ctt aag act aag gaa acc cca tca ctg ggc tcg ggc tac      2160
Phe Thr Arg Leu Lys Thr Lys Glu Thr Pro Ser Leu Gly Ser Gly Tyr
705                 710                 715                 720

gac cct tat tac acc tac tct ggc tct ata ccc tac cta gat gga acc      2208
Asp Pro Tyr Tyr Thr Tyr Ser Gly Ser Ile Pro Tyr Leu Asp Gly Thr
                725                 730                 735

ttt tac ctc aac cac acc ttt aag aag gtg gcc att acc ttt gac tct      2256
Phe Tyr Leu Asn His Thr Phe Lys Lys Val Ala Ile Thr Phe Asp Ser
            740                 745                 750

tct gtc agc tgg cct ggc aat gac cgc ctg ctt acc ccc aac gag ttt      2304
Ser Val Ser Trp Pro Gly Asn Asp Arg Leu Leu Thr Pro Asn Glu Phe
        755                 760                 765

gaa att aag cgc tca gtt gac ggg gag ggt tac aac gtt gcc cag tgt      2352
Glu Ile Lys Arg Ser Val Asp Gly Glu Gly Tyr Asn Val Ala Gln Cys
    770                 775                 780

aac atg acc aaa gac tgg ttc ctg gta caa atg cta gct aac tat aac      2400
Asn Met Thr Lys Asp Trp Phe Leu Val Gln Met Leu Ala Asn Tyr Asn
785                 790                 795                 800

att ggc tac cag ggc ttc tat atc cca gag agc tac aag gac cgc atg      2448
Ile Gly Tyr Gln Gly Phe Tyr Ile Pro Glu Ser Tyr Lys Asp Arg Met
                805                 810                 815

tac tcc ttc ttt aga aac ttc cag ccc atg agc cgt cag gtg gtg gat      2496
Tyr Ser Phe Phe Arg Asn Phe Gln Pro Met Ser Arg Gln Val Val Asp
            820                 825                 830

gat act aaa tac aag gac tac caa cag gtg ggc atc cta cac caa cac      2544
Asp Thr Lys Tyr Lys Asp Tyr Gln Gln Val Gly Ile Leu His Gln His
        835                 840                 845

aac aac tct gga ttt gtt ggc tac ctt gcc ccc acc atg cgc gaa gga      2592
Asn Asn Ser Gly Phe Val Gly Tyr Leu Ala Pro Thr Met Arg Glu Gly
    850                 855                 860

cag gcc tac cct gct aac ttc ccc tat ccg ctt ata ggc aag acc gca      2640
Gln Ala Tyr Pro Ala Asn Phe Pro Tyr Pro Leu Ile Gly Lys Thr Ala
865                 870                 875                 880

gtt gac agc att acc cag aaa aag ttt ctt tgc gat cgc acc ctt tgg      2688
Val Asp Ser Ile Thr Gln Lys Lys Phe Leu Cys Asp Arg Thr Leu Trp
                885                 890                 895

cgc atc cca ttc tcc agt aac ttt atg tcc atg ggc gca ctc aca gac      2736
```

-continued

```
Arg Ile Pro Phe Ser Ser Asn Phe Met Ser Met Gly Ala Leu Thr Asp
            900                 905                 910

ctg ggc caa aac ctt ctc tac gcc aac tcc gcc cac gcg cta gac atg     2784
Leu Gly Gln Asn Leu Leu Tyr Ala Asn Ser Ala His Ala Leu Asp Met
        915                 920                 925

act ttt gag gtg gat ccc atg gac gag ccc acc ctt ctt tat gtt ttg     2832
Thr Phe Glu Val Asp Pro Met Asp Glu Pro Thr Leu Leu Tyr Val Leu
    930                 935                 940

ttt gaa gtc ttt gac gtg gtc cgt gtg cac cag ccg cac cgc ggc gtc     2880
Phe Glu Val Phe Asp Val Val Arg Val His Gln Pro His Arg Gly Val
945                 950                 955                 960

atc gaa acc gtg tac ctg cgc acg ccc ttc tcg gcc ggc aac gcc aca     2928
Ile Glu Thr Val Tyr Leu Arg Thr Pro Phe Ser Ala Gly Asn Ala Thr
                965                 970                 975

aca taa                                                             2934
Thr


<210> SEQ ID NO 20
<211> LENGTH: 2958
<212> TYPE: DNA
<213> ORGANISM: Artificial Sequence
<220> FEATURE:
<223> OTHER INFORMATION: (NANP)20-HVR1 modified Hexon protein
<220> FEATURE:
<221> NAME/KEY: CDS
<222> LOCATION: (1)..(2955)

<400> SEQUENCE: 20

atg gct acc cct tcg atg atg ccg cag tgg tct tac atg cac atc tcg       48
Met Ala Thr Pro Ser Met Met Pro Gln Trp Ser Tyr Met His Ile Ser
1               5                   10                  15

ggc cag gac gcc tcg gag tac ctg agc ccc ggg ctg gtg cag ttt gcc       96
Gly Gln Asp Ala Ser Glu Tyr Leu Ser Pro Gly Leu Val Gln Phe Ala
            20                  25                  30

cgc gcc acc gag acg tac ttc agc ctg aat aac aag ttt aga aac ccc      144
Arg Ala Thr Glu Thr Tyr Phe Ser Leu Asn Asn Lys Phe Arg Asn Pro
        35                  40                  45

acg gtg gcg cct acg cac gac gtg acc aca gac cgg tcc cag cgt ttg      192
Thr Val Ala Pro Thr His Asp Val Thr Thr Asp Arg Ser Gln Arg Leu
    50                  55                  60

acg ctg cgg ttc atc cct gtg gac cgt gag gat act gcg tac tcg tac      240
Thr Leu Arg Phe Ile Pro Val Asp Arg Glu Asp Thr Ala Tyr Ser Tyr
65                  70                  75                  80

aag gcg cgg ttc acc cta gct gtg ggt gat aac cgt gtg ctg gac atg      288
Lys Ala Arg Phe Thr Leu Ala Val Gly Asp Asn Arg Val Leu Asp Met
                85                  90                  95

gct tcc acg tac ttt gac atc cgc ggc gtg ctg gac agg ggc cct act      336
Ala Ser Thr Tyr Phe Asp Ile Arg Gly Val Leu Asp Arg Gly Pro Thr
            100                 105                 110

ttt aag ccc tac tct ggc act gcc tac aac gcc ctg gct ccc aag ggt      384
Phe Lys Pro Tyr Ser Gly Thr Ala Tyr Asn Ala Leu Ala Pro Lys Gly
        115                 120                 125

gcc cca aat cct tgc gaa tgg gat gaa aat gca aat cca aat gca aat      432
Ala Pro Asn Pro Cys Glu Trp Asp Glu Asn Ala Asn Pro Asn Ala Asn
    130                 135                 140

cca aat gca aat cca aat gca aat cca aat gca aat cca aat gca aat      480
Pro Asn Ala Asn Pro Asn Ala Asn Pro Asn Ala Asn Pro Asn Ala Asn
145                 150                 155                 160

cca aat gca aat cca aat gca aat cca aat gca aat cca aat gca aat      528
Pro Asn Ala Asn Pro Asn Ala Asn Pro Asn Ala Asn Pro Asn Ala Asn
                165                 170                 175
```

-continued

```
cca aat gca aat cca aat gca aat cca aac gcg aac ccg aat gct aat      576
Pro Asn Ala Asn Pro Asn Ala Asn Pro Asn Ala Asn Pro Asn Ala Asn
            180                 185                 190

cct aat gca aat cca aat gca aat cca aat gca aat cca aat gca aat      624
Pro Asn Ala Asn Pro Asn Ala Asn Pro Asn Ala Asn Pro Asn Ala Asn
        195                 200                 205

cca aat gca aat cca aat gca aat cca aaa act cac gta ttt ggg cag      672
Pro Asn Ala Asn Pro Asn Ala Asn Pro Lys Thr His Val Phe Gly Gln
    210                 215                 220

gcg cct tat tct ggt ata aat att aca aag gag ggt att caa ata ggt      720
Ala Pro Tyr Ser Gly Ile Asn Ile Thr Lys Glu Gly Ile Gln Ile Gly
225                 230                 235                 240

gtc gaa ggt caa aca cct aaa tat gcc gat aaa aca ttt caa cct gaa      768
Val Glu Gly Gln Thr Pro Lys Tyr Ala Asp Lys Thr Phe Gln Pro Glu
                245                 250                 255

cct caa ata gga gaa tct cag tgg tac gaa aca gaa att aat cat gca      816
Pro Gln Ile Gly Glu Ser Gln Trp Tyr Glu Thr Glu Ile Asn His Ala
            260                 265                 270

gct ggg aga gtc cta aaa aag act acc cca atg aaa cca tgt tac ggt      864
Ala Gly Arg Val Leu Lys Lys Thr Thr Pro Met Lys Pro Cys Tyr Gly
        275                 280                 285

tca tat gca aaa ccc aca aat gaa aat gga ggg caa ggc att ctt gta      912
Ser Tyr Ala Lys Pro Thr Asn Glu Asn Gly Gly Gln Gly Ile Leu Val
    290                 295                 300

aag caa caa aat gga aag cta gaa agt caa gtg gaa atg caa ttt ttc      960
Lys Gln Gln Asn Gly Lys Leu Glu Ser Gln Val Glu Met Gln Phe Phe
305                 310                 315                 320

tca act act gag gca gcc gca ggc aat ggt gat aac ttg act cct aaa     1008
Ser Thr Thr Glu Ala Ala Ala Gly Asn Gly Asp Asn Leu Thr Pro Lys
                325                 330                 335

gtg gta ttg tac agt gaa gat gta gat ata gaa acc cca gac act cat     1056
Val Val Leu Tyr Ser Glu Asp Val Asp Ile Glu Thr Pro Asp Thr His
            340                 345                 350

att tct tac atg ccc act att aag gaa ggt aac tca cga gaa cta atg     1104
Ile Ser Tyr Met Pro Thr Ile Lys Glu Gly Asn Ser Arg Glu Leu Met
        355                 360                 365

ggc caa caa tct atg ccc aac agg cct aat tac att gct ttt agg gac     1152
Gly Gln Gln Ser Met Pro Asn Arg Pro Asn Tyr Ile Ala Phe Arg Asp
    370                 375                 380

aat ttt att ggt cta atg tat tac aac agc acg ggt aat atg ggt gtt     1200
Asn Phe Ile Gly Leu Met Tyr Tyr Asn Ser Thr Gly Asn Met Gly Val
385                 390                 395                 400

ctg gcg ggc caa gca tcg cag ttg aat gct gtt gta gat ttg caa gac     1248
Leu Ala Gly Gln Ala Ser Gln Leu Asn Ala Val Val Asp Leu Gln Asp
                405                 410                 415

aga aac aca gag ctt tca tac cag ctt ttg ctt gat tcc att ggt gat     1296
Arg Asn Thr Glu Leu Ser Tyr Gln Leu Leu Leu Asp Ser Ile Gly Asp
            420                 425                 430

aga acc agg tac ttt tct atg tgg aat cag ctt cca aat tac tgc ttt     1344
Arg Thr Arg Tyr Phe Ser Met Trp Asn Gln Leu Pro Asn Tyr Cys Phe
        435                 440                 445

cca ctg gga ggt gtg att aat aca gag act ctt acc aag gta aaa cct     1392
Pro Leu Gly Gly Val Ile Asn Thr Glu Thr Leu Thr Lys Val Lys Pro
    450                 455                 460

aaa aca ggt cag gaa aat gga tgg gaa aaa gat gct aca gaa ttt tca     1440
Lys Thr Gly Gln Glu Asn Gly Trp Glu Lys Asp Ala Thr Glu Phe Ser
465                 470                 475                 480

gat aaa aat gaa ata aga gtt gga aat aat ttt gcc atg gaa atc aat     1488
Asp Lys Asn Glu Ile Arg Val Gly Asn Asn Phe Ala Met Glu Ile Asn
                485                 490                 495
```

```
cta aat gcc aac ctg tgg aga aat ttc ctg tac tcc aac ata gcg ctg     1536
Leu Asn Ala Asn Leu Trp Arg Asn Phe Leu Tyr Ser Asn Ile Ala Leu
            500                 505                 510

tat ttg ccc gac aag cta aag tac agt cct tcc aac gta aaa att tct     1584
Tyr Leu Pro Asp Lys Leu Lys Tyr Ser Pro Ser Asn Val Lys Ile Ser
        515                 520                 525

gat aac cca aac acc tac gac tac atg aac aag cga gtg gtg gct ccc     1632
Asp Asn Pro Asn Thr Tyr Asp Tyr Met Asn Lys Arg Val Val Ala Pro
    530                 535                 540

ggg cta gtg gac tgc tac att aac ctt gga gca cgc tgg tcc ctt gac     1680
Gly Leu Val Asp Cys Tyr Ile Asn Leu Gly Ala Arg Trp Ser Leu Asp
545                 550                 555                 560

tat atg gac aac gtc aac cca ttt aac cac cac cgc aat gct ggc ctg     1728
Tyr Met Asp Asn Val Asn Pro Phe Asn His His Arg Asn Ala Gly Leu
                565                 570                 575

cgc tac cgc tca atg ttg ctg ggc aat ggt cgc tat gtg ccc ttc cac     1776
Arg Tyr Arg Ser Met Leu Leu Gly Asn Gly Arg Tyr Val Pro Phe His
            580                 585                 590

atc cag gtg cct cag aag ttc ttt gcc att aaa aac ctc ctt ctc ctg     1824
Ile Gln Val Pro Gln Lys Phe Phe Ala Ile Lys Asn Leu Leu Leu Leu
        595                 600                 605

ccg ggc tca tac acc tac gag tgg aac ttc agg aag gat gtt aac atg     1872
Pro Gly Ser Tyr Thr Tyr Glu Trp Asn Phe Arg Lys Asp Val Asn Met
    610                 615                 620

gtt ctg cag agc tcc cta gga aat gac cta agg gtt gac gga gcc agc     1920
Val Leu Gln Ser Ser Leu Gly Asn Asp Leu Arg Val Asp Gly Ala Ser
625                 630                 635                 640

att aag ttt gat agc att tgc ctt tac gcc acc ttc ttc ccc atg gcc     1968
Ile Lys Phe Asp Ser Ile Cys Leu Tyr Ala Thr Phe Phe Pro Met Ala
                645                 650                 655

cac aac acc gcc tcc acg ctt gag gcc atg ctt aga aac gac acc aac     2016
His Asn Thr Ala Ser Thr Leu Glu Ala Met Leu Arg Asn Asp Thr Asn
            660                 665                 670

gac cag tcc ttt aac gac tat ctc tcc gcc gcc aac atg ctc tac cct     2064
Asp Gln Ser Phe Asn Asp Tyr Leu Ser Ala Ala Asn Met Leu Tyr Pro
        675                 680                 685

ata ccc gcc aac gct acc aac gtg ccc ata tcc atc ccc tcc cgc aac     2112
Ile Pro Ala Asn Ala Thr Asn Val Pro Ile Ser Ile Pro Ser Arg Asn
    690                 695                 700

tgg gcg gct ttc cgc ggc tgg gcc ttc acg cgc ctt aag act aag gaa     2160
Trp Ala Ala Phe Arg Gly Trp Ala Phe Thr Arg Leu Lys Thr Lys Glu
705                 710                 715                 720

acc cca tca ctg ggc tcg ggc tac gac cct tat tac acc tac tct ggc     2208
Thr Pro Ser Leu Gly Ser Gly Tyr Asp Pro Tyr Tyr Thr Tyr Ser Gly
                725                 730                 735

tct ata ccc tac cta gat gga acc ttt tac ctc aac cac acc ttt aag     2256
Ser Ile Pro Tyr Leu Asp Gly Thr Phe Tyr Leu Asn His Thr Phe Lys
            740                 745                 750

aag gtg gcc att acc ttt gac tct tct gtc agc tgg cct ggc aat gac     2304
Lys Val Ala Ile Thr Phe Asp Ser Ser Val Ser Trp Pro Gly Asn Asp
        755                 760                 765

cgc ctg ctt acc ccc aac gag ttt gaa att aag cgc tca gtt gac ggg     2352
Arg Leu Leu Thr Pro Asn Glu Phe Glu Ile Lys Arg Ser Val Asp Gly
    770                 775                 780

gag ggt tac aac gtt gcc cag tgt aac atg acc aaa gac tgg ttc ctg     2400
Glu Gly Tyr Asn Val Ala Gln Cys Asn Met Thr Lys Asp Trp Phe Leu
785                 790                 795                 800

gta caa atg cta gct aac tat aac att ggc tac cag ggc ttc tat atc     2448
Val Gln Met Leu Ala Asn Tyr Asn Ile Gly Tyr Gln Gly Phe Tyr Ile
```

```
                805                 810                 815

cca gag agc tac aag gac cgc atg tac tcc ttc ttt aga aac ttc cag     2496
Pro Glu Ser Tyr Lys Asp Arg Met Tyr Ser Phe Phe Arg Asn Phe Gln
            820                 825                 830

ccc atg agc cgt cag gtg gtg gat gat act aaa tac aag gac tac caa     2544
Pro Met Ser Arg Gln Val Val Asp Asp Thr Lys Tyr Lys Asp Tyr Gln
        835                 840                 845

cag gtg ggc atc cta cac caa cac aac aac tct gga ttt gtt ggc tac     2592
Gln Val Gly Ile Leu His Gln His Asn Asn Ser Gly Phe Val Gly Tyr
    850                 855                 860

ctt gcc ccc acc atg cgc gaa gga cag gcc tac cct gct aac ttc ccc     2640
Leu Ala Pro Thr Met Arg Glu Gly Gln Ala Tyr Pro Ala Asn Phe Pro
865                 870                 875                 880

tat ccg ctt ata ggc aag acc gca gtt gac agc att acc cag aaa aag     2688
Tyr Pro Leu Ile Gly Lys Thr Ala Val Asp Ser Ile Thr Gln Lys Lys
                885                 890                 895

ttt ctt tgc gat cgc acc ctt tgg cgc atc cca ttc tcc agt aac ttt     2736
Phe Leu Cys Asp Arg Thr Leu Trp Arg Ile Pro Phe Ser Ser Asn Phe
            900                 905                 910

atg tcc atg ggc gca ctc aca gac ctg ggc caa aac ctt ctc tac gcc     2784
Met Ser Met Gly Ala Leu Thr Asp Leu Gly Gln Asn Leu Leu Tyr Ala
        915                 920                 925

aac tcc gcc cac gcg cta gac atg act ttt gag gtg gat ccc atg gac     2832
Asn Ser Ala His Ala Leu Asp Met Thr Phe Glu Val Asp Pro Met Asp
    930                 935                 940

gag ccc acc ctt ctt tat gtt ttg ttt gaa gtc ttt gac gtg gtc cgt     2880
Glu Pro Thr Leu Leu Tyr Val Leu Phe Glu Val Phe Asp Val Val Arg
945                 950                 955                 960

gtg cac cag ccg cac cgc ggc gtc atc gaa acc gtg tac ctg cgc acg     2928
Val His Gln Pro His Arg Gly Val Ile Glu Thr Val Tyr Leu Arg Thr
                965                 970                 975

ccc ttc tcg gcc ggc aac gcc aca aca taa                             2958
Pro Phe Ser Ala Gly Asn Ala Thr Thr
            980                 985


<210> SEQ ID NO 21
<211> LENGTH: 2982
<212> TYPE: DNA
<213> ORGANISM: Artificial Sequence
<220> FEATURE:
<223> OTHER INFORMATION: (NANP)22-HVR1 modified Hexon protein
<220> FEATURE:
<221> NAME/KEY: CDS
<222> LOCATION: (1)..(2979)

<400> SEQUENCE: 21

atg gct acc cct tcg atg atg ccg cag tgg tct tac atg cac atc tcg       48
Met Ala Thr Pro Ser Met Met Pro Gln Trp Ser Tyr Met His Ile Ser
1               5                   10                  15

ggc cag gac gcc tcg gag tac ctg agc ccc ggg ctg gtg cag ttt gcc       96
Gly Gln Asp Ala Ser Glu Tyr Leu Ser Pro Gly Leu Val Gln Phe Ala
            20                  25                  30

cgc gcc acc gag acg tac ttc agc ctg aat aac aag ttt aga aac ccc      144
Arg Ala Thr Glu Thr Tyr Phe Ser Leu Asn Asn Lys Phe Arg Asn Pro
        35                  40                  45

acg gtg gcg cct acg cac gac gtg acc aca gac cgg tcc cag cgt ttg      192
Thr Val Ala Pro Thr His Asp Val Thr Thr Asp Arg Ser Gln Arg Leu
    50                  55                  60

acg ctg cgg ttc atc cct gtg gac cgt gag gat act gcg tac tcg tac      240
Thr Leu Arg Phe Ile Pro Val Asp Arg Glu Asp Thr Ala Tyr Ser Tyr
65                  70                  75                  80
```

-continued

```
aag gcg cgg ttc acc cta gct gtg ggt gat aac cgt gtg ctg gac atg       288
Lys Ala Arg Phe Thr Leu Ala Val Gly Asp Asn Arg Val Leu Asp Met
                85                  90                  95

gct tcc acg tac ttt gac atc cgc ggc gtg ctg gac agg ggc cct act       336
Ala Ser Thr Tyr Phe Asp Ile Arg Gly Val Leu Asp Arg Gly Pro Thr
            100                 105                 110

ttt aag ccc tac tct ggc act gcc tac aac gcc ctg gct ccc aag ggt       384
Phe Lys Pro Tyr Ser Gly Thr Ala Tyr Asn Ala Leu Ala Pro Lys Gly
        115                 120                 125

gcc cca aat cct tgc gaa tgg gat gaa aat gca aat cca aat gca aat       432
Ala Pro Asn Pro Cys Glu Trp Asp Glu Asn Ala Asn Pro Asn Ala Asn
    130                 135                 140

cca aat gca aat cca aat gca aat cca aat gca aat cca aat gca aat       480
Pro Asn Ala Asn Pro Asn Ala Asn Pro Asn Ala Asn Pro Asn Ala Asn
145                 150                 155                 160

cca aat gca aat cca aat gca aat cca aat gca aat cca aat gca aat       528
Pro Asn Ala Asn Pro Asn Ala Asn Pro Asn Ala Asn Pro Asn Ala Asn
                165                 170                 175

cca aat gca aat cca aat gca aat cca aac gcg aac ccg aat gct aat       576
Pro Asn Ala Asn Pro Asn Ala Asn Pro Asn Ala Asn Pro Asn Ala Asn
            180                 185                 190

cct aat gca aat cca aat gca aat cca aat gca aat cca aat gca aat       624
Pro Asn Ala Asn Pro Asn Ala Asn Pro Asn Ala Asn Pro Asn Ala Asn
        195                 200                 205

cca aat gca aat cca aat gca aat cca aat gca aat cca aat gca aat       672
Pro Asn Ala Asn Pro Asn Ala Asn Pro Asn Ala Asn Pro Asn Ala Asn
    210                 215                 220

cca aaa act cac gta ttt ggg cag gcg cct tat tct ggt ata aat att       720
Pro Lys Thr His Val Phe Gly Gln Ala Pro Tyr Ser Gly Ile Asn Ile
225                 230                 235                 240

aca aag gag ggt att caa ata ggt gtc gaa ggt caa aca cct aaa tat       768
Thr Lys Glu Gly Ile Gln Ile Gly Val Glu Gly Gln Thr Pro Lys Tyr
                245                 250                 255

gcc gat aaa aca ttt caa cct gaa cct caa ata gga gaa tct cag tgg       816
Ala Asp Lys Thr Phe Gln Pro Glu Pro Gln Ile Gly Glu Ser Gln Trp
            260                 265                 270

tac gaa aca gaa att aat cat gca gct ggg aga gtc cta aaa aag act       864
Tyr Glu Thr Glu Ile Asn His Ala Ala Gly Arg Val Leu Lys Lys Thr
        275                 280                 285

acc cca atg aaa cca tgt tac ggt tca tat gca aaa ccc aca aat gaa       912
Thr Pro Met Lys Pro Cys Tyr Gly Ser Tyr Ala Lys Pro Thr Asn Glu
    290                 295                 300

aat gga ggg caa ggc att ctt gta aag caa caa aat gga aag cta gaa       960
Asn Gly Gly Gln Gly Ile Leu Val Lys Gln Gln Asn Gly Lys Leu Glu
305                 310                 315                 320

agt caa gtg gaa atg caa ttt ttc tca act act gag gca gcc gca ggc      1008
Ser Gln Val Glu Met Gln Phe Phe Ser Thr Thr Glu Ala Ala Ala Gly
                325                 330                 335

aat ggt gat aac ttg act cct aaa gtg gta ttg tac agt gaa gat gta      1056
Asn Gly Asp Asn Leu Thr Pro Lys Val Val Leu Tyr Ser Glu Asp Val
            340                 345                 350

gat ata gaa acc cca gac act cat att tct tac atg ccc act att aag      1104
Asp Ile Glu Thr Pro Asp Thr His Ile Ser Tyr Met Pro Thr Ile Lys
        355                 360                 365

gaa ggt aac tca cga gaa cta atg ggc caa caa tct atg ccc aac agg      1152
Glu Gly Asn Ser Arg Glu Leu Met Gly Gln Gln Ser Met Pro Asn Arg
    370                 375                 380

cct aat tac att gct ttt agg gac aat ttt att ggt cta atg tat tac      1200
Pro Asn Tyr Ile Ala Phe Arg Asp Asn Phe Ile Gly Leu Met Tyr Tyr
385                 390                 395                 400
```

```
aac agc acg ggt aat atg ggt gtt ctg gcg ggc caa gca tcg cag ttg      1248
Asn Ser Thr Gly Asn Met Gly Val Leu Ala Gly Gln Ala Ser Gln Leu
                405                 410                 415

aat gct gtt gta gat ttg caa gac aga aac aca gag ctt tca tac cag      1296
Asn Ala Val Val Asp Leu Gln Asp Arg Asn Thr Glu Leu Ser Tyr Gln
            420                 425                 430

ctt ttg ctt gat tcc att ggt gat aga acc agg tac ttt tct atg tgg      1344
Leu Leu Leu Asp Ser Ile Gly Asp Arg Thr Arg Tyr Phe Ser Met Trp
        435                 440                 445

aat cag ctt cca aat tac tgc ttt cca ctg gga ggt gtg att aat aca      1392
Asn Gln Leu Pro Asn Tyr Cys Phe Pro Leu Gly Gly Val Ile Asn Thr
    450                 455                 460

gag act ctt acc aag gta aaa cct aaa aca ggt cag gaa aat gga tgg      1440
Glu Thr Leu Thr Lys Val Lys Pro Lys Thr Gly Gln Glu Asn Gly Trp
465                 470                 475                 480

gaa aaa gat gct aca gaa ttt tca gat aaa aat gaa ata aga gtt gga      1488
Glu Lys Asp Ala Thr Glu Phe Ser Asp Lys Asn Glu Ile Arg Val Gly
                485                 490                 495

aat aat ttt gcc atg gaa atc aat cta aat gcc aac ctg tgg aga aat      1536
Asn Asn Phe Ala Met Glu Ile Asn Leu Asn Ala Asn Leu Trp Arg Asn
            500                 505                 510

ttc ctg tac tcc aac ata gcg ctg tat ttg ccc gac aag cta aag tac      1584
Phe Leu Tyr Ser Asn Ile Ala Leu Tyr Leu Pro Asp Lys Leu Lys Tyr
        515                 520                 525

agt cct tcc aac gta aaa att tct gat aac cca aac acc tac gac tac      1632
Ser Pro Ser Asn Val Lys Ile Ser Asp Asn Pro Asn Thr Tyr Asp Tyr
    530                 535                 540

atg aac aag cga gtg gtg gct ccc ggg cta gtg gac tgc tac att aac      1680
Met Asn Lys Arg Val Val Ala Pro Gly Leu Val Asp Cys Tyr Ile Asn
545                 550                 555                 560

ctt gga gca cgc tgg tcc ctt gac tat atg gac aac gtc aac cca ttt      1728
Leu Gly Ala Arg Trp Ser Leu Asp Tyr Met Asp Asn Val Asn Pro Phe
                565                 570                 575

aac cac cac cgc aat gct ggc ctg cgc tac cgc tca atg ttg ctg ggc      1776
Asn His His Arg Asn Ala Gly Leu Arg Tyr Arg Ser Met Leu Leu Gly
            580                 585                 590

aat ggt cgc tat gtg ccc ttc cac atc cag gtg cct cag aag ttc ttt      1824
Asn Gly Arg Tyr Val Pro Phe His Ile Gln Val Pro Gln Lys Phe Phe
        595                 600                 605

gcc att aaa aac ctc ctt ctc ctg ccg ggc tca tac acc tac gag tgg      1872
Ala Ile Lys Asn Leu Leu Leu Leu Pro Gly Ser Tyr Thr Tyr Glu Trp
    610                 615                 620

aac ttc agg aag gat gtt aac atg gtt ctg cag agc tcc cta gga aat      1920
Asn Phe Arg Lys Asp Val Asn Met Val Leu Gln Ser Ser Leu Gly Asn
625                 630                 635                 640

gac cta agg gtt gac gga gcc agc att aag ttt gat agc att tgc ctt      1968
Asp Leu Arg Val Asp Gly Ala Ser Ile Lys Phe Asp Ser Ile Cys Leu
                645                 650                 655

tac gcc acc ttc ttc ccc atg gcc cac aac acc gcc tcc acg ctt gag      2016
Tyr Ala Thr Phe Phe Pro Met Ala His Asn Thr Ala Ser Thr Leu Glu
            660                 665                 670

gcc atg ctt aga aac gac acc aac gac cag tcc ttt aac gac tat ctc      2064
Ala Met Leu Arg Asn Asp Thr Asn Asp Gln Ser Phe Asn Asp Tyr Leu
        675                 680                 685

tcc gcc gcc aac atg ctc tac cct ata ccc gcc aac gct acc aac gtg      2112
Ser Ala Ala Asn Met Leu Tyr Pro Ile Pro Ala Asn Ala Thr Asn Val
    690                 695                 700

ccc ata tcc atc ccc tcc cgc aac tgg gcg gct ttc cgc ggc tgg gcc      2160
Pro Ile Ser Ile Pro Ser Arg Asn Trp Ala Ala Phe Arg Gly Trp Ala
```

```
705                 710                 715                 720

ttc acg cgc ctt aag act aag gaa acc cca tca ctg ggc tcg ggc tac      2208
Phe Thr Arg Leu Lys Thr Lys Glu Thr Pro Ser Leu Gly Ser Gly Tyr
                725                 730                 735

gac cct tat tac acc tac tct ggc tct ata ccc tac cta gat gga acc      2256
Asp Pro Tyr Tyr Thr Tyr Ser Gly Ser Ile Pro Tyr Leu Asp Gly Thr
            740                 745                 750

ttt tac ctc aac cac acc ttt aag aag gtg gcc att acc ttt gac tct      2304
Phe Tyr Leu Asn His Thr Phe Lys Lys Val Ala Ile Thr Phe Asp Ser
        755                 760                 765

tct gtc agc tgg cct ggc aat gac cgc ctg ctt acc ccc aac gag ttt      2352
Ser Val Ser Trp Pro Gly Asn Asp Arg Leu Leu Thr Pro Asn Glu Phe
    770                 775                 780

gaa att aag cgc tca gtt gac ggg gag ggt tac aac gtt gcc cag tgt      2400
Glu Ile Lys Arg Ser Val Asp Gly Glu Gly Tyr Asn Val Ala Gln Cys
785                 790                 795                 800

aac atg acc aaa gac tgg ttc ctg gta caa atg cta gct aac tat aac      2448
Asn Met Thr Lys Asp Trp Phe Leu Val Gln Met Leu Ala Asn Tyr Asn
                805                 810                 815

att ggc tac cag ggc ttc tat atc cca gag agc tac aag gac cgc atg      2496
Ile Gly Tyr Gln Gly Phe Tyr Ile Pro Glu Ser Tyr Lys Asp Arg Met
            820                 825                 830

tac tcc ttc ttt aga aac ttc cag ccc atg agc cgt cag gtg gtg gat      2544
Tyr Ser Phe Phe Arg Asn Phe Gln Pro Met Ser Arg Gln Val Val Asp
        835                 840                 845

gat act aaa tac aag gac tac caa cag gtg ggc atc cta cac caa cac      2592
Asp Thr Lys Tyr Lys Asp Tyr Gln Gln Val Gly Ile Leu His Gln His
    850                 855                 860

aac aac tct gga ttt gtt ggc tac ctt gcc ccc acc atg cgc gaa gga      2640
Asn Asn Ser Gly Phe Val Gly Tyr Leu Ala Pro Thr Met Arg Glu Gly
865                 870                 875                 880

cag gcc tac cct gct aac ttc ccc tat ccg ctt ata ggc aag acc gca      2688
Gln Ala Tyr Pro Ala Asn Phe Pro Tyr Pro Leu Ile Gly Lys Thr Ala
                885                 890                 895

gtt gac agc att acc cag aaa aag ttt ctt tgc gat cgc acc ctt tgg      2736
Val Asp Ser Ile Thr Gln Lys Lys Phe Leu Cys Asp Arg Thr Leu Trp
            900                 905                 910

cgc atc cca ttc tcc agt aac ttt atg tcc atg ggc gca ctc aca gac      2784
Arg Ile Pro Phe Ser Ser Asn Phe Met Ser Met Gly Ala Leu Thr Asp
        915                 920                 925

ctg ggc caa aac ctt ctc tac gcc aac tcc gcc cac gcg cta gac atg      2832
Leu Gly Gln Asn Leu Leu Tyr Ala Asn Ser Ala His Ala Leu Asp Met
    930                 935                 940

act ttt gag gtg gat ccc atg gac gag ccc acc ctt ctt tat gtt ttg      2880
Thr Phe Glu Val Asp Pro Met Asp Glu Pro Thr Leu Leu Tyr Val Leu
945                 950                 955                 960

ttt gaa gtc ttt gac gtg gtc cgt gtg cac cag ccg cac cgc ggc gtc      2928
Phe Glu Val Phe Asp Val Val Arg Val His Gln Pro His Arg Gly Val
                965                 970                 975

atc gaa acc gtg tac ctg cgc acg ccc ttc tcg gcc ggc aac gcc aca      2976
Ile Glu Thr Val Tyr Leu Arg Thr Pro Phe Ser Ala Gly Asn Ala Thr
            980                 985                 990

aca taa                                                              2982
Thr


<210> SEQ ID NO 22
<211> LENGTH: 3054
<212> TYPE: DNA
<213> ORGANISM: Artificial Sequence
<220> FEATURE:
```

-continued

<223> OTHER INFORMATION: (NANP)28-HVR1 modified Hexon protein
<220> FEATURE:
<221> NAME/KEY: CDS
<222> LOCATION: (1)..(3051)

<400> SEQUENCE: 22 atg gct acc cct tcg atg atg ccg cag tgg tct tac atg cac atc tcg 48
Met Ala Thr Pro Ser Met Met Pro Gln Trp Ser Tyr Met His Ile Ser
1 5 10 15 ggc cag gac gcc tcg gag tac ctg agc ccc ggg ctg gtg cag ttt gcc 96
Gly Gln Asp Ala Ser Glu Tyr Leu Ser Pro Gly Leu Val Gln Phe Ala
20 25 30 cgc gcc acc gag acg tac ttc agc ctg aat aac aag ttt aga aac ccc 144
Arg Ala Thr Glu Thr Tyr Phe Ser Leu Asn Asn Lys Phe Arg Asn Pro
35 40 45 acg gtg gcg cct acg cac gac gtg acc aca gac cgg tcc cag cgt ttg 192
Thr Val Ala Pro Thr His Asp Val Thr Thr Asp Arg Ser Gln Arg Leu
50 55 60 acg ctg cgg ttc atc cct gtg gac cgt gag gat act gcg tac tcg tac 240
Thr Leu Arg Phe Ile Pro Val Asp Arg Glu Asp Thr Ala Tyr Ser Tyr
65 70 75 80 aag gcg cgg ttc acc cta gct gtg ggt gat aac cgt gtg ctg gac atg 288
Lys Ala Arg Phe Thr Leu Ala Val Gly Asp Asn Arg Val Leu Asp Met
85 90 95 gct tcc acg tac ttt gac atc cgc ggc gtg ctg gac agg ggc cct act 336
Ala Ser Thr Tyr Phe Asp Ile Arg Gly Val Leu Asp Arg Gly Pro Thr
100 105 110 ttt aag ccc tac tct ggc act gcc tac aac gcc ctg gct ccc aag ggt 384
Phe Lys Pro Tyr Ser Gly Thr Ala Tyr Asn Ala Leu Ala Pro Lys Gly
115 120 125 gcc cca aat cct tgc gaa tgg gat gaa aac gcc aat cca aat gcg aat 432
Ala Pro Asn Pro Cys Glu Trp Asp Glu Asn Ala Asn Pro Asn Ala Asn
130 135 140 ccc aac gct aat cct aac gca aac ccg aat gct aac cct aac gca aac 480
Pro Asn Ala Asn Pro Asn Ala Asn Pro Asn Ala Asn Pro Asn Ala Asn
145 150 155 160 ccc aac gct aac ccc aac gcg aac ccc aat gcc aac ccc aac gcc aac 528
Pro Asn Ala Asn Pro Asn Ala Asn Pro Asn Ala Asn Pro Asn Ala Asn
165 170 175 ccg aac gcc aat cca aac gct aac cct aat gcc aat cct aat gcc aat 576
Pro Asn Ala Asn Pro Asn Ala Asn Pro Asn Ala Asn Pro Asn Ala Asn
180 185 190 ccg aac gcc aat cca aat gcc aat cca aat gct aat ccc aac aat gcc 624
Pro Asn Ala Asn Pro Asn Ala Asn Pro Asn Ala Asn Pro Asn Ala Asn
195 200 205 ccc aac gcg aac cct aat gcc aac ccc aac gct aat cca aat gcg aac 672
Pro Asn Ala Asn Pro Asn Ala Asn Pro Asn Ala Asn Pro Asn Ala Asn
210 215 220 cct aac gcc aac ccg aat gct aat ccc aat gcc aac ccc aat gct aat 720
Pro Asn Ala Asn Pro Asn Ala Asn Pro Asn Ala Asn Pro Asn Ala Asn
225 230 235 240 ccc aat gcg aac cct aat gcc aat ccc aaa act cac gta ttt ggg cag 768
Pro Asn Ala Asn Pro Asn Ala Asn Pro Lys Thr His Val Phe Gly Gln
245 250 255 gcg cct tat tct ggt ata aat att aca aag gag ggt att caa ata ggt 816
Ala Pro Tyr Ser Gly Ile Asn Ile Thr Lys Glu Gly Ile Gln Ile Gly
260 265 270 gtc gaa ggt caa aca cct aaa tat gcc gat aaa aca ttt caa cct gaa 864
Val Glu Gly Gln Thr Pro Lys Tyr Ala Asp Lys Thr Phe Gln Pro Glu
275 280 285

-continued

```
cct caa ata gga gaa tct cag tgg tac gaa aca gaa att aat cat gca      912
Pro Gln Ile Gly Glu Ser Gln Trp Tyr Glu Thr Glu Ile Asn His Ala
    290                 295                 300

gct ggg aga gtc cta aaa aag act acc cca atg aaa cca tgt tac ggt      960
Ala Gly Arg Val Leu Lys Lys Thr Thr Pro Met Lys Pro Cys Tyr Gly
305                 310                 315                 320

tca tat gca aaa ccc aca aat gaa aat gga ggg caa ggc att ctt gta     1008
Ser Tyr Ala Lys Pro Thr Asn Glu Asn Gly Gly Gln Gly Ile Leu Val
                325                 330                 335

aag caa caa aat gga aag cta gaa agt caa gtg gaa atg caa ttt ttc     1056
Lys Gln Gln Asn Gly Lys Leu Glu Ser Gln Val Glu Met Gln Phe Phe
            340                 345                 350

tca act act gag gca gcc gca ggc aat ggt gat aac ttg act cct aaa     1104
Ser Thr Thr Glu Ala Ala Ala Gly Asn Gly Asp Asn Leu Thr Pro Lys
        355                 360                 365

gtg gta ttg tac agt gaa gat gta gat ata gaa acc cca gac act cat     1152
Val Val Leu Tyr Ser Glu Asp Val Asp Ile Glu Thr Pro Asp Thr His
    370                 375                 380

att tct tac atg ccc act att aag gaa ggt aac tca cga gaa cta atg     1200
Ile Ser Tyr Met Pro Thr Ile Lys Glu Gly Asn Ser Arg Glu Leu Met
385                 390                 395                 400

ggc caa caa tct atg ccc aac agg cct aat tac att gct ttt agg gac     1248
Gly Gln Gln Ser Met Pro Asn Arg Pro Asn Tyr Ile Ala Phe Arg Asp
                405                 410                 415

aat ttt att ggt cta atg tat tac aac agc acg ggt aat atg ggt gtt     1296
Asn Phe Ile Gly Leu Met Tyr Tyr Asn Ser Thr Gly Asn Met Gly Val
            420                 425                 430

ctg gcg ggc caa gca tcg cag ttg aat gct gtt gta gat ttg caa gac     1344
Leu Ala Gly Gln Ala Ser Gln Leu Asn Ala Val Val Asp Leu Gln Asp
        435                 440                 445

aga aac aca gag ctt tca tac cag ctt ttg ctt gat tcc att ggt gat     1392
Arg Asn Thr Glu Leu Ser Tyr Gln Leu Leu Leu Asp Ser Ile Gly Asp
    450                 455                 460

aga acc agg tac ttt tct atg tgg aat cag ctt cca aat tac tgc ttt     1440
Arg Thr Arg Tyr Phe Ser Met Trp Asn Gln Leu Pro Asn Tyr Cys Phe
465                 470                 475                 480

cca ctg gga ggt gtg att aat aca gag act ctt acc aag gta aaa cct     1488
Pro Leu Gly Gly Val Ile Asn Thr Glu Thr Leu Thr Lys Val Lys Pro
                485                 490                 495

aaa aca ggt cag gaa aat gga tgg gaa aaa gat gct aca gaa ttt tca     1536
Lys Thr Gly Gln Glu Asn Gly Trp Glu Lys Asp Ala Thr Glu Phe Ser
            500                 505                 510

gat aaa aat gaa ata aga gtt gga aat aat ttt gcc atg gaa atc aat     1584
Asp Lys Asn Glu Ile Arg Val Gly Asn Asn Phe Ala Met Glu Ile Asn
        515                 520                 525

cta aat gcc aac ctg tgg aga aat ttc ctg tac tcc aac ata gcg ctg     1632
Leu Asn Ala Asn Leu Trp Arg Asn Phe Leu Tyr Ser Asn Ile Ala Leu
    530                 535                 540

tat ttg ccc gac aag cta aag tac agt cct tcc aac gta aaa att tct     1680
Tyr Leu Pro Asp Lys Leu Lys Tyr Ser Pro Ser Asn Val Lys Ile Ser
545                 550                 555                 560

gat aac cca aac acc tac gac tac atg aac aag cga gtg gtg gct ccc     1728
Asp Asn Pro Asn Thr Tyr Asp Tyr Met Asn Lys Arg Val Val Ala Pro
                565                 570                 575

ggg cta gtg gac tgc tac att aac ctt gga gca cgc tgg tcc ctt gac     1776
Gly Leu Val Asp Cys Tyr Ile Asn Leu Gly Ala Arg Trp Ser Leu Asp
            580                 585                 590

tat atg gac aac gtc aac cca ttt aac cac cac cgc aat gct ggc ctg     1824
Tyr Met Asp Asn Val Asn Pro Phe Asn His His Arg Asn Ala Gly Leu
        595                 600                 605
```

-continued

```
cgc tac cgc tca atg ttg ctg ggc aat ggt cgc tat gtg ccc ttc cac     1872
Arg Tyr Arg Ser Met Leu Leu Gly Asn Gly Arg Tyr Val Pro Phe His
    610                 615                 620

atc cag gtg cct cag aag ttc ttt gcc att aaa aac ctc ctt ctc ctg     1920
Ile Gln Val Pro Gln Lys Phe Phe Ala Ile Lys Asn Leu Leu Leu Leu
625                 630                 635                 640

ccg ggc tca tac acc tac gag tgg aac ttc agg aag gat gtt aac atg     1968
Pro Gly Ser Tyr Thr Tyr Glu Trp Asn Phe Arg Lys Asp Val Asn Met
                645                 650                 655

gtt ctg cag agc tcc cta gga aat gac cta agg gtt gac gga gcc agc     2016
Val Leu Gln Ser Ser Leu Gly Asn Asp Leu Arg Val Asp Gly Ala Ser
            660                 665                 670

att aag ttt gat agc att tgc ctt tac gcc acc ttc ttc ccc atg gcc     2064
Ile Lys Phe Asp Ser Ile Cys Leu Tyr Ala Thr Phe Phe Pro Met Ala
        675                 680                 685

cac aac acc gcc tcc acg ctt gag gcc atg ctt aga aac gac acc aac     2112
His Asn Thr Ala Ser Thr Leu Glu Ala Met Leu Arg Asn Asp Thr Asn
    690                 695                 700

gac cag tcc ttt aac gac tat ctc tcc gcc gcc aac atg ctc tac cct     2160
Asp Gln Ser Phe Asn Asp Tyr Leu Ser Ala Ala Asn Met Leu Tyr Pro
705                 710                 715                 720

ata ccc gcc aac gct acc aac gtg ccc ata tcc atc ccc tcc cgc aac     2208
Ile Pro Ala Asn Ala Thr Asn Val Pro Ile Ser Ile Pro Ser Arg Asn
                725                 730                 735

tgg gcg gct ttc cgc ggc tgg gcc ttc acg cgc ctt aag act aag gaa     2256
Trp Ala Ala Phe Arg Gly Trp Ala Phe Thr Arg Leu Lys Thr Lys Glu
            740                 745                 750

acc cca tca ctg ggc tcg ggc tac gac cct tat tac acc tac tct ggc     2304
Thr Pro Ser Leu Gly Ser Gly Tyr Asp Pro Tyr Tyr Thr Tyr Ser Gly
        755                 760                 765

tct ata ccc tac cta gat gga acc ttt tac ctc aac cac acc ttt aag     2352
Ser Ile Pro Tyr Leu Asp Gly Thr Phe Tyr Leu Asn His Thr Phe Lys
    770                 775                 780

aag gtg gcc att acc ttt gac tct tct gtc agc tgg cct ggc aat gac     2400
Lys Val Ala Ile Thr Phe Asp Ser Ser Val Ser Trp Pro Gly Asn Asp
785                 790                 795                 800

cgc ctg ctt acc ccc aac gag ttt gaa att aag cgc tca gtt gac ggg     2448
Arg Leu Leu Thr Pro Asn Glu Phe Glu Ile Lys Arg Ser Val Asp Gly
                805                 810                 815

gag ggt tac aac gtt gcc cag tgt aac atg acc aaa gac tgg ttc ctg     2496
Glu Gly Tyr Asn Val Ala Gln Cys Asn Met Thr Lys Asp Trp Phe Leu
            820                 825                 830

gta caa atg cta gct aac tat aac att ggc tac cag ggc ttc tat atc     2544
Val Gln Met Leu Ala Asn Tyr Asn Ile Gly Tyr Gln Gly Phe Tyr Ile
        835                 840                 845

cca gag agc tac aag gac cgc atg tac tcc ttc ttt aga aac ttc cag     2592
Pro Glu Ser Tyr Lys Asp Arg Met Tyr Ser Phe Phe Arg Asn Phe Gln
    850                 855                 860

ccc atg agc cgt cag gtg gtg gat gat act aaa tac aag gac tac caa     2640
Pro Met Ser Arg Gln Val Val Asp Asp Thr Lys Tyr Lys Asp Tyr Gln
865                 870                 875                 880

cag gtg ggc atc cta cac caa cac aac aac tct gga ttt gtt ggc tac     2688
Gln Val Gly Ile Leu His Gln His Asn Asn Ser Gly Phe Val Gly Tyr
                885                 890                 895

ctt gcc ccc acc atg cgc gaa gga cag gcc tac cct gct aac ttc ccc     2736
Leu Ala Pro Thr Met Arg Glu Gly Gln Ala Tyr Pro Ala Asn Phe Pro
            900                 905                 910

tat ccg ctt ata ggc aag acc gca gtt gac agc att acc cag aaa aag     2784
Tyr Pro Leu Ile Gly Lys Thr Ala Val Asp Ser Ile Thr Gln Lys Lys
```

915 920 925 ttt ctt tgc gat cgc acc ctt tgg cgc atc cca ttc tcc agt aac ttt 2832
Phe Leu Cys Asp Arg Thr Leu Trp Arg Ile Pro Phe Ser Ser Asn Phe
930 935 940 atg tcc atg ggc gca ctc aca gac ctg ggc caa aac ctt ctc tac gcc 2880
Met Ser Met Gly Ala Leu Thr Asp Leu Gly Gln Asn Leu Leu Tyr Ala
945 950 955 960 aac tcc gcc cac gcg cta gac atg act ttt gag gtg gat ccc atg gac 2928
Asn Ser Ala His Ala Leu Asp Met Thr Phe Glu Val Asp Pro Met Asp
965 970 975 gag ccc acc ctt ctt tat gtt ttg ttt gaa gtc ttt gac gtg gtc cgt 2976
Glu Pro Thr Leu Leu Tyr Val Leu Phe Glu Val Phe Asp Val Val Arg
980 985 990 gtg cac cag ccg cac cgc ggc gtc atc gaa acc gtg tac ctg cgc acg 3024
Val His Gln Pro His Arg Gly Val Ile Glu Thr Val Tyr Leu Arg Thr
995 1000 1005 ccc ttc tcg gcc ggc aac gcc aca aca taa 3054
Pro Phe Ser Ala Gly Asn Ala Thr Thr
1010 1015

<210> SEQ ID NO 23
<211> LENGTH: 2928
<212> TYPE: DNA
<213> ORGANISM: Artificial Sequence
<220> FEATURE:
<223> OTHER INFORMATION: (QGPGAP)3-HVR5 modified Hexon protein
<220> FEATURE:
<221> NAME/KEY: CDS
<222> LOCATION: (1)..(2925)

<400> SEQUENCE: 23 atg gct acc cct tcg atg atg ccg cag tgg tct tac atg cac atc tcg 48
Met Ala Thr Pro Ser Met Met Pro Gln Trp Ser Tyr Met His Ile Ser
1 5 10 15 ggc cag gac gcc tcg gag tac ctg agc ccc ggg ctg gtg cag ttt gcc 96
Gly Gln Asp Ala Ser Glu Tyr Leu Ser Pro Gly Leu Val Gln Phe Ala
20 25 30 cgc gcc acc gag acg tac ttc agc ctg aat aac aag ttt aga aac ccc 144
Arg Ala Thr Glu Thr Tyr Phe Ser Leu Asn Asn Lys Phe Arg Asn Pro
35 40 45 acg gtg gcg cct acg cac gac gtg acc aca gac cgg tcc cag cgt ttg 192
Thr Val Ala Pro Thr His Asp Val Thr Thr Asp Arg Ser Gln Arg Leu
50 55 60 acg ctg cgg ttc atc cct gtg gac cgt gag gat act gcg tac tcg tac 240
Thr Leu Arg Phe Ile Pro Val Asp Arg Glu Asp Thr Ala Tyr Ser Tyr
65 70 75 80 aag gcg cgg ttc acc cta gct gtg ggt gat aac cgt gtg ctg gac atg 288
Lys Ala Arg Phe Thr Leu Ala Val Gly Asp Asn Arg Val Leu Asp Met
85 90 95 gct tcc acg tac ttt gac atc cgc ggc gtg ctg gac agg ggc cct act 336
Ala Ser Thr Tyr Phe Asp Ile Arg Gly Val Leu Asp Arg Gly Pro Thr
100 105 110 ttt aag ccc tac tct ggc act gcc tac aac gcc ctg gct ccc aag ggt 384
Phe Lys Pro Tyr Ser Gly Thr Ala Tyr Asn Ala Leu Ala Pro Lys Gly
115 120 125 gcc cca aat cct tgc gaa tgg gat gaa gct gct act gct ctt gaa ata 432
Ala Pro Asn Pro Cys Glu Trp Asp Glu Ala Ala Thr Ala Leu Glu Ile
130 135 140 aac cta gaa gaa gag gac gat gac aac gaa gac gaa gta gac gag caa 480
Asn Leu Glu Glu Glu Asp Asp Asp Asn Glu Asp Glu Val Asp Glu Gln
145 150 155 160

-continued

```
gct gag cag caa aaa act cac gta ttt ggg cag gcg cct tat tct ggt      528
Ala Glu Gln Gln Lys Thr His Val Phe Gly Gln Ala Pro Tyr Ser Gly
                165                 170                 175

ata aat att aca aag gag ggt att caa ata ggt gtc gaa ggt caa aca      576
Ile Asn Ile Thr Lys Glu Gly Ile Gln Ile Gly Val Glu Gly Gln Thr
            180                 185                 190

cct aaa tat gcc gat aaa aca ttt caa cct gaa cct caa ata gga gaa      624
Pro Lys Tyr Ala Asp Lys Thr Phe Gln Pro Glu Pro Gln Ile Gly Glu
        195                 200                 205

tct cag tgg tac gaa aca gaa att aat cat gca gct ggg aga gtc cta      672
Ser Gln Trp Tyr Glu Thr Glu Ile Asn His Ala Ala Gly Arg Val Leu
    210                 215                 220

aaa aag act acc cca atg aaa cca tgt tac ggt tca tat gca aaa ccc      720
Lys Lys Thr Thr Pro Met Lys Pro Cys Tyr Gly Ser Tyr Ala Lys Pro
225                 230                 235                 240

aca aat gaa aat gga ggg caa ggc att ctt gta aag caa caa aat gga      768
Thr Asn Glu Asn Gly Gly Gln Gly Ile Leu Val Lys Gln Gln Asn Gly
                245                 250                 255

aag cta gaa agt caa gtg gaa atg caa ttt ttc tca gct agc cag ggc      816
Lys Leu Glu Ser Gln Val Glu Met Gln Phe Phe Ser Ala Ser Gln Gly
            260                 265                 270

cct gga gct cca cag gga cca ggt gca cct caa ggg cct gga gcc cct      864
Pro Gly Ala Pro Gln Gly Pro Gly Ala Pro Gln Gly Pro Gly Ala Pro
        275                 280                 285

ggc act agc act act gag gca gcc gca ggc aat ggt gat aac ttg act      912
Gly Thr Ser Thr Thr Glu Ala Ala Ala Gly Asn Gly Asp Asn Leu Thr
    290                 295                 300

cct aaa gtg gta ttg tac agt gaa gat gta gat ata gaa acc cca gac      960
Pro Lys Val Val Leu Tyr Ser Glu Asp Val Asp Ile Glu Thr Pro Asp
305                 310                 315                 320

act cat att tct tac atg ccc act att aag gaa ggt aac tca cga gaa     1008
Thr His Ile Ser Tyr Met Pro Thr Ile Lys Glu Gly Asn Ser Arg Glu
                325                 330                 335

cta atg ggc caa caa tct atg ccc aac agg cct aat tac att gct ttt     1056
Leu Met Gly Gln Gln Ser Met Pro Asn Arg Pro Asn Tyr Ile Ala Phe
            340                 345                 350

agg gac aat ttt att ggt cta atg tat tac aac agc acg ggt aat atg     1104
Arg Asp Asn Phe Ile Gly Leu Met Tyr Tyr Asn Ser Thr Gly Asn Met
        355                 360                 365

ggt gtt ctg gcg ggc caa gca tcg cag ttg aat gct gtt gta gat ttg     1152
Gly Val Leu Ala Gly Gln Ala Ser Gln Leu Asn Ala Val Val Asp Leu
    370                 375                 380

caa gac aga aac aca gag ctt tca tac cag ctt ttg ctt gat tcc att     1200
Gln Asp Arg Asn Thr Glu Leu Ser Tyr Gln Leu Leu Leu Asp Ser Ile
385                 390                 395                 400

ggt gat aga acc agg tac ttt tct atg tgg aat cag gct gtt gac agc     1248
Gly Asp Arg Thr Arg Tyr Phe Ser Met Trp Asn Gln Ala Val Asp Ser
                405                 410                 415

tat gat cca gat gtt aga att att gaa aat cat gga act gaa gat gaa     1296
Tyr Asp Pro Asp Val Arg Ile Ile Glu Asn His Gly Thr Glu Asp Glu
            420                 425                 430

ctt cca aat tac tgc ttt cca ctg gga ggt gtg att aat aca gag act     1344
Leu Pro Asn Tyr Cys Phe Pro Leu Gly Gly Val Ile Asn Thr Glu Thr
        435                 440                 445

ctt acc aag gta aaa cct aaa aca ggt cag gaa aat gga tgg gaa aaa     1392
Leu Thr Lys Val Lys Pro Lys Thr Gly Gln Glu Asn Gly Trp Glu Lys
    450                 455                 460

gat gct aca gaa ttt tca gat aaa aat gaa ata aga gtt gga aat aat     1440
Asp Ala Thr Glu Phe Ser Asp Lys Asn Glu Ile Arg Val Gly Asn Asn
465                 470                 475                 480
```

```
ttt gcc atg gaa atc aat cta aat gcc aac ctg tgg aga aat ttc ctg      1488
Phe Ala Met Glu Ile Asn Leu Asn Ala Asn Leu Trp Arg Asn Phe Leu
            485                 490                 495

tac tcc aac ata gcg ctg tat ttg ccc gac aag cta aag tac agt cct      1536
Tyr Ser Asn Ile Ala Leu Tyr Leu Pro Asp Lys Leu Lys Tyr Ser Pro
        500                 505                 510

tcc aac gta aaa att tct gat aac cca aac acc tac gac tac atg aac      1584
Ser Asn Val Lys Ile Ser Asp Asn Pro Asn Thr Tyr Asp Tyr Met Asn
    515                 520                 525

aag cga gtg gtg gct ccc ggg cta gtg gac tgc tac att aac ctt gga      1632
Lys Arg Val Val Ala Pro Gly Leu Val Asp Cys Tyr Ile Asn Leu Gly
    530                 535                 540

gca cgc tgg tcc ctt gac tat atg gac aac gtc aac cca ttt aac cac      1680
Ala Arg Trp Ser Leu Asp Tyr Met Asp Asn Val Asn Pro Phe Asn His
545                 550                 555                 560

cac cgc aat gct ggc ctg cgc tac cgc tca atg ttg ctg ggc aat ggt      1728
His Arg Asn Ala Gly Leu Arg Tyr Arg Ser Met Leu Leu Gly Asn Gly
            565                 570                 575

cgc tat gtg ccc ttc cac atc cag gtg cct cag aag ttc ttt gcc att      1776
Arg Tyr Val Pro Phe His Ile Gln Val Pro Gln Lys Phe Phe Ala Ile
        580                 585                 590

aaa aac ctc ctt ctc ctg ccg ggc tca tac acc tac gag tgg aac ttc      1824
Lys Asn Leu Leu Leu Leu Pro Gly Ser Tyr Thr Tyr Glu Trp Asn Phe
    595                 600                 605

agg aag gat gtt aac atg gtt ctg cag agc tcc cta gga aat gac cta      1872
Arg Lys Asp Val Asn Met Val Leu Gln Ser Ser Leu Gly Asn Asp Leu
    610                 615                 620

agg gtt gac gga gcc agc att aag ttt gat agc att tgc ctt tac gcc      1920
Arg Val Asp Gly Ala Ser Ile Lys Phe Asp Ser Ile Cys Leu Tyr Ala
625                 630                 635                 640

acc ttc ttc ccc atg gcc cac aac acc gcc tcc acg ctt gag gcc atg      1968
Thr Phe Phe Pro Met Ala His Asn Thr Ala Ser Thr Leu Glu Ala Met
            645                 650                 655

ctt aga aac gac acc aac gac cag tcc ttt aac gac tat ctc tcc gcc      2016
Leu Arg Asn Asp Thr Asn Asp Gln Ser Phe Asn Asp Tyr Leu Ser Ala
        660                 665                 670

gcc aac atg ctc tac cct ata ccc gcc aac gct acc aac gtg ccc ata      2064
Ala Asn Met Leu Tyr Pro Ile Pro Ala Asn Ala Thr Asn Val Pro Ile
    675                 680                 685

tcc atc ccc tcc cgc aac tgg gcg gct ttc cgc ggc tgg gcc ttc acg      2112
Ser Ile Pro Ser Arg Asn Trp Ala Ala Phe Arg Gly Trp Ala Phe Thr
    690                 695                 700

cgc ctt aag act aag gaa acc cca tca ctg ggc tcg ggc tac gac cct      2160
Arg Leu Lys Thr Lys Glu Thr Pro Ser Leu Gly Ser Gly Tyr Asp Pro
705                 710                 715                 720

tat tac acc tac tct ggc tct ata ccc tac cta gat gga acc ttt tac      2208
Tyr Tyr Thr Tyr Ser Gly Ser Ile Pro Tyr Leu Asp Gly Thr Phe Tyr
            725                 730                 735

ctc aac cac acc ttt aag aag gtg gcc att acc ttt gac tct tct gtc      2256
Leu Asn His Thr Phe Lys Lys Val Ala Ile Thr Phe Asp Ser Ser Val
        740                 745                 750

agc tgg cct ggc aat gac cgc ctg ctt acc ccc aac gag ttt gaa att      2304
Ser Trp Pro Gly Asn Asp Arg Leu Leu Thr Pro Asn Glu Phe Glu Ile
    755                 760                 765

aag cgc tca gtt gac ggg gag ggt tac aac gtt gcc cag tgt aac atg      2352
Lys Arg Ser Val Asp Gly Glu Gly Tyr Asn Val Ala Gln Cys Asn Met
    770                 775                 780

acc aaa gac tgg ttc ctg gta caa atg cta gct aac tat aac att ggc      2400
Thr Lys Asp Trp Phe Leu Val Gln Met Leu Ala Asn Tyr Asn Ile Gly
```

```
785                 790                 795                 800

tac cag ggc ttc tat atc cca gag agc tac aag gac cgc atg tac tcc      2448
Tyr Gln Gly Phe Tyr Ile Pro Glu Ser Tyr Lys Asp Arg Met Tyr Ser
                805                 810                 815

ttc ttt aga aac ttc cag ccc atg agc cgt cag gtg gtg gat gat act      2496
Phe Phe Arg Asn Phe Gln Pro Met Ser Arg Gln Val Val Asp Asp Thr
            820                 825                 830

aaa tac aag gac tac caa cag gtg ggc atc cta cac caa cac aac aac      2544
Lys Tyr Lys Asp Tyr Gln Gln Val Gly Ile Leu His Gln His Asn Asn
        835                 840                 845

tct gga ttt gtt ggc tac ctt gcc ccc acc atg cgc gaa gga cag gcc      2592
Ser Gly Phe Val Gly Tyr Leu Ala Pro Thr Met Arg Glu Gly Gln Ala
    850                 855                 860

tac cct gct aac ttc ccc tat ccg ctt ata ggc aag acc gca gtt gac      2640
Tyr Pro Ala Asn Phe Pro Tyr Pro Leu Ile Gly Lys Thr Ala Val Asp
865                 870                 875                 880

agc att acc cag aaa aag ttt ctt tgc gat cgc acc ctt tgg cgc atc      2688
Ser Ile Thr Gln Lys Lys Phe Leu Cys Asp Arg Thr Leu Trp Arg Ile
                885                 890                 895

cca ttc tcc agt aac ttt atg tcc atg ggc gca ctc aca gac ctg ggc      2736
Pro Phe Ser Ser Asn Phe Met Ser Met Gly Ala Leu Thr Asp Leu Gly
            900                 905                 910

caa aac ctt ctc tac gcc aac tcc gcc cac gcg cta gac atg act ttt      2784
Gln Asn Leu Leu Tyr Ala Asn Ser Ala His Ala Leu Asp Met Thr Phe
        915                 920                 925

gag gtg gat ccc atg gac gag ccc acc ctt ctt tat gtt ttg ttt gaa      2832
Glu Val Asp Pro Met Asp Glu Pro Thr Leu Leu Tyr Val Leu Phe Glu
    930                 935                 940

gtc ttt gac gtg gtc cgt gtg cac cag ccg cac cgc ggc gtc atc gaa      2880
Val Phe Asp Val Val Arg Val His Gln Pro His Arg Gly Val Ile Glu
945                 950                 955                 960

acc gtg tac ctg cgc acg ccc ttc tcg gcc ggc aac gcc aca aca taa      2928
Thr Val Tyr Leu Arg Thr Pro Phe Ser Ala Gly Asn Ala Thr Thr
                965                 970                 975


<210> SEQ ID NO 24
<211> LENGTH: 1800
<212> TYPE: DNA
<213> ORGANISM: Artificial Sequence
<220> FEATURE:
<223> OTHER INFORMATION: (QGPGAP)3 modified fiber protein
<220> FEATURE:
<221> NAME/KEY: CDS
<222> LOCATION: (1)..(1797)

<400> SEQUENCE: 24

atg aag cgc gca aga ccg tct gaa gat acc ttc aac ccc gtg tat cca        48
Met Lys Arg Ala Arg Pro Ser Glu Asp Thr Phe Asn Pro Val Tyr Pro
1               5                   10                  15

tat gac acg gaa acc ggt cct cca act gtg cct ttt ctt act cct ccc        96
Tyr Asp Thr Glu Thr Gly Pro Pro Thr Val Pro Phe Leu Thr Pro Pro
            20                  25                  30

ttt gta tcc ccc aat ggg ttt caa gag agt ccc cct ggg gta ctc tct       144
Phe Val Ser Pro Asn Gly Phe Gln Glu Ser Pro Pro Gly Val Leu Ser
        35                  40                  45

ttg cgc cta tcc gaa cct cta gtt acc tcc aat ggc atg ctt gcg ctc       192
Leu Arg Leu Ser Glu Pro Leu Val Thr Ser Asn Gly Met Leu Ala Leu
    50                  55                  60

aaa atg ggc aac ggc ctc tct ctg gac gag gcc ggc aac ctt acc tcc       240
Lys Met Gly Asn Gly Leu Ser Leu Asp Glu Ala Gly Asn Leu Thr Ser
65                  70                  75                  80
```

-continued

```
caa aat gta acc act gtg agc cca cct ctc aaa aaa acc aag tca aac      288
Gln Asn Val Thr Thr Val Ser Pro Pro Leu Lys Lys Thr Lys Ser Asn
                 85                  90                  95

ata aac ctg gaa ata tct gca ccc ctc aca gtt acc tca gaa gcc cta      336
Ile Asn Leu Glu Ile Ser Ala Pro Leu Thr Val Thr Ser Glu Ala Leu
            100                 105                 110

act gtg gct gcc gcc gca cct cta atg gtc gcg ggc aac aca ctc acc      384
Thr Val Ala Ala Ala Ala Pro Leu Met Val Ala Gly Asn Thr Leu Thr
        115                 120                 125

atg caa tca cag gcc ccg cta acc gtg cac gac tcc aaa ctt agc att      432
Met Gln Ser Gln Ala Pro Leu Thr Val His Asp Ser Lys Leu Ser Ile
    130                 135                 140

gcc acc caa gga ccc ctc aca gtg tca gaa gga aag cta gcc ctg caa      480
Ala Thr Gln Gly Pro Leu Thr Val Ser Glu Gly Lys Leu Ala Leu Gln
145                 150                 155                 160

aca tca ggc ccc ctc acc acc acc gat agc agt acc ctt act atc act      528
Thr Ser Gly Pro Leu Thr Thr Thr Asp Ser Ser Thr Leu Thr Ile Thr
                165                 170                 175

gcc tca ccc cct cta act act gcc act ggt agc ttg ggc att gac ttg      576
Ala Ser Pro Pro Leu Thr Thr Ala Thr Gly Ser Leu Gly Ile Asp Leu
            180                 185                 190

aaa gag ccc att tat aca caa aat gga aaa cta gga cta aag tac ggg      624
Lys Glu Pro Ile Tyr Thr Gln Asn Gly Lys Leu Gly Leu Lys Tyr Gly
        195                 200                 205

gct cct ttg cat gta aca gac gac cta aac act ttg acc gta gca act      672
Ala Pro Leu His Val Thr Asp Asp Leu Asn Thr Leu Thr Val Ala Thr
    210                 215                 220

ggt cca ggt gtg act att aat aat act tcc ttg caa act aaa gtt act      720
Gly Pro Gly Val Thr Ile Asn Asn Thr Ser Leu Gln Thr Lys Val Thr
225                 230                 235                 240

gga gcc ttg ggt ttt gat tca caa ggc aat atg caa ctt aat gta gca      768
Gly Ala Leu Gly Phe Asp Ser Gln Gly Asn Met Gln Leu Asn Val Ala
                245                 250                 255

gga gga cta agg att gat tct caa aac aga cgc ctt ata ctt gat gtt      816
Gly Gly Leu Arg Ile Asp Ser Gln Asn Arg Arg Leu Ile Leu Asp Val
            260                 265                 270

agt tat ccg ttt gat gct caa aac caa cta aat cta aga cta gga cag      864
Ser Tyr Pro Phe Asp Ala Gln Asn Gln Leu Asn Leu Arg Leu Gly Gln
        275                 280                 285

ggc cct ctt ttt ata aac tca gcc cac aac ttg gat att aac tac aac      912
Gly Pro Leu Phe Ile Asn Ser Ala His Asn Leu Asp Ile Asn Tyr Asn
    290                 295                 300

aaa ggc ctt tac ttg ttt aca gct tca aac aat tcc aaa aag ctt gag      960
Lys Gly Leu Tyr Leu Phe Thr Ala Ser Asn Asn Ser Lys Lys Leu Glu
305                 310                 315                 320

gtt aac cta agc act gcc aag ggg ttg atg ttt gac gct aca gcc ata     1008
Val Asn Leu Ser Thr Ala Lys Gly Leu Met Phe Asp Ala Thr Ala Ile
                325                 330                 335

gcc att aat gca gga gat ggg ctt gaa ttt ggt tca cct aat gca cca     1056
Ala Ile Asn Ala Gly Asp Gly Leu Glu Phe Gly Ser Pro Asn Ala Pro
            340                 345                 350

aac aca aat ccc ctc aaa aca aaa att ggc cat ggc cta gaa ttt gat     1104
Asn Thr Asn Pro Leu Lys Thr Lys Ile Gly His Gly Leu Glu Phe Asp
        355                 360                 365

tca aac aag gct atg gtt cct aaa cta gga act ggc ctt agt ttt gac     1152
Ser Asn Lys Ala Met Val Pro Lys Leu Gly Thr Gly Leu Ser Phe Asp
    370                 375                 380

agc aca ggt gcc att aca gta gga aac aaa aat aat gat aag cta act     1200
Ser Thr Gly Ala Ile Thr Val Gly Asn Lys Asn Asn Asp Lys Leu Thr
385                 390                 395                 400
```

```
ttg tgg acc aca cca gct cca tct cct aac tgt aga cta aat gca gag      1248
Leu Trp Thr Thr Pro Ala Pro Ser Pro Asn Cys Arg Leu Asn Ala Glu
                405                 410                 415

aaa gat gct aaa ctc act ttg gtc tta aca aaa tgt ggc agt caa ata      1296
Lys Asp Ala Lys Leu Thr Leu Val Leu Thr Lys Cys Gly Ser Gln Ile
            420                 425                 430

ctt gct aca gtt tca gtt ttg gct gtt aaa ggc agt ttg gct cca ata      1344
Leu Ala Thr Val Ser Val Leu Ala Val Lys Gly Ser Leu Ala Pro Ile
        435                 440                 445

tct gga aca gtt caa agt gct cat ctt att ata aga ttt gac gaa aat      1392
Ser Gly Thr Val Gln Ser Ala His Leu Ile Ile Arg Phe Asp Glu Asn
    450                 455                 460

gga gtg cta cta aac aat tcc ttc ctg gac cca gaa tat tgg aac ttt      1440
Gly Val Leu Leu Asn Asn Ser Phe Leu Asp Pro Glu Tyr Trp Asn Phe
465                 470                 475                 480

aga aat gga gat ctt act gaa ggc aca gcc tat aca aac gct gtt gga      1488
Arg Asn Gly Asp Leu Thr Glu Gly Thr Ala Tyr Thr Asn Ala Val Gly
                485                 490                 495

ttt atg cct aac cta tca gct tat cca aaa tct cac ggt aaa act gcc      1536
Phe Met Pro Asn Leu Ser Ala Tyr Pro Lys Ser His Gly Lys Thr Ala
            500                 505                 510

aaa agt aac att gtc agt caa gtt tac tta aac gga gac aaa act aaa      1584
Lys Ser Asn Ile Val Ser Gln Val Tyr Leu Asn Gly Asp Lys Thr Lys
        515                 520                 525

cct gta aca cta acc att aca cta aac ggt aca cag gaa aca gga cag      1632
Pro Val Thr Leu Thr Ile Thr Leu Asn Gly Thr Gln Glu Thr Gly Gln
    530                 535                 540

ggc cct gga gct cca cag gga cca ggt gca cct caa ggg cct gga gcc      1680
Gly Pro Gly Ala Pro Gln Gly Pro Gly Ala Pro Gln Gly Pro Gly Ala
545                 550                 555                 560

cct gac aca act cca agt gca tac tct atg tca ttt tca tgg gac tgg      1728
Pro Asp Thr Thr Pro Ser Ala Tyr Ser Met Ser Phe Ser Trp Asp Trp
                565                 570                 575

tct ggc cac aac tac att aat gaa ata ttt gcc aca tcc tct tac act      1776
Ser Gly His Asn Tyr Ile Asn Glu Ile Phe Ala Thr Ser Ser Tyr Thr
            580                 585                 590

ttt tca tac att gcc caa gaa taa                                      1800
Phe Ser Tyr Ile Ala Gln Glu
        595


<210> SEQ ID NO 25
<211> LENGTH: 1794
<212> TYPE: DNA
<213> ORGANISM: Artificial Sequence
<220> FEATURE:
<223> OTHER INFORMATION: (NANP)4 modified fiber protein
<220> FEATURE:
<221> NAME/KEY: CDS
<222> LOCATION: (1)..(1791)

<400> SEQUENCE: 25

atg aag cgc gca aga ccg tct gaa gat acc ttc aac ccc gtg tat cca        48
Met Lys Arg Ala Arg Pro Ser Glu Asp Thr Phe Asn Pro Val Tyr Pro
1               5                   10                  15

tat gac acg gaa acc ggt cct cca act gtg cct ttt ctt act cct ccc        96
Tyr Asp Thr Glu Thr Gly Pro Pro Thr Val Pro Phe Leu Thr Pro Pro
            20                  25                  30

ttt gta tcc ccc aat ggg ttt caa gag agt ccc cct ggg gta ctc tct       144
Phe Val Ser Pro Asn Gly Phe Gln Glu Ser Pro Pro Gly Val Leu Ser
        35                  40                  45

ttg cgc cta tcc gaa cct cta gtt acc tcc aat ggc atg ctt gcg ctc       192
```

-continued

```
Leu Arg Leu Ser Glu Pro Leu Val Thr Ser Asn Gly Met Leu Ala Leu
    50                  55                  60

aaa atg ggc aac ggc ctc tct ctg gac gag gcc ggc aac ctt acc tcc      240
Lys Met Gly Asn Gly Leu Ser Leu Asp Glu Ala Gly Asn Leu Thr Ser
65                  70                  75                  80

caa aat gta acc act gtg agc cca cct ctc aaa aaa acc aag tca aac      288
Gln Asn Val Thr Thr Val Ser Pro Pro Leu Lys Lys Thr Lys Ser Asn
                85                  90                  95

ata aac ctg gaa ata tct gca ccc ctc aca gtt acc tca gaa gcc cta      336
Ile Asn Leu Glu Ile Ser Ala Pro Leu Thr Val Thr Ser Glu Ala Leu
            100                 105                 110

act gtg gct gcc gcc gca cct cta atg gtc gcg ggc aac aca ctc acc      384
Thr Val Ala Ala Ala Ala Pro Leu Met Val Ala Gly Asn Thr Leu Thr
        115                 120                 125

atg caa tca cag gcc ccg cta acc gtg cac gac tcc aaa ctt agc att      432
Met Gln Ser Gln Ala Pro Leu Thr Val His Asp Ser Lys Leu Ser Ile
    130                 135                 140

gcc acc caa gga ccc ctc aca gtg tca gaa gga aag cta gcc ctg caa      480
Ala Thr Gln Gly Pro Leu Thr Val Ser Glu Gly Lys Leu Ala Leu Gln
145                 150                 155                 160

aca tca ggc ccc ctc acc acc acc gat agc agt acc ctt act atc act      528
Thr Ser Gly Pro Leu Thr Thr Thr Asp Ser Ser Thr Leu Thr Ile Thr
                165                 170                 175

gcc tca ccc cct cta act act gcc act ggt agc ttg ggc att gac ttg      576
Ala Ser Pro Pro Leu Thr Thr Ala Thr Gly Ser Leu Gly Ile Asp Leu
            180                 185                 190

aaa gag ccc att tat aca caa aat gga aaa cta gga cta aag tac ggg      624
Lys Glu Pro Ile Tyr Thr Gln Asn Gly Lys Leu Gly Leu Lys Tyr Gly
        195                 200                 205

gct cct ttg cat gta aca gac gac cta aac act ttg acc gta gca act      672
Ala Pro Leu His Val Thr Asp Asp Leu Asn Thr Leu Thr Val Ala Thr
    210                 215                 220

ggt cca ggt gtg act att aat aat act tcc ttg caa act aaa gtt act      720
Gly Pro Gly Val Thr Ile Asn Asn Thr Ser Leu Gln Thr Lys Val Thr
225                 230                 235                 240

gga gcc ttg ggt ttt gat tca caa ggc aat atg caa ctt aat gta gca      768
Gly Ala Leu Gly Phe Asp Ser Gln Gly Asn Met Gln Leu Asn Val Ala
                245                 250                 255

gga gga cta agg att gat tct caa aac aga cgc ctt ata ctt gat gtt      816
Gly Gly Leu Arg Ile Asp Ser Gln Asn Arg Arg Leu Ile Leu Asp Val
            260                 265                 270

agt tat ccg ttt gat gct caa aac caa cta aat cta aga cta gga cag      864
Ser Tyr Pro Phe Asp Ala Gln Asn Gln Leu Asn Leu Arg Leu Gly Gln
        275                 280                 285

ggc cct ctt ttt ata aac tca gcc cac aac ttg gat att aac tac aac      912
Gly Pro Leu Phe Ile Asn Ser Ala His Asn Leu Asp Ile Asn Tyr Asn
    290                 295                 300

aaa ggc ctt tac ttg ttt aca gct tca aac aat tcc aaa aag ctt gag      960
Lys Gly Leu Tyr Leu Phe Thr Ala Ser Asn Asn Ser Lys Lys Leu Glu
305                 310                 315                 320

gtt aac cta agc act gcc aag ggg ttg atg ttt gac gct aca gcc ata     1008
Val Asn Leu Ser Thr Ala Lys Gly Leu Met Phe Asp Ala Thr Ala Ile
                325                 330                 335

gcc att aat gca gga gat ggg ctt gaa ttt ggt tca cct aat gca cca     1056
Ala Ile Asn Ala Gly Asp Gly Leu Glu Phe Gly Ser Pro Asn Ala Pro
            340                 345                 350

aac aca aat ccc ctc aaa aca aaa att ggc cat ggc cta gaa ttt gat     1104
Asn Thr Asn Pro Leu Lys Thr Lys Ile Gly His Gly Leu Glu Phe Asp
        355                 360                 365
```

```
tca aac aag gct atg gtt cct aaa cta gga act ggc ctt agt ttt gac     1152
Ser Asn Lys Ala Met Val Pro Lys Leu Gly Thr Gly Leu Ser Phe Asp
    370                 375                 380

agc aca ggt gcc att aca gta gga aac aaa aat aat gat aag cta act     1200
Ser Thr Gly Ala Ile Thr Val Gly Asn Lys Asn Asn Asp Lys Leu Thr
385                 390                 395                 400

ttg tgg acc aca cca gct cca tct cct aac tgt aga cta aat gca gag     1248
Leu Trp Thr Thr Pro Ala Pro Ser Pro Asn Cys Arg Leu Asn Ala Glu
                405                 410                 415

aaa gat gct aaa ctc act ttg gtc tta aca aaa tgt ggc agt caa ata     1296
Lys Asp Ala Lys Leu Thr Leu Val Leu Thr Lys Cys Gly Ser Gln Ile
            420                 425                 430

ctt gct aca gtt tca gtt ttg gct gtt aaa ggc agt ttg gct cca ata     1344
Leu Ala Thr Val Ser Val Leu Ala Val Lys Gly Ser Leu Ala Pro Ile
        435                 440                 445

tct gga aca gtt caa agt gct cat ctt att ata aga ttt gac gaa aat     1392
Ser Gly Thr Val Gln Ser Ala His Leu Ile Ile Arg Phe Asp Glu Asn
    450                 455                 460

gga gtg cta cta aac aat tcc ttc ctg gac cca gaa tat tgg aac ttt     1440
Gly Val Leu Leu Asn Asn Ser Phe Leu Asp Pro Glu Tyr Trp Asn Phe
465                 470                 475                 480

aga aat gga gat ctt act gaa ggc aca gcc tat aca aac gct gtt gga     1488
Arg Asn Gly Asp Leu Thr Glu Gly Thr Ala Tyr Thr Asn Ala Val Gly
                485                 490                 495

ttt atg cct aac cta tca gct tat cca aaa tct cac ggt aaa act gcc     1536
Phe Met Pro Asn Leu Ser Ala Tyr Pro Lys Ser His Gly Lys Thr Ala
            500                 505                 510

aaa agt aac att gtc agt caa gtt tac tta aac gga gac aaa act aaa     1584
Lys Ser Asn Ile Val Ser Gln Val Tyr Leu Asn Gly Asp Lys Thr Lys
        515                 520                 525

cct gta aca cta acc att aca cta aac ggt aca cag gaa aca gga aac     1632
Pro Val Thr Leu Thr Ile Thr Leu Asn Gly Thr Gln Glu Thr Gly Asn
    530                 535                 540

gct aat ccc aac gct aac cca aat gca aat cct aat gcc aac ccc gac     1680
Ala Asn Pro Asn Ala Asn Pro Asn Ala Asn Pro Asn Ala Asn Pro Asp
545                 550                 555                 560

aca act cca agt gca tac tct atg tca ttt tca tgg gac tgg tct ggc     1728
Thr Thr Pro Ser Ala Tyr Ser Met Ser Phe Ser Trp Asp Trp Ser Gly
                565                 570                 575

cac aac tac att aat gaa ata ttt gcc aca tcc tct tac act ttt tca     1776
His Asn Tyr Ile Asn Glu Ile Phe Ala Thr Ser Ser Tyr Thr Phe Ser
            580                 585                 590

tac att gcc caa gaa taa                                             1794
Tyr Ile Ala Gln Glu
        595
```

<210> SEQ ID NO 26
<211> LENGTH: 684
<212> TYPE: DNA
<213> ORGANISM: Artificial Sequence
<220> FEATURE:
<223> OTHER INFORMATION: P. yoelii CD4+ epitope modified pVII sequence
<220> FEATURE:
<221> NAME/KEY: CDS
<222> LOCATION: (1)..(681)

<400> SEQUENCE: 26

```
atg tcc atc ctt ata tcg ccc agc aat aac aca ggc tgg ggc ctg cgc       48
Met Ser Ile Leu Ile Ser Pro Ser Asn Asn Thr Gly Trp Gly Leu Arg
1               5                   10                  15

ttc cca agc aag atg ttt ggc ggg gcc aag aag cgc tcc gac caa cac       96
Phe Pro Ser Lys Met Phe Gly Gly Ala Lys Lys Arg Ser Asp Gln His
```

```
            20                  25                  30

cca gtg cgc gtg cgc ggg cac tac cgc gcg ccc tgg ggc gcg cac aaa      144
Pro Val Arg Val Arg Gly His Tyr Arg Ala Pro Trp Gly Ala His Lys
        35                  40                  45

cgc ggc cgc act ggg cgc acc acc gtc gat gac gcc atc gac gcg gtg      192
Arg Gly Arg Thr Gly Arg Thr Thr Val Asp Asp Ala Ile Asp Ala Val
    50                  55                  60

gtg gag gag gcg cgc aac tac acg ccc acg ccg cca cca gtg tcc aca      240
Val Glu Glu Ala Arg Asn Tyr Thr Pro Thr Pro Pro Pro Val Ser Thr
65                  70                  75                  80

gtg gac gcg gcc att cag acc gtg gtg cgc gga gcc cgg cgc tat gct      288
Val Asp Ala Ala Ile Gln Thr Val Val Arg Gly Ala Arg Arg Tyr Ala
                85                  90                  95

aaa atg aag aga cgg cgg agg cgc gta gca cgt cgc cac cgc cgc cga      336
Lys Met Lys Arg Arg Arg Arg Arg Val Ala Arg Arg His Arg Arg Arg
            100                 105                 110

ccc ggc act gcc gcc caa cgc gcg gcg gcg gcc ctg ctt aac cgc gca      384
Pro Gly Thr Ala Ala Gln Arg Ala Ala Ala Ala Leu Leu Asn Arg Ala
        115                 120                 125

cgt cgc acc ggc cga cgg gcg gcc atg cgg gcc gct cga agg ctg gcc      432
Arg Arg Thr Gly Arg Arg Ala Ala Met Arg Ala Ala Arg Arg Leu Ala
    130                 135                 140

gcg ggt att gtc act gtg ccc ccc agg tcc agg cga cga gcg gcc gcc      480
Ala Gly Ile Val Thr Val Pro Pro Arg Ser Arg Arg Arg Ala Ala Ala
145                 150                 155                 160

gca gca gcc gcg gcc att agt gct atg act cag ggt cgc agg ggc aac      528
Ala Ala Ala Ala Ala Ile Ser Ala Met Thr Gln Gly Arg Arg Gly Asn
                165                 170                 175

gtg tat tgg gtg cgc gac tcg gtt agc ggc ctg cgc gtg ccc gtg cgc      576
Val Tyr Trp Val Arg Asp Ser Val Ser Gly Leu Arg Val Pro Val Arg
            180                 185                 190

acc cgc ccc ccg cgc aac gtg cgc acc cgc ccc ccg cgc aac tac aac      624
Thr Arg Pro Pro Arg Asn Val Arg Thr Arg Pro Pro Arg Asn Tyr Asn
        195                 200                 205

agg aac atc gtg aac agg ctg ctg ggc gac gcc ctg aac ggc aag ccc      672
Arg Asn Ile Val Asn Arg Leu Leu Gly Asp Ala Leu Asn Gly Lys Pro
    210                 215                 220

gag gag aag tag                                                      684
Glu Glu Lys
225


<210> SEQ ID NO 27
<211> LENGTH: 657
<212> TYPE: DNA
<213> ORGANISM: Artificial Sequence
<220> FEATURE:
<223> OTHER INFORMATION: P. falciparum CD4+ epitope modified pVII-1
      sequence
<220> FEATURE:
<221> NAME/KEY: CDS
<222> LOCATION: (1)..(654)

<400> SEQUENCE: 27

atg tcc atc ctt ata tcg ccc agc aat aac aca ggc tgg ggc ctg cgc       48
Met Ser Ile Leu Ile Ser Pro Ser Asn Asn Thr Gly Trp Gly Leu Arg
1               5                   10                  15

ttc cca agc aag atg ttt ggc ggg gcc aag aag cgc tcc gac caa cac       96
Phe Pro Ser Lys Met Phe Gly Gly Ala Lys Lys Arg Ser Asp Gln His
            20                  25                  30

cca gtg cgc gtg cgc ggg cac tac cgc gcg ccc tgg ggc gcg cac aaa      144
Pro Val Arg Val Arg Gly His Tyr Arg Ala Pro Trp Gly Ala His Lys
        35                  40                  45
```

```
cgc ggc cgc act ggg cgc acc acc gtc gat gac gcc atc gac gcg gtg      192
Arg Gly Arg Thr Gly Arg Thr Thr Val Asp Asp Ala Ile Asp Ala Val
    50                  55                  60

gtg gag gag gcg cgc aac tac acg ccc acg ccg cca cca gtg tcc aca      240
Val Glu Glu Ala Arg Asn Tyr Thr Pro Thr Pro Pro Pro Val Ser Thr
65                  70                  75                  80

gtg gac gcg gcc att cag acc gtg gtg cgc gga gcc cgg cgc tat gct      288
Val Asp Ala Ala Ile Gln Thr Val Val Arg Gly Ala Arg Arg Tyr Ala
                85                  90                  95

aaa atg aag aga cgg cgg agg cgc gta gca cgt cgc cac cgc cgc cga      336
Lys Met Lys Arg Arg Arg Arg Arg Val Ala Arg Arg His Arg Arg Arg
            100                 105                 110

ccc ggc act gcc gcc caa cgc gcg gcg gcg gcc ctg ctt aac cgc gca      384
Pro Gly Thr Ala Ala Gln Arg Ala Ala Ala Ala Leu Leu Asn Arg Ala
        115                 120                 125

cgt cgc acc ggc cga cgg gcg gcc atg cgg gcc gct cga agg ctg gcc      432
Arg Arg Thr Gly Arg Arg Ala Ala Met Arg Ala Ala Arg Arg Leu Ala
    130                 135                 140

gcg ggt att gtc act gtg ccc ccc agg tcc agg cga cga gcg gcc gcc      480
Ala Gly Ile Val Thr Val Pro Pro Arg Ser Arg Arg Arg Ala Ala Ala
145                 150                 155                 160

gca gca gcc gcg gcc att agt gct atg act cag ggt cgc agg ggc aac      528
Ala Ala Ala Ala Ala Ile Ser Ala Met Thr Gln Gly Arg Arg Gly Asn
                165                 170                 175

gtg tat tgg gtg cgc gac tcg gtt agc ggc ctg cgc gtg ccc gtg cgc      576
Val Tyr Trp Val Arg Asp Ser Val Ser Gly Leu Arg Val Pro Val Arg
            180                 185                 190

acc cgc ccc ccg cgc aac gaa tat ttg aac aag att caa aac tcc ctc      624
Thr Arg Pro Pro Arg Asn Glu Tyr Leu Asn Lys Ile Gln Asn Ser Leu
        195                 200                 205

tca aca gaa tgg tct cct tgc agc gtg act tag                          657
Ser Thr Glu Trp Ser Pro Cys Ser Val Thr
    210                 215
```

```
<210> SEQ ID NO 28
<211> LENGTH: 741
<212> TYPE: DNA
<213> ORGANISM: Artificial Sequence
<220> FEATURE:
<223> OTHER INFORMATION: P. falciparum CD4+ epitope modified pVII-2
      sequence
<220> FEATURE:
<221> NAME/KEY: CDS
<222> LOCATION: (1)..(738)

<400> SEQUENCE: 28
```

```
atg tcc atc ctt ata tcg ccc agc aat aac aca ggc tgg ggc ctg cgc       48
Met Ser Ile Leu Ile Ser Pro Ser Asn Asn Thr Gly Trp Gly Leu Arg
1               5                   10                  15

ttc cca agc aag atg ttt ggc ggg gcc aag aag cgc tcc gac caa cac       96
Phe Pro Ser Lys Met Phe Gly Gly Ala Lys Lys Arg Ser Asp Gln His
            20                  25                  30

cca gtg cgc gtg cgc ggg cac tac cgc gcg ccc tgg ggc gcg cac aaa      144
Pro Val Arg Val Arg Gly His Tyr Arg Ala Pro Trp Gly Ala His Lys
        35                  40                  45

cgc ggc cgc act ggg cgc acc acc gtc gat gac gcc atc gac gcg gtg      192
Arg Gly Arg Thr Gly Arg Thr Thr Val Asp Asp Ala Ile Asp Ala Val
    50                  55                  60

gtg gag gag gcg cgc aac tac acg ccc acg ccg cca cca gtg tcc aca      240
Val Glu Glu Ala Arg Asn Tyr Thr Pro Thr Pro Pro Pro Val Ser Thr
65                  70                  75                  80
```

```
gtg gac gcg gcc att cag acc gtg gtg cgc gga gcc gaa tat ttg aac      288
Val Asp Ala Ala Ile Gln Thr Val Val Arg Gly Ala Glu Tyr Leu Asn
                85                  90                  95

aag att caa aac tcc ctc tca aca gaa tgg tct cct tgc agc gtg act      336
Lys Ile Gln Asn Ser Leu Ser Thr Glu Trp Ser Pro Cys Ser Val Thr
            100                 105                 110

cgg cgc tat gct aaa atg aag aga cgg cgg agg cgc gta gca cgt cgc      384
Arg Arg Tyr Ala Lys Met Lys Arg Arg Arg Arg Arg Val Ala Arg Arg
        115                 120                 125

cac cgc cgc cga ccc ggc act gcc gcc caa cgc gcg gcg gcg gcc ctg      432
His Arg Arg Arg Pro Gly Thr Ala Ala Gln Arg Ala Ala Ala Ala Leu
    130                 135                 140

ctt aac cgc gca cgt cgc acc ggc cga cgg gcg gcc atg cgg gcc gct      480
Leu Asn Arg Ala Arg Arg Thr Gly Arg Arg Ala Ala Met Arg Ala Ala
145                 150                 155                 160

cga agg ctg gcc gcg ggt att gtc act gtg ccc ccc agg tcc agg cga      528
Arg Arg Leu Ala Ala Gly Ile Val Thr Val Pro Pro Arg Ser Arg Arg
                165                 170                 175

cga gcg gcc gcc gca gca gcc gcg gcc att agt gct atg act cag ggt      576
Arg Ala Ala Ala Ala Ala Ala Ala Ala Ile Ser Ala Met Thr Gln Gly
            180                 185                 190

cgc agg ggc aac gtg tat tgg gtg cgc gac tcg gtt agc ggc ctg cgc      624
Arg Arg Gly Asn Val Tyr Trp Val Arg Asp Ser Val Ser Gly Leu Arg
        195                 200                 205

gtg ccc gtg cgc acc cgc ccc ccg cgc aac gtg cgc acc cgc ccc ccg      672
Val Pro Val Arg Thr Arg Pro Pro Arg Asn Val Arg Thr Arg Pro Pro
    210                 215                 220

cgc aac tac aac agg aac atc gtg aac agg ctg ctg ggc gac gcc ctg      720
Arg Asn Tyr Asn Arg Asn Ile Val Asn Arg Leu Leu Gly Asp Ala Leu
225                 230                 235                 240

acc cgc ccc ccg cgc aac tag                                          741
Thr Arg Pro Pro Arg Asn
                245
```

<210> SEQ ID NO 29
<211> LENGTH: 681
<212> TYPE: DNA
<213> ORGANISM: Artificial Sequence
<220> FEATURE:
<223> OTHER INFORMATION: P. falciparum CD4+ epitope modified PVII-3 sequence
<220> FEATURE:
<221> NAME/KEY: CDS
<222> LOCATION: (1)..(678)

<400> SEQUENCE: 29

```
atg tcc atc ctt ata tcg ccc agc aat aac aca ggc tgg ggc ctg cgc       48
Met Ser Ile Leu Ile Ser Pro Ser Asn Asn Thr Gly Trp Gly Leu Arg
1               5                   10                  15

ttc cca agc aag atg ttt ggc ggg gcc aag aag cgc tcc gac caa cac       96
Phe Pro Ser Lys Met Phe Gly Gly Ala Lys Lys Arg Ser Asp Gln His
            20                  25                  30

cca gtg cgc gtg cgc ggg cac tac cgc gcg ccc tgg ggc gcg cac aaa      144
Pro Val Arg Val Arg Gly His Tyr Arg Ala Pro Trp Gly Ala His Lys
        35                  40                  45

cgc ggc cgc act ggg cgc acc acc gtc gat gac gcc atc gac gcg gtg      192
Arg Gly Arg Thr Gly Arg Thr Thr Val Asp Asp Ala Ile Asp Ala Val
    50                  55                  60

gtg gag gag gcg cgc aac tac acg ccc acg ccg cca cca gtg tcc aca      240
Val Glu Glu Ala Arg Asn Tyr Thr Pro Thr Pro Pro Pro Val Ser Thr
65                  70                  75                  80

gtg gac gcg gcc att cag acc gtg gtg cgc gga gcc cgg cgc tat gct      288
```

```
Val Asp Ala Ala Ile Gln Thr Val Val Arg Gly Ala Arg Arg Tyr Ala
                85                  90                  95

aaa atg aag aga cgg cgg agg cgc gta gca cgt cgc cac cgc cgc cga      336
Lys Met Lys Arg Arg Arg Arg Arg Val Ala Arg Arg His Arg Arg Arg
            100                 105                 110

ccc ggc act gcc gcc caa cgc gcg gcg gcg gcc ctg ctt aac cgc gca      384
Pro Gly Thr Ala Ala Gln Arg Ala Ala Ala Ala Leu Leu Asn Arg Ala
        115                 120                 125

cgt cgc acc ggc cga cgg gcg gcc atg cgg gcc gct gaa tat ttg aac      432
Arg Arg Thr Gly Arg Arg Ala Ala Met Arg Ala Ala Glu Tyr Leu Asn
    130                 135                 140

aag att caa aac tcc ctc tca aca gaa tgg tct cct tgc agc gtg act      480
Lys Ile Gln Asn Ser Leu Ser Thr Glu Trp Ser Pro Cys Ser Val Thr
145                 150                 155                 160

cga agg ctg gcc gcg ggt att gtc act gtg ccc ccc agg tcc agg cga      528
Arg Arg Leu Ala Ala Gly Ile Val Thr Val Pro Pro Arg Ser Arg Arg
                165                 170                 175

cga gcg gcc gcc gca gca gcc gcg gcc att agt gct atg act cag ggt      576
Arg Ala Ala Ala Ala Ala Ala Ala Ala Ile Ser Ala Met Thr Gln Gly
            180                 185                 190

cgc agg ggc aac gtg tat tgg gtg cgc gac tcg gtt agc ggc ctg cgc      624
Arg Arg Gly Asn Val Tyr Trp Val Arg Asp Ser Val Ser Gly Leu Arg
        195                 200                 205

gtg ccc gtg cgc acc cgc ccc ccg cgc aac gtg cgc acc cgc ccc ccg      672
Val Pro Val Arg Thr Arg Pro Pro Arg Asn Val Arg Thr Arg Pro Pro
    210                 215                 220

cgc aac tag                                                          681
Arg Asn
225


<210> SEQ ID NO 30
<211> LENGTH: 369
<212> TYPE: PRT
<213> ORGANISM: Artificial Sequence
<220> FEATURE:
<223> OTHER INFORMATION: Synthetic Construct

<400> SEQUENCE: 30

Met Lys Lys Cys Thr Ile Leu Val Val Ala Ser Leu Leu Leu Val Asp
1               5                   10                  15

Ser Leu Leu Pro Gly Tyr Gly Gln Asn Lys Ser Val Gln Ala Gln Arg
            20                  25                  30

Asn Leu Asn Glu Leu Cys Tyr Asn Glu Glu Asn Asp Asn Lys Leu Tyr
        35                  40                  45

His Val Leu Asn Ser Lys Asn Gly Lys Ile Tyr Asn Arg Asn Ile Val
    50                  55                  60

Asn Arg Leu Leu Gly Asp Ala Leu Asn Gly Lys Pro Glu Glu Lys Lys
65                  70                  75                  80

Asp Asp Pro Pro Lys Asp Asp Asn Lys Asp Asp Leu Pro Lys Glu Glu
                85                  90                  95

Lys Lys Asp Asp Leu Pro Lys Glu Glu Lys Lys Asp Asp Pro Pro Lys
            100                 105                 110

Asp Pro Lys Lys Asp Asp Pro Pro Lys Glu Ala Gln Asn Lys Leu Asn
        115                 120                 125

Gln Pro Val Val Ala Asp Glu Asn Val Asp Gln Gly Pro Gly Ala Pro
    130                 135                 140

Gln Gly Pro Gly Ala Pro Gln Gly Pro Gly Ala Pro Gln Gly Pro Gly
145                 150                 155                 160
```

Ala Pro Gln Gly Pro Gly Ala Pro Gln Gly Pro Gly Ala Pro Gln Gly
165 170 175

Pro Gly Ala Pro Gln Gly Pro Gly Ala Pro Gln Gly Pro Gly Ala Pro
180 185 190

Gln Gly Pro Gly Ala Pro Gln Gly Pro Gly Ala Pro Gln Gly Pro Gly
195 200 205

Ala Pro Gln Gly Pro Gly Ala Pro Gln Gly Pro Gly Ala Pro Gln Gly
210 215 220

Pro Gly Ala Pro Gln Gly Pro Gly Ala Pro Gln Gly Pro Gly Ala Pro
225 230 235 240

Gln Gly Pro Gly Ala Pro Gln Gly Pro Gly Ala Pro Gln Glu Pro Pro
245 250 255

Gln Gln Pro Pro Gln Gln Pro Pro Gln Gln Pro Pro Gln Gln Pro Pro
260 265 270

Gln Gln Pro Pro Gln Gln Pro Asn Asn Asn Asn Asn Asn Asn Gly Asn
275 280 285

Asn Asn Glu Asp Ser Tyr Val Pro Ser Ala Glu Gln Ile Leu Glu Phe
290 295 300

Val Lys Gln Ile Ser Ser Gln Leu Thr Glu Glu Trp Ser Gln Cys Ser
305 310 315 320

Val Thr Cys Gly Ser Gly Val Arg Val Arg Lys Arg Lys Asn Val Asn
325 330 335

Lys Gln Pro Glu Asn Leu Thr Leu Glu Asp Ile Asp Thr Glu Ile Cys
340 345 350

Lys Met Asp Lys Cys Ser Ser Ile Phe Asn Ile Val Ser Asn Ser Leu
355 360 365

Gly

<210> SEQ ID NO 31
<211> LENGTH: 943
<212> TYPE: PRT
<213> ORGANISM: Artificial Sequence
<220> FEATURE:
<223> OTHER INFORMATION: Synthetic Construct

<400> SEQUENCE: 31

Met Ala Thr Pro Ser Met Met Pro Gln Trp Ser Tyr Met His Ile Ser
1 5 10 15

Gly Gln Asp Ala Ser Glu Tyr Leu Ser Pro Gly Leu Val Gln Phe Ala
20 25 30

Arg Ala Thr Glu Thr Tyr Phe Ser Leu Asn Asn Lys Phe Arg Asn Pro
35 40 45

Thr Val Ala Pro Thr His Asp Val Thr Thr Asp Arg Ser Gln Arg Leu
50 55 60

Thr Leu Arg Phe Ile Pro Val Asp Arg Glu Asp Thr Ala Tyr Ser Tyr
65 70 75 80

Lys Ala Arg Phe Thr Leu Ala Val Gly Asp Asn Arg Val Leu Asp Met
85 90 95

Ala Ser Thr Tyr Phe Asp Ile Arg Gly Val Leu Asp Arg Gly Pro Thr
100 105 110

Phe Lys Pro Tyr Ser Gly Thr Ala Tyr Asn Ala Leu Ala Pro Lys Gly
115 120 125

Ala Pro Asn Pro Cys Glu Trp Asp Glu Gln Gly Pro Gly Ala Pro Gln
130 135 140

Gly Pro Gly Ala Pro Gln Gly Pro Gly Ala Pro Lys Thr His Val Phe

-continued

```
145                 150                 155                 160

Gly Gln Ala Pro Tyr Ser Gly Ile Asn Ile Thr Lys Glu Gly Ile Gln
                165                 170                 175

Ile Gly Val Glu Gly Gln Thr Pro Lys Tyr Ala Asp Lys Thr Phe Gln
            180                 185                 190

Pro Glu Pro Gln Ile Gly Glu Ser Gln Trp Tyr Glu Thr Glu Ile Asn
        195                 200                 205

His Ala Ala Gly Arg Val Leu Lys Lys Thr Thr Pro Met Lys Pro Cys
    210                 215                 220

Tyr Gly Ser Tyr Ala Lys Pro Thr Asn Glu Asn Gly Gly Gln Gly Ile
225                 230                 235                 240

Leu Val Lys Gln Gln Asn Gly Lys Leu Glu Ser Gln Val Glu Met Gln
                245                 250                 255

Phe Phe Ser Thr Thr Glu Ala Ala Ala Gly Asn Gly Asp Asn Leu Thr
            260                 265                 270

Pro Lys Val Val Leu Tyr Ser Glu Asp Val Asp Ile Glu Thr Pro Asp
        275                 280                 285

Thr His Ile Ser Tyr Met Pro Thr Ile Lys Glu Gly Asn Ser Arg Glu
    290                 295                 300

Leu Met Gly Gln Gln Ser Met Pro Asn Arg Pro Asn Tyr Ile Ala Phe
305                 310                 315                 320

Arg Asp Asn Phe Ile Gly Leu Met Tyr Tyr Asn Ser Thr Gly Asn Met
                325                 330                 335

Gly Val Leu Ala Gly Gln Ala Ser Gln Leu Asn Ala Val Val Asp Leu
            340                 345                 350

Gln Asp Arg Asn Thr Glu Leu Ser Tyr Gln Leu Leu Leu Asp Ser Ile
        355                 360                 365

Gly Asp Arg Thr Arg Tyr Phe Ser Met Trp Asn Gln Ala Val Asp Ser
    370                 375                 380

Tyr Asp Pro Asp Val Arg Ile Ile Glu Asn His Gly Thr Glu Asp Glu
385                 390                 395                 400

Leu Pro Asn Tyr Cys Phe Pro Leu Gly Gly Val Ile Asn Thr Glu Thr
                405                 410                 415

Leu Thr Lys Val Lys Pro Lys Thr Gly Gln Glu Asn Gly Trp Glu Lys
            420                 425                 430

Asp Ala Thr Glu Phe Ser Asp Lys Asn Glu Ile Arg Val Gly Asn Asn
        435                 440                 445

Phe Ala Met Glu Ile Asn Leu Asn Ala Asn Leu Trp Arg Asn Phe Leu
    450                 455                 460

Tyr Ser Asn Ile Ala Leu Tyr Leu Pro Asp Lys Leu Lys Tyr Ser Pro
465                 470                 475                 480

Ser Asn Val Lys Ile Ser Asp Asn Pro Asn Thr Tyr Asp Tyr Met Asn
                485                 490                 495

Lys Arg Val Val Ala Pro Gly Leu Val Asp Cys Tyr Ile Asn Leu Gly
            500                 505                 510

Ala Arg Trp Ser Leu Asp Tyr Met Asp Asn Val Asn Pro Phe Asn His
        515                 520                 525

His Arg Asn Ala Gly Leu Arg Tyr Arg Ser Met Leu Leu Gly Asn Gly
    530                 535                 540

Arg Tyr Val Pro Phe His Ile Gln Val Pro Gln Lys Phe Phe Ala Ile
545                 550                 555                 560

Lys Asn Leu Leu Leu Leu Pro Gly Ser Tyr Thr Tyr Glu Trp Asn Phe
                565                 570                 575
```

Arg Lys Asp Val Asn Met Val Leu Gln Ser Ser Leu Gly Asn Asp Leu
580 585 590

Arg Val Asp Gly Ala Ser Ile Lys Phe Asp Ser Ile Cys Leu Tyr Ala
595 600 605

Thr Phe Phe Pro Met Ala His Asn Thr Ala Ser Thr Leu Glu Ala Met
610 615 620

Leu Arg Asn Asp Thr Asn Asp Gln Ser Phe Asn Asp Tyr Leu Ser Ala
625 630 635 640

Ala Asn Met Leu Tyr Pro Ile Pro Ala Asn Ala Thr Asn Val Pro Ile
645 650 655

Ser Ile Pro Ser Arg Asn Trp Ala Ala Phe Arg Gly Trp Ala Phe Thr
660 665 670

Arg Leu Lys Thr Lys Glu Thr Pro Ser Leu Gly Ser Gly Tyr Asp Pro
675 680 685

Tyr Tyr Thr Tyr Ser Gly Ser Ile Pro Tyr Leu Asp Gly Thr Phe Tyr
690 695 700

Leu Asn His Thr Phe Lys Lys Val Ala Ile Thr Phe Asp Ser Ser Val
705 710 715 720

Ser Trp Pro Gly Asn Asp Arg Leu Leu Thr Pro Asn Glu Phe Glu Ile
725 730 735

Lys Arg Ser Val Asp Gly Glu Gly Tyr Asn Val Ala Gln Cys Asn Met
740 745 750

Thr Lys Asp Trp Phe Leu Val Gln Met Leu Ala Asn Tyr Asn Ile Gly
755 760 765

Tyr Gln Gly Phe Tyr Ile Pro Glu Ser Tyr Lys Asp Arg Met Tyr Ser
770 775 780

Phe Phe Arg Asn Phe Gln Pro Met Ser Arg Gln Val Val Asp Asp Thr
785 790 795 800

Lys Tyr Lys Asp Tyr Gln Gln Val Gly Ile Leu His Gln His Asn Asn
805 810 815

Ser Gly Phe Val Gly Tyr Leu Ala Pro Thr Met Arg Glu Gly Gln Ala
820 825 830

Tyr Pro Ala Asn Phe Pro Tyr Pro Leu Ile Gly Lys Thr Ala Val Asp
835 840 845

Ser Ile Thr Gln Lys Lys Phe Leu Cys Asp Arg Thr Leu Trp Arg Ile
850 855 860

Pro Phe Ser Ser Asn Phe Met Ser Met Gly Ala Leu Thr Asp Leu Gly
865 870 875 880

Gln Asn Leu Leu Tyr Ala Asn Ser Ala His Ala Leu Asp Met Thr Phe
885 890 895

Glu Val Asp Pro Met Asp Glu Pro Thr Leu Leu Tyr Val Leu Phe Glu
900 905 910

Val Phe Asp Val Val Arg Val His Gln Pro His Arg Gly Val Ile Glu
915 920 925

Thr Val Tyr Leu Arg Thr Pro Phe Ser Ala Gly Asn Ala Thr Thr
930 935 940

<210> SEQ ID NO 32
<211> LENGTH: 929
<212> TYPE: PRT
<213> ORGANISM: Artificial Sequence
<220> FEATURE:
<223> OTHER INFORMATION: Synthetic Construct

<400> SEQUENCE: 32

-continued

```
Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Asp Glu Gln Gly Pro Gly Ala Pro Gln
    130                 135                 140

Gly Pro Gly Ala Pro Gln Gly Pro Gly Ala Pro Gln Gly Pro Gly Ala
145                 150                 155                 160

Pro Lys Thr His Val Phe Gly Gln Ala Pro Tyr Ser Gly Ile Asn Ile
                165                 170                 175

Thr Lys Glu Gly Ile Gln Ile Gly Val Glu Gly Gln Thr Pro Lys Tyr
            180                 185                 190

Ala Asp Lys Thr Phe Gln Pro Glu Pro Gln Ile Gly Glu Ser Gln Trp
        195                 200                 205

Tyr Glu Thr Glu Ile Asn His Ala Ala Gly Arg Val Leu Lys Lys Thr
    210                 215                 220

Thr Pro Met Lys Pro Cys Tyr Gly Ser Tyr Ala Lys Pro Thr Asn Glu
225                 230                 235                 240

Asn Gly Gly Gln Gly Ile Leu Val Lys Gln Gln Asn Gly Lys Leu Glu
                245                 250                 255

Ser Gln Val Glu Met Gln Phe Phe Ser Thr Thr Glu Ala Ala Ala Gly
            260                 265                 270

Asn Gly Asp Asn Leu Thr Pro Lys Val Val Leu Tyr Ser Glu Asp Val
        275                 280                 285

Asp Ile Glu Thr Pro Asp Thr His Ile Ser Tyr Met Pro Thr Ile Lys
    290                 295                 300

Glu Gly Asn Ser Arg Glu Leu Met Gly Gln Gln Ser Met Pro Asn Arg
305                 310                 315                 320

Pro Asn Tyr Ile Ala Phe Arg Asp Asn Phe Ile Gly Leu Met Tyr Tyr
                325                 330                 335

Asn Ser Thr Gly Asn Met Gly Val Leu Ala Gly Gln Ala Ser Gln Leu
            340                 345                 350

Asn Ala Val Val Asp Leu Gln Asp Arg Asn Thr Glu Leu Ser Tyr Gln
        355                 360                 365

Leu Leu Leu Asp Ser Ile Gly Asp Arg Thr Arg Tyr Phe Ser Met Trp
    370                 375                 380

Asn Gln Leu Pro Asn Tyr Cys Phe Pro Leu Gly Gly Val Ile Asn Thr
385                 390                 395                 400

Glu Thr Leu Thr Lys Val Lys Pro Lys Thr Gly Gln Glu Asn Gly Trp
                405                 410                 415
```

-continued

```
Glu Lys Asp Ala Thr Glu Phe Ser Asp Lys Asn Glu Ile Arg Val Gly
            420                 425                 430

Asn Asn Phe Ala Met Glu Ile Asn Leu Asn Ala Asn Leu Trp Arg Asn
        435                 440                 445

Phe Leu Tyr Ser Asn Ile Ala Leu Tyr Leu Pro Asp Lys Leu Lys Tyr
    450                 455                 460

Ser Pro Ser Asn Val Lys Ile Ser Asp Asn Pro Asn Thr Tyr Asp Tyr
465                 470                 475                 480

Met Asn Lys Arg Val Val Ala Pro Gly Leu Val Asp Cys Tyr Ile Asn
                485                 490                 495

Leu Gly Ala Arg Trp Ser Leu Asp Tyr Met Asp Asn Val Asn Pro Phe
            500                 505                 510

Asn His His Arg Asn Ala Gly Leu Arg Tyr Arg Ser Met Leu Leu Gly
        515                 520                 525

Asn Gly Arg Tyr Val Pro Phe His Ile Gln Val Pro Gln Lys Phe Phe
    530                 535                 540

Ala Ile Lys Asn Leu Leu Leu Leu Pro Gly Ser Tyr Thr Tyr Glu Trp
545                 550                 555                 560

Asn Phe Arg Lys Asp Val Asn Met Val Leu Gln Ser Ser Leu Gly Asn
                565                 570                 575

Asp Leu Arg Val Asp Gly Ala Ser Ile Lys Phe Asp Ser Ile Cys Leu
            580                 585                 590

Tyr Ala Thr Phe Phe Pro Met Ala His Asn Thr Ala Ser Thr Leu Glu
        595                 600                 605

Ala Met Leu Arg Asn Asp Thr Asn Asp Gln Ser Phe Asn Asp Tyr Leu
    610                 615                 620

Ser Ala Ala Asn Met Leu Tyr Pro Ile Pro Ala Asn Ala Thr Asn Val
625                 630                 635                 640

Pro Ile Ser Ile Pro Ser Arg Asn Trp Ala Ala Phe Arg Gly Trp Ala
                645                 650                 655

Phe Thr Arg Leu Lys Thr Lys Glu Thr Pro Ser Leu Gly Ser Gly Tyr
            660                 665                 670

Asp Pro Tyr Tyr Thr Tyr Ser Gly Ser Ile Pro Tyr Leu Asp Gly Thr
        675                 680                 685

Phe Tyr Leu Asn His Thr Phe Lys Lys Val Ala Ile Thr Phe Asp Ser
    690                 695                 700

Ser Val Ser Trp Pro Gly Asn Asp Arg Leu Leu Thr Pro Asn Glu Phe
705                 710                 715                 720

Glu Ile Lys Arg Ser Val Asp Gly Glu Gly Tyr Asn Val Ala Gln Cys
                725                 730                 735

Asn Met Thr Lys Asp Trp Phe Leu Val Gln Met Leu Ala Asn Tyr Asn
            740                 745                 750

Ile Gly Tyr Gln Gly Phe Tyr Ile Pro Glu Ser Tyr Lys Asp Arg Met
        755                 760                 765

Tyr Ser Phe Phe Arg Asn Phe Gln Pro Met Ser Arg Gln Val Val Asp
    770                 775                 780

Asp Thr Lys Tyr Lys Asp Tyr Gln Gln Val Gly Ile Leu His Gln His
785                 790                 795                 800

Asn Asn Ser Gly Phe Val Gly Tyr Leu Ala Pro Thr Met Arg Glu Gly
                805                 810                 815

Gln Ala Tyr Pro Ala Asn Phe Pro Tyr Pro Leu Ile Gly Lys Thr Ala
            820                 825                 830

Val Asp Ser Ile Thr Gln Lys Lys Phe Leu Cys Asp Arg Thr Leu Trp
```

```
        835                 840                 845

Arg Ile Pro Phe Ser Ser Asn Phe Met Ser Met Gly Ala Leu Thr Asp
    850                 855                 860

Leu Gly Gln Asn Leu Leu Tyr Ala Asn Ser Ala His Ala Leu Asp Met
865                 870                 875                 880

Thr Phe Glu Val Asp Pro Met Asp Glu Pro Thr Leu Leu Tyr Val Leu
                885                 890                 895

Phe Glu Val Phe Asp Val Val Arg Val His Gln Pro His Arg Gly Val
            900                 905                 910

Ile Glu Thr Val Tyr Leu Arg Thr Pro Phe Ser Ala Gly Asn Ala Thr
        915                 920                 925

Thr


<210> SEQ ID NO 33
<211> LENGTH: 935
<212> TYPE: PRT
<213> ORGANISM: Artificial Sequence
<220> FEATURE:
<223> OTHER INFORMATION: Synthetic Construct

<400> SEQUENCE: 33

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Asp Glu Gln Gly Pro Gly Ala Pro Gln
    130                 135                 140

Gly Pro Gly Ala Pro Gln Gly Pro Gly Ala Pro Gln Gly Pro Gly Ala
145                 150                 155                 160

Pro Gln Gly Pro Gly Ala Pro Lys Thr His Val Phe Gly Gln Ala Pro
                165                 170                 175

Tyr Ser Gly Ile Asn Ile Thr Lys Glu Gly Ile Gln Ile Gly Val Glu
            180                 185                 190

Gly Gln Thr Pro Lys Tyr Ala Asp Lys Thr Phe Gln Pro Glu Pro Gln
        195                 200                 205

Ile Gly Glu Ser Gln Trp Tyr Glu Thr Glu Ile Asn His Ala Ala Gly
    210                 215                 220

Arg Val Leu Lys Lys Thr Thr Pro Met Lys Pro Cys Tyr Gly Ser Tyr
225                 230                 235                 240

Ala Lys Pro Thr Asn Glu Asn Gly Gly Gln Gly Ile Leu Val Lys Gln
                245                 250                 255

Gln Asn Gly Lys Leu Glu Ser Gln Val Glu Met Gln Phe Phe Ser Thr
            260                 265                 270
```

-continued

```
Thr Glu Ala Ala Ala Gly Asn Gly Asp Asn Leu Thr Pro Lys Val Val
        275                 280                 285

Leu Tyr Ser Glu Asp Val Asp Ile Glu Thr Pro Asp Thr His Ile Ser
    290                 295                 300

Tyr Met Pro Thr Ile Lys Glu Gly Asn Ser Arg Glu Leu Met Gly Gln
305                 310                 315                 320

Gln Ser Met Pro Asn Arg Pro Asn Tyr Ile Ala Phe Arg Asp Asn Phe
                325                 330                 335

Ile Gly Leu Met Tyr Tyr Asn Ser Thr Gly Asn Met Gly Val Leu Ala
            340                 345                 350

Gly Gln Ala Ser Gln Leu Asn Ala Val Val Asp Leu Gln Asp Arg Asn
        355                 360                 365

Thr Glu Leu Ser Tyr Gln Leu Leu Leu Asp Ser Ile Gly Asp Arg Thr
    370                 375                 380

Arg Tyr Phe Ser Met Trp Asn Gln Leu Pro Asn Tyr Cys Phe Pro Leu
385                 390                 395                 400

Gly Gly Val Ile Asn Thr Glu Thr Leu Thr Lys Val Lys Pro Lys Thr
                405                 410                 415

Gly Gln Glu Asn Gly Trp Glu Lys Asp Ala Thr Glu Phe Ser Asp Lys
            420                 425                 430

Asn Glu Ile Arg Val Gly Asn Asn Phe Ala Met Glu Ile Asn Leu Asn
        435                 440                 445

Ala Asn Leu Trp Arg Asn Phe Leu Tyr Ser Asn Ile Ala Leu Tyr Leu
    450                 455                 460

Pro Asp Lys Leu Lys Tyr Ser Pro Ser Asn Val Lys Ile Ser Asp Asn
465                 470                 475                 480

Pro Asn Thr Tyr Asp Tyr Met Asn Lys Arg Val Val Ala Pro Gly Leu
                485                 490                 495

Val Asp Cys Tyr Ile Asn Leu Gly Ala Arg Trp Ser Leu Asp Tyr Met
            500                 505                 510

Asp Asn Val Asn Pro Phe Asn His His Arg Asn Ala Gly Leu Arg Tyr
        515                 520                 525

Arg Ser Met Leu Leu Gly Asn Gly Arg Tyr Val Pro Phe His Ile Gln
    530                 535                 540

Val Pro Gln Lys Phe Phe Ala Ile Lys Asn Leu Leu Leu Leu Pro Gly
545                 550                 555                 560

Ser Tyr Thr Tyr Glu Trp Asn Phe Arg Lys Asp Val Asn Met Val Leu
                565                 570                 575

Gln Ser Ser Leu Gly Asn Asp Leu Arg Val Asp Gly Ala Ser Ile Lys
            580                 585                 590

Phe Asp Ser Ile Cys Leu Tyr Ala Thr Phe Phe Pro Met Ala His Asn
        595                 600                 605

Thr Ala Ser Thr Leu Glu Ala Met Leu Arg Asn Asp Thr Asn Asp Gln
    610                 615                 620

Ser Phe Asn Asp Tyr Leu Ser Ala Ala Asn Met Leu Tyr Pro Ile Pro
625                 630                 635                 640

Ala Asn Ala Thr Asn Val Pro Ile Ser Ile Pro Ser Arg Asn Trp Ala
                645                 650                 655

Ala Phe Arg Gly Trp Ala Phe Thr Arg Leu Lys Thr Lys Glu Thr Pro
            660                 665                 670

Ser Leu Gly Ser Gly Tyr Asp Pro Tyr Tyr Thr Tyr Ser Gly Ser Ile
        675                 680                 685
```

Pro Tyr Leu Asp Gly Thr Phe Tyr Leu Asn His Thr Phe Lys Lys Val
690 695 700

Ala Ile Thr Phe Asp Ser Ser Val Ser Trp Pro Gly Asn Asp Arg Leu
705 710 715 720

Leu Thr Pro Asn Glu Phe Glu Ile Lys Arg Ser Val Asp Gly Glu Gly
725 730 735

Tyr Asn Val Ala Gln Cys Asn Met Thr Lys Asp Trp Phe Leu Val Gln
740 745 750

Met Leu Ala Asn Tyr Asn Ile Gly Tyr Gln Gly Phe Tyr Ile Pro Glu
755 760 765

Ser Tyr Lys Asp Arg Met Tyr Ser Phe Phe Arg Asn Phe Gln Pro Met
770 775 780

Ser Arg Gln Val Val Asp Asp Thr Lys Tyr Lys Asp Tyr Gln Gln Val
785 790 795 800

Gly Ile Leu His Gln His Asn Asn Ser Gly Phe Val Gly Tyr Leu Ala
805 810 815

Pro Thr Met Arg Glu Gly Gln Ala Tyr Pro Ala Asn Phe Pro Tyr Pro
820 825 830

Leu Ile Gly Lys Thr Ala Val Asp Ser Ile Thr Gln Lys Lys Phe Leu
835 840 845

Cys Asp Arg Thr Leu Trp Arg Ile Pro Phe Ser Ser Asn Phe Met Ser
850 855 860

Met Gly Ala Leu Thr Asp Leu Gly Gln Asn Leu Leu Tyr Ala Asn Ser
865 870 875 880

Ala His Ala Leu Asp Met Thr Phe Glu Val Asp Pro Met Asp Glu Pro
885 890 895

Thr Leu Leu Tyr Val Leu Phe Glu Val Phe Asp Val Val Arg Val His
900 905 910

Gln Pro His Arg Gly Val Ile Glu Thr Val Tyr Leu Arg Thr Pro Phe
915 920 925

Ser Ala Gly Asn Ala Thr Thr
930 935

<210> SEQ ID NO 34
<211> LENGTH: 941
<212> TYPE: PRT
<213> ORGANISM: Artificial Sequence
<220> FEATURE:
<223> OTHER INFORMATION: Synthetic Construct

<400> SEQUENCE: 34

Met Ala Thr Pro Ser Met Met Pro Gln Trp Ser Tyr Met His Ile Ser
1 5 10 15

Gly Gln Asp Ala Ser Glu Tyr Leu Ser Pro Gly Leu Val Gln Phe Ala
20 25 30

Arg Ala Thr Glu Thr Tyr Phe Ser Leu Asn Asn Lys Phe Arg Asn Pro
35 40 45

Thr Val Ala Pro Thr His Asp Val Thr Thr Asp Arg Ser Gln Arg Leu
50 55 60

Thr Leu Arg Phe Ile Pro Val Asp Arg Glu Asp Thr Ala Tyr Ser Tyr
65 70 75 80

Lys Ala Arg Phe Thr Leu Ala Val Gly Asp Asn Arg Val Leu Asp Met
85 90 95

Ala Ser Thr Tyr Phe Asp Ile Arg Gly Val Leu Asp Arg Gly Pro Thr
100 105 110

```
Phe Lys Pro Tyr Ser Gly Thr Ala Tyr Asn Ala Leu Ala Pro Lys Gly
        115                 120                 125

Ala Pro Asn Pro Cys Glu Trp Asp Glu Gln Gly Pro Gly Ala Pro Gln
    130                 135                 140

Gly Pro Gly Ala Pro Gln Gly Pro Gly Ala Pro Gln Gly Pro Gly Ala
145                 150                 155                 160

Pro Gln Gly Pro Gly Ala Pro Gln Gly Pro Gly Ala Pro Lys Thr His
                165                 170                 175

Val Phe Gly Gln Ala Pro Tyr Ser Gly Ile Asn Ile Thr Lys Glu Gly
            180                 185                 190

Ile Gln Ile Gly Val Glu Gly Gln Thr Pro Lys Tyr Ala Asp Lys Thr
        195                 200                 205

Phe Gln Pro Glu Pro Gln Ile Gly Glu Ser Gln Trp Tyr Glu Thr Glu
    210                 215                 220

Ile Asn His Ala Ala Gly Arg Val Leu Lys Lys Thr Thr Pro Met Lys
225                 230                 235                 240

Pro Cys Tyr Gly Ser Tyr Ala Lys Pro Thr Asn Glu Asn Gly Gly Gln
                245                 250                 255

Gly Ile Leu Val Lys Gln Gln Asn Gly Lys Leu Glu Ser Gln Val Glu
            260                 265                 270

Met Gln Phe Phe Ser Thr Thr Glu Ala Ala Ala Gly Asn Gly Asp Asn
        275                 280                 285

Leu Thr Pro Lys Val Val Leu Tyr Ser Glu Asp Val Asp Ile Glu Thr
    290                 295                 300

Pro Asp Thr His Ile Ser Tyr Met Pro Thr Ile Lys Glu Gly Asn Ser
305                 310                 315                 320

Arg Glu Leu Met Gly Gln Gln Ser Met Pro Asn Arg Pro Asn Tyr Ile
                325                 330                 335

Ala Phe Arg Asp Asn Phe Ile Gly Leu Met Tyr Tyr Asn Ser Thr Gly
            340                 345                 350

Asn Met Gly Val Leu Ala Gly Gln Ala Ser Gln Leu Asn Ala Val Val
        355                 360                 365

Asp Leu Gln Asp Arg Asn Thr Glu Leu Ser Tyr Gln Leu Leu Leu Asp
    370                 375                 380

Ser Ile Gly Asp Arg Thr Arg Tyr Phe Ser Met Trp Asn Gln Leu Pro
385                 390                 395                 400

Asn Tyr Cys Phe Pro Leu Gly Gly Val Ile Asn Thr Glu Thr Leu Thr
                405                 410                 415

Lys Val Lys Pro Lys Thr Gly Gln Glu Asn Gly Trp Glu Lys Asp Ala
            420                 425                 430

Thr Glu Phe Ser Asp Lys Asn Glu Ile Arg Val Gly Asn Asn Phe Ala
        435                 440                 445

Met Glu Ile Asn Leu Asn Ala Asn Leu Trp Arg Asn Phe Leu Tyr Ser
    450                 455                 460

Asn Ile Ala Leu Tyr Leu Pro Asp Lys Leu Lys Tyr Ser Pro Ser Asn
465                 470                 475                 480

Val Lys Ile Ser Asp Asn Pro Asn Thr Tyr Asp Tyr Met Asn Lys Arg
                485                 490                 495

Val Val Ala Pro Gly Leu Val Asp Cys Tyr Ile Asn Leu Gly Ala Arg
            500                 505                 510

Trp Ser Leu Asp Tyr Met Asp Asn Val Asn Pro Phe Asn His His Arg
        515                 520                 525

Asn Ala Gly Leu Arg Tyr Arg Ser Met Leu Leu Gly Asn Gly Arg Tyr
```

-continued

```
    530                 535                 540

Val Pro Phe His Ile Gln Val Pro Gln Lys Phe Phe Ala Ile Lys Asn
545                 550                 555                 560

Leu Leu Leu Leu Pro Gly Ser Tyr Thr Tyr Glu Trp Asn Phe Arg Lys
                565                 570                 575

Asp Val Asn Met Val Leu Gln Ser Ser Leu Gly Asn Asp Leu Arg Val
            580                 585                 590

Asp Gly Ala Ser Ile Lys Phe Asp Ser Ile Cys Leu Tyr Ala Thr Phe
        595                 600                 605

Phe Pro Met Ala His Asn Thr Ala Ser Thr Leu Glu Ala Met Leu Arg
    610                 615                 620

Asn Asp Thr Asn Asp Gln Ser Phe Asn Asp Tyr Leu Ser Ala Ala Asn
625                 630                 635                 640

Met Leu Tyr Pro Ile Pro Ala Asn Ala Thr Asn Val Pro Ile Ser Ile
                645                 650                 655

Pro Ser Arg Asn Trp Ala Ala Phe Arg Gly Trp Ala Phe Thr Arg Leu
            660                 665                 670

Lys Thr Lys Glu Thr Pro Ser Leu Gly Ser Gly Tyr Asp Pro Tyr Tyr
        675                 680                 685

Thr Tyr Ser Gly Ser Ile Pro Tyr Leu Asp Gly Thr Phe Tyr Leu Asn
    690                 695                 700

His Thr Phe Lys Lys Val Ala Ile Thr Phe Asp Ser Ser Val Ser Trp
705                 710                 715                 720

Pro Gly Asn Asp Arg Leu Leu Thr Pro Asn Glu Phe Glu Ile Lys Arg
                725                 730                 735

Ser Val Asp Gly Glu Gly Tyr Asn Val Ala Gln Cys Asn Met Thr Lys
            740                 745                 750

Asp Trp Phe Leu Val Gln Met Leu Ala Asn Tyr Asn Ile Gly Tyr Gln
        755                 760                 765

Gly Phe Tyr Ile Pro Glu Ser Tyr Lys Asp Arg Met Tyr Ser Phe Phe
    770                 775                 780

Arg Asn Phe Gln Pro Met Ser Arg Gln Val Val Asp Asp Thr Lys Tyr
785                 790                 795                 800

Lys Asp Tyr Gln Gln Val Gly Ile Leu His Gln His Asn Asn Ser Gly
                805                 810                 815

Phe Val Gly Tyr Leu Ala Pro Thr Met Arg Glu Gly Gln Ala Tyr Pro
            820                 825                 830

Ala Asn Phe Pro Tyr Pro Leu Ile Gly Lys Thr Ala Val Asp Ser Ile
        835                 840                 845

Thr Gln Lys Lys Phe Leu Cys Asp Arg Thr Leu Trp Arg Ile Pro Phe
    850                 855                 860

Ser Ser Asn Phe Met Ser Met Gly Ala Leu Thr Asp Leu Gly Gln Asn
865                 870                 875                 880

Leu Leu Tyr Ala Asn Ser Ala His Ala Leu Asp Met Thr Phe Glu Val
                885                 890                 895

Asp Pro Met Asp Glu Pro Thr Leu Leu Tyr Val Leu Phe Glu Val Phe
            900                 905                 910

Asp Val Val Arg Val His Gln Pro His Arg Gly Val Ile Glu Thr Val
        915                 920                 925

Tyr Leu Arg Thr Pro Phe Ser Ala Gly Asn Ala Thr Thr
    930                 935                 940
```

<210> SEQ ID NO 35

<211> LENGTH: 947
<212> TYPE: PRT
<213> ORGANISM: Artificial Sequence
<220> FEATURE:
<223> OTHER INFORMATION: Synthetic Construct

<400> SEQUENCE: 35

```
Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Asp Glu Gln Gly Pro Gly Ala Pro Gln
    130                 135                 140

Gly Pro Gly Ala Pro Gln Gly Pro Gly Ala Pro Gln Gly Pro Gly Ala
145                 150                 155                 160

Pro Gln Gly Pro Gly Ala Pro Gln Gly Pro Gly Ala Pro Gln Gly Pro
                165                 170                 175

Gly Ala Pro Lys Thr His Val Phe Gly Gln Ala Pro Tyr Ser Gly Ile
            180                 185                 190

Asn Ile Thr Lys Glu Gly Ile Gln Ile Gly Val Glu Gly Gln Thr Pro
        195                 200                 205

Lys Tyr Ala Asp Lys Thr Phe Gln Pro Glu Pro Gln Ile Gly Glu Ser
    210                 215                 220

Gln Trp Tyr Glu Thr Glu Ile Asn His Ala Ala Gly Arg Val Leu Lys
225                 230                 235                 240

Lys Thr Thr Pro Met Lys Pro Cys Tyr Gly Ser Tyr Ala Lys Pro Thr
                245                 250                 255

Asn Glu Asn Gly Gly Gln Gly Ile Leu Val Lys Gln Gln Asn Gly Lys
            260                 265                 270

Leu Glu Ser Gln Val Glu Met Gln Phe Phe Ser Thr Thr Glu Ala Ala
        275                 280                 285

Ala Gly Asn Gly Asp Asn Leu Thr Pro Lys Val Val Leu Tyr Ser Glu
    290                 295                 300

Asp Val Asp Ile Glu Thr Pro Asp Thr His Ile Ser Tyr Met Pro Thr
305                 310                 315                 320

Ile Lys Glu Gly Asn Ser Arg Glu Leu Met Gly Gln Gln Ser Met Pro
                325                 330                 335

Asn Arg Pro Asn Tyr Ile Ala Phe Arg Asp Asn Phe Ile Gly Leu Met
            340                 345                 350

Tyr Tyr Asn Ser Thr Gly Asn Met Gly Val Leu Ala Gly Gln Ala Ser
        355                 360                 365

Gln Leu Asn Ala Val Val Asp Leu Gln Asp Arg Asn Thr Glu Leu Ser
    370                 375                 380
```

```
Tyr Gln Leu Leu Leu Asp Ser Ile Gly Asp Arg Thr Arg Tyr Phe Ser
385                 390                 395                 400

Met Trp Asn Gln Leu Pro Asn Tyr Cys Phe Pro Leu Gly Gly Val Ile
                405                 410                 415

Asn Thr Glu Thr Leu Thr Lys Val Lys Pro Lys Thr Gly Gln Glu Asn
            420                 425                 430

Gly Trp Glu Lys Asp Ala Thr Glu Phe Ser Asp Lys Asn Glu Ile Arg
        435                 440                 445

Val Gly Asn Asn Phe Ala Met Glu Ile Asn Leu Asn Ala Asn Leu Trp
    450                 455                 460

Arg Asn Phe Leu Tyr Ser Asn Ile Ala Leu Tyr Leu Pro Asp Lys Leu
465                 470                 475                 480

Lys Tyr Ser Pro Ser Asn Val Lys Ile Ser Asp Asn Pro Asn Thr Tyr
                485                 490                 495

Asp Tyr Met Asn Lys Arg Val Val Ala Pro Gly Leu Val Asp Cys Tyr
            500                 505                 510

Ile Asn Leu Gly Ala Arg Trp Ser Leu Asp Tyr Met Asp Asn Val Asn
        515                 520                 525

Pro Phe Asn His His Arg Asn Ala Gly Leu Arg Tyr Arg Ser Met Leu
    530                 535                 540

Leu Gly Asn Gly Arg Tyr Val Pro Phe His Ile Gln Val Pro Gln Lys
545                 550                 555                 560

Phe Phe Ala Ile Lys Asn Leu Leu Leu Leu Pro Gly Ser Tyr Thr Tyr
                565                 570                 575

Glu Trp Asn Phe Arg Lys Asp Val Asn Met Val Leu Gln Ser Ser Leu
            580                 585                 590

Gly Asn Asp Leu Arg Val Asp Gly Ala Ser Ile Lys Phe Asp Ser Ile
        595                 600                 605

Cys Leu Tyr Ala Thr Phe Phe Pro Met Ala His Asn Thr Ala Ser Thr
    610                 615                 620

Leu Glu Ala Met Leu Arg Asn Asp Thr Asn Asp Gln Ser Phe Asn Asp
625                 630                 635                 640

Tyr Leu Ser Ala Ala Asn Met Leu Tyr Pro Ile Pro Ala Asn Ala Thr
                645                 650                 655

Asn Val Pro Ile Ser Ile Pro Ser Arg Asn Trp Ala Ala Phe Arg Gly
            660                 665                 670

Trp Ala Phe Thr Arg Leu Lys Thr Lys Glu Thr Pro Ser Leu Gly Ser
        675                 680                 685

Gly Tyr Asp Pro Tyr Tyr Thr Tyr Ser Gly Ser Ile Pro Tyr Leu Asp
    690                 695                 700

Gly Thr Phe Tyr Leu Asn His Thr Phe Lys Lys Val Ala Ile Thr Phe
705                 710                 715                 720

Asp Ser Ser Val Ser Trp Pro Gly Asn Asp Arg Leu Leu Thr Pro Asn
                725                 730                 735

Glu Phe Glu Ile Lys Arg Ser Val Asp Gly Glu Gly Tyr Asn Val Ala
            740                 745                 750

Gln Cys Asn Met Thr Lys Asp Trp Phe Leu Val Gln Met Leu Ala Asn
        755                 760                 765

Tyr Asn Ile Gly Tyr Gln Gly Phe Tyr Ile Pro Glu Ser Tyr Lys Asp
    770                 775                 780

Arg Met Tyr Ser Phe Phe Arg Asn Phe Gln Pro Met Ser Arg Gln Val
785                 790                 795                 800
```

```
Val Asp Asp Thr Lys Tyr Lys Asp Tyr Gln Gln Val Gly Ile Leu His
                805                 810                 815

Gln His Asn Asn Ser Gly Phe Val Gly Tyr Leu Ala Pro Thr Met Arg
            820                 825                 830

Glu Gly Gln Ala Tyr Pro Ala Asn Phe Pro Tyr Pro Leu Ile Gly Lys
        835                 840                 845

Thr Ala Val Asp Ser Ile Thr Gln Lys Lys Phe Leu Cys Asp Arg Thr
    850                 855                 860

Leu Trp Arg Ile Pro Phe Ser Ser Asn Phe Met Ser Met Gly Ala Leu
865                 870                 875                 880

Thr Asp Leu Gly Gln Asn Leu Leu Tyr Ala Asn Ser Ala His Ala Leu
                885                 890                 895

Asp Met Thr Phe Glu Val Asp Pro Met Asp Glu Pro Thr Leu Leu Tyr
            900                 905                 910

Val Leu Phe Glu Val Phe Asp Val Val Arg Val His Gln Pro His Arg
        915                 920                 925

Gly Val Ile Glu Thr Val Tyr Leu Arg Thr Pro Phe Ser Ala Gly Asn
    930                 935                 940

Ala Thr Thr
945


<210> SEQ ID NO 36
<211> LENGTH: 953
<212> TYPE: PRT
<213> ORGANISM: Artificial Sequence
<220> FEATURE:
<223> OTHER INFORMATION: Synthetic Construct

<400> SEQUENCE: 36

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Asp Glu Gln Gly Pro Gly Ala Pro Gln
    130                 135                 140

Gly Pro Gly Ala Pro Gln Gly Pro Gly Ala Pro Gln Gly Pro Gly Ala
145                 150                 155                 160

Pro Gln Gly Pro Gly Ala Pro Gln Gly Pro Gly Ala Pro Gln Gly Pro
                165                 170                 175

Gly Ala Pro Gln Gly Pro Gly Ala Pro Lys Thr His Val Phe Gly Gln
            180                 185                 190

Ala Pro Tyr Ser Gly Ile Asn Ile Thr Lys Glu Gly Ile Gln Ile Gly
        195                 200                 205
```

-continued

```
Val Glu Gly Gln Thr Pro Lys Tyr Ala Asp Lys Thr Phe Gln Pro Glu
    210                 215                 220

Pro Gln Ile Gly Glu Ser Gln Trp Tyr Glu Thr Glu Ile Asn His Ala
225                 230                 235                 240

Ala Gly Arg Val Leu Lys Lys Thr Thr Pro Met Lys Pro Cys Tyr Gly
                245                 250                 255

Ser Tyr Ala Lys Pro Thr Asn Glu Asn Gly Gly Gln Gly Ile Leu Val
            260                 265                 270

Lys Gln Gln Asn Gly Lys Leu Glu Ser Gln Val Glu Met Gln Phe Phe
        275                 280                 285

Ser Thr Thr Glu Ala Ala Ala Gly Asn Gly Asp Asn Leu Thr Pro Lys
    290                 295                 300

Val Val Leu Tyr Ser Glu Asp Val Asp Ile Glu Thr Pro Asp Thr His
305                 310                 315                 320

Ile Ser Tyr Met Pro Thr Ile Lys Glu Gly Asn Ser Arg Glu Leu Met
                325                 330                 335

Gly Gln Gln Ser Met Pro Asn Arg Pro Asn Tyr Ile Ala Phe Arg Asp
            340                 345                 350

Asn Phe Ile Gly Leu Met Tyr Tyr Asn Ser Thr Gly Asn Met Gly Val
        355                 360                 365

Leu Ala Gly Gln Ala Ser Gln Leu Asn Ala Val Val Asp Leu Gln Asp
    370                 375                 380

Arg Asn Thr Glu Leu Ser Tyr Gln Leu Leu Leu Asp Ser Ile Gly Asp
385                 390                 395                 400

Arg Thr Arg Tyr Phe Ser Met Trp Asn Gln Leu Pro Asn Tyr Cys Phe
                405                 410                 415

Pro Leu Gly Gly Val Ile Asn Thr Glu Thr Leu Thr Lys Val Lys Pro
            420                 425                 430

Lys Thr Gly Gln Glu Asn Gly Trp Glu Lys Asp Ala Thr Glu Phe Ser
        435                 440                 445

Asp Lys Asn Glu Ile Arg Val Gly Asn Asn Phe Ala Met Glu Ile Asn
    450                 455                 460

Leu Asn Ala Asn Leu Trp Arg Asn Phe Leu Tyr Ser Asn Ile Ala Leu
465                 470                 475                 480

Tyr Leu Pro Asp Lys Leu Lys Tyr Ser Pro Ser Asn Val Lys Ile Ser
                485                 490                 495

Asp Asn Pro Asn Thr Tyr Asp Tyr Met Asn Lys Arg Val Val Ala Pro
            500                 505                 510

Gly Leu Val Asp Cys Tyr Ile Asn Leu Gly Ala Arg Trp Ser Leu Asp
        515                 520                 525

Tyr Met Asp Asn Val Asn Pro Phe Asn His His Arg Asn Ala Gly Leu
    530                 535                 540

Arg Tyr Arg Ser Met Leu Leu Gly Asn Gly Arg Tyr Val Pro Phe His
545                 550                 555                 560

Ile Gln Val Pro Gln Lys Phe Phe Ala Ile Lys Asn Leu Leu Leu Leu
                565                 570                 575

Pro Gly Ser Tyr Thr Tyr Glu Trp Asn Phe Arg Lys Asp Val Asn Met
            580                 585                 590

Val Leu Gln Ser Ser Leu Gly Asn Asp Leu Arg Val Asp Gly Ala Ser
        595                 600                 605

Ile Lys Phe Asp Ser Ile Cys Leu Tyr Ala Thr Phe Phe Pro Met Ala
    610                 615                 620

His Asn Thr Ala Ser Thr Leu Glu Ala Met Leu Arg Asn Asp Thr Asn
```

```
625                 630                 635                 640

Asp Gln Ser Phe Asn Asp Tyr Leu Ser Ala Ala Asn Met Leu Tyr Pro
                645                 650                 655

Ile Pro Ala Asn Ala Thr Asn Val Pro Ile Ser Ile Pro Ser Arg Asn
            660                 665                 670

Trp Ala Ala Phe Arg Gly Trp Ala Phe Thr Arg Leu Lys Thr Lys Glu
        675                 680                 685

Thr Pro Ser Leu Gly Ser Gly Tyr Asp Pro Tyr Tyr Thr Tyr Ser Gly
    690                 695                 700

Ser Ile Pro Tyr Leu Asp Gly Thr Phe Tyr Leu Asn His Thr Phe Lys
705                 710                 715                 720

Lys Val Ala Ile Thr Phe Asp Ser Ser Val Ser Trp Pro Gly Asn Asp
                725                 730                 735

Arg Leu Leu Thr Pro Asn Glu Phe Glu Ile Lys Arg Ser Val Asp Gly
            740                 745                 750

Glu Gly Tyr Asn Val Ala Gln Cys Asn Met Thr Lys Asp Trp Phe Leu
        755                 760                 765

Val Gln Met Leu Ala Asn Tyr Asn Ile Gly Tyr Gln Gly Phe Tyr Ile
    770                 775                 780

Pro Glu Ser Tyr Lys Asp Arg Met Tyr Ser Phe Phe Arg Asn Phe Gln
785                 790                 795                 800

Pro Met Ser Arg Gln Val Val Asp Asp Thr Lys Tyr Lys Asp Tyr Gln
                805                 810                 815

Gln Val Gly Ile Leu His Gln His Asn Asn Ser Gly Phe Val Gly Tyr
            820                 825                 830

Leu Ala Pro Thr Met Arg Glu Gly Gln Ala Tyr Pro Ala Asn Phe Pro
        835                 840                 845

Tyr Pro Leu Ile Gly Lys Thr Ala Val Asp Ser Ile Thr Gln Lys Lys
    850                 855                 860

Phe Leu Cys Asp Arg Thr Leu Trp Arg Ile Pro Phe Ser Ser Asn Phe
865                 870                 875                 880

Met Ser Met Gly Ala Leu Thr Asp Leu Gly Gln Asn Leu Leu Tyr Ala
                885                 890                 895

Asn Ser Ala His Ala Leu Asp Met Thr Phe Glu Val Asp Pro Met Asp
            900                 905                 910

Glu Pro Thr Leu Leu Tyr Val Leu Phe Glu Val Phe Asp Val Val Arg
        915                 920                 925

Val His Gln Pro His Arg Gly Val Ile Glu Thr Val Tyr Leu Arg Thr
    930                 935                 940

Pro Phe Ser Ala Gly Asn Ala Thr Thr
945                 950


<210> SEQ ID NO 37
<211> LENGTH: 959
<212> TYPE: PRT
<213> ORGANISM: Artificial Sequence
<220> FEATURE:
<223> OTHER INFORMATION: Synthetic Construct

<400> SEQUENCE: 37

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
```

-continued

```
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Asp Glu Gln Gly Pro Gly Ala Pro Gln
    130                 135                 140

Gly Pro Gly Ala Pro Gln Gly Pro Gly Ala Pro Gln Gly Pro Gly Ala
145                 150                 155                 160

Pro Gln Gly Pro Gly Ala Pro Gln Gly Pro Gly Ala Pro Gln Gly Pro
                165                 170                 175

Gly Ala Pro Gln Gly Pro Gly Ala Pro Gln Gly Pro Gly Ala Pro Lys
            180                 185                 190

Thr His Val Phe Gly Gln Ala Pro Tyr Ser Gly Ile Asn Ile Thr Lys
        195                 200                 205

Glu Gly Ile Gln Ile Gly Val Glu Gly Gln Thr Pro Lys Tyr Ala Asp
    210                 215                 220

Lys Thr Phe Gln Pro Glu Pro Gln Ile Gly Glu Ser Gln Trp Tyr Glu
225                 230                 235                 240

Thr Glu Ile Asn His Ala Ala Gly Arg Val Leu Lys Lys Thr Thr Pro
                245                 250                 255

Met Lys Pro Cys Tyr Gly Ser Tyr Ala Lys Pro Thr Asn Glu Asn Gly
            260                 265                 270

Gly Gln Gly Ile Leu Val Lys Gln Gln Asn Gly Lys Leu Glu Ser Gln
        275                 280                 285

Val Glu Met Gln Phe Phe Ser Thr Thr Glu Ala Ala Ala Gly Asn Gly
    290                 295                 300

Asp Asn Leu Thr Pro Lys Val Val Leu Tyr Ser Glu Asp Val Asp Ile
305                 310                 315                 320

Glu Thr Pro Asp Thr His Ile Ser Tyr Met Pro Thr Ile Lys Glu Gly
                325                 330                 335

Asn Ser Arg Glu Leu Met Gly Gln Gln Ser Met Pro Asn Arg Pro Asn
            340                 345                 350

Tyr Ile Ala Phe Arg Asp Asn Phe Ile Gly Leu Met Tyr Tyr Asn Ser
        355                 360                 365

Thr Gly Asn Met Gly Val Leu Ala Gly Gln Ala Ser Gln Leu Asn Ala
    370                 375                 380

Val Val Asp Leu Gln Asp Arg Asn Thr Glu Leu Ser Tyr Gln Leu Leu
385                 390                 395                 400

Leu Asp Ser Ile Gly Asp Arg Thr Arg Tyr Phe Ser Met Trp Asn Gln
                405                 410                 415

Leu Pro Asn Tyr Cys Phe Pro Leu Gly Gly Val Ile Asn Thr Glu Thr
            420                 425                 430

Leu Thr Lys Val Lys Pro Lys Thr Gly Gln Glu Asn Gly Trp Glu Lys
        435                 440                 445

Asp Ala Thr Glu Phe Ser Asp Lys Asn Glu Ile Arg Val Gly Asn Asn
    450                 455                 460
```

-continued

```
Phe Ala Met Glu Ile Asn Leu Asn Ala Asn Leu Trp Arg Asn Phe Leu
465                 470                 475                 480

Tyr Ser Asn Ile Ala Leu Tyr Leu Pro Asp Lys Leu Lys Tyr Ser Pro
                485                 490                 495

Ser Asn Val Lys Ile Ser Asp Asn Pro Asn Thr Tyr Asp Tyr Met Asn
            500                 505                 510

Lys Arg Val Val Ala Pro Gly Leu Val Asp Cys Tyr Ile Asn Leu Gly
        515                 520                 525

Ala Arg Trp Ser Leu Asp Tyr Met Asp Asn Val Asn Pro Phe Asn His
    530                 535                 540

His Arg Asn Ala Gly Leu Arg Tyr Arg Ser Met Leu Leu Gly Asn Gly
545                 550                 555                 560

Arg Tyr Val Pro Phe His Ile Gln Val Pro Gln Lys Phe Phe Ala Ile
                565                 570                 575

Lys Asn Leu Leu Leu Leu Pro Gly Ser Tyr Thr Tyr Glu Trp Asn Phe
            580                 585                 590

Arg Lys Asp Val Asn Met Val Leu Gln Ser Ser Leu Gly Asn Asp Leu
        595                 600                 605

Arg Val Asp Gly Ala Ser Ile Lys Phe Asp Ser Ile Cys Leu Tyr Ala
    610                 615                 620

Thr Phe Phe Pro Met Ala His Asn Thr Ala Ser Thr Leu Glu Ala Met
625                 630                 635                 640

Leu Arg Asn Asp Thr Asn Asp Gln Ser Phe Asn Asp Tyr Leu Ser Ala
                645                 650                 655

Ala Asn Met Leu Tyr Pro Ile Pro Ala Asn Ala Thr Asn Val Pro Ile
            660                 665                 670

Ser Ile Pro Ser Arg Asn Trp Ala Ala Phe Arg Gly Trp Ala Phe Thr
        675                 680                 685

Arg Leu Lys Thr Lys Glu Thr Pro Ser Leu Gly Ser Gly Tyr Asp Pro
    690                 695                 700

Tyr Tyr Thr Tyr Ser Gly Ser Ile Pro Tyr Leu Asp Gly Thr Phe Tyr
705                 710                 715                 720

Leu Asn His Thr Phe Lys Lys Val Ala Ile Thr Phe Asp Ser Ser Val
                725                 730                 735

Ser Trp Pro Gly Asn Asp Arg Leu Leu Thr Pro Asn Glu Phe Glu Ile
            740                 745                 750

Lys Arg Ser Val Asp Gly Glu Gly Tyr Asn Val Ala Gln Cys Asn Met
        755                 760                 765

Thr Lys Asp Trp Phe Leu Val Gln Met Leu Ala Asn Tyr Asn Ile Gly
    770                 775                 780

Tyr Gln Gly Phe Tyr Ile Pro Glu Ser Tyr Lys Asp Arg Met Tyr Ser
785                 790                 795                 800

Phe Phe Arg Asn Phe Gln Pro Met Ser Arg Gln Val Val Asp Asp Thr
                805                 810                 815

Lys Tyr Lys Asp Tyr Gln Gln Val Gly Ile Leu His Gln His Asn Asn
            820                 825                 830

Ser Gly Phe Val Gly Tyr Leu Ala Pro Thr Met Arg Glu Gly Gln Ala
        835                 840                 845

Tyr Pro Ala Asn Phe Pro Tyr Pro Leu Ile Gly Lys Thr Ala Val Asp
    850                 855                 860

Ser Ile Thr Gln Lys Lys Phe Leu Cys Asp Arg Thr Leu Trp Arg Ile
865                 870                 875                 880
```

```
Pro Phe Ser Ser Asn Phe Met Ser Met Gly Ala Leu Thr Asp Leu Gly
                885                 890                 895

Gln Asn Leu Leu Tyr Ala Asn Ser Ala His Ala Leu Asp Met Thr Phe
            900                 905                 910

Glu Val Asp Pro Met Asp Glu Pro Thr Leu Leu Tyr Val Leu Phe Glu
        915                 920                 925

Val Phe Asp Val Val Arg Val His Gln Pro His Arg Gly Val Ile Glu
    930                 935                 940

Thr Val Tyr Leu Arg Thr Pro Phe Ser Ala Gly Asn Ala Thr Thr
945                 950                 955


<210> SEQ ID NO 38
<211> LENGTH: 971
<212> TYPE: PRT
<213> ORGANISM: Artificial Sequence
<220> FEATURE:
<223> OTHER INFORMATION: Synthetic Construct

<400> SEQUENCE: 38

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Asp Glu Gln Gly Pro Gly Ala Pro Gln
    130                 135                 140

Gly Pro Gly Ala Pro Gln Gly Pro Gly Ala Pro Gln Gly Pro Gly Ala
145                 150                 155                 160

Pro Gln Gly Pro Gly Ala Pro Gln Gly Pro Gly Ala Pro Gln Gly Pro
                165                 170                 175

Gly Ala Pro Gln Gly Pro Gly Ala Pro Gln Gly Pro Gly Ala Pro Gln
            180                 185                 190

Gly Pro Gly Ala Pro Gln Gly Pro Gly Ala Pro Lys Thr His Val Phe
        195                 200                 205

Gly Gln Ala Pro Tyr Ser Gly Ile Asn Ile Thr Lys Glu Gly Ile Gln
    210                 215                 220

Ile Gly Val Glu Gly Gln Thr Pro Lys Tyr Ala Asp Lys Thr Phe Gln
225                 230                 235                 240

Pro Glu Pro Gln Ile Gly Glu Ser Gln Trp Tyr Glu Thr Glu Ile Asn
                245                 250                 255

His Ala Ala Gly Arg Val Leu Lys Lys Thr Thr Pro Met Lys Pro Cys
            260                 265                 270

Tyr Gly Ser Tyr Ala Lys Pro Thr Asn Glu Asn Gly Gly Gln Gly Ile
        275                 280                 285
```

-continued

```
Leu Val Lys Gln Gln Asn Gly Lys Leu Glu Ser Gln Val Glu Met Gln
    290                 295                 300

Phe Phe Ser Thr Thr Glu Ala Ala Ala Gly Asn Gly Asp Asn Leu Thr
305                 310                 315                 320

Pro Lys Val Val Leu Tyr Ser Glu Asp Val Asp Ile Glu Thr Pro Asp
                325                 330                 335

Thr His Ile Ser Tyr Met Pro Thr Ile Lys Glu Gly Asn Ser Arg Glu
            340                 345                 350

Leu Met Gly Gln Gln Ser Met Pro Asn Arg Pro Asn Tyr Ile Ala Phe
        355                 360                 365

Arg Asp Asn Phe Ile Gly Leu Met Tyr Tyr Asn Ser Thr Gly Asn Met
    370                 375                 380

Gly Val Leu Ala Gly Gln Ala Ser Gln Leu Asn Ala Val Val Asp Leu
385                 390                 395                 400

Gln Asp Arg Asn Thr Glu Leu Ser Tyr Gln Leu Leu Leu Asp Ser Ile
                405                 410                 415

Gly Asp Arg Thr Arg Tyr Phe Ser Met Trp Asn Gln Leu Pro Asn Tyr
            420                 425                 430

Cys Phe Pro Leu Gly Gly Val Ile Asn Thr Glu Thr Leu Thr Lys Val
        435                 440                 445

Lys Pro Lys Thr Gly Gln Glu Asn Gly Trp Glu Lys Asp Ala Thr Glu
    450                 455                 460

Phe Ser Asp Lys Asn Glu Ile Arg Val Gly Asn Asn Phe Ala Met Glu
465                 470                 475                 480

Ile Asn Leu Asn Ala Asn Leu Trp Arg Asn Phe Leu Tyr Ser Asn Ile
                485                 490                 495

Ala Leu Tyr Leu Pro Asp Lys Leu Lys Tyr Ser Pro Ser Asn Val Lys
            500                 505                 510

Ile Ser Asp Asn Pro Asn Thr Tyr Asp Tyr Met Asn Lys Arg Val Val
        515                 520                 525

Ala Pro Gly Leu Val Asp Cys Tyr Ile Asn Leu Gly Ala Arg Trp Ser
    530                 535                 540

Leu Asp Tyr Met Asp Asn Val Asn Pro Phe Asn His His Arg Asn Ala
545                 550                 555                 560

Gly Leu Arg Tyr Arg Ser Met Leu Leu Gly Asn Gly Arg Tyr Val Pro
                565                 570                 575

Phe His Ile Gln Val Pro Gln Lys Phe Phe Ala Ile Lys Asn Leu Leu
            580                 585                 590

Leu Leu Pro Gly Ser Tyr Thr Tyr Glu Trp Asn Phe Arg Lys Asp Val
        595                 600                 605

Asn Met Val Leu Gln Ser Ser Leu Gly Asn Asp Leu Arg Val Asp Gly
    610                 615                 620

Ala Ser Ile Lys Phe Asp Ser Ile Cys Leu Tyr Ala Thr Phe Phe Pro
625                 630                 635                 640

Met Ala His Asn Thr Ala Ser Thr Leu Glu Ala Met Leu Arg Asn Asp
                645                 650                 655

Thr Asn Asp Gln Ser Phe Asn Asp Tyr Leu Ser Ala Ala Asn Met Leu
            660                 665                 670

Tyr Pro Ile Pro Ala Asn Ala Thr Asn Val Pro Ile Ser Ile Pro Ser
        675                 680                 685

Arg Asn Trp Ala Ala Phe Arg Gly Trp Ala Phe Thr Arg Leu Lys Thr
    690                 695                 700

Lys Glu Thr Pro Ser Leu Gly Ser Gly Tyr Asp Pro Tyr Tyr Thr Tyr
```

705 710 715 720

Ser Gly Ser Ile Pro Tyr Leu Asp Gly Thr Phe Tyr Leu Asn His Thr
725 730 735

Phe Lys Lys Val Ala Ile Thr Phe Asp Ser Ser Val Ser Trp Pro Gly
740 745 750

Asn Asp Arg Leu Leu Thr Pro Asn Glu Phe Glu Ile Lys Arg Ser Val
755 760 765

Asp Gly Glu Gly Tyr Asn Val Ala Gln Cys Asn Met Thr Lys Asp Trp
770 775 780

Phe Leu Val Gln Met Leu Ala Asn Tyr Asn Ile Gly Tyr Gln Gly Phe
785 790 795 800

Tyr Ile Pro Glu Ser Tyr Lys Asp Arg Met Tyr Ser Phe Phe Arg Asn
805 810 815

Phe Gln Pro Met Ser Arg Gln Val Val Asp Asp Thr Lys Tyr Lys Asp
820 825 830

Tyr Gln Gln Val Gly Ile Leu His Gln His Asn Asn Ser Gly Phe Val
835 840 845

Gly Tyr Leu Ala Pro Thr Met Arg Glu Gly Gln Ala Tyr Pro Ala Asn
850 855 860

Phe Pro Tyr Pro Leu Ile Gly Lys Thr Ala Val Asp Ser Ile Thr Gln
865 870 875 880

Lys Lys Phe Leu Cys Asp Arg Thr Leu Trp Arg Ile Pro Phe Ser Ser
885 890 895

Asn Phe Met Ser Met Gly Ala Leu Thr Asp Leu Gly Gln Asn Leu Leu
900 905 910

Tyr Ala Asn Ser Ala His Ala Leu Asp Met Thr Phe Glu Val Asp Pro
915 920 925

Met Asp Glu Pro Thr Leu Leu Tyr Val Leu Phe Glu Val Phe Asp Val
930 935 940

Val Arg Val His Gln Pro His Arg Gly Val Ile Glu Thr Val Tyr Leu
945 950 955 960

Arg Thr Pro Phe Ser Ala Gly Asn Ala Thr Thr
965 970

<210> SEQ ID NO 39
<211> LENGTH: 977
<212> TYPE: PRT
<213> ORGANISM: Artificial Sequence
<220> FEATURE:
<223> OTHER INFORMATION: Synthetic Construct

<400> SEQUENCE: 39

Met Ala Thr Pro Ser Met Met Pro Gln Trp Ser Tyr Met His Ile Ser
1 5 10 15

Gly Gln Asp Ala Ser Glu Tyr Leu Ser Pro Gly Leu Val Gln Phe Ala
20 25 30

Arg Ala Thr Glu Thr Tyr Phe Ser Leu Asn Asn Lys Phe Arg Asn Pro
35 40 45

Thr Val Ala Pro Thr His Asp Val Thr Thr Asp Arg Ser Gln Arg Leu
50 55 60

Thr Leu Arg Phe Ile Pro Val Asp Arg Glu Asp Thr Ala Tyr Ser Tyr
65 70 75 80

Lys Ala Arg Phe Thr Leu Ala Val Gly Asp Asn Arg Val Leu Asp Met
85 90 95

Ala Ser Thr Tyr Phe Asp Ile Arg Gly Val Leu Asp Arg Gly Pro Thr

-continued

```
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Asp Glu Gln Gly Pro Gly Ala Pro Gln
    130                 135                 140

Gly Pro Gly Ala Pro Gln Gly Pro Gly Ala Pro Gln Gly Pro Gly Ala
145                 150                 155                 160

Pro Gln Gly Pro Gly Ala Pro Gln Gly Pro Gly Ala Pro Gln Gly Pro
                165                 170                 175

Gly Ala Pro Gln Gly Pro Gly Ala Pro Gln Gly Pro Gly Ala Pro Gln
            180                 185                 190

Gly Pro Gly Ala Pro Gln Gly Pro Gly Ala Pro Gln Gly Pro Gly Ala
        195                 200                 205

Pro Lys Thr His Val Phe Gly Gln Ala Pro Tyr Ser Gly Ile Asn Ile
    210                 215                 220

Thr Lys Glu Gly Ile Gln Ile Gly Val Glu Gly Gln Thr Pro Lys Tyr
225                 230                 235                 240

Ala Asp Lys Thr Phe Gln Pro Glu Pro Gln Ile Gly Glu Ser Gln Trp
                245                 250                 255

Tyr Glu Thr Glu Ile Asn His Ala Ala Gly Arg Val Leu Lys Lys Thr
            260                 265                 270

Thr Pro Met Lys Pro Cys Tyr Gly Ser Tyr Ala Lys Pro Thr Asn Glu
        275                 280                 285

Asn Gly Gly Gln Gly Ile Leu Val Lys Gln Gln Asn Gly Lys Leu Glu
    290                 295                 300

Ser Gln Val Glu Met Gln Phe Phe Ser Thr Thr Glu Ala Ala Ala Gly
305                 310                 315                 320

Asn Gly Asp Asn Leu Thr Pro Lys Val Val Leu Tyr Ser Glu Asp Val
                325                 330                 335

Asp Ile Glu Thr Pro Asp Thr His Ile Ser Tyr Met Pro Thr Ile Lys
            340                 345                 350

Glu Gly Asn Ser Arg Glu Leu Met Gly Gln Gln Ser Met Pro Asn Arg
        355                 360                 365

Pro Asn Tyr Ile Ala Phe Arg Asp Asn Phe Ile Gly Leu Met Tyr Tyr
    370                 375                 380

Asn Ser Thr Gly Asn Met Gly Val Leu Ala Gly Gln Ala Ser Gln Leu
385                 390                 395                 400

Asn Ala Val Val Asp Leu Gln Asp Arg Asn Thr Glu Leu Ser Tyr Gln
                405                 410                 415

Leu Leu Leu Asp Ser Ile Gly Asp Arg Thr Arg Tyr Phe Ser Met Trp
            420                 425                 430

Asn Gln Leu Pro Asn Tyr Cys Phe Pro Leu Gly Gly Val Ile Asn Thr
        435                 440                 445

Glu Thr Leu Thr Lys Val Lys Pro Lys Thr Gly Gln Glu Asn Gly Trp
    450                 455                 460

Glu Lys Asp Ala Thr Glu Phe Ser Asp Lys Asn Glu Ile Arg Val Gly
465                 470                 475                 480

Asn Asn Phe Ala Met Glu Ile Asn Leu Asn Ala Asn Leu Trp Arg Asn
                485                 490                 495

Phe Leu Tyr Ser Asn Ile Ala Leu Tyr Leu Pro Asp Lys Leu Lys Tyr
            500                 505                 510

Ser Pro Ser Asn Val Lys Ile Ser Asp Asn Pro Asn Thr Tyr Asp Tyr
        515                 520                 525
```

-continued

```
Met Asn Lys Arg Val Val Ala Pro Gly Leu Val Asp Cys Tyr Ile Asn
    530                 535                 540

Leu Gly Ala Arg Trp Ser Leu Asp Tyr Met Asp Asn Val Asn Pro Phe
545                 550                 555                 560

Asn His His Arg Asn Ala Gly Leu Arg Tyr Arg Ser Met Leu Leu Gly
                565                 570                 575

Asn Gly Arg Tyr Val Pro Phe His Ile Gln Val Pro Gln Lys Phe Phe
            580                 585                 590

Ala Ile Lys Asn Leu Leu Leu Leu Pro Gly Ser Tyr Thr Tyr Glu Trp
        595                 600                 605

Asn Phe Arg Lys Asp Val Asn Met Val Leu Gln Ser Ser Leu Gly Asn
    610                 615                 620

Asp Leu Arg Val Asp Gly Ala Ser Ile Lys Phe Asp Ser Ile Cys Leu
625                 630                 635                 640

Tyr Ala Thr Phe Phe Pro Met Ala His Asn Thr Ala Ser Thr Leu Glu
                645                 650                 655

Ala Met Leu Arg Asn Asp Thr Asn Asp Gln Ser Phe Asn Asp Tyr Leu
            660                 665                 670

Ser Ala Ala Asn Met Leu Tyr Pro Ile Pro Ala Asn Ala Thr Asn Val
        675                 680                 685

Pro Ile Ser Ile Pro Ser Arg Asn Trp Ala Ala Phe Arg Leu Leu Thr
    690                 695                 700

Pro Asn Glu Phe Glu Ile Lys Arg Ser Val Asp Gly Glu Gly Tyr Asn
705                 710                 715                 720

Asp Pro Tyr Tyr Thr Tyr Ser Gly Ser Ile Pro Tyr Leu Asp Gly Thr
                725                 730                 735

Phe Tyr Leu Asn His Thr Phe Lys Lys Val Ala Ile Thr Phe Asp Ser
            740                 745                 750

Ser Val Ser Trp Pro Gly Asn Asp Arg Leu Leu Thr Pro Asn Glu Phe
        755                 760                 765

Glu Ile Lys Arg Ser Val Asp Gly Glu Gly Tyr Asn Val Ala Gln Cys
    770                 775                 780

Asn Met Thr Lys Asp Trp Phe Leu Val Gln Met Leu Ala Asn Tyr Asn
785                 790                 795                 800

Ile Gly Tyr Gln Gly Phe Tyr Ile Pro Glu Ser Tyr Lys Asp Arg Met
                805                 810                 815

Tyr Ser Phe Phe Arg Asn Phe Gln Pro Met Ser Arg Gln Val Val Asp
            820                 825                 830

Asp Thr Lys Tyr Lys Asp Tyr Gln Gln Val Gly Ile Leu His Gln His
        835                 840                 845

Asn Asn Ser Gly Phe Val Gly Tyr Leu Ala Pro Thr Met Arg Glu Gly
    850                 855                 860

Gln Ala Tyr Pro Ala Asn Phe Pro Tyr Pro Leu Ile Gly Lys Thr Ala
865                 870                 875                 880

Val Asp Ser Ile Thr Gln Lys Lys Phe Leu Cys Asp Arg Thr Leu Trp
                885                 890                 895

Arg Ile Pro Phe Ser Ser Asn Phe Met Ser Met Gly Ala Leu Thr Asp
            900                 905                 910

Leu Gly Gln Asn Leu Leu Tyr Ala Asn Ser Ala His Ala Leu Asp Met
        915                 920                 925

Thr Phe Glu Val Asp Pro Met Asp Glu Pro Thr Leu Leu Tyr Val Leu
    930                 935                 940
```

-continued

```
Phe Glu Val Phe Asp Val Val Arg Val His Gln Pro His Arg Gly Val
945                 950                 955                 960

Ile Glu Thr Val Tyr Leu Arg Thr Pro Phe Ser Ala Gly Asn Ala Thr
                965                 970                 975

Thr
```

<210> SEQ ID NO 40
<211> LENGTH: 975
<212> TYPE: PRT
<213> ORGANISM: Artificial Sequence
<220> FEATURE:
<223> OTHER INFORMATION: Synthetic Construct

<400> SEQUENCE: 40

```
Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Asp Glu Ala Ala Thr Ala Leu Glu Ile
    130                 135                 140

Asn Leu Glu Glu Glu Asp Asp Asp Asn Glu Asp Glu Val Asp Glu Gln
145                 150                 155                 160

Ala Glu Gln Gln Lys Thr His Val Phe Gly Gln Ala Pro Tyr Ser Gly
                165                 170                 175

Ile Asn Ile Thr Lys Glu Gly Ile Gln Ile Gly Val Glu Gly Gln Thr
            180                 185                 190

Pro Lys Tyr Ala Asp Lys Thr Phe Gln Pro Glu Pro Gln Ile Gly Glu
        195                 200                 205

Ser Gln Trp Tyr Glu Thr Glu Ile Asn His Ala Ala Gly Arg Val Leu
    210                 215                 220

Lys Lys Thr Thr Pro Met Lys Pro Cys Tyr Gly Ser Tyr Ala Lys Pro
225                 230                 235                 240

Thr Asn Glu Asn Gly Gly Gln Gly Ile Leu Val Lys Gln Gln Asn Gly
                245                 250                 255

Lys Leu Glu Ser Gln Val Glu Met Gln Phe Phe Ser Ala Ser Gln Gly
            260                 265                 270

Pro Gly Ala Pro Gln Gly Pro Gly Ala Pro Gln Gly Pro Gly Ala Pro
        275                 280                 285

Gly Thr Ser Thr Thr Glu Ala Ala Ala Gly Asn Gly Asp Asn Leu Thr
    290                 295                 300

Pro Lys Val Val Leu Tyr Ser Glu Asp Val Asp Ile Glu Thr Pro Asp
305                 310                 315                 320

Thr His Ile Ser Tyr Met Pro Thr Ile Lys Glu Gly Asn Ser Arg Glu
```

```
                325                 330                 335

Leu Met Gly Gln Gln Ser Met Pro Asn Arg Pro Asn Tyr Ile Ala Phe
            340                 345                 350

Arg Asp Asn Phe Ile Gly Leu Met Tyr Tyr Asn Ser Thr Gly Asn Met
        355                 360                 365

Gly Val Leu Ala Gly Gln Ala Ser Gln Leu Asn Ala Val Val Asp Leu
    370                 375                 380

Gln Asp Arg Asn Thr Glu Leu Ser Tyr Gln Leu Leu Leu Asp Ser Ile
385                 390                 395                 400

Gly Asp Arg Thr Arg Tyr Phe Ser Met Trp Asn Gln Ala Val Asp Ser
                405                 410                 415

Tyr Asp Pro Asp Val Arg Ile Ile Glu Asn His Gly Thr Glu Asp Glu
            420                 425                 430

Leu Pro Asn Tyr Cys Phe Pro Leu Gly Gly Val Ile Asn Thr Glu Thr
        435                 440                 445

Leu Thr Lys Val Lys Pro Lys Thr Gly Gln Glu Asn Gly Trp Glu Lys
    450                 455                 460

Asp Ala Thr Glu Phe Ser Asp Lys Asn Glu Ile Arg Val Gly Asn Asn
465                 470                 475                 480

Phe Ala Met Glu Ile Asn Leu Asn Ala Asn Leu Trp Arg Asn Phe Leu
                485                 490                 495

Tyr Ser Asn Ile Ala Leu Tyr Leu Pro Asp Lys Leu Lys Tyr Ser Pro
            500                 505                 510

Ser Asn Val Lys Ile Ser Asp Asn Pro Asn Thr Tyr Asp Tyr Met Asn
        515                 520                 525

Lys Arg Val Val Ala Pro Gly Leu Val Asp Cys Tyr Ile Asn Leu Gly
    530                 535                 540

Ala Arg Trp Ser Leu Asp Tyr Met Asp Asn Val Asn Pro Phe Asn His
545                 550                 555                 560

His Arg Asn Ala Gly Leu Arg Tyr Arg Ser Met Leu Leu Gly Asn Gly
                565                 570                 575

Arg Tyr Val Pro Phe His Ile Gln Val Pro Gln Lys Phe Phe Ala Ile
            580                 585                 590

Lys Asn Leu Leu Leu Leu Pro Gly Ser Tyr Thr Tyr Glu Trp Asn Phe
        595                 600                 605

Arg Lys Asp Val Asn Met Val Leu Gln Ser Ser Leu Gly Asn Asp Leu
    610                 615                 620

Arg Val Asp Gly Ala Ser Ile Lys Phe Asp Ser Ile Cys Leu Tyr Ala
625                 630                 635                 640

Thr Phe Phe Pro Met Ala His Asn Thr Ala Ser Thr Leu Glu Ala Met
                645                 650                 655

Leu Arg Asn Asp Thr Asn Asp Gln Ser Phe Asn Asp Tyr Leu Ser Ala
            660                 665                 670

Ala Asn Met Leu Tyr Pro Ile Pro Ala Asn Ala Thr Asn Val Pro Ile
        675                 680                 685

Ser Ile Pro Ser Arg Asn Trp Ala Ala Phe Arg Gly Trp Ala Phe Thr
    690                 695                 700

Arg Leu Lys Thr Lys Glu Thr Pro Ser Leu Gly Ser Gly Tyr Asp Pro
705                 710                 715                 720

Tyr Tyr Thr Tyr Ser Gly Ser Ile Pro Tyr Leu Asp Gly Thr Phe Tyr
                725                 730                 735

Leu Asn His Thr Phe Lys Lys Val Ala Ile Thr Phe Asp Ser Ser Val
            740                 745                 750
```

Ser Trp Pro Gly Asn Asp Arg Leu Leu Thr Pro Asn Glu Phe Glu Ile
755 760 765

Lys Arg Ser Val Asp Gly Glu Gly Tyr Asn Val Ala Gln Cys Asn Met
770 775 780

Thr Lys Asp Trp Phe Leu Val Gln Met Leu Ala Asn Tyr Asn Ile Gly
785 790 795 800

Tyr Gln Gly Phe Tyr Ile Pro Glu Ser Tyr Lys Asp Arg Met Tyr Ser
805 810 815

Phe Phe Arg Asn Phe Gln Pro Met Ser Arg Gln Val Val Asp Asp Thr
820 825 830

Lys Tyr Lys Asp Tyr Gln Gln Val Gly Ile Leu His Gln His Asn Asn
835 840 845

Ser Gly Phe Val Gly Tyr Leu Ala Pro Thr Met Arg Glu Gly Gln Ala
850 855 860

Tyr Pro Ala Asn Phe Pro Tyr Pro Leu Ile Gly Lys Thr Ala Val Asp
865 870 875 880

Ser Ile Thr Gln Lys Lys Phe Leu Cys Asp Arg Thr Leu Trp Arg Ile
885 890 895

Pro Phe Ser Ser Asn Phe Met Ser Met Gly Ala Leu Thr Asp Leu Gly
900 905 910

Gln Asn Leu Leu Tyr Ala Asn Ser Ala His Ala Leu Asp Met Thr Phe
915 920 925

Glu Val Asp Pro Met Asp Glu Pro Thr Leu Leu Tyr Val Leu Phe Glu
930 935 940

Val Phe Asp Val Val Arg Val His Gln Pro His Arg Gly Val Ile Glu
945 950 955 960

Thr Val Tyr Leu Arg Thr Pro Phe Ser Ala Gly Asn Ala Thr Thr
965 970 975

<210> SEQ ID NO 41
<211> LENGTH: 599
<212> TYPE: PRT
<213> ORGANISM: Artificial Sequence
<220> FEATURE:
<223> OTHER INFORMATION: Synthetic Construct

<400> SEQUENCE: 41

Met Lys Arg Ala Arg Pro Ser Glu Asp Thr Phe Asn Pro Val Tyr Pro
1 5 10 15

Tyr Asp Thr Glu Thr Gly Pro Pro Thr Val Pro Phe Leu Thr Pro Pro
20 25 30

Phe Val Ser Pro Asn Gly Phe Gln Glu Ser Pro Pro Gly Val Leu Ser
35 40 45

Leu Arg Leu Ser Glu Pro Leu Val Thr Ser Asn Gly Met Leu Ala Leu
50 55 60

Lys Met Gly Asn Gly Leu Ser Leu Asp Glu Ala Gly Asn Leu Thr Ser
65 70 75 80

Gln Asn Val Thr Thr Val Ser Pro Pro Leu Lys Lys Thr Lys Ser Asn
85 90 95

Ile Asn Leu Glu Ile Ser Ala Pro Leu Thr Val Thr Ser Glu Ala Leu
100 105 110

Thr Val Ala Ala Ala Ala Pro Leu Met Val Ala Gly Asn Thr Leu Thr
115 120 125

Met Gln Ser Gln Ala Pro Leu Thr Val His Asp Ser Lys Leu Ser Ile
130 135 140

-continued

```
Ala Thr Gln Gly Pro Leu Thr Val Ser Glu Gly Lys Leu Ala Leu Gln
145                 150                 155                 160

Thr Ser Gly Pro Leu Thr Thr Thr Asp Ser Ser Thr Leu Thr Ile Thr
                165                 170                 175

Ala Ser Pro Pro Leu Thr Thr Ala Thr Gly Ser Leu Gly Ile Asp Leu
            180                 185                 190

Lys Glu Pro Ile Tyr Thr Gln Asn Gly Lys Leu Gly Leu Lys Tyr Gly
        195                 200                 205

Ala Pro Leu His Val Thr Asp Asp Leu Asn Thr Leu Thr Val Ala Thr
    210                 215                 220

Gly Pro Gly Val Thr Ile Asn Asn Thr Ser Leu Gln Thr Lys Val Thr
225                 230                 235                 240

Gly Ala Leu Gly Phe Asp Ser Gln Gly Asn Met Gln Leu Asn Val Ala
                245                 250                 255

Gly Gly Leu Arg Ile Asp Ser Gln Asn Arg Arg Leu Ile Leu Asp Val
            260                 265                 270

Ser Tyr Pro Phe Asp Ala Gln Asn Gln Leu Asn Leu Arg Leu Gly Gln
        275                 280                 285

Gly Pro Leu Phe Ile Asn Ser Ala His Asn Leu Asp Ile Asn Tyr Asn
    290                 295                 300

Lys Gly Leu Tyr Leu Phe Thr Ala Ser Asn Asn Ser Lys Lys Leu Glu
305                 310                 315                 320

Val Asn Leu Ser Thr Ala Lys Gly Leu Met Phe Asp Ala Thr Ala Ile
                325                 330                 335

Ala Ile Asn Ala Gly Asp Gly Leu Glu Phe Gly Ser Pro Asn Ala Pro
            340                 345                 350

Asn Thr Asn Pro Leu Lys Thr Lys Ile Gly His Gly Leu Glu Phe Asp
        355                 360                 365

Ser Asn Lys Ala Met Val Pro Lys Leu Gly Thr Gly Leu Ser Phe Asp
    370                 375                 380

Ser Thr Gly Ala Ile Thr Val Gly Asn Lys Asn Asn Asp Lys Leu Thr
385                 390                 395                 400

Leu Trp Thr Thr Pro Ala Pro Ser Pro Asn Cys Arg Leu Asn Ala Glu
                405                 410                 415

Lys Asp Ala Lys Leu Thr Leu Val Leu Thr Lys Cys Gly Ser Gln Ile
            420                 425                 430

Leu Ala Thr Val Ser Val Leu Ala Val Lys Gly Ser Leu Ala Pro Ile
        435                 440                 445

Ser Gly Thr Val Gln Ser Ala His Leu Ile Ile Arg Phe Asp Glu Asn
    450                 455                 460

Gly Val Leu Leu Asn Asn Ser Phe Leu Asp Pro Glu Tyr Trp Asn Phe
465                 470                 475                 480

Arg Asn Gly Asp Leu Thr Glu Gly Thr Ala Tyr Thr Asn Ala Val Gly
                485                 490                 495

Phe Met Pro Asn Leu Ser Ala Tyr Pro Lys Ser His Gly Lys Thr Ala
            500                 505                 510

Lys Ser Asn Ile Val Ser Gln Val Tyr Leu Asn Gly Asp Lys Thr Lys
        515                 520                 525

Pro Val Thr Leu Thr Ile Thr Leu Asn Gly Thr Gln Glu Thr Gly Gln
    530                 535                 540

Gly Pro Gly Ala Pro Gln Gly Pro Gly Ala Pro Gln Gly Pro Gly Ala
545                 550                 555                 560
```

```
Pro Asp Thr Thr Pro Ser Ala Tyr Ser Met Ser Phe Ser Trp Asp Trp
                565                 570                 575

Ser Gly His Asn Tyr Ile Asn Glu Ile Phe Ala Thr Ser Ser Tyr Thr
            580                 585                 590

Phe Ser Tyr Ile Ala Gln Glu
        595


<210> SEQ ID NO 42
<211> LENGTH: 227
<212> TYPE: PRT
<213> ORGANISM: Artificial Sequence
<220> FEATURE:
<223> OTHER INFORMATION: Synthetic Construct

<400> SEQUENCE: 42

Met Ser Ile Leu Ile Ser Pro Ser Asn Asn Thr Gly Trp Gly Leu Arg
1               5                   10                  15

Phe Pro Ser Lys Met Phe Gly Gly Ala Lys Lys Arg Ser Asp Gln His
            20                  25                  30

Pro Val Arg Val Arg Gly His Tyr Arg Ala Pro Trp Gly Ala His Lys
        35                  40                  45

Arg Gly Arg Thr Gly Arg Thr Thr Val Asp Asp Ala Ile Asp Ala Val
    50                  55                  60

Val Glu Glu Ala Arg Asn Tyr Thr Pro Thr Pro Pro Pro Val Ser Thr
65                  70                  75                  80

Val Asp Ala Ala Ile Gln Thr Val Val Arg Gly Ala Arg Arg Tyr Ala
                85                  90                  95

Lys Met Lys Arg Arg Arg Arg Arg Val Ala Arg Arg His Arg Arg Arg
            100                 105                 110

Pro Gly Thr Ala Ala Gln Arg Ala Ala Ala Ala Leu Leu Asn Arg Ala
        115                 120                 125

Arg Arg Thr Gly Arg Arg Ala Ala Met Arg Ala Ala Arg Arg Leu Ala
    130                 135                 140

Ala Gly Ile Val Thr Val Pro Pro Arg Ser Arg Arg Arg Ala Ala Ala
145                 150                 155                 160

Ala Ala Ala Ala Ala Ile Ser Ala Met Thr Gln Gly Arg Arg Gly Asn
                165                 170                 175

Val Tyr Trp Val Arg Asp Ser Val Ser Gly Leu Arg Val Pro Val Arg
            180                 185                 190

Thr Arg Pro Pro Arg Asn Val Arg Thr Arg Pro Pro Arg Asn Tyr Asn
        195                 200                 205

Arg Asn Ile Val Asn Arg Leu Leu Gly Asp Ala Leu Asn Gly Lys Pro
    210                 215                 220

Glu Glu Lys
225


<210> SEQ ID NO 43
<211> LENGTH: 374
<212> TYPE: PRT
<213> ORGANISM: Artificial Sequence
<220> FEATURE:
<223> OTHER INFORMATION: Synthetic Construct

<400> SEQUENCE: 43

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30
```

```
Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Glu Asp Asn Glu Lys Leu Arg Lys Pro Lys His Lys Lys Leu Lys Gln
                85                  90                  95

Pro Ala Asp Gly Asn Pro Asp Pro Asn Ala Asn Pro Asn Val Asp Pro
            100                 105                 110

Asn Ala Asn Pro Asn Val Asp Pro Asn Ala Asn Pro Asn Val Asp Pro
        115                 120                 125

Asn Ala Asn Pro Asn Ala Asn Pro Asn Ala Asn Pro Asn Ala Asn Pro
    130                 135                 140

Asn Ala Asn Pro Asn Ala Asn Pro Asn Ala Asn Pro Asn Ala Asn Pro
145                 150                 155                 160

Asn Ala Asn Pro Asn Ala Asn Pro Asn Ala Asn Pro Asn Ala Asn Pro
                165                 170                 175

Asn Ala Asn Pro Asn Ala Asn Pro Asn Ala Asn Pro Asn Ala Asn Pro
            180                 185                 190

Asn Ala Asn Pro Asn Val Asp Pro Asn Ala Asn Pro Asn Ala Asn Pro
        195                 200                 205

Asn Ala Asn Pro Asn Ala Asn Pro Asn Ala Asn Pro Asn Ala Asn Pro
    210                 215                 220

Asn Ala Asn Pro Asn Ala Asn Pro Asn Ala Asn Pro Asn Ala Asn Pro
225                 230                 235                 240

Asn Ala Asn Pro Asn Ala Asn Pro Asn Ala Asn Pro Asn Ala Asn Pro
                245                 250                 255

Asn Ala Asn Pro Asn Ala Asn Pro Asn Ala Asn Pro Asn Ala Asn Pro
            260                 265                 270

Asn Lys Asn Asn Gln Gly Asn Gly Gln Gly His Asn Met Pro Asn Asp
        275                 280                 285

Pro Asn Arg Asn Val Asp Glu Asn Ala Asn Ala Asn Ser Ala Val Lys
    290                 295                 300

Asn Asn Asn Asn Glu Glu Pro Ser Asp Lys His Ile Lys Glu Tyr Leu
305                 310                 315                 320

Asn Lys Ile Gln Asn Ser Leu Ser Thr Glu Trp Ser Pro Cys Ser Val
                325                 330                 335

Thr Cys Gly Asn Gly Ile Gln Val Arg Ile Lys Pro Gly Ser Ala Asn
            340                 345                 350

Lys Pro Lys Asp Glu Leu Asp Tyr Ala Asn Asp Ile Glu Lys Lys Ile
        355                 360                 365

Cys Lys Met Glu Lys Cys
    370
```

<210> SEQ ID NO 44
<211> LENGTH: 941
<212> TYPE: PRT
<213> ORGANISM: Artificial Sequence
<220> FEATURE:
<223> OTHER INFORMATION: Synthetic Construct

<400> SEQUENCE: 44

```
Met Ala Thr Pro Ser Met Met Pro Gln Trp Ser Tyr Met His Ile Ser
1               5                   10                  15
```

-continued

```
Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Asp Glu Asn Ala Asn Pro Asn Ala Asn
    130                 135                 140

Pro Asn Ala Asn Pro Asn Ala Asn Pro Lys Thr His Val Phe Gly Gln
145                 150                 155                 160

Ala Pro Tyr Ser Gly Ile Asn Ile Thr Lys Glu Gly Ile Gln Ile Gly
                165                 170                 175

Val Glu Gly Gln Thr Pro Lys Tyr Ala Asp Lys Thr Phe Gln Pro Glu
            180                 185                 190

Pro Gln Ile Gly Glu Ser Gln Trp Tyr Glu Thr Glu Ile Asn His Ala
        195                 200                 205

Ala Gly Arg Val Leu Lys Lys Thr Thr Pro Met Lys Pro Cys Tyr Gly
    210                 215                 220

Ser Tyr Ala Lys Pro Thr Asn Glu Asn Gly Gly Gln Gly Ile Leu Val
225                 230                 235                 240

Lys Gln Gln Asn Gly Lys Leu Glu Ser Gln Val Glu Met Gln Phe Phe
                245                 250                 255

Ser Thr Thr Glu Ala Ala Ala Gly Asn Gly Asp Asn Leu Thr Pro Lys
            260                 265                 270

Val Val Leu Tyr Ser Glu Asp Val Asp Ile Glu Thr Pro Asp Thr His
        275                 280                 285

Ile Ser Tyr Met Pro Thr Ile Lys Glu Gly Asn Ser Arg Glu Leu Met
    290                 295                 300

Gly Gln Gln Ser Met Pro Asn Arg Pro Asn Tyr Ile Ala Phe Arg Asp
305                 310                 315                 320

Asn Phe Ile Gly Leu Met Tyr Tyr Asn Ser Thr Gly Asn Met Gly Val
                325                 330                 335

Leu Ala Gly Gln Ala Ser Gln Leu Asn Ala Val Val Asp Leu Gln Asp
            340                 345                 350

Arg Asn Thr Glu Leu Ser Tyr Gln Leu Leu Leu Asp Ser Ile Gly Asp
        355                 360                 365

Arg Thr Arg Tyr Phe Ser Met Trp Asn Gln Ala Val Asp Ser Tyr Asp
    370                 375                 380

Pro Asp Val Arg Ile Ile Glu Asn His Gly Thr Glu Asp Glu Leu Pro
385                 390                 395                 400

Asn Tyr Cys Phe Pro Leu Gly Gly Val Ile Asn Thr Glu Thr Leu Thr
                405                 410                 415

Lys Val Lys Pro Lys Thr Gly Gln Glu Asn Gly Trp Glu Lys Asp Ala
            420                 425                 430
```

```
Thr Glu Phe Ser Asp Lys Asn Glu Ile Arg Val Gly Asn Asn Phe Ala
        435                 440                 445

Met Glu Ile Asn Leu Asn Ala Asn Leu Trp Arg Asn Phe Leu Tyr Ser
    450                 455                 460

Asn Ile Ala Leu Tyr Leu Pro Asp Lys Leu Lys Tyr Ser Pro Ser Asn
465                 470                 475                 480

Val Lys Ile Ser Asp Asn Pro Asn Thr Tyr Asp Tyr Met Asn Lys Arg
                485                 490                 495

Val Val Ala Pro Gly Leu Val Asp Cys Tyr Ile Asn Leu Gly Ala Arg
            500                 505                 510

Trp Ser Leu Asp Tyr Met Asp Asn Val Asn Pro Phe Asn His His Arg
        515                 520                 525

Asn Ala Gly Leu Arg Tyr Arg Ser Met Leu Leu Gly Asn Gly Arg Tyr
    530                 535                 540

Val Pro Phe His Ile Gln Val Pro Gln Lys Phe Phe Ala Ile Lys Asn
545                 550                 555                 560

Leu Leu Leu Leu Pro Gly Ser Tyr Thr Tyr Glu Trp Asn Phe Arg Lys
                565                 570                 575

Asp Val Asn Met Val Leu Gln Ser Ser Leu Gly Asn Asp Leu Arg Val
            580                 585                 590

Asp Gly Ala Ser Ile Lys Phe Asp Ser Ile Cys Leu Tyr Ala Thr Phe
        595                 600                 605

Phe Pro Met Ala His Asn Thr Ala Ser Thr Leu Glu Ala Met Leu Arg
    610                 615                 620

Asn Asp Thr Asn Asp Gln Ser Phe Asn Asp Tyr Leu Ser Ala Ala Asn
625                 630                 635                 640

Met Leu Tyr Pro Ile Pro Ala Asn Ala Thr Asn Val Pro Ile Ser Ile
                645                 650                 655

Pro Ser Arg Asn Trp Ala Ala Phe Arg Gly Trp Ala Phe Thr Arg Leu
            660                 665                 670

Lys Thr Lys Glu Thr Pro Ser Leu Gly Ser Gly Tyr Asp Pro Tyr Tyr
        675                 680                 685

Thr Tyr Ser Gly Ser Ile Pro Tyr Leu Asp Gly Thr Phe Tyr Leu Asn
    690                 695                 700

His Thr Phe Lys Lys Val Ala Ile Thr Phe Asp Ser Ser Val Ser Trp
705                 710                 715                 720

Pro Gly Asn Asp Arg Leu Leu Thr Pro Asn Glu Phe Glu Ile Lys Arg
                725                 730                 735

Ser Val Asp Gly Glu Gly Tyr Asn Val Ala Gln Cys Asn Met Thr Lys
            740                 745                 750

Asp Trp Phe Leu Val Gln Met Leu Ala Asn Tyr Asn Ile Gly Tyr Gln
        755                 760                 765

Gly Phe Tyr Ile Pro Glu Ser Tyr Lys Asp Arg Met Tyr Ser Phe Phe
    770                 775                 780

Arg Asn Phe Gln Pro Met Ser Arg Gln Val Val Asp Asp Thr Lys Tyr
785                 790                 795                 800

Lys Asp Tyr Gln Gln Val Gly Ile Leu His Gln His Asn Asn Ser Gly
                805                 810                 815

Phe Val Gly Tyr Leu Ala Pro Thr Met Arg Glu Gly Gln Ala Tyr Pro
            820                 825                 830

Ala Asn Phe Pro Tyr Pro Leu Ile Gly Lys Thr Ala Val Asp Ser Ile
        835                 840                 845

Thr Gln Lys Lys Phe Leu Cys Asp Arg Thr Leu Trp Arg Ile Pro Phe
```

```
    850                 855                 860

Ser Ser Asn Phe Met Ser Met Gly Ala Leu Thr Asp Leu Gly Gln Asn
865                 870                 875                 880

Leu Leu Tyr Ala Asn Ser Ala His Ala Leu Asp Met Thr Phe Glu Val
                885                 890                 895

Asp Pro Met Asp Glu Pro Thr Leu Leu Tyr Val Leu Phe Glu Val Phe
            900                 905                 910

Asp Val Val Arg Val His Gln Pro His Arg Gly Val Ile Glu Thr Val
        915                 920                 925

Tyr Leu Arg Thr Pro Phe Ser Ala Gly Asn Ala Thr Thr
    930                 935                 940


<210> SEQ ID NO 45
<211> LENGTH: 929
<212> TYPE: PRT
<213> ORGANISM: Artificial Sequence
<220> FEATURE:
<223> OTHER INFORMATION: Synthetic Construct

<400> SEQUENCE: 45

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Asp Glu Asn Ala Asn Pro Asn Ala Asn
    130                 135                 140

Pro Asn Ala Asn Pro Asn Ala Asn Pro Asn Ala Asn Pro Asn Ala Asn
145                 150                 155                 160

Pro Lys Thr His Val Phe Gly Gln Ala Pro Tyr Ser Gly Ile Asn Ile
                165                 170                 175

Thr Lys Glu Gly Ile Gln Ile Gly Val Glu Gly Gln Thr Pro Lys Tyr
            180                 185                 190

Ala Asp Lys Thr Phe Gln Pro Glu Pro Gln Ile Gly Glu Ser Gln Trp
        195                 200                 205

Tyr Glu Thr Glu Ile Asn His Ala Ala Gly Arg Val Leu Lys Lys Thr
    210                 215                 220

Thr Pro Met Lys Pro Cys Tyr Gly Ser Tyr Ala Lys Pro Thr Asn Glu
225                 230                 235                 240

Asn Gly Gly Gln Gly Ile Leu Val Lys Gln Gln Asn Gly Lys Leu Glu
                245                 250                 255

Ser Gln Val Glu Met Gln Phe Phe Ser Thr Thr Glu Ala Ala Ala Gly
            260                 265                 270

Asn Gly Asp Asn Leu Thr Pro Lys Val Val Leu Tyr Ser Glu Asp Val
```

```
        275                 280                 285

Asp Ile Glu Thr Pro Asp Thr His Ile Ser Tyr Met Pro Thr Ile Lys
    290                 295                 300

Glu Gly Asn Ser Arg Glu Leu Met Gly Gln Gln Ser Met Pro Asn Arg
305                 310                 315                 320

Pro Asn Tyr Ile Ala Phe Arg Asp Asn Phe Ile Gly Leu Met Tyr Tyr
                325                 330                 335

Asn Ser Thr Gly Asn Met Gly Val Leu Ala Gly Gln Ala Ser Gln Leu
            340                 345                 350

Asn Ala Val Val Asp Leu Gln Asp Arg Asn Thr Glu Leu Ser Tyr Gln
        355                 360                 365

Leu Leu Leu Asp Ser Ile Gly Asp Arg Thr Arg Tyr Phe Ser Met Trp
    370                 375                 380

Asn Gln Leu Pro Asn Tyr Cys Phe Pro Leu Gly Gly Val Ile Asn Thr
385                 390                 395                 400

Glu Thr Leu Thr Lys Val Lys Pro Lys Thr Gly Gln Glu Asn Gly Trp
                405                 410                 415

Glu Lys Asp Ala Thr Glu Phe Ser Asp Lys Asn Glu Ile Arg Val Gly
            420                 425                 430

Asn Asn Phe Ala Met Glu Ile Asn Leu Asn Ala Asn Leu Trp Arg Asn
        435                 440                 445

Phe Leu Tyr Ser Asn Ile Ala Leu Tyr Leu Pro Asp Lys Leu Lys Tyr
    450                 455                 460

Ser Pro Ser Asn Val Lys Ile Ser Asp Asn Pro Asn Thr Tyr Asp Tyr
465                 470                 475                 480

Met Asn Lys Arg Val Val Ala Pro Gly Leu Val Asp Cys Tyr Ile Asn
                485                 490                 495

Leu Gly Ala Arg Trp Ser Leu Asp Tyr Met Asp Asn Val Asn Pro Phe
            500                 505                 510

Asn His His Arg Asn Ala Gly Leu Arg Tyr Arg Ser Met Leu Leu Gly
        515                 520                 525

Asn Gly Arg Tyr Val Pro Phe His Ile Gln Val Pro Gln Lys Phe Phe
    530                 535                 540

Ala Ile Lys Asn Leu Leu Leu Leu Pro Gly Ser Tyr Thr Tyr Glu Trp
545                 550                 555                 560

Asn Phe Arg Lys Asp Val Asn Met Val Leu Gln Ser Ser Leu Gly Asn
                565                 570                 575

Asp Leu Arg Val Asp Gly Ala Ser Ile Lys Phe Asp Ser Ile Cys Leu
            580                 585                 590

Tyr Ala Thr Phe Phe Pro Met Ala His Asn Thr Ala Ser Thr Leu Glu
        595                 600                 605

Ala Met Leu Arg Asn Asp Thr Asn Asp Gln Ser Phe Asn Asp Tyr Leu
    610                 615                 620

Ser Ala Ala Asn Met Leu Tyr Pro Ile Pro Ala Asn Ala Thr Asn Val
625                 630                 635                 640

Pro Ile Ser Ile Pro Ser Arg Asn Trp Ala Ala Phe Arg Gly Trp Ala
                645                 650                 655

Phe Thr Arg Leu Lys Thr Lys Glu Thr Pro Ser Leu Gly Ser Gly Tyr
            660                 665                 670

Asp Pro Tyr Tyr Thr Tyr Ser Gly Ser Ile Pro Tyr Leu Asp Gly Thr
        675                 680                 685

Phe Tyr Leu Asn His Thr Phe Lys Lys Val Ala Ile Thr Phe Asp Ser
    690                 695                 700
```

Ser Val Ser Trp Pro Gly Asn Asp Arg Leu Leu Thr Pro Asn Glu Phe
705 710 715 720

Glu Ile Lys Arg Ser Val Asp Gly Glu Gly Tyr Asn Val Ala Gln Cys
725 730 735

Asn Met Thr Lys Asp Trp Phe Leu Val Gln Met Leu Ala Asn Tyr Asn
740 745 750

Ile Gly Tyr Gln Gly Phe Tyr Ile Pro Glu Ser Tyr Lys Asp Arg Met
755 760 765

Tyr Ser Phe Phe Arg Asn Phe Gln Pro Met Ser Arg Gln Val Val Asp
770 775 780

Asp Thr Lys Tyr Lys Asp Tyr Gln Gln Val Gly Ile Leu His Gln His
785 790 795 800

Asn Asn Ser Gly Phe Val Gly Tyr Leu Ala Pro Thr Met Arg Glu Gly
805 810 815

Gln Ala Tyr Pro Ala Asn Phe Pro Tyr Pro Leu Ile Gly Lys Thr Ala
820 825 830

Val Asp Ser Ile Thr Gln Lys Lys Phe Leu Cys Asp Arg Thr Leu Trp
835 840 845

Arg Ile Pro Phe Ser Ser Asn Phe Met Ser Met Gly Ala Leu Thr Asp
850 855 860

Leu Gly Gln Asn Leu Leu Tyr Ala Asn Ser Ala His Ala Leu Asp Met
865 870 875 880

Thr Phe Glu Val Asp Pro Met Asp Glu Pro Thr Leu Leu Tyr Val Leu
885 890 895

Phe Glu Val Phe Asp Val Val Arg Val His Gln Pro His Arg Gly Val
900 905 910

Ile Glu Thr Val Tyr Leu Arg Thr Pro Phe Ser Ala Gly Asn Ala Thr
915 920 925

Thr

<210> SEQ ID NO 46
<211> LENGTH: 937
<212> TYPE: PRT
<213> ORGANISM: Artificial Sequence
<220> FEATURE:
<223> OTHER INFORMATION: Synthetic Construct

<400> SEQUENCE: 46

Met Ala Thr Pro Ser Met Met Pro Gln Trp Ser Tyr Met His Ile Ser
1 5 10 15

Gly Gln Asp Ala Ser Glu Tyr Leu Ser Pro Gly Leu Val Gln Phe Ala
20 25 30

Arg Ala Thr Glu Thr Tyr Phe Ser Leu Asn Asn Lys Phe Arg Asn Pro
35 40 45

Thr Val Ala Pro Thr His Asp Val Thr Thr Asp Arg Ser Gln Arg Leu
50 55 60

Thr Leu Arg Phe Ile Pro Val Asp Arg Glu Asp Thr Ala Tyr Ser Tyr
65 70 75 80

Lys Ala Arg Phe Thr Leu Ala Val Gly Asp Asn Arg Val Leu Asp Met
85 90 95

Ala Ser Thr Tyr Phe Asp Ile Arg Gly Val Leu Asp Arg Gly Pro Thr
100 105 110

Phe Lys Pro Tyr Ser Gly Thr Ala Tyr Asn Ala Leu Ala Pro Lys Gly
115 120 125

-continued

```
Ala Pro Asn Pro Cys Glu Trp Asp Glu Asn Ala Asn Pro Asn Ala Asn
    130                 135                 140

Pro Asn Ala Asn Pro Asn Ala Asn Pro Asn Ala Asn Pro Asn Ala Asn
145                 150                 155                 160

Pro Asn Ala Asn Pro Asn Ala Asn Pro Lys Thr His Val Phe Gly Gln
                165                 170                 175

Ala Pro Tyr Ser Gly Ile Asn Ile Thr Lys Glu Gly Ile Gln Ile Gly
            180                 185                 190

Val Glu Gly Gln Thr Pro Lys Tyr Ala Asp Lys Thr Phe Gln Pro Glu
        195                 200                 205

Pro Gln Ile Gly Glu Ser Gln Trp Tyr Glu Thr Glu Ile Asn His Ala
    210                 215                 220

Ala Gly Arg Val Leu Lys Lys Thr Thr Pro Met Lys Pro Cys Tyr Gly
225                 230                 235                 240

Ser Tyr Ala Lys Pro Thr Asn Glu Asn Gly Gly Gln Gly Ile Leu Val
                245                 250                 255

Lys Gln Gln Asn Gly Lys Leu Glu Ser Gln Val Glu Met Gln Phe Phe
            260                 265                 270

Ser Thr Thr Glu Ala Ala Ala Gly Asn Gly Asp Asn Leu Thr Pro Lys
        275                 280                 285

Val Val Leu Tyr Ser Glu Asp Val Asp Ile Glu Thr Pro Asp Thr His
    290                 295                 300

Ile Ser Tyr Met Pro Thr Ile Lys Glu Gly Asn Ser Arg Glu Leu Met
305                 310                 315                 320

Gly Gln Gln Ser Met Pro Asn Arg Pro Asn Tyr Ile Ala Phe Arg Asp
                325                 330                 335

Asn Phe Ile Gly Leu Met Tyr Tyr Asn Ser Thr Gly Asn Met Gly Val
            340                 345                 350

Leu Ala Gly Gln Ala Ser Gln Leu Asn Ala Val Val Asp Leu Gln Asp
        355                 360                 365

Arg Asn Thr Glu Leu Ser Tyr Gln Leu Leu Leu Asp Ser Ile Gly Asp
    370                 375                 380

Arg Thr Arg Tyr Phe Ser Met Trp Asn Gln Leu Pro Asn Tyr Cys Phe
385                 390                 395                 400

Pro Leu Gly Gly Val Ile Asn Thr Glu Thr Leu Thr Lys Val Lys Pro
                405                 410                 415

Lys Thr Gly Gln Glu Asn Gly Trp Glu Lys Asp Ala Thr Glu Phe Ser
            420                 425                 430

Asp Lys Asn Glu Ile Arg Val Gly Asn Asn Phe Ala Met Glu Ile Asn
        435                 440                 445

Leu Asn Ala Asn Leu Trp Arg Asn Phe Leu Tyr Ser Asn Ile Ala Leu
    450                 455                 460

Tyr Leu Pro Asp Lys Leu Lys Tyr Ser Pro Ser Asn Val Lys Ile Ser
465                 470                 475                 480

Asp Asn Pro Asn Thr Tyr Asp Tyr Met Asn Lys Arg Val Val Ala Pro
                485                 490                 495

Gly Leu Val Asp Cys Tyr Ile Asn Leu Gly Ala Arg Trp Ser Leu Asp
            500                 505                 510

Tyr Met Asp Asn Val Asn Pro Phe Asn His His Arg Asn Ala Gly Leu
        515                 520                 525

Arg Tyr Arg Ser Met Leu Leu Gly Asn Gly Arg Tyr Val Pro Phe His
    530                 535                 540

Ile Gln Val Pro Gln Lys Phe Phe Ala Ile Lys Asn Leu Leu Leu Leu
```

```
545                 550                 555                 560

Pro Gly Ser Tyr Thr Tyr Glu Trp Asn Phe Arg Lys Asp Val Asn Met
                565                 570                 575

Val Leu Gln Ser Ser Leu Gly Asn Asp Leu Arg Val Asp Gly Ala Ser
            580                 585                 590

Ile Lys Phe Asp Ser Ile Cys Leu Tyr Ala Thr Phe Phe Pro Met Ala
        595                 600                 605

His Asn Thr Ala Ser Thr Leu Glu Ala Met Leu Arg Asn Asp Thr Asn
    610                 615                 620

Asp Gln Ser Phe Asn Asp Tyr Leu Ser Ala Ala Asn Met Leu Tyr Pro
625                 630                 635                 640

Ile Pro Ala Asn Ala Thr Asn Val Pro Ile Ser Ile Pro Ser Arg Asn
                645                 650                 655

Trp Ala Ala Phe Arg Gly Trp Ala Phe Thr Arg Leu Lys Thr Lys Glu
            660                 665                 670

Thr Pro Ser Leu Gly Ser Gly Tyr Asp Pro Tyr Tyr Thr Tyr Ser Gly
        675                 680                 685

Ser Ile Pro Tyr Leu Asp Gly Thr Phe Tyr Leu Asn His Thr Phe Lys
    690                 695                 700

Lys Val Ala Ile Thr Phe Asp Ser Ser Val Ser Trp Pro Gly Asn Asp
705                 710                 715                 720

Arg Leu Leu Thr Pro Asn Glu Phe Glu Ile Lys Arg Ser Val Asp Gly
                725                 730                 735

Glu Gly Tyr Asn Val Ala Gln Cys Asn Met Thr Lys Asp Trp Phe Leu
            740                 745                 750

Val Gln Met Leu Ala Asn Tyr Asn Ile Gly Tyr Gln Gly Phe Tyr Ile
        755                 760                 765

Pro Glu Ser Tyr Lys Asp Arg Met Tyr Ser Phe Phe Arg Asn Phe Gln
    770                 775                 780

Pro Met Ser Arg Gln Val Val Asp Asp Thr Lys Tyr Lys Asp Tyr Gln
785                 790                 795                 800

Gln Val Gly Ile Leu His Gln His Asn Asn Ser Gly Phe Val Gly Tyr
                805                 810                 815

Leu Ala Pro Thr Met Arg Glu Gly Gln Ala Tyr Pro Ala Asn Phe Pro
            820                 825                 830

Tyr Pro Leu Ile Gly Lys Thr Ala Val Asp Ser Ile Thr Gln Lys Lys
        835                 840                 845

Phe Leu Cys Asp Arg Thr Leu Trp Arg Ile Pro Phe Ser Ser Asn Phe
    850                 855                 860

Met Ser Met Gly Ala Leu Thr Asp Leu Gly Gln Asn Leu Leu Tyr Ala
865                 870                 875                 880

Asn Ser Ala His Ala Leu Asp Met Thr Phe Glu Val Asp Pro Met Asp
                885                 890                 895

Glu Pro Thr Leu Leu Tyr Val Leu Phe Glu Val Phe Asp Val Val Arg
            900                 905                 910

Val His Gln Pro His Arg Gly Val Ile Glu Thr Val Tyr Leu Arg Thr
        915                 920                 925

Pro Phe Ser Ala Gly Asn Ala Thr Thr
    930                 935
```

<210> SEQ ID NO 47
<211> LENGTH: 945
<212> TYPE: PRT
<213> ORGANISM: Artificial Sequence
<220> FEATURE:
<223> OTHER INFORMATION: Synthetic Construct

<400> SEQUENCE: 47

```
Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Asp Glu Asn Ala Asn Pro Asn Ala Asn
    130                 135                 140

Pro Asn Ala Asn Pro Asn Ala Asn Pro Asn Ala Asn Pro Asn Ala Asn
145                 150                 155                 160

Pro Asn Ala Asn Pro Asn Ala Asn Pro Asn Ala Asn Pro Asn Ala Asn
                165                 170                 175

Pro Lys Thr His Val Phe Gly Gln Ala Pro Tyr Ser Gly Ile Asn Ile
            180                 185                 190

Thr Lys Glu Gly Ile Gln Ile Gly Val Glu Gly Gln Thr Pro Lys Tyr
        195                 200                 205

Ala Asp Lys Thr Phe Gln Pro Glu Pro Gln Ile Gly Glu Ser Gln Trp
    210                 215                 220

Tyr Glu Thr Glu Ile Asn His Ala Ala Gly Arg Val Leu Lys Lys Thr
225                 230                 235                 240

Thr Pro Met Lys Pro Cys Tyr Gly Ser Tyr Ala Lys Pro Thr Asn Glu
                245                 250                 255

Asn Gly Gly Gln Gly Ile Leu Val Lys Gln Gln Asn Gly Lys Leu Glu
            260                 265                 270

Ser Gln Val Glu Met Gln Phe Phe Ser Thr Thr Glu Ala Ala Ala Gly
        275                 280                 285

Asn Gly Asp Asn Leu Thr Pro Lys Val Val Leu Tyr Ser Glu Asp Val
    290                 295                 300

Asp Ile Glu Thr Pro Asp Thr His Ile Ser Tyr Met Pro Thr Ile Lys
305                 310                 315                 320

Glu Gly Asn Ser Arg Glu Leu Met Gly Gln Gln Ser Met Pro Asn Arg
                325                 330                 335

Pro Asn Tyr Ile Ala Phe Arg Asp Asn Phe Ile Gly Leu Met Tyr Tyr
            340                 345                 350

Asn Ser Thr Gly Asn Met Gly Val Leu Ala Gly Gln Ala Ser Gln Leu
        355                 360                 365

Asn Ala Val Val Asp Leu Gln Asp Arg Asn Thr Glu Leu Ser Tyr Gln
    370                 375                 380

Leu Leu Leu Asp Ser Ile Gly Asp Arg Thr Arg Tyr Phe Ser Met Trp
385                 390                 395                 400
```

-continued

```
Asn Gln Leu Pro Asn Tyr Cys Phe Pro Leu Gly Gly Val Ile Asn Thr
                405                 410                 415

Glu Thr Leu Thr Lys Val Lys Pro Lys Thr Gly Gln Glu Asn Gly Trp
            420                 425                 430

Glu Lys Asp Ala Thr Glu Phe Ser Asp Lys Asn Glu Ile Arg Val Gly
        435                 440                 445

Asn Asn Phe Ala Met Glu Ile Asn Leu Asn Ala Asn Leu Trp Arg Asn
    450                 455                 460

Phe Leu Tyr Ser Asn Ile Ala Leu Tyr Leu Pro Asp Lys Leu Lys Tyr
465                 470                 475                 480

Ser Pro Ser Asn Val Lys Ile Ser Asp Asn Pro Asn Thr Tyr Asp Tyr
                485                 490                 495

Met Asn Lys Arg Val Val Ala Pro Gly Leu Val Asp Cys Tyr Ile Asn
            500                 505                 510

Leu Gly Ala Arg Trp Ser Leu Asp Tyr Met Asp Asn Val Asn Pro Phe
        515                 520                 525

Asn His His Arg Asn Ala Gly Leu Arg Tyr Arg Ser Met Leu Leu Gly
    530                 535                 540

Asn Gly Arg Tyr Val Pro Phe His Ile Gln Val Pro Gln Lys Phe Phe
545                 550                 555                 560

Ala Ile Lys Asn Leu Leu Leu Leu Pro Gly Ser Tyr Thr Tyr Glu Trp
                565                 570                 575

Asn Phe Arg Lys Asp Val Asn Met Val Leu Gln Ser Ser Leu Gly Asn
            580                 585                 590

Asp Leu Arg Val Asp Gly Ala Ser Ile Lys Phe Asp Ser Ile Cys Leu
        595                 600                 605

Tyr Ala Thr Phe Phe Pro Met Ala His Asn Thr Ala Ser Thr Leu Glu
    610                 615                 620

Ala Met Leu Arg Asn Asp Thr Asn Asp Gln Ser Phe Asn Asp Tyr Leu
625                 630                 635                 640

Ser Ala Ala Asn Met Leu Tyr Pro Ile Pro Ala Asn Ala Thr Asn Val
                645                 650                 655

Pro Ile Ser Ile Pro Ser Arg Asn Trp Ala Ala Phe Arg Gly Trp Ala
            660                 665                 670

Phe Thr Arg Leu Lys Thr Lys Glu Thr Pro Ser Leu Gly Ser Gly Tyr
        675                 680                 685

Asp Pro Tyr Tyr Thr Tyr Ser Gly Ser Ile Pro Tyr Leu Asp Gly Thr
    690                 695                 700

Phe Tyr Leu Asn His Thr Phe Lys Lys Val Ala Ile Thr Phe Asp Ser
705                 710                 715                 720

Ser Val Ser Trp Pro Gly Asn Asp Arg Leu Leu Thr Pro Asn Glu Phe
                725                 730                 735

Glu Ile Lys Arg Ser Val Asp Gly Glu Gly Tyr Asn Val Ala Gln Cys
            740                 745                 750

Asn Met Thr Lys Asp Trp Phe Leu Val Gln Met Leu Ala Asn Tyr Asn
        755                 760                 765

Ile Gly Tyr Gln Gly Phe Tyr Ile Pro Glu Ser Tyr Lys Asp Arg Met
    770                 775                 780

Tyr Ser Phe Phe Arg Asn Phe Gln Pro Met Ser Arg Gln Val Val Asp
785                 790                 795                 800

Asp Thr Lys Tyr Lys Asp Tyr Gln Gln Val Gly Ile Leu His Gln His
                805                 810                 815
```

```
Asn Asn Ser Gly Phe Val Gly Tyr Leu Ala Pro Thr Met Arg Glu Gly
            820                 825                 830

Gln Ala Tyr Pro Ala Asn Phe Pro Tyr Pro Leu Ile Gly Lys Thr Ala
        835                 840                 845

Val Asp Ser Ile Thr Gln Lys Lys Phe Leu Cys Asp Arg Thr Leu Trp
    850                 855                 860

Arg Ile Pro Phe Ser Ser Asn Phe Met Ser Met Gly Ala Leu Thr Asp
865                 870                 875                 880

Leu Gly Gln Asn Leu Leu Tyr Ala Asn Ser Ala His Ala Leu Asp Met
                885                 890                 895

Thr Phe Glu Val Asp Pro Met Asp Glu Pro Thr Leu Leu Tyr Val Leu
            900                 905                 910

Phe Glu Val Phe Asp Val Val Arg Val His Gln Pro His Arg Gly Val
        915                 920                 925

Ile Glu Thr Val Tyr Leu Arg Thr Pro Phe Ser Ala Gly Asn Ala Thr
    930                 935                 940

Thr
945


<210> SEQ ID NO 48
<211> LENGTH: 953
<212> TYPE: PRT
<213> ORGANISM: Artificial Sequence
<220> FEATURE:
<223> OTHER INFORMATION: Synthetic Construct

<400> SEQUENCE: 48

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Asp Glu Asn Ala Asn Pro Asn Ala Asn
    130                 135                 140

Pro Asn Ala Asn Pro Asn Ala Asn Pro Asn Ala Asn Pro Asn Ala Asn
145                 150                 155                 160

Pro Asn Ala Asn Pro Asn Ala Asn Pro Asn Ala Asn Pro Asn Ala Asn
                165                 170                 175

Pro Asn Ala Asn Pro Asn Ala Asn Pro Lys Thr His Val Phe Gly Gln
            180                 185                 190

Ala Pro Tyr Ser Gly Ile Asn Ile Thr Lys Glu Gly Ile Gln Ile Gly
        195                 200                 205

Val Glu Gly Gln Thr Pro Lys Tyr Ala Asp Lys Thr Phe Gln Pro Glu
    210                 215                 220
```

-continued

```
Pro Gln Ile Gly Glu Ser Gln Trp Tyr Glu Thr Glu Ile Asn His Ala
225                 230                 235                 240

Ala Gly Arg Val Leu Lys Lys Thr Thr Pro Met Lys Pro Cys Tyr Gly
                245                 250                 255

Ser Tyr Ala Lys Pro Thr Asn Glu Asn Gly Gly Gln Gly Ile Leu Val
            260                 265                 270

Lys Gln Gln Asn Gly Lys Leu Glu Ser Gln Val Glu Met Gln Phe Phe
        275                 280                 285

Ser Thr Thr Glu Ala Ala Ala Gly Asn Gly Asp Asn Leu Thr Pro Lys
    290                 295                 300

Val Val Leu Tyr Ser Glu Asp Val Asp Ile Glu Thr Pro Asp Thr His
305                 310                 315                 320

Ile Ser Tyr Met Pro Thr Ile Lys Glu Gly Asn Ser Arg Glu Leu Met
                325                 330                 335

Gly Gln Gln Ser Met Pro Asn Arg Pro Asn Tyr Ile Ala Phe Arg Asp
            340                 345                 350

Asn Phe Ile Gly Leu Met Tyr Tyr Asn Ser Thr Gly Asn Met Gly Val
        355                 360                 365

Leu Ala Gly Gln Ala Ser Gln Leu Asn Ala Val Val Asp Leu Gln Asp
    370                 375                 380

Arg Asn Thr Glu Leu Ser Tyr Gln Leu Leu Leu Asp Ser Ile Gly Asp
385                 390                 395                 400

Arg Thr Arg Tyr Phe Ser Met Trp Asn Gln Leu Pro Asn Tyr Cys Phe
                405                 410                 415

Pro Leu Gly Gly Val Ile Asn Thr Glu Thr Leu Thr Lys Val Lys Pro
            420                 425                 430

Lys Thr Gly Gln Glu Asn Gly Trp Glu Lys Asp Ala Thr Glu Phe Ser
        435                 440                 445

Asp Lys Asn Glu Ile Arg Val Gly Asn Asn Phe Ala Met Glu Ile Asn
    450                 455                 460

Leu Asn Ala Asn Leu Trp Arg Asn Phe Leu Tyr Ser Asn Ile Ala Leu
465                 470                 475                 480

Tyr Leu Pro Asp Lys Leu Lys Tyr Ser Pro Ser Asn Val Lys Ile Ser
                485                 490                 495

Asp Asn Pro Asn Thr Tyr Asp Tyr Met Asn Lys Arg Val Val Ala Pro
            500                 505                 510

Gly Leu Val Asp Cys Tyr Ile Asn Leu Gly Ala Arg Trp Ser Leu Asp
        515                 520                 525

Tyr Met Asp Asn Val Asn Pro Phe Asn His His Arg Asn Ala Gly Leu
    530                 535                 540

Arg Tyr Arg Ser Met Leu Leu Gly Asn Gly Arg Tyr Val Pro Phe His
545                 550                 555                 560

Ile Gln Val Pro Gln Lys Phe Phe Ala Ile Lys Asn Leu Leu Leu Leu
                565                 570                 575

Pro Gly Ser Tyr Thr Tyr Glu Trp Asn Phe Arg Lys Asp Val Asn Met
            580                 585                 590

Val Leu Gln Ser Ser Leu Gly Asn Asp Leu Arg Val Asp Gly Ala Ser
        595                 600                 605

Ile Lys Phe Asp Ser Ile Cys Leu Tyr Ala Thr Phe Phe Pro Met Ala
    610                 615                 620

His Asn Thr Ala Ser Thr Leu Glu Ala Met Leu Arg Asn Asp Thr Asn
625                 630                 635                 640

Asp Gln Ser Phe Asn Asp Tyr Leu Ser Ala Ala Asn Met Leu Tyr Pro
```

```
                645                 650                 655

Ile Pro Ala Asn Ala Thr Asn Val Pro Ile Ser Ile Pro Ser Arg Asn
            660                 665                 670

Trp Ala Ala Phe Arg Gly Trp Ala Phe Thr Arg Leu Lys Thr Lys Glu
        675                 680                 685

Thr Pro Ser Leu Gly Ser Gly Tyr Asp Pro Tyr Tyr Thr Tyr Ser Gly
    690                 695                 700

Ser Ile Pro Tyr Leu Asp Gly Thr Phe Tyr Leu Asn His Thr Phe Lys
705                 710                 715                 720

Lys Val Ala Ile Thr Phe Asp Ser Ser Val Ser Trp Pro Gly Asn Asp
                725                 730                 735

Arg Leu Leu Thr Pro Asn Glu Phe Glu Ile Lys Arg Ser Val Asp Gly
            740                 745                 750

Glu Gly Tyr Asn Val Ala Gln Cys Asn Met Thr Lys Asp Trp Phe Leu
        755                 760                 765

Val Gln Met Leu Ala Asn Tyr Asn Ile Gly Tyr Gln Gly Phe Tyr Ile
    770                 775                 780

Pro Glu Ser Tyr Lys Asp Arg Met Tyr Ser Phe Phe Arg Asn Phe Gln
785                 790                 795                 800

Pro Met Ser Arg Gln Val Val Asp Asp Thr Lys Tyr Lys Asp Tyr Gln
                805                 810                 815

Gln Val Gly Ile Leu His Gln His Asn Asn Ser Gly Phe Val Gly Tyr
            820                 825                 830

Leu Ala Pro Thr Met Arg Glu Gly Gln Ala Tyr Pro Ala Asn Phe Pro
        835                 840                 845

Tyr Pro Leu Ile Gly Lys Thr Ala Val Asp Ser Ile Thr Gln Lys Lys
    850                 855                 860

Phe Leu Cys Asp Arg Thr Leu Trp Arg Ile Pro Phe Ser Ser Asn Phe
865                 870                 875                 880

Met Ser Met Gly Ala Leu Thr Asp Leu Gly Gln Asn Leu Leu Tyr Ala
                885                 890                 895

Asn Ser Ala His Ala Leu Asp Met Thr Phe Glu Val Asp Pro Met Asp
            900                 905                 910

Glu Pro Thr Leu Leu Tyr Val Leu Phe Glu Val Phe Asp Val Val Arg
        915                 920                 925

Val His Gln Pro His Arg Gly Val Ile Glu Thr Val Tyr Leu Arg Thr
    930                 935                 940

Pro Phe Ser Ala Gly Asn Ala Thr Thr
945                 950


<210> SEQ ID NO 49
<211> LENGTH: 961
<212> TYPE: PRT
<213> ORGANISM: Artificial Sequence
<220> FEATURE:
<223> OTHER INFORMATION: Synthetic Construct

<400> SEQUENCE: 49

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
```

```
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Asp Glu Asn Ala Asn Pro Asn Ala Asn
    130                 135                 140

Pro Asn Ala Asn Pro Asn Ala Asn Pro Asn Ala Asn Pro Asn Ala Asn
145                 150                 155                 160

Pro Asn Ala Asn Pro Asn Ala Asn Pro Asn Ala Asn Pro Asn Ala Asn
                165                 170                 175

Pro Asn Ala Asn Pro Asn Ala Asn Pro Asn Ala Asn Pro Asn Ala Asn
            180                 185                 190

Pro Lys Thr His Val Phe Gly Gln Ala Pro Tyr Ser Gly Ile Asn Ile
        195                 200                 205

Thr Lys Glu Gly Ile Gln Ile Gly Val Glu Gly Gln Thr Pro Lys Tyr
    210                 215                 220

Ala Asp Lys Thr Phe Gln Pro Glu Pro Gln Ile Gly Glu Ser Gln Trp
225                 230                 235                 240

Tyr Glu Thr Glu Ile Asn His Ala Ala Gly Arg Val Leu Lys Lys Thr
                245                 250                 255

Thr Pro Met Lys Pro Cys Tyr Gly Ser Tyr Ala Lys Pro Thr Asn Glu
            260                 265                 270

Asn Gly Gly Gln Gly Ile Leu Val Lys Gln Gln Asn Gly Lys Leu Glu
        275                 280                 285

Ser Gln Val Glu Met Gln Phe Phe Ser Thr Thr Glu Ala Ala Ala Gly
    290                 295                 300

Asn Gly Asp Asn Leu Thr Pro Lys Val Val Leu Tyr Ser Glu Asp Val
305                 310                 315                 320

Asp Ile Glu Thr Pro Asp Thr His Ile Ser Tyr Met Pro Thr Ile Lys
                325                 330                 335

Glu Gly Asn Ser Arg Glu Leu Met Gly Gln Gln Ser Met Pro Asn Arg
            340                 345                 350

Pro Asn Tyr Ile Ala Phe Arg Asp Asn Phe Ile Gly Leu Met Tyr Tyr
        355                 360                 365

Asn Ser Thr Gly Asn Met Gly Val Leu Ala Gly Gln Ala Ser Gln Leu
    370                 375                 380

Asn Ala Val Val Asp Leu Gln Asp Arg Asn Thr Glu Leu Ser Tyr Gln
385                 390                 395                 400

Leu Leu Leu Asp Ser Ile Gly Asp Arg Thr Arg Tyr Phe Ser Met Trp
                405                 410                 415

Asn Gln Leu Pro Asn Tyr Cys Phe Pro Leu Gly Gly Val Ile Asn Thr
            420                 425                 430

Glu Thr Leu Thr Lys Val Lys Pro Lys Thr Gly Gln Glu Asn Gly Trp
        435                 440                 445

Glu Lys Asp Ala Thr Glu Phe Ser Asp Lys Asn Glu Ile Arg Val Gly
    450                 455                 460

Asn Asn Phe Ala Met Glu Ile Asn Leu Asn Ala Asn Leu Trp Arg Asn
465                 470                 475                 480
```

-continued

```
Phe Leu Tyr Ser Asn Ile Ala Leu Tyr Leu Pro Asp Lys Leu Lys Tyr
                485                 490                 495

Ser Pro Ser Asn Val Lys Ile Ser Asp Asn Pro Asn Thr Tyr Asp Tyr
            500                 505                 510

Met Asn Lys Arg Val Val Ala Pro Gly Leu Val Asp Cys Tyr Ile Asn
        515                 520                 525

Leu Gly Ala Arg Trp Ser Leu Asp Tyr Met Asp Asn Val Asn Pro Phe
    530                 535                 540

Asn His His Arg Asn Ala Gly Leu Arg Tyr Arg Ser Met Leu Leu Gly
545                 550                 555                 560

Asn Gly Arg Tyr Val Pro Phe His Ile Gln Val Pro Gln Lys Phe Phe
                565                 570                 575

Ala Ile Lys Asn Leu Leu Leu Leu Pro Gly Ser Tyr Thr Tyr Glu Trp
            580                 585                 590

Asn Phe Arg Lys Asp Val Asn Met Val Leu Gln Ser Ser Leu Gly Asn
        595                 600                 605

Asp Leu Arg Val Asp Gly Ala Ser Ile Lys Phe Asp Ser Ile Cys Leu
    610                 615                 620

Tyr Ala Thr Phe Phe Pro Met Ala His Asn Thr Ala Ser Thr Leu Glu
625                 630                 635                 640

Ala Met Leu Arg Asn Asp Thr Asn Asp Gln Ser Phe Asn Asp Tyr Leu
                645                 650                 655

Ser Ala Ala Asn Met Leu Tyr Pro Ile Pro Ala Asn Ala Thr Asn Val
            660                 665                 670

Pro Ile Ser Ile Pro Ser Arg Asn Trp Ala Ala Phe Arg Gly Trp Ala
        675                 680                 685

Phe Thr Arg Leu Lys Thr Lys Glu Thr Pro Ser Leu Gly Ser Gly Tyr
    690                 695                 700

Asp Pro Tyr Tyr Thr Tyr Ser Gly Ser Ile Pro Tyr Leu Asp Gly Thr
705                 710                 715                 720

Phe Tyr Leu Asn His Thr Phe Lys Lys Val Ala Ile Thr Phe Asp Ser
                725                 730                 735

Ser Val Ser Trp Pro Gly Asn Asp Arg Leu Leu Thr Pro Asn Glu Phe
            740                 745                 750

Glu Ile Lys Arg Ser Val Asp Gly Glu Gly Tyr Asn Val Ala Gln Cys
        755                 760                 765

Asn Met Thr Lys Asp Trp Phe Leu Val Gln Met Leu Ala Asn Tyr Asn
    770                 775                 780

Ile Gly Tyr Gln Gly Phe Tyr Ile Pro Glu Ser Tyr Lys Asp Arg Met
785                 790                 795                 800

Tyr Ser Phe Phe Arg Asn Phe Gln Pro Met Ser Arg Gln Val Val Asp
                805                 810                 815

Asp Thr Lys Tyr Lys Asp Tyr Gln Gln Val Gly Ile Leu His Gln His
            820                 825                 830

Asn Asn Ser Gly Phe Val Gly Tyr Leu Ala Pro Thr Met Arg Glu Gly
        835                 840                 845

Gln Ala Tyr Pro Ala Asn Phe Pro Tyr Pro Leu Ile Gly Lys Thr Ala
    850                 855                 860

Val Asp Ser Ile Thr Gln Lys Lys Phe Leu Cys Asp Arg Thr Leu Trp
865                 870                 875                 880

Arg Ile Pro Phe Ser Ser Asn Phe Met Ser Met Gly Ala Leu Thr Asp
                885                 890                 895
```

```
Leu Gly Gln Asn Leu Leu Tyr Ala Asn Ser Ala His Ala Leu Asp Met
            900                 905                 910

Thr Phe Glu Val Asp Pro Met Asp Glu Pro Thr Leu Leu Tyr Val Leu
        915                 920                 925

Phe Glu Val Phe Asp Val Val Arg Val His Gln Pro His Arg Gly Val
    930                 935                 940

Ile Glu Thr Val Tyr Leu Arg Thr Pro Phe Ser Ala Gly Asn Ala Thr
945                 950                 955                 960

Thr


<210> SEQ ID NO 50
<211> LENGTH: 969
<212> TYPE: PRT
<213> ORGANISM: Artificial Sequence
<220> FEATURE:
<223> OTHER INFORMATION: Synthetic Construct

<400> SEQUENCE: 50

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Asp Glu Asn Ala Asn Pro Asn Ala Asn
    130                 135                 140

Pro Asn Ala Asn Pro Asn Ala Asn Pro Asn Ala Asn Pro Asn Ala Asn
145                 150                 155                 160

Pro Asn Ala Asn Pro Asn Ala Asn Pro Asn Ala Asn Pro Asn Ala Asn
                165                 170                 175

Pro Asn Ala Asn Pro Asn Ala Asn Pro Asn Ala Asn Pro Asn Ala Asn
            180                 185                 190

Pro Asn Ala Asn Pro Asn Ala Asn Pro Lys Thr His Val Phe Gly Gln
        195                 200                 205

Ala Pro Tyr Ser Gly Ile Asn Ile Thr Lys Glu Gly Ile Gln Ile Gly
    210                 215                 220

Val Glu Gly Gln Thr Pro Lys Tyr Ala Asp Lys Thr Phe Gln Pro Glu
225                 230                 235                 240

Pro Gln Ile Gly Glu Ser Gln Trp Tyr Glu Thr Glu Ile Asn His Ala
                245                 250                 255

Ala Gly Arg Val Leu Lys Lys Thr Thr Pro Met Lys Pro Cys Tyr Gly
            260                 265                 270

Ser Tyr Ala Lys Pro Thr Asn Glu Asn Gly Gly Gln Gly Ile Leu Val
        275                 280                 285

Lys Gln Gln Asn Gly Lys Leu Glu Ser Gln Val Glu Met Gln Phe Phe
```

```
    290                 295                 300

Ser Thr Thr Glu Ala Ala Ala Gly Asn Gly Asp Asn Leu Thr Pro Lys
305                 310                 315                 320

Val Val Leu Tyr Ser Glu Asp Val Asp Ile Glu Thr Pro Asp Thr His
                325                 330                 335

Ile Ser Tyr Met Pro Thr Ile Lys Glu Gly Asn Ser Arg Glu Leu Met
            340                 345                 350

Gly Gln Gln Ser Met Pro Asn Arg Pro Asn Tyr Ile Ala Phe Arg Asp
        355                 360                 365

Asn Phe Ile Gly Leu Met Tyr Tyr Asn Ser Thr Gly Asn Met Gly Val
    370                 375                 380

Leu Ala Gly Gln Ala Ser Gln Leu Asn Ala Val Val Asp Leu Gln Asp
385                 390                 395                 400

Arg Asn Thr Glu Leu Ser Tyr Gln Leu Leu Leu Asp Ser Ile Gly Asp
                405                 410                 415

Arg Thr Arg Tyr Phe Ser Met Trp Asn Gln Leu Pro Asn Tyr Cys Phe
            420                 425                 430

Pro Leu Gly Gly Val Ile Asn Thr Glu Thr Leu Thr Lys Val Lys Pro
        435                 440                 445

Lys Thr Gly Gln Glu Asn Gly Trp Glu Lys Asp Ala Thr Glu Phe Ser
    450                 455                 460

Asp Lys Asn Glu Ile Arg Val Gly Asn Asn Phe Ala Met Glu Ile Asn
465                 470                 475                 480

Leu Asn Ala Asn Leu Trp Arg Asn Phe Leu Tyr Ser Asn Ile Ala Leu
                485                 490                 495

Tyr Leu Pro Asp Lys Leu Lys Tyr Ser Pro Ser Asn Val Lys Ile Ser
            500                 505                 510

Asp Asn Pro Asn Thr Tyr Asp Tyr Met Asn Lys Arg Val Val Ala Pro
        515                 520                 525

Gly Leu Val Asp Cys Tyr Ile Asn Leu Gly Ala Arg Trp Ser Leu Asp
    530                 535                 540

Tyr Met Asp Asn Val Asn Pro Phe Asn His His Arg Asn Ala Gly Leu
545                 550                 555                 560

Arg Tyr Arg Ser Met Leu Leu Gly Asn Gly Arg Tyr Val Pro Phe His
                565                 570                 575

Ile Gln Val Pro Gln Lys Phe Phe Ala Ile Lys Asn Leu Leu Leu Leu
            580                 585                 590

Pro Gly Ser Tyr Thr Tyr Glu Trp Asn Phe Arg Lys Asp Val Asn Met
        595                 600                 605

Val Leu Gln Ser Ser Leu Gly Asn Asp Leu Arg Val Asp Gly Ala Ser
    610                 615                 620

Ile Lys Phe Asp Ser Ile Cys Leu Tyr Ala Thr Phe Phe Pro Met Ala
625                 630                 635                 640

His Asn Thr Ala Ser Thr Leu Glu Ala Met Leu Arg Asn Asp Thr Asn
                645                 650                 655

Asp Gln Ser Phe Asn Asp Tyr Leu Ser Ala Ala Asn Met Leu Tyr Pro
            660                 665                 670

Ile Pro Ala Asn Ala Thr Asn Val Pro Ile Ser Ile Pro Ser Arg Asn
        675                 680                 685

Trp Ala Ala Phe Arg Gly Trp Ala Phe Thr Arg Leu Lys Thr Lys Glu
    690                 695                 700

Thr Pro Ser Leu Gly Ser Gly Tyr Asp Pro Tyr Tyr Thr Tyr Ser Gly
705                 710                 715                 720
```

Ser Ile Pro Tyr Leu Asp Gly Thr Phe Tyr Leu Asn His Thr Phe Lys
725 730 735

Lys Val Ala Ile Thr Phe Asp Ser Ser Val Ser Trp Pro Gly Asn Asp
740 745 750

Arg Leu Leu Thr Pro Asn Glu Phe Glu Ile Lys Arg Ser Val Asp Gly
755 760 765

Glu Gly Tyr Asn Val Ala Gln Cys Asn Met Thr Lys Asp Trp Phe Leu
770 775 780

Val Gln Met Leu Ala Asn Tyr Asn Ile Gly Tyr Gln Gly Phe Tyr Ile
785 790 795 800

Pro Glu Ser Tyr Lys Asp Arg Met Tyr Ser Phe Phe Arg Asn Phe Gln
805 810 815

Pro Met Ser Arg Gln Val Val Asp Asp Thr Lys Tyr Lys Asp Tyr Gln
820 825 830

Gln Val Gly Ile Leu His Gln His Asn Asn Ser Gly Phe Val Gly Tyr
835 840 845

Leu Ala Pro Thr Met Arg Glu Gly Gln Ala Tyr Pro Ala Asn Phe Pro
850 855 860

Tyr Pro Leu Ile Gly Lys Thr Ala Val Asp Ser Ile Thr Gln Lys Lys
865 870 875 880

Phe Leu Cys Asp Arg Thr Leu Trp Arg Ile Pro Phe Ser Ser Asn Phe
885 890 895

Met Ser Met Gly Ala Leu Thr Asp Leu Gly Gln Asn Leu Leu Tyr Ala
900 905 910

Asn Ser Ala His Ala Leu Asp Met Thr Phe Glu Val Asp Pro Met Asp
915 920 925

Glu Pro Thr Leu Leu Tyr Val Leu Phe Glu Val Phe Asp Val Val Arg
930 935 940

Val His Gln Pro His Arg Gly Val Ile Glu Thr Val Tyr Leu Arg Thr
945 950 955 960

Pro Phe Ser Ala Gly Asn Ala Thr Thr
965

<210> SEQ ID NO 51
<211> LENGTH: 977
<212> TYPE: PRT
<213> ORGANISM: Artificial Sequence
<220> FEATURE:
<223> OTHER INFORMATION: Synthetic Construct

<400> SEQUENCE: 51

Met Ala Thr Pro Ser Met Met Pro Gln Trp Ser Tyr Met His Ile Ser
1 5 10 15

Gly Gln Asp Ala Ser Glu Tyr Leu Ser Pro Gly Leu Val Gln Phe Ala
20 25 30

Arg Ala Thr Glu Thr Tyr Phe Ser Leu Asn Asn Lys Phe Arg Asn Pro
35 40 45

Thr Val Ala Pro Thr His Asp Val Thr Thr Asp Arg Ser Gln Arg Leu
50 55 60

Thr Leu Arg Phe Ile Pro Val Asp Arg Glu Asp Thr Ala Tyr Ser Tyr
65 70 75 80

Lys Ala Arg Phe Thr Leu Ala Val Gly Asp Asn Arg Val Leu Asp Met
85 90 95

Ala Ser Thr Tyr Phe Asp Ile Arg Gly Val Leu Asp Arg Gly Pro Thr
100 105 110

-continued

```
Phe Lys Pro Tyr Ser Gly Thr Ala Tyr Asn Ala Leu Ala Pro Lys Gly
        115                 120                 125

Ala Pro Asn Pro Cys Glu Trp Asp Glu Asn Ala Asn Pro Asn Ala Asn
    130                 135                 140

Pro Asn Ala Asn Pro Asn Ala Asn Pro Asn Ala Asn Pro Asn Ala Asn
145                 150                 155                 160

Pro Asn Ala Asn Pro Asn Ala Asn Pro Asn Ala Asn Pro Asn Ala Asn
                165                 170                 175

Pro Asn Ala Asn Pro Asn Ala Asn Pro Asn Ala Asn Pro Asn Ala Asn
            180                 185                 190

Pro Asn Ala Asn Pro Asn Ala Asn Pro Asn Ala Asn Pro Asn Ala Asn
        195                 200                 205

Pro Lys Thr His Val Phe Gly Gln Ala Pro Tyr Ser Gly Ile Asn Ile
    210                 215                 220

Thr Lys Glu Gly Ile Gln Ile Gly Val Glu Gly Gln Thr Pro Lys Tyr
225                 230                 235                 240

Ala Asp Lys Thr Phe Gln Pro Glu Pro Gln Ile Gly Glu Ser Gln Trp
                245                 250                 255

Tyr Glu Thr Glu Ile Asn His Ala Ala Gly Arg Val Leu Lys Lys Thr
            260                 265                 270

Thr Pro Met Lys Pro Cys Tyr Gly Ser Tyr Ala Lys Pro Thr Asn Glu
        275                 280                 285

Asn Gly Gly Gln Gly Ile Leu Val Lys Gln Gln Asn Gly Lys Leu Glu
    290                 295                 300

Ser Gln Val Glu Met Gln Phe Phe Ser Thr Thr Glu Ala Ala Ala Gly
305                 310                 315                 320

Asn Gly Asp Asn Leu Thr Pro Lys Val Val Leu Tyr Ser Glu Asp Val
                325                 330                 335

Asp Ile Glu Thr Pro Asp Thr His Ile Ser Tyr Met Pro Thr Ile Lys
            340                 345                 350

Glu Gly Asn Ser Arg Glu Leu Met Gly Gln Gln Ser Met Pro Asn Arg
        355                 360                 365

Pro Asn Tyr Ile Ala Phe Arg Asp Asn Phe Ile Gly Leu Met Tyr Tyr
    370                 375                 380

Asn Ser Thr Gly Asn Met Gly Val Leu Ala Gly Gln Ala Ser Gln Leu
385                 390                 395                 400

Asn Ala Val Val Asp Leu Gln Asp Arg Asn Thr Glu Leu Ser Tyr Gln
                405                 410                 415

Leu Leu Leu Asp Ser Ile Gly Asp Arg Thr Arg Tyr Phe Ser Met Trp
            420                 425                 430

Asn Gln Leu Pro Asn Tyr Cys Phe Pro Leu Gly Gly Val Ile Asn Thr
        435                 440                 445

Glu Thr Leu Thr Lys Val Lys Pro Lys Thr Gly Gln Glu Asn Gly Trp
    450                 455                 460

Glu Lys Asp Ala Thr Glu Phe Ser Asp Lys Asn Glu Ile Arg Val Gly
465                 470                 475                 480

Asn Asn Phe Ala Met Glu Ile Asn Leu Asn Ala Asn Leu Trp Arg Asn
                485                 490                 495

Phe Leu Tyr Ser Asn Ile Ala Leu Tyr Leu Pro Asp Lys Leu Lys Tyr
            500                 505                 510

Ser Pro Ser Asn Val Lys Ile Ser Asp Asn Pro Asn Thr Tyr Asp Tyr
        515                 520                 525
```

-continued

```
Met Asn Lys Arg Val Val Ala Pro Gly Leu Val Asp Cys Tyr Ile Asn
    530                 535                 540

Leu Gly Ala Arg Trp Ser Leu Asp Tyr Met Asp Asn Val Asn Pro Phe
545                 550                 555                 560

Asn His His Arg Asn Ala Gly Leu Arg Tyr Arg Ser Met Leu Leu Gly
                565                 570                 575

Asn Gly Arg Tyr Val Pro Phe His Ile Gln Val Pro Gln Lys Phe Phe
            580                 585                 590

Ala Ile Lys Asn Leu Leu Leu Leu Pro Gly Ser Tyr Thr Tyr Glu Trp
        595                 600                 605

Asn Phe Arg Lys Asp Val Asn Met Val Leu Gln Ser Ser Leu Gly Asn
    610                 615                 620

Asp Leu Arg Val Asp Gly Ala Ser Ile Lys Phe Asp Ser Ile Cys Leu
625                 630                 635                 640

Tyr Ala Thr Phe Phe Pro Met Ala His Asn Thr Ala Ser Thr Leu Glu
                645                 650                 655

Ala Met Leu Arg Asn Asp Thr Asn Asp Gln Ser Phe Asn Asp Tyr Leu
            660                 665                 670

Ser Ala Ala Asn Met Leu Tyr Pro Ile Pro Ala Asn Ala Thr Asn Val
        675                 680                 685

Pro Ile Ser Ile Pro Ser Arg Asn Trp Ala Ala Phe Arg Gly Trp Ala
    690                 695                 700

Phe Thr Arg Leu Lys Thr Lys Glu Thr Pro Ser Leu Gly Ser Gly Tyr
705                 710                 715                 720

Asp Pro Tyr Tyr Thr Tyr Ser Gly Ser Ile Pro Tyr Leu Asp Gly Thr
                725                 730                 735

Phe Tyr Leu Asn His Thr Phe Lys Lys Val Ala Ile Thr Phe Asp Ser
            740                 745                 750

Ser Val Ser Trp Pro Gly Asn Asp Arg Leu Leu Thr Pro Asn Glu Phe
        755                 760                 765

Glu Ile Lys Arg Ser Val Asp Gly Glu Gly Tyr Asn Val Ala Gln Cys
    770                 775                 780

Asn Met Thr Lys Asp Trp Phe Leu Val Gln Met Leu Ala Asn Tyr Asn
785                 790                 795                 800

Ile Gly Tyr Gln Gly Phe Tyr Ile Pro Glu Ser Tyr Lys Asp Arg Met
                805                 810                 815

Tyr Ser Phe Phe Arg Asn Phe Gln Pro Met Ser Arg Gln Val Val Asp
            820                 825                 830

Asp Thr Lys Tyr Lys Asp Tyr Gln Gln Val Gly Ile Leu His Gln His
        835                 840                 845

Asn Asn Ser Gly Phe Val Gly Tyr Leu Ala Pro Thr Met Arg Glu Gly
    850                 855                 860

Gln Ala Tyr Pro Ala Asn Phe Pro Tyr Pro Leu Ile Gly Lys Thr Ala
865                 870                 875                 880

Val Asp Ser Ile Thr Gln Lys Lys Phe Leu Cys Asp Arg Thr Leu Trp
                885                 890                 895

Arg Ile Pro Phe Ser Ser Asn Phe Met Ser Met Gly Ala Leu Thr Asp
            900                 905                 910

Leu Gly Gln Asn Leu Leu Tyr Ala Asn Ser Ala His Ala Leu Asp Met
        915                 920                 925

Thr Phe Glu Val Asp Pro Met Asp Glu Pro Thr Leu Leu Tyr Val Leu
    930                 935                 940

Phe Glu Val Phe Asp Val Val Arg Val His Gln Pro His Arg Gly Val
```

945 950 955 960

Ile Glu Thr Val Tyr Leu Arg Thr Pro Phe Ser Ala Gly Asn Ala Thr
965 970 975

Thr

<210> SEQ ID NO 52
<211> LENGTH: 985
<212> TYPE: PRT
<213> ORGANISM: Artificial Sequence
<220> FEATURE:
<223> OTHER INFORMATION: Synthetic Construct

<400> SEQUENCE: 52

Met Ala Thr Pro Ser Met Met Pro Gln Trp Ser Tyr Met His Ile Ser
1 5 10 15

Gly Gln Asp Ala Ser Glu Tyr Leu Ser Pro Gly Leu Val Gln Phe Ala
20 25 30

Arg Ala Thr Glu Thr Tyr Phe Ser Leu Asn Asn Lys Phe Arg Asn Pro
35 40 45

Thr Val Ala Pro Thr His Asp Val Thr Thr Asp Arg Ser Gln Arg Leu
50 55 60

Thr Leu Arg Phe Ile Pro Val Asp Arg Glu Asp Thr Ala Tyr Ser Tyr
65 70 75 80

Lys Ala Arg Phe Thr Leu Ala Val Gly Asp Asn Arg Val Leu Asp Met
85 90 95

Ala Ser Thr Tyr Phe Asp Ile Arg Gly Val Leu Asp Arg Gly Pro Thr
100 105 110

Phe Lys Pro Tyr Ser Gly Thr Ala Tyr Asn Ala Leu Ala Pro Lys Gly
115 120 125

Ala Pro Asn Pro Cys Glu Trp Asp Glu Asn Ala Asn Pro Asn Ala Asn
130 135 140

Pro Asn Ala Asn Pro Asn Ala Asn Pro Asn Ala Asn Pro Asn Ala Asn
145 150 155 160

Pro Asn Ala Asn Pro Asn Ala Asn Pro Asn Ala Asn Pro Asn Ala Asn
165 170 175

Pro Asn Ala Asn Pro Asn Ala Asn Pro Asn Ala Asn Pro Asn Ala Asn
180 185 190

Pro Asn Ala Asn Pro Asn Ala Asn Pro Asn Ala Asn Pro Asn Ala Asn
195 200 205

Pro Asn Ala Asn Pro Asn Ala Asn Pro Lys Thr His Val Phe Gly Gln
210 215 220

Ala Pro Tyr Ser Gly Ile Asn Ile Thr Lys Glu Gly Ile Gln Ile Gly
225 230 235 240

Val Glu Gly Gln Thr Pro Lys Tyr Ala Asp Lys Thr Phe Gln Pro Glu
245 250 255

Pro Gln Ile Gly Glu Ser Gln Trp Tyr Glu Thr Glu Ile Asn His Ala
260 265 270

Ala Gly Arg Val Leu Lys Lys Thr Thr Pro Met Lys Pro Cys Tyr Gly
275 280 285

Ser Tyr Ala Lys Pro Thr Asn Glu Asn Gly Gly Gln Gly Ile Leu Val
290 295 300

Lys Gln Gln Asn Gly Lys Leu Glu Ser Gln Val Glu Met Gln Phe Phe
305 310 315 320

Ser Thr Thr Glu Ala Ala Ala Gly Asn Gly Asp Asn Leu Thr Pro Lys
325 330 335

-continued

```
Val Val Leu Tyr Ser Glu Asp Val Asp Ile Glu Thr Pro Asp Thr His
            340                 345                 350

Ile Ser Tyr Met Pro Thr Ile Lys Glu Gly Asn Ser Arg Glu Leu Met
        355                 360                 365

Gly Gln Gln Ser Met Pro Asn Arg Pro Asn Tyr Ile Ala Phe Arg Asp
    370                 375                 380

Asn Phe Ile Gly Leu Met Tyr Tyr Asn Ser Thr Gly Asn Met Gly Val
385                 390                 395                 400

Leu Ala Gly Gln Ala Ser Gln Leu Asn Ala Val Val Asp Leu Gln Asp
                405                 410                 415

Arg Asn Thr Glu Leu Ser Tyr Gln Leu Leu Leu Asp Ser Ile Gly Asp
            420                 425                 430

Arg Thr Arg Tyr Phe Ser Met Trp Asn Gln Leu Pro Asn Tyr Cys Phe
        435                 440                 445

Pro Leu Gly Gly Val Ile Asn Thr Glu Thr Leu Thr Lys Val Lys Pro
    450                 455                 460

Lys Thr Gly Gln Glu Asn Gly Trp Glu Lys Asp Ala Thr Glu Phe Ser
465                 470                 475                 480

Asp Lys Asn Glu Ile Arg Val Gly Asn Asn Phe Ala Met Glu Ile Asn
                485                 490                 495

Leu Asn Ala Asn Leu Trp Arg Asn Phe Leu Tyr Ser Asn Ile Ala Leu
            500                 505                 510

Tyr Leu Pro Asp Lys Leu Lys Tyr Ser Pro Ser Asn Val Lys Ile Ser
        515                 520                 525

Asp Asn Pro Asn Thr Tyr Asp Tyr Met Asn Lys Arg Val Val Ala Pro
    530                 535                 540

Gly Leu Val Asp Cys Tyr Ile Asn Leu Gly Ala Arg Trp Ser Leu Asp
545                 550                 555                 560

Tyr Met Asp Asn Val Asn Pro Phe Asn His His Arg Asn Ala Gly Leu
                565                 570                 575

Arg Tyr Arg Ser Met Leu Leu Gly Asn Gly Arg Tyr Val Pro Phe His
            580                 585                 590

Ile Gln Val Pro Gln Lys Phe Phe Ala Ile Lys Asn Leu Leu Leu Leu
        595                 600                 605

Pro Gly Ser Tyr Thr Tyr Glu Trp Asn Phe Arg Lys Asp Val Asn Met
    610                 615                 620

Val Leu Gln Ser Ser Leu Gly Asn Asp Leu Arg Val Asp Gly Ala Ser
625                 630                 635                 640

Ile Lys Phe Asp Ser Ile Cys Leu Tyr Ala Thr Phe Phe Pro Met Ala
                645                 650                 655

His Asn Thr Ala Ser Thr Leu Glu Ala Met Leu Arg Asn Asp Thr Asn
            660                 665                 670

Asp Gln Ser Phe Asn Asp Tyr Leu Ser Ala Ala Asn Met Leu Tyr Pro
        675                 680                 685

Ile Pro Ala Asn Ala Thr Asn Val Pro Ile Ser Ile Pro Ser Arg Asn
    690                 695                 700

Trp Ala Ala Phe Arg Gly Trp Ala Phe Thr Arg Leu Lys Thr Lys Glu
705                 710                 715                 720

Thr Pro Ser Leu Gly Ser Gly Tyr Asp Pro Tyr Tyr Thr Tyr Ser Gly
                725                 730                 735

Ser Ile Pro Tyr Leu Asp Gly Thr Phe Tyr Leu Asn His Thr Phe Lys
            740                 745                 750
```

Lys Val Ala Ile Thr Phe Asp Ser Ser Val Ser Trp Pro Gly Asn Asp
755 760 765

Arg Leu Leu Thr Pro Asn Glu Phe Glu Ile Lys Arg Ser Val Asp Gly
770 775 780

Glu Gly Tyr Asn Val Ala Gln Cys Asn Met Thr Lys Asp Trp Phe Leu
785 790 795 800

Val Gln Met Leu Ala Asn Tyr Asn Ile Gly Tyr Gln Gly Phe Tyr Ile
805 810 815

Pro Glu Ser Tyr Lys Asp Arg Met Tyr Ser Phe Phe Arg Asn Phe Gln
820 825 830

Pro Met Ser Arg Gln Val Val Asp Asp Thr Lys Tyr Lys Asp Tyr Gln
835 840 845

Gln Val Gly Ile Leu His Gln His Asn Asn Ser Gly Phe Val Gly Tyr
850 855 860

Leu Ala Pro Thr Met Arg Glu Gly Gln Ala Tyr Pro Ala Asn Phe Pro
865 870 875 880

Tyr Pro Leu Ile Gly Lys Thr Ala Val Asp Ser Ile Thr Gln Lys Lys
885 890 895

Phe Leu Cys Asp Arg Thr Leu Trp Arg Ile Pro Phe Ser Ser Asn Phe
900 905 910

Met Ser Met Gly Ala Leu Thr Asp Leu Gly Gln Asn Leu Leu Tyr Ala
915 920 925

Asn Ser Ala His Ala Leu Asp Met Thr Phe Glu Val Asp Pro Met Asp
930 935 940

Glu Pro Thr Leu Leu Tyr Val Leu Phe Glu Val Phe Asp Val Val Arg
945 950 955 960

Val His Gln Pro His Arg Gly Val Ile Glu Thr Val Tyr Leu Arg Thr
965 970 975

Pro Phe Ser Ala Gly Asn Ala Thr Thr
980 985

<210> SEQ ID NO 53
<211> LENGTH: 993
<212> TYPE: PRT
<213> ORGANISM: Artificial Sequence
<220> FEATURE:
<223> OTHER INFORMATION: Synthetic Construct

<400> SEQUENCE: 53

Met Ala Thr Pro Ser Met Met Pro Gln Trp Ser Tyr Met His Ile Ser
1 5 10 15

Gly Gln Asp Ala Ser Glu Tyr Leu Ser Pro Gly Leu Val Gln Phe Ala
20 25 30

Arg Ala Thr Glu Thr Tyr Phe Ser Leu Asn Asn Lys Phe Arg Asn Pro
35 40 45

Thr Val Ala Pro Thr His Asp Val Thr Thr Asp Arg Ser Gln Arg Leu
50 55 60

Thr Leu Arg Phe Ile Pro Val Asp Arg Glu Asp Thr Ala Tyr Ser Tyr
65 70 75 80

Lys Ala Arg Phe Thr Leu Ala Val Gly Asp Asn Arg Val Leu Asp Met
85 90 95

Ala Ser Thr Tyr Phe Asp Ile Arg Gly Val Leu Asp Arg Gly Pro Thr
100 105 110

Phe Lys Pro Tyr Ser Gly Thr Ala Tyr Asn Ala Leu Ala Pro Lys Gly
115 120 125

-continued

```
Ala Pro Asn Pro Cys Glu Trp Asp Glu Asn Ala Asn Pro Asn Ala Asn
    130                 135                 140

Pro Asn Ala Asn Pro Asn Ala Asn Pro Asn Ala Asn Pro Asn Ala Asn
145                 150                 155                 160

Pro Asn Ala Asn Pro Asn Ala Asn Pro Asn Ala Asn Pro Asn Ala Asn
                165                 170                 175

Pro Asn Ala Asn Pro Asn Ala Asn Pro Asn Ala Asn Pro Asn Ala Asn
            180                 185                 190

Pro Asn Ala Asn Pro Asn Ala Asn Pro Asn Ala Asn Pro Asn Ala Asn
        195                 200                 205

Pro Asn Ala Asn Pro Asn Ala Asn Pro Asn Ala Asn Pro Asn Ala Asn
    210                 215                 220

Pro Lys Thr His Val Phe Gly Gln Ala Pro Tyr Ser Gly Ile Asn Ile
225                 230                 235                 240

Thr Lys Glu Gly Ile Gln Ile Gly Val Glu Gly Gln Thr Pro Lys Tyr
                245                 250                 255

Ala Asp Lys Thr Phe Gln Pro Glu Pro Gln Ile Gly Glu Ser Gln Trp
            260                 265                 270

Tyr Glu Thr Glu Ile Asn His Ala Ala Gly Arg Val Leu Lys Lys Thr
        275                 280                 285

Thr Pro Met Lys Pro Cys Tyr Gly Ser Tyr Ala Lys Pro Thr Asn Glu
    290                 295                 300

Asn Gly Gly Gln Gly Ile Leu Val Lys Gln Gln Asn Gly Lys Leu Glu
305                 310                 315                 320

Ser Gln Val Glu Met Gln Phe Phe Ser Thr Thr Glu Ala Ala Ala Gly
                325                 330                 335

Asn Gly Asp Asn Leu Thr Pro Lys Val Val Leu Tyr Ser Glu Asp Val
            340                 345                 350

Asp Ile Glu Thr Pro Asp Thr His Ile Ser Tyr Met Pro Thr Ile Lys
        355                 360                 365

Glu Gly Asn Ser Arg Glu Leu Met Gly Gln Gln Ser Met Pro Asn Arg
    370                 375                 380

Pro Asn Tyr Ile Ala Phe Arg Asp Asn Phe Ile Gly Leu Met Tyr Tyr
385                 390                 395                 400

Asn Ser Thr Gly Asn Met Gly Val Leu Ala Gly Gln Ala Ser Gln Leu
                405                 410                 415

Asn Ala Val Val Asp Leu Gln Asp Arg Asn Thr Glu Leu Ser Tyr Gln
            420                 425                 430

Leu Leu Leu Asp Ser Ile Gly Asp Arg Thr Arg Tyr Phe Ser Met Trp
        435                 440                 445

Asn Gln Leu Pro Asn Tyr Cys Phe Pro Leu Gly Gly Val Ile Asn Thr
    450                 455                 460

Glu Thr Leu Thr Lys Val Lys Pro Lys Thr Gly Gln Glu Asn Gly Trp
465                 470                 475                 480

Glu Lys Asp Ala Thr Glu Phe Ser Asp Lys Asn Glu Ile Arg Val Gly
                485                 490                 495

Asn Asn Phe Ala Met Glu Ile Asn Leu Asn Ala Asn Leu Trp Arg Asn
            500                 505                 510

Phe Leu Tyr Ser Asn Ile Ala Leu Tyr Leu Pro Asp Lys Leu Lys Tyr
        515                 520                 525

Ser Pro Ser Asn Val Lys Ile Ser Asp Asn Pro Asn Thr Tyr Asp Tyr
    530                 535                 540

Met Asn Lys Arg Val Val Ala Pro Gly Leu Val Asp Cys Tyr Ile Asn
```

-continued 545 550 555 560

Leu Gly Ala Arg Trp Ser Leu Asp Tyr Met Asp Asn Val Asn Pro Phe
565 570 575

Asn His His Arg Asn Ala Gly Leu Arg Tyr Arg Ser Met Leu Leu Gly
580 585 590

Asn Gly Arg Tyr Val Pro Phe His Ile Gln Val Pro Gln Lys Phe Phe
595 600 605

Ala Ile Lys Asn Leu Leu Leu Leu Pro Gly Ser Tyr Thr Tyr Glu Trp
610 615 620

Asn Phe Arg Lys Asp Val Asn Met Val Leu Gln Ser Ser Leu Gly Asn
625 630 635 640

Asp Leu Arg Val Asp Gly Ala Ser Ile Lys Phe Asp Ser Ile Cys Leu
645 650 655

Tyr Ala Thr Phe Phe Pro Met Ala His Asn Thr Ala Ser Thr Leu Glu
660 665 670

Ala Met Leu Arg Asn Asp Thr Asn Asp Gln Ser Phe Asn Asp Tyr Leu
675 680 685

Ser Ala Ala Asn Met Leu Tyr Pro Ile Pro Ala Asn Ala Thr Asn Val
690 695 700

Pro Ile Ser Ile Pro Ser Arg Asn Trp Ala Ala Phe Arg Gly Trp Ala
705 710 715 720

Phe Thr Arg Leu Lys Thr Lys Glu Thr Pro Ser Leu Gly Ser Gly Tyr
725 730 735

Asp Pro Tyr Tyr Thr Tyr Ser Gly Ser Ile Pro Tyr Leu Asp Gly Thr
740 745 750

Phe Tyr Leu Asn His Thr Phe Lys Lys Val Ala Ile Thr Phe Asp Ser
755 760 765

Ser Val Ser Trp Pro Gly Asn Asp Arg Leu Leu Thr Pro Asn Glu Phe
770 775 780

Glu Ile Lys Arg Ser Val Asp Gly Glu Gly Tyr Asn Val Ala Gln Cys
785 790 795 800

Asn Met Thr Lys Asp Trp Phe Leu Val Gln Met Leu Ala Asn Tyr Asn
805 810 815

Ile Gly Tyr Gln Gly Phe Tyr Ile Pro Glu Ser Tyr Lys Asp Arg Met
820 825 830

Tyr Ser Phe Phe Arg Asn Phe Gln Pro Met Ser Arg Gln Val Val Asp
835 840 845

Asp Thr Lys Tyr Lys Asp Tyr Gln Gln Val Gly Ile Leu His Gln His
850 855 860

Asn Asn Ser Gly Phe Val Gly Tyr Leu Ala Pro Thr Met Arg Glu Gly
865 870 875 880

Gln Ala Tyr Pro Ala Asn Phe Pro Tyr Pro Leu Ile Gly Lys Thr Ala
885 890 895

Val Asp Ser Ile Thr Gln Lys Lys Phe Leu Cys Asp Arg Thr Leu Trp
900 905 910

Arg Ile Pro Phe Ser Ser Asn Phe Met Ser Met Gly Ala Leu Thr Asp
915 920 925

Leu Gly Gln Asn Leu Leu Tyr Ala Asn Ser Ala His Ala Leu Asp Met
930 935 940

Thr Phe Glu Val Asp Pro Met Asp Glu Pro Thr Leu Leu Tyr Val Leu
945 950 955 960

Phe Glu Val Phe Asp Val Val Arg Val His Gln Pro His Arg Gly Val
965 970 975

```
Ile Glu Thr Val Tyr Leu Arg Thr Pro Phe Ser Ala Gly Asn Ala Thr
            980                 985                 990

Thr


<210> SEQ ID NO 54
<211> LENGTH: 1017
<212> TYPE: PRT
<213> ORGANISM: Artificial Sequence
<220> FEATURE:
<223> OTHER INFORMATION: Synthetic Construct

<400> SEQUENCE: 54

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Asp Glu Asn Ala Asn Pro Asn Ala Asn
    130                 135                 140

Pro Asn Ala Asn Pro Asn Ala Asn Pro Asn Ala Asn Pro Asn Ala Asn
145                 150                 155                 160

Pro Asn Ala Asn Pro Asn Ala Asn Pro Asn Ala Asn Pro Asn Ala Asn
                165                 170                 175

Pro Asn Ala Asn Pro Asn Ala Asn Pro Asn Ala Asn Pro Asn Ala Asn
            180                 185                 190

Pro Asn Ala Asn Pro Asn Ala Asn Pro Asn Ala Asn Pro Asn Ala Asn
        195                 200                 205

Pro Asn Ala Asn Pro Asn Ala Asn Pro Asn Ala Asn Pro Asn Ala Asn
    210                 215                 220

Pro Asn Ala Asn Pro Asn Ala Asn Pro Asn Ala Asn Pro Asn Ala Asn
225                 230                 235                 240

Pro Asn Ala Asn Pro Asn Ala Asn Pro Lys Thr His Val Phe Gly Gln
                245                 250                 255

Ala Pro Tyr Ser Gly Ile Asn Ile Thr Lys Glu Gly Ile Gln Ile Gly
            260                 265                 270

Val Glu Gly Gln Thr Pro Lys Tyr Ala Asp Lys Thr Phe Gln Pro Glu
        275                 280                 285

Pro Gln Ile Gly Glu Ser Gln Trp Tyr Glu Thr Glu Ile Asn His Ala
    290                 295                 300

Ala Gly Arg Val Leu Lys Lys Thr Thr Pro Met Lys Pro Cys Tyr Gly
305                 310                 315                 320

Ser Tyr Ala Lys Pro Thr Asn Glu Asn Gly Gly Gln Gly Ile Leu Val
                325                 330                 335
```

```
Lys Gln Gln Asn Gly Lys Leu Glu Ser Gln Val Glu Met Gln Phe Phe
            340                 345                 350

Ser Thr Thr Glu Ala Ala Ala Gly Asn Gly Asp Asn Leu Thr Pro Lys
        355                 360                 365

Val Val Leu Tyr Ser Glu Asp Val Asp Ile Glu Thr Pro Asp Thr His
    370                 375                 380

Ile Ser Tyr Met Pro Thr Ile Lys Glu Gly Asn Ser Arg Glu Leu Met
385                 390                 395                 400

Gly Gln Gln Ser Met Pro Asn Arg Pro Asn Tyr Ile Ala Phe Arg Asp
                405                 410                 415

Asn Phe Ile Gly Leu Met Tyr Tyr Asn Ser Thr Gly Asn Met Gly Val
            420                 425                 430

Leu Ala Gly Gln Ala Ser Gln Leu Asn Ala Val Val Asp Leu Gln Asp
        435                 440                 445

Arg Asn Thr Glu Leu Ser Tyr Gln Leu Leu Leu Asp Ser Ile Gly Asp
    450                 455                 460

Arg Thr Arg Tyr Phe Ser Met Trp Asn Gln Leu Pro Asn Tyr Cys Phe
465                 470                 475                 480

Pro Leu Gly Gly Val Ile Asn Thr Glu Thr Leu Thr Lys Val Lys Pro
                485                 490                 495

Lys Thr Gly Gln Glu Asn Gly Trp Glu Lys Asp Ala Thr Glu Phe Ser
            500                 505                 510

Asp Lys Asn Glu Ile Arg Val Gly Asn Asn Phe Ala Met Glu Ile Asn
        515                 520                 525

Leu Asn Ala Asn Leu Trp Arg Asn Phe Leu Tyr Ser Asn Ile Ala Leu
    530                 535                 540

Tyr Leu Pro Asp Lys Leu Lys Tyr Ser Pro Ser Asn Val Lys Ile Ser
545                 550                 555                 560

Asp Asn Pro Asn Thr Tyr Asp Tyr Met Asn Lys Arg Val Val Ala Pro
                565                 570                 575

Gly Leu Val Asp Cys Tyr Ile Asn Leu Gly Ala Arg Trp Ser Leu Asp
            580                 585                 590

Tyr Met Asp Asn Val Asn Pro Phe Asn His His Arg Asn Ala Gly Leu
        595                 600                 605

Arg Tyr Arg Ser Met Leu Leu Gly Asn Gly Arg Tyr Val Pro Phe His
    610                 615                 620

Ile Gln Val Pro Gln Lys Phe Phe Ala Ile Lys Asn Leu Leu Leu Leu
625                 630                 635                 640

Pro Gly Ser Tyr Thr Tyr Glu Trp Asn Phe Arg Lys Asp Val Asn Met
                645                 650                 655

Val Leu Gln Ser Ser Leu Gly Asn Asp Leu Arg Val Asp Gly Ala Ser
            660                 665                 670

Ile Lys Phe Asp Ser Ile Cys Leu Tyr Ala Thr Phe Phe Pro Met Ala
        675                 680                 685

His Asn Thr Ala Ser Thr Leu Glu Ala Met Leu Arg Asn Asp Thr Asn
    690                 695                 700

Asp Gln Ser Phe Asn Asp Tyr Leu Ser Ala Ala Asn Met Leu Tyr Pro
705                 710                 715                 720

Ile Pro Ala Asn Ala Thr Asn Val Pro Ile Ser Ile Pro Ser Arg Asn
                725                 730                 735

Trp Ala Ala Phe Arg Gly Trp Ala Phe Thr Arg Leu Lys Thr Lys Glu
            740                 745                 750

Thr Pro Ser Leu Gly Ser Gly Tyr Asp Pro Tyr Tyr Thr Tyr Ser Gly
```

```
        755                 760                 765

Ser Ile Pro Tyr Leu Asp Gly Thr Phe Tyr Leu Asn His Thr Phe Lys
    770                 775                 780

Lys Val Ala Ile Thr Phe Asp Ser Ser Val Ser Trp Pro Gly Asn Asp
785                 790                 795                 800

Arg Leu Leu Thr Pro Asn Glu Phe Glu Ile Lys Arg Ser Val Asp Gly
                805                 810                 815

Glu Gly Tyr Asn Val Ala Gln Cys Asn Met Thr Lys Asp Trp Phe Leu
            820                 825                 830

Val Gln Met Leu Ala Asn Tyr Asn Ile Gly Tyr Gln Gly Phe Tyr Ile
        835                 840                 845

Pro Glu Ser Tyr Lys Asp Arg Met Tyr Ser Phe Phe Arg Asn Phe Gln
    850                 855                 860

Pro Met Ser Arg Gln Val Val Asp Asp Thr Lys Tyr Lys Asp Tyr Gln
865                 870                 875                 880

Gln Val Gly Ile Leu His Gln His Asn Asn Ser Gly Phe Val Gly Tyr
                885                 890                 895

Leu Ala Pro Thr Met Arg Glu Gly Gln Ala Tyr Pro Ala Asn Phe Pro
            900                 905                 910

Tyr Pro Leu Ile Gly Lys Thr Ala Val Asp Ser Ile Thr Gln Lys Lys
        915                 920                 925

Phe Leu Cys Asp Arg Thr Leu Trp Arg Ile Pro Phe Ser Ser Asn Phe
    930                 935                 940

Met Ser Met Gly Ala Leu Thr Asp Leu Gly Gln Asn Leu Leu Tyr Ala
945                 950                 955                 960

Asn Ser Ala His Ala Leu Asp Met Thr Phe Glu Val Asp Pro Met Asp
                965                 970                 975

Glu Pro Thr Leu Leu Tyr Val Leu Phe Glu Val Phe Asp Val Val Arg
            980                 985                 990

Val His Gln Pro His Arg Gly Val  Ile Glu Thr Val Tyr  Leu Arg Thr
        995                 1000                1005

Pro Phe  Ser Ala Gly Asn Ala  Thr Thr
    1010                1015


<210> SEQ ID NO 55
<211> LENGTH: 597
<212> TYPE: PRT
<213> ORGANISM: Artificial Sequence
<220> FEATURE:
<223> OTHER INFORMATION: Synthetic Construct

<400> SEQUENCE: 55

Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
            20                  25                  30

Phe Val Ser Pro Asn Gly Phe Gln Glu Ser Pro Pro Gly Val Leu Ser
        35                  40                  45

Leu Arg Leu Ser Glu Pro Leu Val Thr Ser Asn Gly Met Leu Ala Leu
    50                  55                  60

Lys Met Gly Asn Gly Leu Ser Leu Asp Glu Ala Gly Asn Leu Thr Ser
65                  70                  75                  80

Gln Asn Val Thr Thr Val Ser Pro Pro Leu Lys Lys Thr Lys Ser Asn
                85                  90                  95

Ile Asn Leu Glu Ile Ser Ala Pro Leu Thr Val Thr Ser Glu Ala Leu
```

-continued

```
            100                 105                 110

Thr Val Ala Ala Ala Ala Pro Leu Met Val Ala Gly Asn Thr Leu Thr
        115                 120                 125

Met Gln Ser Gln Ala Pro Leu Thr Val His Asp Ser Lys Leu Ser Ile
    130                 135                 140

Ala Thr Gln Gly Pro Leu Thr Val Ser Glu Gly Lys Leu Ala Leu Gln
145                 150                 155                 160

Thr Ser Gly Pro Leu Thr Thr Thr Asp Ser Ser Thr Leu Thr Ile Thr
                165                 170                 175

Ala Ser Pro Pro Leu Thr Thr Ala Thr Gly Ser Leu Gly Ile Asp Leu
            180                 185                 190

Lys Glu Pro Ile Tyr Thr Gln Asn Gly Lys Leu Gly Leu Lys Tyr Gly
        195                 200                 205

Ala Pro Leu His Val Thr Asp Asp Leu Asn Thr Leu Thr Val Ala Thr
    210                 215                 220

Gly Pro Gly Val Thr Ile Asn Asn Thr Ser Leu Gln Thr Lys Val Thr
225                 230                 235                 240

Gly Ala Leu Gly Phe Asp Ser Gln Gly Asn Met Gln Leu Asn Val Ala
                245                 250                 255

Gly Gly Leu Arg Ile Asp Ser Gln Asn Arg Arg Leu Ile Leu Asp Val
            260                 265                 270

Ser Tyr Pro Phe Asp Ala Gln Asn Gln Leu Asn Leu Arg Leu Gly Gln
        275                 280                 285

Gly Pro Leu Phe Ile Asn Ser Ala His Asn Leu Asp Ile Asn Tyr Asn
    290                 295                 300

Lys Gly Leu Tyr Leu Phe Thr Ala Ser Asn Asn Ser Lys Lys Leu Glu
305                 310                 315                 320

Val Asn Leu Ser Thr Ala Lys Gly Leu Met Phe Asp Ala Thr Ala Ile
                325                 330                 335

Ala Ile Asn Ala Gly Asp Gly Leu Glu Phe Gly Ser Pro Asn Ala Pro
            340                 345                 350

Asn Thr Asn Pro Leu Lys Thr Lys Ile Gly His Gly Leu Glu Phe Asp
        355                 360                 365

Ser Asn Lys Ala Met Val Pro Lys Leu Gly Thr Gly Leu Ser Phe Asp
    370                 375                 380

Ser Thr Gly Ala Ile Thr Val Gly Asn Lys Asn Asn Asp Lys Leu Thr
385                 390                 395                 400

Leu Trp Thr Thr Pro Ala Pro Ser Pro Asn Cys Arg Leu Asn Ala Glu
                405                 410                 415

Lys Asp Ala Lys Leu Thr Leu Val Leu Thr Lys Cys Gly Ser Gln Ile
            420                 425                 430

Leu Ala Thr Val Ser Val Leu Ala Val Lys Gly Ser Leu Ala Pro Ile
        435                 440                 445

Ser Gly Thr Val Gln Ser Ala His Leu Ile Ile Arg Phe Asp Glu Asn
    450                 455                 460

Gly Val Leu Leu Asn Asn Ser Phe Leu Asp Pro Glu Tyr Trp Asn Phe
465                 470                 475                 480

Arg Asn Gly Asp Leu Thr Glu Gly Thr Ala Tyr Thr Asn Ala Val Gly
                485                 490                 495

Phe Met Pro Asn Leu Ser Ala Tyr Pro Lys Ser His Gly Lys Thr Ala
            500                 505                 510

Lys Ser Asn Ile Val Ser Gln Val Tyr Leu Asn Gly Asp Lys Thr Lys
        515                 520                 525
```

```
Pro Val Thr Leu Thr Ile Thr Leu Asn Gly Thr Gln Glu Thr Gly Asn
    530                 535                 540

Ala Asn Pro Asn Ala Asn Pro Asn Ala Asn Pro Asn Ala Asn Pro Asp
545                 550                 555                 560

Thr Thr Pro Ser Ala Tyr Ser Met Ser Phe Ser Trp Asp Trp Ser Gly
                565                 570                 575

His Asn Tyr Ile Asn Glu Ile Phe Ala Thr Ser Ser Tyr Thr Phe Ser
            580                 585                 590

Tyr Ile Ala Gln Glu
        595


<210> SEQ ID NO 56
<211> LENGTH: 218
<212> TYPE: PRT
<213> ORGANISM: Artificial Sequence
<220> FEATURE:
<223> OTHER INFORMATION: Synthetic Construct

<400> SEQUENCE: 56

Met Ser Ile Leu Ile Ser Pro Ser Asn Asn Thr Gly Trp Gly Leu Arg
1               5                   10                  15

Phe Pro Ser Lys Met Phe Gly Gly Ala Lys Lys Arg Ser Asp Gln His
            20                  25                  30

Pro Val Arg Val Arg Gly His Tyr Arg Ala Pro Trp Gly Ala His Lys
        35                  40                  45

Arg Gly Arg Thr Gly Arg Thr Thr Val Asp Asp Ala Ile Asp Ala Val
    50                  55                  60

Val Glu Glu Ala Arg Asn Tyr Thr Pro Thr Pro Pro Pro Val Ser Thr
65                  70                  75                  80

Val Asp Ala Ala Ile Gln Thr Val Val Arg Gly Ala Arg Arg Tyr Ala
                85                  90                  95

Lys Met Lys Arg Arg Arg Arg Arg Val Ala Arg Arg His Arg Arg Arg
            100                 105                 110

Pro Gly Thr Ala Ala Gln Arg Ala Ala Ala Ala Leu Leu Asn Arg Ala
        115                 120                 125

Arg Arg Thr Gly Arg Arg Ala Ala Met Arg Ala Ala Arg Arg Leu Ala
    130                 135                 140

Ala Gly Ile Val Thr Val Pro Pro Arg Ser Arg Arg Arg Ala Ala Ala
145                 150                 155                 160

Ala Ala Ala Ala Ala Ile Ser Ala Met Thr Gln Gly Arg Arg Gly Asn
                165                 170                 175

Val Tyr Trp Val Arg Asp Ser Val Ser Gly Leu Arg Val Pro Val Arg
            180                 185                 190

Thr Arg Pro Pro Arg Asn Glu Tyr Leu Asn Lys Ile Gln Asn Ser Leu
        195                 200                 205

Ser Thr Glu Trp Ser Pro Cys Ser Val Thr
    210                 215


<210> SEQ ID NO 57
<211> LENGTH: 246
<212> TYPE: PRT
<213> ORGANISM: Artificial Sequence
<220> FEATURE:
<223> OTHER INFORMATION: Synthetic Construct

<400> SEQUENCE: 57

Met Ser Ile Leu Ile Ser Pro Ser Asn Asn Thr Gly Trp Gly Leu Arg
```

-continued 1 5 10 15

Phe Pro Ser Lys Met Phe Gly Gly Ala Lys Lys Arg Ser Asp Gln His
20 25 30

Pro Val Arg Val Arg Gly His Tyr Arg Ala Pro Trp Gly Ala His Lys
35 40 45

Arg Gly Arg Thr Gly Arg Thr Thr Val Asp Asp Ala Ile Asp Ala Val
50 55 60

Val Glu Glu Ala Arg Asn Tyr Thr Pro Thr Pro Pro Pro Val Ser Thr
65 70 75 80

Val Asp Ala Ala Ile Gln Thr Val Val Arg Gly Ala Glu Tyr Leu Asn
85 90 95

Lys Ile Gln Asn Ser Leu Ser Thr Glu Trp Ser Pro Cys Ser Val Thr
100 105 110

Arg Arg Tyr Ala Lys Met Lys Arg Arg Arg Arg Arg Val Ala Arg Arg
115 120 125

His Arg Arg Arg Pro Gly Thr Ala Ala Gln Arg Ala Ala Ala Ala Leu
130 135 140

Leu Asn Arg Ala Arg Arg Thr Gly Arg Arg Ala Ala Met Arg Ala Ala
145 150 155 160

Arg Arg Leu Ala Ala Gly Ile Val Thr Val Pro Pro Arg Ser Arg Arg
165 170 175

Arg Ala Ala Ala Ala Ala Ala Ala Ala Ile Ser Ala Met Thr Gln Gly
180 185 190

Arg Arg Gly Asn Val Tyr Trp Val Arg Asp Ser Val Ser Gly Leu Arg
195 200 205

Val Pro Val Arg Thr Arg Pro Pro Arg Asn Val Arg Thr Arg Pro Pro
210 215 220

Arg Asn Tyr Asn Arg Asn Ile Val Asn Arg Leu Leu Gly Asp Ala Leu
225 230 235 240

Thr Arg Pro Pro Arg Asn
245

<210> SEQ ID NO 58
<211> LENGTH: 226
<212> TYPE: PRT
<213> ORGANISM: Artificial Sequence
<220> FEATURE:
<223> OTHER INFORMATION: Synthetic Construct

<400> SEQUENCE: 58

Met Ser Ile Leu Ile Ser Pro Ser Asn Asn Thr Gly Trp Gly Leu Arg
1 5 10 15

Phe Pro Ser Lys Met Phe Gly Gly Ala Lys Lys Arg Ser Asp Gln His
20 25 30

Pro Val Arg Val Arg Gly His Tyr Arg Ala Pro Trp Gly Ala His Lys
35 40 45

Arg Gly Arg Thr Gly Arg Thr Thr Val Asp Asp Ala Ile Asp Ala Val
50 55 60

Val Glu Glu Ala Arg Asn Tyr Thr Pro Thr Pro Pro Pro Val Ser Thr
65 70 75 80

Val Asp Ala Ala Ile Gln Thr Val Val Arg Gly Ala Arg Arg Tyr Ala
85 90 95

Lys Met Lys Arg Arg Arg Arg Arg Val Ala Arg Arg His Arg Arg Arg
100 105 110

Pro Gly Thr Ala Ala Gln Arg Ala Ala Ala Ala Leu Leu Asn Arg Ala

```
        115                 120                 125

Arg Arg Thr Gly Arg Arg Ala Ala Met Arg Ala Ala Glu Tyr Leu Asn
    130                 135                 140

Lys Ile Gln Asn Ser Leu Ser Thr Glu Trp Ser Pro Cys Ser Val Thr
145                 150                 155                 160

Arg Arg Leu Ala Ala Gly Ile Val Thr Val Pro Pro Arg Ser Arg Arg
                165                 170                 175

Arg Ala Ala Ala Ala Ala Ala Ala Ala Ile Ser Ala Met Thr Gln Gly
            180                 185                 190

Arg Arg Gly Asn Val Tyr Trp Val Arg Asp Ser Val Ser Gly Leu Arg
        195                 200                 205

Val Pro Val Arg Thr Arg Pro Pro Arg Asn Val Arg Thr Arg Pro Pro
    210                 215                 220

Arg Asn
225


<210> SEQ ID NO 59
<211> LENGTH: 6
<212> TYPE: PRT
<213> ORGANISM: Plasmodium yoelii

<400> SEQUENCE: 59

Gln Gly Pro Gly Ala Pro
1               5


<210> SEQ ID NO 60
<211> LENGTH: 4
<212> TYPE: PRT
<213> ORGANISM: Plasmodium falciparum

<400> SEQUENCE: 60

Asn Ala Asn Pro
1


<210> SEQ ID NO 61
<211> LENGTH: 21
<212> TYPE: PRT
<213> ORGANISM: Plasmodium yoelii

<400> SEQUENCE: 61

Tyr Asn Arg Asn Ile Val Asn Arg Leu Leu Gly Asp Ala Leu Asn Gly
1               5                   10                  15

Lys Pro Glu Glu Lys
            20


<210> SEQ ID NO 62
<211> LENGTH: 20
<212> TYPE: PRT
<213> ORGANISM: Plasmodium falciparum

<400> SEQUENCE: 62

Glu Tyr Leu Asn Lys Ile Gln Asn Ser Leu Ser Thr Glu Trp Ser Pro
1               5                   10                  15

Cys Ser Val Thr
            20


<210> SEQ ID NO 63
<211> LENGTH: 9
<212> TYPE: PRT
<213> ORGANISM: Plasmodium vivax
```

-continued

```
<400> SEQUENCE: 63

Ala Asn Gly Ala Gly Asn Gln Pro Gly
1               5


<210> SEQ ID NO 64
<211> LENGTH: 4
<212> TYPE: PRT
<213> ORGANISM: Plasmodium malariae

<400> SEQUENCE: 64

Asn Ala Ala Gly
1


<210> SEQ ID NO 65
<211> LENGTH: 4
<212> TYPE: PRT
<213> ORGANISM: Plasmodium yoelii

<400> SEQUENCE: 65

Gln Gln Pro Pro
1


<210> SEQ ID NO 66
<211> LENGTH: 9
<212> TYPE: PRT
<213> ORGANISM: Plasmodium yoelii

<400> SEQUENCE: 66

Ser Tyr Val Pro Ser Ala Glu Gln Ile
1               5
```

MODIFICATION OF RECOMBINANT ADENOVIRUS WITH IMMUNOGENIC PLASMODIUM CIRCUMSPOROZOITE PROTEIN EPITOPES

CROSS-REFERENCE TO RELATED APPLICATIONS

This application is a continuation of International Application No. PCT/US10/045,952, filed Aug. 18, 2010, which claims priority to and is a continuation-in-part of International Application No. PCT/US09/054,212, filed on Aug. 18, 2009, both of which are incorporated by reference in their entirety, as if fully set forth herein.

STATEMENT REGARDING FEDERALLY SPONSORED RESEARCH

This invention was made with government support under Grant No. 1R01AI081510-01A1 awarded by the National Institute of Allergy and Infectious Diseases (NIAID), an institute that is part of the National Institutes of Health. The government has certain rights in the invention.

FIELD OF THE INVENTION

The invention relates to the field of medicine and biotechnology. More particularly, the invention relates to the use of capsid-modified adenoviral vectors to induce a potent immune response to a malaria parasite antigen such as *Plasmodium* circumsporozoite protein, which are suitable for vaccines against malaria.

BACKGROUND

Malaria is a severe disease that ranks among the most prevalent infections in tropical areas throughout the world. Approximately 300-500 million people become infected yearly, with relatively high rates of morbidity and mortality. Severe morbidity and mortality occur particularly in young children and in adults migrating to a malaria endemic area without having undergone prior malaria exposure. The World Health Organization (WHO) estimates that 2-3 million children die of malaria in Africa alone, every year. The widespread occurrence and the increasing incidence of malaria in many countries, caused by drug-resistant parasites (*Plasmodium falciparum*, recently also *Plasmodium vivax*) and insecticide-resistant vectors (Anopheles mosquitoes), underscore the need for developing new methods for the control of this disease (Nussenzweig and Long 1994).

Malaria parasites have a complicated life cycle consisting of pre-erythrocytic, erythrocytic and sexual parasitic forms, representing a potential target for the development of a malaria vaccine. The pre-erythrocytic and erythrocytic forms are found in the host, while the sexual forms occur in the vector. Immunization with live-attenuated irradiated sporozoites (IrSp) has been shown to induce sterile protection (i.e., complete resistance against parasite challenge) in mice (Nussenzweig et al. 1967), non-human primates (Gwadz et al. 1979) and human (Clyde et al. 1973, Edelman et al. 1993). Protection conferred by IrSp is mediated by sporozoite neutralization by both humoral (B cell) and cellular (T cell) immune responses (Tsuji et al. 2001). Although an IrSp vaccination is an attractive solution, the only way to obtain sporozoites is by dissecting mosquito salivary glands, and there is currently no known technology to grow large numbers of sporozoites in vitro. Therefore, an alternate vaccine vector that can elicit an equally strong protective immunity against malaria is needed.

One promising target for such a vaccine vector is the circumsporozoite (CS) protein, which is expressed on the surface of the sporozoite. Effective neutralizing antibodies are directed against the immunodominant, species specific, repeat domains of the circumsporozoite (CS) protein. In *Plasmodium falciparum* (human malaria parasite), the repeats $(NANP)_n$ are conserved among isolates from all areas of the world. This central repeat contains multiple repeat of B cell epitopes, and, therefore, the CS protein can induce a strong humoral immune response by triggering B cells (Tsuji et al. 2001). At the C-terminal region of the CS protein, there are several T cell epitopes, which can induce a significant cellular immune response (Tsuji et al. 2001). The humoral (antibody) response can eliminate parasites by interacting and neutralizing the infectivity of sporozoites (extra-cellular parasite) prior to entering hepatocyte, whereas the cellular (T cell) response can attack EEF (an intra-cellular parasite) by secreting interferon-gamma. These immune responses prevent the EEFs from maturing and dividing rapidly to form thousands of merozoites that reenter the blood and infect erythrocytes causing the disease we recognize as malaria.

One CS-based malarial vaccine that is currently undergoing human trials is GlaxoSmithKline's RTS, S, fusion protein of the Hepatitis B surface antigen and a portion of *Plasmodium falciparum* circumsporozoite protein (PfCSP) in a form of virus-like particle (International Patent Application No. PCT/EP1992/002591 to SmithKline Beecham Biologicals S.A., filed Nov. 11, 1992), has been shown to decrease malaria infection in clinical trials (Alonso et al. 2004, Alonso et al. 2005, Bejon et al. 2008). RTS, S induces an anti-PfCSP humoral immune response, but a relatively weak PfCSP-specific cellular (CD8+) response (Kester et al. 2008), which might be the reason for the relatively weak protection by RTS, S. In contrast, adenovirus-based malaria vaccines can induce a protective cellular immune response (International Patent Application No. PCT/EP2003/051019, filed Dec. 16, 2003, Rodrigues et al. 1997). However, there are currently two obstacles that limit the use of an adenovirus-based platform as a malaria vaccine: (1) lack of a capability of inducing a potent humoral response against a transgene product, and (2) pre-existing immunity to adenovirus, especially adenovirus serotype 5, which hampers the immunogenicity of adenovirus-based vaccine.

One approach that has recently been taken in an attempt to augment adenovirus-induced humoral response is to insert a B cell antigenic epitope (e.g., a bacterial or viral epitope) in adenovirus capsid proteins such as Hexon, Fiber, Penton and pIX (Worgall et al. 2005, McConnell et al. 2006, Krause et al. 2006, Worgall et al. 2007).

In addition, to circumvent pre-existing immunity to adenovirus serotype 5 (Ad5), other adenovirus serotypes with lower seroprevalence, such as adenovirus serotype 11, 35, 26, 48, 49 and 50, have been evaluated as a vaccine platform and shown to induce immune response to a transgene in spite of the presence of anti-Ad5 immunity (International Patent Application No. PCT/EP2005/055183 to Crucell Holland B.V., filed Oct. 12, 2005, Abbink et al. 2007). Substitution of Ad5 Hexon, which is the target capsid protein of neutralizing antibody, with that of other serotypes has also been constructed in order to escape pre-existing anti-Ad5 immunity (Wu et al. 2002, Roberts et al. 2006).

There is, however, no improved adenoviral vector reported to have overcome the two obstacles at the same time in applying an adenoviral vector to a malaria vaccine mentioned above. Given that seroprevalence to Ad5 is high in malaria endemic areas (Ophorst et al. 2006.), there is a need for an adenovirus-based malaria vaccine that induces both protective humoral and cellular immune responses even in the presence of pre-exiting immunity to adenovirus.

SUMMARY

The present disclosure relates to various adenovirus protein modifications to augment immune response to a transgene of a recombinant adenoviral vaccine and to circumvent pre-existing anti-adenovirus immunity.

More specifically, one embodiment is directed to a recombinant adenovirus derived from a recombinant adenovirus plasmid vector, wherein the recombinant adenovirus plasmid vector comprises a nucleotide sequence encoding (i) a *Plasmodium* circumsporozoite protein, or antigenic portion thereof, operably linked to a heterologous promoter: and (ii) a modified capsid or core protein, wherein an immunogenic epitope of *Plasmodium* circumsporozoite has been inserted into or replaces at least part of a capsid or core protein.

In some embodiments, the *Plasmodium* circumsporozoite protein further comprises a *Plasmodium falciparum* or *Plasmodium yoelii* circumsporozoite protein. The circumsporozoite protein may further comprise a codon-optimized *Plasmodium falciparum* or *Plasmodium yoelii* circumsporozoite protein, and in some aspects, may be encoded by the nucleotide sequence of SEQ ID NO:2 or SEQ ID NO:1, respectively.

In other embodiments, the immunogenic epitope further comprises a B cell epitope of *Plasmodium* circumsporozoite protein. The B cell epitope may be incorporated in a modified capsid protein, and in some aspects, the capsid protein may comprise a Hexon hypervariable region (HVR). The HVR may further comprise HVR1 or HVR5, wherein a portion of HVR1 or HVR5 is replaced with the B cell epitope. In other aspects, the capsid protein may further comprise a capsid Fiber protein wherein the B cell epitope is inserted into the Fiber protein. In some aspects, the B cell epitope is a *Plasmodium falciparum* circumsporozoite protein B cell epitope, wherein the B cell epitope is a repeat sequence, for example, $(NANP)_n$ (SEQ ID NO:60), wherein the repeat sequence may be $(NANP)_4$, $(NANP)_6$, $(NANP)_8$, $(NANP)_{10}$, $(NANP)_{12}$, $(NANP)_{14}$, $(NANP)_{16}$, $(NANP)_{18}$, $(NANP)_{20}$, $(NANP)_{22}$ or $(NANP)_{28}$. In other aspects, the B cell epitope is a *Plasmodium yoelii* circumsporozoite protein B cell epitope, wherein the B cell epitope is a repeat sequence, for example, $(QGPGAP)_n$ (SEQ ID NO:59), wherein the repeat sequence may be $(QGPGAP)_3$, $(QGPGAP)_4$, $(QGPGAP)_5$, $(QGPGAP)_6$, $(QGPGAP)_7$, $(QGPGAP)_8$, $(QGPGAP)_9$, $(QGPGAP)_{11}$, or $(QGPGAP)_{12}$.

In yet other embodiments, the immunogenic epitope further comprises a CD4+ or CD8+ T cell epitope of *Plasmodium* circumsporozoite protein. The CD4+ or CD8+ T cell epitope may be incorporated in a modified capsid or core protein. In some aspects, the capsid protein may comprise a Hexon hypervariable region (HVR). The HVR may further comprise HVR1 wherein a portion of HVR1 is replaced with the CD4+ or CD8+ T cell epitope. In other aspects, the core protein further comprises a pVII protein and a CD4+ T cell epitope is inserted into the pVII protein. In some aspects the CD4+ T cell epitope is a *Plasmodium falciparum* circumsporozoite CD4+ T cell epitope, wherein the CD4+ T cell epitope is EYLNKIQNSLSTEWSPCSVT (SEQ ID NO:62). In other aspects the CD4+ T cell epitope is a *Plasmodium yoelii* circumsporozoite CD4+ T cell epitope, wherein the CD4+ T cell epitope is YNRNIVNRLLGDALNGKPEEK (SEQ ID NO:61)

Other embodiments are directed to a pharmaceutical composition or malaria vaccine composition comprising a recombinant adenovirus according to the above embodiments. Further embodiments include a method of treating, preventing, or diagnosing malaria, comprising administering a therapeutic amount of the pharmaceutical composition or malaria vaccine composition in accordance with the above embodiments.

In another embodiment, a method for treatment comprising administering a prime-boost vaccination, wherein a subject is given a series of increasing dosages or same dosages at a given time interval. The time interval may be any length sufficient to generate a humoral and/or cellular immune response. For example, as described below, the interval may be, but is not limited to, once every 3 weeks.

BRIEF DESCRIPTION OF THE DRAWINGS

FIG. 9 is the nucleic acid sequence of codon-optimized *Plasmodium yoelii* circumsporozoite protein (PyCS, SEQ ID NO:1) and the corresponding amino acid sequence (SEQ ID NO:30)

FIG. 10 is the nucleic acid sequence of codon-optimized *Plasmodium falciparum* circumsporozoite protein (PfCSP, SEQ ID NO:2) and the corresponding amino acid sequence (SEQ ID NO:43)

FIGS. 11A-C is the nucleic acid and amino acid sequences of a modified Hexon having three repeats of the PyCS B cell epitope sequence $(QGPGAP)_n$, (SEQ ID NO:59; n=3) in HVR1 (SEQ ID NO:3, nucleic acid; SEQ ID NO:31, amino acid). The inserted $(QGPGAP)_3$ sequence is underlined.

FIGS. 12A-C is the nucleic acid and amino acid sequences of a modified Hexon having four repeats of the PyCS B cell epitope sequence $(QGPGAP)_n$, (SEQ ID NO:59; n=4) in HVR1 (SEQ ID NO:4, nucleic acid; SEQ ID NO: 32, amino acid). The inserted $(QGPGAP)_4$ sequence is underlined.

FIGS. 13A-C is the nucleic acid and amino acid sequences of modified Hexon having five repeats of the PyCS B cell epitope sequence $(QGPGAP)_n$, (SEQ ID NO:59; n=5) in HVR1 (SEQ ID NO:5, nucleic acid; SEQ ID NO: 33, amino acid). The inserted $(QGPGAP)_5$ sequence is underlined.

FIGS. 14A-C is the nucleic acid and amino acid sequences of modified Hexon having six repeats of the PyCS B cell epitope sequence $(QGPGAP)_n$, (SEQ ID NO:59; n=6) in HVR1 (SEQ ID NO:6, nucleic acid; SEQ ID NO: 34, amino acid). The inserted $(QGPGAP)_6$ sequence is underlined.

FIGS. 15A-C is the nucleic acid and amino acid sequences of modified Hexon having seven repeats of the PyCS B cell epitope sequence $(QGPGAP)_n$, (SEQ ID NO:59; n=7) in HVR1 (SEQ ID NO:7, nucleic acid; SEQ ID NO: 35, amino acid). The inserted $(QGPGAP)_7$ sequence is underlined.

FIGS. 16A-C is the nucleic acid and amino acid sequences of modified Hexon having eight repeats of the PyCS B cell epitope sequence $(QGPGAP)_n$, (SEQ ID NO:59; n=8) in HVR1 (SEQ ID NO:8, nucleic acid; SEQ ID NO: 36, amino acid). The inserted $(QGPGAP)_8$ sequence is underlined.

FIGS. 17A-C is the nucleic acid and amino acid sequences of modified Hexon having nine repeats of the PyCS B cell epitope sequence $(QGPGAP)_n$, (SEQ ID NO:59; n=9) in HVR1 (SEQ ID NO:9, nucleic acid; SEQ ID NO: 37, amino acid). The inserted $(QGPGAP)_9$ sequence is underlined.

FIGS. 18A-C is the nucleic acid and amino acid sequences of modified Hexon having eleven repeats of the PyCS B cell epitope sequence $(QGPGAP)_n$, (SEQ ID NO:59; n=11) in HVR1 (SEQ ID NO:10, nucleic acid; SEQ ID NO: 38, amino acid). The inserted $(QGPGAP)_{11}$ sequence is underlined.

FIGS. 19A-C is the nucleic acid and amino acid sequences of modified Hexon having twelve repeats of the PyCS B cell epitope sequence $(QGPGAP)_n$, (SEQ ID NO:59; n=12) in HVR1 (SEQ ID NO:11, nucleic acid; SEQ ID NO: 39, amino acid). The inserted $(QGPGAP)_{12}$ sequence is underlined.

FIGS. 20A-C is the nucleic acid and amino acid sequences of modified Hexon having four repeats of the PfCSP B cell epitope sequence $(NANP)_n$, (SEQ ID NO:60; n=4) in HVR1 (SEQ ID NO:12, nucleic acid; SEQ ID NO: 44, amino acid). The inserted $(NANP)_4$ sequence is underlined.

FIGS. 21A-C is the nucleic acid and amino acid sequences of modified Hexon having six repeats of the PfCSP B cell epitope sequence $(NANP)_n$, (SEQ ID NO:60; n=6) in HVR1 (SEQ ID NO:13, nucleic acid; SEQ ID NO: 45, amino acid). The inserted $(NANP)_6$ sequence is underlined.

FIGS. 22A-C is the nucleic acid and amino acid sequences of modified Hexon having eight repeats of the PfCSP B cell epitope sequence $(NANP)_n$, (SEQ ID NO:60; n=8) in HVR1 (SEQ ID NO:14, nucleic acid; SEQ ID NO: 46, amino acid). The inserted $(NANP)_8$ sequence is underlined.

FIGS. 23A-C is the nucleic acid and amino acid sequences of modified Hexon having ten repeats of the PfCSP B cell epitope sequence $(NANP)_n$, (SEQ ID NO:60; n=10) in HVR1 (SEQ ID NO:15, nucleic acid; SEQ ID NO: 47, amino acid). The inserted $(NANP)_{10}$ sequence is underlined.

FIGS. 24A-C is the nucleic acid and amino acid sequences of modified Hexon having twelve repeats of the PfCSP B cell epitope sequence $(NANP)_n$, (SEQ ID NO:60; n=12) in HVR1 (SEQ ID NO:16, nucleic acid; SEQ ID NO: 48, amino acid). The inserted $(NANP)_{12}$ sequence is underlined.

FIGS. 25A-C is the nucleic acid and amino acid sequences of modified Hexon having fourteen repeats of the PfCSP B cell epitope sequence $(NANP)_n$, (SEQ ID NO:60; n=14) in HVR1 (SEQ ID NO:17, nucleic acid; SEQ ID NO: 49, amino acid). The inserted $(NANP)_{14}$ sequence is underlined.

FIGS. 26A-C is the nucleic acid and amino acid sequences of modified Hexon having sixteen repeats of the PfCSP B cell epitope sequence $(NANP)_n$, (SEQ ID NO:60; n=16) in HVR1 (SEQ ID NO:18, nucleic acid; SEQ ID NO: 50, amino acid). The inserted $(NANP)_{16}$ sequence is underlined.

FIGS. 27A-C is the nucleic acid and amino acid sequences of modified Hexon having eighteen repeats of the PfCSP B cell epitope sequence $(NANP)_n$, (SEQ ID NO:60; n=18) in HVR1 (SEQ ID NO:19, nucleic acid; SEQ ID NO: 51, amino acid). The inserted $(NANP)_{18}$ sequence is underlined.

FIGS. 28A-C is the nucleic acid and amino acid sequences of modified Hexon having twenty repeats of the PfCSP B cell epitope sequence $(NANP)_n$, (SEQ ID NO:60; n=20) in HVR1 (SEQ ID NO:20, nucleic acid; SEQ ID NO: 52, amino acid). The inserted $(NANP)_{20}$ sequence is underlined.

FIGS. 29A-C is the nucleic acid and amino acid sequences of modified Hexon having twenty-two repeats of the PfCSP B cell epitope sequence $(NANP)_n$, (SEQ ID NO:60; n=22) in HVR1 (SEQ ID NO:21, nucleic acid; SEQ ID NO: 53, amino acid). The inserted $(NANP)_{22}$ sequence is underlined.

FIGS. 30A-C is the nucleic acid and amino acid sequences of modified Hexon having twenty-eight repeats of the PfCSP B cell epitope sequence $(NANP)_n$, (SEQ ID NO:60; n=28) in HVR1 (SEQ ID NO:22, nucleic acid; SEQ ID NO: 54, amino acid). The inserted $(NANP)_{28}$ sequence is underlined.

FIGS. 31A-C is the nucleic acid and amino acid sequences of modified Hexon having three repeats of the PyCS B cell epitope sequence $(QGPGAP)_n$, (SEQ ID NO:59; n=3) in HVR5 (SEQ ID NO:23, nucleic acid; SEQ ID NO:40, amino acid). The inserted $(QGPGAP)_3$ sequence is underlined.

FIGS. 32A-C is the nucleic acid and amino acid sequences of modified Fiber having three repeats of the PyCS B cell epitope sequence $(QGPGAP)_n$, (SEQ ID NO:59; n=3) in Fiber (SEQ ID NO:24, nucleic acid; SEQ ID NO:41, amino acid). The inserted $(QGPGAP)_3$ sequence is underlined.

FIGS. 33A-B is the nucleic acid and amino acid sequences of modified Fiber having four repeats of the PfCSP B cell epitope sequence $(NANP)_n$, (SEQ ID NO:60; n=4) in Fiber (SEQ ID NO:25, nucleic acid; SEQ ID NO:55, amino acid). The inserted $(NANP)_4$ sequence is underlined.

FIG. 34 is the nucleic acid and amino acid sequences of the modified pVII having the PyCS CD4+ epitope sequence YNRNIVNRLLGDALNGKPEEK, (SEQ ID NO:61) at the N-terminus of pVII (SEQ ID NO:26, nucleic acid; SEQ ID NO:42, amino acid). The inserted YNRNIVNRLL-GDALNGKPEEK sequence is underlined.

FIG. 35 is the nucleic acid and amino acid sequences of the modified pVII having the PfCSP CD4+ epitope sequence EYLNKIQNSLSTEWSPCSVT, (SEQ ID NO:62) at the C-terminus of pVII (pVII-1; SEQ ID NO:27, nucleic acid; SEQ ID NO:56, amino acid). The inserted EYLNKIQNSLSTEWSPCSVT sequence is underlined.

FIG. 36 is the nucleic acid and amino acid sequences of the modified pVII having the PfCSP CD4+ epitope sequence EYLNKIQNSLSTEWSPCSVT, (SEQ ID NO:62) before the first Nuclear Localization Signal (NLS) of pVII (pVII-2; SEQ ID NO:28, nucleic acid; SEQ ID NO:57, amino acid). The inserted EYLNKIQNSLSTEWSPCSVT sequence is underlined.

FIG. 37 is the nucleic acid and amino acid sequences of the modified pVII having the PfCSP CD4+ epitope sequence EYLNKIQNSLSTEWSPCSVT, (SEQ ID NO:62) between the two NLSs of pVII (pVII-3; SEQ ID NO:29, nucleic acid; SEQ ID NO:58, amino acid). The inserted EYLNKIQNSLSTEWSPCSVT sequence is underlined.

FIG. 53 shows schematic diagrams of the structure of the adenovirus pVII proteins with the PfCSP CD4+ epitope sequence EYLNKIQNSLSTEWSPCSVT (SEQ ID NO:62) inserted at the before the first Nuclear Localization Signal (NLS) of pVII (PfCD4-pVII-2; SEQ ID NO:28, nucleic acid; SEQ ID NO:57, amino acid) and between the two NLSs of pVII (PfCD4-pVII-3; SEQ ID NO:29, nucleic acid; SEQ ID NO:58, amino acid) (A) and the results of silver staining to confirm the epitope insertion into pVII (B).

MEANS FOR SOLVING THE PROBLEMS

Figure 1:
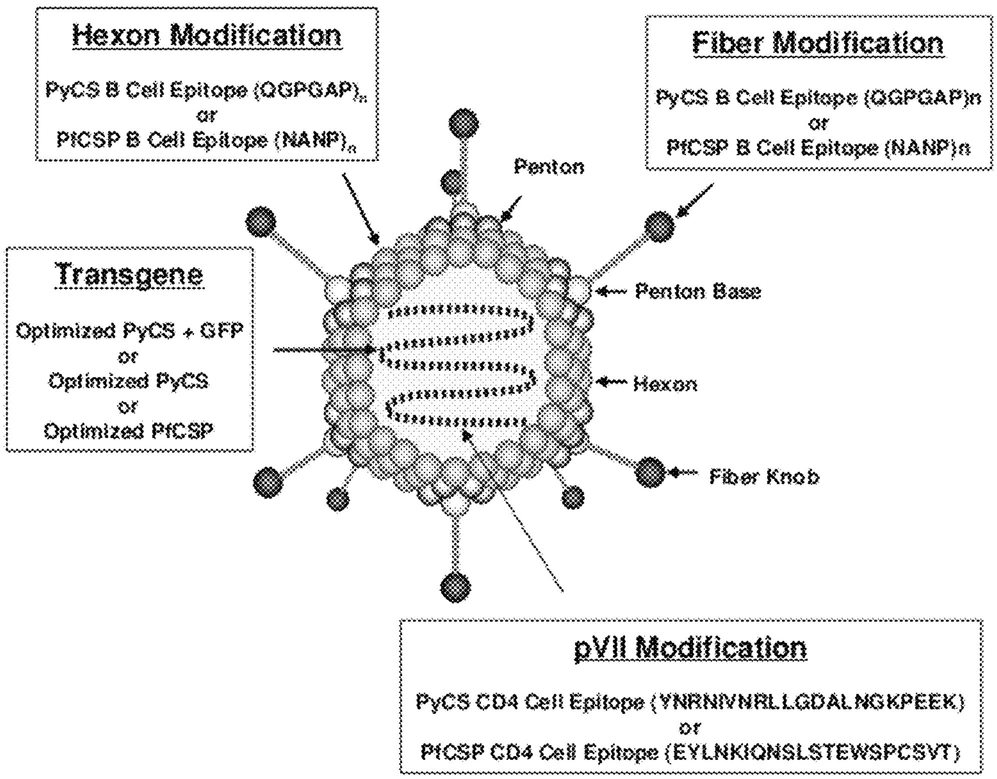
FIG. 1 is a schematic diagram of a capsid-modified recombinant adenovirus in accordance with embodiments of the disclosure.

The present inventors have found a novel recombinant adenovirus having a novel, capsid-modified structure that is derived from a recombinant adenovirus plasmid vector. The recombinant adenovirus is capable of infecting mammalian cells, causing the cells to express a *Plasmodium* circumsporozoite protein. The recombinant adenovirus also has one or more capsid proteins that have been modified by having a desired immunogenic antigen, such as B cell epitope, T cell epitope of *Plasmodium* circumsporozoite protein. The recombinant adenovirus is obtained by the method of transfecting cells with the linearized recombinant adenovirus plasmid vector. Using the obtained recombinant adenovirus, the present inventors carried out extensive research on pharmaceuticals containing as an active ingredient a recombinant adenovirus having malaria infection preventive and therapeutic effects. As a result, the inventors found that the obtained recombinant adenovirus has the desired pharmaceutical effects.

DETAILED DESCRIPTION

The following description provides specific details for a thorough understanding of, and enabling description for, embodiments of the disclosure. However, one skilled in the art will understand that the disclosure may be practiced without these details. In other instances, well-known structures and functions have not been shown or described in detail to avoid unnecessarily obscuring the description of the embodiments of the disclosure.

The abbreviations used for the amino acids, peptides, base sequences, and nucleic acids in the present disclosure are based on the abbreviations specified in the IUPAC-IUB Communication on Biochemical Nomenclature, Eur. J. Biochem., 138: 9 (1984), "Guideline for Preparing Specifications Including Base Sequences and Amino Acid Sequences" (United States Patent and Trademark Office), and those commonly used in this technical field.

A "nucleotide sequence," "polynucleotide" or "DNA molecule" as contemplated by the current disclosure, may include double strand DNA or single strand DNA (i.e., a sense chain and an antisense chain constituting the double strand DNA), and is not limited to a full length thereof. Nucleotide sequences encoding an immunogenic foreign gene, such as those disclosed herein below, encompass double strand DNA containing genomic DNA, single strand DNA (sense chain) containing cDNA, single strand DNA (antisense chain) having a sequence complementary to the sense chain, synthetic DNA, and fragments thereof, unless otherwise mentioned.

Nucleotide sequences, polynucleotides or DNA molecules as used herein are not limited to the functional region, and may include at least one of an expression suppression region, a coding region, a leader sequence, an exon, and an intron. Further, examples of nucleotide sequences or polynucleotides may include RNA or DNA. A polypeptide containing a specific amino acid sequence and a polynucleotide containing a specific DNA sequence may include fragments, homologs, derivatives, and mutants of the polynucleotide. Examples of mutants of a nucleotide sequence or polynucleotide (such as mutant DNA), include naturally occurring allelic mutants; artificial mutants; and mutants having deletion, substitution, addition, and/or insertion. It should be understood that such mutants encode polypeptides having substantially the same function as the polypeptide encoded by the original non-mutated polynucleotide.

The present disclosure relates to a recombinant adenovirus that can express an antigenic determinant of a *Plasmodium* parasite, and comprises one or more modified capsid and/or core proteins. The recombinant adenovirus is derived from a recombinant adenovirus plasmid vector, the generation of which is described in the Examples below. The use of adenovirus as a vector is discussed further below. The recombinant adenovirus plasmid vectors described herein may be used as a malaria vaccine or pharmaceutical composition, wherein both humoral and cellular immune responses against the *Plasmodium* parasite are induced.

The *Plasmodium* parasite may be selected from any of the known *Plasmodium* (*P.*) species, for example, *P. falciparum, P. malariae, P. ovale, P. vivax, P. knowlesi, P. berghei, P. chabaudi* and *P. yoelii*. In some embodiments, the antigenic determinant is derived from the rodent-specific *Plasmodium yoelii* or the human-specific *Plasmodium falciparum*

In one embodiment, a recombinant adenovirus capsid-modified plasmid vector (also described as a recombinant adenovirus plasmid vector herein) is a plasmid that encodes and produces a capsid and/or core-modified recombinant adenovirus (also described as a recombinant adenovirus herein) that has a structure comprising one or more modified capsid and/or core proteins. In accordance with the embodiments of the disclosure, the modification of the capsid and/or core proteins may be accomplished by insertion of at least one immunogenic epitope of a *Plasmodium* circumsporozoite protein. Alternatively, at least part of the capsid and/or core protein may be deleted and replaced by at least one immunogenic epitope of a *Plasmodium* circumsporozoite protein. In some embodiments, the immunogenic epitope is a B-cell and/or T-cell epitope of a *Plasmodium* circumsporozoite protein. The addition of a B cell or T cell epitope may serve to enhance the efficacy of an adenoviral vector used as a malaria vaccine by establishing or enhancing the humoral immune response to the CS protein. The modified capsid and core proteins and their significance with respect to their use in the recombinant adenovirus described herein are discussed further below.

The one or more modified capsid and/or core proteins may be a modified Hexon protein, a modified Fiber protein, a modified pVII protein or a combination thereof. In one embodiment, a portion of a Hexon hypervariable region (HVR) and/or a portion of Fiber protein is replaced by at least one B-cell and/or T-cell epitope of a *Plasmodium* circumsporozoite protein. Alternatively, one or more B-cell and/or T cell epitope of a *Plasmodium* circumsporozoite protein may be inserted in the Fiber protein or Hexon HVR. In some aspects, the modified HVR may be HVR1, HVR2, HVR3, HVR4, HVR5, HVR6 or HVR7. In other aspects, the modified HVR may be HVR1 or HVR5. In some embodiments, the HVR-modified Hexon may have a nucleic acid sequence of SEQ ID NO:3 (FIG. 11), SEQ ID NO:4 (FIG. 12), SEQ ID NO:5 (FIG. 13), SEQ ID NO:6 (FIG. 14), SEQ ID NO:7 (FIG. 15), SEQ ID NO:8 (FIG. 16), SEQ ID NO:9 (FIG. 17), SEQ ID NO:10 (FIG. 18), SEQ ID NO:11 (FIG. 19), SEQ ID NO:12 (FIG. 20), SEQ ID NO:13 (FIG. 21), SEQ ID NO:14 (FIG. 22), SEQ ID NO:15 (FIG. 23), SEQ ID NO:16 (FIG. 24), SEQ ID NO:17 (FIG. 25), SEQ ID NO:18 (FIG. 26), SEQ ID NO:19 (FIG. 27), SEQ ID NO:20 (FIG. 28), SEQ ID NO:21 (FIG. 29), SEQ ID NO:22 (FIG. 30), or SEQ ID NO:23 (FIG. 31). In other embodiments, the modified Fiber protein may have a nucleic acid sequence of SEQ ID NO:24 (FIG. 32) or SEQ ID NO:25 (FIG. 33).

In another embodiment, a T-cell epitope of a *Plasmodium* circumsporozoite protein may be inserted into an adenovirus core pVII protein at any of the following sites: the C-terminus, before the first Nuclear Localization Signal (NLS) or between the two NLS. Alternatively, a T-cell epitope of a *Plasmodium* circumsporozoite protein may replace a portion of the pVII protein. In some embodiments, the modified pVII protein may have a nucleic acid sequence of SEQ ID NO:26 (FIG. 34), SEQ ID NO:27 (FIG. 35), SEQ ID NO:28 (FIG. 36) or SEQ ID NO:29 (FIG. 37).

In the recombinant adenovirus may express a transgenic protein or recombinant transgenic protein. In some embodiments, the transgenic protein or recombinant transgenic protein is a *Plasmodium* circumsporozoite protein or an antigenic determinant that is encoded by a recombinant adenovirus plasmid vector as described herein, and is expressed by a recombinant adenovirus produced by said recombinant adenovirus plasmid vector after infection of one or more host cells, Thus, in some embodiments, the recombinant adenovirus plasmid vectors comprise a nucleotide sequence encoding a recombinant transgenic protein. In one embodiment, the recombinant transgenic protein may comprise an antigenic determinant of *P. yoelii*, a rodent-specific parasite, wherein the antigenic determinant comprises a *P. yoelii* circumsporozoite (CS) protein gene or an antigenic portion thereof. In another embodiment, the recombinant transgenic protein may comprise an antigenic determinant of *P. falciparum*, a human-specific parasite, wherein the antigenic determinant comprises a *P. falciparum* circumsporozoite gene (CS) protein or an antigenic portion thereof. The *P. falciparum* CS protein has demonstrated prevention of malaria when used as the basis of active immunization in humans against mosquito-borne infection. The antigenic determinant may further comprise an immunogenic epitope, such as a B cell and/or T cell epitope.

In some embodiments, the CS protein is codon-optimized for enhanced expression in a subject. Codon-optimization is based on the required amino acid content, the general optimal codon usage in the subject of interest as well as any aspects that should be avoided to ensure proper expression. Such aspects may be splice donor or acceptor sites, stop codons, polyadenylation (pA) signals, GC- and AT-rich sequences, internal TATA boxes, or any other aspects known in the art. In some embodiments, the DNA sequence of the codon-optimized CS transgene is shown in FIG. 9 (SEQ ID NO:1, *P. yoelii*) and FIG. 10 (SEQ ID NO: 2, *P. falciparum*).

Figure 2:
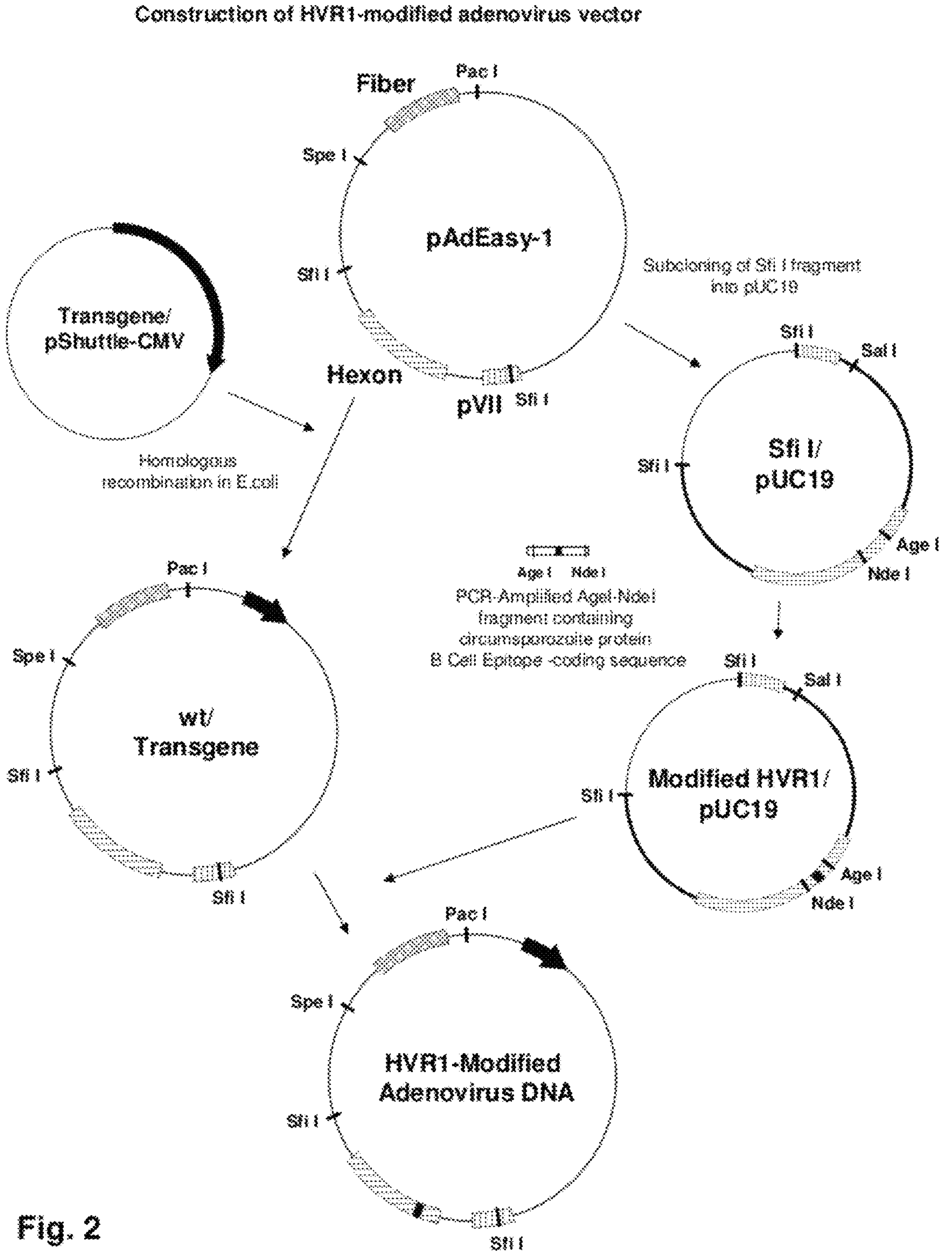
FIG. 2 is a schematic diagram illustrating the construction of the HVR1-Modified Adenovirus DNA of an HVR1-modified recombinant adenovirus plasmid vector.
Figure 4:
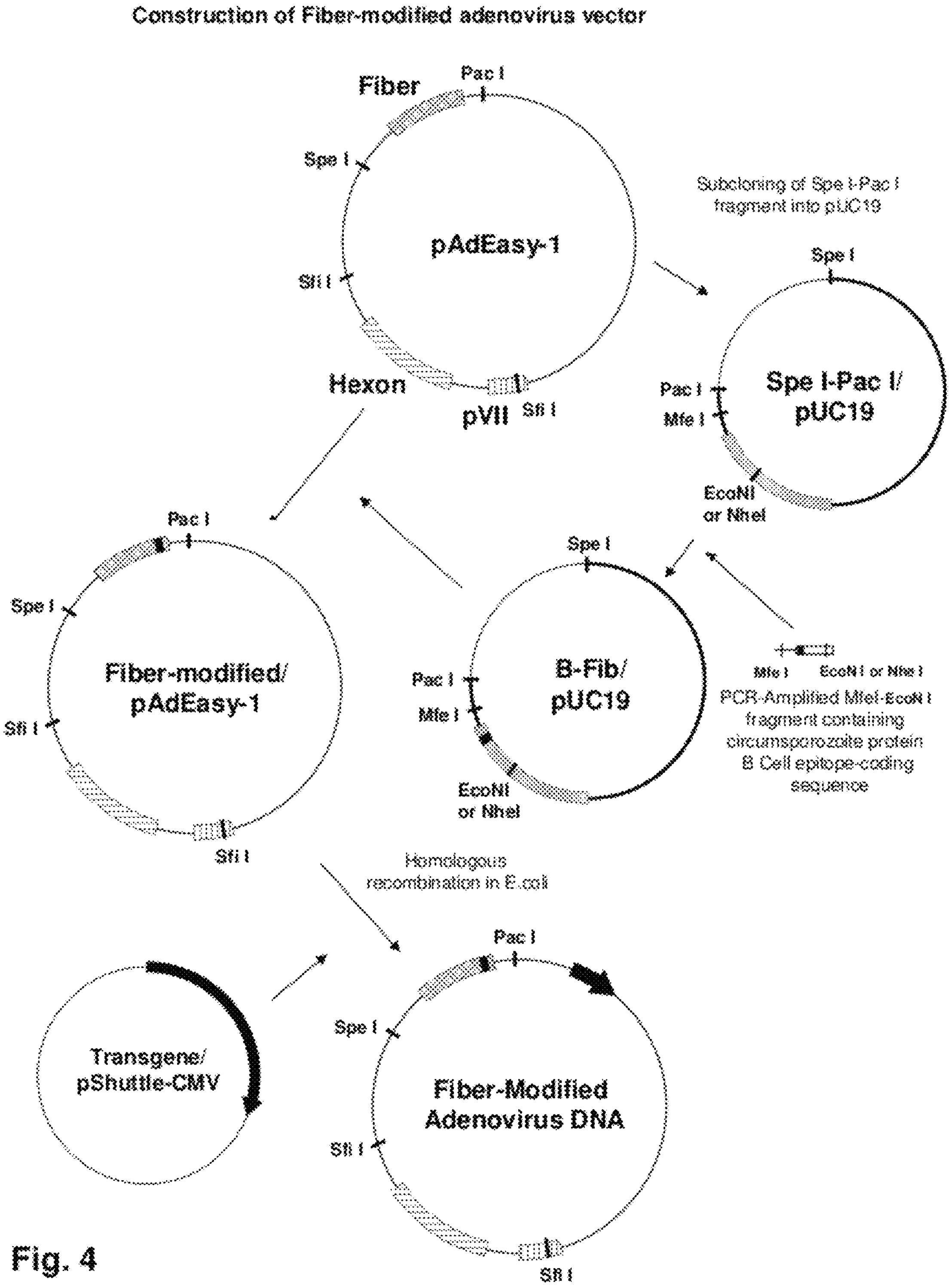
FIG. 4 is a schematic diagram illustrating the construction of the Fiber-Modified Adenovirus DNA of a Fiber-modified recombinant adenovirus plasmid vector.
Figure 5:
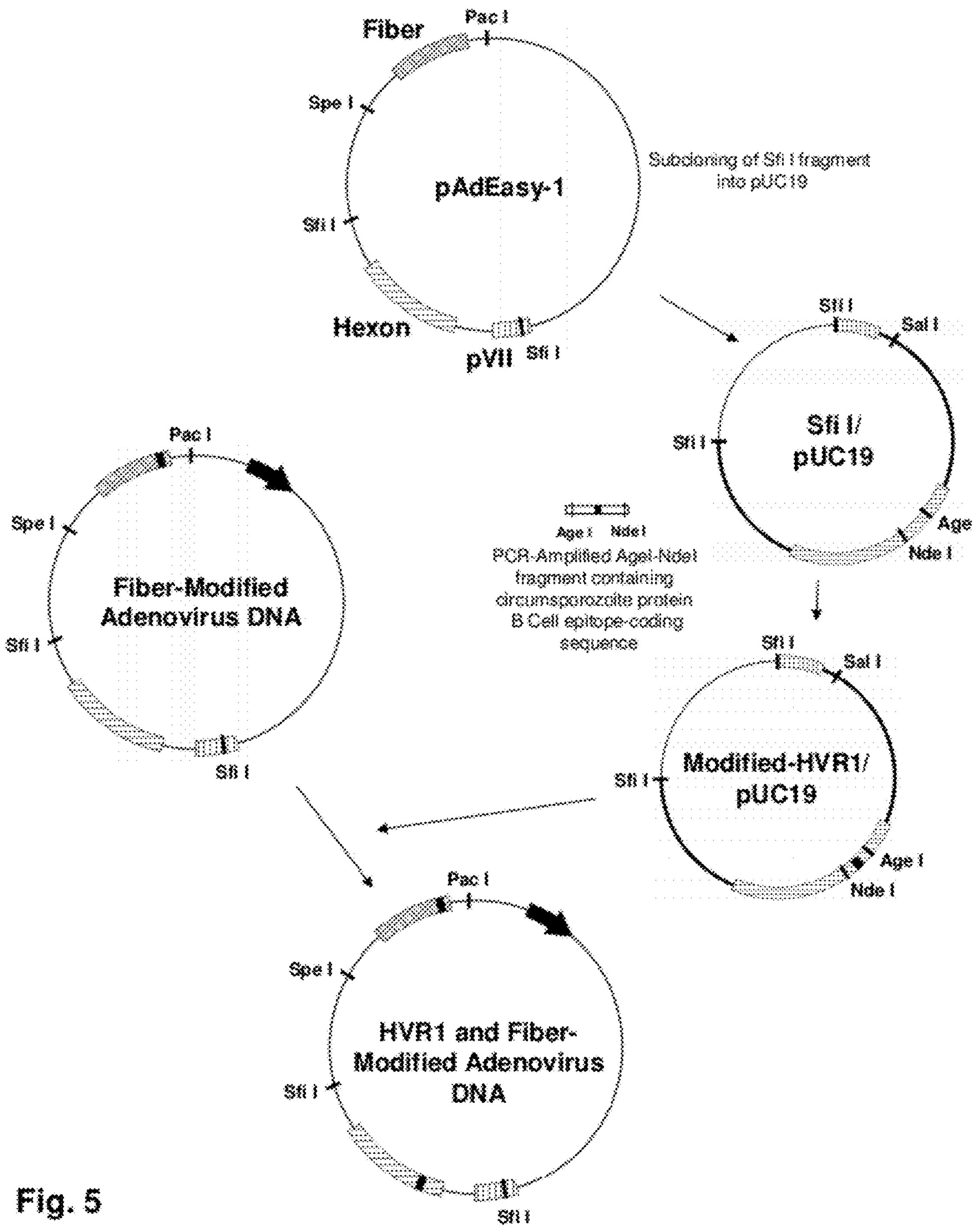
FIG. 5 is a schematic diagram illustrating the construction of the HVR1 and Fiber-Modified Adenovirus DNA of an HVR1 and Fiber-modified recombinant adenovirus plasmid vector.
Figure 6:
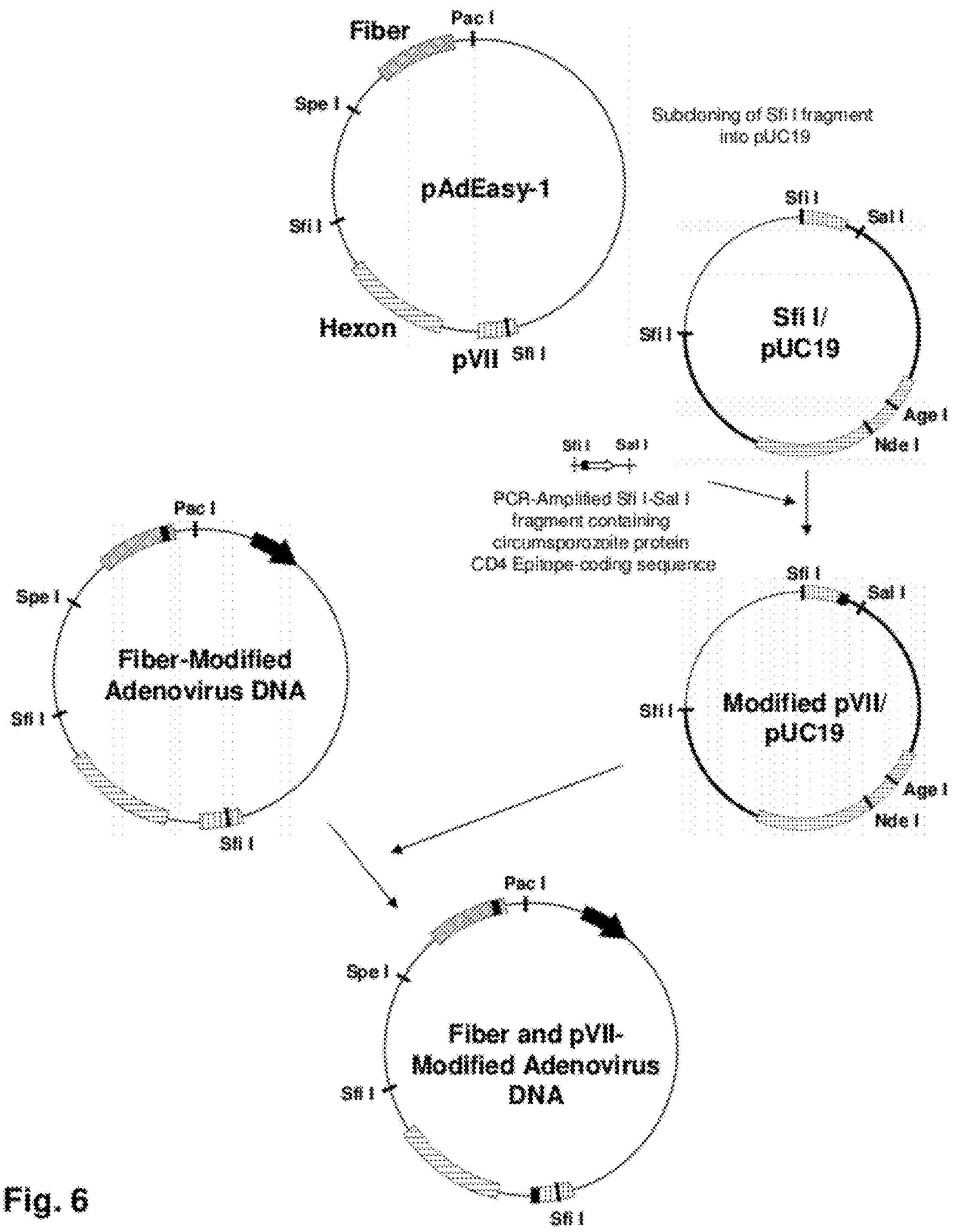
FIG. 6 is a schematic diagram illustrating the construction of the Fiber and pVII-Modified Adenovirus DNA of a Fiber and pVII-modified recombinant adenovirus plasmid vector.
Figure 7:
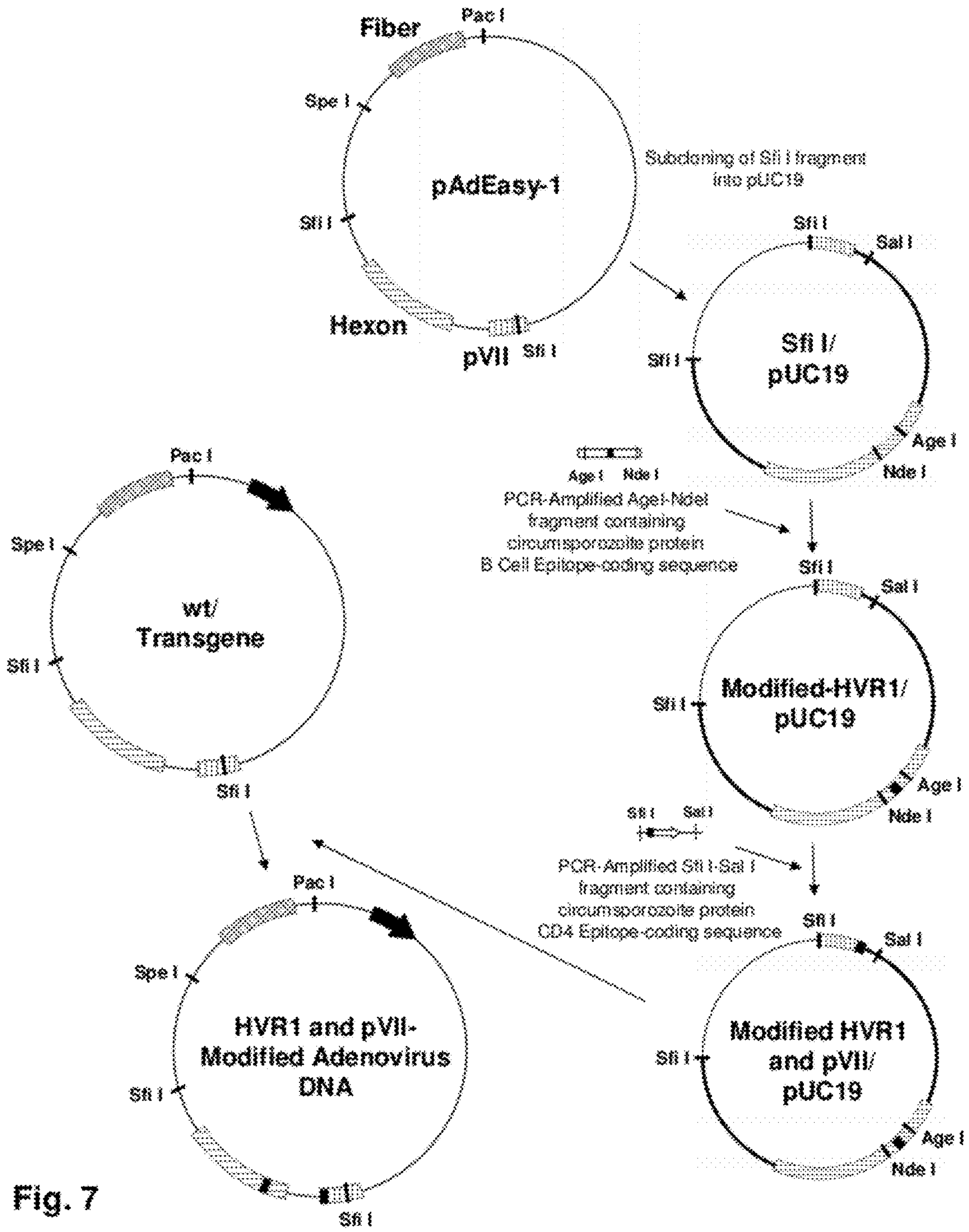
FIG. 7 is a schematic diagram illustrating the construction of the HVR1 and pVII-Modified Adenovirus DNA of an HVR1 and pVII-modified recombinant adenovirus plasmid vector.
Figure 8:
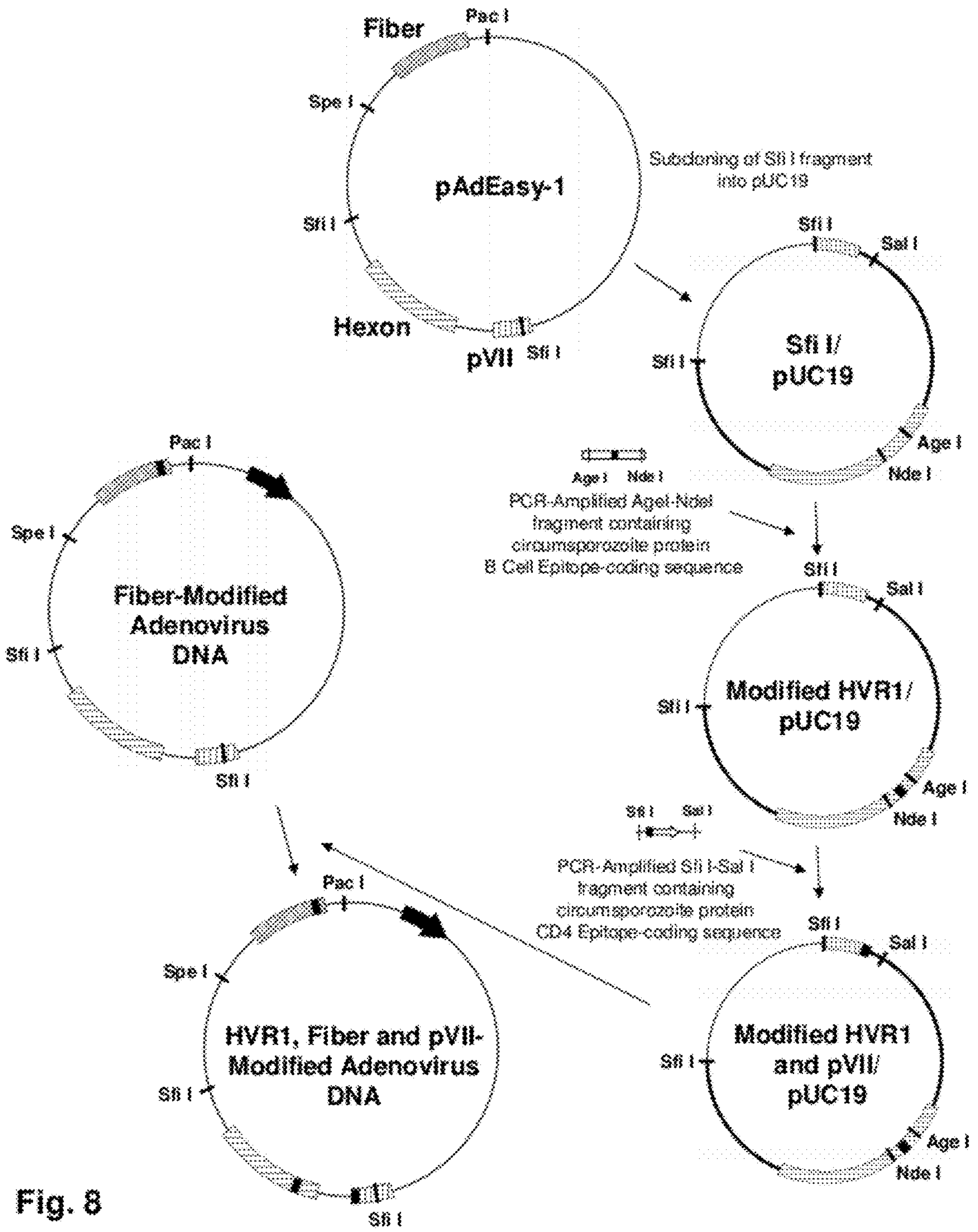
FIG. 8 is a schematic diagram illustrating the construction of the HVR1, Fiber and pVII-Modified Adenovirus DNA of an HVR1, Fiber and pVII-modified recombinant adenovirus plasmid vector.

In some embodiments, the recombinant adenovirus plasmid vector may be one of the following modified *P. falciparum* recombinant adenovirus plasmid vectors: HVR1-modified adenovirus vector (NANP-HVR1/PfCSP) constructed as shown in FIG. 2, using a B cell epitope coding sequence of $(NANP)_n$ (SEQ ID NO:60); Fiber-modified adenovirus vector (NANP-Fib/PfCSP) constructed as shown in FIG. 4, using a B cell epitope coding sequence of $(NANP)_n$ (SEQ ID NO:60); HVR1 and Fiber-modified adenovirus vector (NANP-HVR1/B-Fib/PfCSP) constructed as shown in FIG. 5, using a B cell epitope coding sequence of $(NANP)_n$ (SEQ ID NO:60); HVR1 and pVII-modified adenovirus vector (NANP-HVR1/CD4-pVII/PfCSP) constructed as shown in FIG. 7, using a B cell epitope of $(NANP)_n$ (SEQ ID NO:60) and a CD4 epitope coding sequence of EYLNKIQNSLSTEWSPCSVT (SEQ ID NO:62); Fiber and pVII-modified adenovirus vector (NANP-Fib/CD4-pVII/PfCSP) constructed as shown in FIG. 6, using a B cell epitope of $(NANP)_n$ (SEQ ID NO:60) and a CD4 epitope coding sequence of EYLNKIQNSLSTEWSPCSVT (SEQ ID NO:62); and HVR1, Fiber and pVII-modified adenovirus vector (NANP-HVR1/Fib/CD4-pVII/PfCSP) constructed as shown in FIG. 8, using a B cell epitope of $(NANP)_n$ (SEQ ID NO:60) and a CD4 epitope coding sequence of EYLNKIQNSLSTEWSPCSVT (SEQ ID NO:62).

In other embodiments, the recombinant adenovirus plasmid vector may be one of the following modified *P. yoelii* recombinant adenovirus plasmid vectors: HVR1-modified adenovirus vector (QGPGAP-HVR1/PyCS) constructed as shown in FIG. 2, using a B cell epitope coding sequence of $(QGPGAP)_n$ (SEQ ID NO:59); Fiber-modified adenovirus vector (QGPGAP-Fib/PyCS) constructed as shown in FIG. 4, using a B cell epitope coding sequence of $(QGPGAP)_n$ (SEQ ID NO:59); HVR1 and Fiber-modified adenovirus vector (QGPGAP-HVR1/B-Fib/PyCS) constructed as shown in FIG. 5, using a B cell epitope coding sequence of $(QGPGAP)_n$ (SEQ ID NO:59); HVR1 and pVII-modified adenovirus vector (QGPGAP-HVR1/CD4-pVII/PyCS) constructed as shown in FIG. 7, using a B cell epitope of $(QGPGAP)_n$ (SEQ ID NO:59) and a CD4 epitope coding sequence of YNRNIVNRLLGDALNGKPEEK, (SEQ ID NO:61); Fiber and pVII-modified adenovirus vector (QGPGAP-Fib/CD4-pVII/PyCS) constructed as shown in FIG. 6, using a B cell epitope of $(QGPGAP)_n$ (SEQ ID NO:59) and a CD4 epitope coding sequence of YNRNIVNRLLGDALNGKPEEK, (SEQ ID NO:61); and HVR1, Fiber and pVII-modified adenovirus vector (QGPGAP-HVR1/Fib/CD4-pVII/PyCS) constructed as shown in FIG. 8, using a B cell epitope of $(QGPGAP)_n$ (SEQ ID NO:59) and a CD4 epitope coding sequence of YNRNIVNRLLGDALNGKPEEK, (SEQ ID NO:61).

In other embodiments, a recombinant adenovirus may be produced by one of the following modified *P. falciparum* or *P. yoelii* recombinant adenovirus plasmid vectors: NANP-HVR1/PfCSP or QGPGAP-HVR1/PyCS (FIG. 2), NANP-Fib/PfCSP or QGPGAP-Fib/PyCS (FIG. 4), NANP-HVR1/B-Fib/PfCSP or QGPGAP-HVR1/B-Fib/PyCS (FIG. 5), NANP-HVR1/CD4-pVII/PfCSP or QGPGAP-HVR1/CD4-pVII/PyCS (FIG. 7), NANP-Fib/CD4-pVII/PfCSP or QGPGAP-Fib/CD4-pVII/PyCS (FIG. 6), NANP-HVR1/Fib/CD4-pVII/PfCSP or QGPGAP-HVR1/Fib/CD4-pVII/PyCS (FIG. 8). The recombinant adenovirus may be produced in accordance with the methods described herein for producing a recombinant adenovirus plasmid vector with the ability to express a recombinant transgenic protein (e.g., *Plasmodium* CS protein) in mammalian host cells.

Purification of a recombinant adenovirus may be performed by using known virus purification methods. For example, purification of 0.5 to 1.0 mL of a stock virus obtained by the method of producing a recombinant adenovirus protein by inoculating insect cells ($1\times10^7$ cells/10 cm dish), such as AD293 cells. The culture supernatant is then collected several days after the infection, and a virus pellet obtained by centrifugation is suspended in a buffer, such as PBS (Phosphate Buffered Saline). The resulting suspension is subjected to a sucrose gradient of 10 to 60% and then centrifuged (25,000 rpm for 60 minutes at 4° C.) to collect a virus band. The collected virus is further suspended in PBS, subsequently centrifuged under the same conditions as above, and the resulting purified recombinant virus pellet is stored at 4° C. in a buffer, such as PBS.

Another embodiment is directed to a pharmaceutical composition essentially comprising at least one active ingredient. In one embodiment, an active ingredient of the pharmaceutical composition may comprise a recombinant adenovirus, which may be obtained by the genetic engineering techniques described herein. More specifically, the active ingredient may be a recombinant adenovirus comprising modified capsid and/or core proteins, wherein a portion of a Hexon hypervariable region (HVR), a portion of Fiber protein, a portion of pVII protein or a combination thereof is replaced by at least one immunogenic epitope of *Plasmodium* circumsporozoite protein. Alternatively, one or more B-cell and/or T cell epitope of a *Plasmodium* circumsporozoite protein may be inserted in the Fiber protein, Hexon HVR or pVII protein. The recombinant adenovirus plasmid vector further comprises a transgenic protein or recombinant transgenic protein that is expressed by the recombinant adenovirus after infecting one or more host cells. The transgenic protein or recombinant transgenic protein may be a *Plasmodium* circumsporozoite protein or a malaria antigen of a *Plasmodium* circumsporozoite protein, wherein the malaria antigen comprises at least one immunogenic epitope (e.g., a B cell or T cell epitope) of *Plasmodium* circumsporozoite protein.

In some embodiments, the active ingredient of the pharmaceutical composition is a recombinant adenovirus derived from a recombinant adenovirus plasmid vector, wherein the recombinant adenovirus plasmid vector is one of the following modified *P. falciparum* or *P. yoelii* recombinant adenovirus plasmid vectors: NANP-HVR1/PfCSP or QGPGAP-HVR1/PyCS (FIG. 2), NANP-Fib/PfCSP or QGPGAP-Fib/PyCS (FIG. 4), NANP-HVR1/B-Fib/PfCSP or QGPGAP-HVR1/B-Fib/PyCS (FIG. 5), NANP-HVR1/CD4-pVII/PfCSP or QGPGAP-HVR1/CD4-pVII/PyCS (FIG. 7), NANP-Fib/CD4-pVII/PfCSP or QGPGAP-Fib/CD4-pVII/PyCS (FIG. 6), NANP-HVR1/Fib/CD4-pVII/PfCSP or QGPGAP-HVR1/Fib/CD4-pVII/PyCS (FIG. 8). These recombinant adenovirus plasmid vectors are capable of producing recombinant adenoviruses when transfected into cells (e.g., AD293 cells) and wherein the recombinant transgenic protein may be expressed in mammalian cells, including human cells.

When given to a subject, a pharmaceutical composition having an active ingredient is a recombinant adenovirus as described herein enhances malaria infection-preventing effects against a malaria infectious antigen and reduces the infectivity titer, as described further in the Examples below. Thus, the recombinant adenovirus may be used for the treatment of malaria infections associated with infection of target cells and tissues. Examples of target cells affected by such malaria infection include blood cells, hepatic cells, renal cells, brain cells, lung cells, epithelial cells, and muscular cells. Examples of tissues comprising such cells include the lung, liver, kidney, brain, arteries and veins, the stomach, intestines, urethra, skin, and muscle.

In some aspects, the pharmaceutical composition may enhance malaria infection-preventing effects against infectious antigens, for example, malaria antigens such as sporozoite surface antigens (Circumsporozoite Protein (CSP) and Thrombospondin Related Adhesive Protein (TRAP)) of malaria parasites, merozoite surface membrane protein (MSPI), malaria S antigen secreted from erythrocytes infected with malaria, and *P. falciparum* Erythrocyte Membrane Protein-1 (PfEMPI) protein present in the knobs of erythrocytes infected with malaria. The pharmaceutical composition may enhance malaria infection-preventing effects against a *Plasmodium* parasite, selected from any known *Plasmodium* (P) species, for example, *P. falciparum, P. malariae, P. ovale, P. vivax, P. knowlesi, P. berghei, P. chabaudi* and *P. yoelii*, by reducing the infectivity titer. When administered to a subject, a reduction of the infectivity titer by the pharmaceutical composition may result in an increased survival, disease-free survival, or infection-free survival period and survival, disease-free survival, or infection-free survival rate when compared to subjects not administered the pharmaceutical composition. Thus, in some aspects, the pharmaceutical composition is useful as a preventive or therapeutic agent for malaria infections caused by pathogens such as *Plasmodium*. In further aspects, the pharmaceutical composition is useful as a preventive or therapeutic agent for complications resulting from a malaria infection caused by pathogens such as *Plasmodium*.

The infection-preventing effect of the recombinant adenovirus of the present invention in a subject can be provided, for example, by administering the pharmaceutical composition containing the capsid-modified recombinant adenovirus of the present invention and additives for pharmaceutical administration to vertebrates, particularly mammals, including humans, by intramuscular (i.m.), subcutaneous (s.c.), intracutaneous (i.c.), intradermal (i.d.), intraperitoneal (i.p.), nasal, or respiratory route, and then immunizing the vertebrates with the pharmaceutical composition containing the recombinant adenovirus described herein as an active ingredient several times. To evaluate the infection-preventing effect, the survival rate, disease-free survival, or infection-free survival of subjects immunized with the pharmaceutical composition several times followed by infection by a target pathogen (such as a selected *Plasmodium* species) may be compared with the survival rate, disease-free survival, or infection-free survival of subjects not given the pharmaceutical composition.

In some embodiments, the pharmaceutical composition may additionally comprise a pharmaceutically effective amount of capsid and/or core-modified recombinant adenovirus as described herein and a pharmaceutically acceptable carrier, which is described further below.

Another embodiment is directed to a vaccine composition essentially comprising at least one active ingredient. In one embodiment, an active ingredient of the vaccine composition may comprise a recombinant adenovirus, derived from a recombinant adenovirus plasmid vector as described herein. More specifically, the active ingredient may be a recombinant adenovirus comprising modified capsid or core proteins, wherein a portion of a Hexon hypervariable region (HVR), a portion of Fiber protein, a portion of pVII protein or a combination thereof are replaced by at least one immunogenic epitope of *Plasmodium* circumsporozoite protein. Alternatively, at least one immunogenic epitope of a *Plasmodium* circumsporozoite protein may be inserted in the pVII protein, Fiber protein or Hexon HVR, or a combination thereof. In some embodiments, the active ingredient of the vaccine composition may be derived from a recombinant adenovirus plasmid vector illustrated in FIGS. 2-8, for example, NANP-HVR1/PfCSP or QGPGAP-HVR1/PyCS (FIG. 2), NANP-Fib/PfCSP or QGPGAP-Fib/PyCS (FIG. 4), NANP-HVR1/B-Fib/PfCSP or QGPGAP-HVR1/B-Fib/PyCS (FIG. 5), NANP-HVR1/CD4-pVII/PfCSP or QGPGAP-HVR1/CD4-pVII/PyCS (FIG. 7), NANP-Fib/CD4-pVII/PfCSP or QGPGAP-Fib/CD4-pVII/PyCS (FIG. 6), NANP-HVR1/Fib/CD4-pVII/PfCSP or QGPGAP-HVR1/Fib/CD4-pVII/PyCS (FIG. 8).

In some aspects, the vaccine composition, when administered to a subject, first comprises a recombinant adenovirus having one or more antigenic portions of a *Plasmodium* CS protein (i.e., a B cell epitope, T cell epitope or both) inserted into or replacing at least a part of a capsid or core protein. The vaccine composition may then express a recombinant transgenic protein, wherein the recombinant transgenic protein is a *Plasmodium* CS protein comprising a B cell epitope, T cell epitope or both. The antigenic portions of the *Plasmodium* CS protein are found in the recombinant transgenic protein and the modified capsid or core proteins promote or enhance acquired humoral immunity, cellular immunity, or both as described in the Examples below. Thus, in some aspects, the recombinant adenovirus as described herein is useful as a vaccine to promote or enhance humoral immunity, cellular immunity, or both.

In further embodiments, the vaccine composition may enhance infection-preventing effects against infectious antigens, for example, malaria antigens such as sporozoite surface antigens (CSP and TRAP) of malaria parasites, merozoite surface membrane protein MSPI, malaria S antigen secreted from erythrocytes infected with malaria, PfEMPI protein present in the knobs of erythrocytes infected with malaria, Serine-Rich Antigen (SERA) protein, Tyrosine-Rich Acidic Matrix Protein (TRAMP), and Apical Membrane Antigen-1 (AMAI) protein. Further, a reduced infectivity titer (e.g., the viral infectivity titer) resulting from administration of a vaccine composition described herein may result in an increased survival, disease-free survival or infection-free survival period and survival, disease-free survival or infection-free survival rate when compared to subjects not administered the vaccine composition. Thus, in some aspects, the vaccine composition is also useful as a preventive or therapeutic agent for malaria infections caused by pathogens such as *Plasmodium*. In further aspects, the vaccine composition is also useful as a preventive or therapeutic agent for complications resulting from a malaria infection by pathogens such as *Plasmodium*.

A vaccine composition as described herein may comprise a therapeutically effective amount of a recombinant adenovirus as described herein, and further comprising a pharmaceutically acceptable carrier according to a standard method. Examples of acceptable carriers include physiologically acceptable solutions, such as sterile saline and sterile buffered saline.

In some embodiments, the vaccine or pharmaceutical composition may be used in combination with a pharmaceutically effective amount of an adjuvant to enhance the anti-malaria effects. Any immunologic adjuvant that may stimulate the immune system and increase the response to a vaccine, without having any specific antigenic effect itself may be used as the adjuvant. Many immunologic adjuvants mimic evolutionarily conserved molecules known as pathogen-associated molecular patterns (PAMPs) and are recognized by a set of immune receptors known as Toll-like Receptors (TLRs). Examples of adjuvants that may be used in accordance with the embodiments described herein include Freund's complete adjuvant, Freund's incomplete adjuvant, double stranded RNA (a TLR3 ligand), LPS, LPS analogs such as monophosphoryl lipid A (MPL) (a TLR4 ligand), flagellin (a TLR5 ligand), lipoproteins, lipopeptides, single stranded RNA, single stranded DNA, imidazoquinolin analogs (TLR7 and TLR8 ligands), CpG DNA (a TLR9 ligand), Ribi's adjuvant (monophosphoryl-lipid A/trehalose dicorynoycolate), glycolipids (α-GalCer analogs), unmethylated CpG islands, oil emulsion, liposomes, virosomes, saponins (active fractions of saponin such as QS21), muramyl dipeptide, alum, aluminum hydroxide, squalene, BCG, cytokines such as GM-CSF and IL-12, chemokines such as MIP 1-α and RANTES, N-acetylmuramine-L-alanyl-D-isoglutamine (MDP), thymosin αI and MF59. The amount of adjuvant used can be suitably selected according to the degree of symptoms, such as softening of the skin, pain, erythema, fever, headache, and muscular pain, which might be expressed as part of the immune response in humans or animals after the administration of this type of vaccine.

In some embodiments, the vaccine or pharmaceutical composition described herein may be used in combination with other known pharmaceutical products, such as immune response-promoting peptides and antibacterial agents (synthetic antibacterial agents). The vaccine or pharmaceutical composition may further comprise other drugs and additives. Examples of drugs or additives that may be used in conjunction with a vaccine or pharmaceutical composition described herein include drugs that aid intracellular uptake of the recombinant adenovirus or recombinant transgenic protein of the present invention, liposome and other drugs and/or additives that facilitate transfection, (e.g., fluorocarbon emulsifiers, cochleates, tubules, golden particles, biodegradable microspheres, and cationic polymers).

In some embodiments, the amount of the active ingredient contained in the vaccine or pharmaceutical composition described herein may be selected from a wide range of concentrations, Virus Particle Unit (VPU), Plaque Forming Unit (PFU), weight to volume percent (w/v %) or other quantitative measure of active ingredient amount, as long as it is a therapeutically or pharmaceutically effective amount. The dosage of the vaccine or pharmaceutical composition may be appropriately selected from a wide range according to the desired therapeutic effect, the administration method (administration route), the therapeutic period, the patient's age, gender, and other conditions, etc.

In some aspects, when a recombinant adenovirus is administered to a human subject as an active ingredient of the vaccine or pharmaceutical composition, the dosage of the recombinant adenovirus may be administered in an amount approximately corresponding to $10^2$ to $10^{14}$ PFU, preferably $10^5$ to $10^{12}$ PFU, and more preferably $10^6$ to $10^{10}$ PFU per patient, calculated as the PFU of the recombinant virus.

In further aspects, when a recombinant adenovirus is administered to a subject as an active ingredient of the vaccine or pharmaceutical composition, the dosage may be selected from a wide range in terms of the amount of expressible DNA introduced into the vaccine host or the amount of transcribed RNA. The dosage also depends on the strength of the transcription and translation promoters used in any transfer vectors used.

In some embodiments, the vaccine composition or pharmaceutical composition described herein may be administered by directly injecting a recombinant adenovirus suspension prepared by suspending the recombinant adenovirus in PBS (phosphate buffered saline) or saline into a local site (e.g., into the lung tissue, liver, muscle or brain), by nasal or respiratory inhalation, or by intravascular (i.v.) (e.g., intra-arterial, intravenous, and portal venous), subcutaneous (s.c.), intracutaneous (i.c.), intradermal (i.d.), or intraperitoneal (i.p.) administration. The vaccine or pharmaceutical composition of the present invention may be administered more than once. More specifically, after the initial administration, one or more additional vaccinations may be given as a booster. One or more booster administrations can enhance the desired effect. After the administration of the vaccine or pharmaceutical composition, booster immunization with a pharmaceutical composition containing the recombinant adenovirus as described herein may be performed.

In further embodiments, use of various other adjuvants, drugs or additives with the vaccine of the invention, as discussed above, may enhance the therapeutic effect achieved by the administration of the vaccine or pharmaceutical composition. The pharmaceutically acceptable carrier may contain a trace amount of additives, such as substances that enhance the isotonicity and chemical stability. Such additives should be non-toxic to a human or other mammalian subject in the dosage and concentration used, and examples thereof include buffers such as phosphoric acid, citric acid, succinic acid, acetic acid, and other organic acids, and salts thereof; antioxidants such as ascorbic acid; low molecular weight (e.g., less than about 10 residues) polypeptides (e.g., polyarginine and tripeptide) proteins (e.g., serum albumin, gelatin, and immunoglobulin); amino acids (e.g., glycine, glutamic acid, aspartic acid, and arginine); monosaccharides, disaccharides, and other carbohydrates (e.g., cellulose and derivatives thereof, glucose, mannose, and dextrin), chelating agents (e.g., EDTA); sugar alcohols (e.g., mannitol and sorbitol); counterions (e.g., sodium); nonionic surfactants (e.g., polysorbate and poloxamer); and PEG.

The vaccine or pharmaceutical composition containing a recombinant adenovirus described herein may be stored as an aqueous solution or a lyophilized product in a unit or multiple dose container such as a sealed ampoule or a vial. Another embodiment further provides a method of preventing malaria infection, or a method of treating malaria comprising administering an effective amount of the recombinant adenoviral vaccine, formulation, or pharmaceutical composition.

The present invention further provides a method of immunostimulation comprising administering an effective amount of a recombinant adenoviral vaccine composition, formulation, pharmaceutical composition or a combination thereof to a subject. Subjects may include humans, animals (such as mammals, birds, reptiles, fish, and amphibians), or any other subjects that may become infected with a malaria parasite. Malaria parasites may include a *Plasmodium* parasite, selected from any of known *Plasmodium* (P) species, for example, *P. falciparum, P. malariae, P. ovale, P. vivax, P. knowlesi, P. berghei, P. chabaudi* and *P. yoelii.*

In some embodiments, a recombinant adenovirus as described herein may be formed alone or may be together with a pharmaceutically acceptable carrier into a vaccine composition, formulation, or pharmaceutical composition, and administered to the subject. The administration route may be, for example, any administration route mentioned above. The pharmaceutically acceptable carrier for use in the present invention can be suitably selected from carriers commonly used in this technical field, according to the form of the pharmaceutical composition to be produced. For example, when the pharmacological composition is formed into an aqueous solution, purified water (sterile water) or a physiological buffer solution can be used as the carrier. When the pharmaceutical composition is formed into other appropriate solutions, organic esters capable of being injected, such as glycol, glycerol and olive oil may be used as the carrier. The composition may contain stabilizers, excipients and other commonly used substances in this technical field, and particularly in the field of vaccine formulations.

In further embodiments, the amount of recombinant adenovirus used in a vaccine composition, formulation, or pharmaceutical composition may be suitably selected from a wide range of concentrations, VPU, PFU, weight to volume percent (w/v %) or other quantitative measure of active ingredient amount. In some aspects, a suitable range of recombinant adenovirus in the composition is preferably about 0.0002 to about 0.2 (w/v %), and more preferably 0.001 to 0.1 (w/v %). The method of administration of a recombinant adenovirus vaccine composition, formulation, or pharmaceutical composition according to some embodiments may be suitably selected according to the dosage form, the patient's age, gender and other conditions such as the severity of the disease. A suitable dosage form is a form for parenteral administration, such as injections, drops, nasal drops, and inhalants. When the composition is formed into an injection or drops, the injection can be intravenously administered and mixed with a replacement fluid such as a glucose solution or an amino acid solution as appropriate, or can be administered intramuscularly (i.m.), intracutaneously (i.c.), subcutaneously (s.c.) intradermally (i.d.), or intraperitoneally (i.p.).

In other embodiments, the daily dosage of a recombinant adenovirus vaccine composition, formulation, or pharmaceutical composition may vary depending on the subject's condition, body weight, age, gender, etc. In some aspects, the dosage of a recombinant adenovirus is administered in an amount of approximately 0.001 to 100 mg per kg of body weight per day. The vaccine, formulation, or composition of the invention may be administered in one or more administrations per day.

In further embodiments, when a recombinant adenovirus is administered to a human subject as an active ingredient of the vaccine composition, formulation or pharmaceutical composition, the dosage of the recombinant adenovirus is administered in an amount approximately corresponding to $10^2$ to $10^{14}$ PFU, preferably $10^5$ to $10^{12}$ PFU, and more preferably $10^6$ to $10^{10}$ PFU per patient, calculated as the PFU of the recombinant adenovirus particle. The vaccine composition of the present invention should be administered according to Good Medical Practice, considering the clinical condition (for example, the condition to be prevented or treated) of each patient, the delivery site of the vaccine composition containing the recombinant adenovirus, the target tissue, the administration method, the dosage regimen, and other factors known to those skilled in the art. Therefore, the proper dosage of the vaccine composition herein is determined in consideration of the above.

Yet another embodiment of the disclosure relates to a method of treating or preventing a malaria infection in a subject, the method comprising administering an immunologic or therapeutic amount of a malaria vaccine composition comprising a recombinant adenovirus. The recombinant adenovirus of the malaria vaccine may comprise an antigenic determinant of a *Plasmodium* parasite, and may further comprise one or more modified capsid or core proteins. An immunologic, pharmacologic or therapeutic amount may be any suitable amount wherein a potent immune response is generated against one or more antigenic portions of the (CS) protein (i.e., the transgene, B cell epitope, or CD4+ T cell epitope) such that malarial infection is prevented or reduced in severity.

When a subject is first exposed or "primed" to an adenovirus vector, the immune system produces neutralizing antibodies against that specific vector. The immune response to the adenovirus is generally directed against the capsid proteins. Therefore, subsequent exposure to the same adenovirus vector, or "boosts," can reduce the efficacy of transgene expression. Therefore, in some embodiments, the method of treating or preventing a malaria infection described above may comprise a priming step using a first recombinant adenovirus vector followed by one or more boosting steps using one or more different recombinant adenovirus vectors. This method may be used in subjects that have not yet been exposed to a wild-type adenovirus, or in a subject that has been previously exposed to a wild-type adenovirus vector, wherein the priming step recombinant adenovirus vector is used to circumvent existing adenovirus immunity. Further embodiments and examples are described below.

Adenovirus as a Vector

Adenoviruses are non-enveloped DNA viruses comprising a set of viral capsid proteins (described below) and a viral genome, that have been widely used to deliver one or more therapeutic or antigenic transgene to a variety of cells in vitro and in vivo. Many adenovirus serotypes exist. Of the known adenovirus serotypes, serotype 5 (Ad5) is preferably used as a vector for foreign gene transduction because of its strong infectivity in vivo (Abbink et al. 2007). Expression of the antigenic transgene may be controlled by any promoter or enhancer element known in the art. Promoters which may be used to control gene expression include, but are not limited to, cytomegalovirus immediate early promoter (CMV), simian virus 40 (SV40) early promoter, cellular polypeptide chain elongation factor 1 alpha (EF1) promoter, Rous sarcoma virus (RSV) promoter, and tetracycline-regulated (TR) promoter. A polyadenylation (pA) signal after the coding sequence may also be used for efficient transcription and translation. The recombinant adenovirus vector described herein may be replication-defective, having a deletion at least in the E1 region of the adenoviral genome, since the E1 region is required for replication, transcription, translation and packaging processes. In some aspects, the E2, E3 and/or E4 regions may also be deleted. In further aspects, a Kozak consensus sequence may be used for a more efficient translation (Kozak 1987).

The adenovirus (Ad) system is an attractive vector for the development of recombinant vaccines for a number of reasons. One reason is that recombinant adenoviral vectors infect most mammalian cell types (both replicative and non-replicative), including, but not limited to, mouse and human cell types. Thus, the same vector may be used successfully in mouse models and human clinical trials alike. Another reason is that any transferred genetic information remains epichromosomal, avoiding insertional mutagenesis and alteration of the cellular genotype (Crystal 1995). Yet another reason is that the transgene remains unaltered after successive rounds of viral replication. Other advantages of using adenovirus include that recombinant adenovirus: 1) has a high virion stability, 2) is well tolerated, 3) may be grown at high titer, 4) can accommodate large transgenes, 5) has a genome that has been extensively studied for many years such that the complete DNA sequence of several serotypes is known, facilitating the manipulation of the Ad genome by recombinant DNA techniques (Graham and Prevec 1992).

In one embodiment, the adenovirus vaccine platform is used as a viral vector for development of a vaccine that targets a pre-erythrocytic malaria parasite, and provides protection from malaria infection. Among known recombinant viral vectors (Rodrigues et al. 1997, Bruña-Romero et al. 2001, Anderson et al. 2004, Tao et al. 2005), adenovirus has been shown to be a suitable viral vector for a malaria vaccine because it can induce a strong protective cellular immune response to pre-erythrocytic malaria parasites (Rodrigues et al. 1997). The malaria parasite may be any one of the *Plasmodium* family. In some embodiments, the targeted parasite may be *P. yoelii* or *P. falciparum*.

Adenovirus Vectors Expressing PyCS as a Transgene Elicits a Malaria-Specific CD8+ T Cell Response Adenovirus is an attractive vector for inducing a significant CD8+ T cell-mediated protective immunity against malaria (Rodrigues et al. 1997, Rodrigues et al. 1998). The immunogenicity of a recombinant adenovirus expressing the *P. yoelii* (a rodent malaria parasite) CS protein, AdPyCS, was determined using a rodent malaria model. The inoculation of mice with AdPyCS induces complete immunity in a significant proportion of mice, preventing the occurrence of parasitemia (Rodrigues et al. 1997). This protective effect is primarily mediated by CD8+ T cells, as evidenced by depletion of the T cell population and is corroborated by the fact that AdPyCS was unable to induce high titers of antibody response against malaria parasites.

To quantitatively measure the infectivity of capsid-modified adenovirus, the shuttle vector may contain a GFP expression cassette and cloning sites for a transgene. The resulting shuttle vector (GFP/pShuttle-CMV) has dual pCMV promoters and SV40pAs for a transgene and GFP from pmaxGFP (Amaxa, Germany). The optimized PyCS fragment was inserted into KpnI and HindIII sites of GFP/pShuttle-CMV.

The immunogenicity of Ad(PyCS+GFP) was determined by measuring the magnitude of the CS-specific CD8+ T cell response and the level of protective immunity against the plasmodial liver stages. Administration of Ad(PyCS+GFP) via different routes, at an optimal dose, $10^{10}$ viral particle (v.p.) elicited the same pattern of anti-malarial protective responses that AdPyCS was shown to elicit, with the s.c. and i.m. routes inducing the strongest response resulted in the highest degree of liver stage inhibition in mice challenged with live *P. yoelii* sporozoites. This illustrates that as a vaccine, Ad(PyCS+GFP) behaves equivalently to AdPyCS (Rodrigues et al 1997), and is a potentially useful tool in determining the in vivo tropism of AdPyCS.

Adenovirus Capsid and Core Proteins

The studies above confirm that recombinant adenoviral vectors expressing a CS protein elicit a strong cellular immune response by CD8+ T cells, but no appreciable humoral response. Therefore, because the humoral response to wild-type adenovirus can often be attributed to capsid proteins, recombinant adenoviral vectors with modified capsid and core proteins were constructed to 1) enhance humoral immunity via B cell activation, 2) enhance humoral immunity via T helper cell activation, and 3) circumvent existing adenoviral immunity.

Adenovirus is a non-enveloped naked double stranded DNA virus with an icosahedral shape, having 20 faces of equilateral triangles. The adenovirus capsid consists of 252 capsomers, of which 240 are Hexon trimers and 12 are penton pentamers. A Fiber protein, which projects from each penton base, mediates attachment to host cells by interaction with the cellular receptor. A secondary interaction occurs between the RGD (Asp-Arg-Gly) motif in the penton base with αvβ3, αvβ5 and similar integrins, facilitating subsequent internalization of adenovirus into the cell (Mathias et al. 1994, Wickham et al. 1993). Most of the adenovirus use the coxsackie-adenovirus receptor, CAR, as a cellular receptor (Bergelson et al. 1997). In addition, MHC class I molecules, VCAM, and heparan sulfate, are shown to mediate attachment and entry of Ad5 (Chu et al. 2001, Hong et al. 1997). Following entry via endocytosis, the Ad5 rapidly escapes from endocytic compartments into the cytosol (Meier and Greber 2003, Leopold and Crystal 2007). The virion then translocates to the nucleus using microtubules. The Fiber protein is shed as the earliest capsid protein in the process (Nakano et al. 2000, Hong et al 2003). Adenoviruses of different serotypes demonstrate different trafficking patterns (Miyazawa et al. 1999, Miyazawa et al. 2001). Changing or modifying the Fiber protein can impact trafficking, which may be particularly important with regard to antigen processing and presentation, following infection of antigen presenting cells (APC).

The adenovirus Fiber is a trimer divided into Fiber tail, shaft and knob domains (Henry et al. 1994, Rux and Burnett 2004, Chroboczek et al. 1995). The three dimensional structure of the knob domain is known, and together with mutagenesis studies, these studies allow the areas involved in CAR interaction and trimerization to be visualized (Kirby et al. 1999, Xia et al. 1995). The Fiber shaft projects from the virion and the Fiber knob contains the Coxsackie and Adenovirus Receptor (CAR) interaction domain (Roelvink et al. 1999, Bewley et al. 1999). The CAR-binding site of the Fiber knob consists primarily of residues from the AB loop and CD loop and extends secondarily to the FG and HI loop and the B, E and F β sheets (Roelvink et al. 1999, Bewley et al. 1999). The HI loop has been the best studied insertion site on the Fiber knob (Worgall et al. 2004, Mizuguchi and Hayakawa 2004, Koizumi et al. 2003, Belousova et al. 2002, Noureddini and Curiel 2005, Nicklin et al. 2001), and incorporation of an epitope into the HI loop (residue 543 and 544) resulted in potent anti-epitope immunity (Krause et al. 2006). Therefore, an immunodominant CS-derived B cell epitope was initially inserted into the HI loop of the Fiber protein.

Hexon is the most abundant protein of the adenovirus capsid with 720 copies per virion. In the mature virus, Hexon exists as homotrimeric capsomeres which make up the facets of the icosahedral virion (Rux and Burnett 2004). The crystal structures of adenovirus serotypes 2 and 5 (Ad2 and Ad5) Hexons have been solved, revealing a complex molecular architecture (Athapilly et al. 1994, Roberts et al. 1986, Rux and Burnett 2000). The base of each monomeric subunit consists of two beta-barrel motifs that are present in the capsid proteins of many icosahedral viruses. Three long loops (DE1, FG1, and FG2) extend out from the base structure to form the tower region of each molecule (Rux and Burnett 2004). Sequences within these loop domains protrude to the surface of the capsid to form the exterior of the virion. Alignments from different adenovirus serotypes show that the sequences located on the capsid exterior are poorly conserved in both length and amino acid sequence (Crawford-Miksza and Schnurr 1996). Furthermore, it has been shown that the sequences located in these poorly conserved domains, termed hypervariable regions (HVRs), contain the determinants against which serotype-specific antibodies are produced (Top 1975, Rux and Burnett 2000, Top et al. 1971).

Based on early sequence alignments, seven HVRs were identified throughout the Hexon molecule (Crawford-Miksza and Schnurr 1996, Roberts et al 2006). Because the HVRs are poorly conserved between serotypes and do not appear to be involved in maintaining the structural integrity of Hexon, small changes could be made to these domains without affecting the viability of the virus (Rux and Burnett 2000). For example a hexahistidine tag can be inserted into HVR2, HVR3, HVR5, HVR6, and HVR7 without compromising virus viability (Wu et al. 2005). Thus, Hexon HVRs are often used as targets to efficiently induce an antibody response against peptides located in Hexon HVRs (Worgall et al. 2005, Crompton et al. 1994). Due to its poor conservation in length between serotypes and its position on the outermost surface of the adenovirus capsid (Rux and Burnett 2000, Crawford-Miksza and Schnurr 1996), Hexon HVR5 was initially chosen as a site for epitope insertion. Further, the crystal structure of Hexon indicates that HVR5 is a flexible loop on the capsid surface, suggesting that HVR5 can accommodate relatively large peptides without compromising the structural integrity of the capsid (Roberts et al. 1986). Hexon-specific CD4+ and CD8+ epitopes have recently been identified (Leen et al. 2008), and the CD4+ T cell response to adenovirus is focused against conserved residues within the Hexon protein in humans (Onion et al. 2007, Heemskerk et al. 2006).

The adenovirus core is composed of the viral genome and four core proteins. The terminal protein (TP) is covalently linked to the 5' end of each linear viral DNA strand at two copies per virion. Noncovalently and nonspecifically bound to the viral DNA through arginine-rich portions are three other core proteins mu (μ), V (pV) and VII (pVII). pVII is the major core protein contributing roughly 700-800 copies per virion, and serves as a histone-like center around which viral DNA is wrapped to form nucleosome structures.

Modification of Adenovirus Capsid Proteins to Enhance Humoral Immunity

In some embodiments, circumsporozoite (CS) adenoviral vectors that have an immunodominant CS protein B epitope in an adenovirus capsid protein (inserted in the Hexon or Fiber) are described. The transgene may be under a promoter such as CMV to augment cell-mediated and humoral immune responses to CS protein.

A central repeat region is the conserved structure of CS protein among *Plasmodium* species, and antibody against this repeat sequence has been shown to have sporozoite neutralizing activity. Examples of a repeat sequence in *Plasmodium* CS protein are $(NANP)_n$ repeat (*P. falciparum*; SEQ ID NO:60), ANGAGNQPG repeat (*P. vivax*; SEQ ID NO:63) and NAAG repeat (*P. malariae*; SEQ ID NO:64), which can be inserted into adenovirus capsid proteins. In some embodiments, four or more $(NANP)_n$ repeats (SEQ ID NO:60) of PfCSP may be inserted into HVR1 of adenovirus serotype 5 Hexon. In some embodiments, two, four, six, eight, ten, fourteen, sixteen, eighteen, twenty, twenty-two, twenty-four, twenty-six, or twenty-eight $(NANP)_n$ repeats (SEQ ID NO:60; n=2, 4, 6, 8, 10, 12, 14, 16, 18, 20, 22, 24, 26, 28) of PfCSP are inserted into HVR1 of adenovirus serotype 5 Hexon. The $(NANP)_n$ repeat sequence may be additionally inserted in the in the HI loop of Fiber.

In some embodiments, immunodominant neutralizing B cell epitopes to CS were mapped to develop improved CS protein adenovirus vaccines. Mice immunized with recombinant *P. yoelii* CS protein (PyCS) generated high titers against the two major immunodominant B epitopes, QGPGAP (SEQ ID NO:59) and QQPP (SEQ ID NO:65), but the in vitro neutralization assay indicated that the humoral immune response to QGPGAP epitope (SEQ ID NO:59) itself may account for neutralizing activity because the neutralization could be reversed by adding $(QGPGAP)_3$ peptide (SEQ ID NO:59; n=3) to the medium. In some embodiments, three or more $(QGPGAP)_n$ repeats (SEQ ID NO:59) of PyCS are inserted into HVR1 of adenovirus serotype 5 Hexon. In some embodiments, three, four, five, six, seven, eight, nine, ten, eleven, or twelve $(QGPGAP)_n$ repeats (SEQ ID NO:59; n=3, 4, 5, 6, 7, 8, 9, 10, 11, 12) of PyCS may be inserted into HVR1 of adenovirus serotype 5 Hexon. The $(QGPGAP)_n$ repeat sequence may be additionally inserted in the in the HI loop of Fiber.

The B cell epitope peptide should be presented on the surface of adenovirus virions so that immune system can recognize the epitope efficiently. Such insertion sites could be HVRs of Hexon and Loop structures in Fiber, and different insertion sites can be combined.

Modification of Adenovirus Capsid and Core Proteins to Enhance T Helper Cell Activation In another embodiment, a CD4+ epitope specific to the transgene used in an adenoviral vector may be incorporated into adenovirus proteins such as pVII, pV and Hexon to augment immunogenicity of the adenoviral-based vaccine. Professional antigen presenting cells (APC) such as dendritic cells (DC) and B cells can uptake particulated pathogens like virus particles via endocytosis and present CD4+ epitopes in the pathogen to CD4+ T cells which acts as helper cells for humoral and/or cellular immune responses. pVII and Hexon may easily be used as adenovirus target proteins to insert antigenic CD4+ peptides because of high copy number of pVII (700-800 copies) and Hexon (720 copies) in one virion.

Modification of Adenovirus Capsid Proteins to Circumvent Existing Adenovirus Immunity In some embodiments, adenovirus Fiber and Hexon capsid proteins may be modified to insert a B cell or T helper cell epitope to overcome existing immunity to adenovirus and/or enhance the humoral response to an adenovirus vaccine. An estimated 80% of young adults in human population have circulating neutralizing antibodies to adenovirus (Douglas 2007), especially to serotype 5 (Ad5). In studies utilizing adenovirus as a gene therapy vector, it was found that the presence of neutralizing antibodies in animals limits the expression of transgenes delivered by adenovirus. In addition to neutralizing antibodies, CD8+ T cell responses also contributed to the limitation of recombinant gene expression (Yang et al. 1995, Yang et al 1996). Such pre-existing immunity to adenovirus has previously been reported to inhibit the efficacy of a recombinant adenovirus vaccine (Papp et al. 1999) and also reduces immunogenicity of adenovirus-based vaccines in a clinical trial (Priddy et al. 2008).

Hexon is a major target for anti-Ad capsid immune responses (Roy et al. 2005, Wohlfart 1988), and is likely responsible for the potent adjuvant effect of adenovirus, including the induction of CD4+ and CD8+ T cell responses. Therefore, one strategy that has been employed to circumvent pre-existing anti-adenovirus immunity is to replace all or part of the Hexon with a different protein, for example, rare serotypes such as adenovirus 11, 24, 26 and 35. Because Hexon is a major target of anti-adenovirus neutralizing antibody (Youil et al. 2002, Sumida et al. 2005), the entire Hexon or HVRs of Hexon may be swapped with the rare serotypes (Wu et al. 2002, Roberts et al. 2006).

In another strategy as described in one embodiment herein, an adenoviral Hexon may be modified by replacement of HVR1 or HVR5 with an antigenic peptide to circumvent pre-existing anti-adenovirus immunity or anti-adenovirus neutralizing antibody induced by previous vaccination with adenoviral vector. In some embodiments, an antigenic peptide may be an immunogenic epitope of *Plasmodium* CS protein, and in certain aspects, the epitope may comprise a central repeat sequence, CD4+ epitope sequence or CD8+ epitope sequence.

Repeat administration with an Ad vector of the same serotype is prevented due to anti-Ad immunity following immunization. Therefore, many Ad vaccines impede boosting of the vaccine by preventing expression and presentation of the antigen encoded by the transgene (Yang 1995, Hackett et al. 2000, Harvey et al. 1999, Mastrangeli et al. 1996). The addition of a specific epitope to the Ad capsid, such as those described in the examples below, may reduce or eliminate this impediment according to some embodiments.

The following examples are provided to better illustrate the embodiments and are not to be interpreted as limiting the scope of any claimed embodiment. The extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLE 1

Construction of Capsid-Modified *Plasmodium* Circumsporozoite Protein Adenovirus Plasmid Vectors and Recombinant Adenovirus Particles Epitope Mapping First, an immunodominant neutralizing B cell epitope in PyCS was chosen. Naïve Balb/c mice were immunized with recombinant PyCS-protein with incomplete freund adjuvant three times and the pooled serum was used to determine the critical epitope of neutralizing antibody.

Briefly, in the neutralizing assay, human CD81 expressing HepG2 cells were used as target cells. CD81 is a molecule necessary for malaria parasites to form parasitophorous vacuoles in hepatocytes where they multiply and develop into schizonts (Silvie et al 2006), thus greatly increasing the in vitro infectivity of sporozoites.

In this assay, PyCS synthetic peptides were added to the wells to block peptide specific antibody. The results of epitope mapping indicated that the PyCS central repeat sequence, QGPGAP (SEQ ID NO:59), is a more potent neutralizing epitope in PyCS than QQPP (SEQ ID NO:65). Therefore, insertion of the $(QGPGAP)_n$ epitope (SEQ ID NO:59) was used to modify adenovirus capsid proteins, Hexon and/or Fiber.

Construction of Capsid-Modified Plasmid Vectors

Adenovirus shuttle vector pShuttle-CMV (STRATAGENE) was modified by inserting a GFP-expression cassette under the cloning site. First, BsmBI-SacI fragment (pCMV+GFP) and SacI-BsmBI fragment (SV40 poly A signal) of pmaxGFP (Lonza, Cologne, Germany) were blunted and inserted into the blunted SalI and KpnI sites of pUC19 respectively. The BamHI-EcoRI fragment of the resulting pCMV-GFP/pUC19 was inserted into the same sites of SV40pA/pUC19 to create SV40pA-pCMV-GFP fragment. The fragment was blunted and inserted into the EcoRV site of pShuttle-CMV. The resulting shuttle vector (GFP/pShuttle-CMV) has dual pCMV promoters and SV40pAs for a transgene and GFP.

Another modification of the Adenovirus shuttle vector pShuttle-CMV was done to replace the CMV promoter region with CMV5 promoter from pQBI-AdCMV5 (QBIOgene). The SgrAI-KpnI fragment of pShuttle-CMV was replaced with the fragment containing the CMV5 promoter sequence and the upstream sequence from CMV promoter in pShuttle-CMV to construct pShuttle-CMV5 vector.

The *P. yoelii* CS (PyCS) gene was codon-optimized except for the $(QGPGAP)_n$ repeats (SEQ ID NO:59) by overlapping PCR reaction based on JCat codon-optimization algorithm (http://www jcat de/).

The PfCSP amino acid sequence of *P. falciparum* 3D7 strain was used as a template sequence for codon-optimization. Codon-optimization for protein expression in humans was done by Integrated DNA Technologies' (Coralville, Iowa USA) optimization software. DNA fragments that encode whole PfCSP except for the GPI-anchored motif at the C-terminus (FIG. 10; SEQ ID NO:2) were synthesized by Integrated DNA Technologies Codon-optimized PyCS gene (FIG. 9; SEQ ID NO:1) or PfCSP gene (FIG. 10; SEQ ID NO:2) was inserted into KpnI and HindIII sites of pShuttle-CMV, pShuttle-CMV5, or GFP/pShuttle-CMV. The resulting *Plasmodium* circumsporozoite protein coding adenovirus shuttle vectors were used for homologous recombination with AdEasy-1 to construct adenovirus genome which has *Plasmodium* circumsporozoite antigenic gene and intact adenovirus protein coding sequences. Briefly, *Plasmodium* circumsporozoite protein coding adenovirus shuttle vectors were linearized by PmeI digestion, and *E. coli* BJ5183 cells were co-transformed with the linearized shuttle vector and pAdEasy-1 vector (Bruna-Romero et al 2003) for homologous recombination.

Modification of adenovirus capsid proteins is summarized and illustrated in FIG. 1. Modification of HVR1 sequence in the adenovirus genome DNA is illustrated in FIG. 2. Briefly, AdEasy-1 was digested with SfiI and the 6.4 kbp fragment was subcloned into EcoRI and PstI sites of pUC19 using EcoRI-SfiI and PstI-SfiI linker oligomers. To replace HVR1 with a *Plasmodium* circumsporozoite protein B cell epitope, the region containing AgeI and NdeI sites was amplified by two-step PCR using primers which have the epitope sequence instead of HVR1 sequence. The PCR product was digested with AgeI and NdeI, and then used to replace the native AgeI-NdeI region of SfiI fragment in SfiI/pUC19 vector. After confirming the sequence, the SfiI fragment of adenovirus genome DNA was replaced with the SfiI fragment containing the circumsporozoite epitope sequence to produce an HVR1-modified Hexon. In some embodiments, an HVR-modified Hexon may have a nucleic acid sequence of SEQ ID NO:3 (FIG. 11), SEQ ID NO:4 (FIG. 12), SEQ ID NO:5 (FIG. 13), SEQ ID NO:6 (FIG. 14), SEQ ID NO:7 (FIG. 15), SEQ ID NO:8 (FIG. 16), SEQ ID NO:9 (FIG. 17), SEQ ID NO:10 (FIG. 18), SEQ ID NO:11 (FIG. 19), SEQ ID NO:12 (FIG. 20), SEQ ID NO:13 (FIG. 21), SEQ ID NO:14 (FIG. 22), SEQ ID NO:15 (FIG. 23), SEQ ID NO:16 (FIG. 24), SEQ ID NO:17 (FIG. 25), SEQ ID NO:18 (FIG. 26), SEQ ID NO:19 (FIG. 27), SEQ ID NO:20 (FIG. 28), SEQ ID NO:21 (FIG. 29), SEQ ID NO:22 (FIG. 30), or SEQ ID NO:23 (FIG. 31).

To insert $(NANP)_{28}$ (SEQ ID NO:60; n=28) in HVR1, a part of the central repeat region of codon-optimized PfCSP was amplified by PCR using primers having hexon-specific sequence at 5' and NANP-specific sequence at 3', and the resulting DNA fragment was inserted into the AgeI-NdeI region by second PCR.

Figure 3:
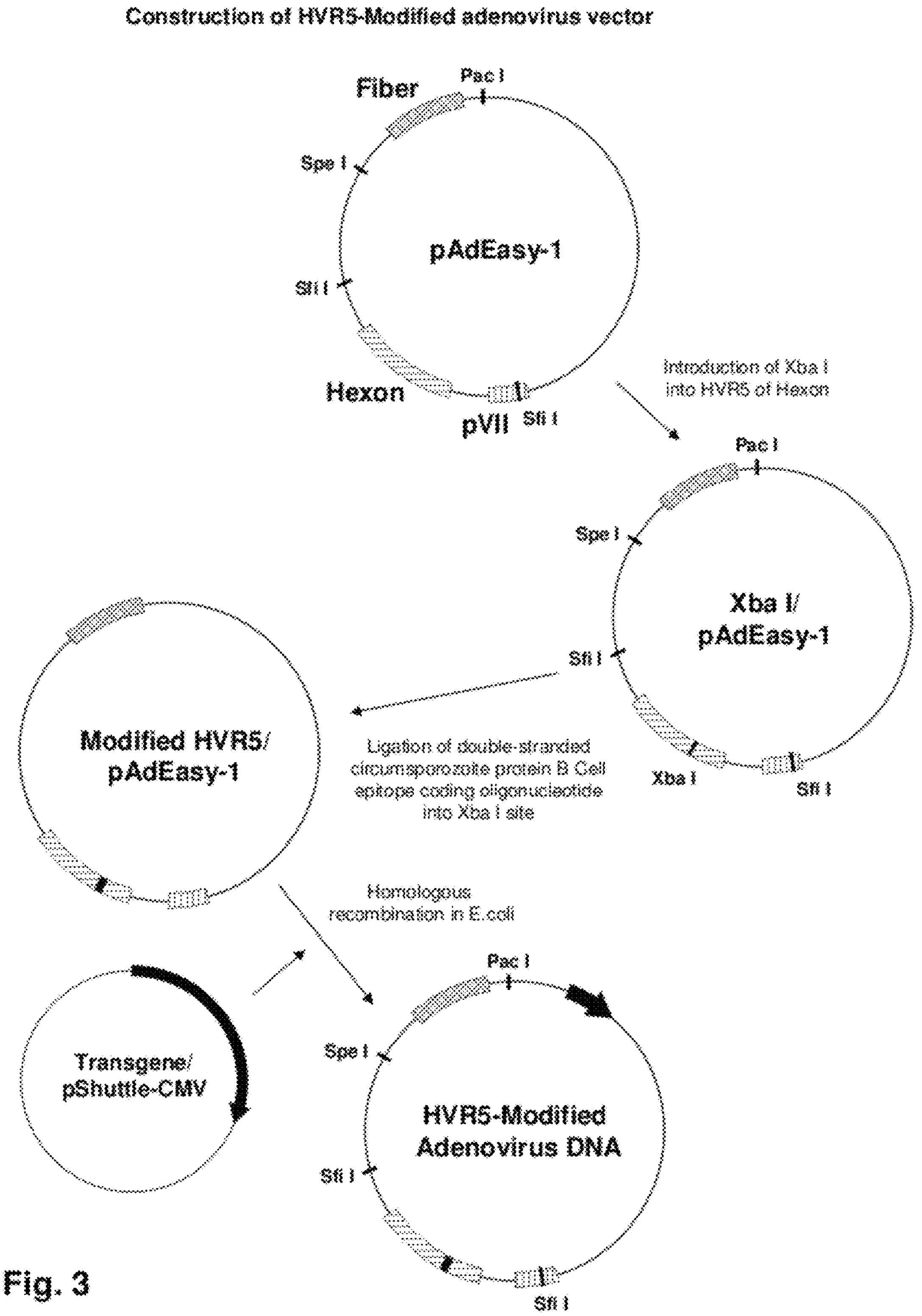
FIG. 3 is a schematic diagram illustrating the construction of the HVR5-Modified Adenovirus DNA of an HVR5-modified recombinant adenovirus plasmid vector.

For HVR5-modification, as illustrated in FIG. 3, XbaI site was introduced into HVR5 in the L1 Loop of Hexon in AdEasy-1 and then synthesized, phosphorylated double strand oligomer coding the *Plasmodium* circumsporozoite protein epitope was inserted into the XbaI site. The insertion was confirmed by sequencing (FIG. 31; SEQ ID NO:23).

For Fiber-modification, as illustrated in FIG. 4, the SpeI-PacI fragment of AdEasy-1 was subcloned into EcoRI and PstI sites of pUC19 using EcoRI-Pact and PstI-SpeI linker oligomers. To insert a *Plasmodium* circumsporozoite protein B-cell epitope sequence into HI loop of Fiber knob, the region containing EcoNI (or NheI) and MfeI sites was amplified by two-step PCR using primers which have the epitope sequence. The PCR product was digested with EcoNI (or NheI) and MfeI, and then used to replace the native EcoNI (or NheI)-MfeI region of Fiber in SpeI-PacI/pUC19 vector. After confirming the sequence (FIG. 32, SEQ ID NO:24; FIG. 33, SEQ ID NO:25), the SpeI-Pact fragment of AdEasy-1 was replaced with the SpeI-Pact fragment containing the epitope sequence. The resulting Fiber-modified adenovirus DNA was used for homologous recombination with *Plasmodium* circumsporozoite protein coding adenovirus shuttle vector to produce Fiber-modified *Plasmodium* circumsporozoite protein adenovirus DNA.

To construct HVR1 and Fiber-modified adenovirus DNA which has two epitope insertions, SfiI-SfiI fragment of Fiber-modified adenovirus DNA was replaced with SfiI-SfiI fragment having the circumsporozoite protein epitope in HVR1 as illustrated in FIG. 5.

To modify the C-terminus of pVII, the region containing Sfi I and Sal I sites was amplified by two-step PCR using primers which have the circumsporozoite protein epitope sequence. The PCR product was digested with SfiI and SalI, and then used to replace the native SfiI-SalI region of SfiI/pUC19 vector (FIGS. 6, 7 and 8). After confirming the sequence (FIG. 34, SEQ ID NO:26; FIG. 35, SEQ ID NO:27), the SfiI-SfiI fragment of HVR1 and/or Fiber-modified circumsporozoite protein adenovirus DNA was replaced with SfiI-SfiI fragment having the circumsporozoite protein epitope in pVII.

To insert the circumsporozoite protein CD4+ epitope sequence EYLNKIQNSLSTEWSPCSVT (SEQ ID NO:62) in the middle of pVII, about 7.7 kb fragment of pAdEasy-1 was prepared by RsrII digestion and cloned between the EcoRI and HindIII sites of pUC19 plasmid using RsrII linker (RsrII/pUC19). The region containing AscI and BglII sites in RsrII/pUC19 was amplified by two-step PCR using primers which have the epitope sequence. The PCR product was digested with AscI and BglII, and then used to replace the native AscI and BglII region in RsrII/pUC19 plasmid. After confirming the sequence of the replaced region (FIG. 36, SEQ ID NO:28; FIG. 37, SEQ ID NO:29), the RsrII fragment of HVR1-modified adenovirus DNA was replaced with the RsrII fragment containing the epitope sequence.

The recombinant adenoviruses listed in Table 1 (*P. yoelii*) and Table 2 (*P. falciparum*) below were produced to evaluate the effect of epitope insertion on infectivity, immunogenicity and sensitivity to pre-existing, anti-adenovirus immunity. Recombinant adenovirus vectors used were replication defective, E1 and E3-deleted adenovirus serotype 5 (STRATAGENE). FIG. 1 shows the schematic structure of capsid-modified *Plasmodium* circumsporozoite protein recombinant adenovirus.

TABLE 1

Recombinant adenoviruses (*Plasmodium yoelii* circumsporozoite protein)

| Antigen | Recombinant Adenovirus | Promoter | Transgene | Adenovirus Protein | Insertion Site | Position (a.a.) | Inserted Sequence | Length |
|---|---|---|---|---|---|---|---|---|
| *P. yoelii* circumsporozoite protein (PyCS) | wt/Empty | CMV | None | Hexon | — | — | — | — |
| | | | | Fiber | — | — | — | — |
| | | | | pVII | — | — | — | — |
| | wt/GFP | CMV | GFP | Hexon | — | — | — | — |
| | | | | Fiber | — | — | — | — |
| | | | | pVII | — | — | — | — |
| | wt/PyCS-GFP | CMV | PyCS + GFP | Hexon | — | — | — | — |
| | | | | Fiber | — | — | — | — |
| | | | | pVII | — | — | — | — |
| | $(QGPGAP)_3$-HVR1/PyCS-GFP | CMV | PyCS + GFP | Hexon | HVR1 | from 138 to 164 | $(QGPGAP)_3$ | 18 |
| | | | | Fiber | — | — | — | — |
| | | | | pVII | — | — | — | — |
| | $(QGPGAP)_3$-HVR5/PyCS-GFP | CMV | PyCS + GFP | Hexon | HVR5 | between 268 and 269 | $(QGPGAP)_3$ | 18 |
| | | | | Fiber | — | — | — | — |
| | | | | pVII | — | — | — | — |
| | $(QGPGAP)_3$-Fib/PyCS-GFP | CMV | PyCS + GFP | Hexon | — | — | — | — |
| | | | | Fiber | HI Loop | between 543 and 544 | $(QGPGAP)_3$ | 18 |
| | | | | pVII | — | — | — | — |
| | $(QGPGAP)_3$-HVR1/Fib/PyCS-GFP | CMV | PyCS + GFP | Hexon | HVR1 | from 138 to 164 | $(QGPGAP)_3$ | 18 |
| | | | | Fiber | HI Loop | between 543 and 544 | $(QGPGAP)_3$ | 18 |
| | | | | pVII | — | — | — | — |
| | $(QGPGAP)_3$-Fib/PyCD4-pVII-1/PyCS-GFP | CMV | PyCS + GFP | Hexon | — | — | — | — |
| | | | | Fiber | HI Loop | between 543 and 544 | $(QGPGAP)_3$ | 18 |
| | | | | pVII | C-terminus | between 198 and STOP Codon | YNRNIVNRLLGDALNGKPEEK | 21 |
| | wt/cmv5-PyCS | CMV5 | PyCS | Hexon | — | — | — | — |
| | | | | Fiber | — | — | — | — |
| | | | | pVII | — | — | — | — |
| | $(QGPGAP)_3$-HVR1/cmv5-PyCS | CMV5 | PyCS | Hexon | HVR1 | from 138 to 164 | $(QGPGAP)_3$ | 18 |
| | | | | Fiber | — | — | — | — |
| | | | | pVII | — | — | — | — |
| | $(QGPGAP)_4$-HVR1/cmv5-PyCS | CMV5 | PyCS | Hexon | HVR1 | from 138 to 164 | $(QGPGAP)_4$ | 24 |
| | | | | Fiber | — | — | — | — |
| | | | | pVII | — | — | — | — |
| | $(QGPGAP)_5$-HVR1/cmv5-PyCS | CMV5 | PyCS | Hexon | HVR1 | from 138 to 164 | $(QGPGAP)_5$ | 30 |
| | | | | Fiber | — | — | — | — |
| | | | | pVII | — | — | — | — |
| | $(QGPGAP)_6$-HVR1/cmv5-PyCS | CMV5 | PyCS | Hexon | HVR1 | from 138 to 164 | $(QGPGAP)_6$ | 36 |
| | | | | Fiber | — | — | — | — |
| | | | | pVII | — | — | — | — |
| | $(QGPGAP)_7$-HVR1/cmv5-PyCS | CMV5 | PyCS | Hexon | HVR1 | from 138 to 164 | $(QGPGAP)_7$ | 42 |
| | | | | Fiber | — | — | — | — |
| | | | | pVII | — | — | — | — |
| | $(QGPGAP)_8$-HVR1/cmv5-PyCS | CMV5 | PyCS | Hexon | HVR1 | from 138 to 164 | $(QGPGAP)_8$ | 48 |
| | | | | Fiber | — | — | — | — |
| | | | | pVII | — | — | — | — |
| | $(QGPGAP)_9$-HVR1/cmv5-PyCS | CMV5 | PyCS | Hexon | HVR1 | from 138 to 164 | $(QGPGAP)_9$ | 54 |
| | | | | Fiber | — | — | — | — |
| | | | | pVII | — | — | — | — |
| | $(QGPGAP)_{11}$-HVR1/cmv5-PyCS | CMV5 | PyCS | Hexon | HVR1 | from 138 to 164 | $(QGPGAP)_{11}$ | 66 |
| | | | | Fiber | — | — | — | — |
| | | | | pVII | — | — | — | — |
| | $(QGPGAP)_{12}$-HVR1/cmv5-PyCS | CMV5 | PyCS | Hexon | HVR1 | from 138 to 164 | $(QGPGAP)_{12}$ | 72 |
| | | | | Fiber | — | — | — | — |
| | | | | pVII | — | — | — | — |

TABLE 2

Recombinant adenoviruses (*Plasmodium falciparum* circumsporozoite protein)

| Antigen | Recombinant Adenovirus | Promoter | Transgene | Adenovirus Protein | Insertion Site | Position (a.a.) | Inserted Sequence | Length |
|---|---|---|---|---|---|---|---|---|
| *P. falciparum* circumsporozoite protein (PfCSP) | wt/PfCSP | CMV | PfCSP | Hexon | — | — | — | — |
| | | | | Fiber | — | — | — | — |
| | | | | pVII | — | — | — | — |
| | $(NANP)_4$-HVR1/PfCSP | CMV | PfCSP | Hexon | HVR1 | from 138 to 164 | $(NANP)_4$ | 16 |
| | | | | Fiber | — | — | — | — |
| | | | | pVII | — | — | — | — |
| | $(NANP)_4$- | CMV | PfCSP | Hexon | — | — | — | — |

TABLE 2-continued

Recombinant adenoviruses (*Plasmodium falciparum* circumsporozoite protein)

| Antigen | Recombinant Adenovirus | Pro-moter | Trans-gene | Adeno-virus Protein | Insertion Site | Position (a.a.) | Inserted Sequence | Length |
|---|---|---|---|---|---|---|---|---|
| | Fib/PfCSP | | | Fiber | HI Loop | between 543 and 544 | $(NANP)_4$ | 16 |
| | | | | pVII | — | — | — | — |
| | $(NANP)_4$-HVR1/Fib/PfCSP | CMV | PfCSP | Hexon | HVR1 | from 138 to 164 | $(NANP)_4$ | 16 |
| | | | | Fiber | HI Loop | between 543 and 544 | $(NANP)_4$ | 16 |
| | | | | pVII | — | — | — | — |
| | $(NANP)_6$-HVR1/PfCSP | CMV | PfCSP | Hexon | HVR1 | from 138 to 164 | $(NANP)_6$ | 24 |
| | | | | Fiber | — | — | — | — |
| | | | | pVII | — | — | — | — |
| | $(NANP)_8$-HVR1/PfCSP | CMV | PfCSP | Hexon | HVR1 | from 138 to 164 | $(NANP)_8$ | 32 |
| | | | | Fiber | — | — | — | — |
| | | | | pVII | — | — | — | — |
| | $(NANP)_{10}$-HVR1/PfCSP | CMV | PfCSP | Hexon | HVR1 | from 138 to 164 | $(NANP)_{10}$ | 40 |
| | | | | Fiber | — | — | — | — |
| | | | | pVII | — | — | — | — |
| | $(NANP)_{12}$-HVR1/PfCSP | CMV | PfCSP | Hexon | HVR1 | from 138 to 164 | $(NANP)_{12}$ | 48 |
| | | | | Fiber | — | — | — | — |
| | | | | pVII | — | — | — | — |
| | $(NANP)_{14}$-HVR1/PfCSP | CMV | PfCSP | Hexon | HVR1 | from 138 to 164 | $(NANP)_{14}$ | 56 |
| | | | | Fiber | — | — | — | — |
| | | | | pVII | — | — | — | — |
| | $(NANP)_{16}$-HVR1/PfCSP | CMV | PfCSP | Hexon | HVR1 | from 138 to 164 | $(NANP)_{16}$ | 64 |
| | | | | Fiber | — | — | — | — |
| | | | | pVII | — | — | — | — |
| | $(NANP)_{18}$-HVR1/PfCSP | CMV | PfCSP | Hexon | HVR1 | from 138 to 164 | $(NANP)_{18}$ | 72 |
| | | | | Fiber | — | — | — | — |
| | | | | pVII | — | — | — | — |
| | $(NANP)_{20}$-HVR1/PfCSP | CMV | PfCSP | Hexon | HVR1 | from 138 to 164 | $(NANP)_{20}$ | 80 |
| | | | | Fiber | — | — | — | — |
| | | | | pVII | — | — | — | — |
| | $(NANP)_{22}$-HVR1/PfCSP | CMV | PfCSP | Hexon | HVR1 | from 138 to 164 | $(NANP)_{22}$ | 88 |
| | | | | Fiber | — | — | — | — |
| | | | | pVII | — | — | — | — |
| | wt/cmv5-PfCSP | CMV5 | PfCSP | Hexon | — | — | — | — |
| | | | | Fiber | — | — | — | — |
| | | | | pVII | — | — | — | — |
| | $(NANP)_{22}$-HVR1/cmv5-PfCSP | CMV5 | PfCSP | Hexon | HVR1 | from 138 to 164 | $(NANP)_{22}$ | 88 |
| | | | | Fiber | — | — | — | — |
| | | | | pVII | — | — | — | — |
| | $(NANP)_{28}$-HVR1/cmv5-PfCSP | CMV5 | PfCSP | Hexon | HVR1 | from 138 to 164 | $(NANP)_{17}(NVDP)_1(NANP)_{10}$ | 112 |
| | | | | Fiber | — | — | — | — |
| | | | | pVII | — | — | — | — |
| | $(NANP)_4$-HVR1/PfCD4-pVII-1/PfCSP | CMV | PfCSP | Hexon | HVR1 | from 138 to 164 | $(NANP)_4$ | 16 |
| | | | | Fiber | — | — | — | — |
| | | | | pVII | C-terminus | between 198 and STOP Codon | EYLNKIQNSLSTEWSPCSVT | 20 |
| | $(NANP)_4$-Fib/PfCD4-pVII-1/PfCSP | CMV | PfCSP | Hexon | — | — | — | — |
| | | | | Fiber | HI Loop | between 543 and 544 | $(NANP)_4$ | 16 |
| | | | | pVII | C-terminus | between 198 and STOP Codon | EYLNKIQNSLSTEWSPCSVT | 20 |
| | $(NANP)_4$-HVR1/Fib/PfCD4-pVII-1/PfCSP | CMV | PfCSP | Hexon | HVR1 | from 138 to 164 | $(NANP)_4$ | 16 |
| | | | | Fiber | — | — | — | — |
| | | | | pVII | C-terminus | between 198 and STOP Codon | EYLNKIQNSLSTEWSPCSVT | 20 |
| | $(NANP)_4$-HVR1/PfCD4-pVII-2/PfCSP | CMV | PfCSP | Hexon | HVR1 | from 138 to 164 | $(NANP)_4$ | 16 |
| | | | | Fiber | — | — | — | — |
| | | | | pVII | Middle | between 92 and 93 Codon | EYLNKIQNSLSTEWSPCSVT | 20 |
| | $(NANP)_4$-HVR1/PfCD4-pVII-3/PfCSP | CMV | PfCSP | Hexon | HVR1 | from 138 to 164 | $(NANP)_4$ | 16 |
| | | | | Fiber | — | — | — | — |
| | | | | pVII | Middle | between 140 and 141 Codon | EYLNKIQNSLSTEWSPCSVT | 20 |
| | $(NANP)_{22}$-HVR1/PfCD4-pVII-3/cmv5-PfCSP | CMV5 | PfCSP | Hexon | HVR1 | from 138 to 164 | $(NANP)_{22}$ | 88 |
| | | | | Fiber | — | — | — | — |
| | | | | pVII | Middle | between 140 and 141 Codon | EYLNKIQNSLSTEWSPCSVT | 20 |
| | $(NANP)_{28}$-HVR1/PfCD4-pVII-3/cmv5-PfCSP | CMV5 | PfCSP | Hexon | HVR1 | from 138 to 164 | $(NANP)_{17}(NVDP)_1(NANP)_{10}$ | 112 |
| | | | | Fiber | — | — | — | — |
| | | | | pVII | Middle | between 140 and 141 Codon | EYLNKIQNSLSTEWSPCSVT | 20 |

The capsid-modified adenovirus genome DNA plasmid was purified, linearized by PacI digestion, and used for transfection of AD293 cells.

Adenovirus particles were prepared from the transfected AD293 cells by four rounds of freeze/thaw and used for further virus amplification. After the last amplification, adenovirus particles were purified by CsCl gradient centrifugation. The band was then collected and dialyzed against dialysis buffer to remove CsCl. Virus particle (v.p.) was calculated based on O.D. 260 (1 O.D.260=$1.25\times10^{12}$ v.p./mL) (Bruna-Romero et al. 2003).

During the adenovirus amplification procedure, small differences in adenovirus growth were observed among capsid-modified adenoviruses, demonstrating that adenovirus infectivity and productivity was not adversely affected by the modification.

EXAMPLE 2

*Plasmodium yoelli* Circumsporozoite Protein-Specific Immune Response

Validation of *Plasmodium yoelii* Recombinant Adenoviruses

Figure 38:
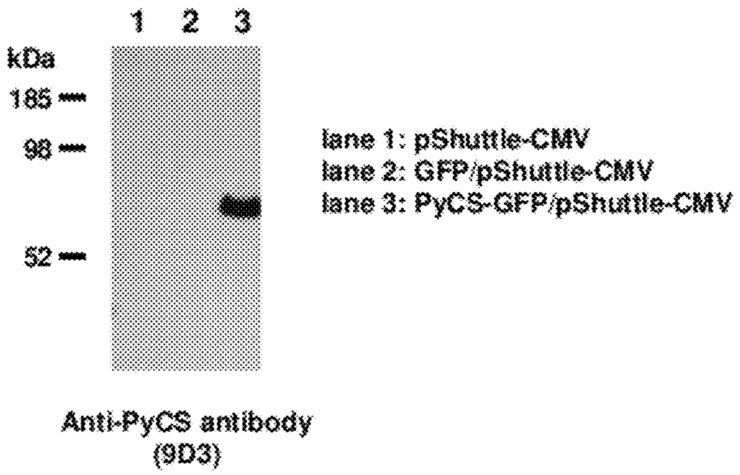
FIG. 38 shows PyCS protein expression in AD293 cells after transient transfection with PyCS-GFP/pShuttle-CMV. PyCS protein was detected by western blotting using mouse monoclonal anti-PyCS antibody (9D3).

*Plasmodium* circumsporozoite protein coding adenovirus shuttle vectors were used for transient transfection to confirm *Plasmodium* circumsporozoite protein expression using AD293 cells (FIG. 38). 24 hours after transfection, cells were lysed in SDS sample buffer followed by SDS PAGE electrophoresis and western blotting with anti-PyCS monoclonal antibody (9D3).

Figure 39:
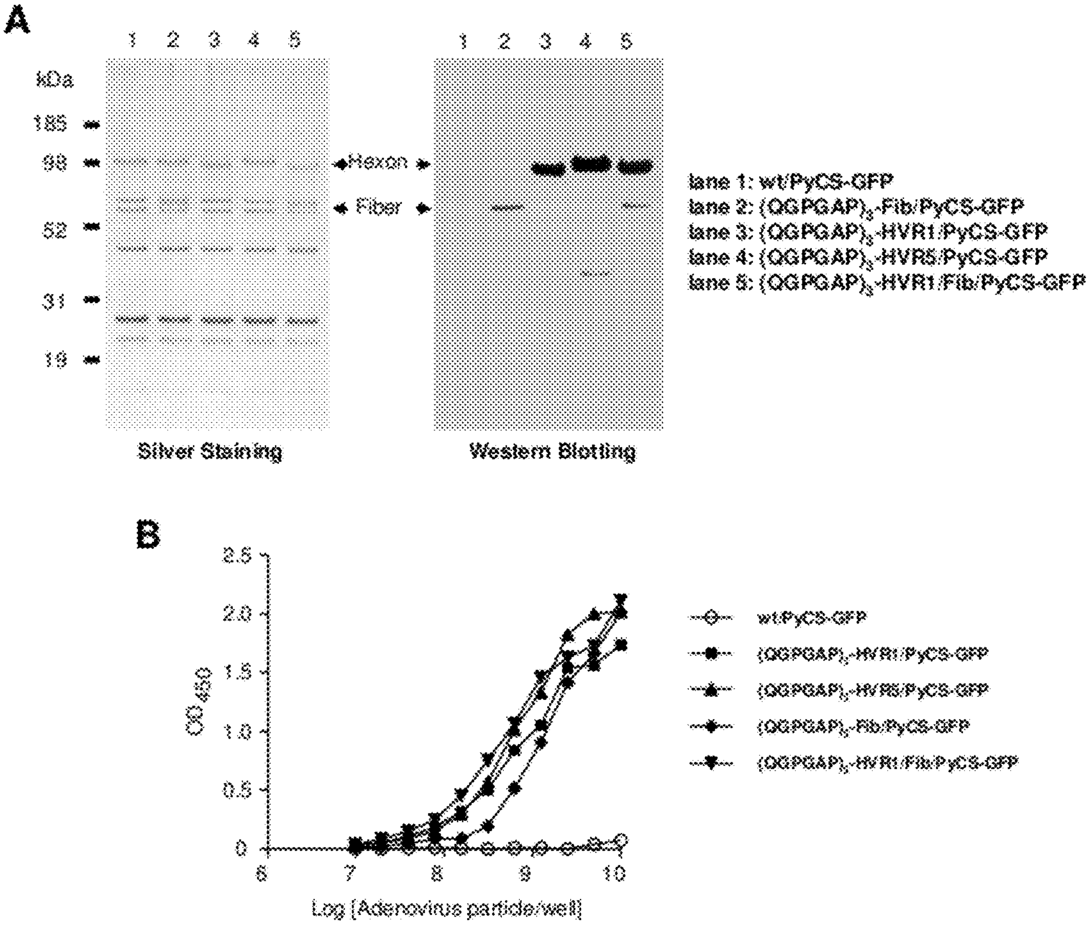
FIG. 39 shows the results of silver staining and western blotting (A) and ELISA assay (B) of the purified capsid-modified recombinant PyCS-GFP adenoviruses to confirm the $(QGPGAP)_3$ epitope (SEQ ID NO:59; n=3) insertion into adenovirus capsid proteins. In the ELISA assay, ELISA plates were coated directly with purified adenoviruses and the inserted epitope in adenovirus particles was detected with anti-PyCS antibody.
Figure 40:
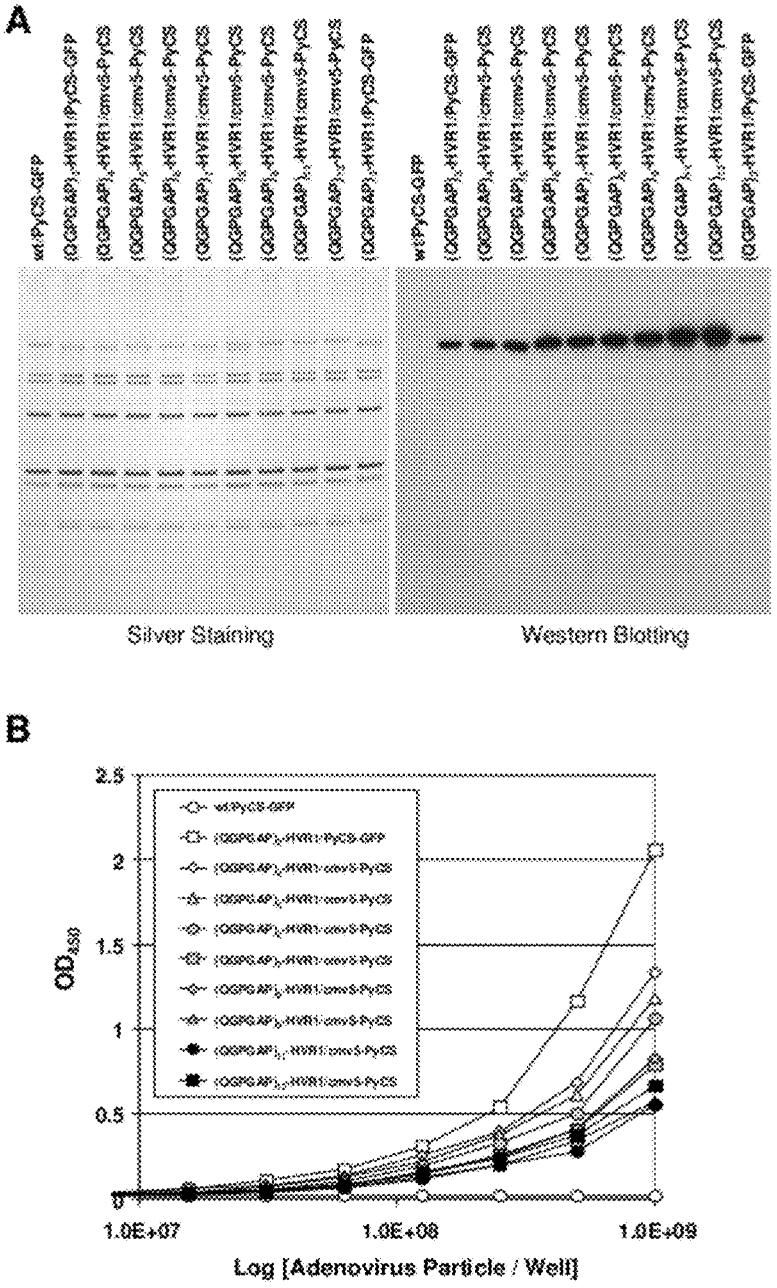
FIG. 40 shows the results of silver staining and western blotting (A) and ELISA assay (B) of the purified capsid-modified recombinant PyCS adenoviruses to confirm the $(QGPGAP)_n$ epitope (SEQ ID NO:59) insertion into adenovirus capsid proteins. In the ELISA assay, ELISA plates were coated directly with purified adenoviruses and the inserted epitope in adenovirus particles was detected with anti-PyCS antibody.

To confirm the epitope insertion into adenovirus capsid proteins, purified recombinant adenoviruses were analyzed by SDS-PAGE ($2\times10^9$ v.p./lane) and Western blot ($1\times10^9$ v.p./lane) with anti-sporozoite antibody which recognizes the $(QGPGAP)_n$ (SEQ ID NO:59) repeats were done as shown in FIGS. 39A and 40A. The intensity of the bands in FIG. 39A correlated with the copy number of the capsid protein in an adenovirus virion: the copy number of Fiber (36 copies per virion) is twenty-times less than Hexon (720 copies per virion). The lower band in lane 4 in FIG. 39A is likely a degraded Hexon. The intensity of the bands in FIG. 40A correlated with the number of $(QGPGAP)_n$ (SEQ ID NO:59) repeats inserted into HVR1.

To assess whether the PyCS-B epitope was exposed to the outside of adenovirus virion, serially diluted purified recombinant adenovirus particles were coated onto Enzyme-Linked Immunosorbent Assay (ELISA) plate and detected with anti-PyCS antibody that recognizes $(QGPGAP)_n$ (SEQ ID NO:59) repeats. The antibody recognized all the capsid-modified adenoviruses (FIGS. 39B and 40B). The results of ELISA assay suggest that the PyCS-B epitope incorporated in capsid proteins were well exposed to the outside of adenovirus virions.

*Plasmodium Yoelii* Circumsporozoite Protein-Specific Immune Response after Immunization with Capsid-Modified PyCS Adenovirus Six- to eight-week old female BALB/c mice were purchased from Taconic (Hudson, N.Y., USA) and maintained under standard conditions in the Laboratory Animal Research Center of The Rockefeller University. For immunization, adenoviruses were diluted in PBS and injected intramuscularly at indicated doses.

Figure 41:
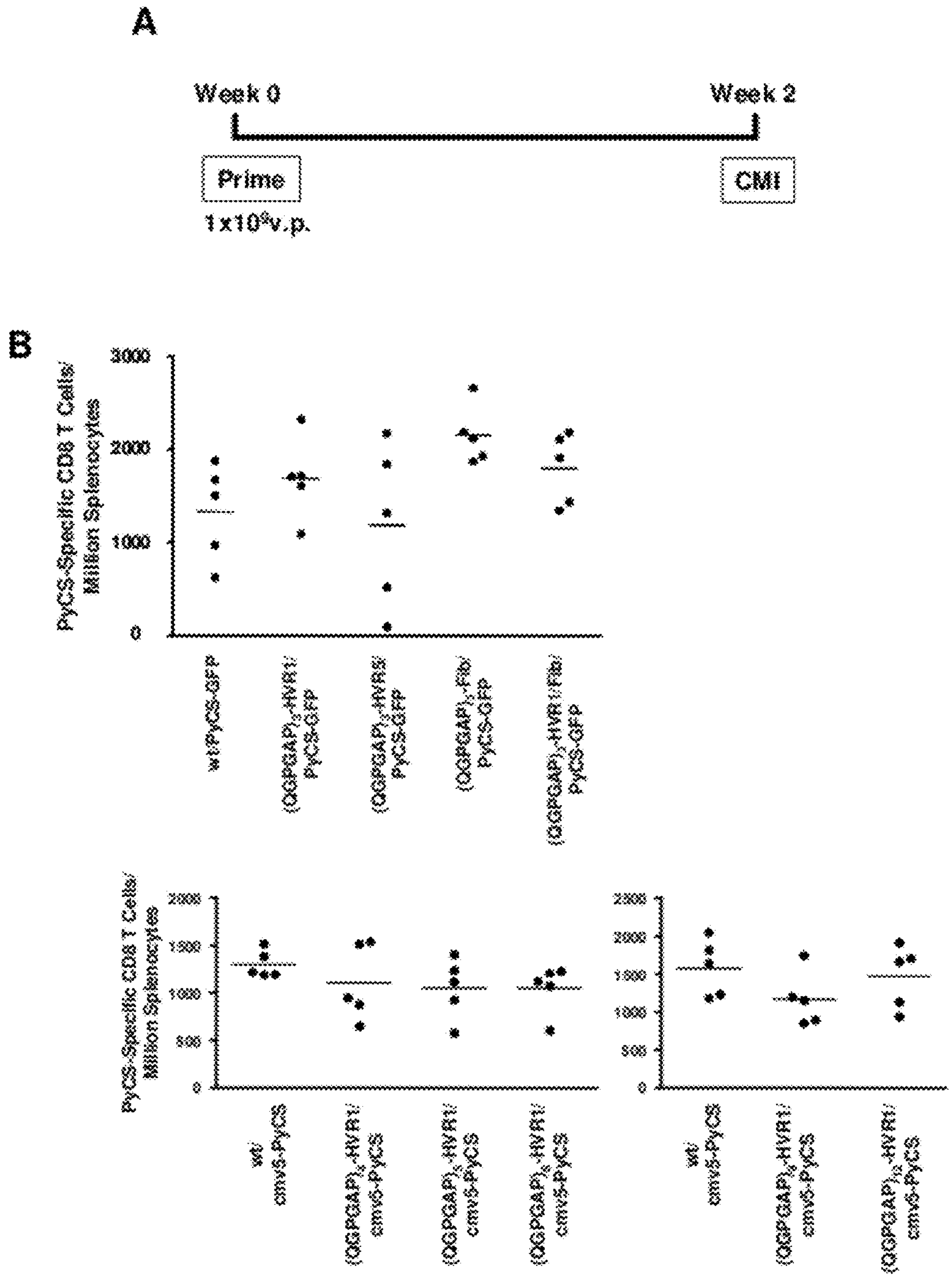
FIG. 41 illustrates a single immunization regimen with capsid-modified PyCS adenoviruses having $(QGPGAP)_n$ repeats (SEQ ID NO:59, n=3, 4, 5, 6, 9, 12) (A) and PyCS-specific CD8+ response two weeks after immunization (B).

To evaluate the immunogenicity of recombinant adenoviruses after a single immunization, groups of naïve BALB/c mice (five per group) were immunized with $1\times10^9$v.p. of various recombinant PyCS adenoviruses intramuscularly and PyCS-specific cell-mediated immune responses (CMI) were measured by ELISPOT 2 weeks after immunization (FIG. 41A).

The number of PyCS-specific, IFN-γ-secreting CD8+ T cells in the spleens of immunized mice were determined by an ELISPOT assay, using a synthetic peptide corresponding to the CD8+ T cell epitope (SYVPSAEQI; SEQ ID NO:66) within the PyCS protein. Briefly, 96 well nitrocellulose plates (Milititer HA, Millipore) were coated overnight with anti-mouse interferon γ mAb, R4. After overnight incubation at room temperature, the wells were washed repeatedly with culture medium and blocked with culture medium for 4 hours. $5\times10^5$ Splenocytes from immunized mice were added to the ELISPOT wells in the presence or absence of 10 μg/mL CD8+ T cell epitope peptide and incubated 24 hours at 37° C. and 5% $CO_2$. After extensive washing of the plates with PBS containing 0.05% Tween 20 (PBST), biotinylated anti-mouse interferon γ mAb, XMG1.2, in PBST were added and incubated overnight at 40° C. After washing with PBST, the plates will be incubated with peroxidase-labeled avidin (eBiosciences). The spots were developed by adding AEC substrate (BD Biosciences).

All of the capsid-modified adenoviruses induced comparable level of CMI to adenoviruses having intact capsid protein at this dose (FIG. 41B).

Figure 42:
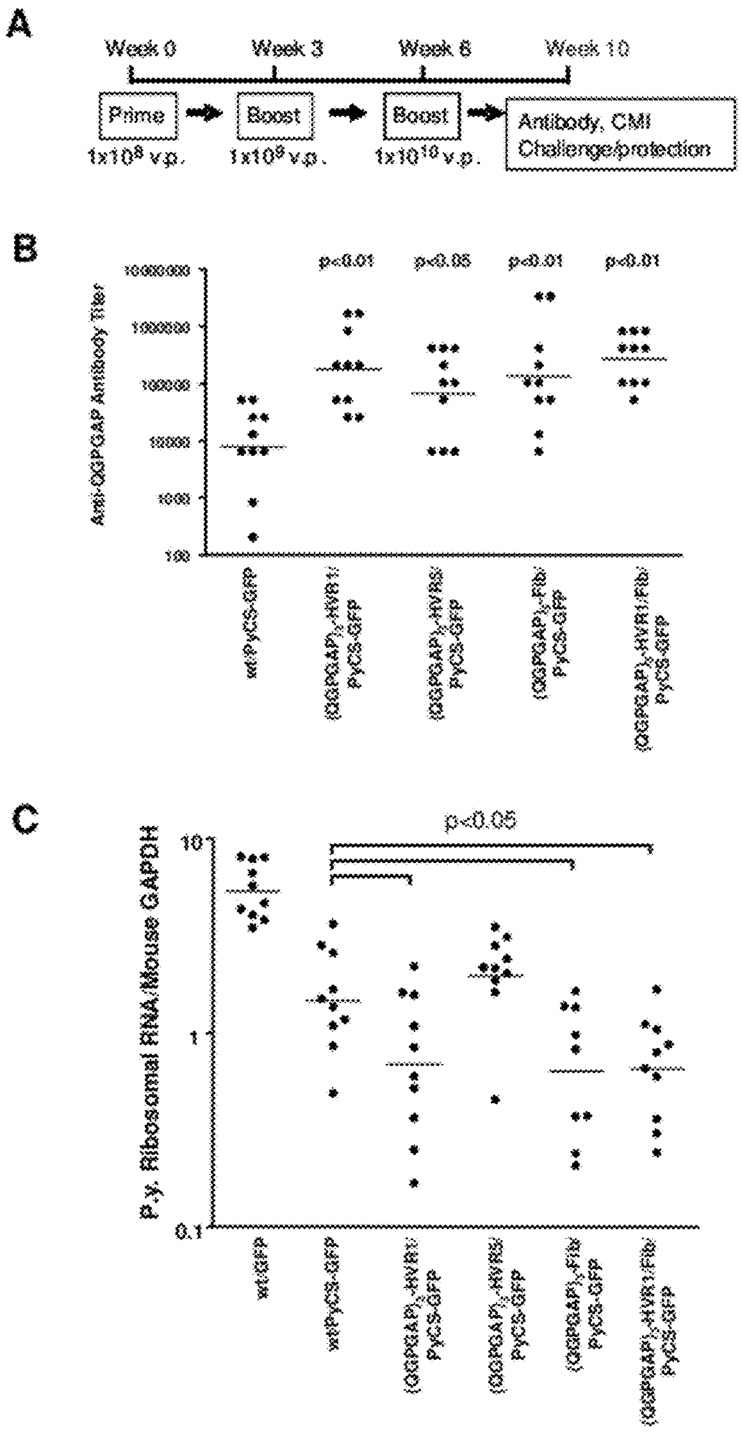
FIG. 42 illustrates a prime and boost immunization regimen with capsid-modified PyCS adenoviruses having $(QGPGAP)_n$ repeats (SEQ ID NO:59, n=3) (A), PyCS-specific humoral responses at week 10 (B), and malaria parasite burden in liver 42 hours after sporozoite challenge (C).

Next, naïve BALB/c mice were given multiple doses of recombinant adenoviruses with increasing doses, i.e. $1\times10^8$, $1\times10^9$, and $1\times10^{10}$ v.p., at 3 week intervals, as shown in FIG. 42A. PyCS-specific humoral response was determined by ELISA. Five microliters of blood was collected from tail vein of the immunized mice and diluted in 495 μl of PBS, and then the samples were centrifuged at 5,000 rpm for 5 min to prepare diluted plasma samples (×100). Maxisorp ELISA plates were coated with 5 μg/ml CS-specific peptide ($(QGPGAP)_3$; SEQ ID NO:59, n=3) in 0.1 M Sodium Carbonate Buffer (pH 9.5) at 4° C. for overnight. Plates were washed and blocked with 1× Diluent for 2 hours at room temperature. The plates were washed again and 100 μl of serially twofold-diluted plasma or serum in 1× Diluent was added to the plates and the plates were incubated for one hour at room temperature. The plates were washed and incubated with 100 μl of HRP-labeled goat anti-mouse IgG antibody. All of the peptides were synthesized by Biosyntheis (Lewisville, Tex., USA).

Using this immunization regimen, all capsid-modified adenoviruses induced a significantly higher level of anti-$(QGPGAP)_3$ antibody response than wt/PyCS-GFP at week 10 (FIG. 42B).

To determine the vaccine efficacy of capsid-modified adenovirus, the immunized mice were challenged with $2\times10^4$ infectious *P. yoelii* sporozoites via tail vein injection at week 10. Parasite burden 42 hours after sporozoite challenge was determined by quantifying the amounts of parasite-specific ribosomal RNA in mouse liver and described as a ratio of the absolute copy number of parasite ribosomal RNA to that of mouse GAPDH mRNA. For statistical analysis, the values were log-transformed and then one-way ANOVA followed by a Dunnett's test was employed to determine the differences.

Vaccinations with $(QGPGAP)_3$—HVR1/PyCS-GFP, $(QGPGAP)_3$-Fib/PyCS-GFP or $(QGPGAP)_3$—HVR1/Fib/PyCS-GFP induced a higher level of protection than wt/PyCS-GFP, resulting in a significantly lower parasite burden in the malaria challenged mice (FIG. 42C).

Next, the functionality of PyCS-specific antibody induced by capsid-modified adenoviruses was evaluated. First, to test whether the sera of adenovirus-immunized mice at week 10 (FIG. 42A) could recognize intact sporozoites, an indirect immunofluorescene assay (IFA) was performed. In IFA, air-dried sporozoites on multi-spot glass slides were incubated with 3% Bovine Serum albumin (BSA) in PBS for one hour and then incubated with diluted sera for one hour. After washing, the slides were incubated with fluorescent-labeled secondary antibody for one hour. The slides were washed and IFA titers were determined as the highest dilution producing fluorescence under a fluorescent microscope. Both (QGPGAP)$_3$-HVR1/PyCS-GFP and (QGPGAP)$_3$-HVR1/Fib/PyCS-GFP induced a highest IFA titer against sporozoites (FIG. 43A), indicating that the insertion of (QGPGAP)$_3$ epitope in HVR1 of adenovirus Hexon enabled PyCS adenovirus to elicit a robust antibody response against not only a synthetic peptide, but also a native epitope present in the malaria parasites.

Second, to determine whether mice immunized with capsid-modified adenovirus (FIG. 42A) developed "functional" antibodies that could neutralize the infectivity of sporozoites, an in vitro sporozoite neutralization assay was performed.

In the in vitro neutralizing assay, *P. yoelii* sporozoites were added to CD81/HepG2 in a 96-well plate in the presence of 30-fold diluted pooled serum from adenovirus-immunized mice. After a two-hour incubation, uninfected sporozoites were washed out with medium and then the cells were cultured for 42 hours. Relative amount of parasite ribosomal RNA to human GAPDH mRNA was measured by real-time PCR (Ophorst et al. 2006).

Figure 43:
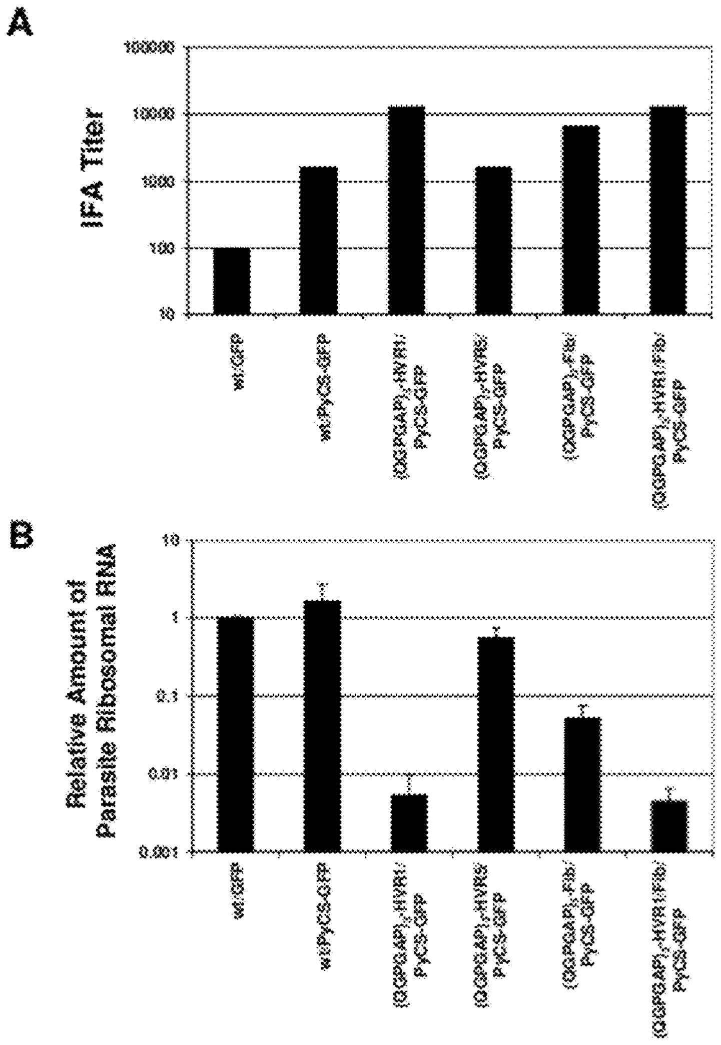
FIG. 43 illustrates anti-sporozoite antibody titer determined by indirect immunofluorescene assay (IFA) (A) and in vitro sporozoite neutralizing activity (B) of pooled serum samples prepared from mice given the regimen in FIG. 42.

The pooled serum samples from mice immunized with capsid-modified adenovirus, particularly $(QGPGAP)_3$-HVR1/PyCS-GFP and $(QGPGAP)_3$-HVR1/Fib/PyCS-GFP, almost completely inhibited (99%) the sporozoite infectivity in vitro (FIG. 43B). It is noted that the degree of inhibition in this assay was inversely correlated with the IFA titers shown in FIG. 43A.

Protection from Blood Stage Malaria Infection

Next it was determined whether immunization with capsid-modified rAd protects mice from developing a blood-stage malaria infection after sporozoite challenge. The experiments were performed twice and in each experiment, 20 BALB/c mice in each group were immunized three times with wt/PyCS-GFP or $(QGPGAP)_3$-HVR1/PyCS-GFP as shown in FIG. 42A and at 4 weeks after the last immunization, the mice were intravenously challenged with 50 *P. yoelli* sporozoites. Giemsa-stained blood smears were analyzed from 3 to 12 days after challenge to detect blood stage malaria parasite infection. In the wt/CS-GFP immunized group, 30 out of 40 mice (75%) were infected whereas 35 out of 40 (87.5%) became infected in the naïve group (Table 3, below). $(QGPGAP)_3$—HVR1/CS-GFP immunized mice were more protected than wt/CS-GFP; only 15 out of 40 (37.5%) of which became infected, which is consistent with the result of protection experiment measured by parasite burden in liver (FIG. 42C).

TABLE 3

Detection of blood stage malaria parasite infection after immunization with wt/PyCS-GFP or $(QGPGAP)_3$-HVR1/PyCS-GFP.

| Immunization | No. of Mice (Chllenged) | No. of Mice (Infected) | Protection (%) |
|---|---|---|---|
| Experiment 1 | | | |
| None | 20 | 18 | 10 |
| wt/PyCS-GFP | 20 | 14 | 30 |
| $(QGPGAP)_3$-HVR1/PyCS-GFP | 20 | 10 | 50 |

TABLE 3-continued

Detection of blood stage malaria parasite infection after immunization with wt/PyCS-GFP or $(QGPGAP)_3$-HVR1/PyCS-GFP.

| Immunization | No. of Mice (Chllenged) | No. of Mice (Infected) | Protection (%) |
|---|---|---|---|
| Experiment 2 | | | |
| None | 20 | 17 | 15 |
| wt/PyCS-GFP | 20 | 16 | 20 |
| $(QGPGAP)_3$-HVR1/PyCS-GFP | 20 | 5 | 75 |
| Total | | | |
| None | 40 | 35 | 87.5 |
| wt/PyCS-GFP | 40 | 30 | 75 |
| $(QGPGAP)_3$-HVR1/PyCS-GFP | 40 | 15 | 37.5 |

Prime-Boost Immunization 1

Figure 44:
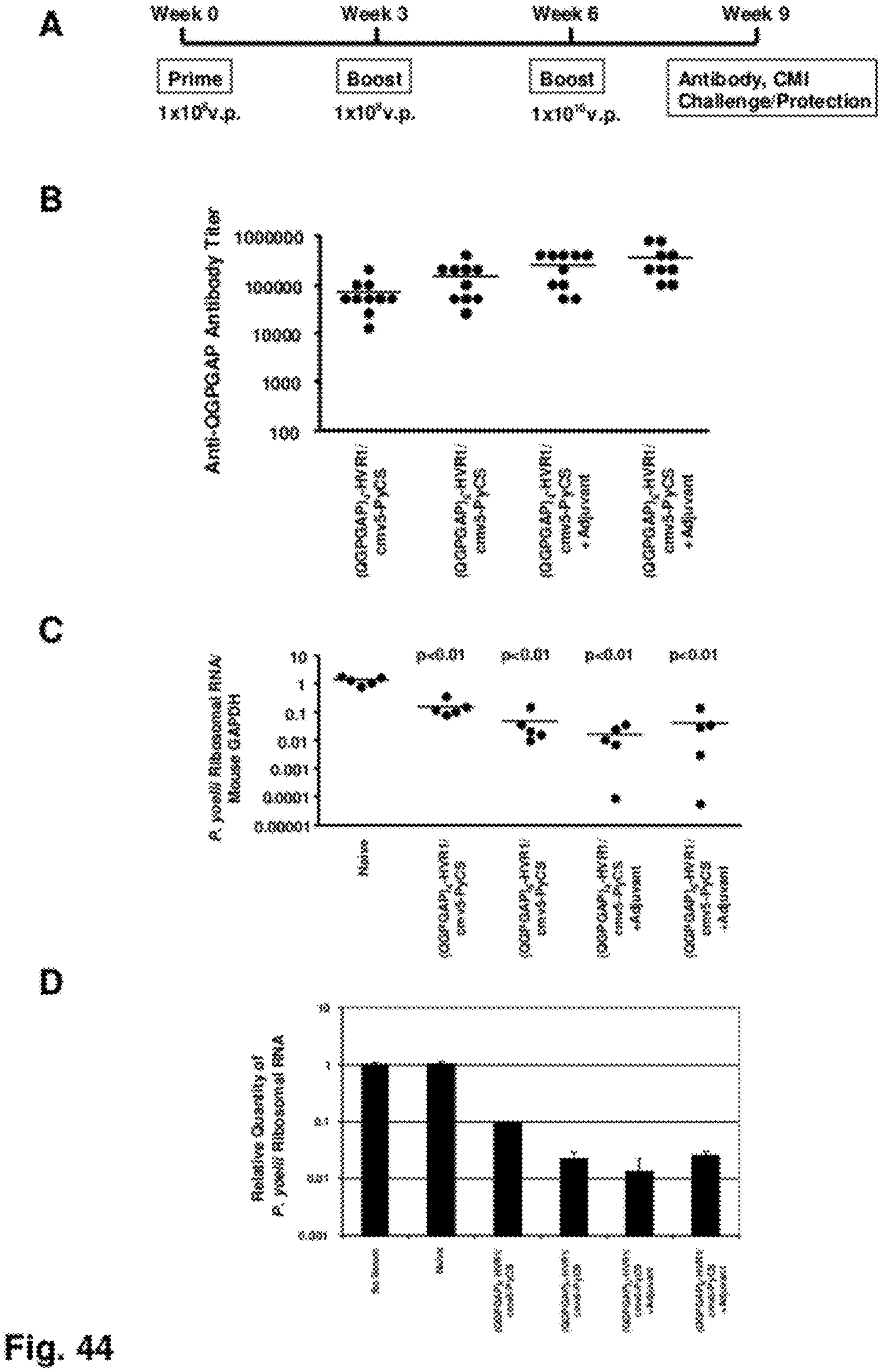
FIG. 44 illustrates a prime and boost immunization regimen with capsid-modified PyCS adenoviruses having $(QGPGAP)_n$ repeats (SEQ ID NO:59, n=4, 6) in HVR1(A), PyCS-specific humoral responses at week 9 (B), malaria parasite burden in liver 42 hours after sporozoite challenge (C), and in vitro sporozoite neutralizing activity of pooled serum samples (D). Mice were immunized with or without adjuvant.

Next, naïve BALB/c mice were given "boosts" of HVR1-modified PyCS adenoviruses which have four or six repeats of $(QGPGAP)_n$ (SEQ ID NO:59; n=4, 6) with or without the adjuvant at multiple increasing doses (i.e. $1\times10^8$, $1\times10^9$, and $1\times10^{10}$ v.p.) at 3 week intervals, as shown in FIG. 44A. The adjuvant used in this experiment is Sigma Adjuvant System (Sigma-Aldrich) containing 200 μg/mL Saponin (Sigma-Aldrich). A vial of Sigma Adjuvant System (1 mL) contains 0.5 mg Monophosphoryl Lipid A (detoxified endotoxin) from *Salmonella minnesota* and 0.5 mg synthetic Trehalose Dicorynomycolate in 2% oil (squalene)-Tween 80 in water. Adenovirus solution was mixed with the equal amount of the adjuvant before the immunization. One hundred microliters of the adenovirus-adjuvant mixture was injected intramuscularly. PyCS-specific humoral and cell-mediated immune responses were measured as described above. A trend was observed that HVR1-modified adenovirus having six repeats induced higher antibody titer than that having four repeats and the use of adjuvant augmented the antibody titer (FIG. 44B). In contrast, there was no effect of the adjuvant on CMI (data not shown).

To determine the vaccine efficacy of HVR1-modified PyCS adenovirus, five mice in each group were challenged with $2\times10^4$ infectious *P. yoelii* sporozoites via tail vein injection at week 9. Parasite burden 42 hours after sporozoite challenge was determined as described above. For statistical analysis, the values were log-transformed and then one-way ANOVA followed by a Dunnett's test was employed to determine the differences. There was a trend that HVR1-modified adenovirus having six repeats reduced parasite burden more than that having four repeats and the use of adjuvant augmented the protection (FIG. 44C).

To evaluate the functionality of antibody induced by HVR1-modified PyCS adenoviruses, we performed an in vitro sporozoite neutralization assay as described above. Pooled serum samples from mice immunized with HVR1-modified PyCS adenoviruses at week 9 neutralized sporozoite invasion at 50-fold dilution (FIG. 44D).

Prime-Boost Immunization 2

Figure 45:
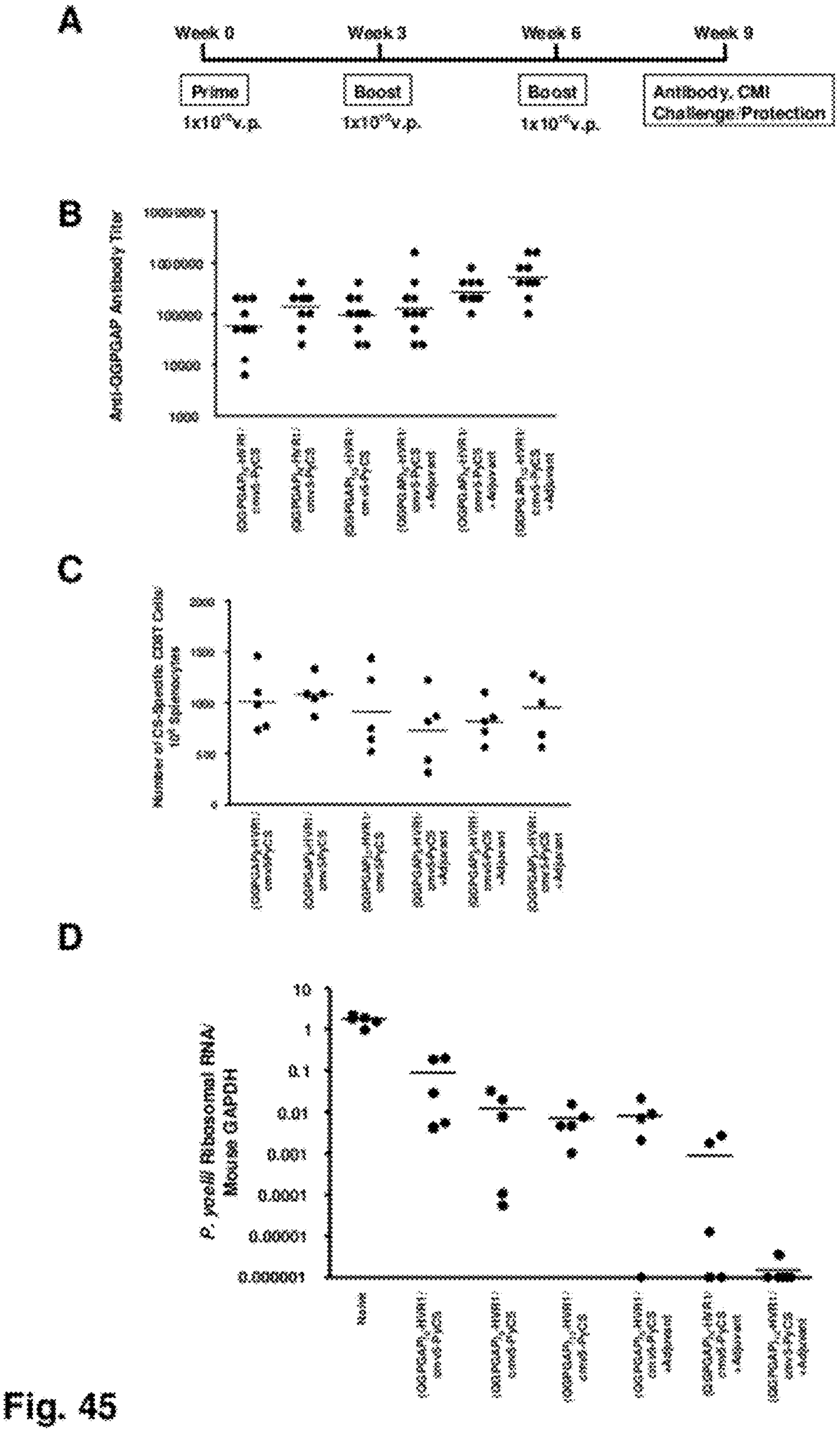
FIG. 45 illustrates a prime and boost immunization regimen with capsid-modified PyCS adenoviruses having $(QGPGAP)_n$ repeats (SEQ ID NO:59, n=6, 9, 12) in HVR1(A), PyCS-specific humoral responses at week 9 (B), PyCS-specific CD8+ T cell responses at week 9 (C), and malaria parasite burden in liver 42 hours after sporozoite challenge (D). Mice were immunized with or without adjuvant.

Naïve BALB/c mice were given "boosts' of HVR1-modified PyCS adenoviruses which have six, nine, or twelve repeats of $(QGPGAP)_n$ (SEQ ID NO: 59; n=6, 9, 12) with or without the adjuvant at three doses of $1\times10^{10}$ v.p. at 3 week intervals, as shown in FIG. 45A. The adjuvant used in this experiment is Sigma Adjuvant System (Sigma-Aldrich) containing 200 μg/mL Saponin (Sigma-Aldrich). Adenovirus solution was mixed with the equal amount of the adjuvant before the immunization. PyCS-specific humoral and cell-mediated immune responses were measured as described above. HVR1-modified PyCS adenovirus which has twelve repeats of $(QGPGAP)_n$ (SEQ ID NO:59; n=12) with the adjuvant induced the highest antibody titer among the groups at week 9 (FIG. 45B). With respect to PyCS-specific CMI, there was no difference among the groups, indicating that the longer epitope insertion up to twelve does not impair adenovirus infectivity in vivo (FIG. 45C). Further, the adjuvant did not affect the ability of adenovirus to induce CMI (FIG. 45C).

To determine the vaccine efficacy of HVR1-modified PyCS adenovirus, five mice in each group were challenged with $2\times10^4$ infectious *P. yoelii* sporozoites via tail vein injection at week 9. Parasite burden 42 hours after sporozoite challenge was determined as described above. All of the HVR-1 modified PyCS adenovirus having $(QGPGAP)_n$ repeats (SEQ ID NO:59, n=6, 9, 12), with or without adjuvant, showed increased protection. However, HVR1-modified PyCS adenovirus having twelve repeats of $(QGPGAP)_n$ (SEQ ID NO:59, n=12) with the adjuvant showed the best protection (FIG. 45D), which was significantly more protective that any other treatment.

EXAMPLE 3

*Plasmodium falciparum* Circumsporozoite Protein-Specific Immune Response

Validation of *Plasmodium falciparum* Recombinant Adenoviruses

Figure 46:
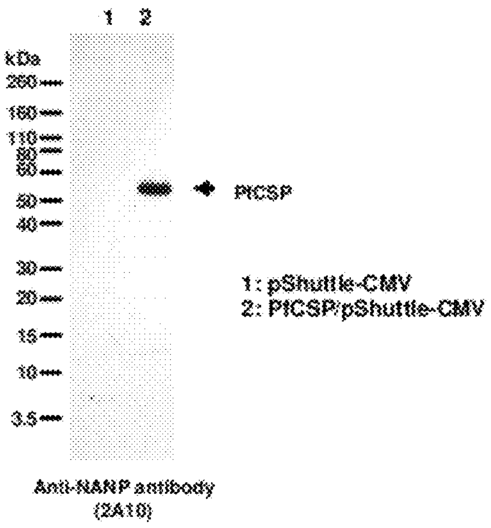
FIG. 46 shows PfCSP protein expression in AD293 cells after transient transfection with PfCSP/pShuttle-CMV. PfCSP was detected by western blotting using mouse monoclonal anti-NANP antibody (2A10).

*Plasmodium* circumsporozoite protein coding adenovirus shuttle vectors were used for transient transfection to confirm *Plasmodium* circumsporozoite protein expression using AD293 cells (FIG. 46A). 24 hours after transfection, cells were lysed in SDS sample buffer followed by SDS PAGE electrophoresis and western blotting with anti-NANP monoclonal antibody (2A10).

Figure 47:
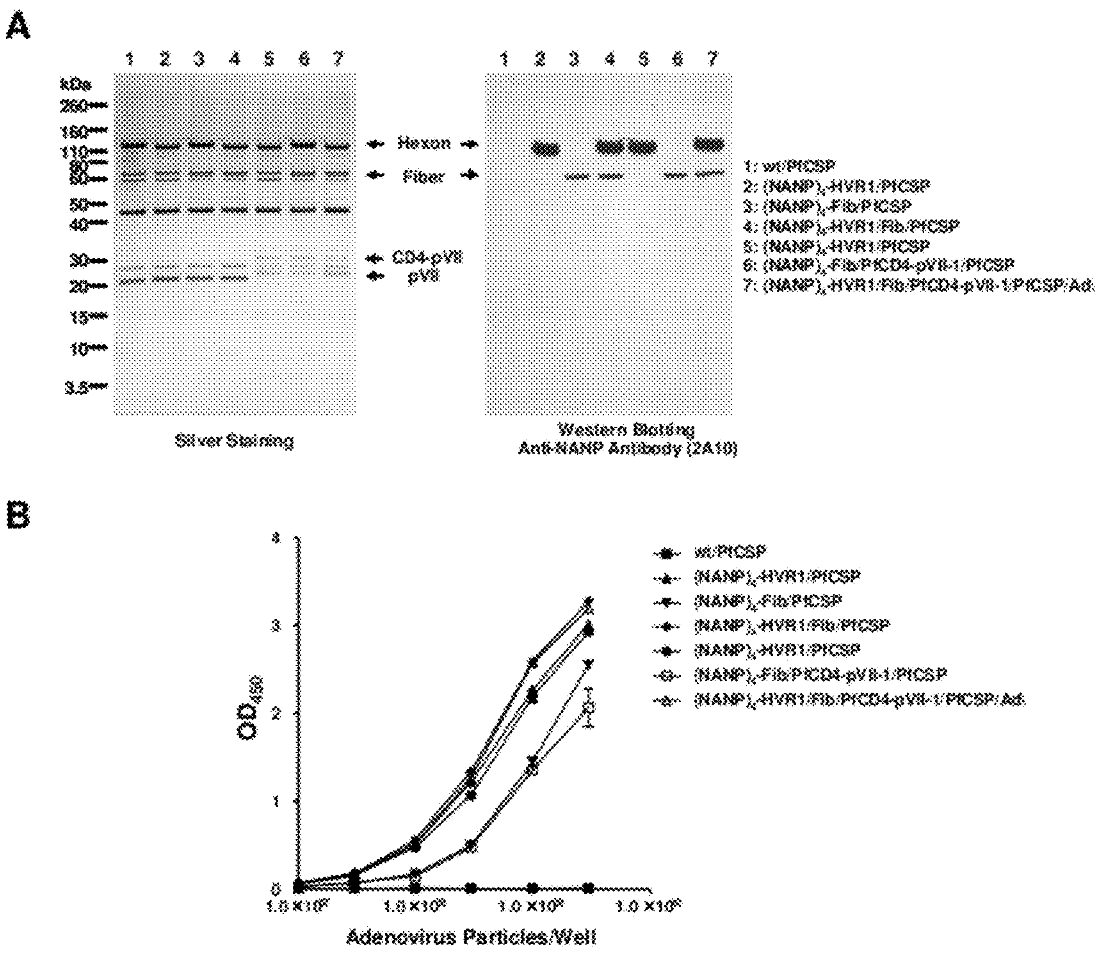
FIG. 47 illustrates the results of silver staining and western blotting (A), and ELISA assay (B) of the purified capsid-modified recombinant PfCSP adenoviruses to confirm the $(NANP)_4$ epitope (SEQ ID NO:60; n=4) insertion into adenovirus capsid proteins. The inserted $(NANP)_4$ epitope (SEQ ID NO:60; n=4) was detected with mouse monoclonal anti-NANP antibody (2A10). In the ELISA assay, ELISA plates were coated directly with purified adenoviruses.
Figure 48:
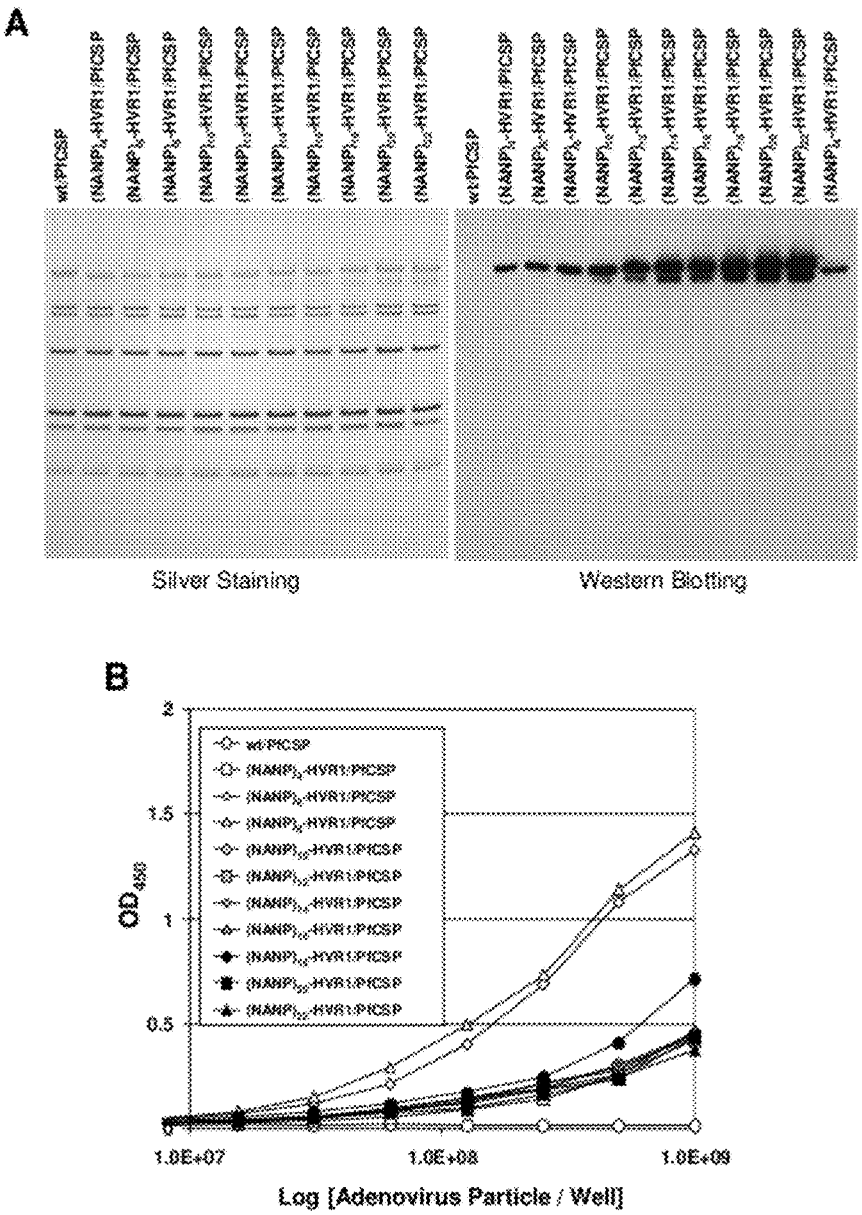
FIG. 48 shows the results of silver staining and western blotting (A) and ELISA assay (B) of the purified capsid-modified recombinant PfCSP adenoviruses to confirm the $(NANP)_n$ epitope (SEQ ID NO:60; n=4, 6, 8, 10, 12, 14, 16, 18, 20, 22) insertion into adenovirus capsid proteins. In the ELISA assay, ELISA plates were coated directly with purified adenoviruses and the inserted epitope in adenovirus particles was detected with anti-PfCSP antibody (2A10).

To confirm the epitope insertion into adenovirus capsid proteins, purified recombinant adenoviruses were analyzed by SDS-PAGE ($2\times10^9$ v.p./lane) and Western blot ($1\times10^9$ v.p./lane) with anti-sporozoite antibody which recognizes the $(NANP)_n$ (SEQ ID NO:60) repeats were done as shown in FIGS. 47A and 48A. The intensity of the bands in FIG. 47A correlated with the copy number of the capsid protein in an adenovirus virion: the copy number of Fiber (36 copies per virion) is twenty-times less than Hexon (720 copies per virion). The intensity of the bands in FIG. 48A correlated with the number of NANP repeat HVR1.

To assess whether the PfCSP-B epitope was exposed to the outside of adenovirus virion, serially diluted purified recombinant adenovirus particles were coated onto Enzyme-Linked Immunosorbent Assay (ELISA) plate and detected with anti-PyCS antibody that recognizes $(NANP)_n$ (SEQ ID NO:60) repeats. The antibody recognized all the capsid-modified adenoviruses (FIGS. 47B and 48B). The results of ELISA assay suggest that the PfCSP-B epitope incorporated in capsid proteins were well exposed to the outside of adenovirus virions.

Prime-Boost Immunization 3

Figure 49:
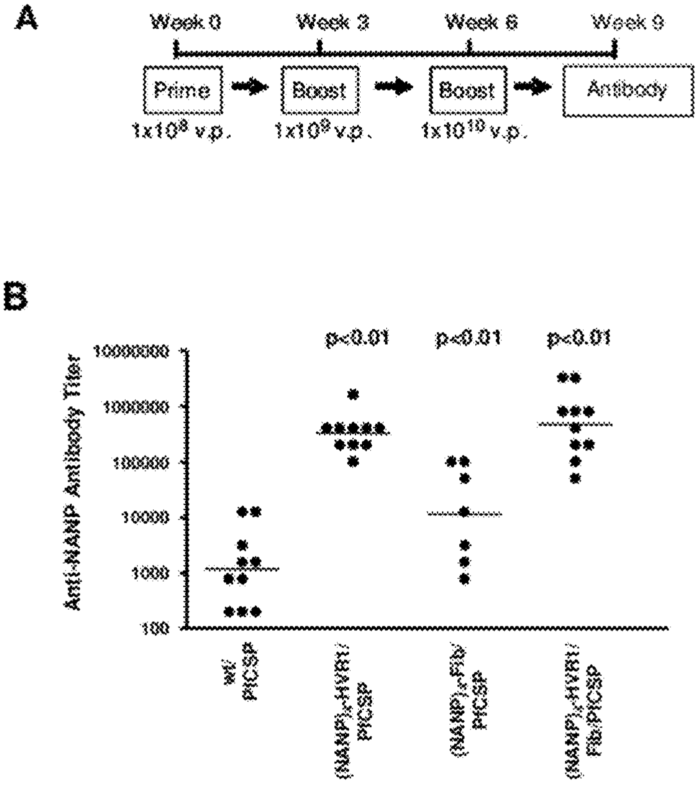
FIG. 49 illustrates the prime and boast immunization regimen with capsid-modified recombinant PfCSP adenoviruses having $(NANP)_4$ (SEQ ID NO:60; n=4) (A) and PfCSP-specific humoral responses at week 9 (B).

Naïve BALB/c mice were given multiple, increasing doses of recombinant PfCSP adenoviruses (i.e., $1\times10^8$, $1\times10^9$, and $1\times10^{10}$v.p.) at 3 week intervals as shown in FIG. 49A. PfCSP-specific humoral response was determined by ELISA as described above using ELISA plates coated with 1 μg/ml $(T1B)_4$, a CS repeat peptide which contains a $(NANP)_n$ repeat sequence (SEQ ID NO:60) (Calvo-Calle et al 2006). For statistical analysis, the values were log-transformed and one-way ANOVA followed by a Dunnett's test was employed to determine the differences between wt/PfCSP and capsid-modified adenoviruses. All capsid-modified adenoviruses induced statistically higher anti-NANP antibody titer than wt/PfCSP.

Prime-Boost Immunization 4

Figure 50:
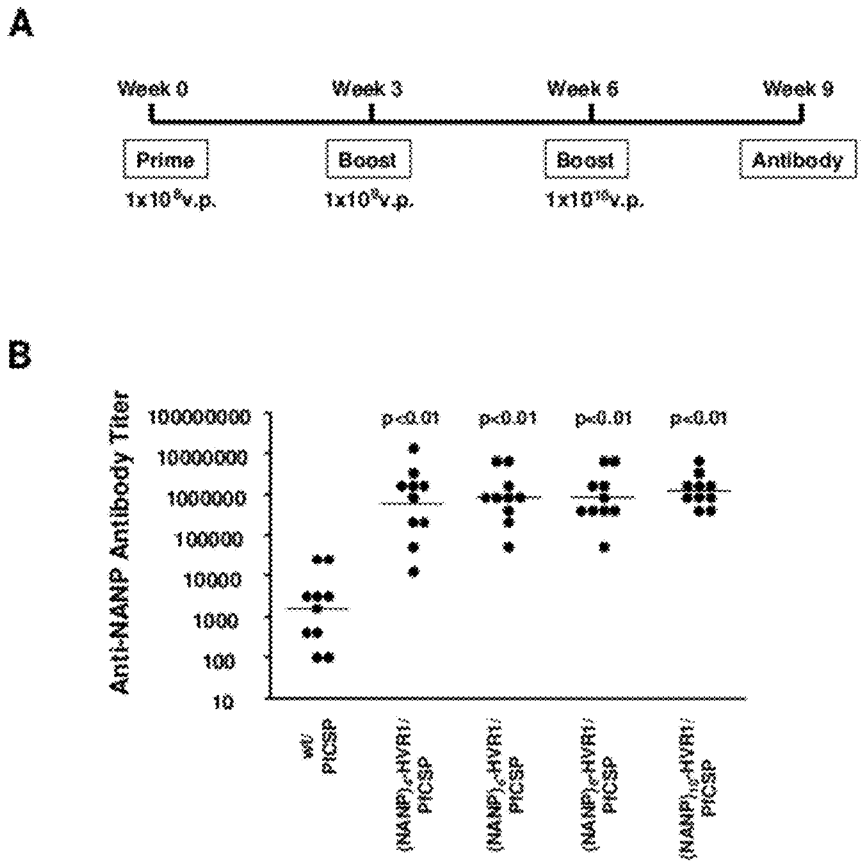
FIG. 50 illustrates the prime and boast immunization regimen with capsid-modified recombinant PfCSP adenoviruses having $(NANP)_n$ (SEQ ID NO:60; n=4, 6, 8, 10) in HVR1 (A) and PfCSP-specific humoral responses at week 9 (B).

Next, naïve BALB/c mice were given "boosts' of HVR1-modified PfCSP adenoviruses which have four, six, eight, or ten repeats of $(NANP)_n$ (SEQ ID NO:60; n=4, 6, 8, 10) with at multiple increasing doses (i.e., $1\times10^8$, $1\times10^9$, and $1\times10^{10}$ v.p.) at 3 week intervals, as shown in FIG. 50A. PfCSP-specific humoral immune responses were measured as described above. All of the HVR1-modified adenoviruses induced significantly higher anti-NANP antibody titer than wt/PfCSP at week 9 (FIG. 50B). For statistical analysis, the values were log-transformed and then one-way ANOVA followed by a Dunnett's test was employed to determine the differences.

Prime-Boost Immunization 5

Figure 51:
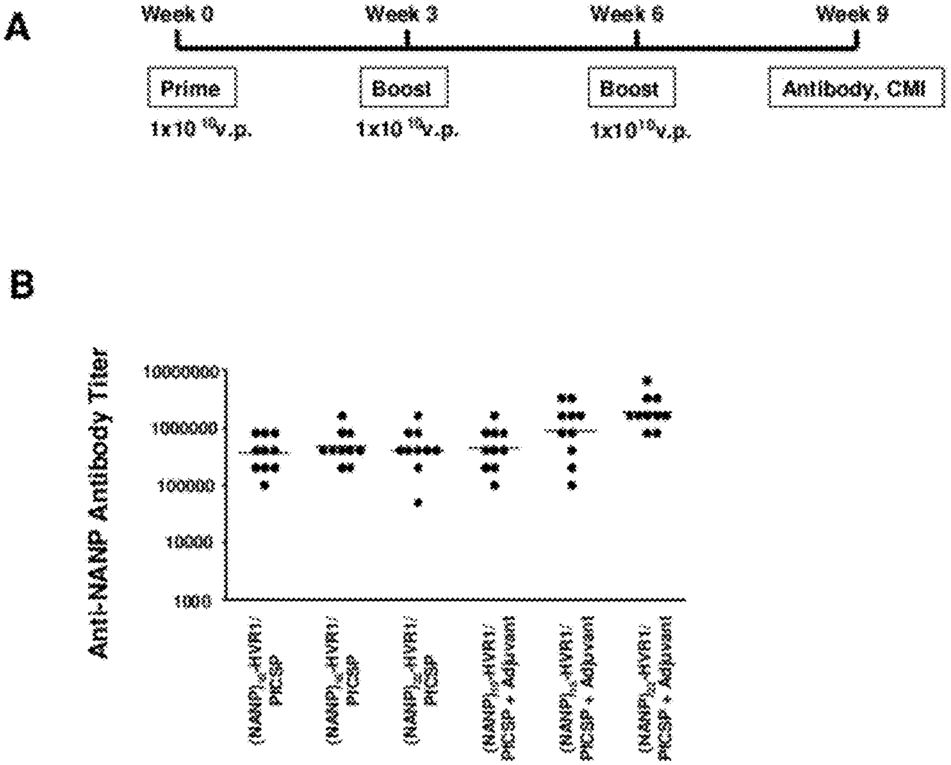
FIG. 51 illustrates the prime and boast immunization regimen with capsid-modified recombinant PfCSP adenoviruses having $(NANP)_n$ (SEQ ID NO:60; n=10, 16, 22) in HVR1 (A) and PfCSP-specific humoral responses at week 9 (B). Mice were immunized with or without adjuvant.

Naïve BALB/c mice were given "boosts" of HVR1-modified adenoviruses which have ten, sixteen, or twenty-two repeats of $(NANP)_n$ (SEQ ID NO:60; n=10, 16, 22) with or without the adjuvant at three doses of $1\times10^{10}$ v.p. at 3 week intervals, as shown in FIG. 51A. The adjuvant used in this experiment is Sigma Adjuvant System (Sigma-Aldrich) containing 200 μg/mL Saponin (Sigma-Aldrich). Adenovirus solution was mixed with the equal amount of the adjuvant before the immunization. PfCSP-specific humoral immune response was measured as described above, and it was determined that HVR1-modified adenoviruses with longer B cell epitope induced higher antibody titer (FIG. 51B).

EXAMPLE 4

PVCS CD4 Epitope Insertion into Adenovirus Core Protein pVII

Figure 52:
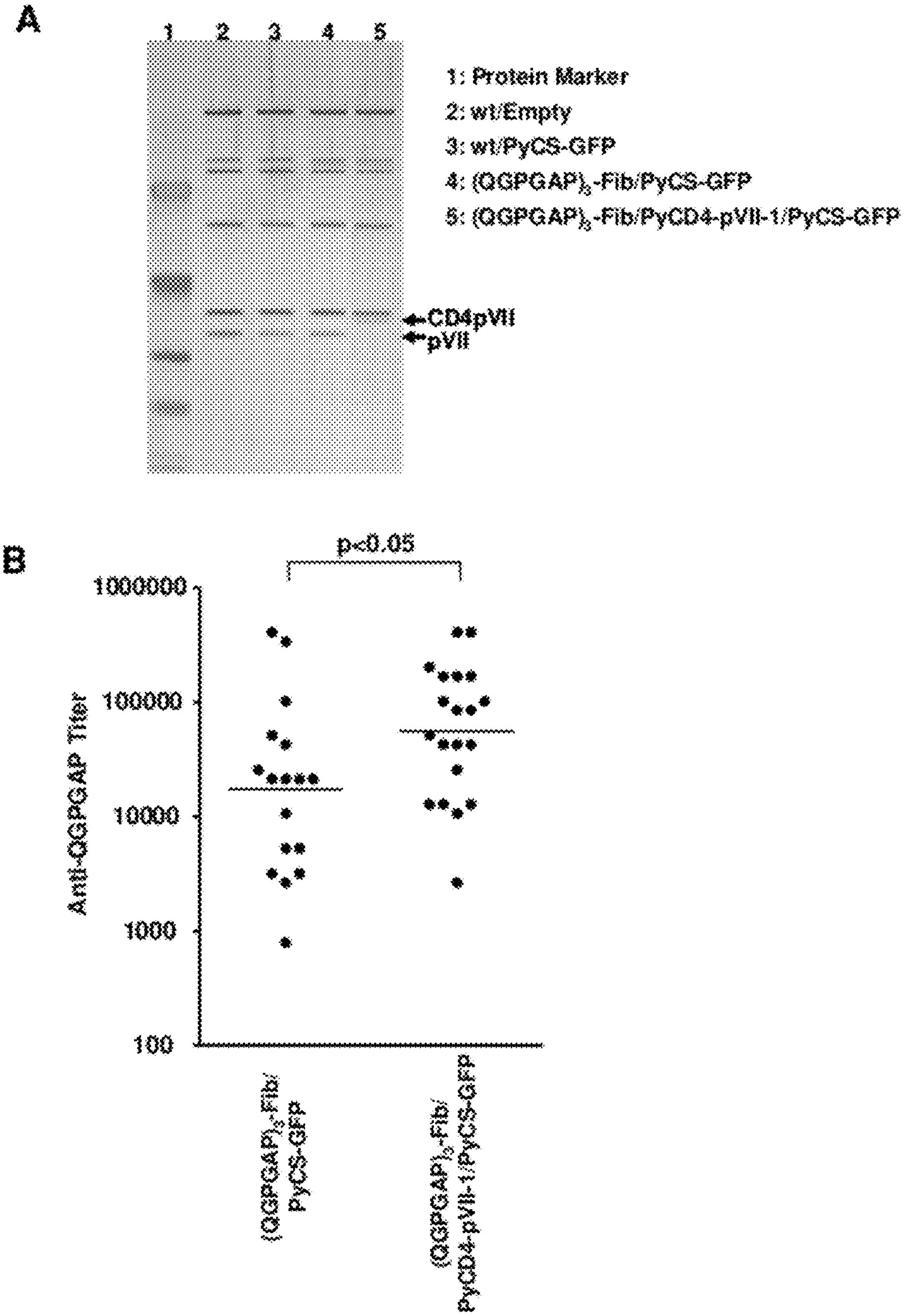
FIG. 52 illustrates the result of sliver staining analysis of purified $(QGPGAP)_3$-modified Fiber and pVII-1 ($(QGPGAP)_3$-Fib/CD4-pVII-1/PyCS-GFP) adenovirus (A) and anti-QGPGAP antibody titer at week 10 in mice immunized with $(QGPGAP)_3$-Fib/PyCS-GFP or $(QGPGAP)_3$-Fib/CD4-pVII-1/PyCS-GFP as described in FIG. 49 (B). The results of two independent experiments were plotted in the figure after normalization with the median antibody titers in B-Fib/PyCS-GFP-immunized group.

Antigen-specific CD4 T cells are required for antigen-specific B cell development and proliferation. Therefore to determine whether it would be possible to enhance PyCS-specific humoral immune response induced by capsid-modified adenovirus by inserting PyCS CD4 epitope in adenovirus protein, $(QGPGAP)_3$-Fib/PyCS-GFP that has PyCS CD4 epitope in pVII ($(QGPGAP)_3$-Fib/CD4-pVII-1/PyCS-GFP) was constructed. pVII is one of the adenovirus core proteins and the copy number per virion is 700-800, which is ideal for efficient CD4 epitope presentation onto MHC class II molecule. As shown in FIG. 52A, the pVII band is shifted by PyCS CD4 epitope insertion into pVII on a SDS-PAGE gel.

To test the effect of PyCS CD4 epitope insertion into pVII, naïve BALB/c mice were immunized with $(QGPGAP)_3$-Fib/PyCS-GFP or $(QGPGAP)_3$-Fib/CD4-pVII-1/PyCS-GFP as shown in FIG. 42A and anti-QGPGAP antibody titer was determined by ELISA at week 10. $(QGPGAP)_3$-Fib/CD4-pVII-1/PyCS-GFP induced significantly higher anti-QGPGAP antibody titer than $(QGPGAP)_3$-Fib/PyCS-GFP (FIG. 52B), and that indicated PyCS CD4 epitope insertion into pVII augmented humoral immune response induced by capsid-modified adenovirus.

PfCSP CD4 Epitope Insertion into Adenovirus Core Protein pVII

To evaluate the effect of PfCSP CD4+ epitope insertion into different positions in adenovirus core protein pVII on adenovirus-induced immune response, HVR1-modified PfCSP adenoviruses having the PfCSP CD4+ epitope just before the first Nuclear localization Signal (NLS) or between the two NLSs were constructed (FIG. 53A).

To confirm the epitope insertion into pVII, purified recombinant adenoviruses were analyzed by SDS-PAGE as described above. As shown in FIG. 53B, the pVII bands of $(NANP)_4$—HVR1/CD4-pVII-2/PfCSP and $(NANP)_4$—HVR1/CD4-pVII-3/PfCSP were shifted upward because of the epitope insertion.

Figure 54:
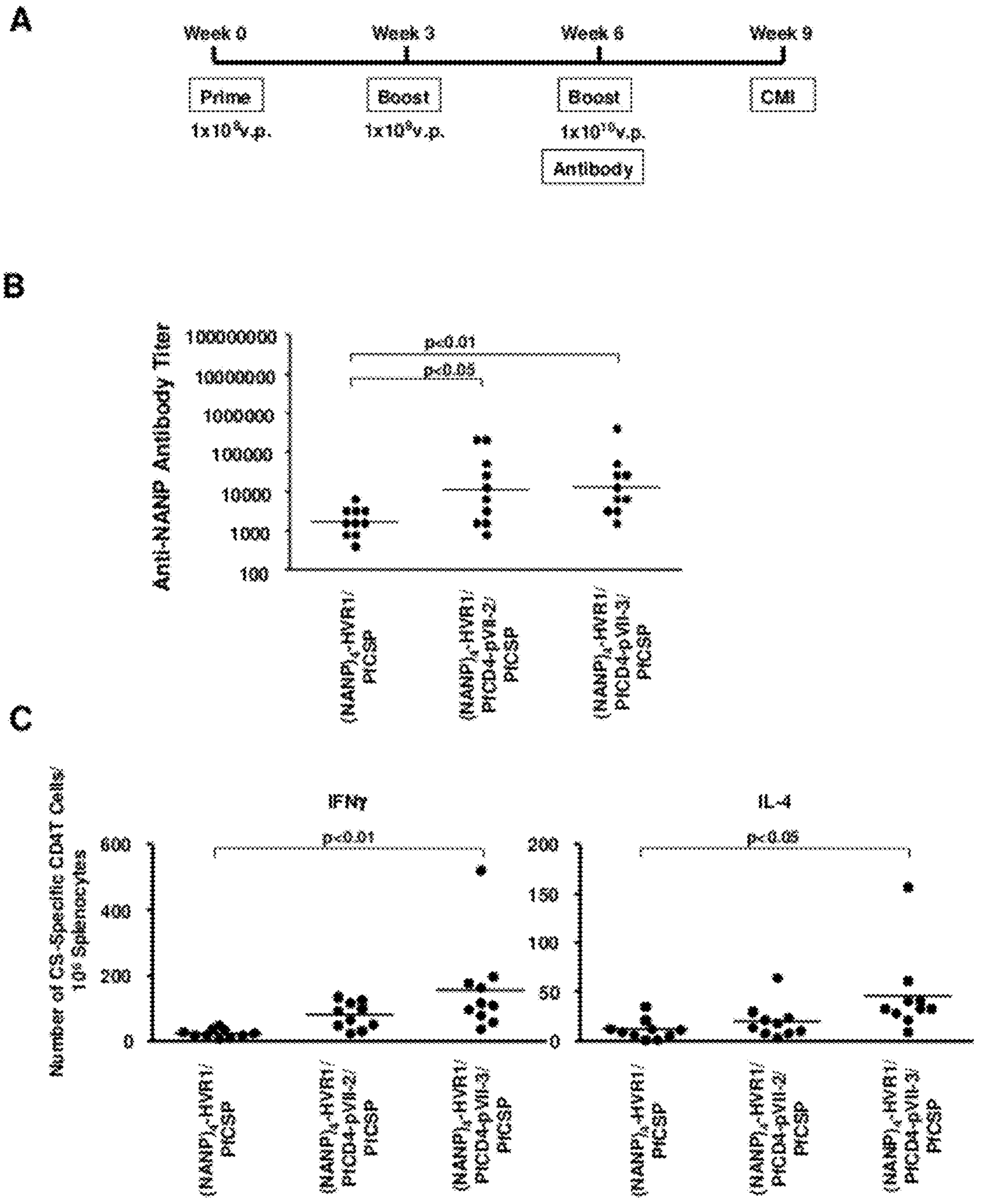
FIG. 54 illustrates the prime and boast immunization regimen with HVR1 and pVII-modified recombinant PfCSP adenoviruses (A), PfCSP-specific humoral responses at week 6 (B), and PfCSP-specific CD4+ (EYLNKIQNSLSTEWSPCSVT; SEQ ID NO:62) response at week 9 (C).

PfCSP-Specific Immune Response Induced by HVR1 and pVII-Modified PfCSP Adenovirus Next, naïve BALB/c mice were given "boosts' of HVR1 and pVII-modified PfCSP adenoviruses which have four repeats of NANP in HVR1 and the PfCD4+ epitope in pVII with at multiple increasing doses (i.e., $1\times10^8$, $1\times10^9$, and $1\times10^{10}$v.p.) at 3 week intervals, as shown in FIG. 54A. PfCSP-specific humoral immune responses were measured as described above. $(NANP)_4$—HVR1/CD4-pVII-2/PfCSP and $(NANP)_4$—HVR1/CD4-pVII-3/PfCSP induced significantly higher anti-NANP antibody titer than $(NANP)_4$—HVR1/PfCSP at week 6 (FIG. 54B). In terms of CMI, $(NANP)_4$—HVR1/CD4-pVII-3/PfCSP induced significantly higher IFNγ and IL-4-secreting PfCSP-specific CD4+ T cells than $(NANP)_4$—HVR1/PfCSP (FIG. 54C).

EXAMPLE 5

Effect of Capsid-Modification on Anti-Adenovirus Immunity

Figure 55:
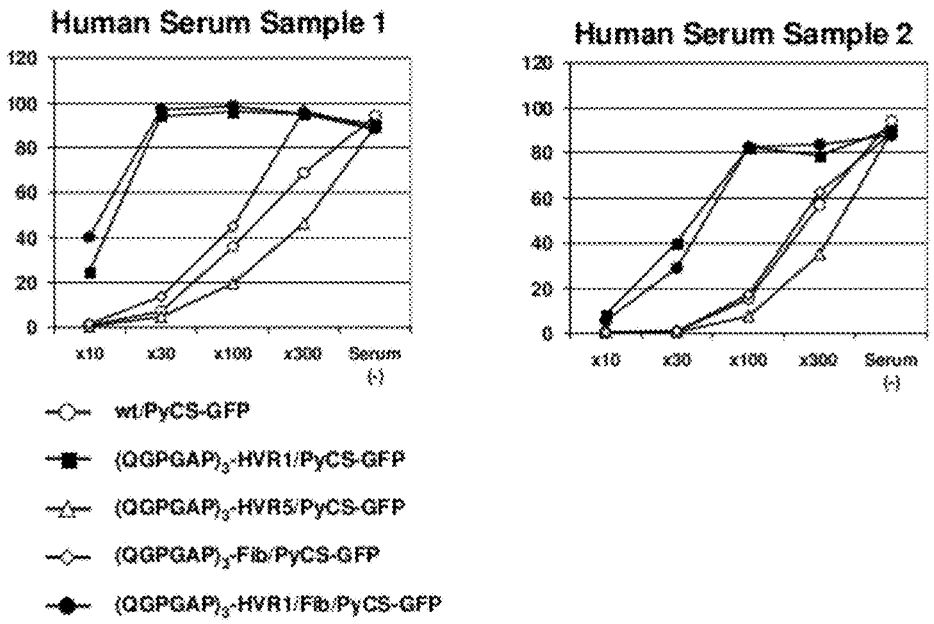
FIG. 55 illustrates in vitro neutralization of recombinant adenovirus by human serum samples. AD293 cells were infected with recombinant adenoviruses in the presence of diluted human serum for overnight and GFP expression was measured as a marker of infection.

For the in vitro adenovirus neutralization experiments, serum was added to the AD293 cells at the indicated dilutions prior to the adenovirus infection. Caucasian serum samples were obtained from Innovative Research (Novi, Mich., USA). All flow cytometry data was analyzed with FlowJo v8.8 software (Tree Star, Inc, Ashland, Oreg., USA). AD293 cells were infected with each capsid-modified adenovirus in the presence of human adenovirus neutralizing serum samples at the indicated dilution followed by measuring GFP expression by flow cytometry. A replacement of HVR1 with the PyCS-B epitope clearly made the adenovirus resilient to anti-adenovirus serotype 5 sera, whereas the modification of HVR5 or Fiber had no effect (FIG. 55).

Figure 56:
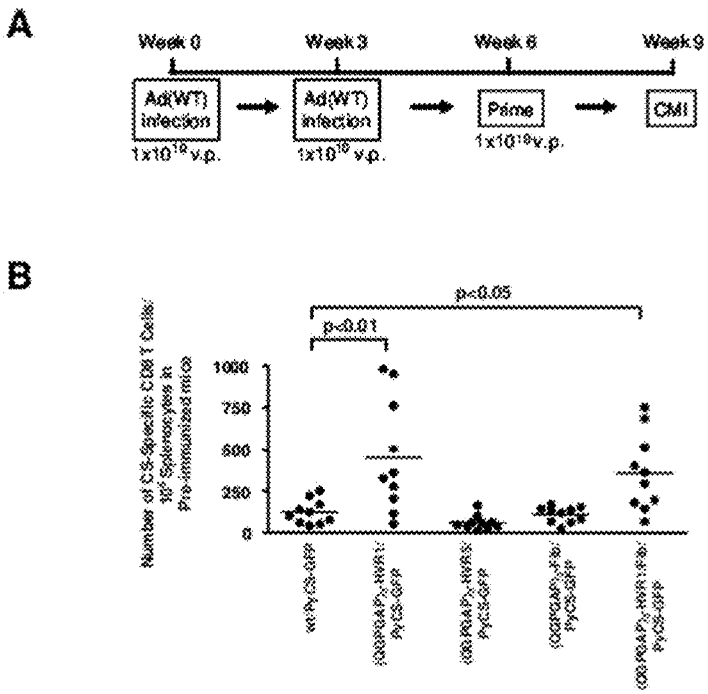
FIG. 56 illustrates the effect of anti-adenovirus immunity on the induction of PyCS-specific T cell response by capsid-modified PyCS-GFP adenoviruses in vivo. (A) is the brief description of the study design. (B) shows PyCS-specific CD8+ T cell response in mice immunized with wild-type (wt)/empty adenovirus twice followed by priming with capsid-modified PyCS-GFP adenoviruses.

Next, it was determined whether HVR1 is a critical molecule for the neutralization in vivo. For this purpose, mice were infected with $1\times10^{10}$ v.p. wt/Empty adenovirus twice to mount sufficient pre-existing anti-adenovirus immunity (FIG. 56A) and randomized based on their anti-adenovirus antibody titers, as determined by ELISA. The mice were then given a single immunizing dose of capsid-modified adenovirus or unmodified adenovirus, and the level of PyCS-specific CD8+ T cell response was measured as described above. Only vaccination with $(QGPGAP)_3$-HVR1/PyCS-GFP or $(QGPGAP)_3$-HVR1/Fib/PyCS-GFP was able to induce a significantly more potent CS-specific CD8+ T cell response, compared to that induced by other capsid-modified or unmodified adenovirus (FIG. 56B).

Figure 57:
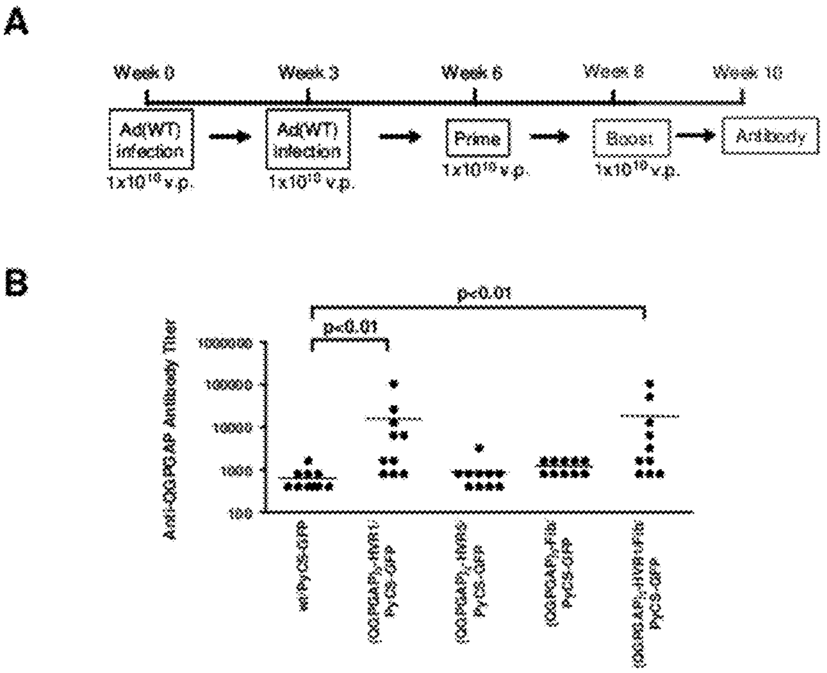
FIG. 57 illustrates the effect of anti-adenovirus immunity on the induction of PyCS-specific humoral immune response by capsid-modified PyCS-GFP adenoviruses in vivo. (A) is the brief description of the study design. (B) shows PyCS-specific humoral immune response in mice immunized with wild-type (wt)/empty adenovirus twice followed by two doses of capsid-modified PyCS-GFP adenoviruses.

The level of antibody response against $(QGPGAP)_3$ epitope was also measured, which is expressed on the capsid proteins of rAd, in mice infected with wt/Empty Ad followed by vaccination with capsid-modified rAd (FIG. 57A). Only mice vaccinated with $(QGPGAP)_3$—HVR1/PyCS-GFP and $(QGPGAP)_3$—HVR1/Fib/PyCS-GFP were able to mount a significantly higher titer of anti-QGPGAP antibody than those vaccinated with wt/PyCS-GFP (FIG. 57B).

The examples described above are meant to more fully illustrate the embodiments and are not to be interpreted as limiting the scope of any claimed embodiment. In addition, the references cited within the disclosure, and all references listed below are hereby incorporated by reference in their entirety as if fully set forth herein.

REFERENCES

Abbink, P., Lemckert, A. A., Ewald, B. A., Lynch, D. M., Denholtz, M., et al. 2007. Comparative seroprevalence and immunogenicity of six rare serotype recombinant adenovirus vaccine vectors from subgroups B and D. *J Virol.* 81:4654-4663.

Alonso, P. L., Sacarlal, J., Aponte, J. J., Leach, A., Macete, E., et al. 2004. Efficacy of the RTS,S/AS02A vaccine against *Plasmodium falciparum* infection and disease in young African children: randomised controlled trial. *Lancet.* 364:1411-1420.

Alonso, P. L., Sacarlal, J., Aponte, J. J., Leach, A., Macete, E., et al. 2005. Duration of protection with RTS,S/AS02A malaria vaccine in prevention of *Plasmodium falciparum* disease in Mozambican children: single-blind extended follow-up of a randomised controlled trial. *Lancet.* 366: 2012-2018.

Anderson, R. J., Hannan, C. M., Gilbert, S. C., Laidlaw, S. M., Sheu, E. G., et al. 2004. Enhanced CD8+ T cell immune responses and protection elicited against *Plasmodium berghei* malaria by prime boost immunization regimens using a novel attenuated fowlpox virus. *J Immunol.* 172:3094-3100.

Athappilly, F. K., Murali, R., Rux, J. J., Cai, Z. & Burnett, R. M. The refined crystal structure of Hexon, the major coat protein of adenovirus type 2, at 2.9 A resolution. *Journal of molecular biology* 242, 430-455 (1994).

Barrat, F. J., Meeker, T, Gregorio, J, Chan, J. H., Uematsu, S., et al. Nucleic acids of mammalian origin can act as endogenous ligands for Toll-like receptors and may promote systemic lupus erythematosus. *J Exp Med.* 202, 1131-1139 (2005)

Bejon, P., Lusingu, J., Olotu, A., Leach, A., Lievens, M., et al. 2008. Efficacy of RTS,S/AS01 E vaccine against malaria in children 5 to 17 months of age. *N Engl J Med.* 359:2521-2532.

Belousova, N., Krendelchtchikova, V., Curiel, D. T. & Krasnykh, V. Modulation of adenovirus vector tropism via incorporation of polypeptide ligands into the Fiber protein. *Journal of virology* 76, 8621-8631 (2002).

Bergelson, J. M. et al. Isolation of a common receptor for Coxsackie B viruses and adenoviruses 2 and 5. *Science* (New York, N.Y. 275, 1320-1323 (1997).

Bewley, M. C., Springer, K., Zhang, Y. B., Freimuth, P. & Flanagan, J. M. Structural analysis of the mechanism of adenovirus binding to its human cellular receptor, CAR. *Science* (New York, N.Y. 286, 1579-1583 (1999).

Bruña-Romero, O., Schmieg, J., Del Val, M., Buschle, M. & Tsuji, M. The dendritic cell-specific chemokine, dendritic cell-derived CC chemokine 1, enhances protective cell-mediated immunity to murine malaria. *J Immunol* 170, 3195-3203 (2003). Hong, S. S., Karayan, L., Tournier, J., Curiel, D. T. & Boulanger, P. A. Adenovirus type 5 Fiber knob binds to MHC class 1 alpha2 domain at the surface of human epithelial and B lymphoblastoid cells. *The EMBO journal* 16, 2294-2306 (1997).

Bruna-Romero, O., González-Aseguinolaza, G., Hafalla, J. C., Tsuji, M., and Nussenzweig, R. S. 2001. Complete, long-lasting protection against malaria of mice primed and boosted with two distinct viral vectors expressing the same plasmodial antigen. *Proc Natl Acad Sci USA.* 98:11491-11496.

Bruna-Romero, O., Rocha, C. D., Tsuji, M. & Gazzinelli, R. T. Enhanced protective immunity against malaria by vaccination with a recombinant adenovirus encoding the circumsporozoite protein of *Plasmodium* lacking the GPI-anchoring motif. *Vaccine* 22, 3575-3584 (2004).

Calvo-Calle, J. M., Oliveira, G. A., Watta, C. O., Soverow, J., Parra-Lopez, C., et al. 2006. A linear peptide containing minimal T- and B-cell epitopes of *Plasmodium falciparum* circumsporozoite protein elicits protection against transgenic sporozoite challenge. *Infect Immun.* 74:6929-6939.

Clyde, D. F., Most, H., McCarthy, V. C., and Vanderberg, J. P. 1973. Immunization of man against sporozite-induced falciparum malaria. *Am J Med Sci.* 266:169-177.

Chroboczek, J., Ruigrok, R. W. & Cusack, S. Adenovirus Fiber. *Current topics in microbiology and immunology* 199 (Pt 1), 163-200 (1995).

Chu, Y., Heistad, D., Cybulsky, M. I. & Davidson, B. L. Vascular cell adhesion molecule-1 augments adenovirus-mediated gene transfer. *Arterioscler Thromb Vasc Biol* 21, 238-242 (2001).

Crawford-Miksza, L. & Schnurr, D. P. Analysis of 15 adenovirus Hexon proteins reveals the location and structure of seven hypervariable regions containing serotype-specific residues. *Journal of virology* 70, 1836-1844 (1996).

Crompton, J., Toogood, C. I., Wallis, N. & Hay, R. T. Expression of a foreign epitope on the surface of the adenovirus Hexon. *The Journal of general virology* 75 (Pt 1), 133-139 (1994).

Crystal, R. G. Transfer of genes to humans: early lessons and obstacles to success. *Science* (New York, N. Y 270, 404-410 (1995).

Douglas, J. T. Adenoviral vectors for gene therapy. *Molecular biotechnology* 36, 71-80 (2007).

Edelman, R., Hoffman, S. L., Davis, J. R., Beier, M., Sztein, M. B., et al. 1993. Long-term persistence of sterile immunity in a volunteer immunized with X-irradiated *Plasmodium falciparum* sporozoites. *J Infect Dis.* 168: 1066-1070.

Grillot, D., Valmori, D., Lambert, P. H., Corradin, G., and Del Giudice, G. 1993. Presentation of T cell epitopes assembled as multiple-antigen peptides to murine and human T lymphocytes. *Infect Immun.* 61:3064-3067.

Graham, F. L. & Prevec, L. Adenovirus-based expression vectors and recombinant vaccines. *Biotechnology* (Reading, Mass. 20, 363-390 (1992).

Gwadz, R. W., Cochrane, A. H., Nussenzweig, V., and Nussenzweig, R. S. 1979. Preliminary studies on vaccination of rhesus monkeys with irradiated sporozoites of *Plasmodium* knowlesi and characterization of surface antigens of these parasites. *Bull World Health Organ.* 57 Suppl 1:165-173.

Hackett, N. R. et al. Use of quantitative TaqMan real-time PCR to track the time-dependent distribution of gene transfer vectors in vivo. *Mol Ther* 2, 649-656 (2000).

Harvey, B. G. et al. Airway epithelial CFTR mRNA expression in cystic fibrosis patients after repetitive administration of a recombinant adenovirus. *The Journal of clinical investigation* 104, 1245-1255 (1999).

Heemskerk, B. et al. Adenovirus-specific CD4+ T cell clones recognizing endogenous antigen inhibit viral replication in vitro through cognate interaction. *J Immunol* 177, 8851-8859 (2006).

Henry, L. J., Xia, D., Wilke, M. E., Deisenhofer, J. & Gerard, R. D. Characterization of the knob domain of the adenovirus type 5 Fiber protein expressed in *Escherichia coli. Journal of virology* 68, 5239-5246 (1994).

Hong, S. S., Habib, N. A., Franqueville, L., Jensen, S. & Boulanger, P. A. Identification of adenovirus (ad) penton base neutralizing epitopes by use of sera from patients who had received conditionally replicative ad (addl 1520) for treatment of liver tumors. *Journal of virology* 77, 10366-10375 (2003).

Kester, K. E., Cummings, J. F., Ockenhouse, C. F., Nielsen, R., Hall, B. T., et al. 2008. Phase 2a trial of 0, 1, and 3 month and 0, 7, and 28 day immunization schedules of malaria vaccine RTS,S/AS02 in malaria-naïve adults at the Walter Reed Army Institute of Research. *Vaccine.* 26:2191-2202.

Kirby, I. et al. Mutations in the DG loop of adenovirus type 5 Fiber knob protein abolish highaffinity binding to its cellular receptor CAR. *Journal of virology* 73, 9508-9514 (1999).

Koizumi, N., Mizuguchi, H., Utoguchi, N., Watanabe, Y. & Hayakawa, T. Generation of Fiber-modified adenovirus vectors containing heterologous peptides in both the HI loop and C terminus of the Fiber knob. *The journal of gene medicine* 5, 267-276 (2003).

Kozak M. 1987. An analysis of 5'-noncoding sequences from 699 vertebrate messenger RNAs. *Nucleic Acids Res.* 15:8125-148.

Krause, A., Joh, J. H., Hackett, N. R., Roelvink, P. W., Bruder, J. T., et al. 2006. Epitopes expressed in different adenovirus capsid proteins induce different levels of epitope-specific immunity. *J Virol.* 80:5523-5530.

Labow, D., Lee, S., Ginsberg, R. J., Crystal, R. G. & Korst, R. J. Adenovirus vector-mediated gene transfer to regional lymph nodes. *Human gene therapy* 11, 759-769 (2000).

Leen, A. M. et al. Identification of Hexon-specific CD4 and CD8 T cell epitopes for vaccine and immunotherapy. *Journal of virology* 82, 546-554 (2008).

Leopold, P. L. & Crystal, R. G. Intracellular trafficking of adenovirus: many means to many ends. *Advanced drug delivery reviews* 59, 810-821 (2007).

Mastrangeli, A. et al. "Sero-switch" adenovirus-mediated in vivo gene transfer: circumvention of anti-adenovirus humoral immune defenses against repeat adenovirus vector administration by changing the adenovirus serotype. *Human gene therapy* 7, 79-87 (1996).

Mathias, P., Wickham, T., Moore, M. & Nemerow, G. Multiple adenovirus serotypes use alpha v integrins for infection. *Journal of virology* 68, 6811-6814 (1994).

McConnell, M. J., Danthinne, X., and Imperiale, M. J. 2006. Characterization of a permissive epitope insertion site in adenovirus Hexon. *J Virol.* 80:5361-5370.

Meier, O. & Greber, U. F. Adenovirus endocytosis. *The journal of gene medicine* 5, 451-462 (2003).

Miyazawa, N. et al. Fiber swap between adenovirus subgroups B and C alters intracellular trafficking of adenovirus gene transfer vectors. *Journal of virology* 73, 6056-6065 (1999).

Miyazawa, N., Crystal, R. G. & Leopold, P. L. Adenovirus serotype 7 retention in a late endosomal compartment prior to cytosol escape is modulated by Fiber protein. *Journal of virology* 75, 1387-1400 (2001).

Mizuguchi, H. & Hayakawa, T. Targeted adenovirus vectors. *Human gene therapy* 15, 1034-1044 (2004).

Nakano, M. Y., Boucke, K., Suomalainen, M., Stidwill, R. P. & Greber, U. F. The first step of adenovirus type 2 disassembly occurs at the cell surface, independently of endocytosis and escape to the cytosol. *Journal of virology* 74, 7085-7095 (2000).

Nicklin, S. A. et al. Ablating adenovirus type 5 Fiber-CAR binding and HI loop insertion of the SIGYPLP peptide generate an endothelial cell-selective adenovirus. *Mol Ther* 4, 534-542 (2001).

Noureddini, S. C. & Curiel, D. T. Genetic targeting strategies for adenovirus. *Molecular pharmaceutics* 2, 341-347 (2005).

Nussenzweig, R. S., Vanderberg, J., Most, H., and Orton, C. 1967. Protective immunity produced by the injection of x-irradiated sporozoites of *plasmodium berghei. Nature.* 216:160-162.

Nussenzweig, R. S. & Long, C. A. Malaria vaccines: multiple targets. *Science* (New York, N.Y. 265, 1381-1383 (1994).

Onion, D. et al. The CD4+ T cell response to adenovirus is focused against conserved residues within the Hexon protein. *The Journal of general virology* 88, 2417-2425 (2007).

Ophorst, O. J., Radosević, K., Havenga, M. J., Pau, M. G., Holterman, L., et al. 2006. Immunogenicity and protection of a recombinant human adenovirus serotype 35-based malaria vaccine against *Plasmodium yoelii* in mice. *Infect Immun.* 74:313-320.

Oualikene, W., Gonin, P. & Eloit, M. Short and long term dissemination of deletion mutants of adenovirus in permissive (cotton rat) and non-permissive (mouse) species. *The Journal of general virology* 75 (Pt 10), 2765-2768 (1994).

Priddy, F. H., Brown, D., Kublin, J., Monahan, K., Wright, D. P., et al. 2008. Safety and immunogenicity of a replication-incompetent adenovirus type 5 HIV-1 clade B gag/pol/nef vaccine in healthy adults. *Clin Infect Dis.* 46:1769-1781.

Roberts, M. M., White, J. L., Grutter, M. G. & Burnett, R. M. Three-dimensional structure of the adenovirus major coat protein Hexon. *Science* (New York, N.Y. 232, 1148-1151 (1986).

Roberts, D. M., Nanda, A., Havenga, M. J., Abbink, P., Lynch, D. M., et al. 2006. Hexon-chimaeric adenovirus serotype 5 vectors circumvent pre-existing anti-vector immunity. *Nature.* 441:239-243.

Rodrigues, E. G., Zavala, F., Eichinger, D., Wilson, J. M., and Tsuji, M. 1997. Single immunizing dose of recombinant adenovirus efficiently induces CD8+ T cell-mediated protective immunity against malaria. *J Immunol.* 158:1268-1274.

Rodrigues, E. G., Zavala, F., Nussenzweig, R. S., Wilson, J. M. & Tsuji, M. Efficient induction of protective antimalaria immunity by recombinant adenovirus. *Vaccine* 16, 1812-1817 (1998).

Roelvink, P. W., Mi Lee, G., Einfeld, D. A., Kovesdi, I. & Wickham, T. J. Identification of a conserved receptor-binding site on the Fiber proteins of CAR-recognizing adenoviridae. *Science* (New York, N. Y 286, 1568-1571 (1999).

Rux, J. J. & Burnett, R. M. Type-specific epitope locations revealed by X-ray crystallographic study of adenovirus type 5 Hexon. *Mol Ther* 1, 18-30 (2000).

Rux, J. J. & Burnett, R. M. Adenovirus structure. *Human gene therapy* 15, 1167-1176 (2004).

Roy, S. et al. Use of chimeric adenoviral vectors to assess capsid neutralization determinants. *Virology* 333, 207-214 (2005).

Silvie, O., Greco, C., Franetich, J. F., Dubart-Kupperschmitt, A., Hannoun, L., et al. 2006. Expression of human CD81 differently affects host cell susceptibility to malaria sporozoites depending on the *Plasmodium* species. *Cell Microbiol.* 8:1134-1146.

Sumida, S. M., Truitt, D. M., Lemckert, A. A., Vogels, R., Custers, J. H., et al. 2005. Neutralizing antibodies to adenovirus serotype 5 vaccine vectors are directed primarily against the adenovirus Hexon protein. *J Immunol.* 174:7179-7185.

Sun, P., Schwenk, R., White, K., Stoute, J. A., Cohen, J., et al. 2003. Protective immunity induced with malaria vaccine, RTS,S, is linked to *Plasmodium falciparum* circumsporozoite protein-specific CD4+ and CD8+ T cells producing IFN-gamma. *J. Immunol.* 171:6961-6967.

Tao, D., Barba-Spaeth, G., Rai, U., Nussenzweig, V., Rice, C. M., and Nussenzweig, R. S. 2005. Yellow fever 17D as a vaccine vector for microbial CTL epitopes: protection in a rodent malaria model. *J Exp Med.* 201:201-209.

Teramoto, S. et al. Investigation of effects of anesthesia and age on aspiration in mice through LacZ gene transfer by recombinant E1-deleted adenovirus vectors. *American journal of respiratory and critical care medicine* 158, 1914-1919 (1998).

Top, F. H., Jr., Dudding, B. A., Russell, P. K. & Buescher, E. L. Control of respiratory disease in recruits with types 4 and 7 adenovirus vaccines. *American journal of epidemiology* 94, 142-146 (1971).

Top, F. H., Jr. Control of adenovirus acute respiratory disease in U. S. Army trainees. *Yale J Biol Med* 48, 185-195 (1975).

Tsuji, M., Romero, P., Nussenzweig, R. S., and Zavala, F. 1990. CD4+ cytolytic T cell clone confers protection against murine malaria. *J Exp Med.* 172:1353-1357.

Tsuji, M., Rodrigues, E. G. & Nussenzweig, S. Progress toward a malaria vaccine: efficient induction of protective anti-malaria immunity. *Biol Chem* 382, 553-570 (2001).

Wickham, T. J., Mathias, P., Cheresh, D. A. & Nemerow, G. R. Integrins alpha v beta 3 and alpha v beta 5 promote adenovirus internalization but not virus attachment. *Cell* 73, 309-319 (1993).

Wohlfart, C. Neutralization of adenoviruses: kinetics, stoichiometry, and mechanisms. *Journal of virology* 62, 2321-2328 (1988).

Worgall, S. et al. Modification to the capsid of the adenovirus vector that enhances dendritic cell infection and transgene-specific cellular immune responses. *Journal of virology* 78, 2572-2580 (2004).

Worgall, S., Krause, A., Rivara, M., Hee, K. K., Vintayen, E. V., et al. 2005. Protection against *P. aeruginosa* with an adenovirus vector containing an OprF epitope in the capsid. *J Clin Invest.* 115:1281-1289.

Worgall, S., Krause, A., Qiu, J., Joh, J., Hackett, N. R., and Crystal, R. G. 2007. Protective immunity to *pseudomonas aeruginosa* induced with a capsid-modified adenovirus expressing *P. aeruginosa* OprF. *J Virol.* 81:13801-13808.

Wu, H., Dmitriev, I., Kashentseva, E., Seki, T., Wang, M., et al. 2002. Construction and characterization of adenovirus serotype 5 packaged by serotype 3 Hexon. *J Virol.* 76:12775-12782.

Wu, H. et al. Identification of sites in adenovirus Hexon for foreign peptide incorporation. *Journal of virology* 79, 3382-3390 (2005).

Xia, D., Henry, L., Gerard, R. D. & Deisenhofer, J. Structure of the receptor binding domain of adenovirus type 5 Fiber protein. *Current topics in microbiology and immunology* 199 (Pt 1), 39-46 (1995).

Yang, Y., Li, Q., Ertl, H. C. & Wilson, J. M. Cellular and humoral immune responses to viral antigens create barriers to lung-directed gene therapy with recombinant adenoviruses. *Journal of virology* 69, 2004-2015 (1995).

Youil, R., Toner, T. J., Su, Q., Chen, M., Tang, A., et al. 2002. Hexon gene switch strategy for the generation of chimeric recombinant adenovirus. *Hum Gene Ther.* 13: 311-320.

What is claimed is:

1. A recombinant adenovirus derived from a recombinant adenovirus plasmid vector, wherein the recombinant adenovirus plasmid vector comprises a nucleotide sequence encoding:

a *Plasmodium falciparum* circumsporozoite protein gene, or antigenic portion thereof, operably linked to a heterologous promoter sequence, and one or more modified capsid and/or core protein genes, wherein an immunogenic epitope sequence of *Plasmodium falciparum* circumsporozoite has been inserted into or replaces at least part of the one or more capsid and/or core protein genes;

wherein the immunogenic epitope sequence is a B cell epitope sequence selected from $(NANP)_{12}$, $(NANP)_{14}$, $(NANP)_{16}$, $(NANP)_{18}$, $(NANP)_{20}$, $(NANP)_{22}$; and wherein the core protein gene further comprises a pVII protein gene and a CD4+T cell epitope sequence that is inserted into the pVII protein gene.

2. The adenovirus of claim 1, wherein the *Plasmodium falciparum* circumsporozoite protein gene further comprises a codon-optimized *Plasmodium falciparum* circumsporozoite protein gene.

3. A recombinant adenovirus derived from a recombinant adenovirus plasmid vector, wherein the recombinant adenovirus plasmid vector comprises a nucleotide sequence encoding:

a *Plasmodium falciparum* circumsporozoite protein gene, or antigenic portion thereof, operably linked to a heterologous promoter sequence, and one or more modified capsid and/or core protein genes, wherein an immunogenic epitope sequence of *Plasmodium falciparum* circumsporozoite has been inserted into or replaces at least part of the one or more capsid and/or core protein genes;

wherein the immunogenic epitope sequence is a B cell epitope sequence selected from $(NANP)_{12}$, $(NANP)_{14}$, $(NANP)_{16}$, $(NANP)_{18}$, $(NANP)_{20}$, $(NANP)_{22}$; and wherein the *Plasmodium falciparum* circumsporozoite protein gene further comprises a codon-optimized *Plasmodium falciparum* circumsporozoite protein gene encoded by SEQ ID NO:2.

4. The adenovirus of claim 1, wherein the capsid protein gene further comprises a Hexon hypervariable region (HVR) sequence.

5. The adenovirus of claim 4, wherein the HVR sequence further comprises an HVR1 or HVR5 sequence and the B cell epitope sequence:

a) is inserted in the HVR1 or HVR5 sequence; or b) replaces a portion of the HVR1 or HVR5 sequence.

6. A recombinant adenovirus derived from a recombinant adenovirus plasmid vector, wherein the recombinant adenovirus plasmid vector comprises a nucleotide sequence encoding:

a *Plasmodium falciparum* circumsporozoite protein gene, or antigenic portion thereof, operably linked to a heterologous promoter sequence, and one or more modified capsid and/or core protein genes encoded by a nucleic acid sequence selected from the group consisting of SEQ ID NO:16, SEQ ID NO:17, SEQ ID NO:18, SEQ ID NO:19, SEQ ID NO:20, SEQ ID NO:21, or SEQ ID NO:22, wherein an immunogenic epitope sequence of *Plasmodium falciparum* circumsporozoite has been inserted into or replaces at least part of the one or more capsid and/or core protein genes;

wherein the immunogenic epitope sequence is a B cell epitope sequence selected from $(NANP)_{12}$, $(NANP)_{14}$, $(NANP)_{16}$, $(NANP)_{18}$, $(NANP)_{20}$, $(NANP)_{22}$, wherein the capsid protein gene further comprises a Hexon hypervariable region (HVR) sequence; and wherein the HVR sequence further comprises an HVR1 or HVR5 sequence and the B cell epitope sequence:

a) is inserted in the HVR1 or HVR5 sequence; or b) replaces a portion of the HVR1 or HVR5 sequence.

7. The adenovirus of claim 1, wherein the one or more modified capsid and/or core protein genes comprises a capsid Fiber protein gene and the B cell epitope sequence is inserted into the Fiber protein gene.

8. A recombinant adenovirus derived from a recombinant adenovirus plasmid vector, wherein the recombinant adenovirus plasmid vector comprises a nucleotide sequence encoding:

a *Plasmodium falciparum* circumsporozoite protein gene, or antigenic portion thereof, operably linked to a heterologous promoter sequence, and one or more modified capsid and/or core protein genes comprising a capsid Fiber protein gene and the B cell epitope sequence is inserted into the Fiber protein gene, wherein an immunogenic epitope sequence of *Plasmodium falciparum* circumsporozoite has been inserted into or replaces at least part of the one or more capsid and/or core protein genes;

wherein the immunogenic epitope sequence is a B cell epitope sequence selected from $(NANP)_{12}$, $(NANP)_{14}$, $(NANP)_{16}$, $(NANP)_{18}$, $(NANP)_{20}$, $(NANP)_{22}$; and wherein the modified capsid protein gene is encoded by SEQ ID NO:24 or SEQ ID NO:25.

9. A recombinant adenovirus derived from a recombinant adenovirus plasmid vector, wherein the recombinant adenovirus plasmid vector comprises a nucleotide sequence encoding:

a *Plasmodium falciparum* circumsporozoite protein gene, or antigenic portion thereof, operably linked to a heterologous promoter sequence, and one or more modified capsid and/or core protein genes comprising a capsid Fiber protein gene and the B cell epitope sequence is inserted into the Fiber protein gene, wherein an immunogenic epitope sequence of *Plasmodium falciparum* circumsporozoite has been inserted into or replaces at least part of the one or more capsid and/or core protein genes;

wherein the immunogenic epitope sequence is a B cell epitope sequence selected from $(NANP)_{12}$, $(NANP)_{14}$, $(NANP)_{16}$, $(NANP)_{18}$, $(NANP)_{20}$, $(NANP)_{22}$;

wherein the core protein gene further comprises a pVII protein gene and a CD4+T cell epitope sequence that is inserted into the pVII protein gene; and wherein the modified core protein gene is encoded by SEQ ID NO:26, SEQ ID NO:27, SEQ ID NO:28 or SEQ ID NO:29.

10. The adenovirus of claim 1 or claim 9, wherein the CD4+T cell epitope sequence is a *Plasmodium falciparum* circumsporozoite protein gene CD4+T cell epitope sequence.

11. The adenovirus of claim 1 or 9, wherein the CD4+T cell epitope sequence is EYLNKIQNSLSTEWSPCSVT (SEQ ID NO:62).

12. The adenovirus of claim 1, wherein the adenovirus is produced from any one of the recombinant adenovirus plasmid vectors selected from the group consisting of an HVR1-modified adenovirus vector, a Fiber-modified adenovirus vector, an HVR1 and Fiber-modified adenovirus vector, a Fiber and pVII-modified adenovirus vector, an HVR1 and pVII-modified adenovirus vector and an HVR1, Fiber and pVII-modified adenovirus vector.

13. A recombinant adenovirus derived from a recombinant adenovirus plasmid vector, wherein the recombinant adenovirus plasmid vector comprises a nucleotide sequence encoding:

a *Plasmodium falciparum* circumsporozoite protein gene, or antigenic portion thereof, operably linked to a heterologous promoter sequence, and one or more modified capsid and/or core protein genes, wherein an immunogenic epitope sequence of *Plasmodium falciparum* circumsporozoite has been inserted into or replaces at least part of the one or more capsid and/or core protein genes; and wherein the core protein gene comprises a pVII protein gene and a CD4+T cell epitope sequence is inserted into the pVII protein gene.

14. The adenovirus of claim 13 wherein the modified core protein gene is encoded by SEQ ID NO:27, SEQ ID NO:28 or SEQ ID NO:29.

15. The adenovirus as in any of claims 13, wherein the CD4+T cell epitope sequence is a *Plasmodium falciparum* circumsporozoite protein gene CD4+T cell epitope sequence.

16. The adenovirus of claim 13, wherein the CD4+T cell epitope sequence is EYLNKIQNSLSTEWSPCSVT (SEQ ID NO:62).

* * * * *